United States Patent
Nie et al.

(10) Patent No.: US 11,203,584 B2
(45) Date of Patent: Dec. 21, 2021

(54) NITROGEN-CONTAINING COMPOUND, ELECTRONIC ELEMENT AND ELECTRONIC DEVICE

(71) Applicant: Shaanxi Lighte Optoelectronics Material Co., Ltd., Shaanxi (CN)

(72) Inventors: Qiqi Nie, Shaanxi (CN); Jiamei Cao, Shaanxi (CN); Tiantian Ma, Shaanxi (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 17/109,611

(22) Filed: Dec. 2, 2020

(65) Prior Publication Data
US 2021/0206741 A1  Jul. 8, 2021

(30) Foreign Application Priority Data

Dec. 31, 2019 (CN) .......................... 201911415821.0

(51) Int. Cl.
*H01L 51/00* (2006.01)
*H01L 51/50* (2006.01)
(Continued)

(52) U.S. Cl.
CPC .......... *C07D 333/76* (2013.01); *C07C 211/54* (2013.01); *C07D 209/82* (2013.01);
(Continued)

(58) Field of Classification Search
CPC .. C07D 333/76; C07D 471/04; C07D 209/86; C07D 265/38; C07D 7/0816;
(Continued)

(56) References Cited

U.S. PATENT DOCUMENTS

2004/0124766 A1*  7/2004  Nakagawa .......... H01L 51/0073
                                                            313/504
2009/0302758 A1* 12/2009  Saitoh ................ H01L 51/5048
                                                            313/506
(Continued)

FOREIGN PATENT DOCUMENTS

CN       107459466 A     12/2017
CN       110128279 A      8/2019
(Continued)

OTHER PUBLICATIONS

Google Patents translation for KR 20190118514A (publication date Oct. 2019). (Year: 2019).*

(Continued)

*Primary Examiner* — Dawn L Garrett

(74) *Attorney, Agent, or Firm* — Tucker Ellis LLP

(57) ABSTRACT

The present disclosure provides a nitrogen-containing compound, an electronic element and an electronic device, which belongs to the technical field of organic materials. The nitrogen-containing compound has a structure of Chemical Formula 1, wherein $R_1$ and $R_2$ are each independently selected from hydrogen or a group represented by Chemical Formula 1-1, and one and only one of $R_1$ and $R_2$ has the group of Chemical Formula 1-1; when $R_1$ or $R_2$ is selected from hydrogen, said $R_1$ and $R_2$ may be replaced by $R_4$. The nitrogen-containing compound can improve the performance of electronic elements.

5 Claims, 2 Drawing Sheets

(51) Int. Cl.
| | |
|---|---|
| *C07D 333/76* | (2006.01) |
| *C07C 211/54* | (2006.01) |
| *C07D 209/82* | (2006.01) |
| *C07D 209/86* | (2006.01) |
| *C07D 209/88* | (2006.01) |
| *C07D 213/36* | (2006.01) |
| *C07D 215/12* | (2006.01) |
| *C07D 265/38* | (2006.01) |
| *C07D 307/91* | (2006.01) |
| *C07D 311/80* | (2006.01) |
| *C07D 319/24* | (2006.01) |
| *C07D 339/08* | (2006.01) |
| *C07D 403/12* | (2006.01) |
| *C07D 405/12* | (2006.01) |
| *C07D 409/12* | (2006.01) |
| *C07D 471/04* | (2006.01) |
| *C07F 7/08* | (2006.01) |

(52) U.S. Cl.
CPC ......... *C07D 209/86* (2013.01); *C07D 209/88* (2013.01); *C07D 213/36* (2013.01); *C07D 215/12* (2013.01); *C07D 265/38* (2013.01); *C07D 307/91* (2013.01); *C07D 311/80* (2013.01); *C07D 319/24* (2013.01); *C07D 339/08* (2013.01); *C07D 403/12* (2013.01); *C07D 405/12* (2013.01); *C07D 409/12* (2013.01); *C07D 471/04* (2013.01); *C07F 7/0816* (2013.01); *H01L 51/006* (2013.01); *H01L 51/0059* (2013.01); *H01L 51/0061* (2013.01); *H01L 51/0067* (2013.01); *H01L 51/0072* (2013.01); *H01L 51/0073* (2013.01); *H01L 51/0074* (2013.01); *H01L 51/5064* (2013.01)

(58) Field of Classification Search
CPC .. C07D 209/88; C07D 213/36; C07D 339/08; C07D 215/12; C07D 311/80; C07D 319/24; C07D 405/12; C07D 307/91; C07D 403/12; C07D 409/12; C07D 209/82; H01L 51/0061; H01L 51/006; H01L 51/0074; H01L 51/0067; H01L 51/0073; H01L 51/0072; H01L 51/0059; H01L 51/5064; C07C 211/54
See application file for complete search history.

(56) References Cited

U.S. PATENT DOCUMENTS

| | | | |
|---|---|---|---|
| 2014/0291586 A1* | 10/2014 | Buesing | C09K 11/06 252/500 |
| 2016/0126469 A1* | 5/2016 | Nakano | H01L 51/006 257/40 |
| 2016/0133849 A1* | 5/2016 | Miyake | H01L 51/0061 549/460 |
| 2016/0372677 A1* | 12/2016 | Miyake | H01L 51/0058 |
| 2021/0130295 A1* | 5/2021 | Kim | H01L 51/006 |

FOREIGN PATENT DOCUMENTS

| | | | |
|---|---|---|---|
| CN | 111138298 A | | 5/2020 |
| CN | 111995533 A | * | 11/2020 |
| EP | 2194110 A1 | * | 6/2010 |
| KR | 20190035567 A | | 4/2019 |
| KR | 20190118514 A | | 10/2019 |
| KR | 20190118515 A | | 10/2019 |
| KR | 20200037732 A | | 4/2020 |
| WO | 2020050623 A1 | | 3/2020 |
| WO | 2020080849 A1 | | 4/2020 |
| WO | 2020080872 A1 | | 4/2020 |
| WO | 2020248943 A1 | | 12/2020 |

OTHER PUBLICATIONS

Synthetic Metals, 143, (2004), pp. 215-220. (Year: 2004).*
Search Report regarding corresponding PCT App. No. PCT/CN2020/ 105862; dated Oct. 28, 2020.
Written Opinion regarding corresponding PCT App. No. PCT/ CN2020/105862; dated Oct. 28, 2020.
First Office Action regarding related CN App. No. 201911415821.0; dated Jul. 6, 2020.
The Extended European Search Report from the European Application No. 20211926.9, dated Feb. 12, 2021, 8 pages.

\* cited by examiner

NITROGEN-CONTAINING COMPOUND, ELECTRONIC ELEMENT AND ELECTRONIC DEVICE

CROSS-REFERENCE OF RELATED APPLICATIONS

The present disclosure claims the priority of the application having the Chinese patent application No. CN201911415821.0, the filing date of Dec. 31, 2019, and the title of "Nitrogen-containing compound, electronic element and electronic device", whose entire content is specifically incorporated into this disclosure by reference in its entirety.

TECHNICAL FIELD

The present disclosure relates to the technical field of organic materials, in particular to a nitrogen-containing compound, an electronic element using the nitrogen-containing compound, and an electronic device using the electronic element.

BACKGROUND

With the development of electronic technology and the advancement of materials science, the application range of electronic components for realizing electroluminescence or photoelectric conversion becomes more and more extensive. Such electronic component usually includes a cathode and an anode disposed opposite to each other, and a functional layer disposed between the cathode and the anode. The functional layer is composed of multiple organic or inorganic film layers, and generally includes an energy conversion layer, a hole transporting layer disposed between the energy conversion layer and the anode, and an electron transporting layer disposed between the energy conversion layer and the cathode.

For example, when the electronic component is an organic electroluminescent device, it generally includes an anode, a hole transporting layer, an electroluminescent layer as an energy conversion layer, an electron transporting layer and a cathode, which are sequentially stacked. When a voltage is applied to between anode and cathode, the two electrodes generate an electric field. Under the action of the electric field, the electrons on the cathode side move to the electroluminescent layer, while the holes on the anode side move to the electroluminescent layer, so the electrons and the holes combine in the electroluminescent layer to form excitons, and the excitons are in an excited state and release energy outwards, which in turn makes the electroluminescent layer emit light outward. In order to improve the performance of electronic components that realize electroluminescence or photoelectric conversion, an electron blocking layer may also be provided between the energy conversion layer and the hole transporting layer.

In electronic components that realize electroluminescence or photoelectric conversion, the hole transport performance of the film layer disposed between the anode and the energy conversion layer has an important influence on the performance of the electronic components. As recited in patent documents such as Chinese Patent Application CN201710407382.3, the fluorene group-containing compound may be used for the hole transporting layer. However, the performance of the existing hole transporting layer materials containing fluorene groups needs to be further improved.

The above information disclosed in the background is only for enhancing the understanding of the background of the present disclosure, so it may include information that does not constitute prior art known to those skilled in the art.

SUMMARY

The object of the present disclosure is to provide a nitrogen-containing compound, an electronic element and an electronic device to improve the performance of the electronic element and the electronic device.

In order to achieve the above-mentioned object of the disclosure, the present disclosure adopts the following technical solutions.

According to the first aspect of the present disclosure, there is provided a nitrogen-containing compound having the structure shown in Chemical Formula 1:

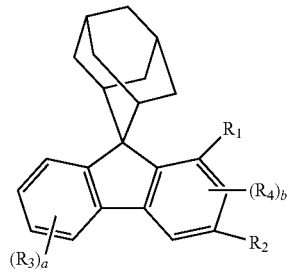

Chemical Formula 1

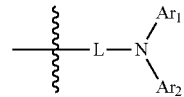

Chemical Formula 1-1 wherein ⁃⁃⁃ represents a chemical bond;

$R_1$ and $R_2$ are each independently selected from hydrogen or a group represented by Chemical Formula 1-1, and one and only one of $R_1$ and $R_2$ has the group represented by Chemical Formula 1-1; when $R_1$ or $R_2$ is selected from hydrogen, said $R_1$ and $R_2$ may be replaced by $R_4$;

$R_3$, $R_4$ are each independently selected from the group consisting of deuterium, halogen, cyano, a heteroaryl having 3 to 20 carbon atoms, an aryl having 6 to 20 carbon atoms, a trialkylsily having 3 to 12 carbon atoms, an arylsilyl having 8 to 12 carbon atoms, an alkyl having 1 to 10 carbon atoms, a haloalkyl having 1 to 10 carbon atoms, an alkenyl having 2 to 6 carbon atoms, an alkynyl having 2 to 6 carbon atoms, a cycloalkyl having 3 to 20 carbon atoms, a heterocycloalkyl having 2 to 10 carbon atoms, a cycloalkenyl having 5 to 10 carbon atoms, a heterocycloalkenyl having 4 to 10 carbon atoms, an alkoxy having 1 to 10 carbon atoms, an alkylthio having 1 to 10 carbon atoms, an aryloxy having 6 to 18 carbon atoms, an arylthio having 6 to 18 carbon atoms and a phosphoroxy having 6 to 18 carbon atoms;

a is selected from 0, 1, 2, 3, or 4; when a is greater than or equal to 2, any two $R_3$ are the same or different;

b is selected from 0, 1, 2, or 3; when b is greater than or equal to 2, any two $R_4$ are the same or different;

L is selected from single bond, a substituted or unsubstituted arylene having 6 to 30 carbon atoms, or a substituted or unsubstituted heteroarylene having 3 to 30 carbon atoms;

$Ar_1$ and $Ar_2$ are each independently selected from the following substituted or unsubstituted groups: an alkyl having 1 to 20 carbon atoms, a cycloalkyl having 3 to 20 carbon atoms, an aryl having 6 to 30 carbon atoms, or a heteroaryl having 3 to 30 carbon atoms, and $Ar_1$ and $Ar_2$ are not 9,9-diphenyl fluorenyl.

According to the second aspect of the present disclosure, there is provided an electronic element including an anode and a cathode disposed opposite to each other, and a functional layer disposed between the anode and the cathode, wherein the functional layer contains the above-mentioned nitrogen-containing compound. According to an embodiment of the present disclosure, the electronic element is an organic electroluminescence device. According to another embodiment of the present disclosure, the electronic element is a solar cell.

According to the third aspect of the present disclosure, there is provided an electronic device including the above-mentioned electronic element.

The nitrogen-containing compound of the present disclosure introduces an adamantane structure at the side of the fluorene to enhance the electron density of the fluorene ring and the conjugate system of the entire compound through the hyperconjugation effect, which can enhance the hole conductivity and electron tolerance of the nitrogen-containing compound. At the same time, the luminous efficiency and lifetime of the organic electroluminescent device using the nitrogen-containing compound may be improved, and the conversion efficiency and lifetime of the photoelectric conversion device using the nitrogen-containing compound may be improved. The adamantyl group is introduced between the branches of the triarylamine which is originally a near-plane structure, rather than at the end of it. The large steric hindrance of the adamantyl group can finely adjust the bonding angle and conjugation degree of the amine and each aryl group, thereby obtain HOMO value suitable for the material of the adjacent layer. It reduces the operating voltage of the organic electroluminescent device, and increases the open circuit voltage of the photoelectric conversion device. In addition, the introduction of adamantyl can also increase the molecular weight of the nitrogen-containing compound and reduce the molecular symmetry, increase the glass transition temperature and evaporation temperature of the compound of the present disclosure, and can control the crystallinity of the nitrogen-containing compound, makes the nitrogen-containing compound have better physical and thermal stability when being mass-produced, which facilitates the mass production stability of the electronic elements such as organic electroluminescent devices and photoelectric conversion devices.

BRIEF DESCRIPTION OF THE DRAWINGS

The above and other features and advantages of the present disclosure will become more apparent by describing in detail exemplary embodiments thereof with reference to the drawings.

Figure 1:
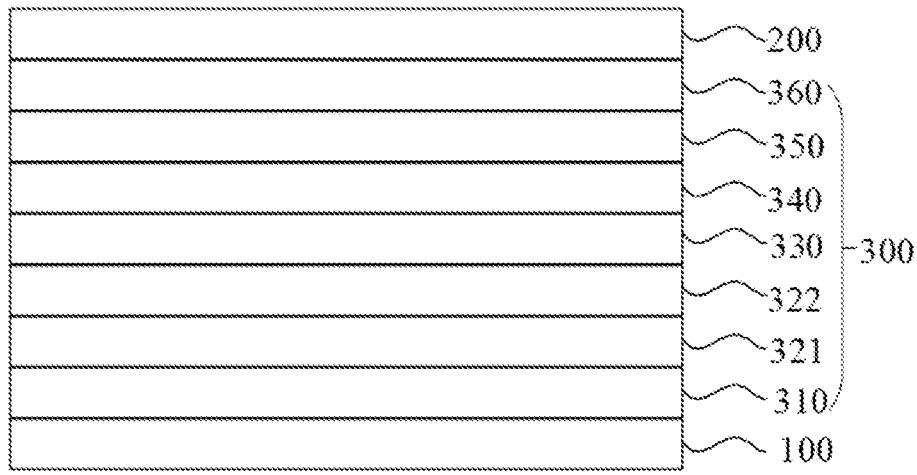
FIG. 1 is a schematic structural diagram of an organic electroluminescent device according to an embodiment of the present disclosure.

The reference symbols of the main elements in the figure are as follows:
100, anode;
200, cathode;
300, functional layer;
310, hole injecting layer;
321, hole transporting layer;
322, electron blocking layer;
330, organic electroluminescent layer;
340, hole blocking layer;
350, electron transporting layer;
360, electron injecting layer;
370, photoelectric conversion layer;
400, the first electronic device;
500, the second electronic device.

DETAILED DESCRIPTION

Exemplary embodiments will now be described more fully with reference to the drawings. However, the exemplary embodiments may be implemented in various forms, and should not be construed as being limited to the examples set forth herein; on the contrary, providing these embodiments makes the present disclosure more comprehensive and complete, and will fully convey the concept of the exemplary embodiments to those skilled in the art. The described features, structures, or characteristics may be combined in one or more embodiments in any suitable manner. In the following description, many specific details are provided to give a full understanding of the embodiments of the present disclosure.

In the figures, the area and layer thickness may be exaggerated for clarity. The same reference symbols in the figures denote the same or similar structures, and thus their detailed description will be omitted.

The described features, structures, or characteristics may be combined in one or more embodiments in any suitable manner. In the following description, many specific details are provided to give a full understanding of the embodiments of the present disclosure. However, those skilled in the art will realize that the technical solutions of the present disclosure may be practiced without one or more of the specific details, or other methods, components, materials, etc. may be used. In other cases, well-known structures, materials, or operations are not shown or described in detail to avoid obscuring the main technical ideas of the present disclosure.

In the present disclosure, when $R_1$ or $R_2$ is selected from hydrogen, said $R_1$ and $R_2$ may be replaced by $R_4$. It means that when one of $R_1$ and $R_2$ is selected from hydrogen, the one selected from hydrogen may be replaced by $R_4$ or not. For example, when $R_2$ is selected from Chemical Formula 1-1 and $R_1$ is selected from hydrogen, $R_1$ may or may not be replaced by $R_4$. Specifically, Chemical Formula 1 may include, but not limit to,

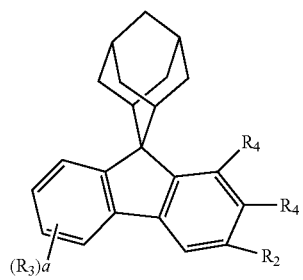

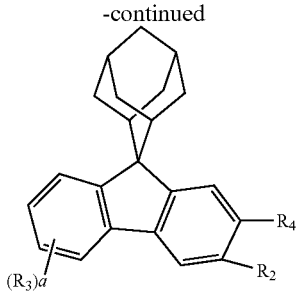

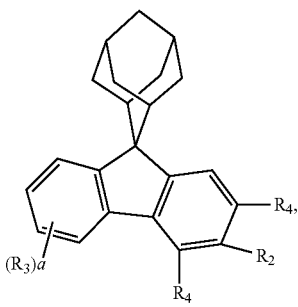

in which any two R₄ are the same or different.

In the present disclosure, since adamantane has a three-dimensional structure, in the structure diagram of the compound, because of the different drawing angles, it will show different plane shapes, among which, the ring structures formed on each 9,9-dimethylfluorene all refer to adamantine, and the connection location between the two group is the same. For example, the following four structures are the same:

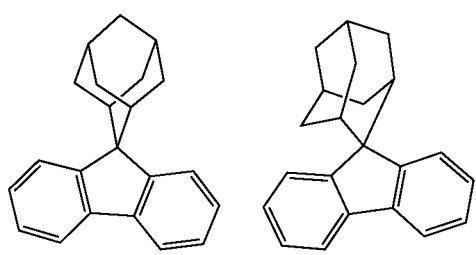

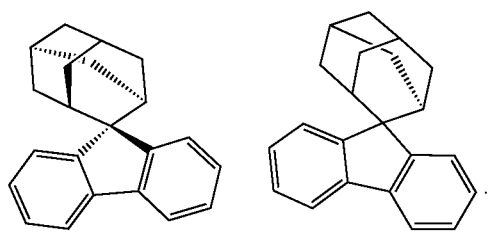

The present disclosure provides a nitrogen-containing compound having a structure shown in Chemical Formula 1:

Chemical Formula 1

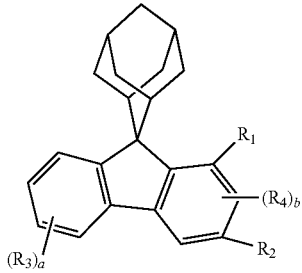

Chemical Formula 1-1

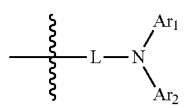

wherein $-\xi-$ represents a chemical bond;

$R_1$ and $R_2$ are each independently selected from hydrogen or a group represented by Chemical Formula 1-1, and one and only one of $R_1$ and $R_2$ has the group represented by Chemical Formula 1-1; when $R_1$ or $R_2$ is selected from hydrogen, said $R_1$ and $R_2$ may be replaced by $R_4$;

$R_3$, $R_4$ are each independently selected the group consisting of deuterium, halogen, cyano, a heteroaryl having 3 to 20 carbon atoms, an aryl having 6 to 20 carbon atoms, a trialkylsily having 3 to 12 carbon atoms, an arylsilyl having 8 to 12 carbon atoms, an alkyl having 1 to 10 carbon atoms, a haloalkyl having 1 to 10 carbon atoms, an alkenyl 2 to 6 carbon atoms, an alkynyl having 2 to 6 carbon atoms, a cycloalkyl having 3 to 20 carbon atoms, a heterocycloalkyl having 3 to 20 carbon atoms, a cycloalkenyl having 5 to 10 carbon atoms, a heterocycloalkenyl having 4 to 10 carbon atoms, an alkoxy having 1 to 10 carbon atoms, an alkylthio having 1 to 10 carbon atoms, an aryloxy having 6 to 18 carbon atoms, an arylthio having 6 to 18 carbon atoms and a phosphoroxy having 6 to 18 carbon atoms;

a is selected from 0, 1, 2, 3, or 4; when a is greater than or equal to 2, any two $R_3$ are the same or different;

b is selected from 0, 1, 2, or 3, when b is greater than or equal to 2, any two $R_4$ are the same or different;

L is selected from single bond, a substituted or unsubstituted arylene having 6 to 30 carbon atoms, a substituted or unsubstituted heteroarylene having 3 to 30 carbon atoms;

$Ar_1$ and $Ar_2$ are each independently selected from the following substituted or unsubstituted groups: an alkyl having 1 to 20 carbon atoms, a cycloalkyl having 3 to 20 carbon atoms, an aryl having 6 to 30 carbon atoms, or a heteroaryl having 3 to 30 carbon atoms, and $Ar_1$ and $Ar_2$ are not 9,9-diphenyl fluorenyl. Alternatively, neither $Ar_1$ nor $Ar_2$ is spirobifluorenyl.

Optionally, the substituents of L, $Ar_1$ and $Ar_2$ are each independently selected from deuterium, halogen, cyano, a heteroaryl having 3 to 18 carbon atoms, an aryl having 6 to 18 carbon atoms, a haloaryl having 6 to 20 carbon atoms, a trialkylsilyl having 3 to 12 carbon atoms, an arylsilyl having 8 to 12 carbon atoms, an alkyl having 1 to 10 carbon atoms, a haloalkyl having 1 to 10 carbon atoms, an alkenyl having 2 to 6 carbon atoms, an alkynyl having 2 to 6 carbon atoms, a cycloalkyl having 3 to 10 carbon atoms, a heterocycloalkyl having 2 to 10 carbon atoms, a cycloalkenyl having 5 to 10 carbon atoms, a heterocyclic alkenyl having 4 to 10 carbon atoms, an alkoxy having 1 to 10 carbon atoms, an alkylthio having 1 to 10 carbon atoms, an aryloxy having 6 to 18 carbon atoms, an arylthio having 6 to 18 carbon atoms, and a phosphoryloxy having 6 to 18 carbon atoms.

Also optionally, the substituents of $Ar_1$ and/or $Ar_2$ are triphenylsilyl.

In the present disclosure, the number of carbon atoms of L, $Ar_1$ and $Ar_2$ refers to all the number of carbon atoms. For example, if L is selected from substituted arylene having 12 carbon atoms, all the carbon atoms of the arylene and the substituents thereon are 12.

In the present disclosure, the expressions "each . . . independently" and " . . . each independently" and " . . . independently selected" may be interchangeable, and should be interpreted broadly. They may mean that in different groups, specific options expressed between the same symbols do not affect each other, or it can mean that in the same group, specific options expressed between the same symbols do not affect each other. For example, "

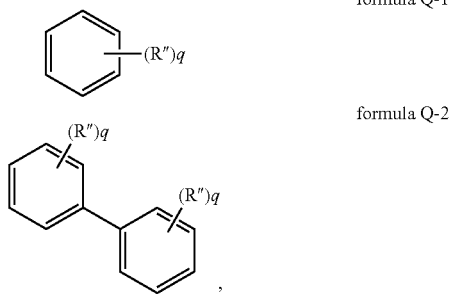

formula Q-1 formula Q-2 wherein each q is independently 0, 1, 2, or 3, and each R" is independently selected from hydrogen, deuterium, fluorine, or chlorine", means that: formula Q-1 represents that there are q substituents R" on the benzene ring, each R" may be the same or different, and the options of each R" do not affect each other; formula Q-2 represents that there are q substituents R" on each benzene ring of the biphenyl. The number q of the R" substituents on the two benzene rings may be the same or different, each R" may be the same or different, and the options of each R" do not affect each other.

In the present disclosure, the term "substituted or unsubstituted" means that there is no substituent or is substituted by one or more substituents. These substituents include, but are not limited to, deuterium (D), halogen (such as, F, Cl, Br), cyano, alkyl, alkenyl, alkynyl, haloalkyl, aryl, heteroaryl, aryloxy, arylthio, cycloalkyl, heterocycloalkyl, etc.

In the present disclosure, unless otherwise indicated, "hetero" means that at least one heteroatom such as B, N, O, S, or P is included in one functional group and the remaining atoms are carbon and hydrogen. The unsubstituted alkyl group may be a "saturated alkyl group" without any double or triple bonds.

In the present disclosure, "alkyl" may include linear or branched alkyl. The alkyl group may have 1 to 20 carbon atoms. In the present disclosure, a numerical range such as "1 to 20" refers to each integer in the given range. For example, "1 to 20 carbon atoms" refers to an alkyl having 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. The alkyl group may also be a alkyl group with 1 to 10 carbon atoms. The alkyl group may also be a lower alkyl group with 1 to 6 carbon atoms. In addition, the alkyl group may be substituted or unsubstituted.

Preferably, the alkyl group is selected from alkyl groups with 1 to 10 carbon atoms, and specific examples thereof include, but are not limited to, methyl, ethyl, propyl, isopropyl, n-butyl, isobutyl, sec-butyl, tert-butyl, pentyl and hexyl.

In the present disclosure, "alkenyl" refers to a hydrocarbon group containing one or more double bonds in a linear or branched hydrocarbon chain. The alkenyl group may be unsubstituted or substituted. An alkenyl group can have 1 to 20 carbon atoms, and whenever it appears herein, a numerical range such as "1 to 20" refers to each integer in the given range. For example, "1 to 20 carbon atoms" means that it can include alkenyl having 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. For example, the alkenyl group may be vinyl, butadienyl, or 1,3,5-hexatrienyl.

In the present disclosure, "cycloalkyl" refers to a saturated hydrocarbon containing an alicyclic structure, which includes monocyclic and fused ring structures. The cycloalkyl group may have 3 to 20 carbon atoms, and a numerical range such as "3 to 20" refers to each integer in the given range. For example, "3 to 20 carbon atoms" means that it can include a cycloalkyl having 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. The cycloalkyl group may be a small ring, an ordinary ring, or a large ring with 3 to 20 carbon atoms. Cycloalkyl groups may have a structure selected from monocyclic rings (single ring), bicyclic rings (two rings), polycyclic rings (three or more rings). Cycloalkyl may also have a structure of spiro ring (two rings sharing one carbon atom-spiro ring), fused ring (two rings sharing two carbon atoms), and bridge ring (two rings sharing more than two carbon atoms). In addition, the cycloalkyl group may be substituted or unsubstituted.

Preferably, the cycloalkyl group is selected from cycloalkyl groups having 3 to 10 carbon atoms, and specific examples thereof include, but are not limited to, cyclopropyl, cyclobutyl, cyclopentyl, cyclohexyl, and adamantyl.

In the present disclosure, "aryl" refers to an optional functional group or substituent derived from an aromatic hydrocarbon ring. The aryl group may be a monocyclic aryl group or a polycyclic aryl group. In other words, the aryl group may be a monocyclic aryl group, or a fused ring aryl group, and the aryl group may also be a polycyclic aryl group, which is formed by two or more monocyclic aryls conjugatedly connected through a carbon-carbon bond, formed by a monocyclic aryl and a fused ring aryl conjugatedly connected by a carbon-carbon bond, or formed by two or more fused ring aryl groups conjugatedly connected by a carbon-carbon bond. That is, two or more aryl groups conjugatedly connected through a carbon-carbon bond can also be regarded as aryl groups in the present disclosure. Among them, the aryl group does not contain heteroatoms such as B, N, O, S, or P. For example, biphenyl, terphenyl and the like are aryl groups in the present disclosure. Examples of aryl groups may include phenyl, naphthyl, fluorenyl, anthryl, phenanthryl, biphenyl, terphenyl, quaterphenyl, quinquephenyl, sexiphenyl, benzo[9,10] phenanthryl, pyrenyl, benzofluoranthenyl, chrysen, fluorenyl, etc., which are not limited thereto. The "aryl" in the present disclosure may contain 6 to 30 carbon atoms. In some embodiments, the number of carbon atoms in the aryl group may be 6 to 25; and in other embodiments, the number of carbon atoms in the aryl group may be 6 to 18; and in another embodiments, the number of carbon atoms in the aryl group may be 6 to 13. For example, the number of carbon atoms in the aryl group may be 6, 12, 13, 18, 20, 25, or 30. Of course, the number of carbon atoms may be other numbers, which will not be listed here.

In the present disclosure, the number of ring-forming carbon atoms refers to the number of carbon atoms located on the aromatic ring of a substituted or unsubstituted aryl and a substituted or unsubstituted heteroaryl. It should be noted that the carbon atoms of the aryl and heteroaryl as substituents are also considered on the ring-forming carbon atoms, and the number of carbon atoms of other substituents is not counted. For example, the number of ring-forming carbon atoms of fluorenyl is 13, the number of ring-forming carbon atoms of 9,9-dimethylfluorenyl is 13, and the number of ring-forming carbon atoms of diphenylfluorenyl is 25. The number of ring-forming carbon atoms of the aryl having 6 to 20 ring-forming carbon atoms may be, for example, 6 to 20, 6 to 18, 6 to 14, or 6 to 10, but it is not limited thereto.

In the present disclosure, substituted aryl refers to one or more hydrogen atoms in the aryl group being substituted by other groups. For example, at least one hydrogen atom is substituted by deuterium, F, Cl, I, CN, hydroxyl, amino, branched alkyl, linear alkyl, cycloalkyl, alkoxy, alkylamino, or other groups. It should be understood that the substituted aryl group having 18 carbon atoms means that the total number of carbon atoms of the aryl group and the substituents on the aryl group is 18. For example, the number of carbon atoms in 9,9-dimethylfluorenyl is 15, and the number of carbon atoms in both 9,9-diphenylfluorenyl and spirodifluorenyl is 25. Among them, biphenyl may be interpreted as aryl or substituted phenyl.

In the present disclosure, the fluorenyl group may be substituted, and the substituted fluorenyl group may be

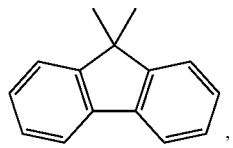

and may also be

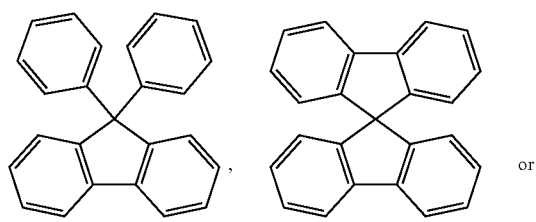 or

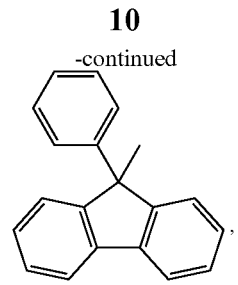

etc.

In the present disclosure, the "heteroaryl" refers to a heteroaryl group including at least one of B, O, N, P, Si, and S as a hetero atom. The heteroaryl group may be a monocyclic heteroaryl group or a polycyclic heteroaryl group. In other words, the heteroaryl group may be a single aromatic ring system or a polycyclic ring system formed by more aromatic rings conjugatedly connected through a carbon-carbon bond where any aromatic ring is an aromatic monocyclic ring or an aromatic fused ring. Exemplary the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridopyrimidinyl, pyridopyrazinyl, pyrazinopyrazinyl, isoquinolyl, indolyl, carbazolyl, N-arylcarbazolyl, N-heteroarylcarbazolyl, N-alkylcarbazolyl, benzoxazolyl, benzimidazoly, benzothiazolyl, benzocarbazolyl, benzothienyl, dibenzothienyl, thienothienyl, benzofuranyl, phenanthrolinyl, isoxazolyl, thiadiazolyl, benzothiazoly, phenothiazinyl, dibenzosilyl, dibenzofuranyl, phenyl substituted dibenzofuranyl, dibenzofuranyl substituted phenyl, etc., which are not limited thereto. Among them, thienyl, furyl, phenanthrolinyl, etc. are heteroaryl groups of a single aromatic ring system, and N-arylcarbazolyl, N-heteroarylcarbazolyl, phenyl substituted dibenzofuranyl, diphenylfuranyl substituted phenyl and the like are heteroaryl groups of multiple aromatic ring systems conjugatedly connected through a carbon-carbon bond.

In the present disclosure, the number of ring-forming carbon atoms refers to the total number of carbon atoms on the aromatic ring. For example, the heteroaryl group having 3 to 20 ring-forming carbon atoms refers to the number of carbon atoms of the heteroaryl ring in the heteroaryl group is 3 to 20, and the carbon atoms of the substituent on the heteroaryl group are not counted. The number of ring-forming carbon atoms in the heteroaryl group may be 3 to 20, 3 to 18, 4 to 18, 3 to 12, 3 to 8, but not limited thereto.

In the present disclosure, substituted heteroaryl means that one or more hydrogen atoms in the heteroaryl group being substituted by other group. For example, at least one hydrogen atom is substituted by deuterium, F, Cl, Br, CN, amino, alkyl, haloalkyl, cycloalkyl, aryloxy, arylthio, silyl, alkylamino, arylamino, boranyl, phosphino, or other groups.

In the present disclosure, the interpretation of aryl may be applied to arylene, and the interpretation of heteroaryl may also be applied to heteroarylene.

In the present disclosure, the halogen may be fluorine, chlorine, bromine, or iodine.

The nitrogen-containing compound of the present disclosure may be used in the preparation of organic electroluminescent devices and photoelectric conversion devices, especially suitable for the preparation of the electron blocking layer (also known as hole assist layer, or second hole transporting layer, etc.) of the organic electroluminescent devices and photoelectric conversion devices, so as to improve the efficiency and lifetime of the organic electroluminescent devices and photoelectric conversion devices, reduce the operating voltage of organic electroluminescent devices, increase the open circuit voltage of photoelectric conversion devices, and improve the mass production stability of the photoelectric conversion devices and the organic electroluminescent devices.

Optionally, $Ar_1$ and $Ar_2$ are each independently selected from the following substituted or unsubstituted groups: an aryl group having 6 to 20 carbon atoms or a heteroaryl group having 3 to 20 carbon atoms.

Preferably, L is selected from single bond, a substituted or unsubstituted arylene group having 6 to 20 ring-forming carbon atoms, or a substituted or unsubstituted heteroarylene group having 3 to 20 ring-forming carbon atoms.

In some embodiments, L is selected from the group consisting of single bond and the following groups:

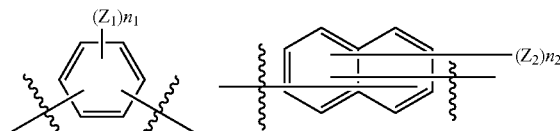
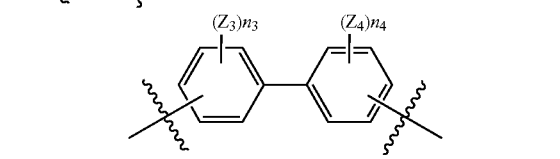
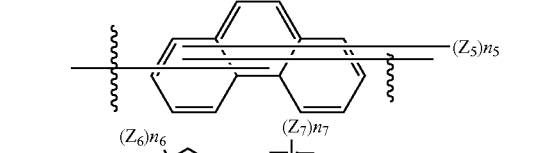
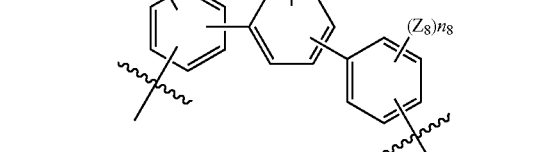
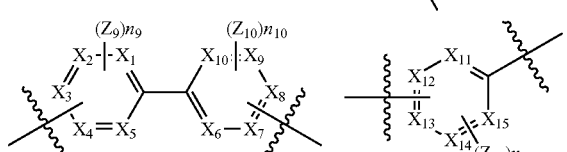
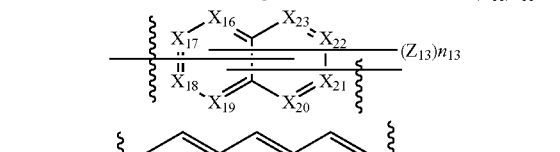
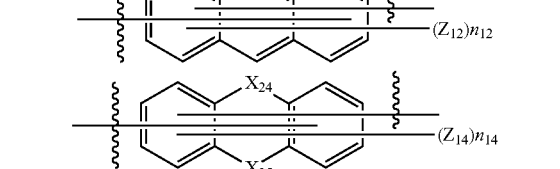

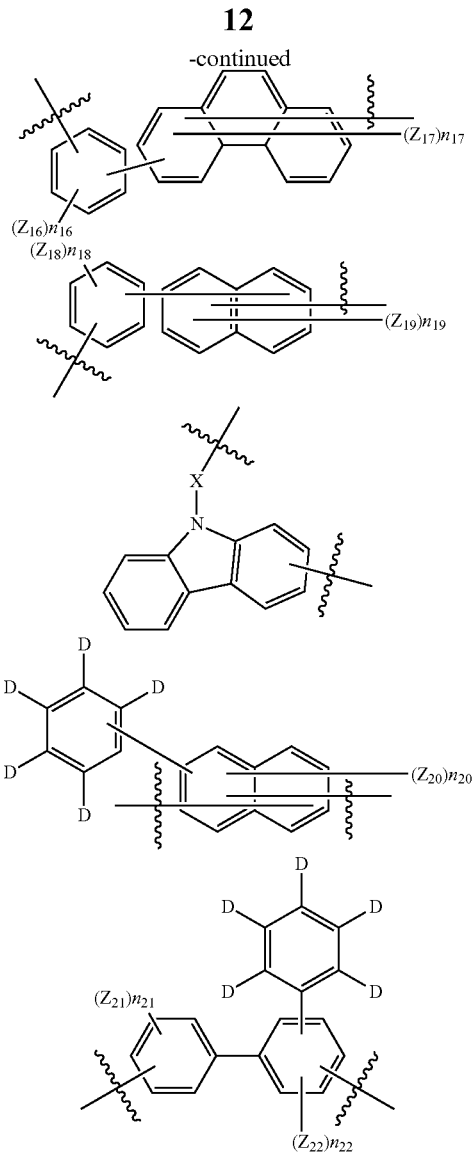

wherein ⁓⁂⁓ represents a chemical bond, $Z_1$ to $Z_{22}$ are each independently selected from hydrogen, deuterium, halogen, cyano, an alkyl having 1 to 6 carbon atoms, a haloalkyl having 1 to 6 carbon atoms, an alkoxy having 1 to 6 carbon atoms, an aryloxy having 6 to 18 carbon atoms, an arylthio having 6 to 18 carbon atoms, an aryl having 6 to 20 carbon atoms, a haloaryl having 6 to 20 carbon atoms, a heteroaryl having 3 to 20 carbon atoms, a silyl having 3 to 12 carbon atoms, or a cycloalkyl having 3 to 10 carbon atoms;

X is selected from a substituted or unsubstituted alkylene having 1 to 10 carbon atoms, a substituted or unsubstituted cycloalkylene having 3 to 10 carbon atoms, a substituted or unsubstituted arylene having 6 to 20 carbon atoms, or a substituted or unsubstituted heteroarylene having 3 to 20 carbon atoms;

$X_1$ to $X_{10}$ are each independently selected from C or N, and at least one of $X_1$ to $X_{10}$ is N;

$X_1$ to $X_{15}$ are each independently selected from C or N, and at least one of to $X_{15}$ is N;

$X_{16}$ to $X_{23}$ are each independently selected from C or N, and at least one of $X_{16}$ to $X_{23}$ is N;

$X_{24}$ and $X_{25}$ are each independently selected from single bond, $C(R_5R_6)$, $N(R_7)$, O, S, $Si(R_5R_6)$, or Se; preferably, $X_{24}$ and $X_{25}$ are not single bonds at the same time;

$R_5$ to $R_7$ are each selected from hydrogen, deuterium, a substituted or unsubstituted alkyl having 1 to 10 carbon atoms, a substituted or unsubstituted aryl having 6 to 20 carbon atoms, or a substituted or unsubstituted heteroaryl having 3 to 20 carbon atoms;

$X_{26}$ and $X_{27}$ are each independently selected from C or N, and at least one of $X_{26}$ and $X_{27}$ is N;

$n_1$, $n_3$, $n_4$, $n_5$, $n_7$, $n_8$, $n_9$, $n_{16}$, $n_{18}$, and $n_{21}$ are each independently selected from 1, 2, 3, or 4;

$n_{10}$, $n_{11}$ and, $n_{22}$ are each independently selected from 1, 2, or 3;

$n_{13}$ and $n_{20}$ are selected from 1, 2, 3, 4, or 5;

$n_2$, $n_{14}$ and $n_{19}$ are each independently selected from 1, 2, 3, 4, 5, or 6;

$n_{15}$ is selected from 1, 2, 3, 4, 5, 6, or 7;

$n_5$, $n_{12}$ and $n_{17}$ are each independently selected from 1, 2, 3, 4, 5, 6, 7, or 8.

Optionally, X is an alkylene group having 1 to 4 carbon atoms, a cycloalkylene group having 5 to 10 carbon atoms, an arylene group having 6 to 12 carbon atoms, or a heteroarylene having 3 to 12 carbon atoms. Specific examples of X include, but are not limited to, methylene, phenylene and the like.

Optionally, $R_5$ to $R_7$ are each independently selected from hydrogen, deuterium, an alkyl group having 1 to 4 carbon atoms, an aryl group having 6 to 12 carbon atoms, or a heteroaryl group having 3 to 12 carbon atoms. Specific examples of $R_5$ to $R_7$ include, but are not limited to, methyl, tert-butyl, phenyl and the like.

Also optionally, $Z_1$ is an aryl group having 6 to 20 carbon atoms substituted by deuterium, for example, a phenyl group substituted by deuterium.

According to an embodiment, L is selected from the group consisting of single bond and the following groups:

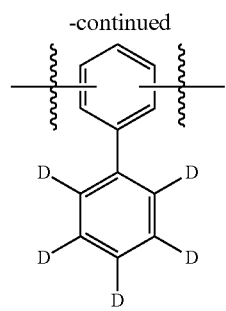
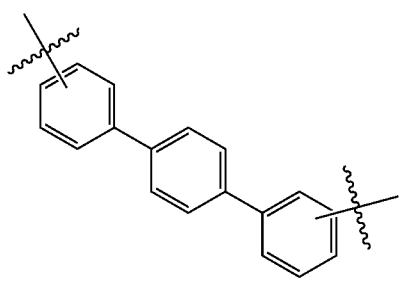
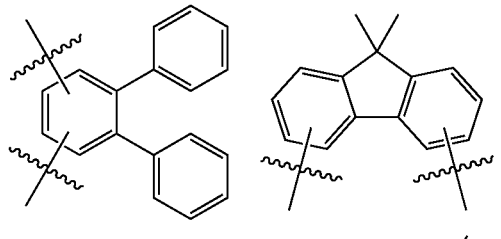
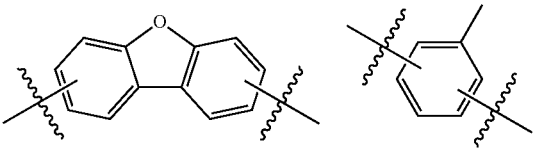
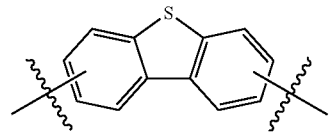
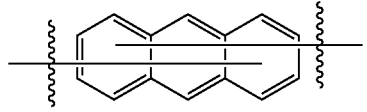
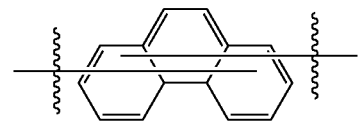
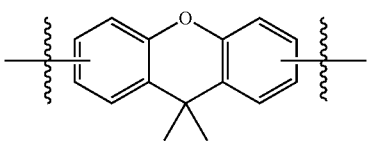
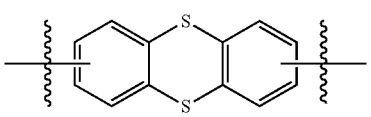
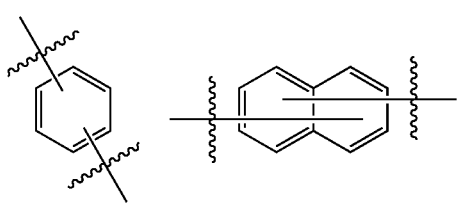
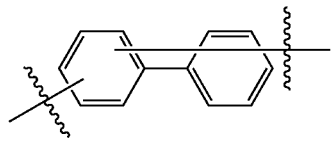
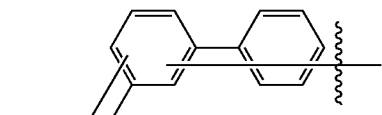
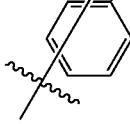

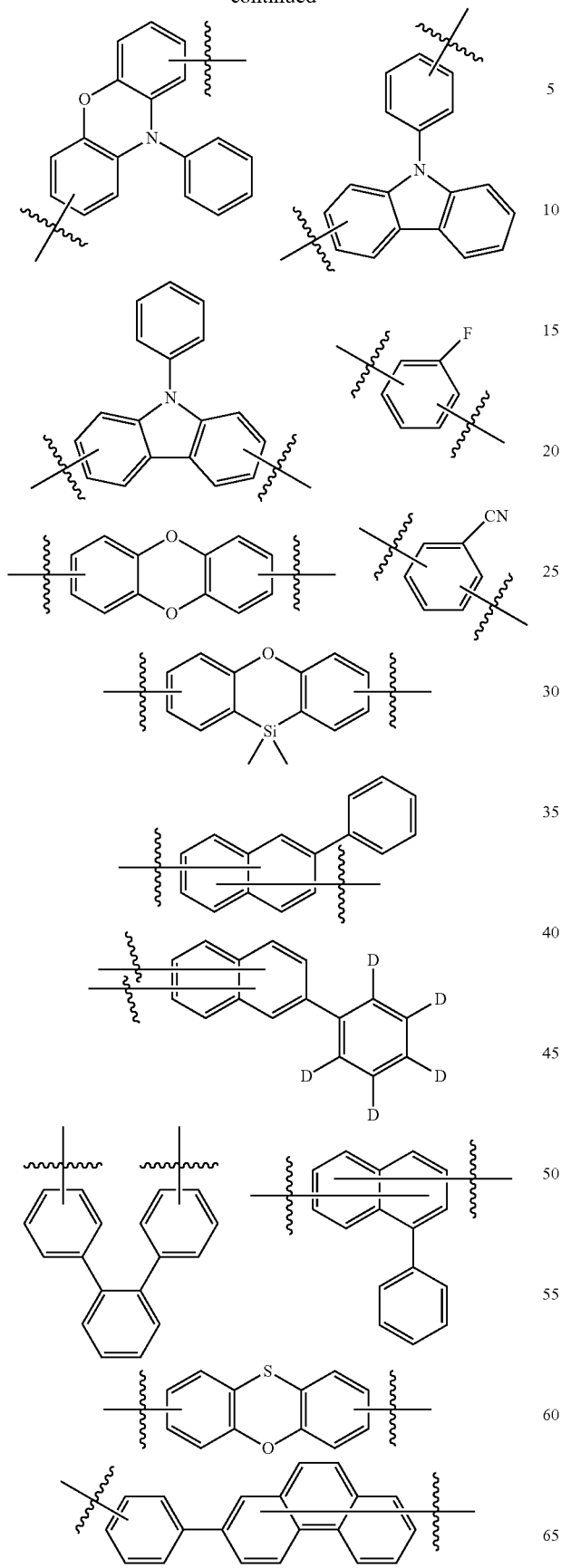
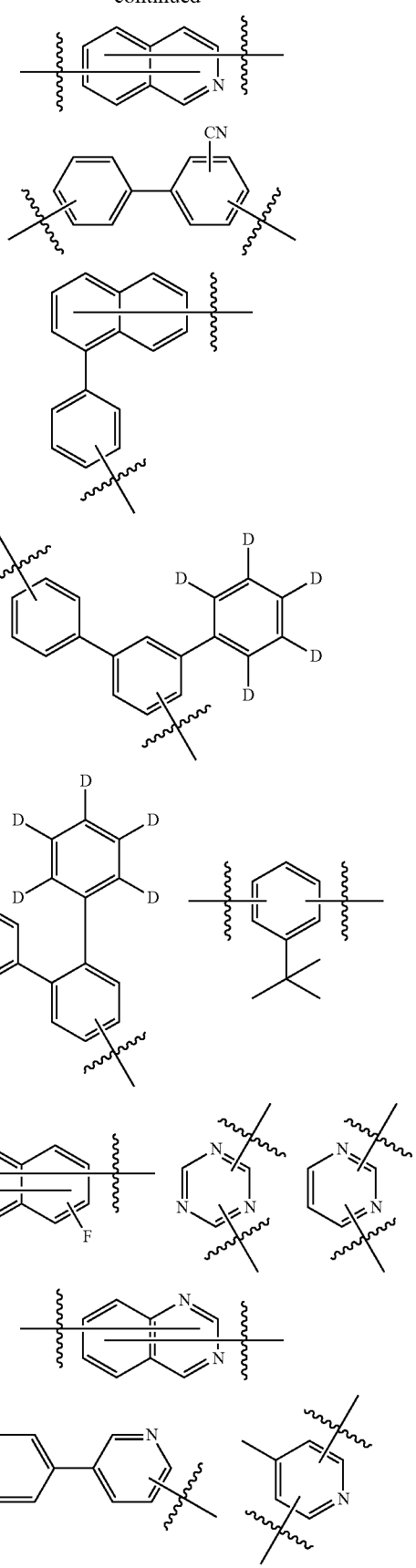

-continued
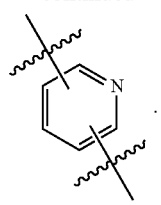
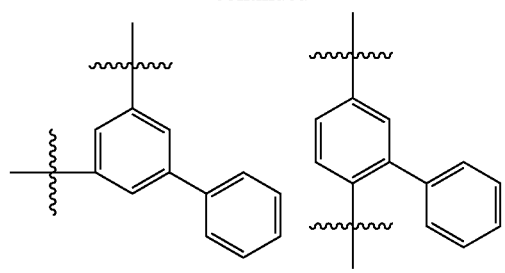
Further optionally, L is selected from the group consisting of single bond and the following groups:
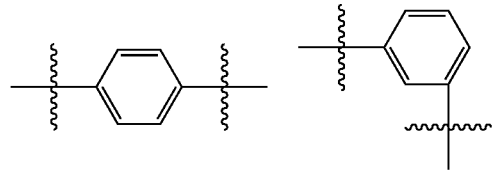
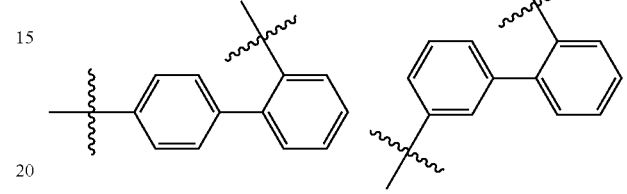
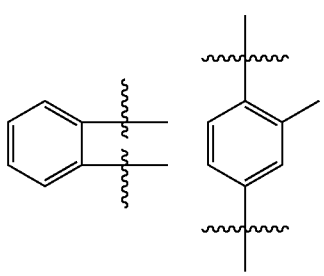
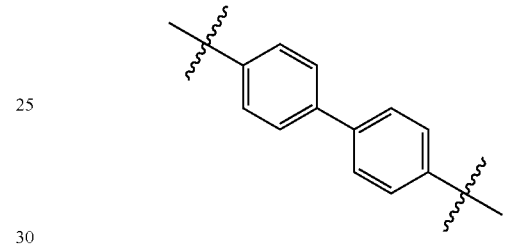
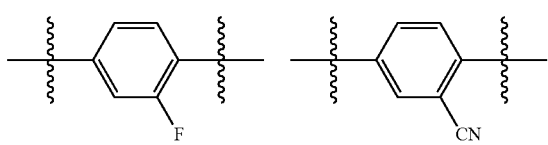
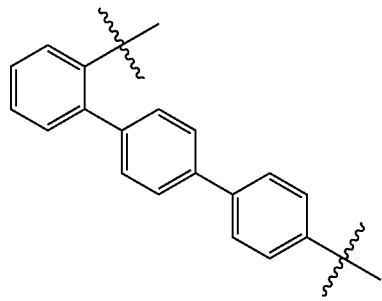
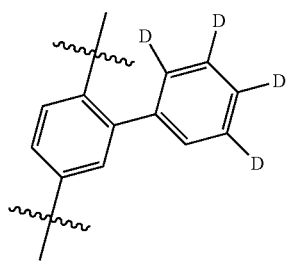
lp;1p
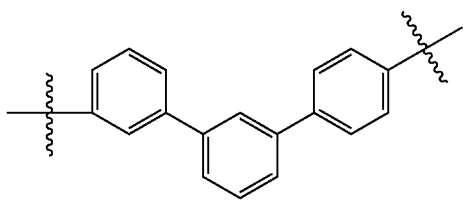
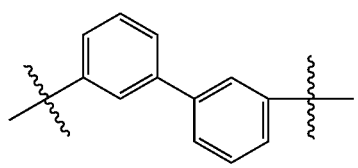
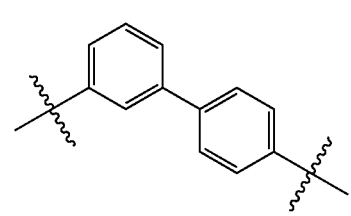
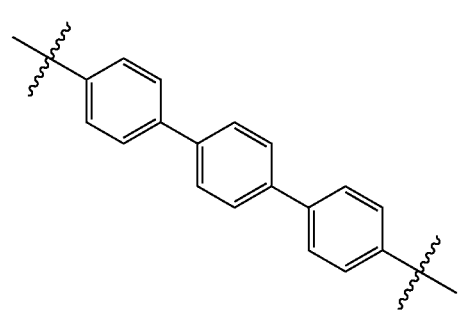

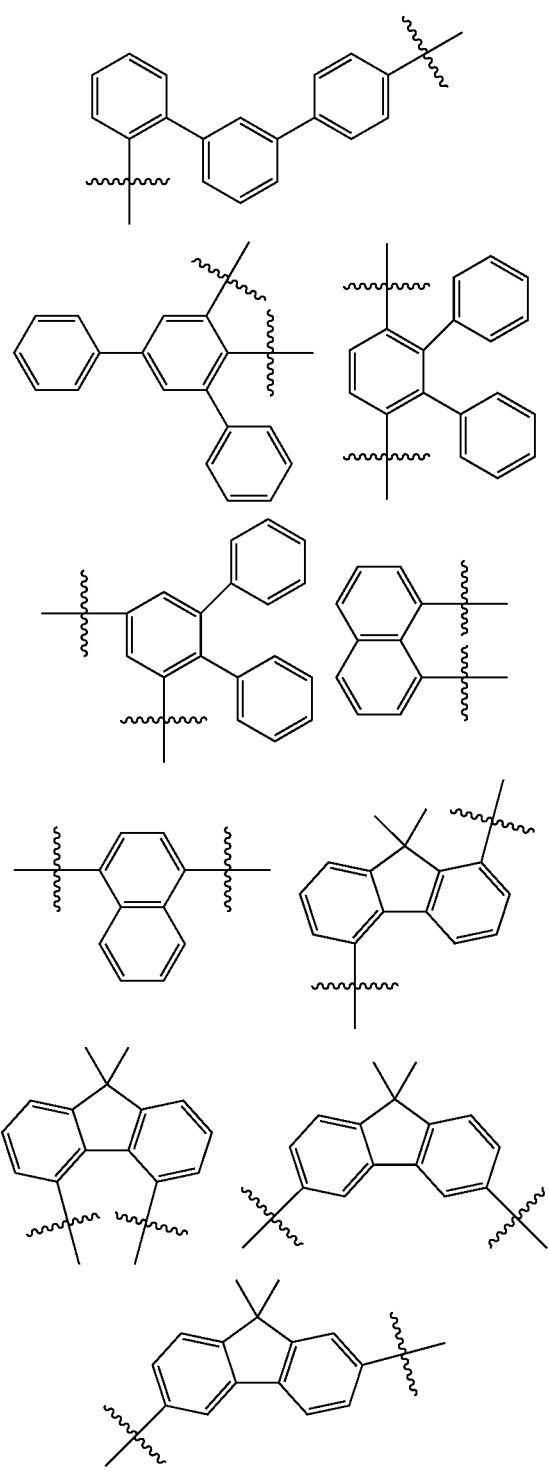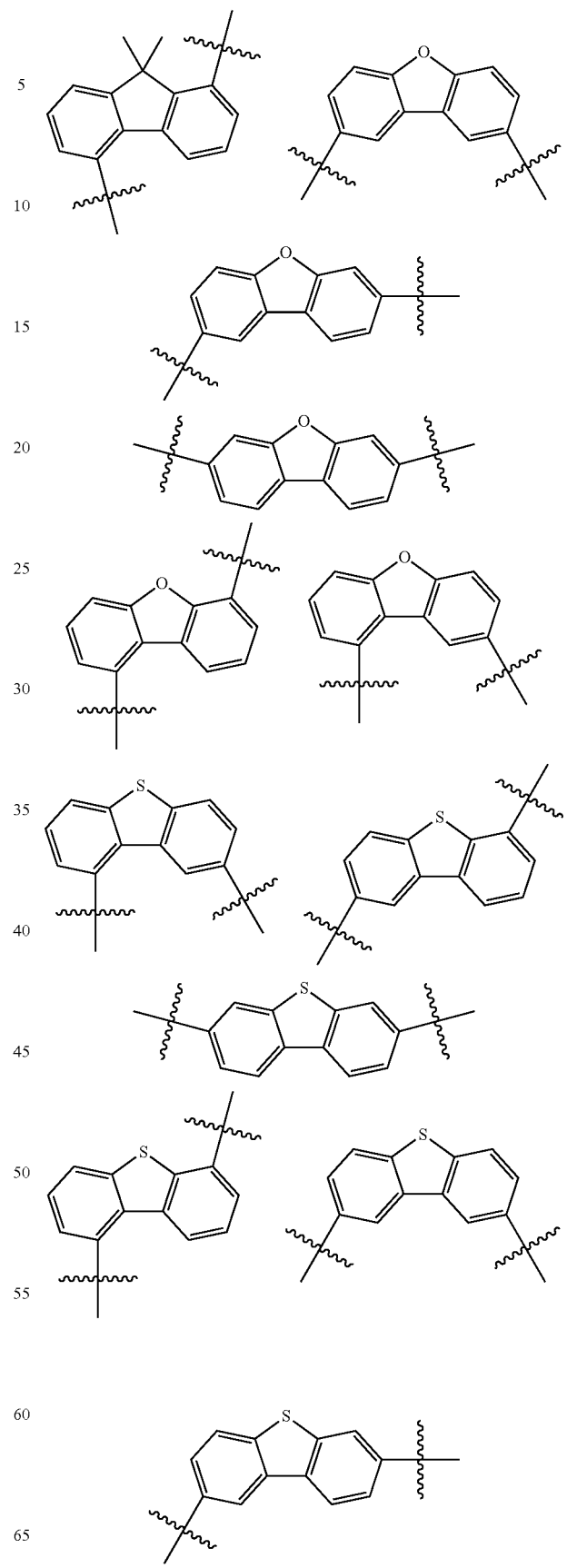

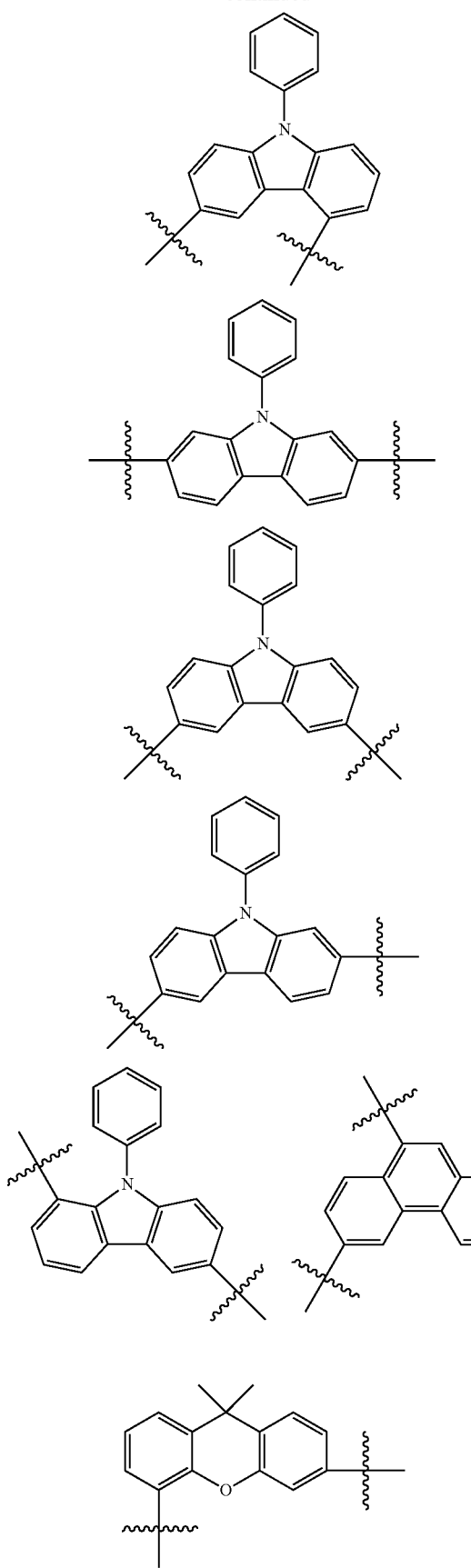

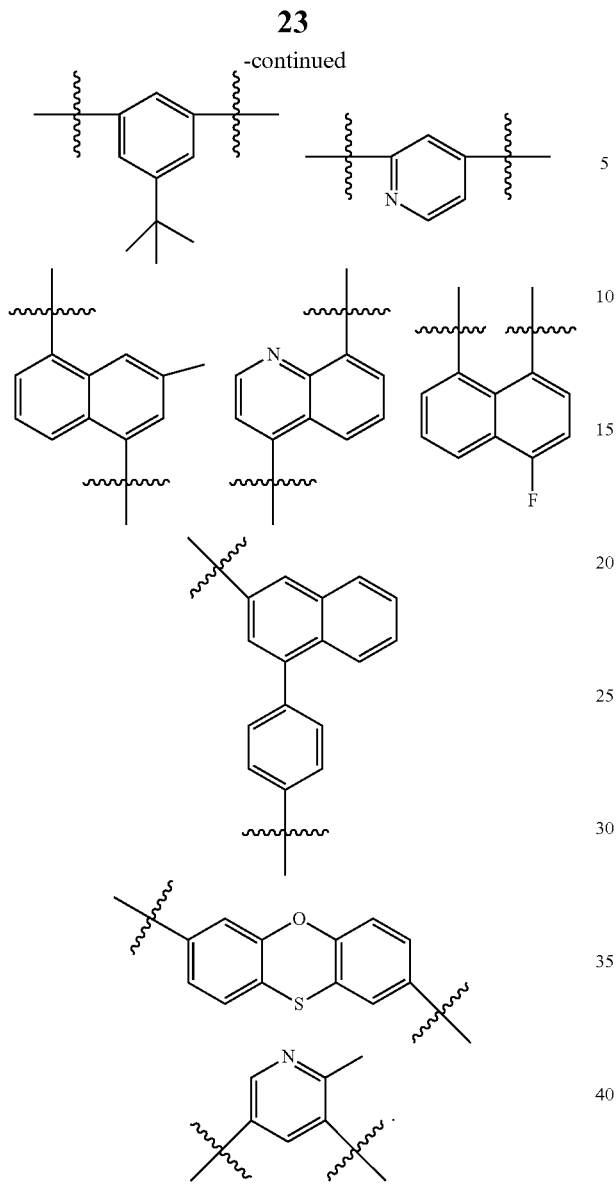

Optionally, $Ar_1$ and $Ar_2$ are each independently selected from the following substituted or unsubstituted groups: an aryl group having 6 to 20 carbon atoms, or a heteroaryl group having 3 to 20 carbon atoms.

Optionally, $Ar_1$ and $Ar_2$ are each independently selected from the following substituted or unsubstituted groups: an aryl group having 6 to 20 ring-forming carbon atoms, or a heteroaryl group having 5 to 20 ring-forming carbon atoms.

In some embodiments, $Ar_1$ and $Ar_2$ are each independently selected from the group consisting of the following groups:

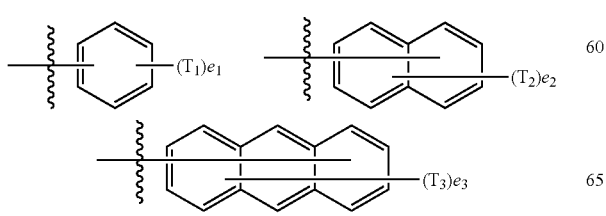

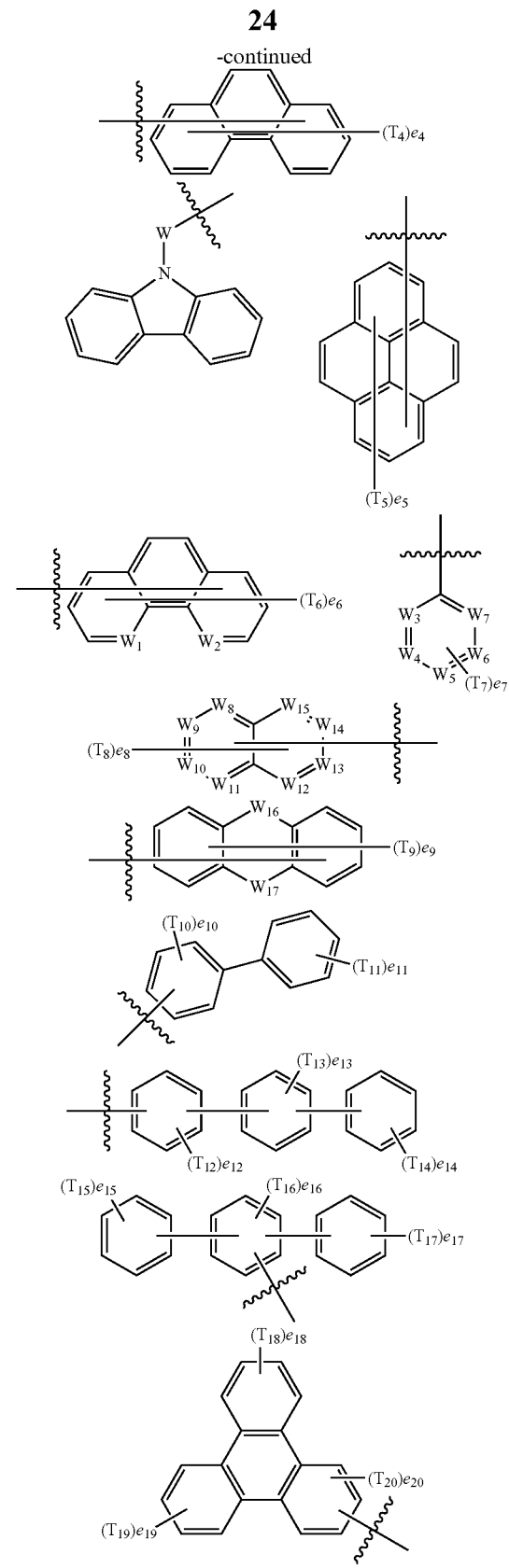

wherein ⁃⁄⁃ represents a chemical bond;

$T_1$ to $T_{20}$ are each independently selected from hydrogen, deuterium, halogen, cyano, an alkyl having 1 to 6 carbon atoms, a haloalkyl having 1 to 6 carbon atoms, an alkoxy having 1 to 6 carbon atoms, an aryloxy group having 6 to 18 carbon atoms, an arylthio having 6 to 18 carbon atoms, an aryl having 6 to 20 carbon atoms, a haloaryl having 6 to 20 carbon atoms, a heteroaryl having 3 to 20 carbon atoms, a silyl having 3 to 12 carbon atoms, or a cycloalkyl having 3 to 10 carbon atoms;

W is selected from a substituted or unsubstituted alkylene having 1 to 10 carbon atoms, a substituted or unsubstituted cycloalkylene having 3 to 10 carbon atoms, a substituted or unsubstituted arylene having 6 to 20 carbon atoms, or a substituted or unsubstituted heteroarylene having 3 to 20 carbon atoms;

$W_1$ and $W_2$ are each independently selected from C or N, and at least one of $W_1$ and $W_2$ is N;

$W_3$ to $W_7$ are each independently selected from C or N, and at least one of $W_3$ to $W_7$ is N;

$W_6$ to $W_{16}$ are each independently selected from C or N, and at least one of $W_8$ to $W_{15}$ is N;

$W_{16}$ and $W_{17}$ are each independently selected from single bond, $C(R_9R_{10})$, $N(R_{11})$, O, S, $Si(R_9R_{10})$, or Se; preferably, $W_{16}$ and $W_{17}$ are not single bonds at the same time;

$R_9$ and $R_{10}$ are the same or different, and each independently selected from hydrogen, deuterium, a substituted or unsubstituted alkyl having 1 to 6 carbon atoms, a substituted or unsubstituted aryl having 7 to 18 carbon atoms, or a substituted or unsubstituted heteroaryl having 3 to 18 carbon atoms;

$R_8$ is selected from hydrogen, deuterium, a substituted or unsubstituted alkyl having 1 to 6 carbon atoms, a substituted or unsubstituted aryl having 6 to 20 carbon atoms, or a substituted or unsubstituted heteroaryl having 3 to 20 carbon atoms;

$e_1$, $e_{11}$, $e_{14}$, $e_{15}$ and $e_{17}$ are each independently selected from 1, 2, 3, 4, or 5;

$e_{16}$ and $e_{20}$ are each independently selected from 1, 2, or 3;

$e_2$ and $e_9$ are each independently selected from 1, 2, 3, 4, 5, 6, or 7;

$e_3$, $e_4$ and $e_5$ are each independently selected from 1, 2, 3, 4, 5, 6, 7, 8, or 9;

$e_6$ is selected from 1, 2, 3, 4, 5, 6, 7 or 8;

$e_7$, $e_{10}$, $e_{12}$, $e_{13}$, $e_{18}$ and $e_{19}$ are each independently selected from 1, 2, 3, or 4;

$e_8$ is selected from 1, 2, 3, 4, 5, or 6.

Optionally, W is an alkylene group having 1 to 4 carbon atoms, a cycloalkylene group having 5 to 10 carbon atoms, an arylene group having 6 to 12 carbon atoms, or a heteroarylene group having 3 to 12 carbon atoms. Specific examples of W include, but are not limited to, methylene, phenylene and the like.

Optionally, $R_9$ and $R_{10}$ are each independently selected from hydrogen, deuterium, or an alkyl group having 1 to 4 carbon atoms. Specific examples of $R_9$ and $R_{10}$ include, but are not limited to, methyl, tert-butyl and the like.

Optionally, $R_8$ is selected from hydrogen, deuterium, an alkyl group having 1 to 6 carbon atoms, an aryl group having 6 to 12 carbon atoms, or a heteroaryl group having 3 to 12 carbon atoms. Specific examples of $R_8$ include, but are not limited to, methyl, phenyl and the like.

Further optionally, $T_1$ is an aryl group having 6 to 20 carbon atoms substituted by deuterium, for example, a phenyl group substituted by deuterium.

Optionally, $Ar_1$ and $Ar_2$ are each independently selected from the group consisting of the following groups:

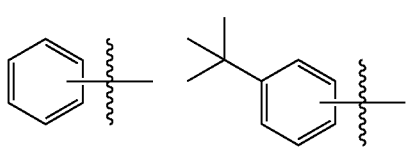
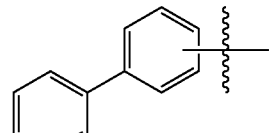
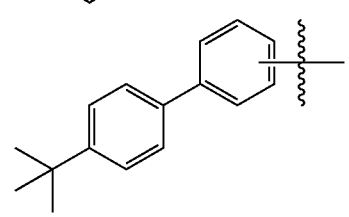
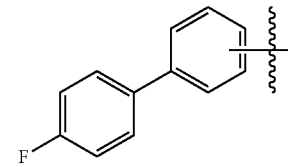
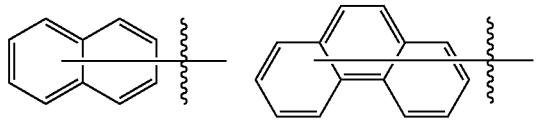
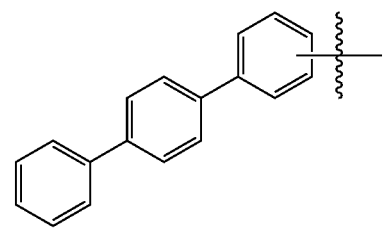
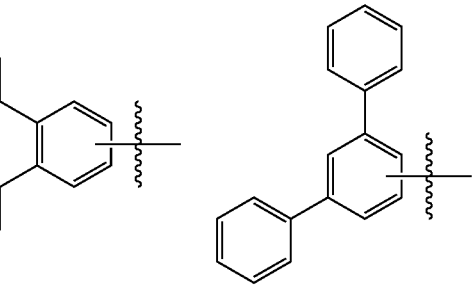
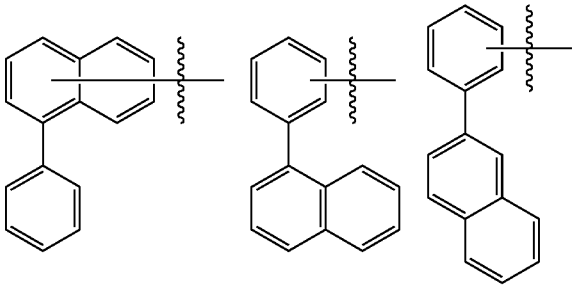

-continued
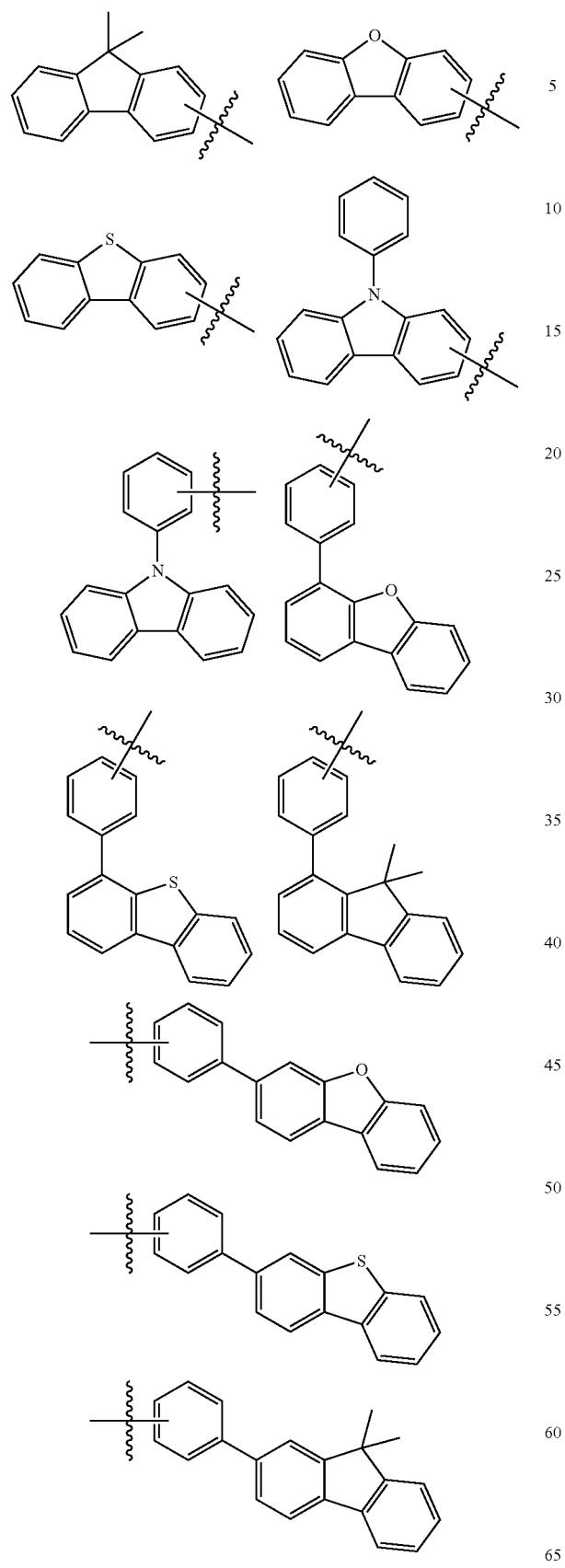
-continued
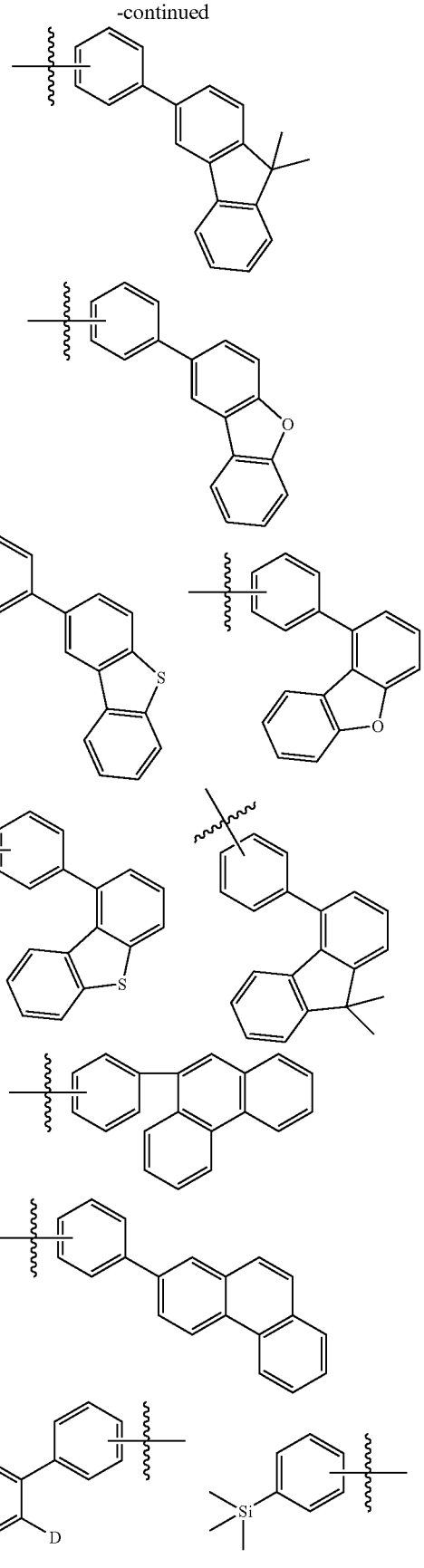

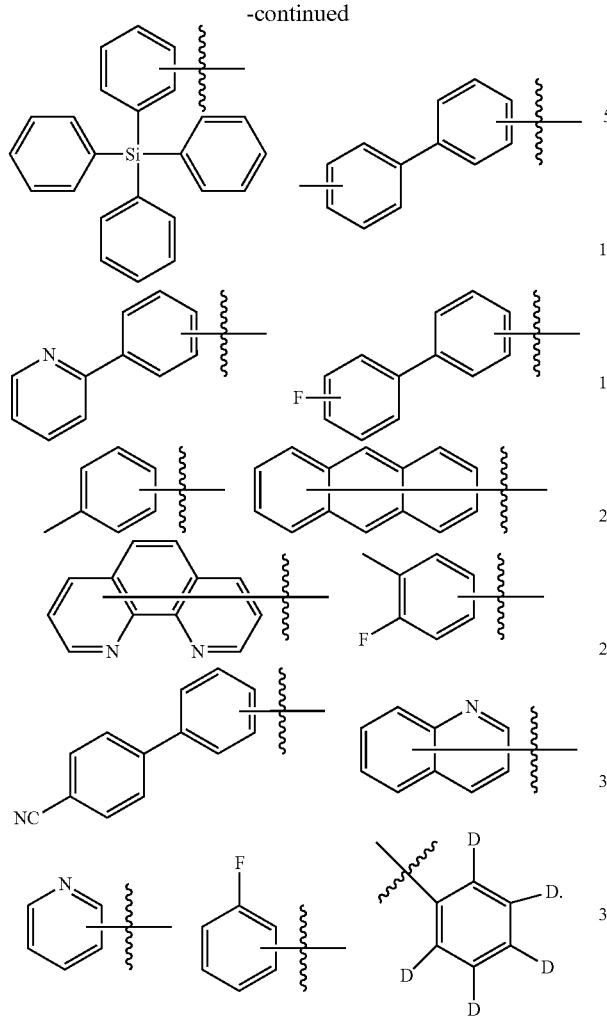
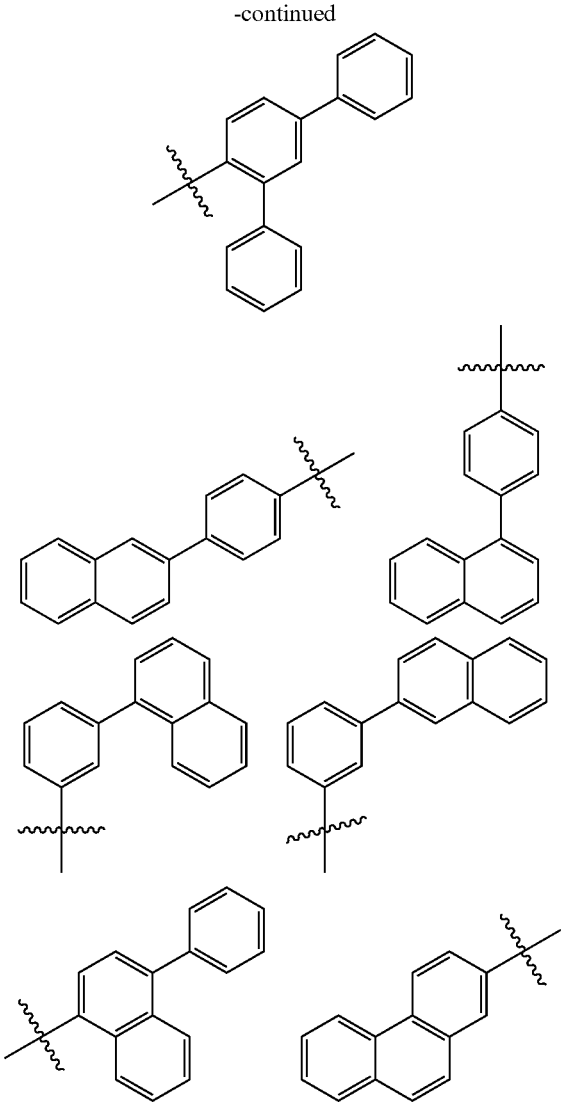
Further optionally, Ar₁ and Ar₂ are each independently selected from the group consisting of the following groups:
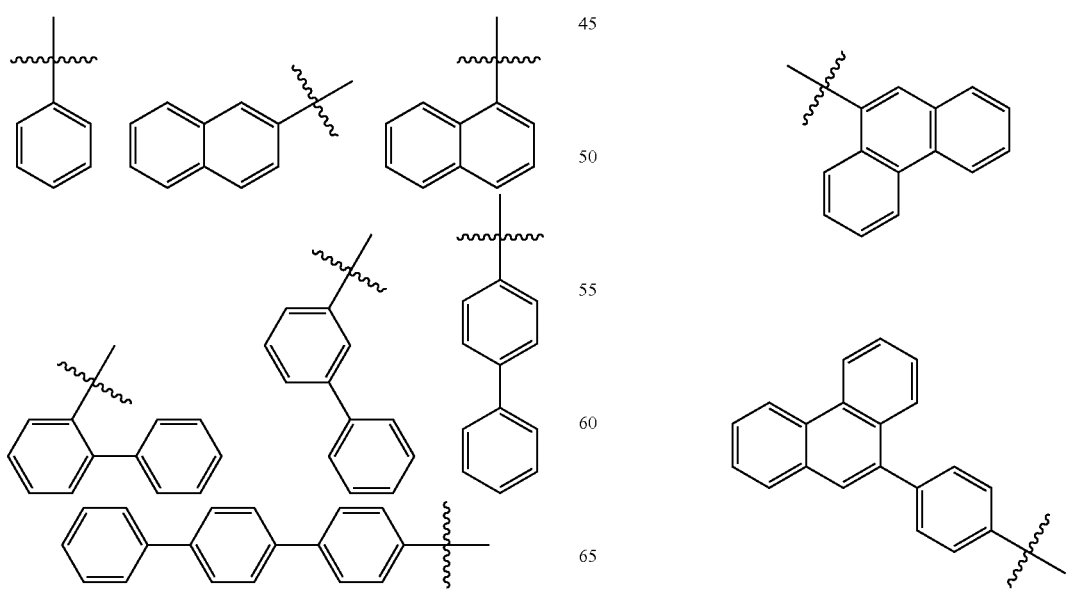

31
-continued
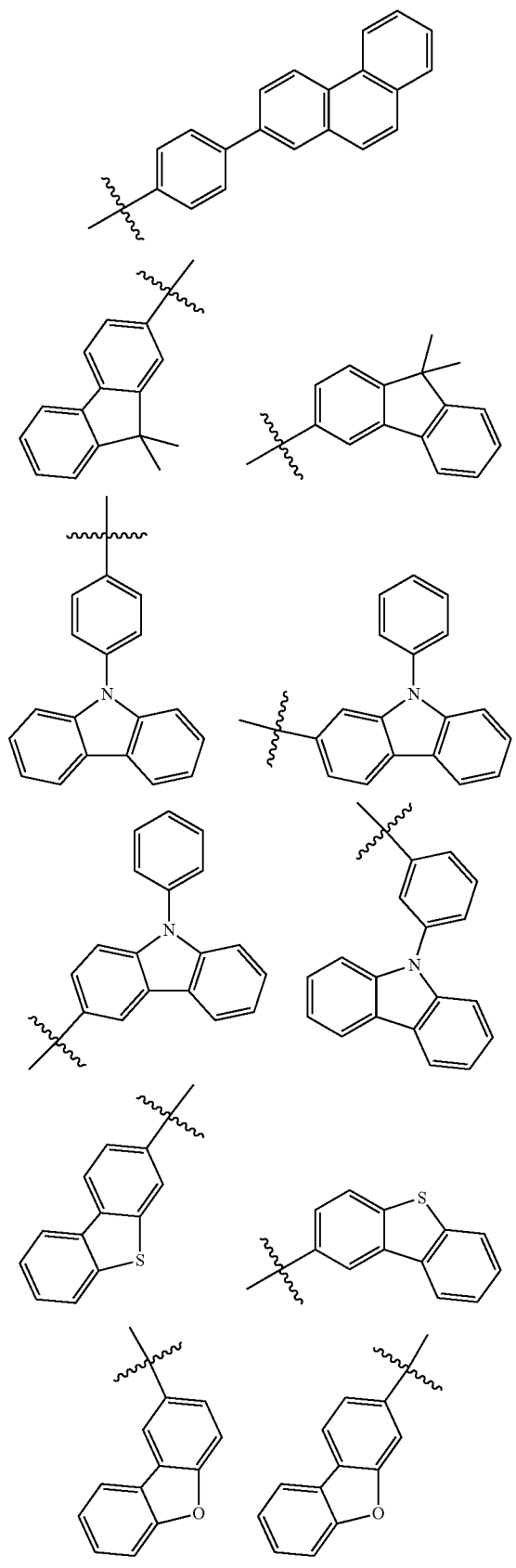
32
-continued
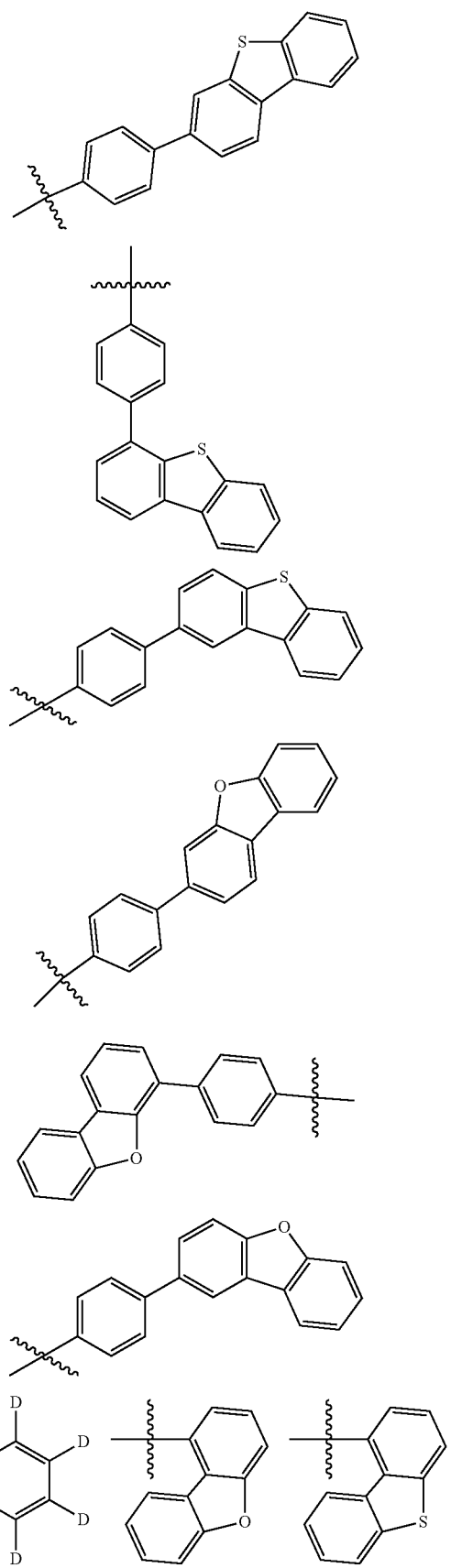

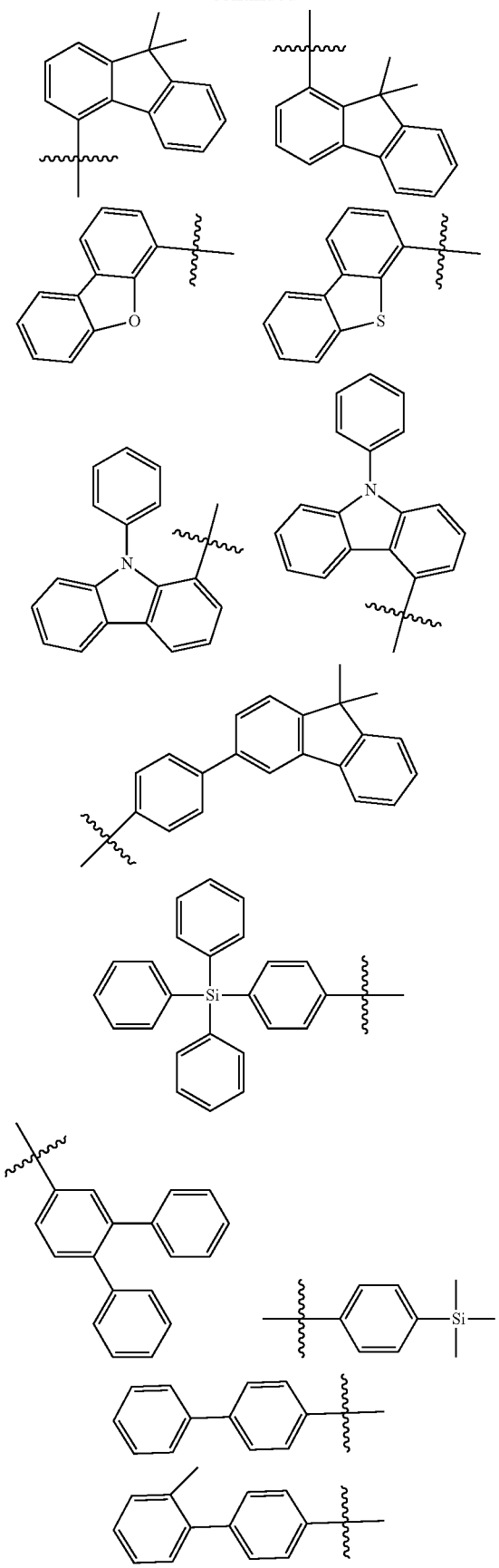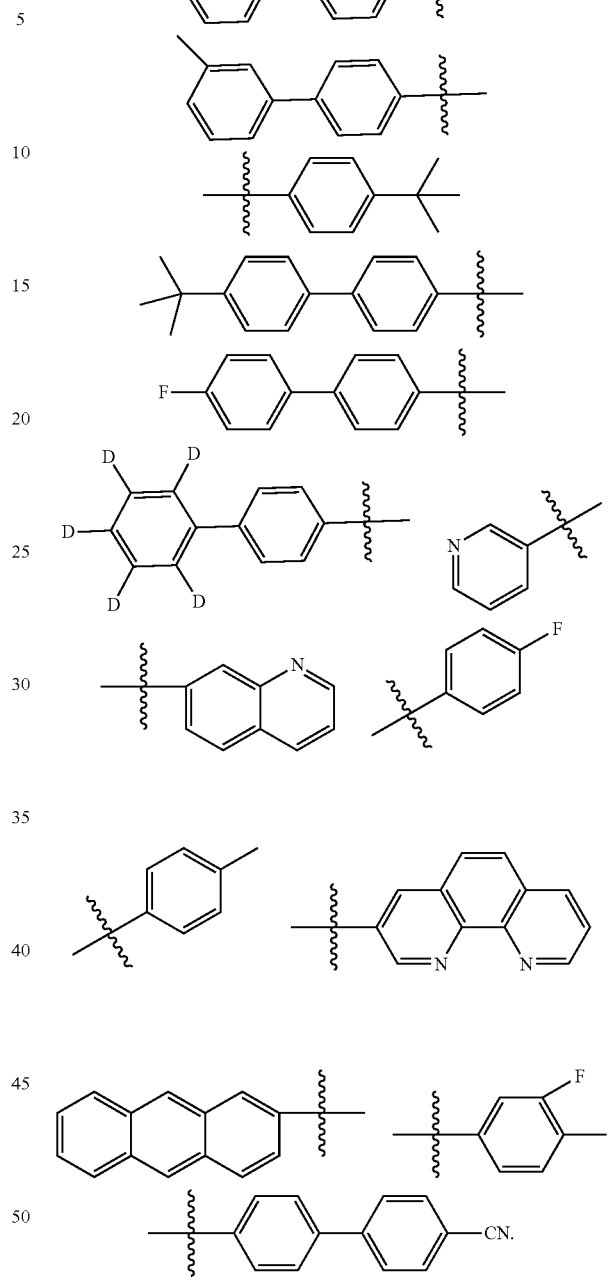

Optionally, $R_3$ and $R_4$ are each independently selected from deuterium, fluorine, cyano, an aryl group having 6 to 18 carbon atoms, a heteroaryl group having 5 to 18 carbon atoms, an alkyl group having 1 to 6 carbon atoms, or a cycloalkyl group having 3 to 10 carbon atoms. Specific examples of $R_3$ and $R_4$ include, but are not limited to, deuterium, fluorine, cyano, methyl, tert-butyl, phenyl, cyclopentyl, cyclohexyl, pyridyl and the like.

Also optionally, $R_3$ and/or $R_4$ are phenyl substituted by deuterium.

Optionally, the nitrogen-containing compound is selected from the group consisting of the following compounds:

1
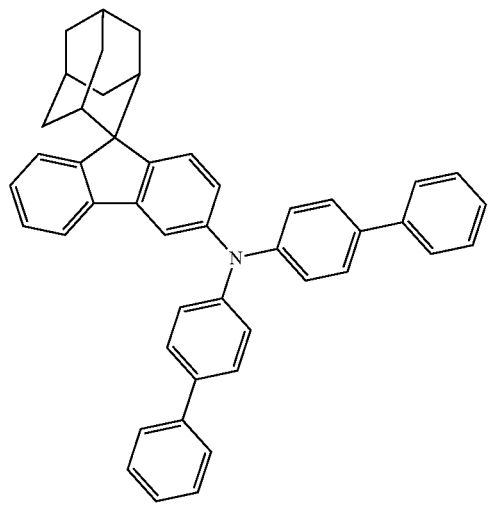
2
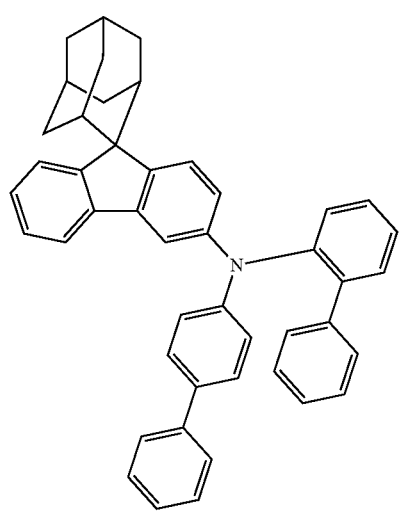
3
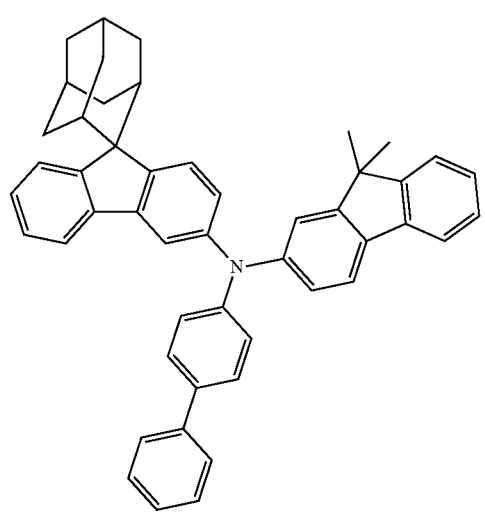
-continued
4
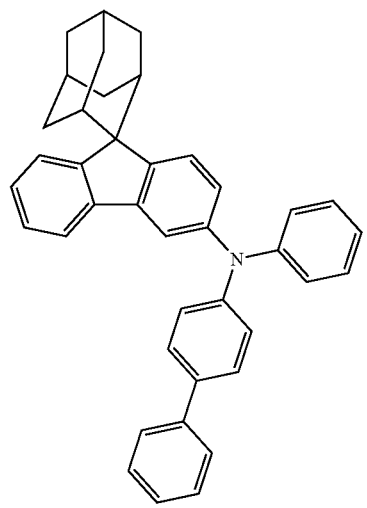
5
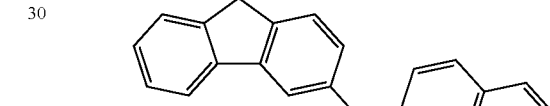
6
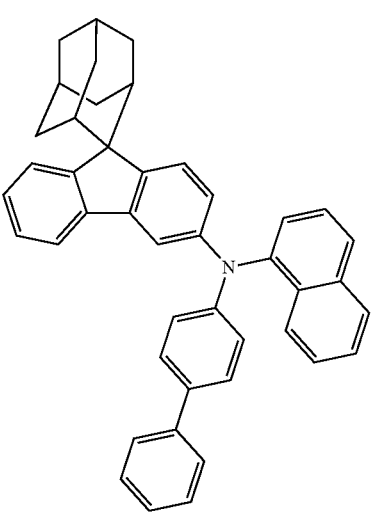

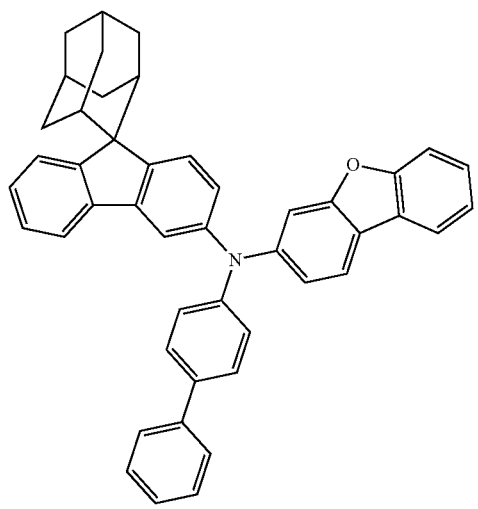
7
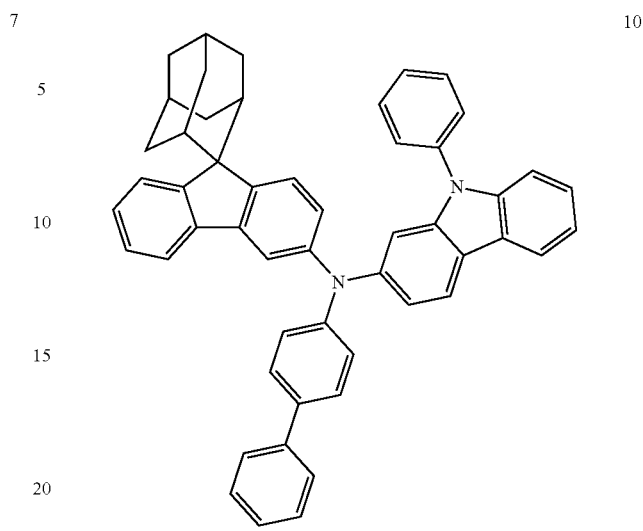
10
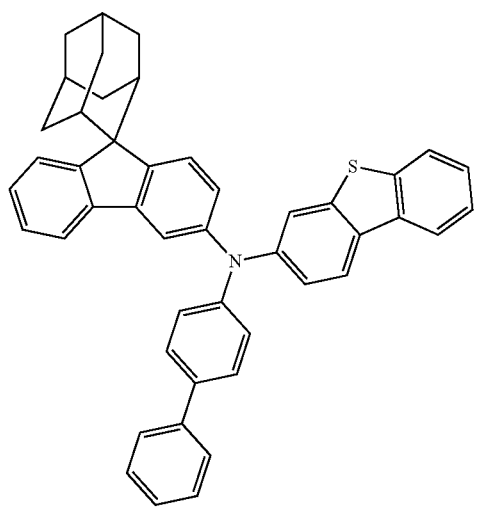
8
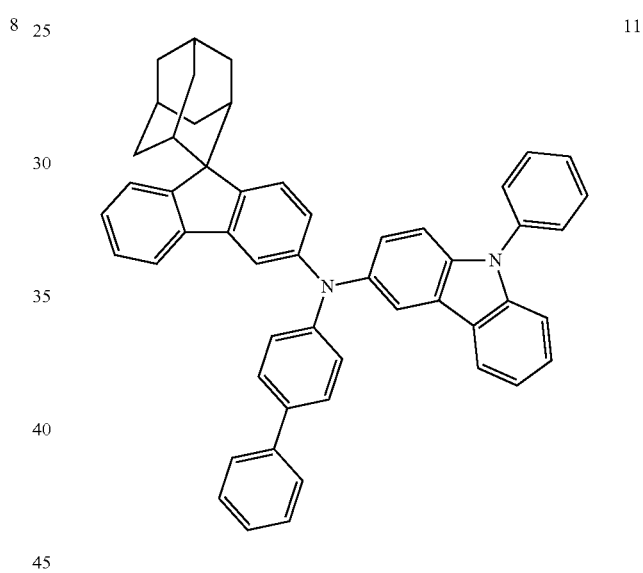
11
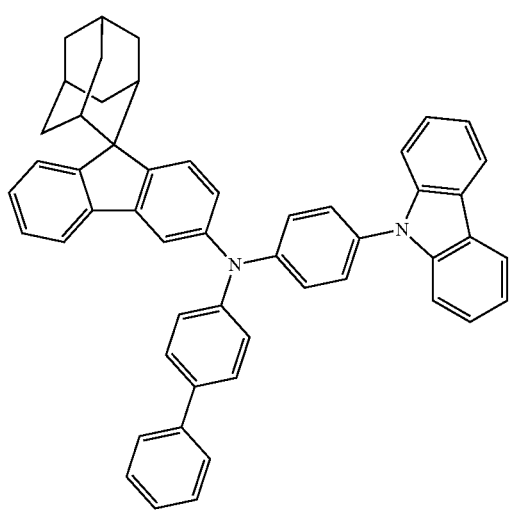
9
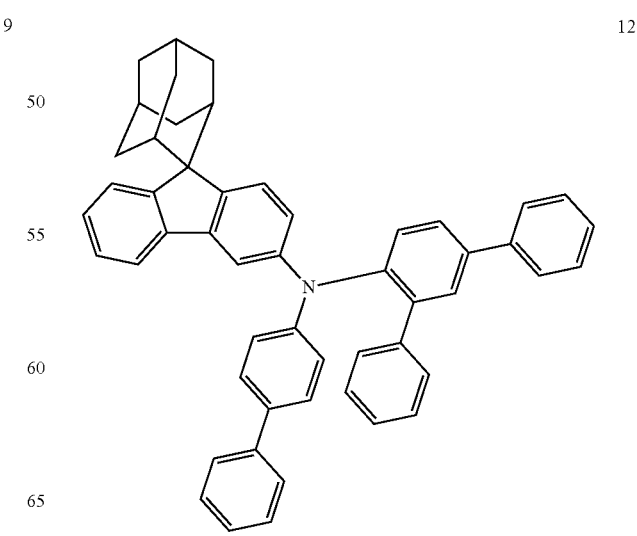
12

13
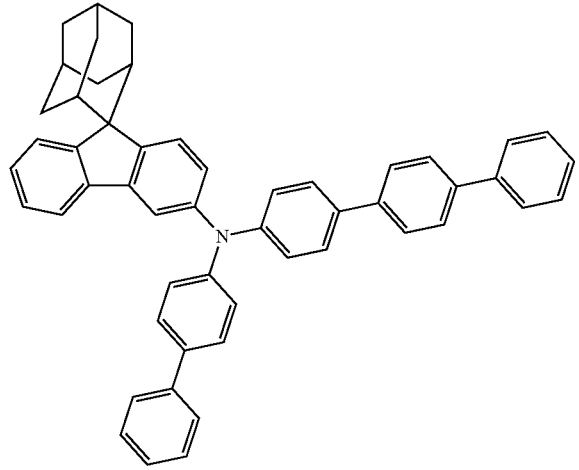
14
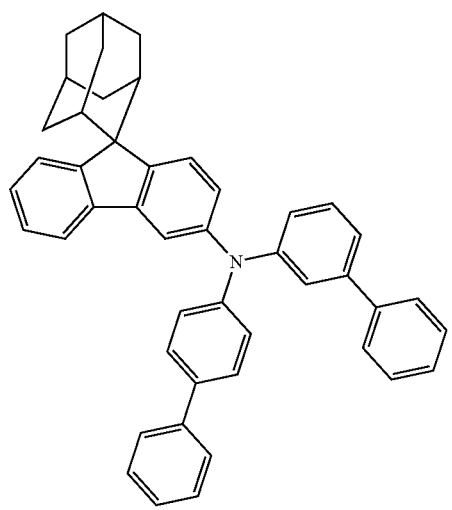
15
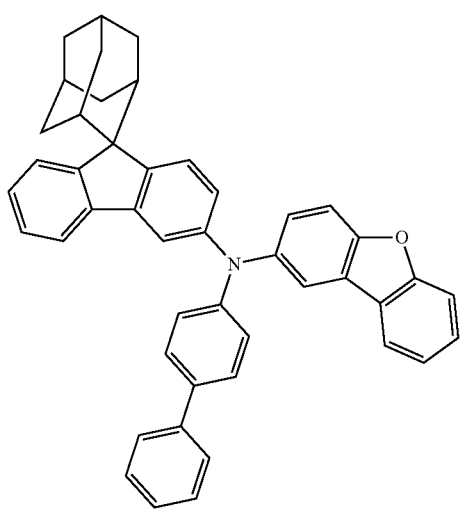
16
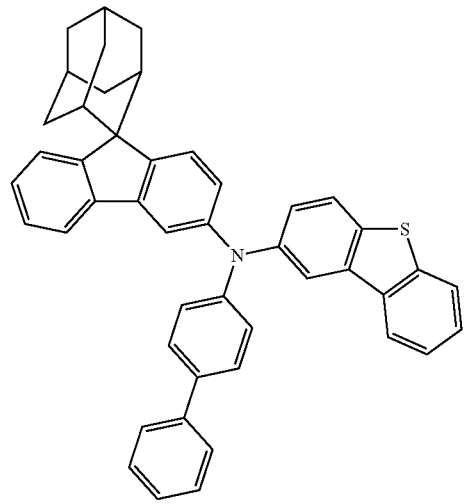
17
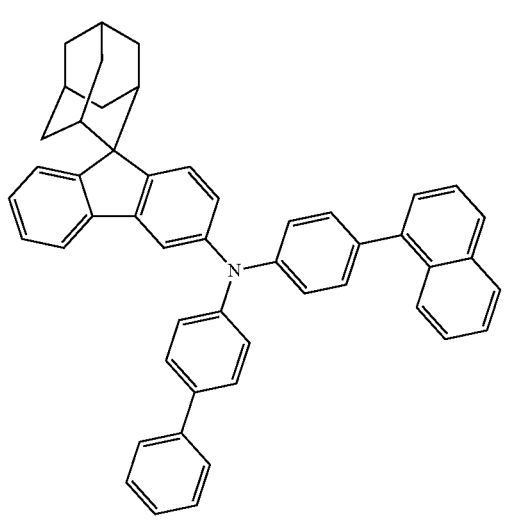
18
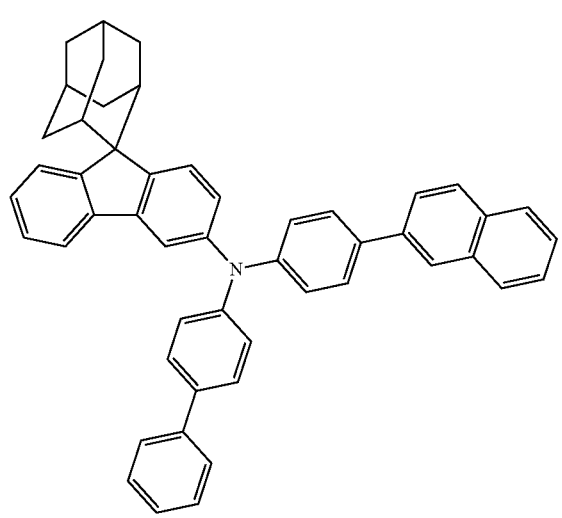

19
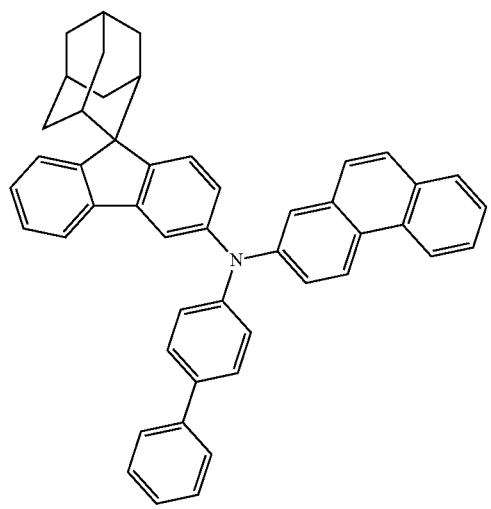
20
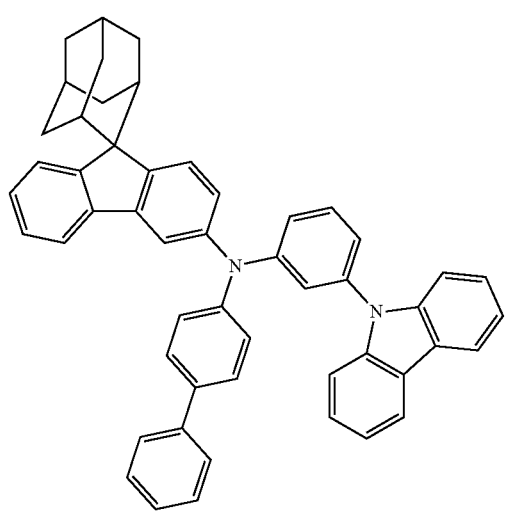
21
22
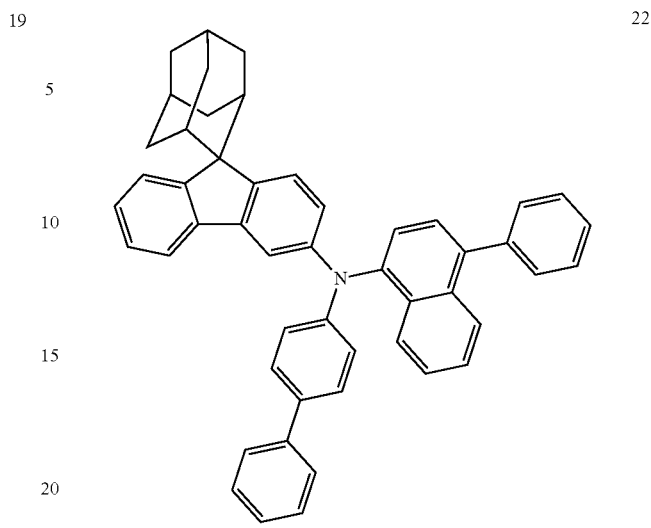
23
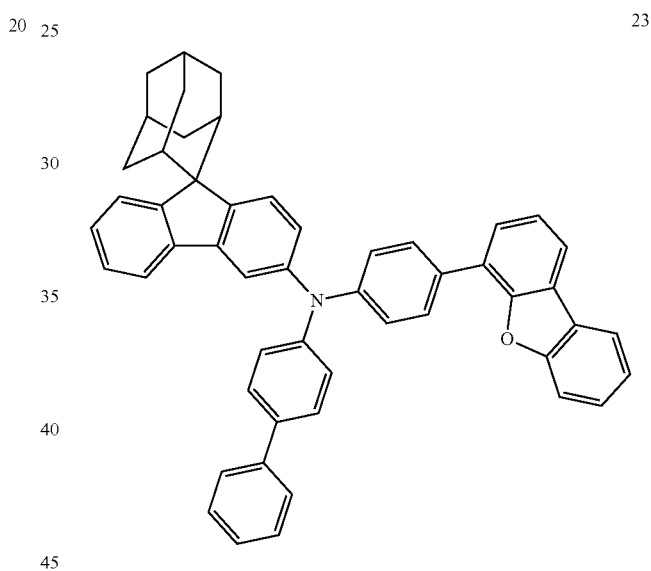
24
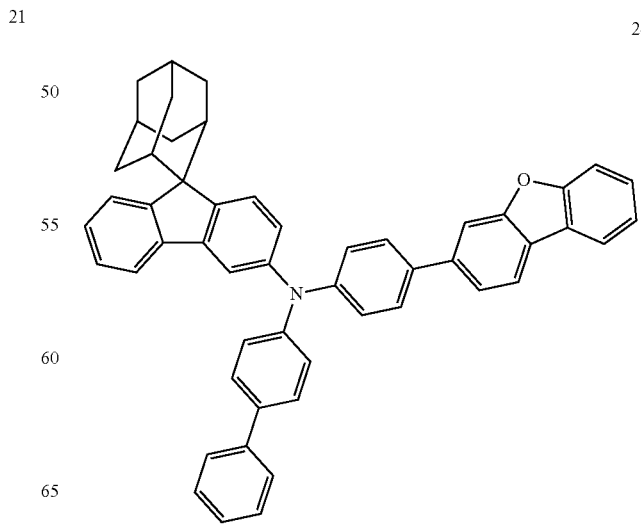

25
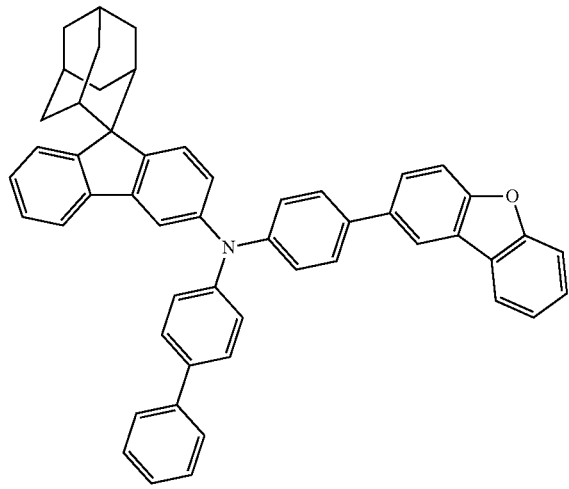
28
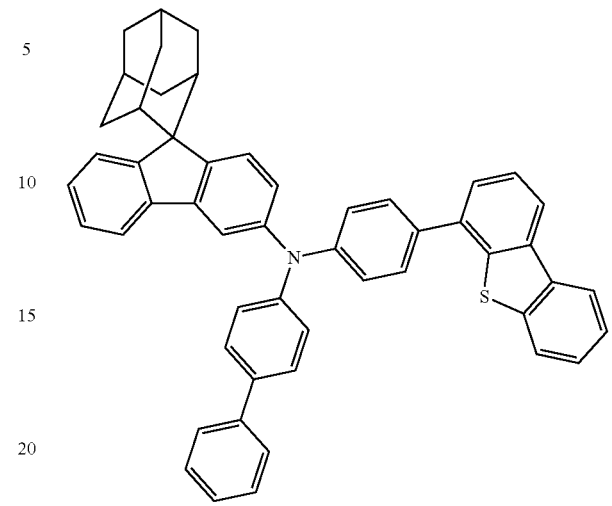
26
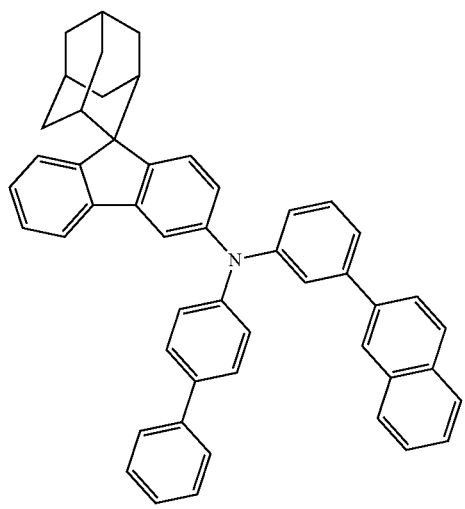
29
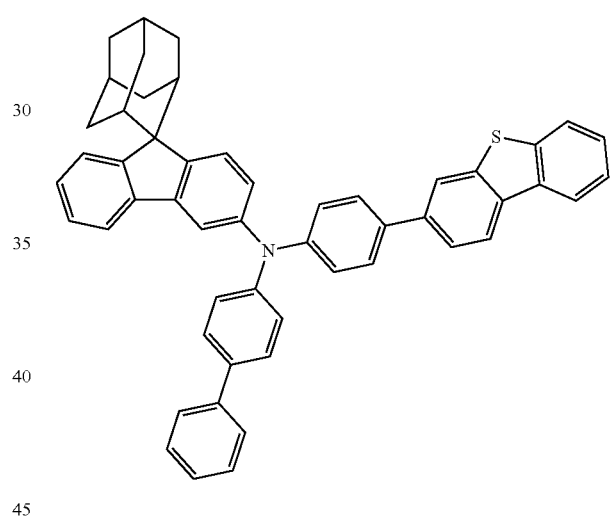
27
30
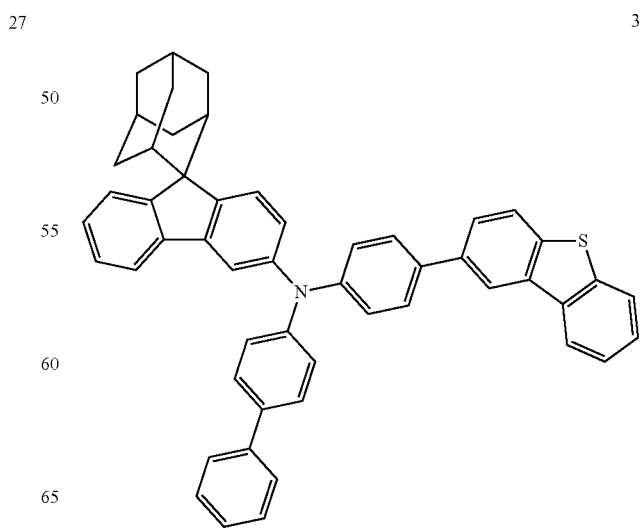

31
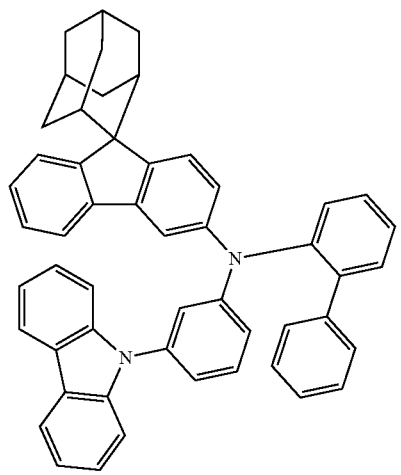
32
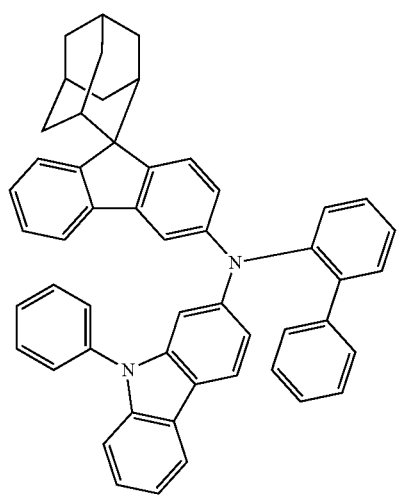
33
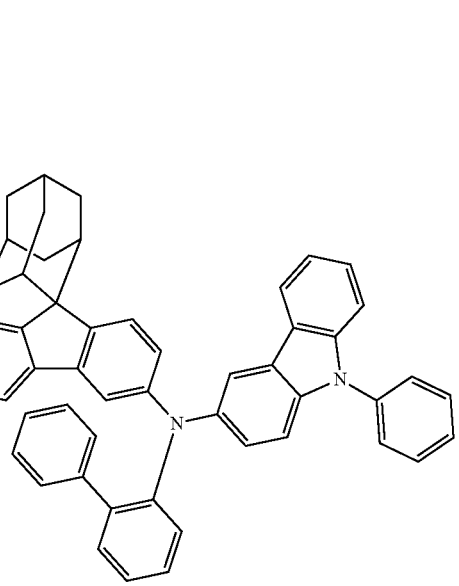
34
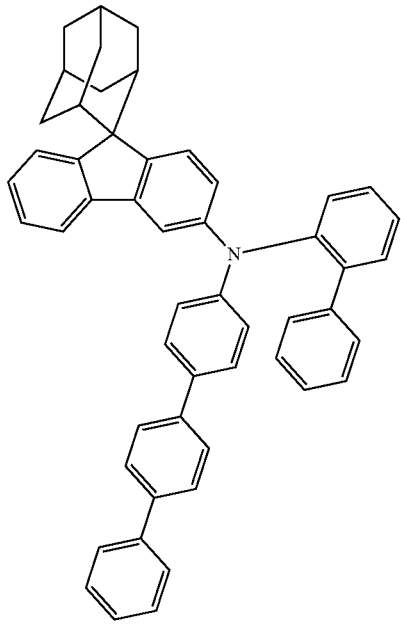
35
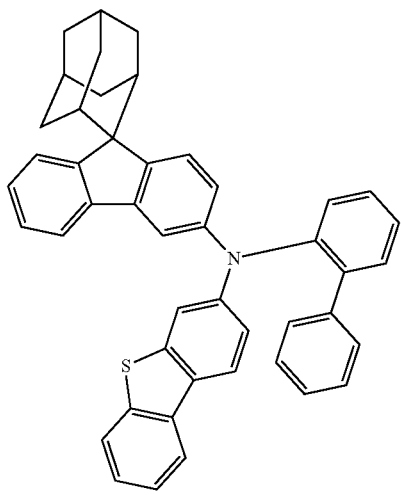
36
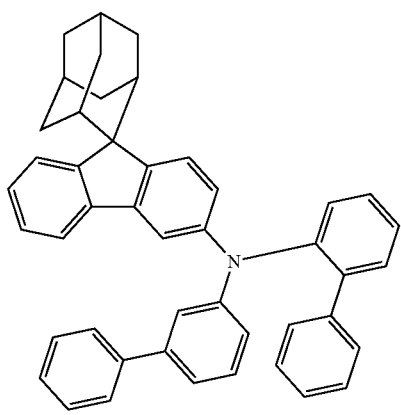

37
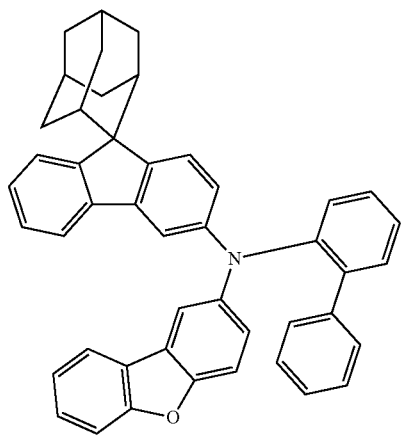
38
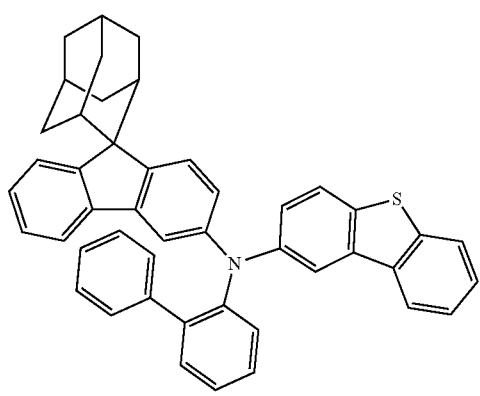
39
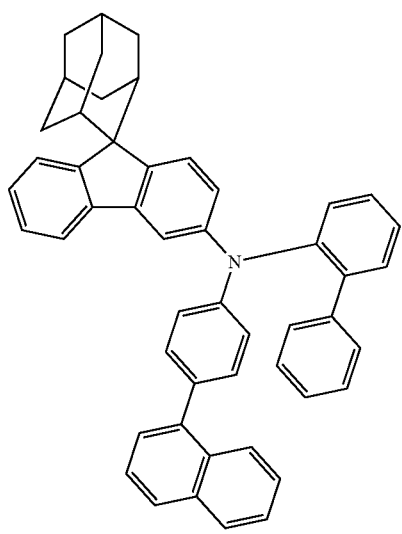
40
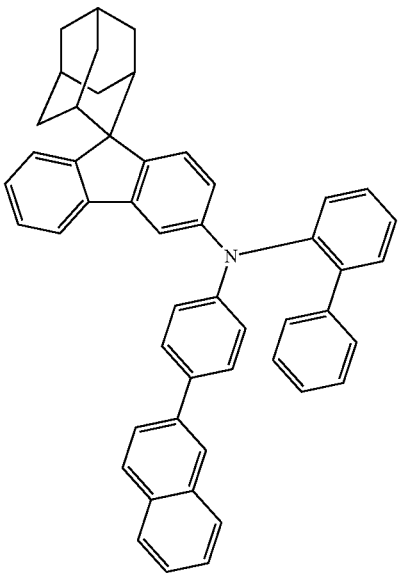
41
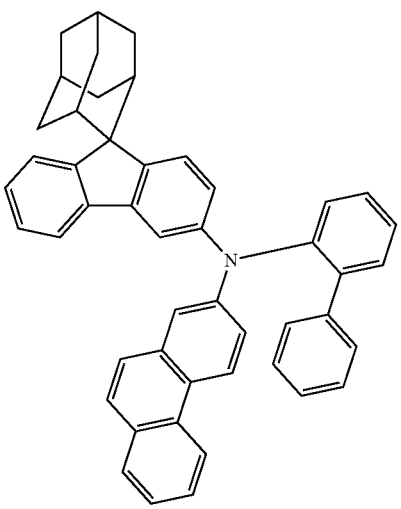
42
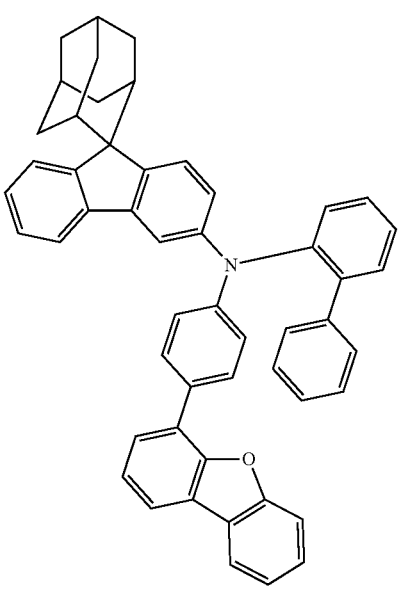

43
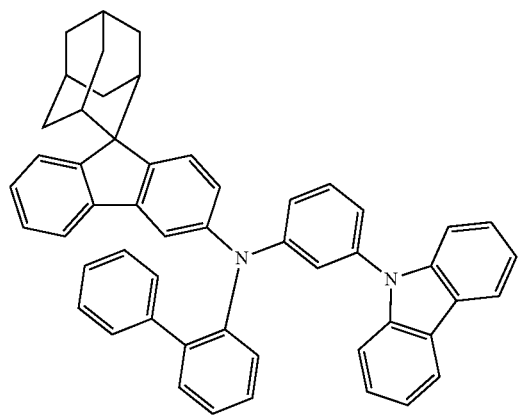
44
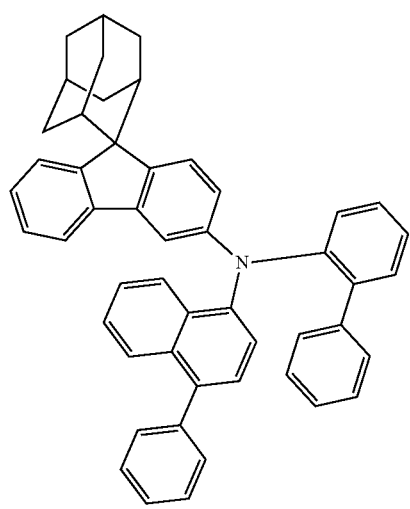
45
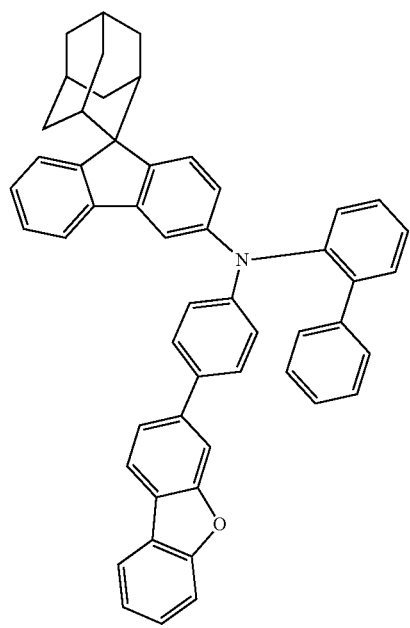
46
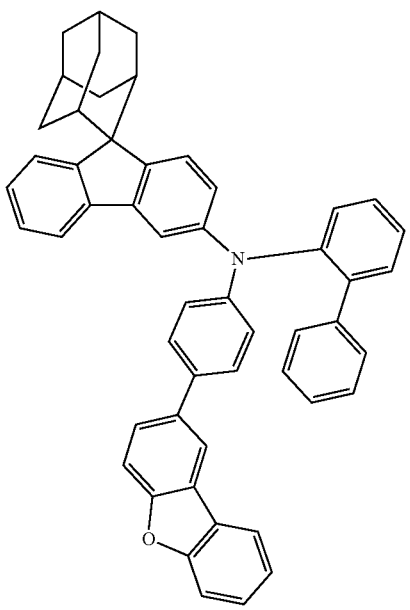
47
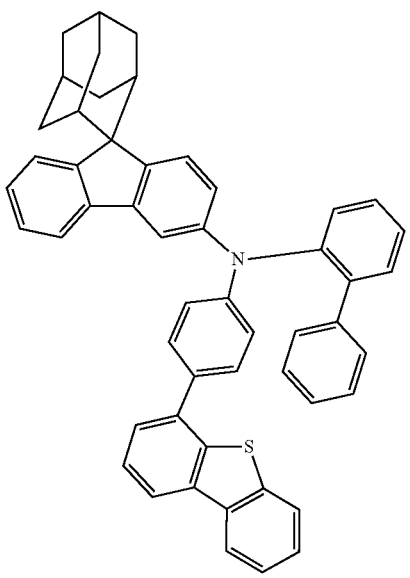
48
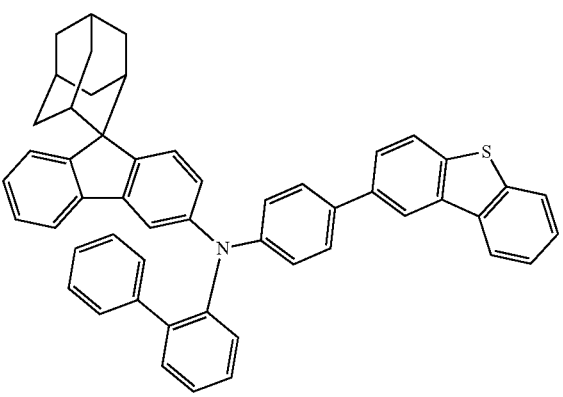

49
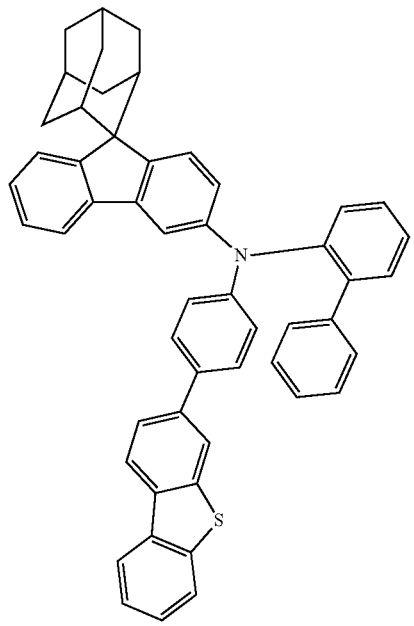
50
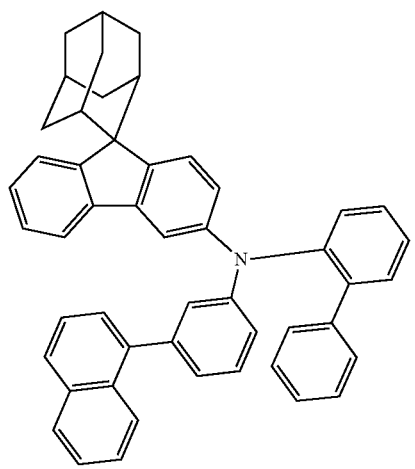
51
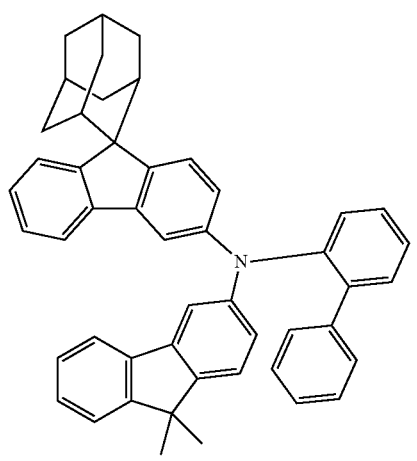
52
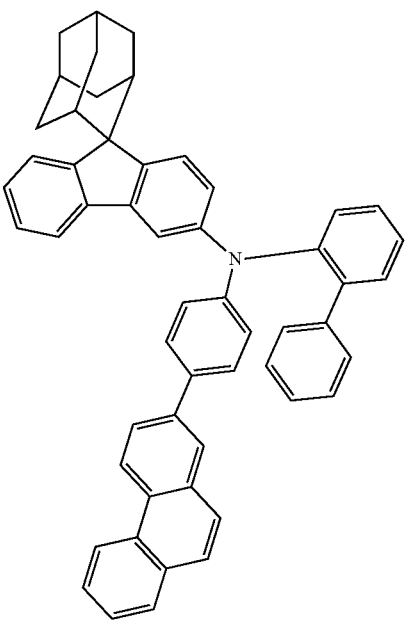
53
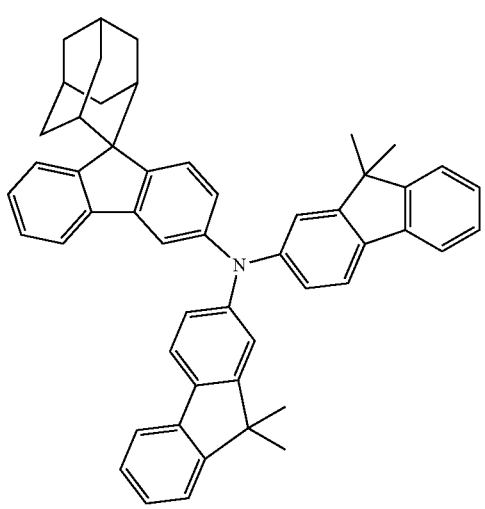

55
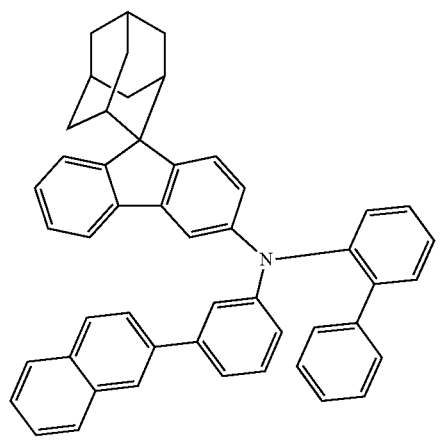
56
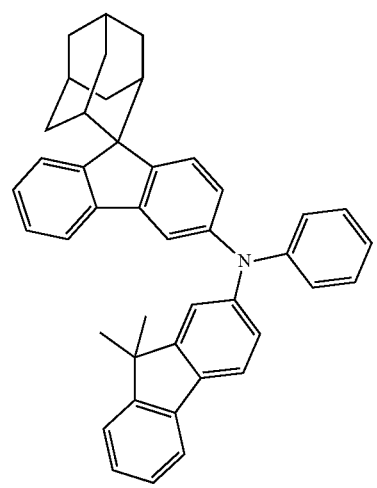
57
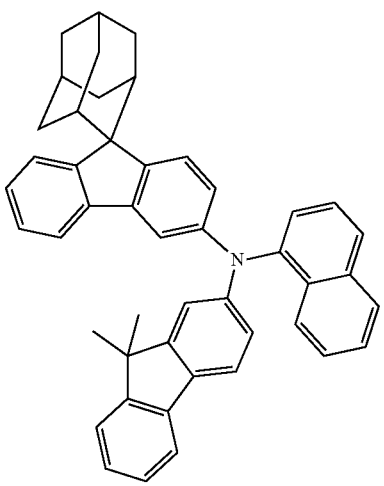
58
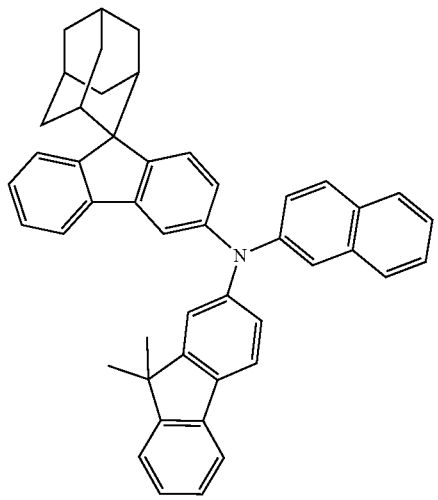
59
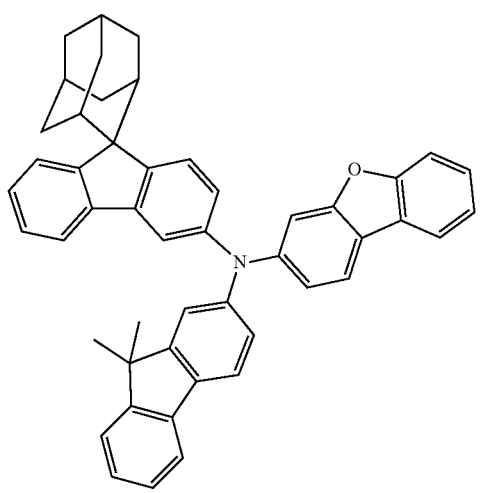
60
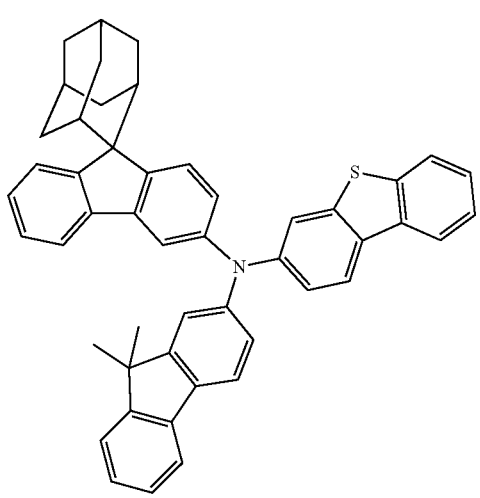

61
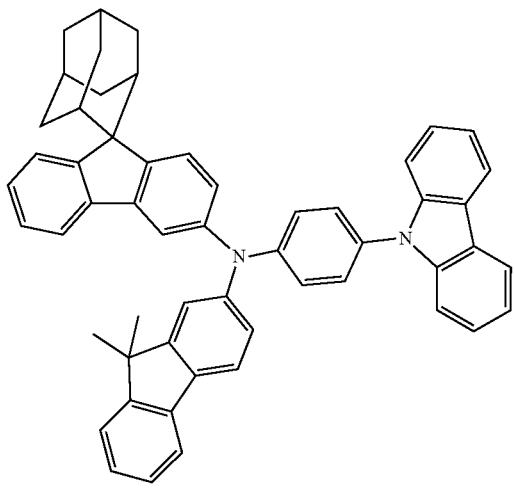
62
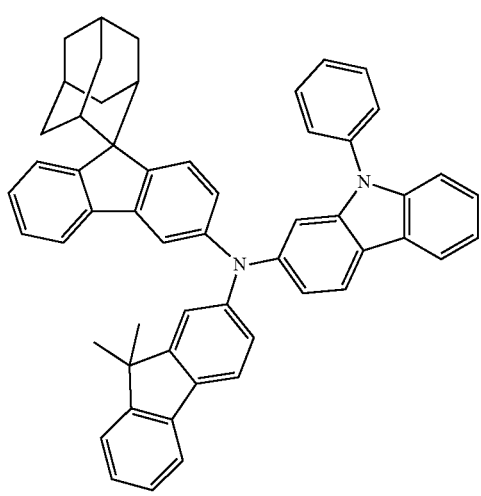
63
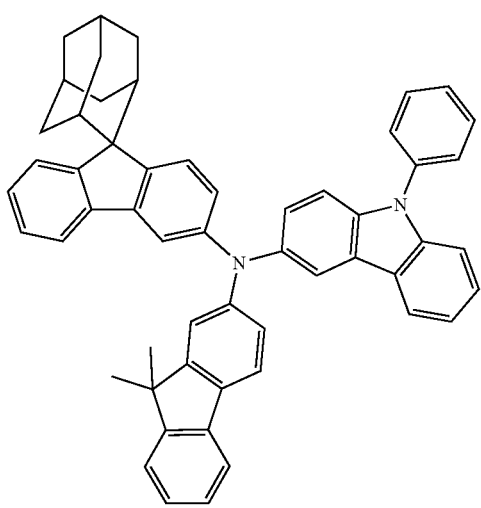
64
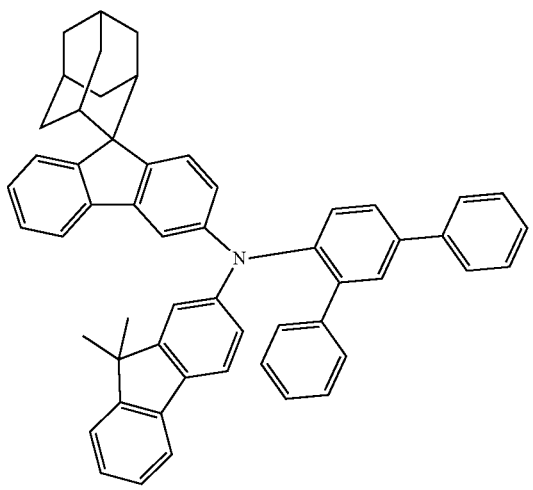
65
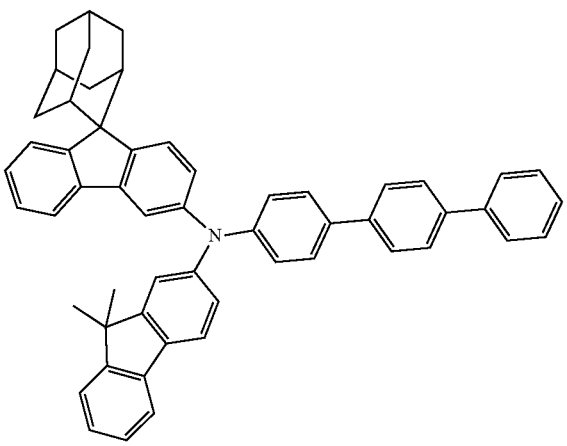
66
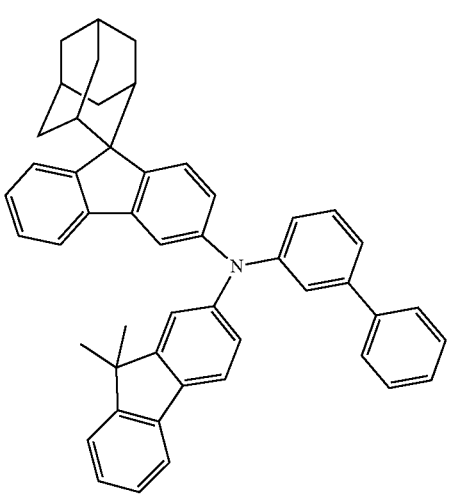

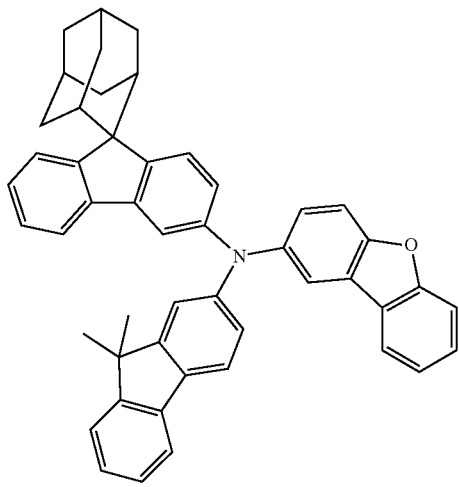
67
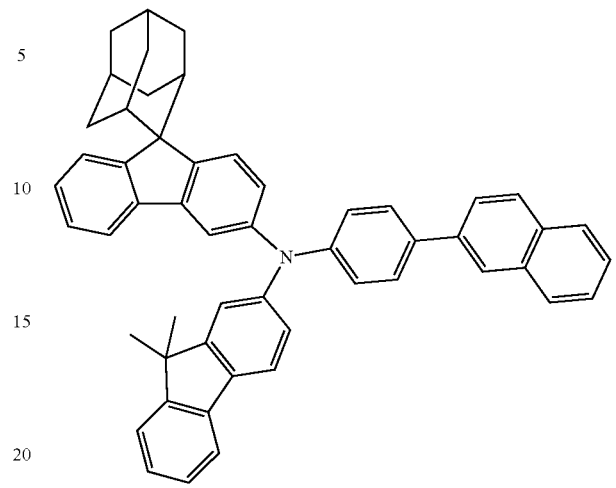
70
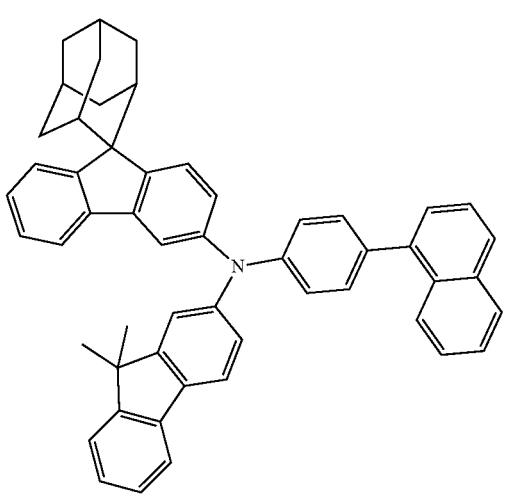
68
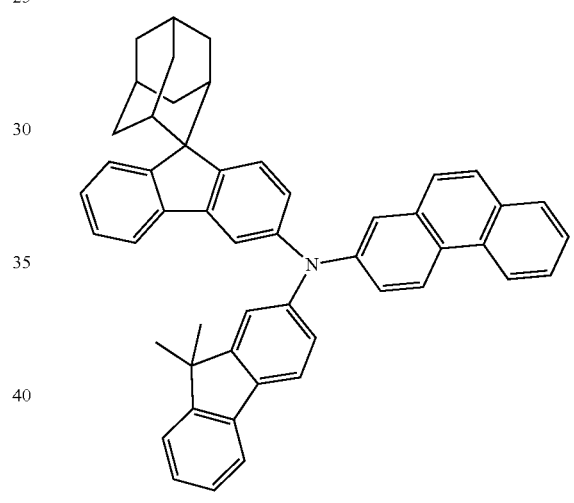
71
69
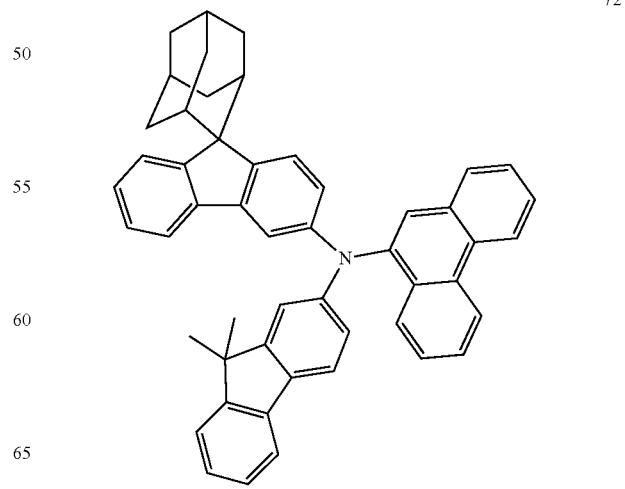
72

73
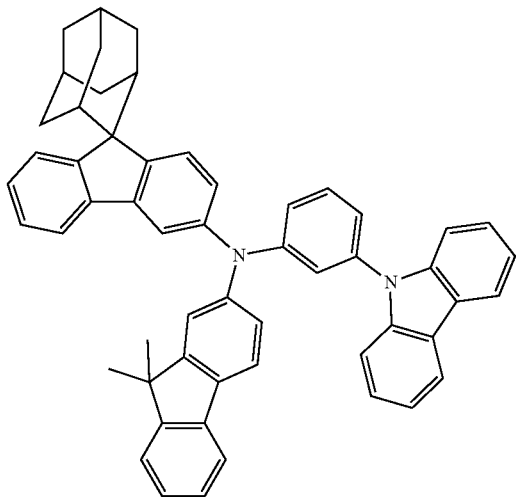
74
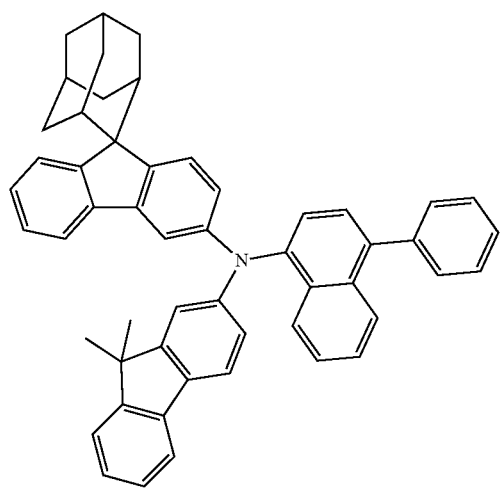
75
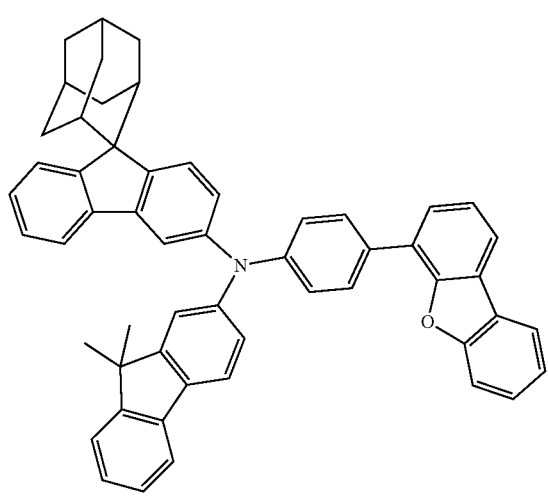
76
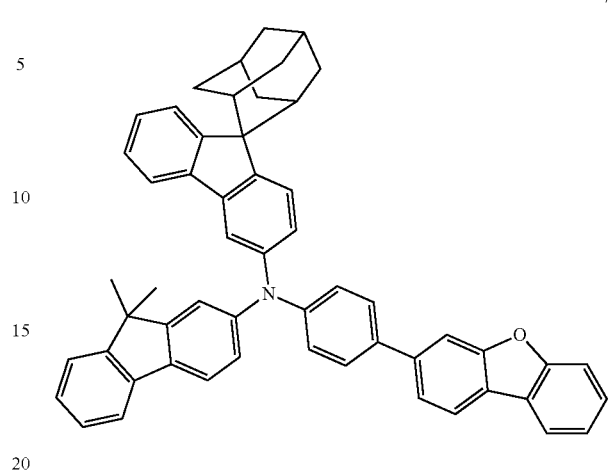
77
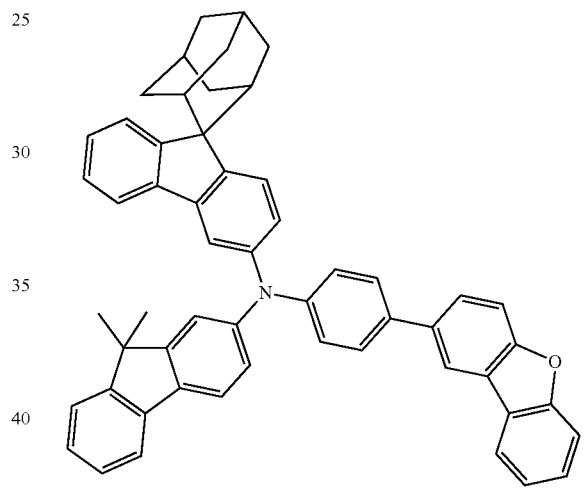
78
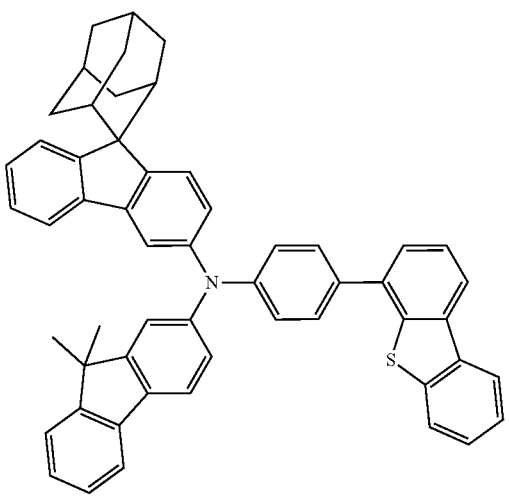

79
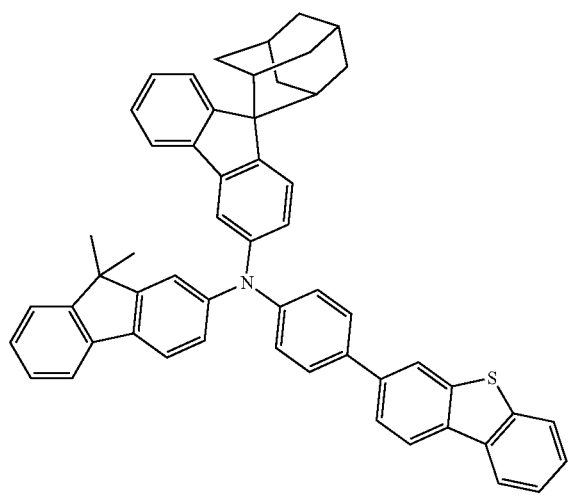
80
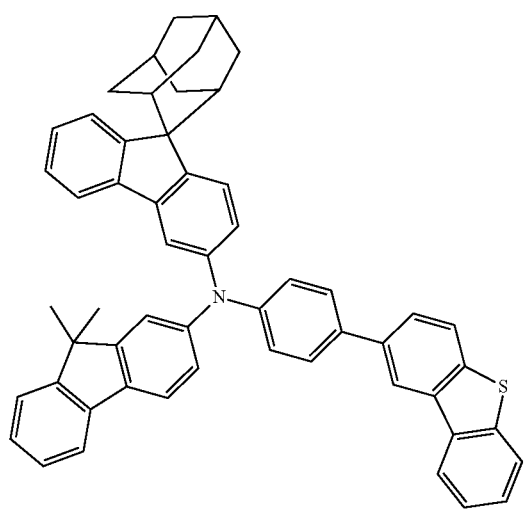
81
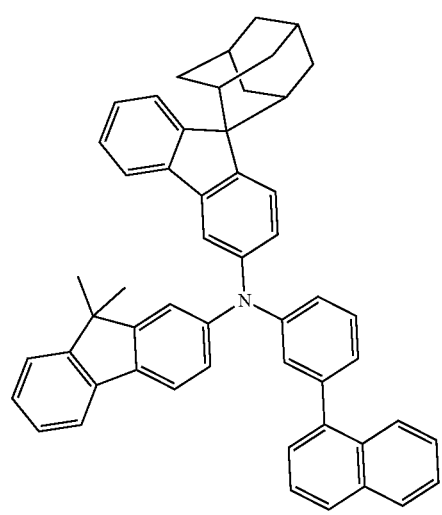
82
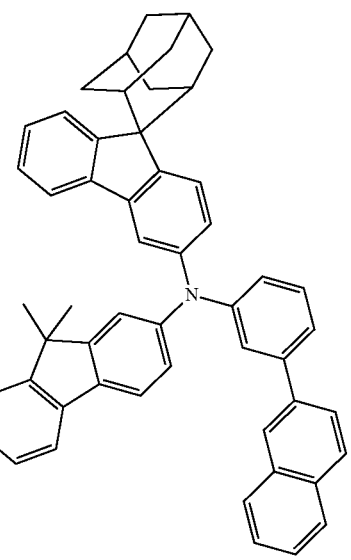
83
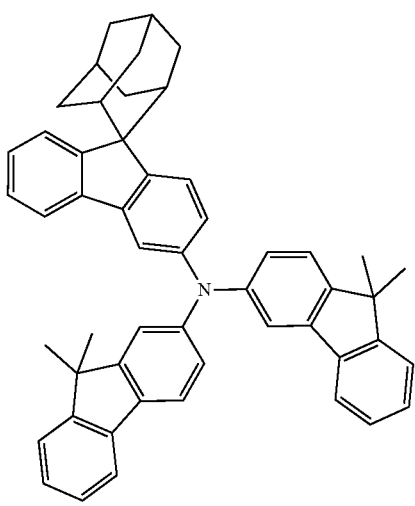
84
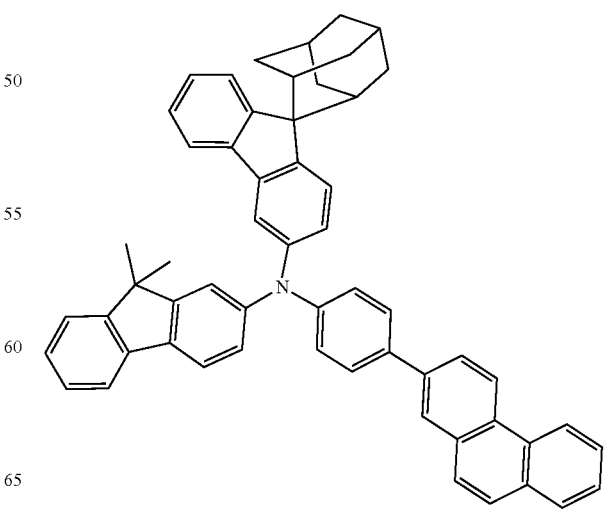

85
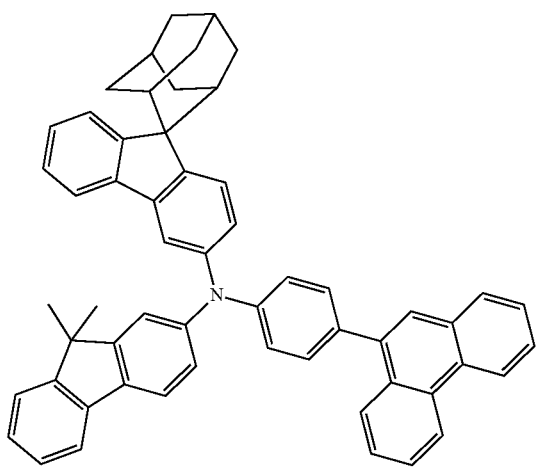
86
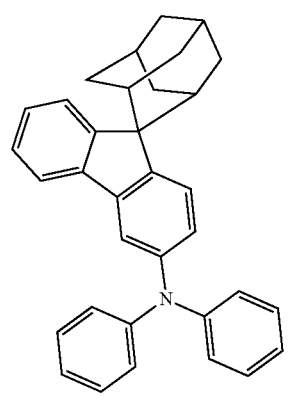
87
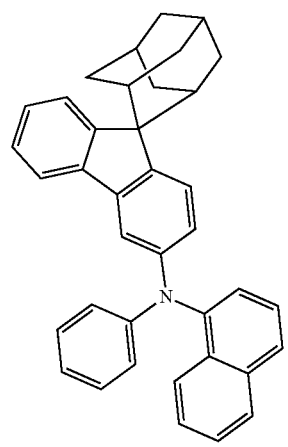
88
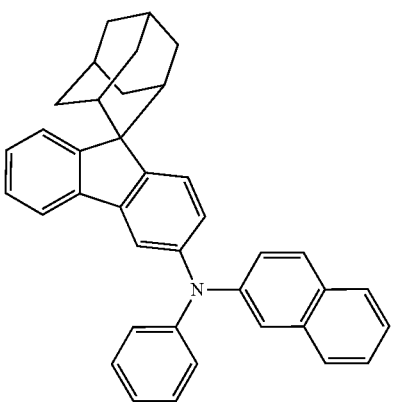
89
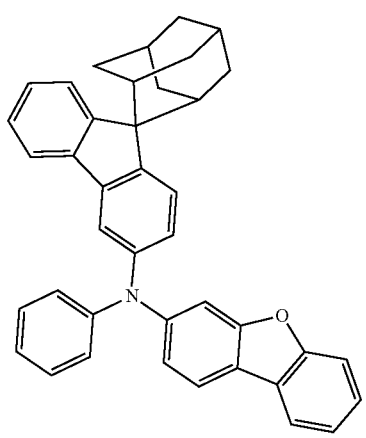
90
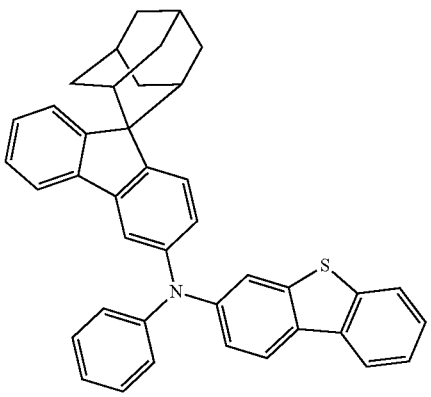

91
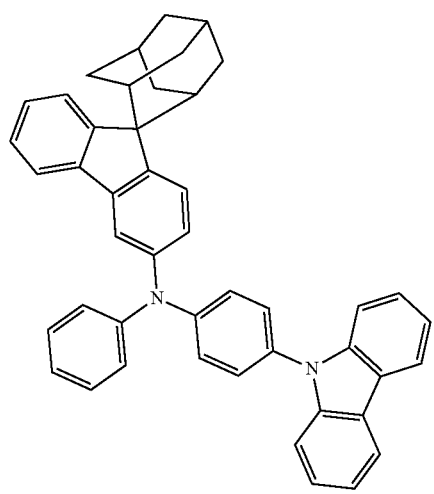
92
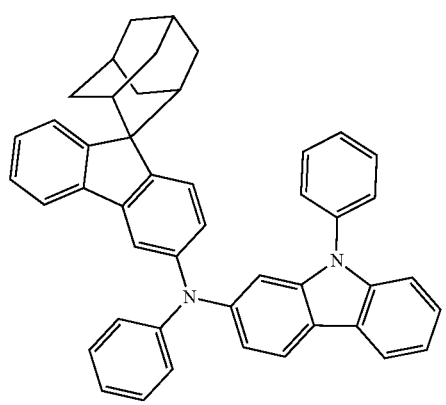
93
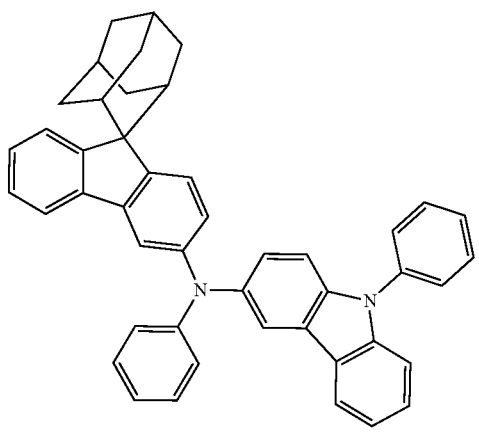
94
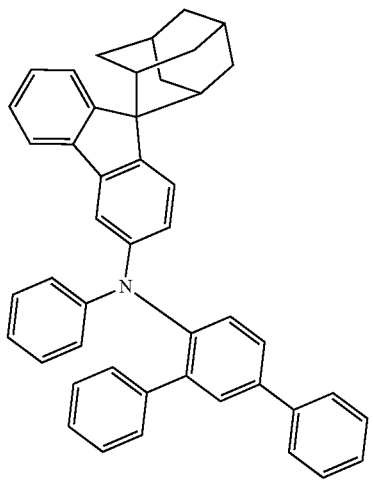
95
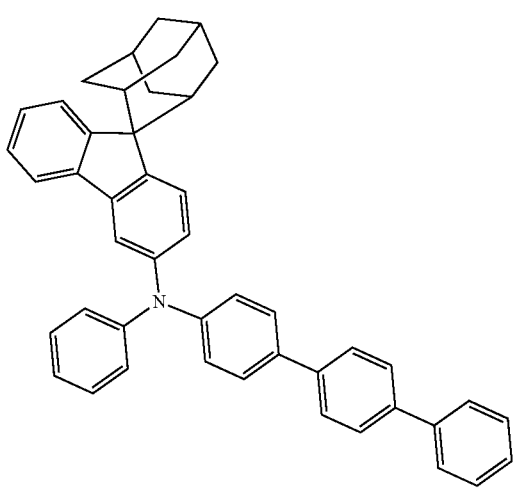
96
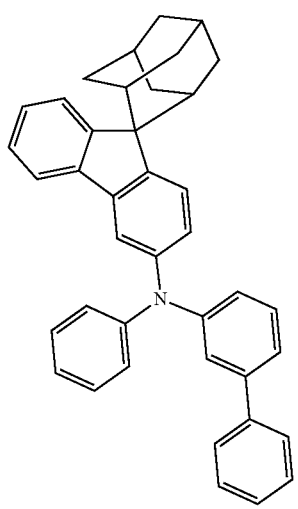

97
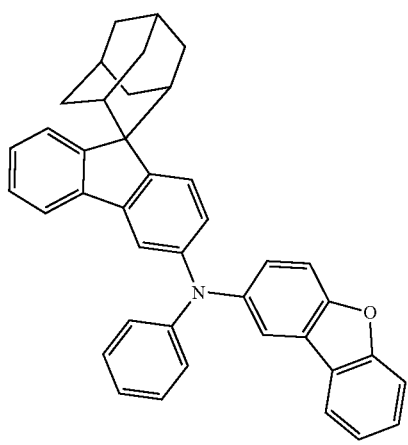
98
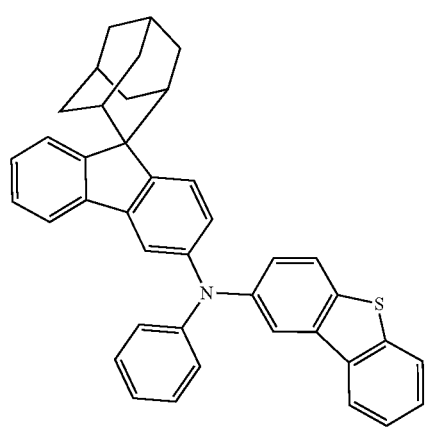
99
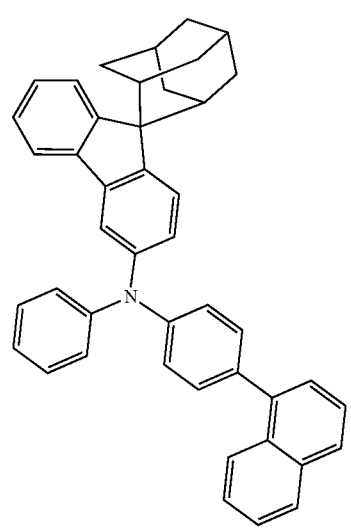
100
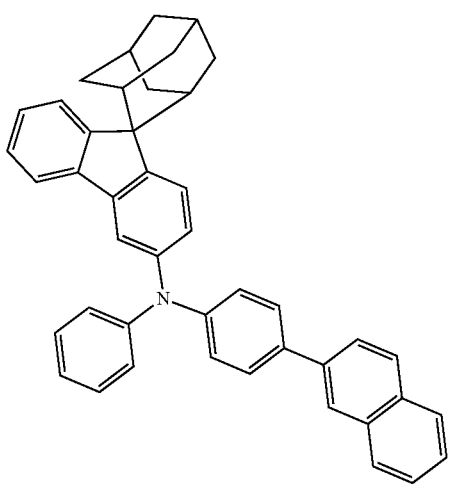
101
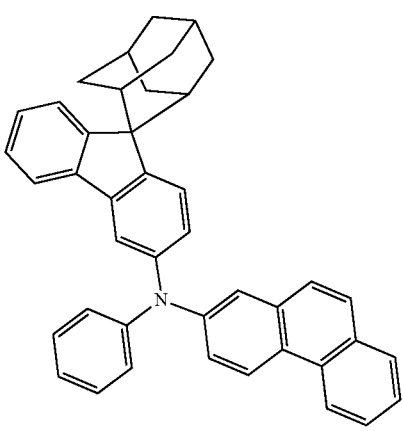
102
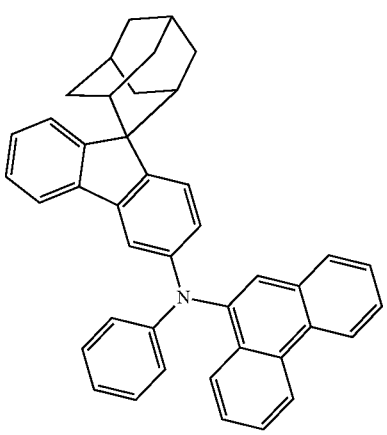

103 
104 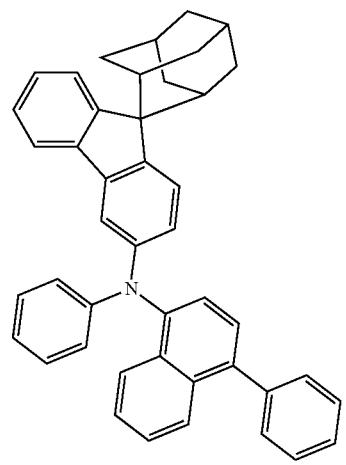
105 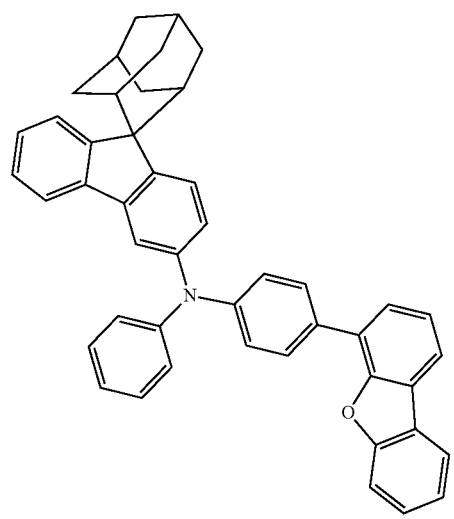
106 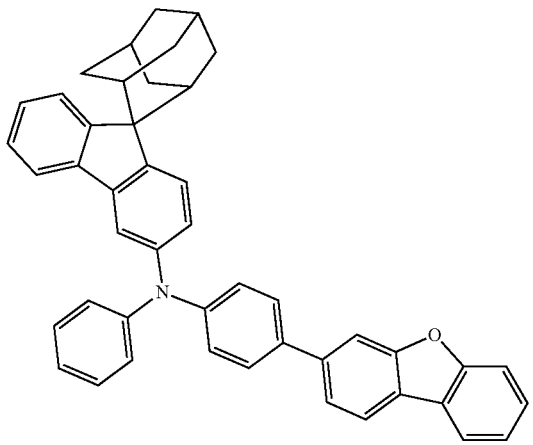
107 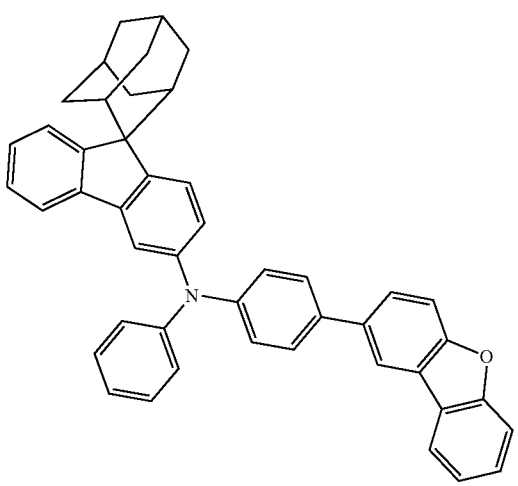
108 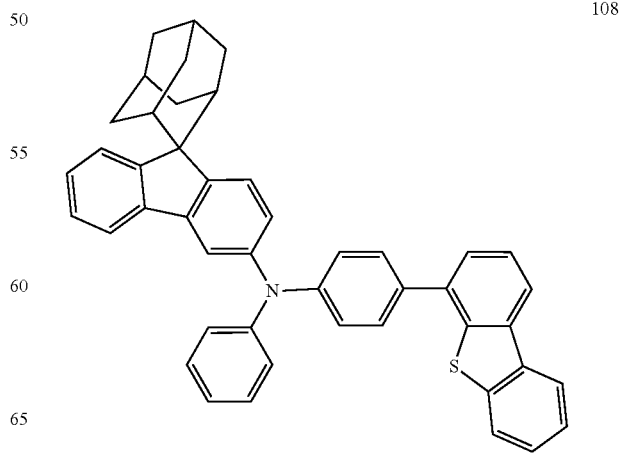

109
110
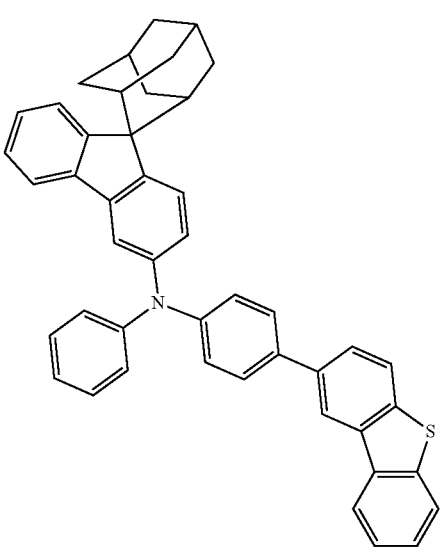
111
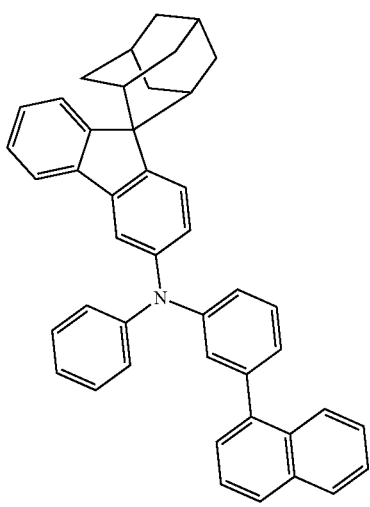
112
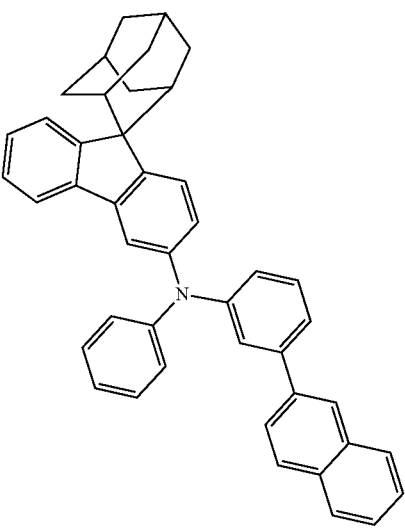
113
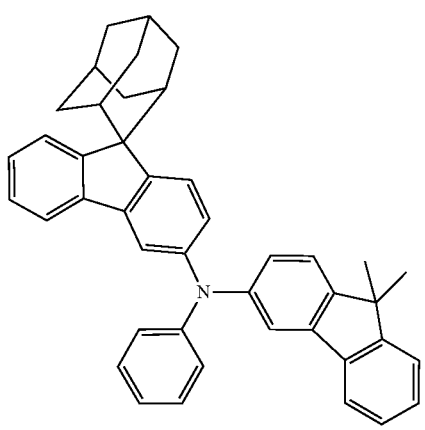
114

115 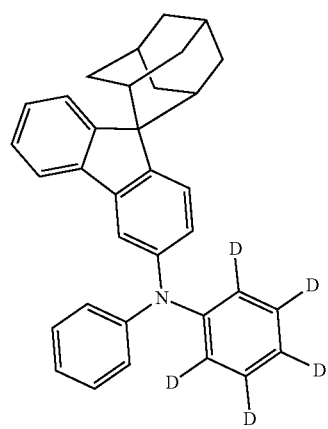
116 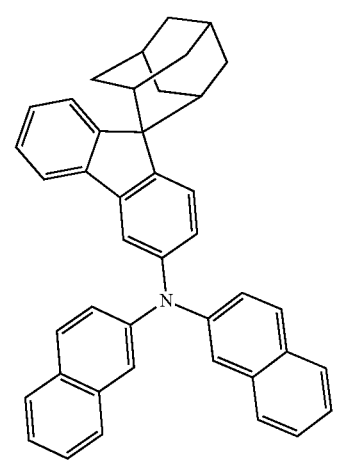
117 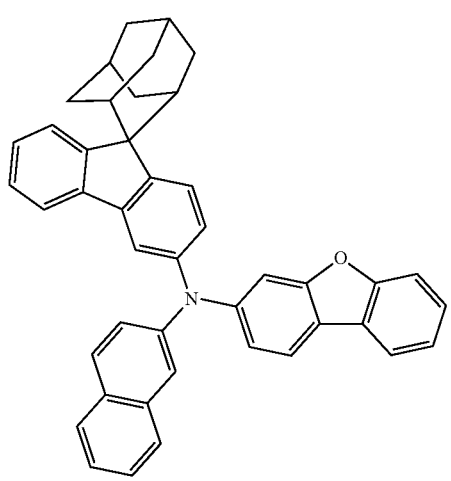
118 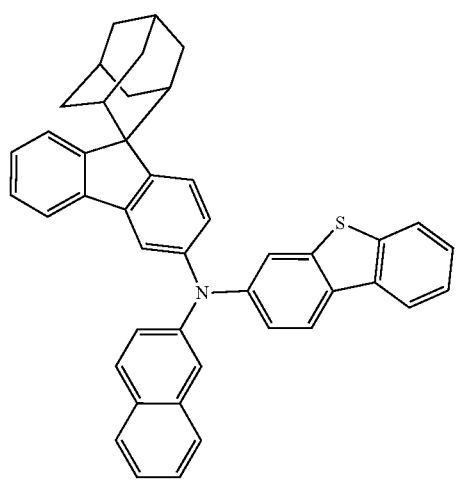
119 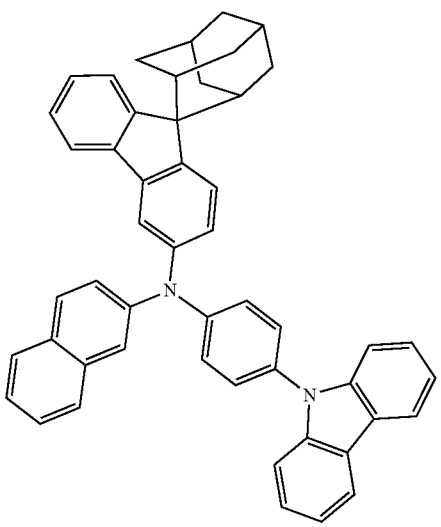
120 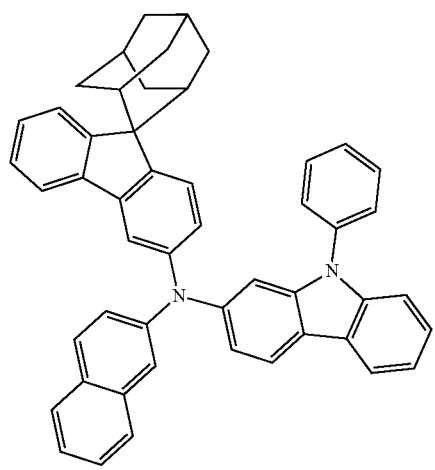

121
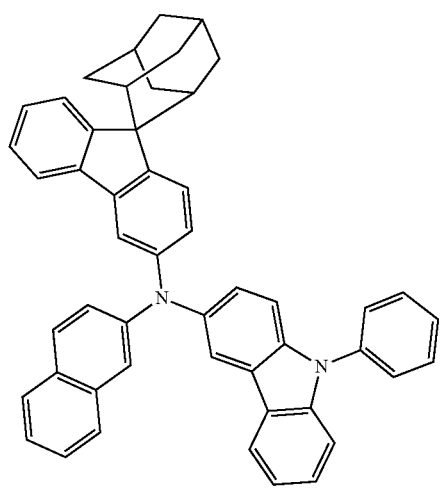
124
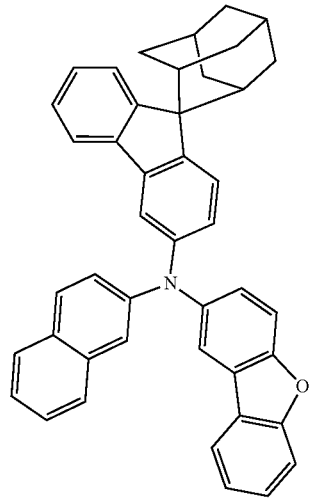
122
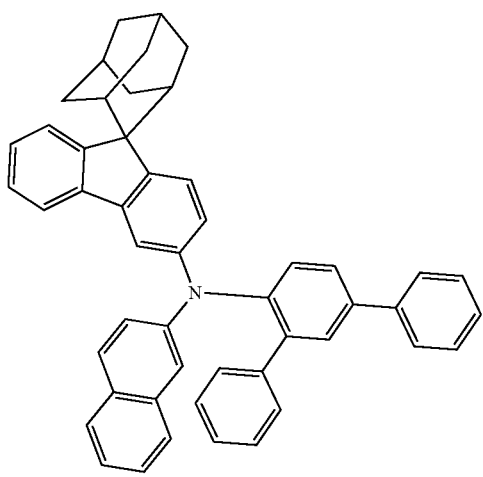
125
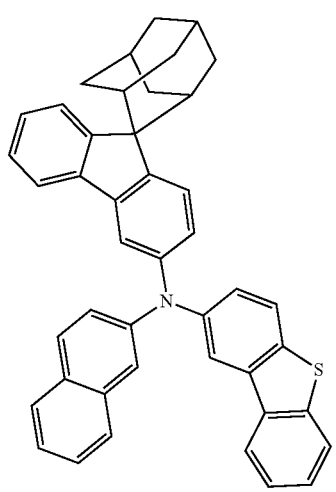
123
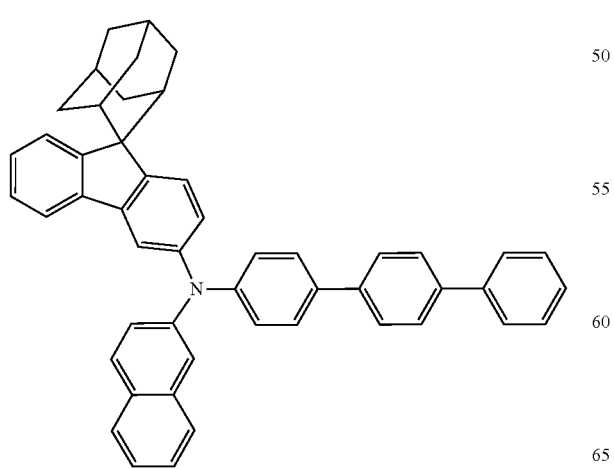
126
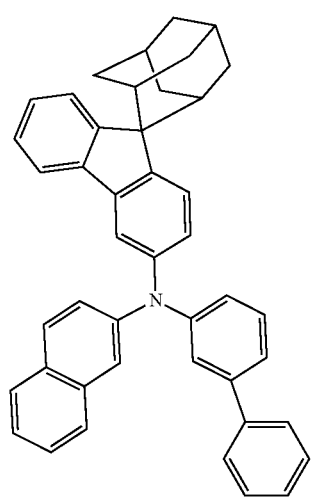

127
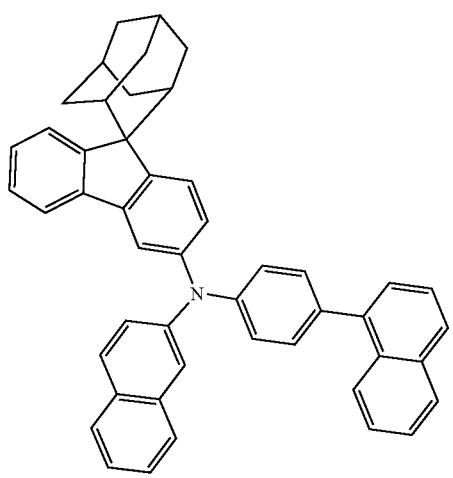
128
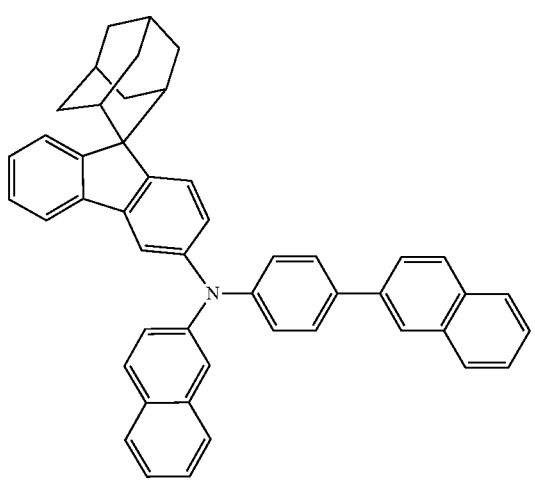
129
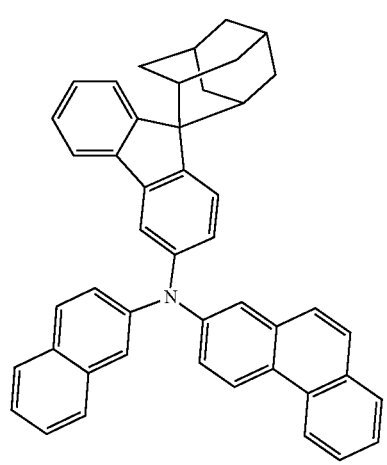
130
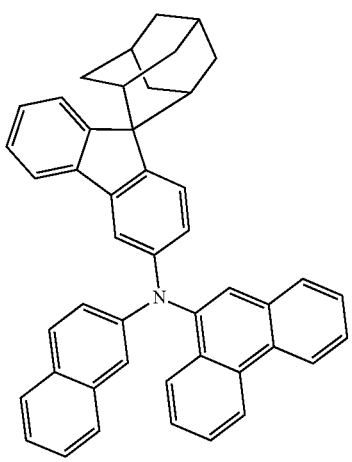
131
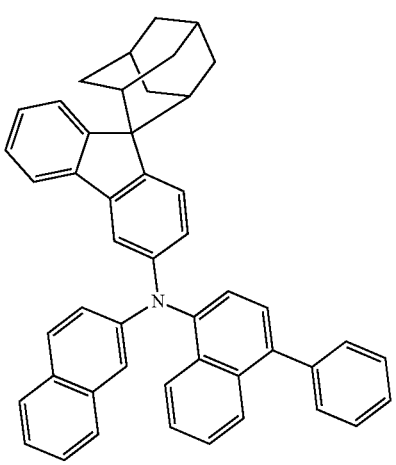
132
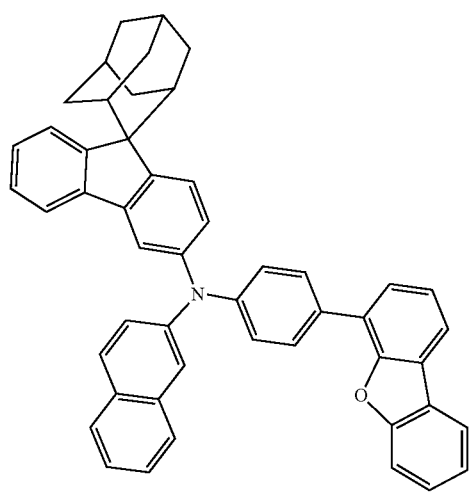

133
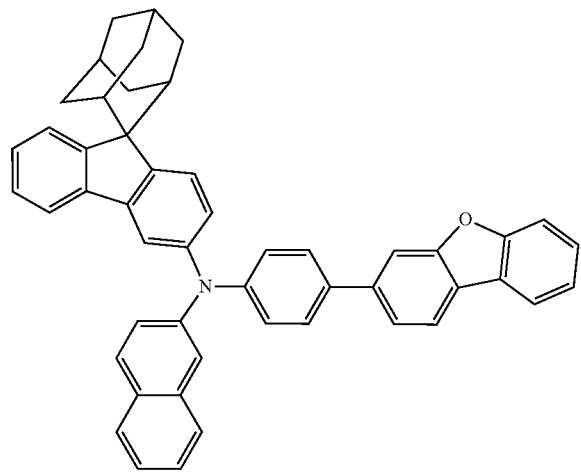
134
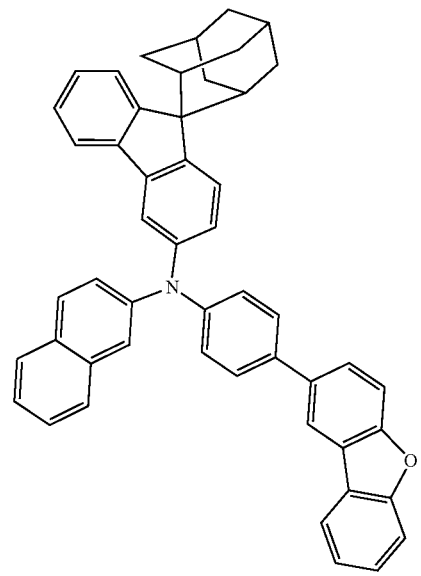
135
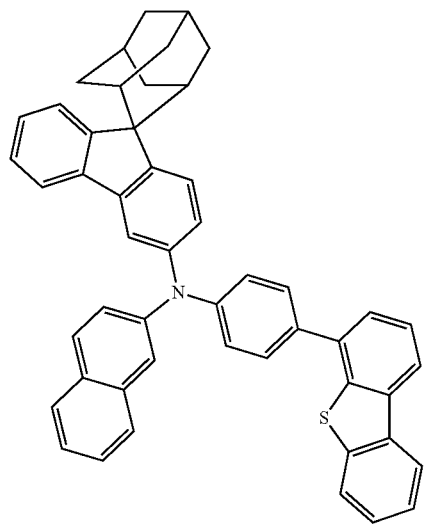
136
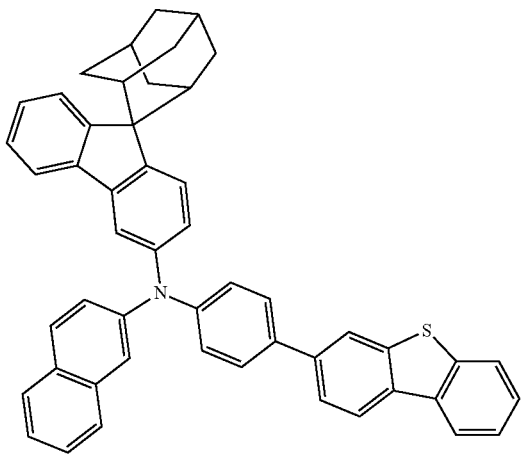
137
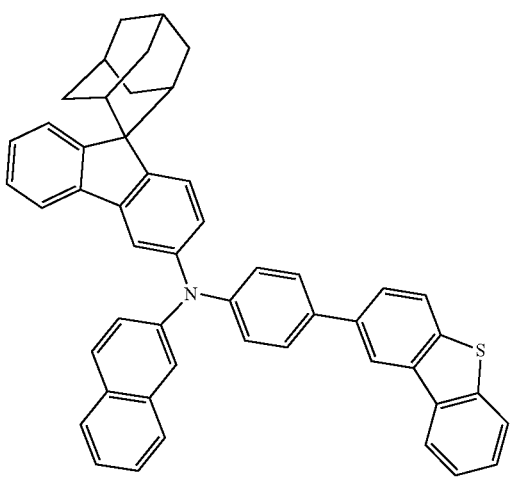
138
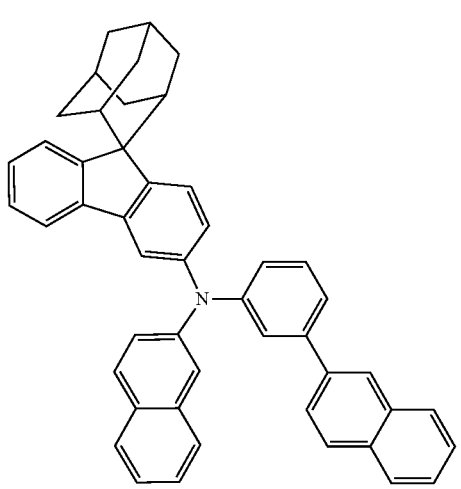

139 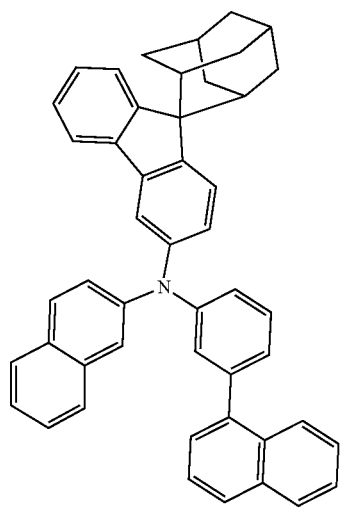
140 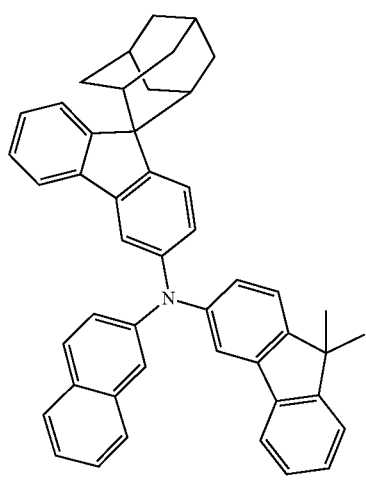
141 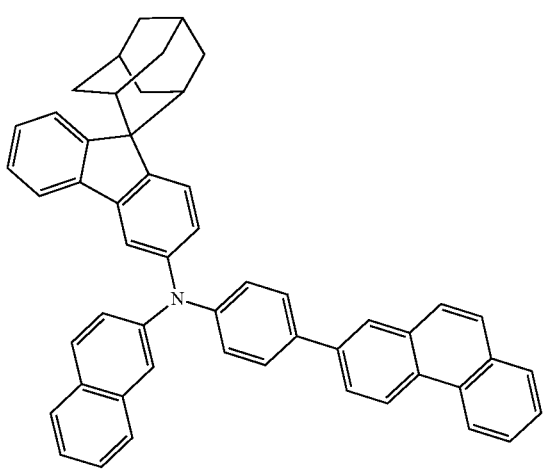
142 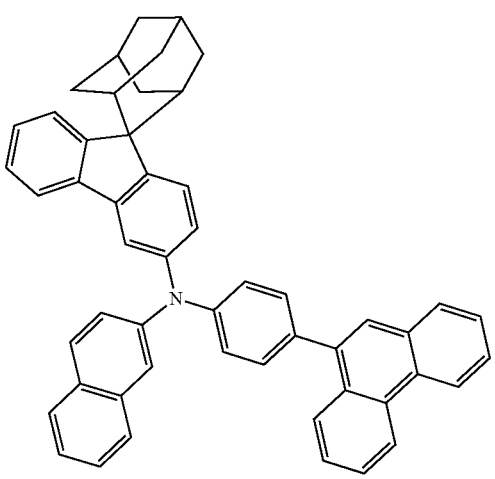
143 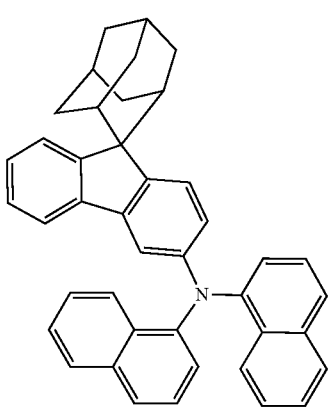
144 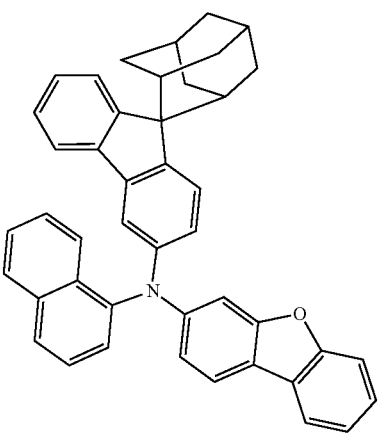

145
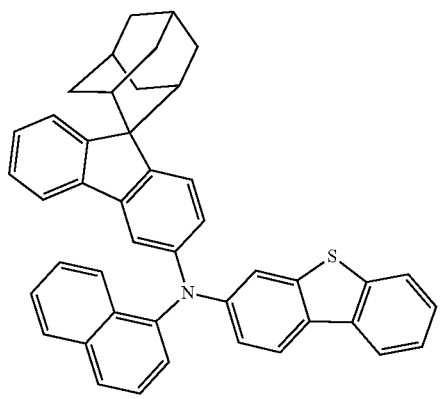
146
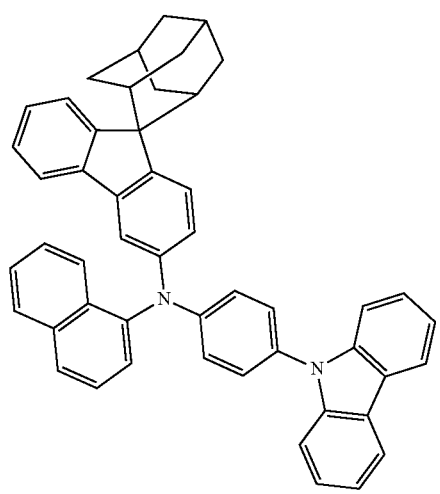
147
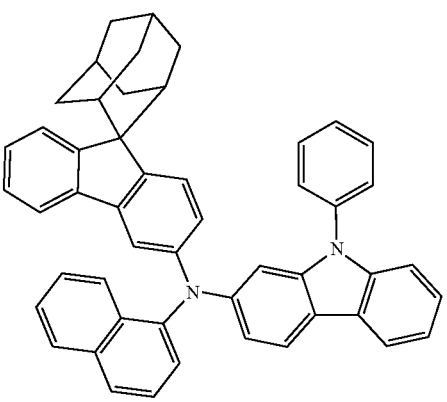
148
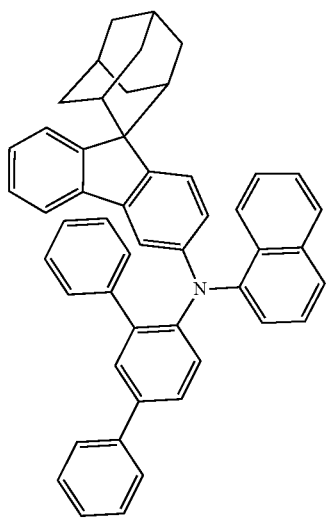
149
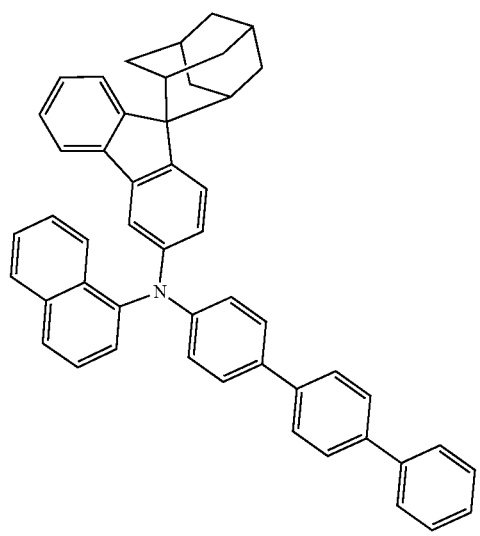
150
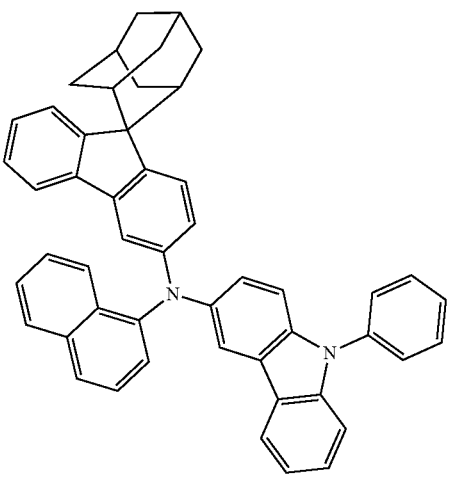

151 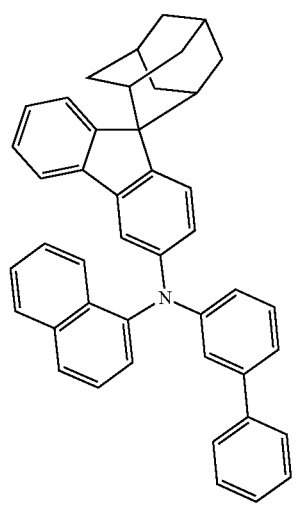
152 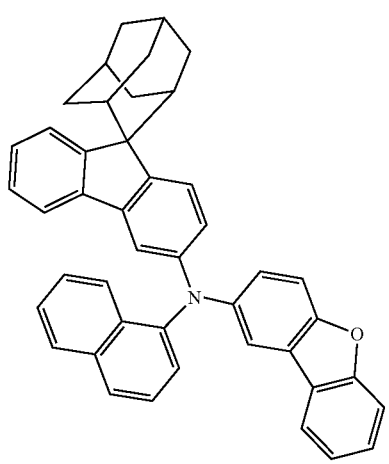
153 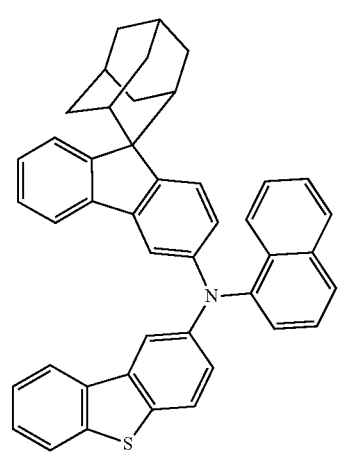
154 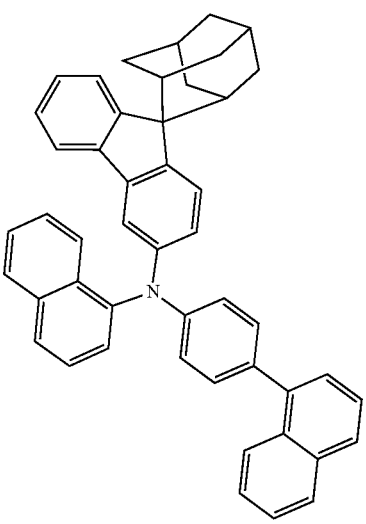
155 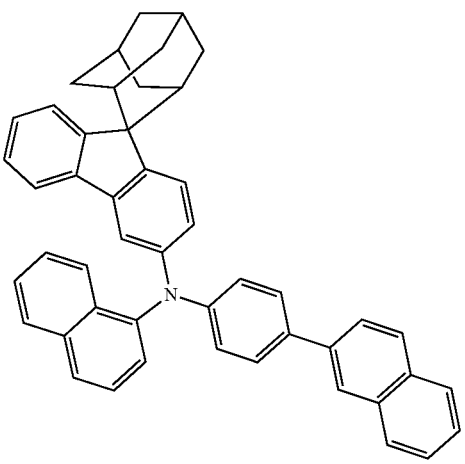
156 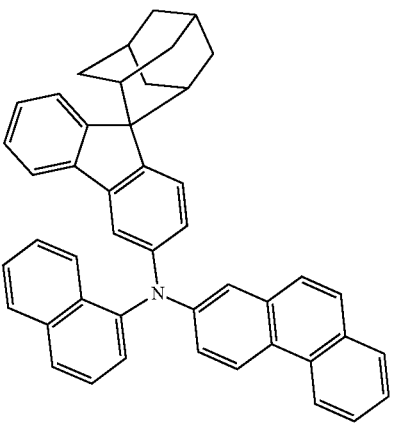

157
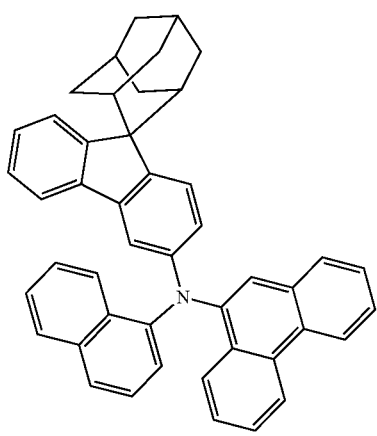
158
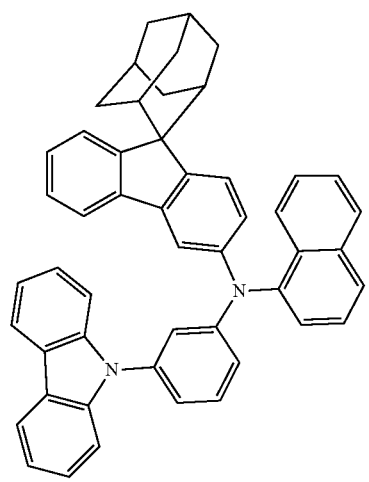
159
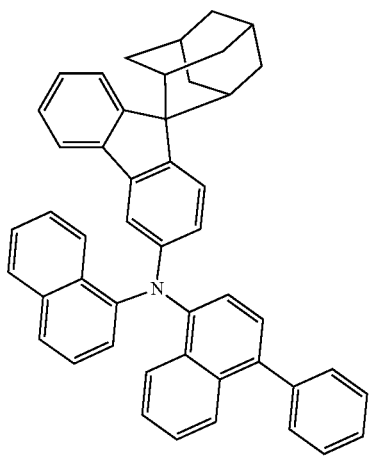
160
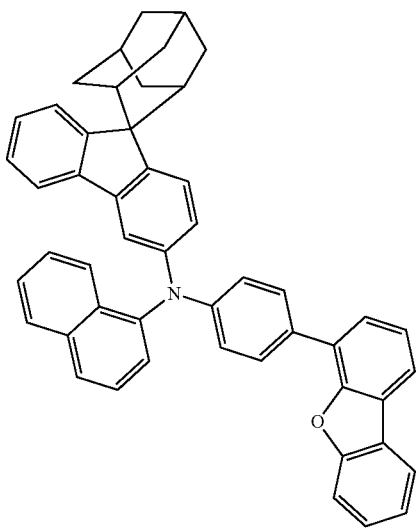
161
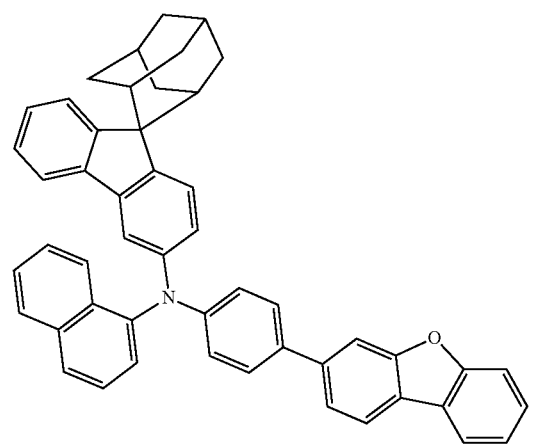
162
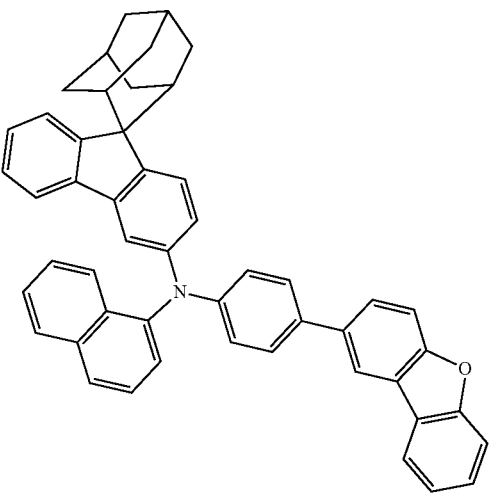

163
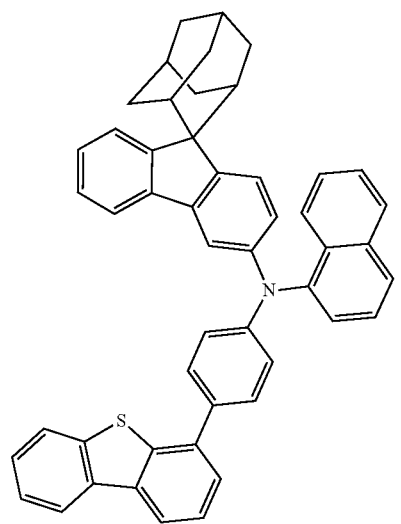
164
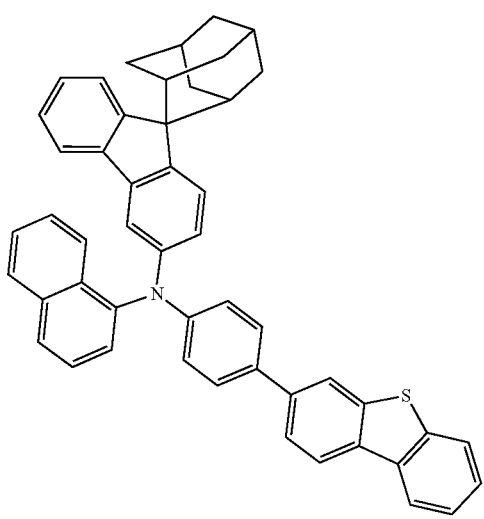
165
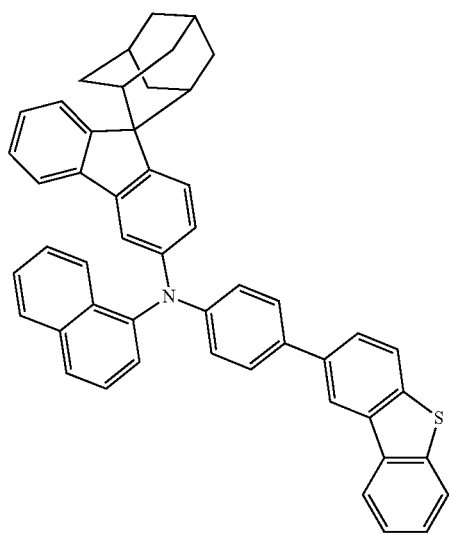
166
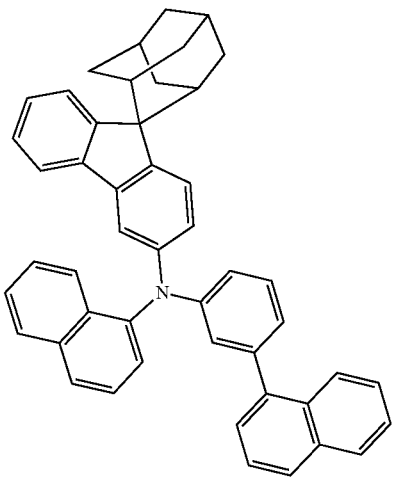
167
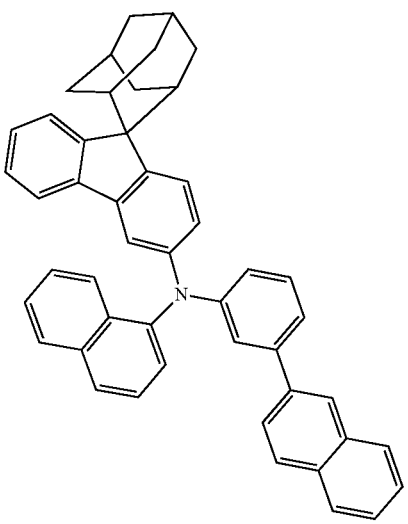
168
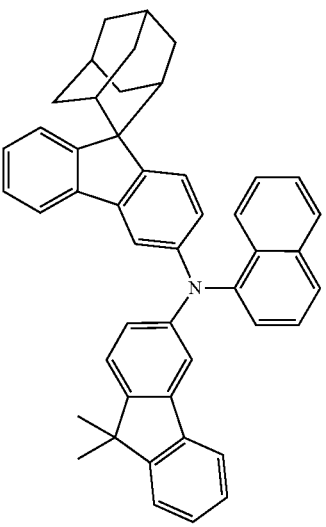

169
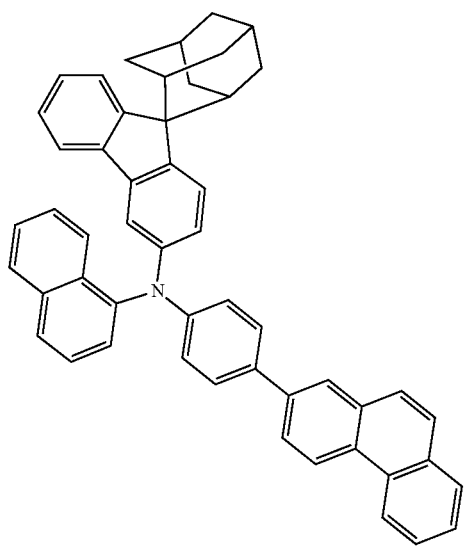
170
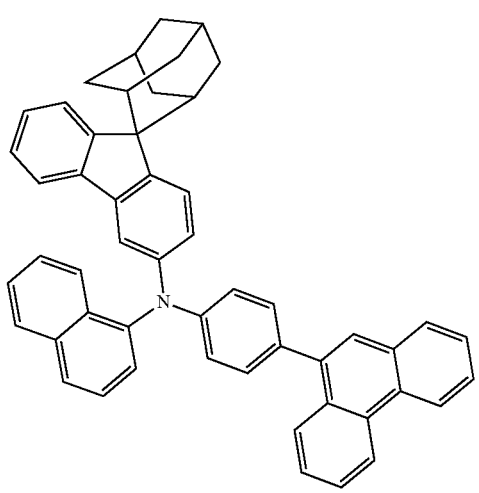
171
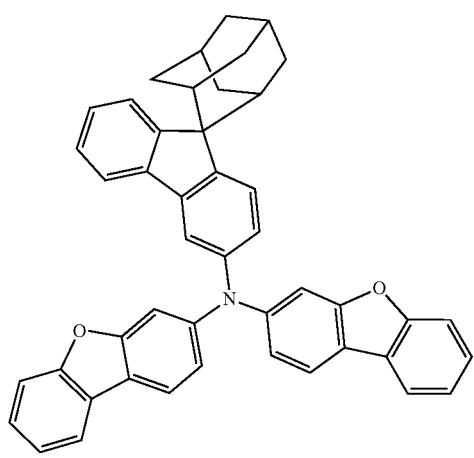
172
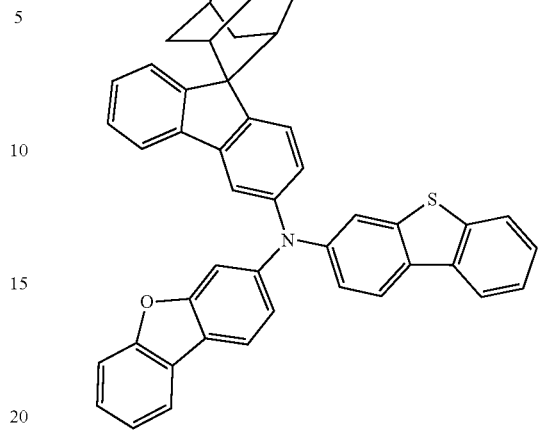
173
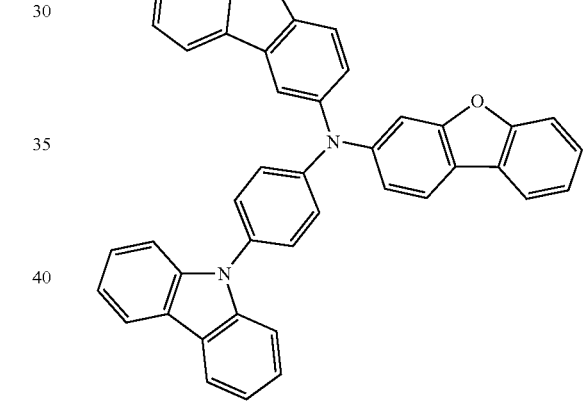
174
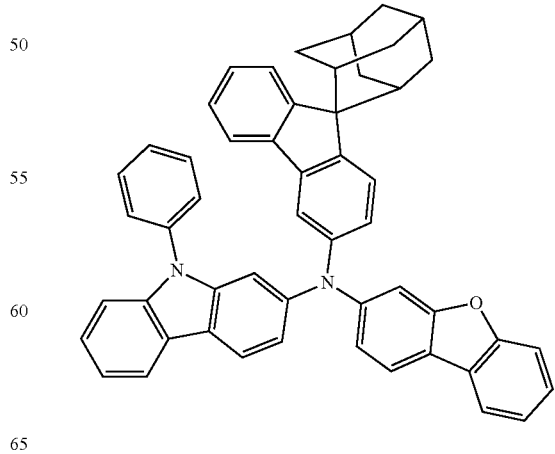

175
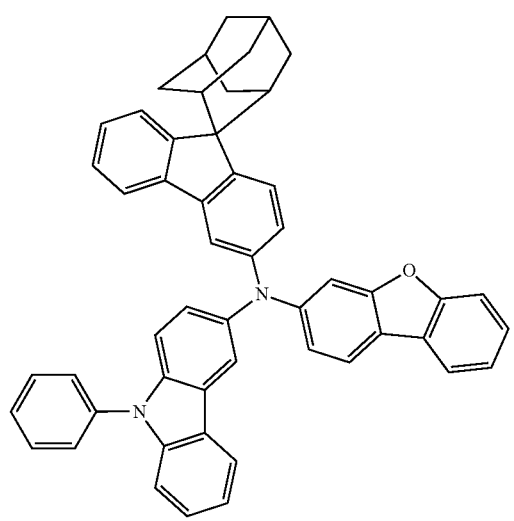
176
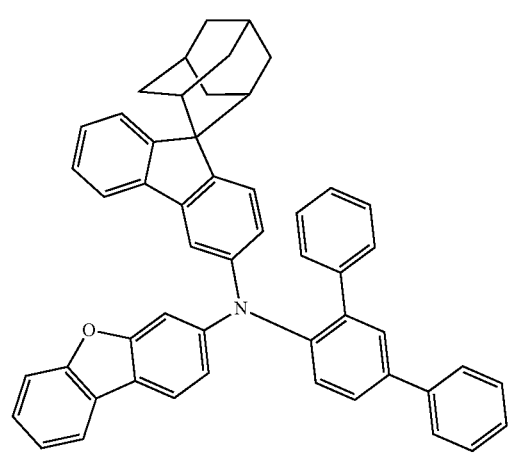
177
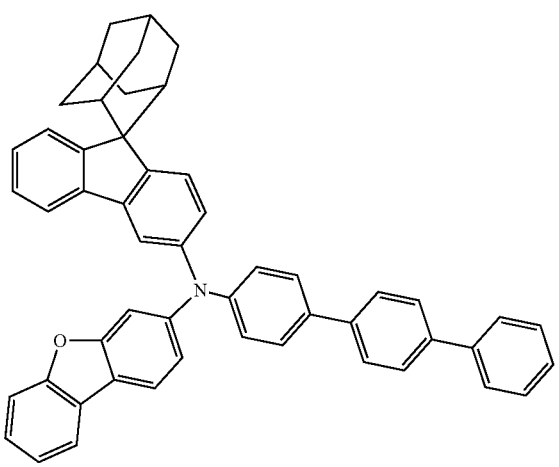
178
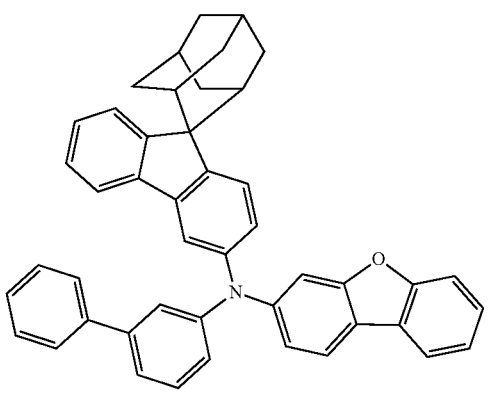
179
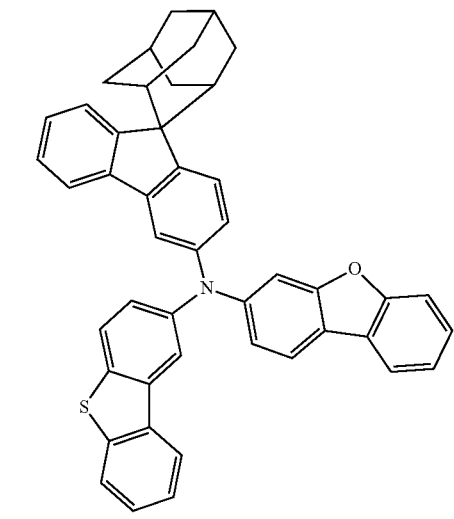
180

181
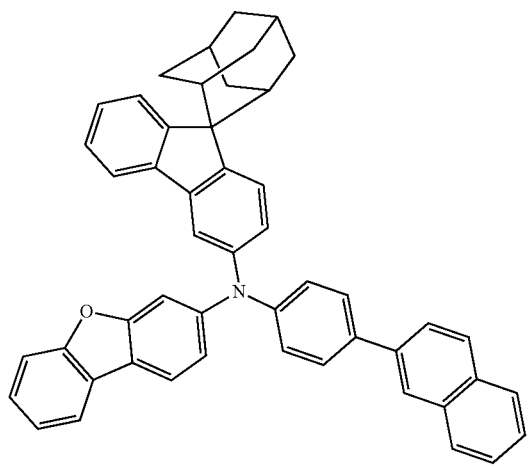
182
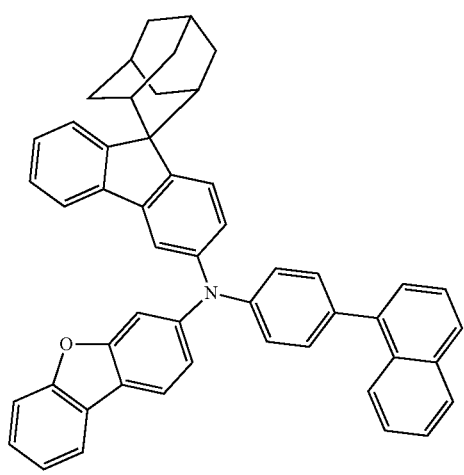
183
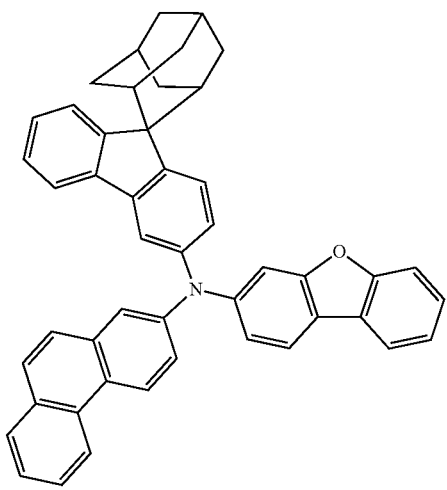
184
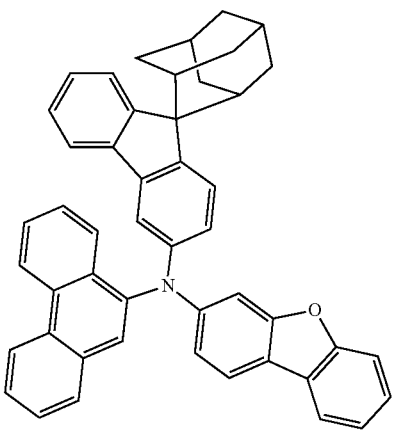
185
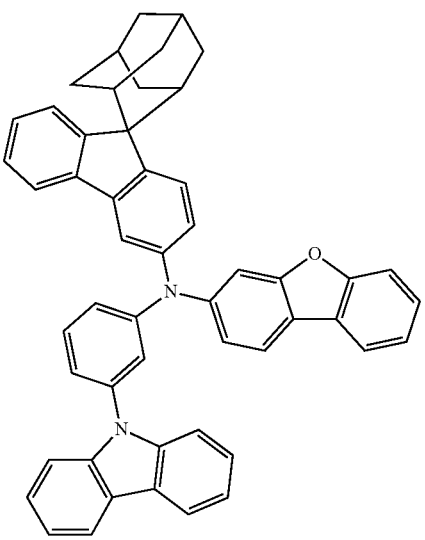
186
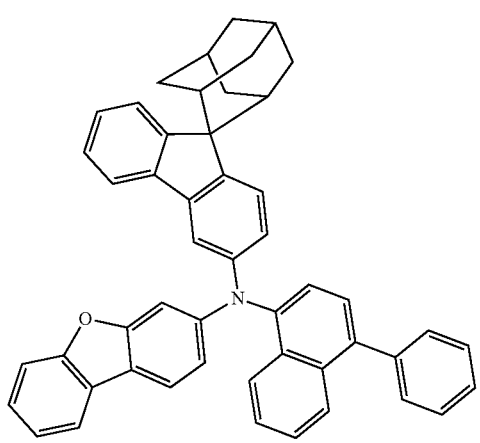

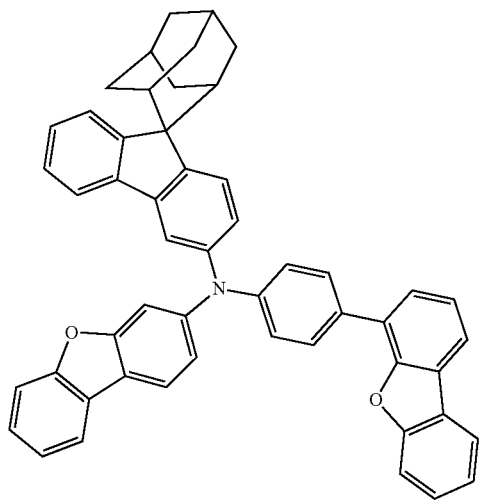
187
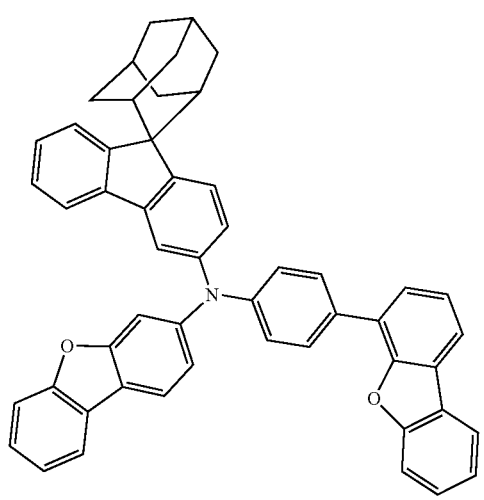
187
188
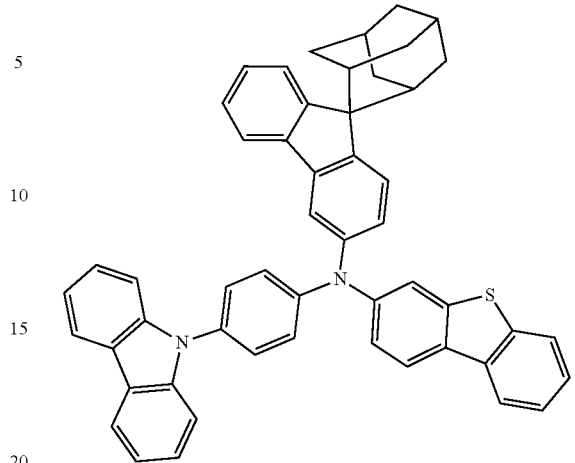
189
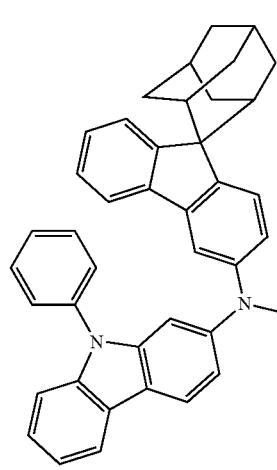
190
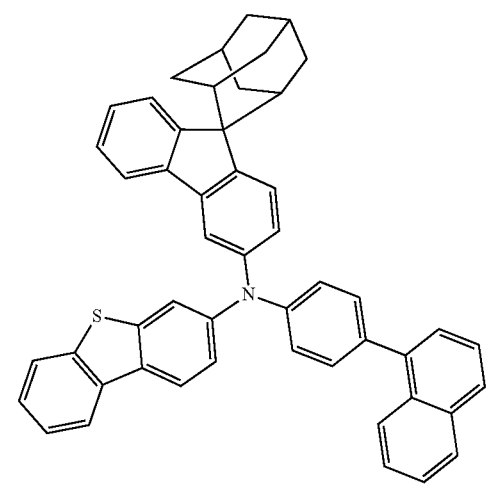
191

192
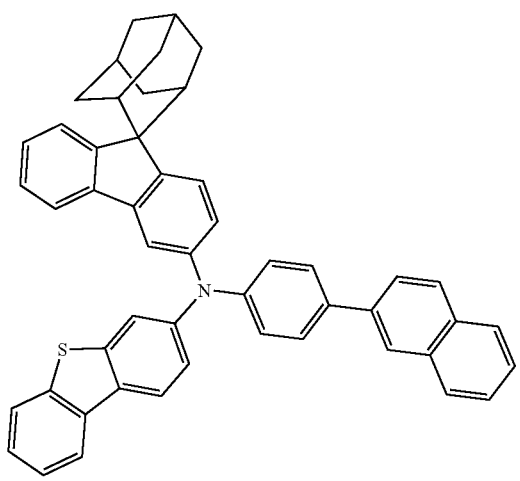
193
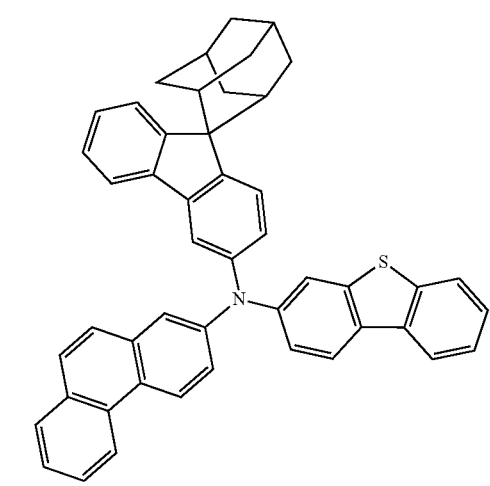
194
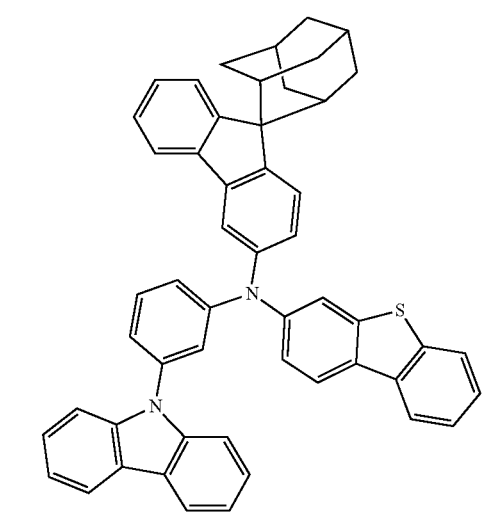
195
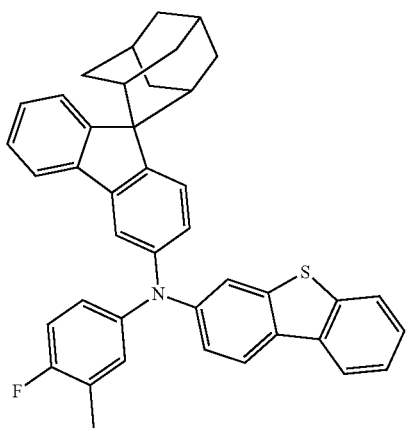
196
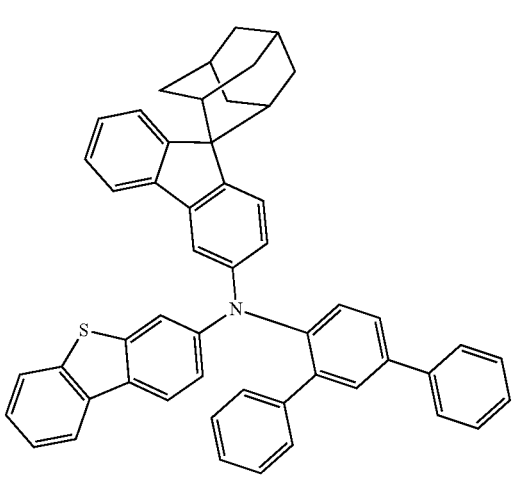
197
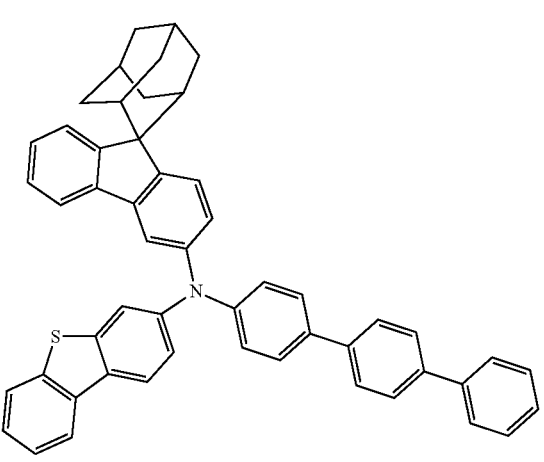

-continued
198
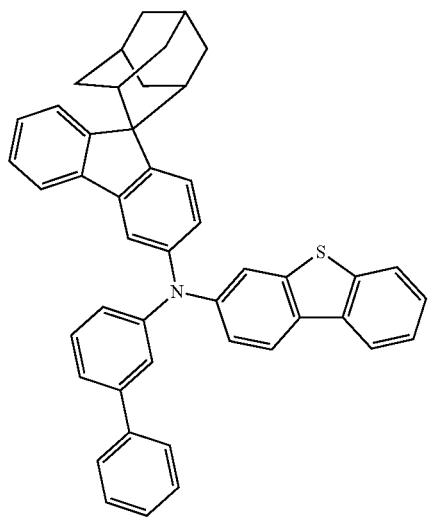
199
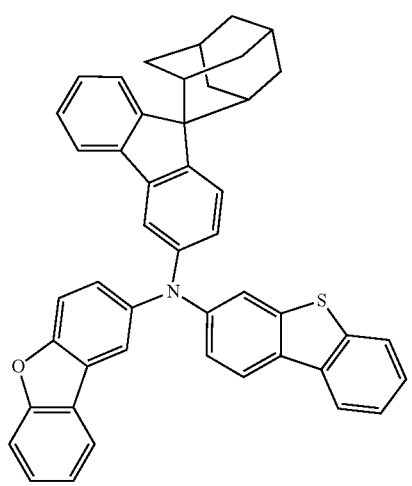
200
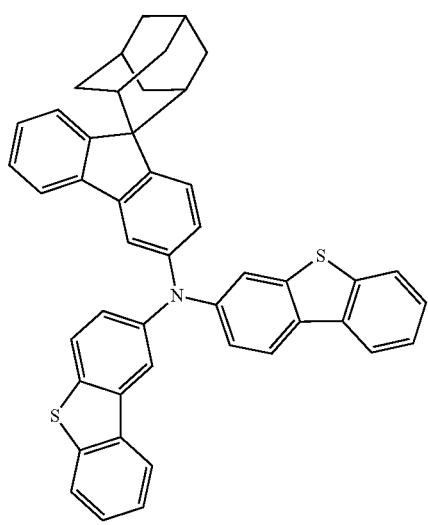
201
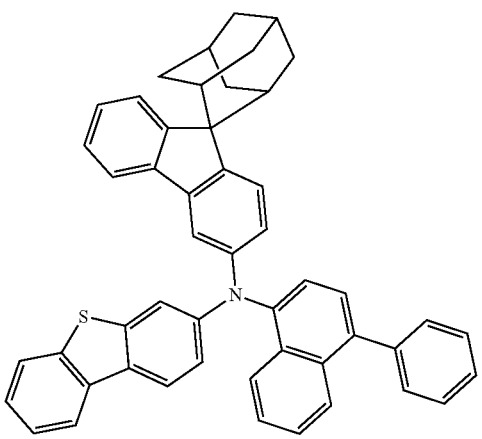
202
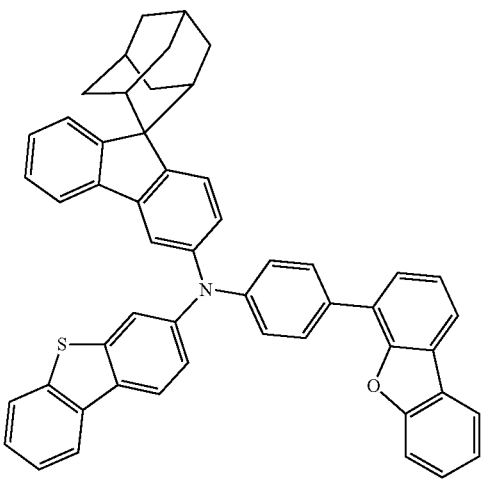
203
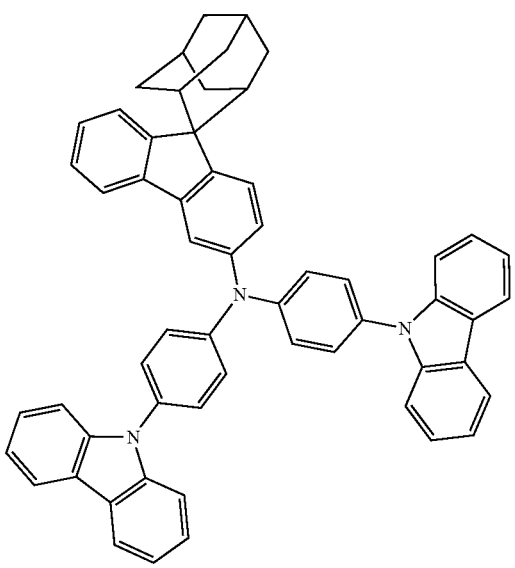

-continued
204
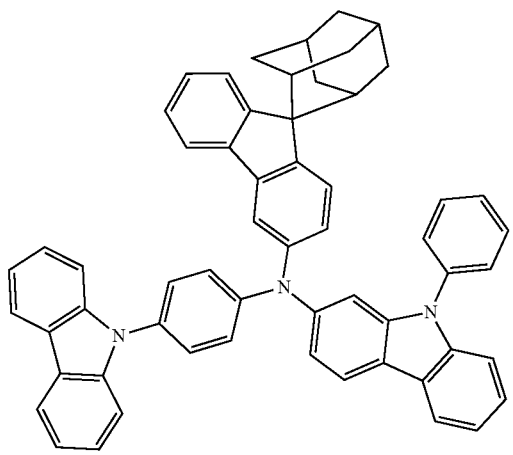
205
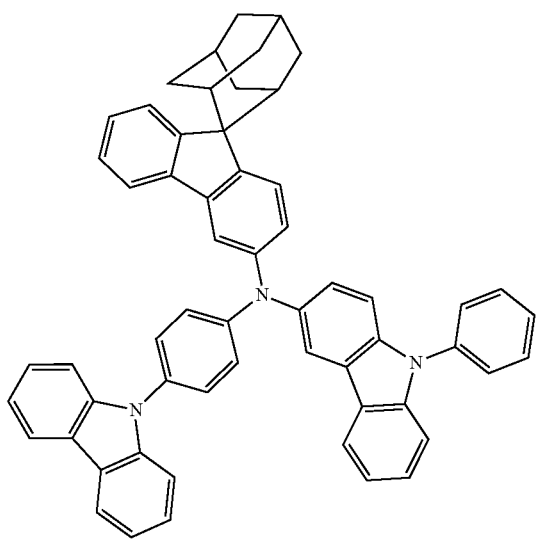
206
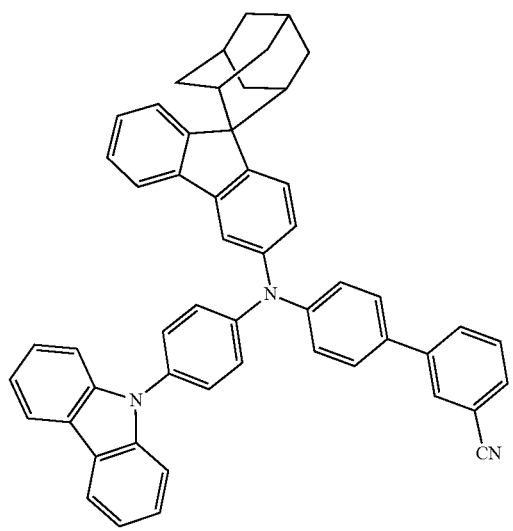
-continued
207
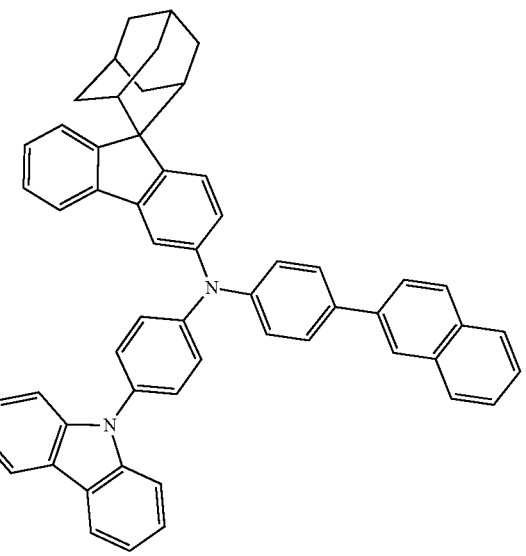
208
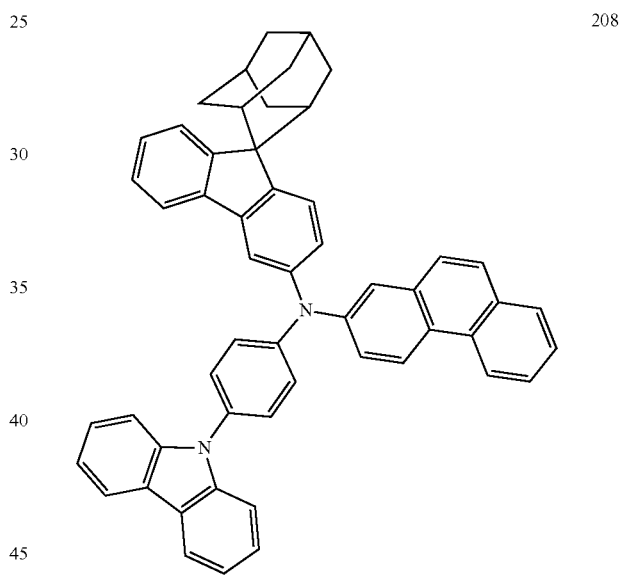
209
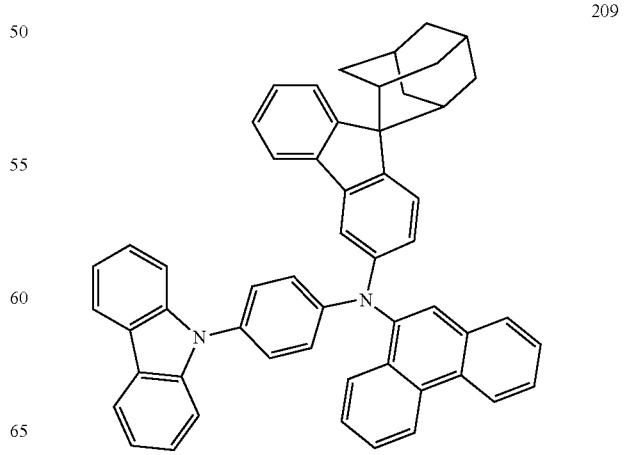

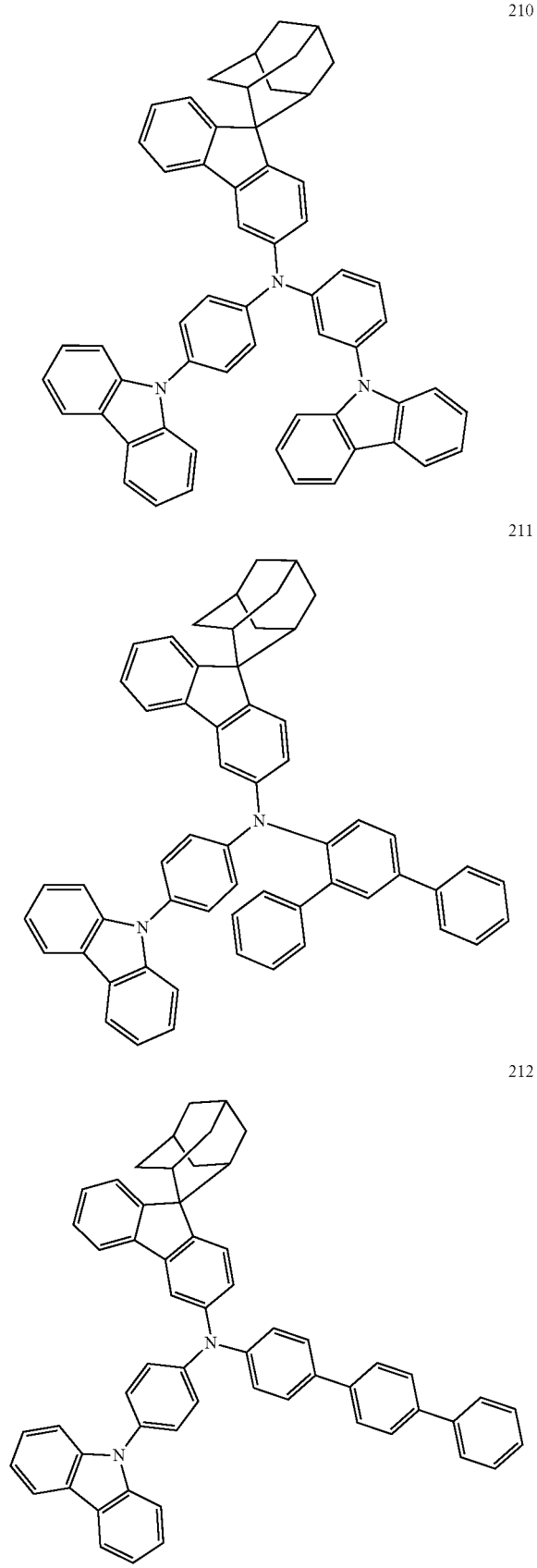 [SMILES: c1cc(N(c2ccc(-n3c4ccccc4c4ccccc43)cc2)c2ccc3c(c2)-c2ccccc2C32C3CC4CC(C3)CC2C4)cc(-n2c3ccccc3c3ccccc32)c1 ; c1ccc(-c2ccc(N(c3ccc(-n4c5ccccc5c5ccccc54)cc3)c3ccc4c(c3)-c3ccccc3C43C4CC5CC(C4)CC3C5)c(-c3ccccc3)c2)cc1 ; c1ccc(-c2ccc(-c3ccc(N(c4ccc(-n5c6ccccc6c6ccccc65)cc4)c4ccc5c(c4)-c4ccccc4C54C5CC6CC(C5)CC4C6)cc3)cc2)cc1]
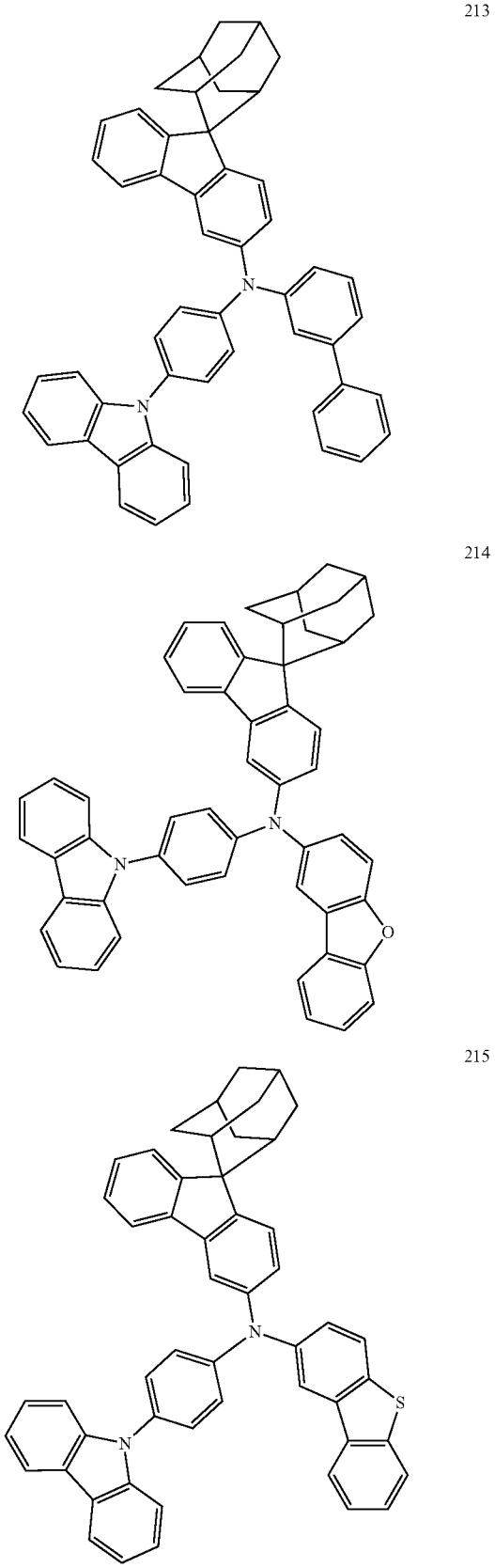 [SMILES: c1ccc(-c2cccc(N(c3ccc(-n4c5ccccc5c5ccccc54)cc3)c3ccc4c(c3)-c3ccccc3C43C4CC5CC(C4)CC3C5)c2)cc1 ; c1ccc2c(c1)-c1cc(N(c3ccc(-n4c5ccccc5c5ccccc54)cc3)c3ccc4oc5ccccc5c4c3)ccc1C21C2CC3CC(C2)CC1C3 ; c1ccc2c(c1)-c1cc(N(c3ccc(-n4c5ccccc5c5ccccc54)cc3)c3ccc4sc5ccccc5c4c3)ccc1C21C2CC3CC(C2)CC1C3]

216
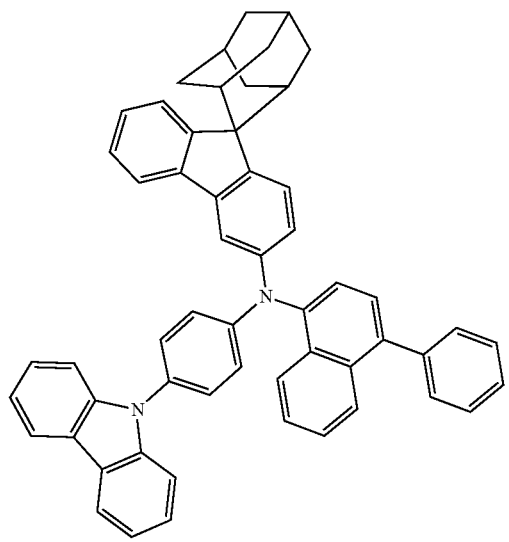
217
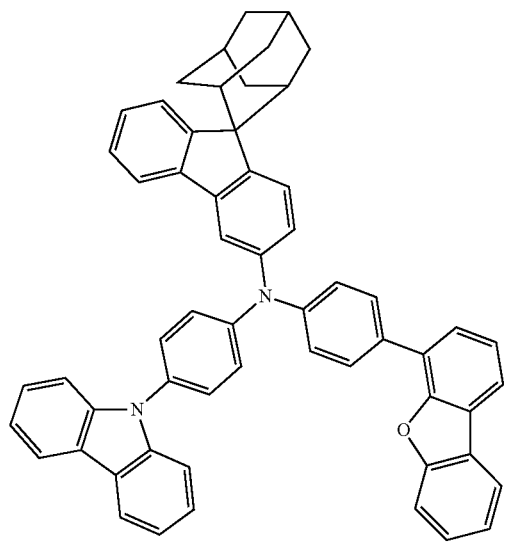
218
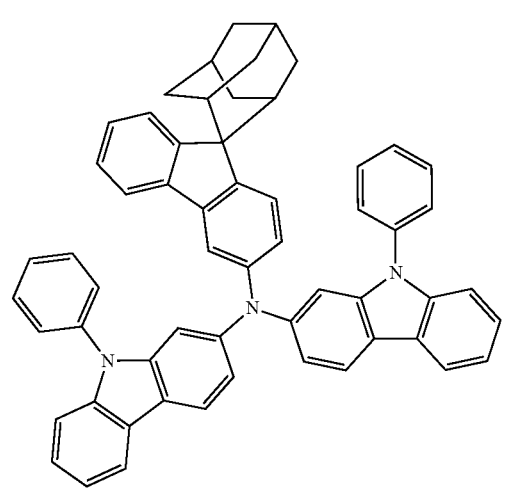
219
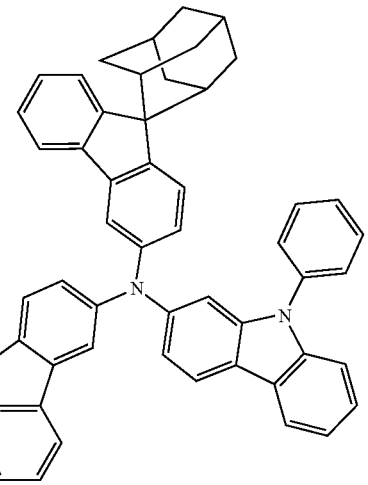
220
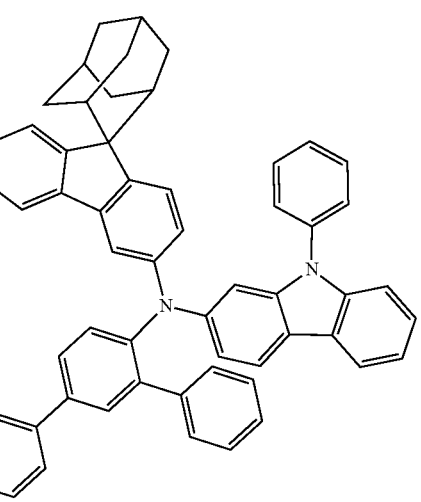
221
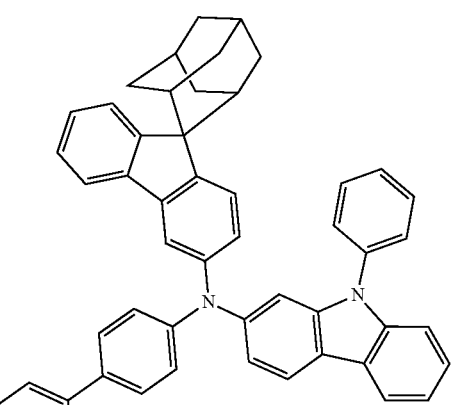

222
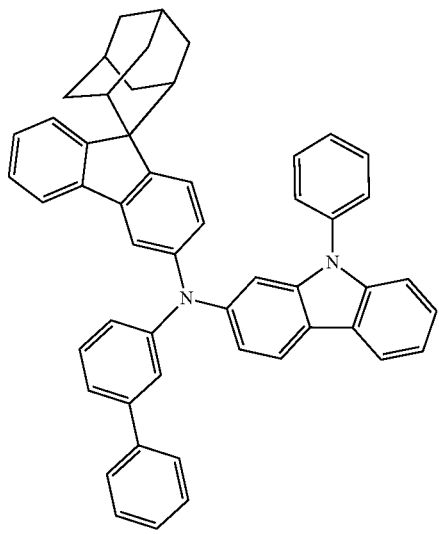
225
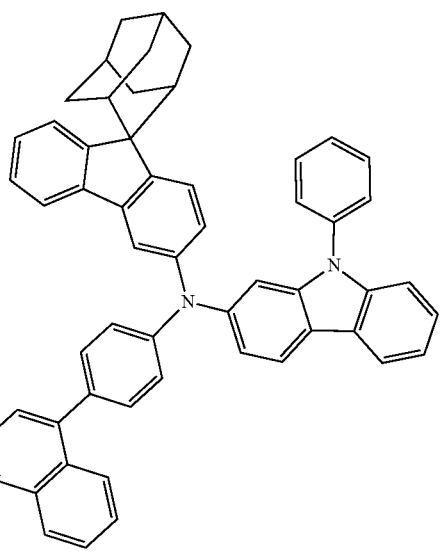
223
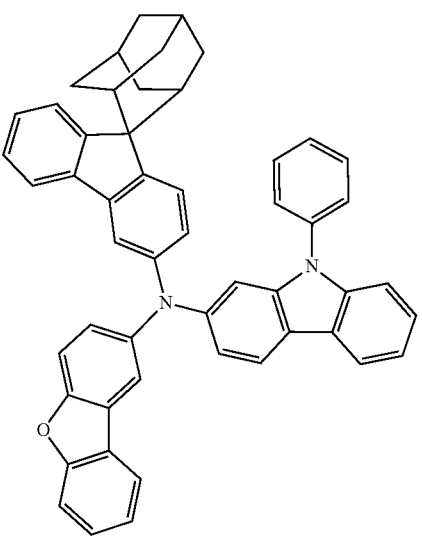
224
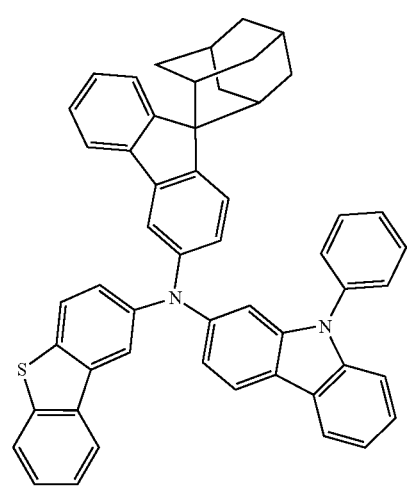
226

227
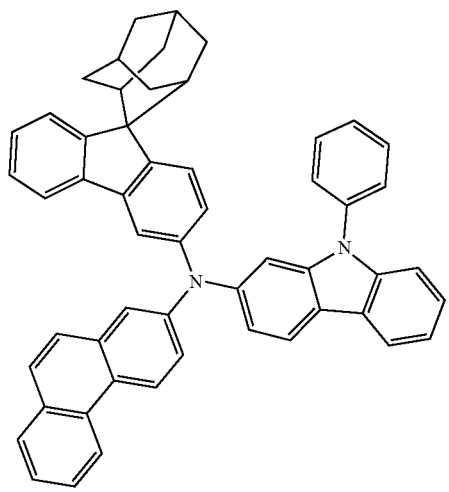
228
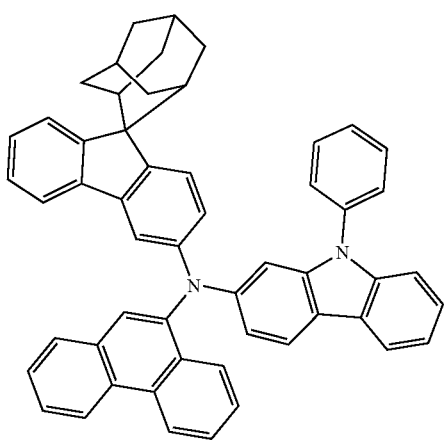
229
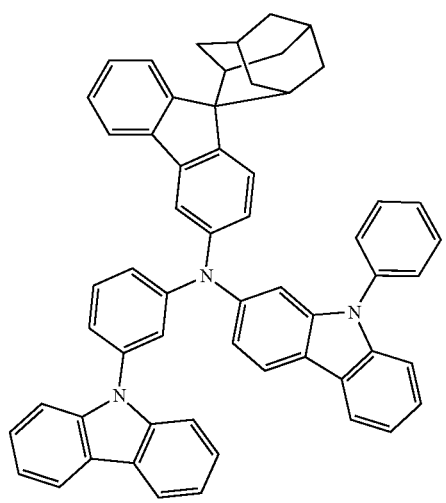
230
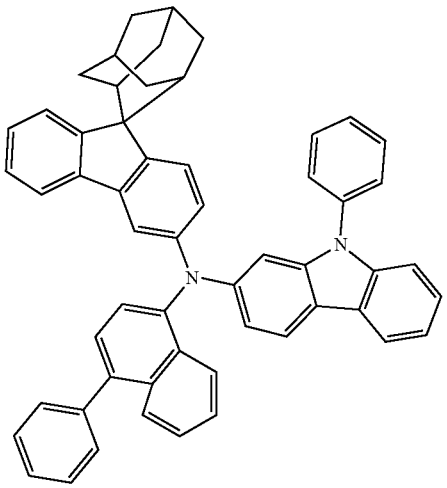
231
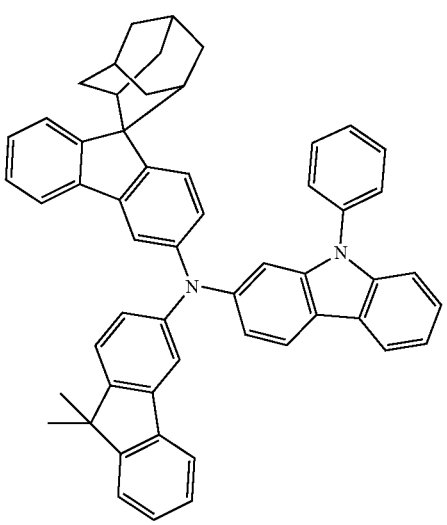
232
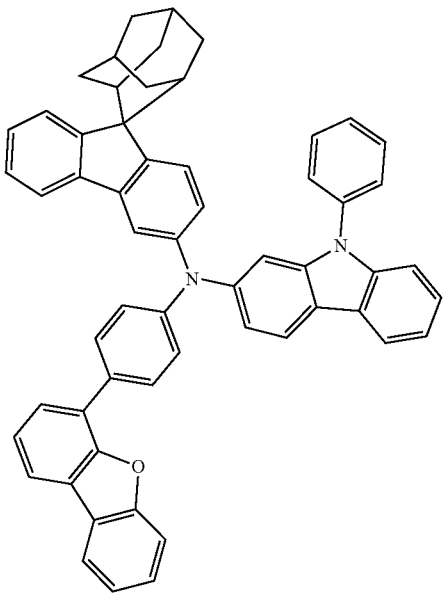

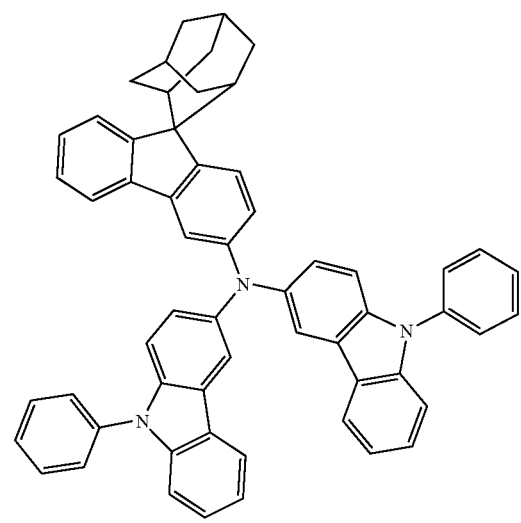
233
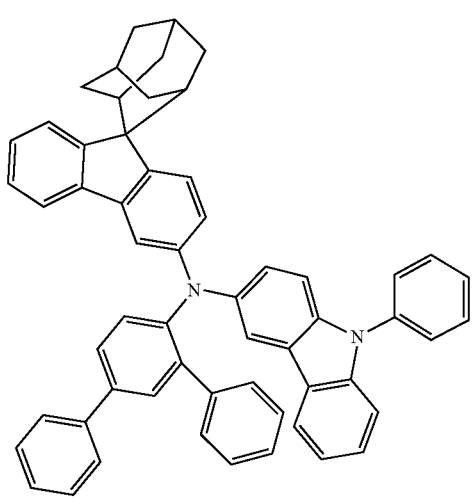
234
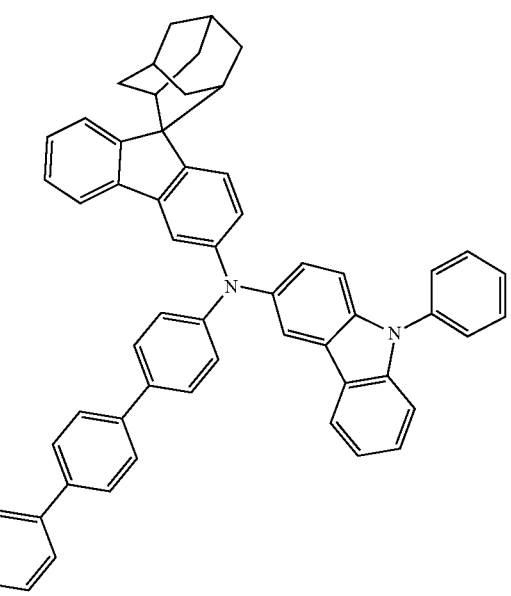
235
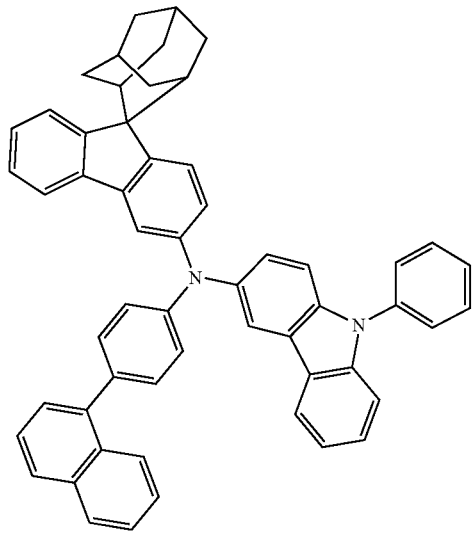
236
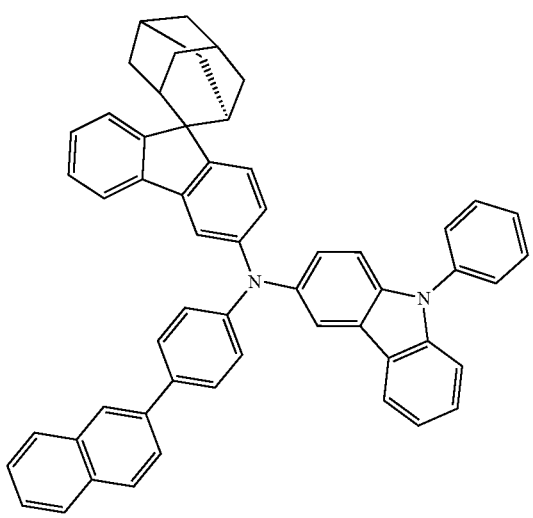
237
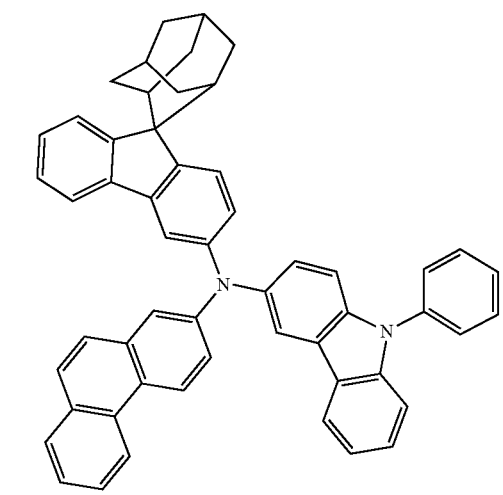
238

239
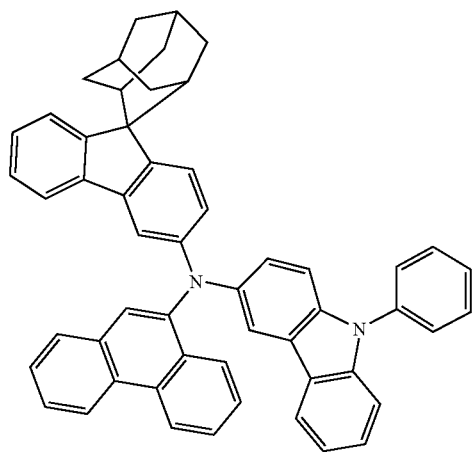
240
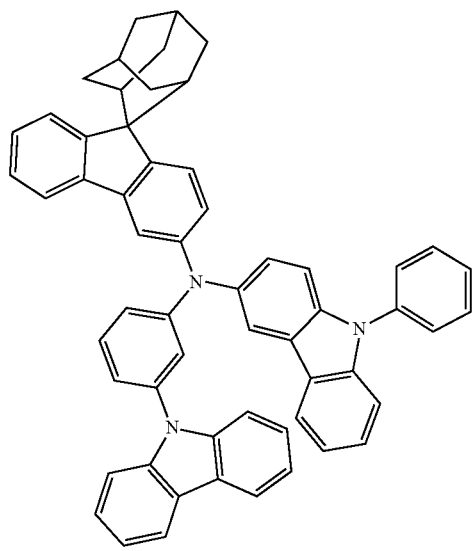
241
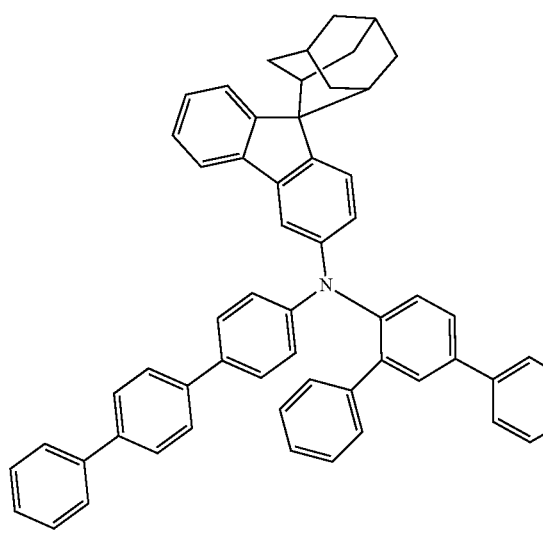
242
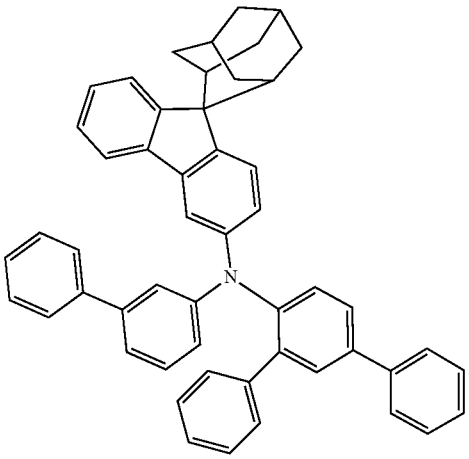
243
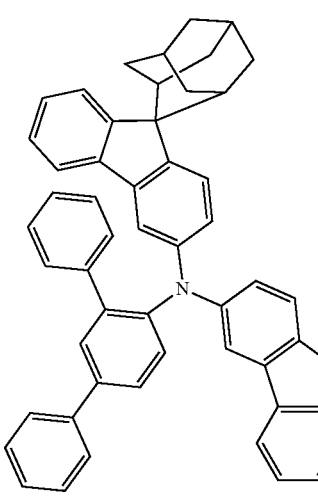
244
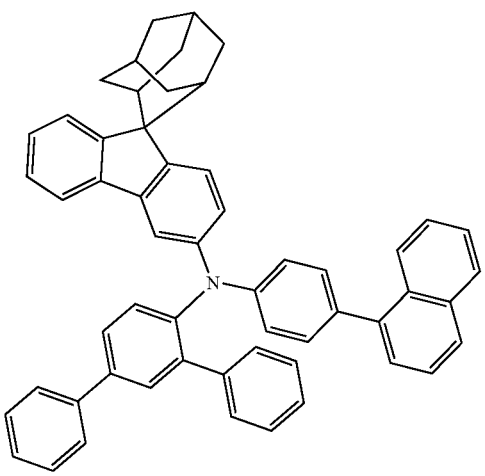

245
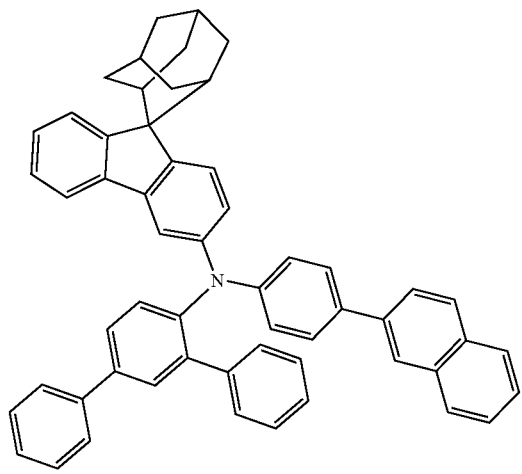
246
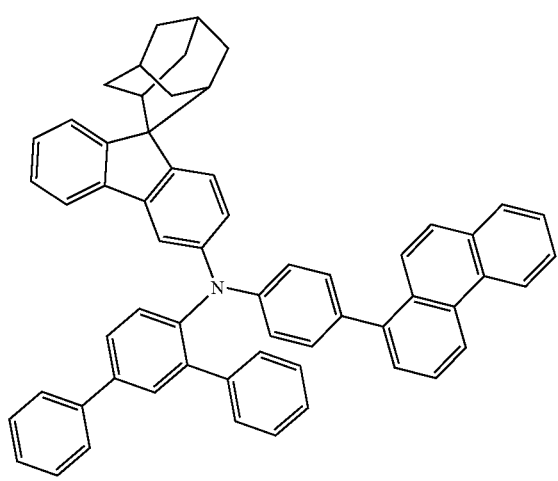
247
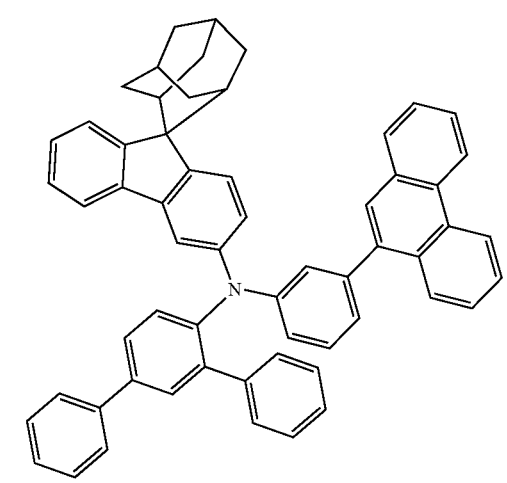
248
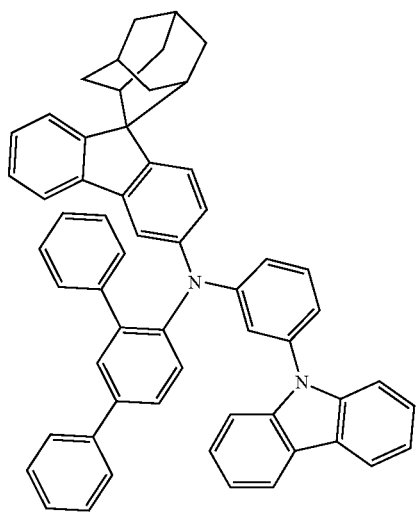
249
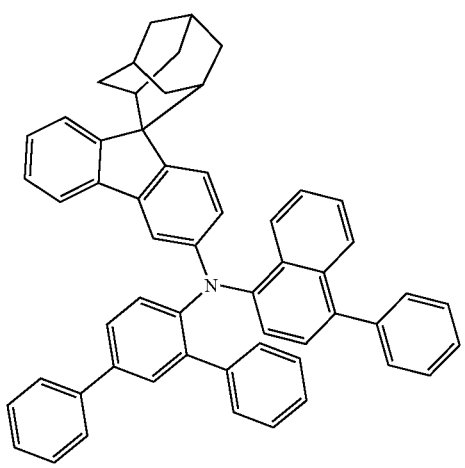
250
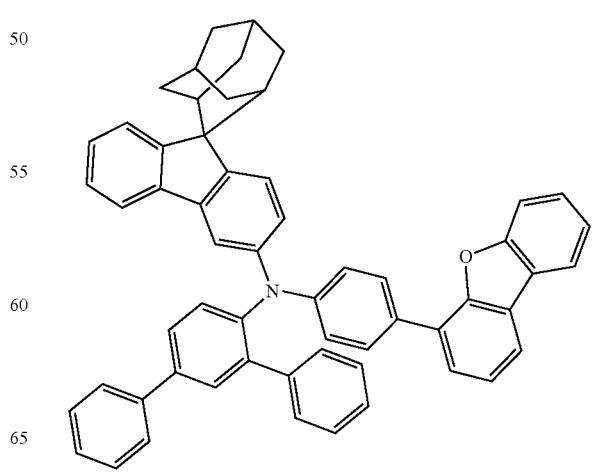

251
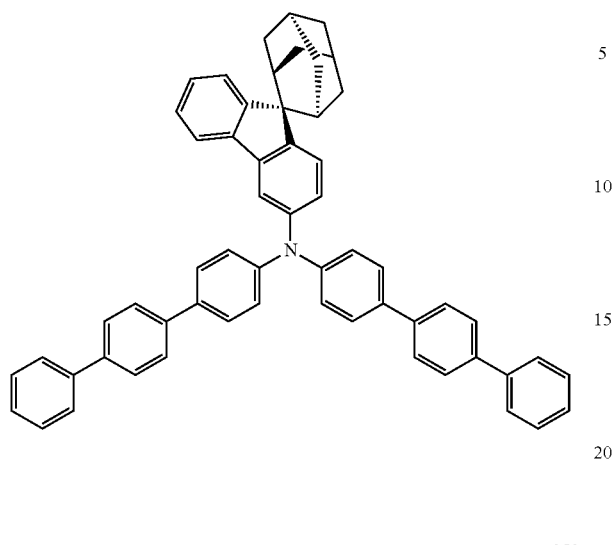
252
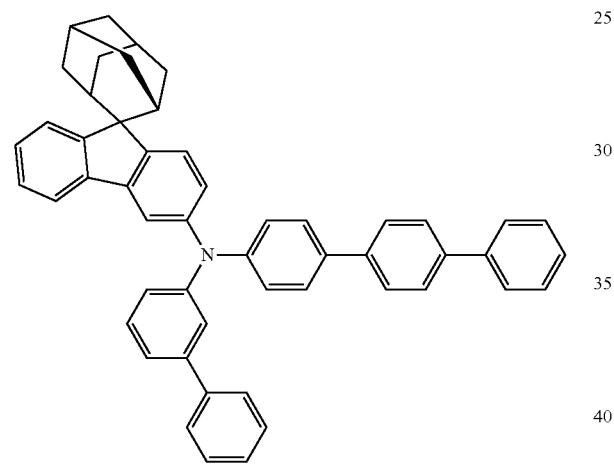
253
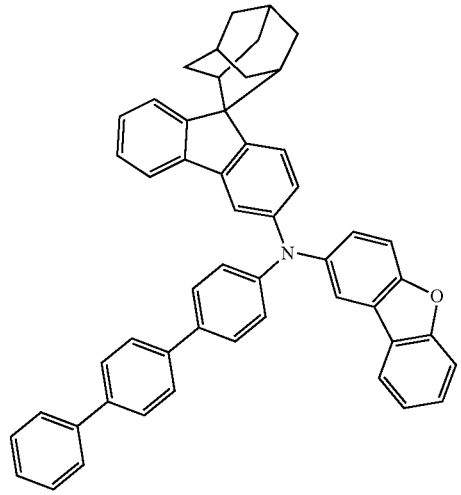
254
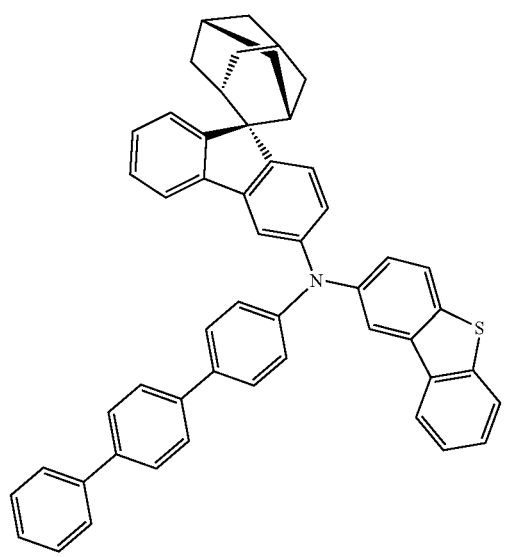
255
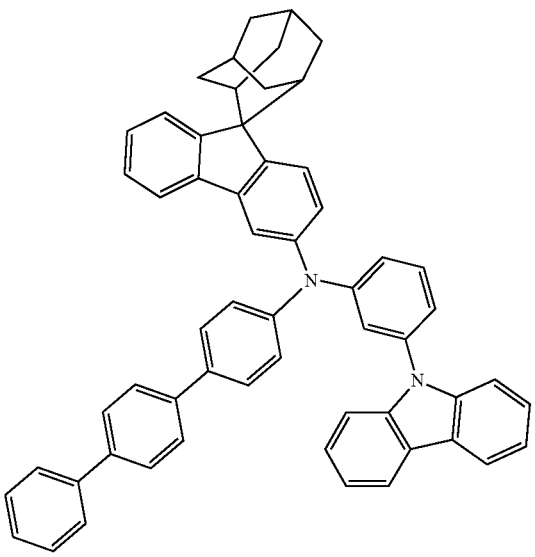

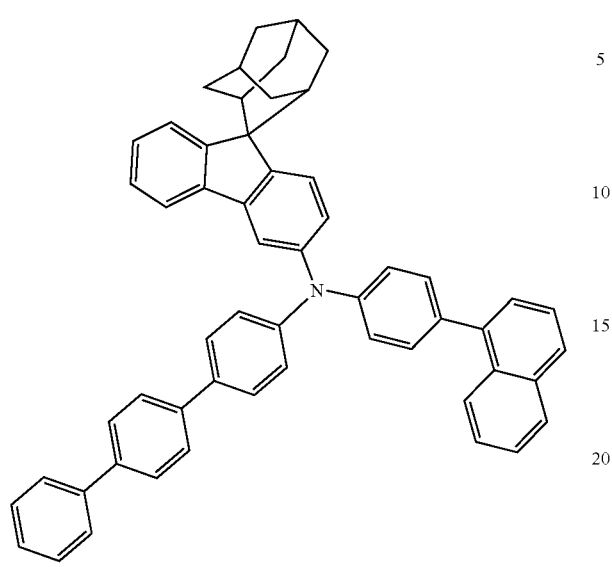
256
257
258
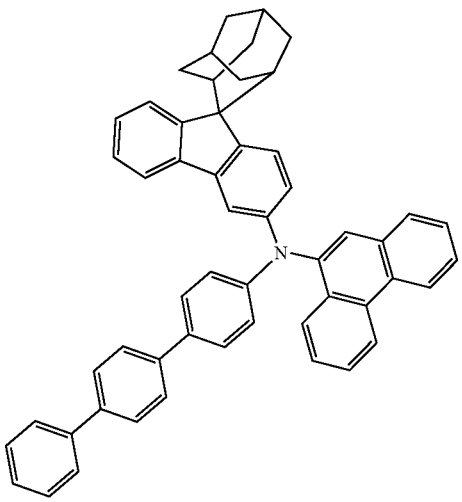
259
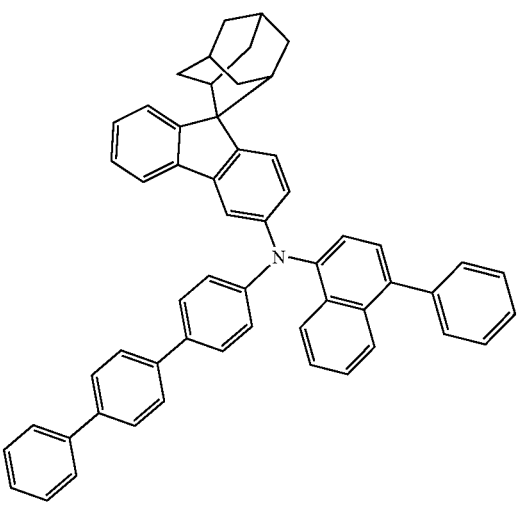
260
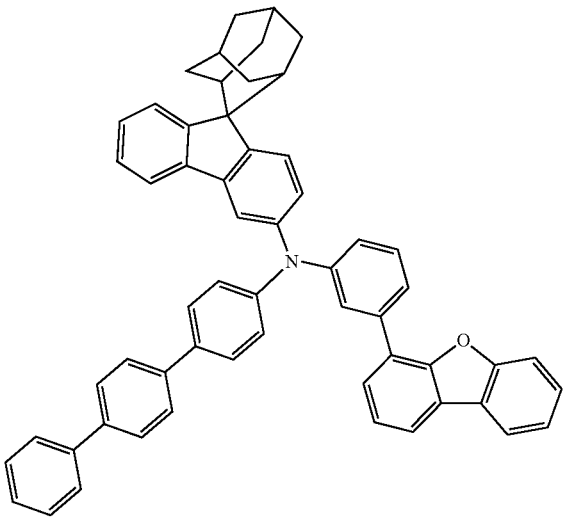
261

262 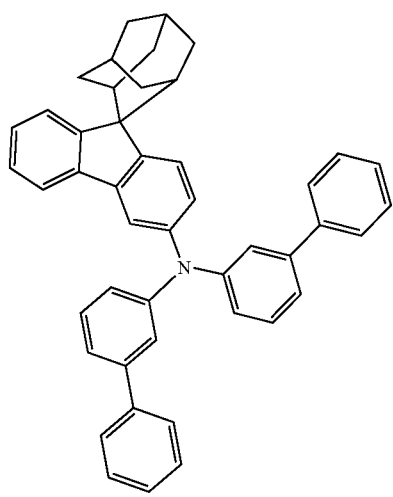
263 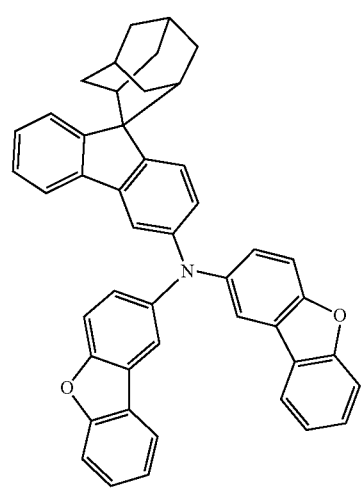
264 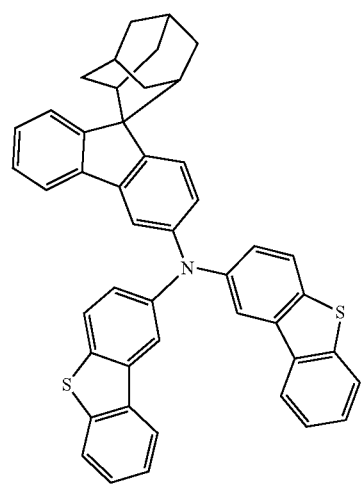
265 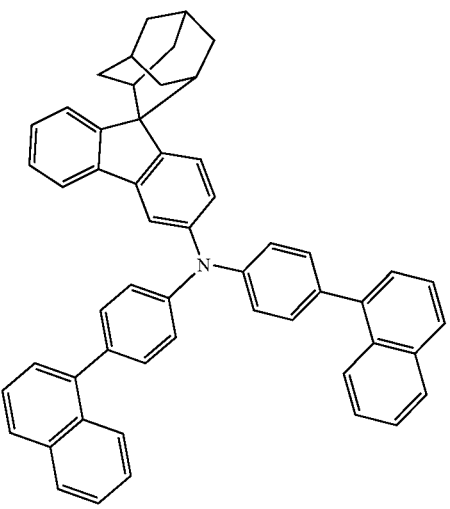
266 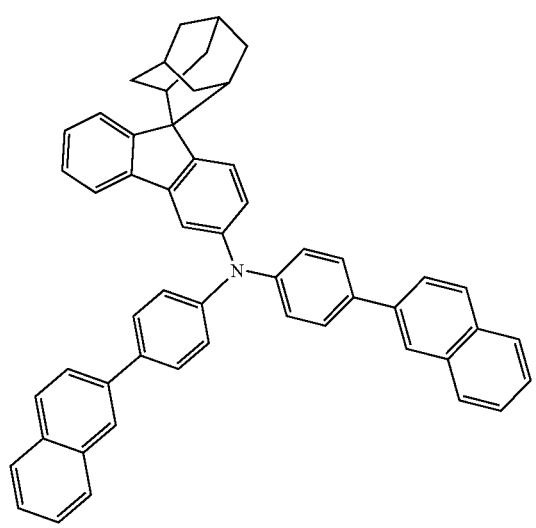
267 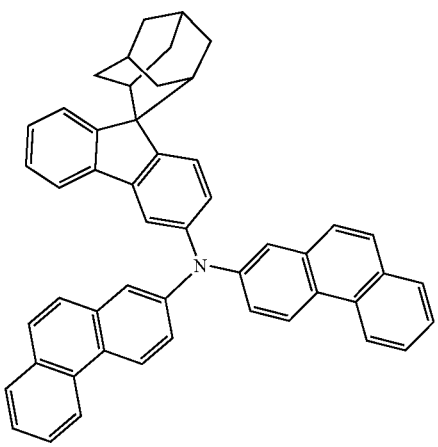

268
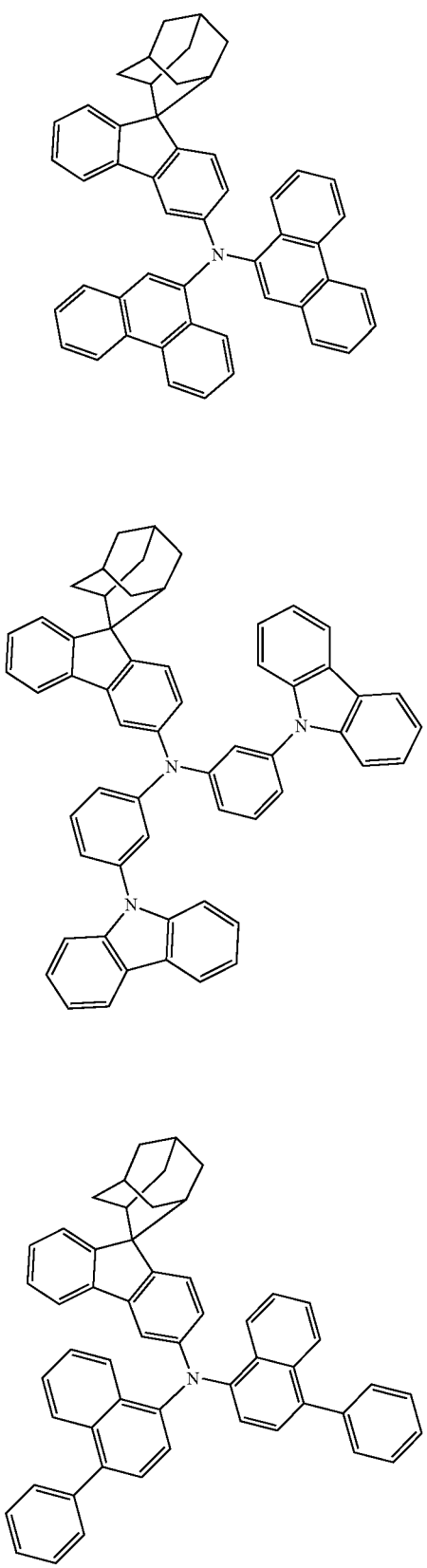
269
270
271
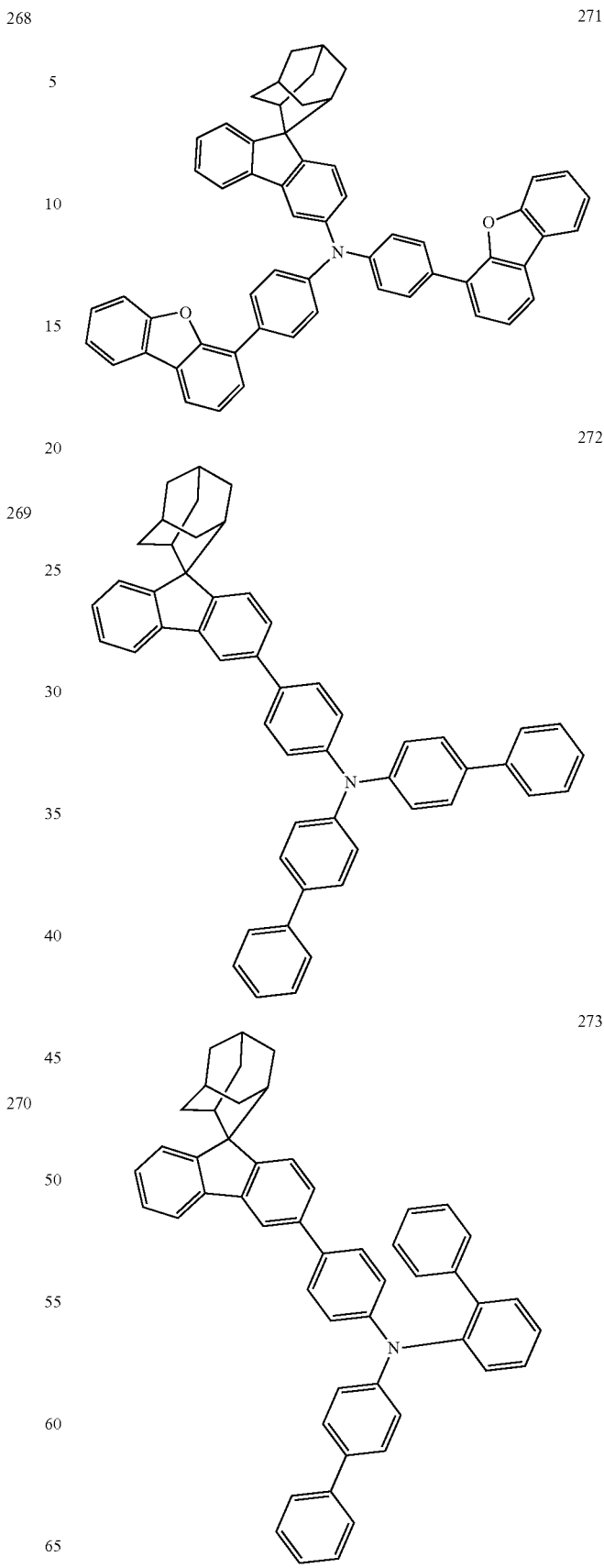
272
273

127
-continued
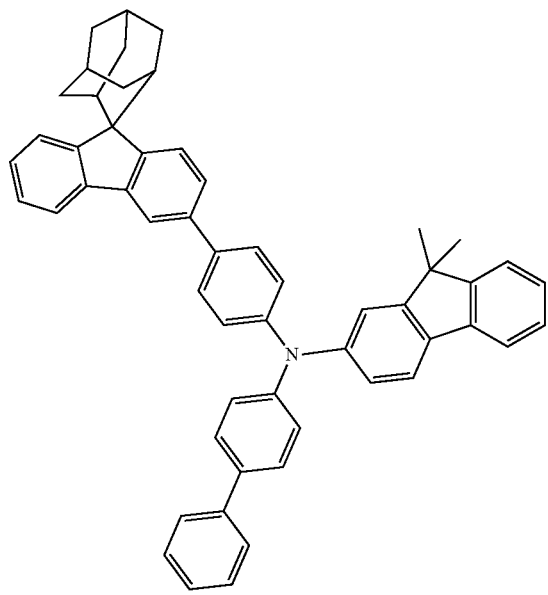
274
128
-continued
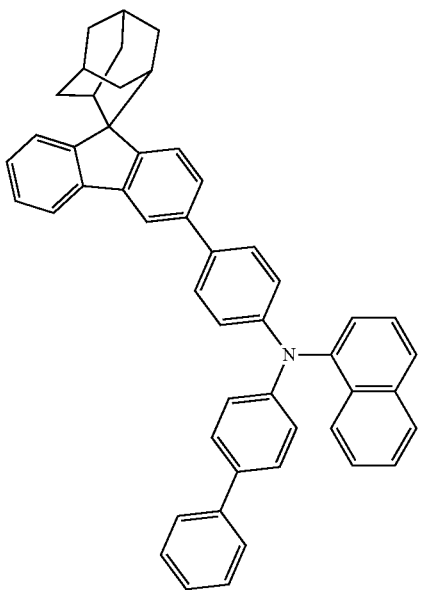
276
275
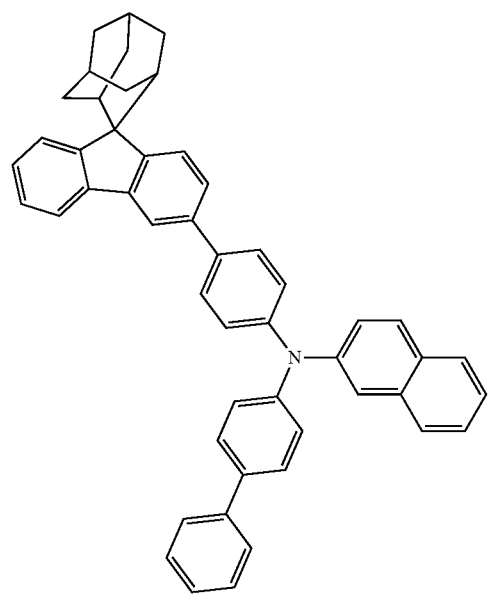
277
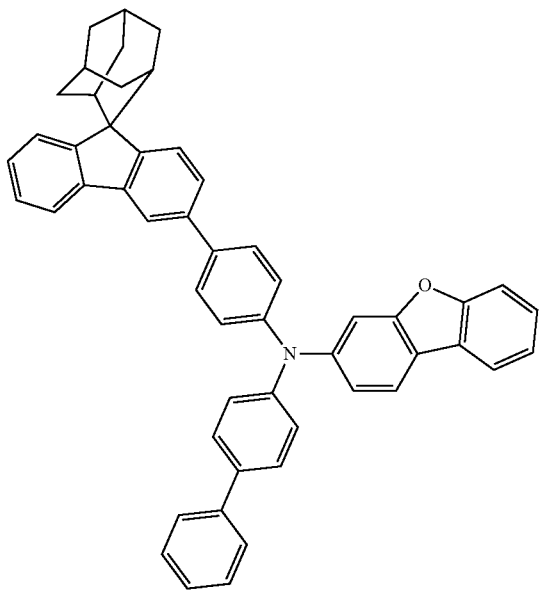

278
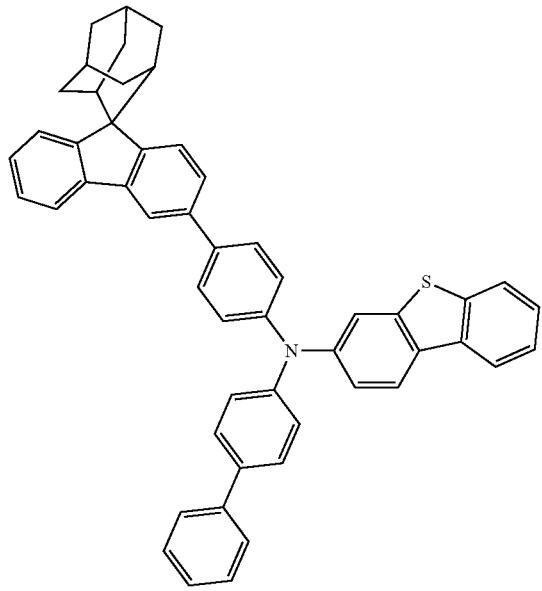
279
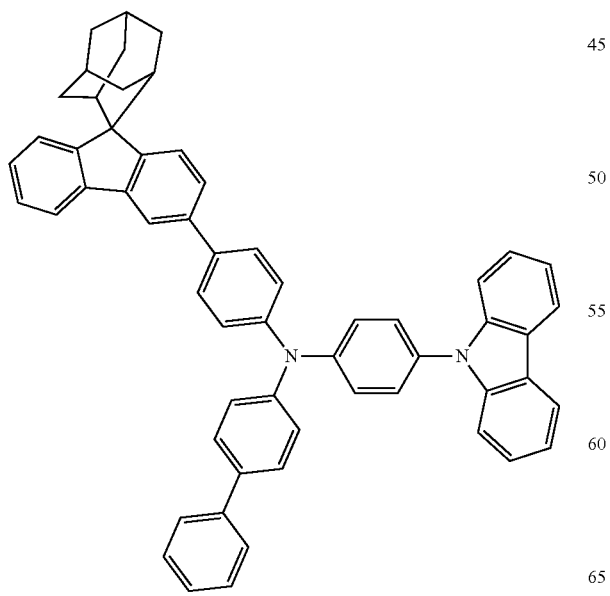
280
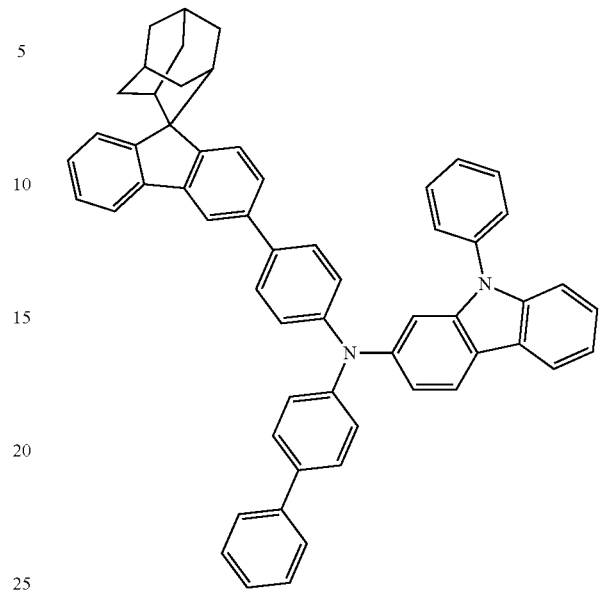
281
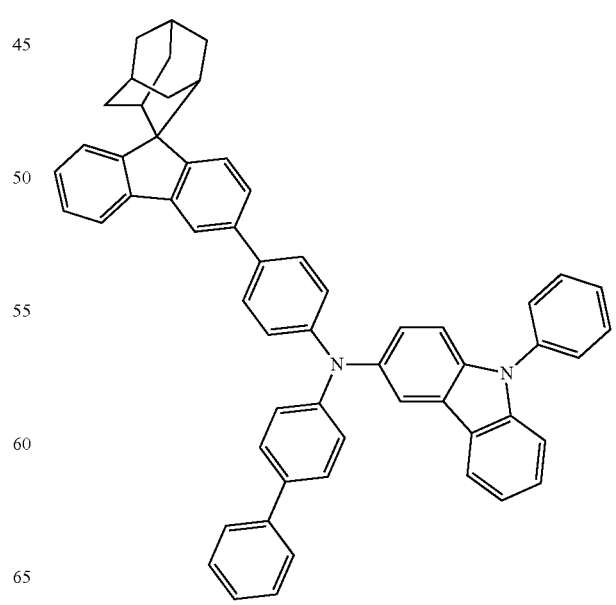

131
-continued
282
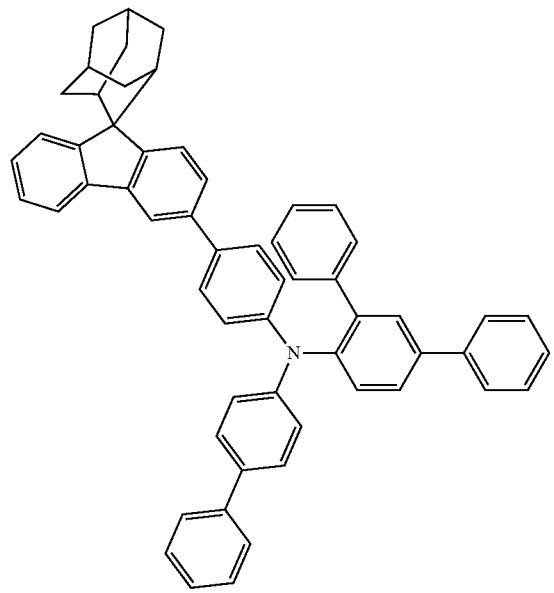
284
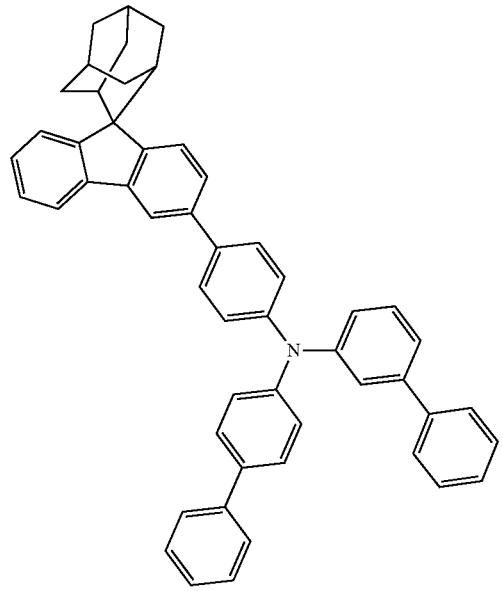
283
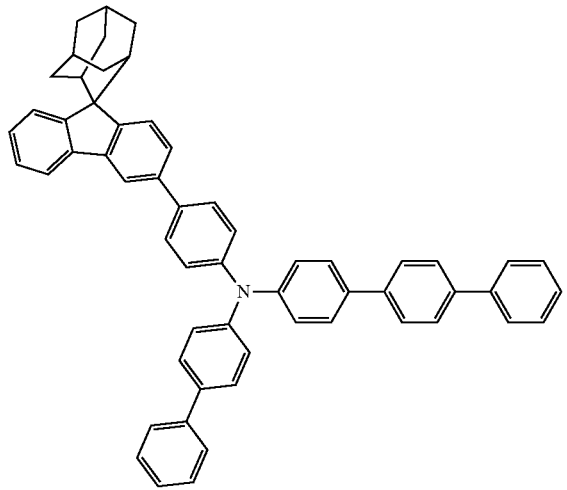
285
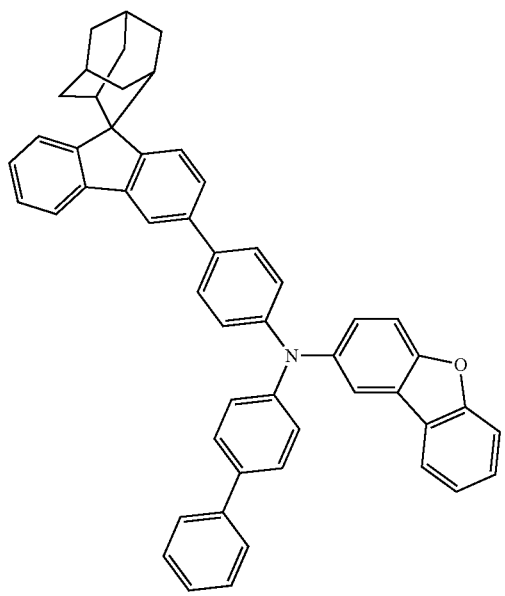

286
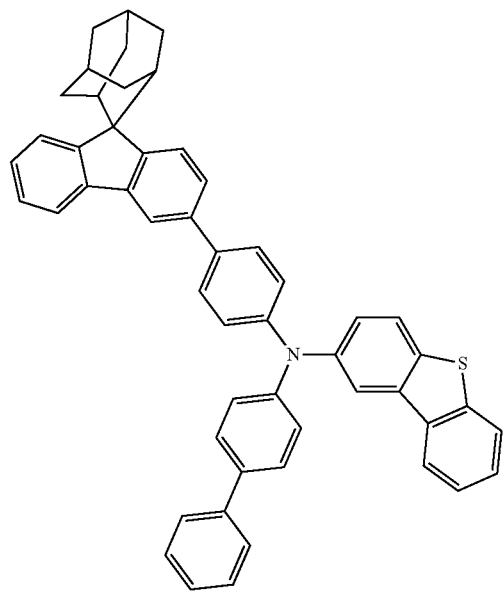
287
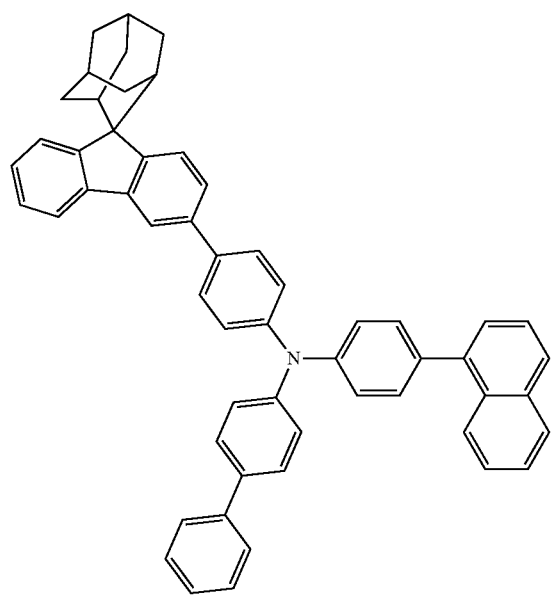
288
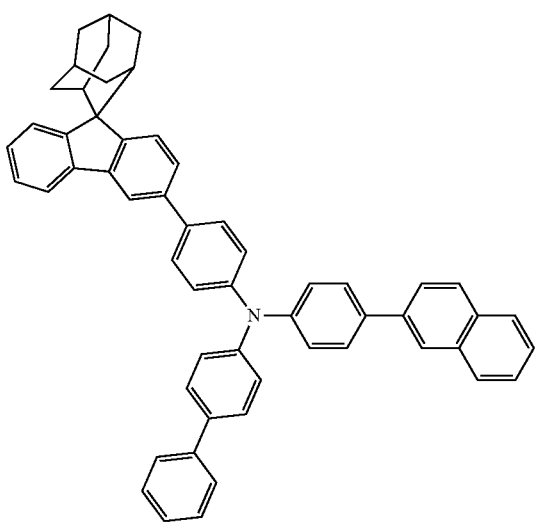
289
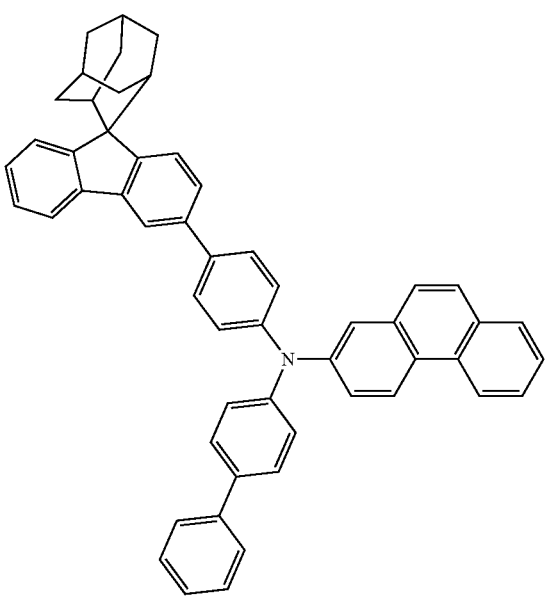

290
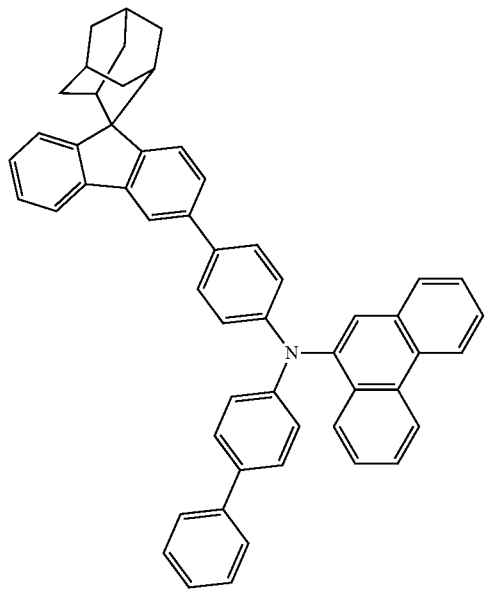
291
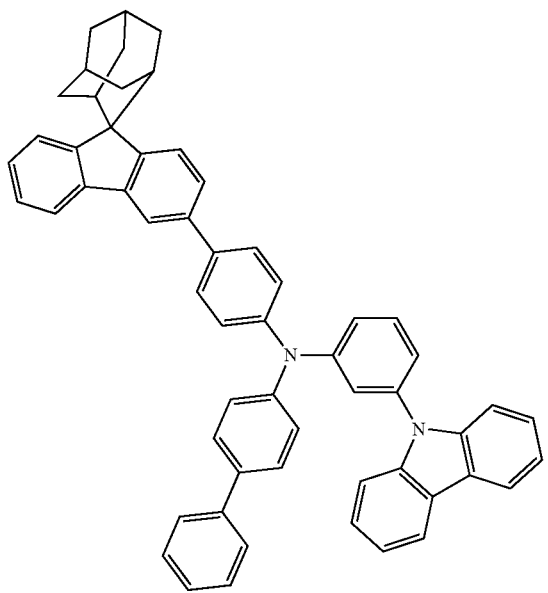
292
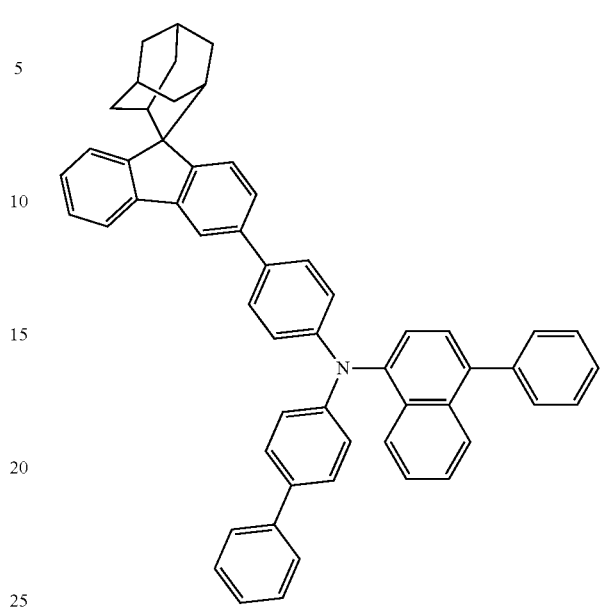
293
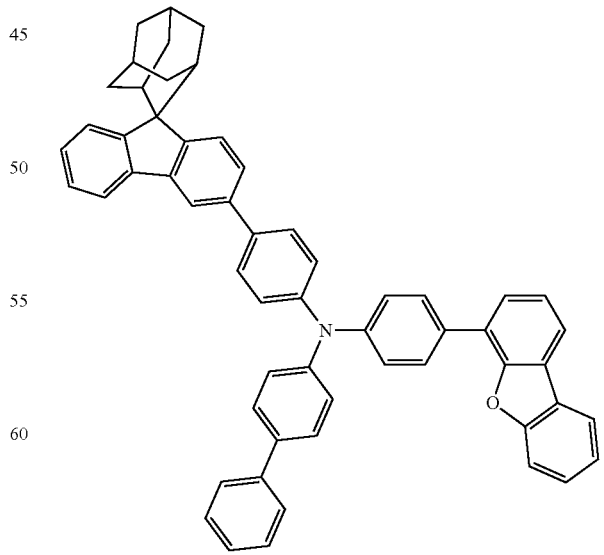

294
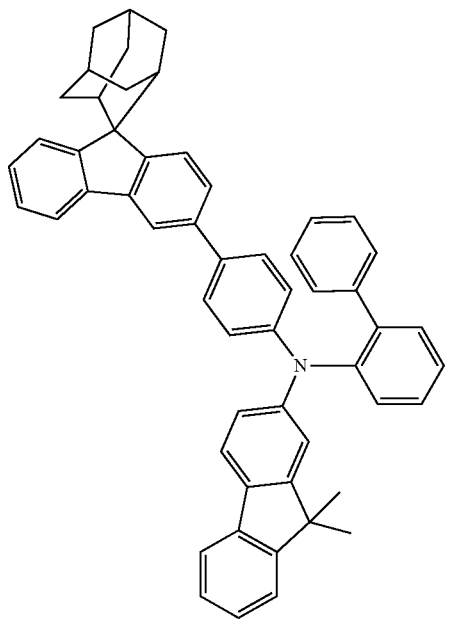
295
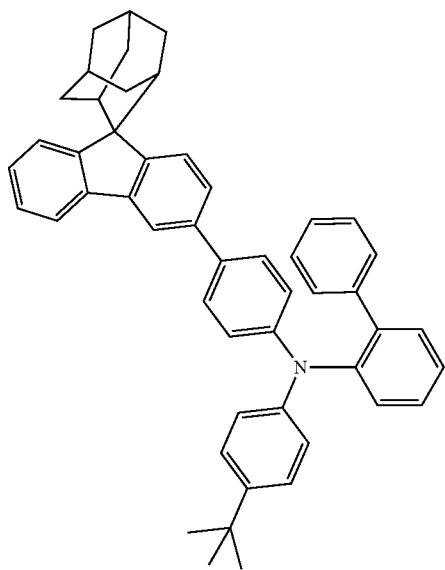
296
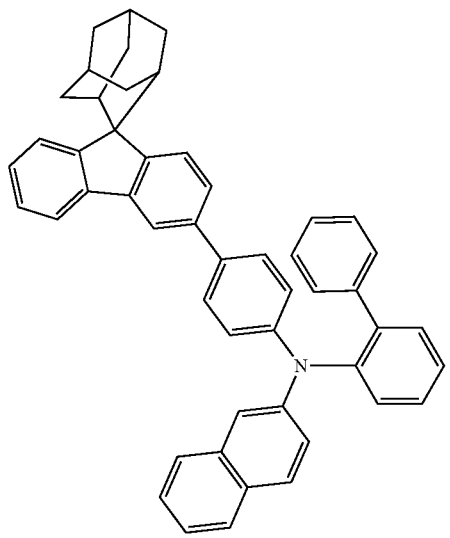
297
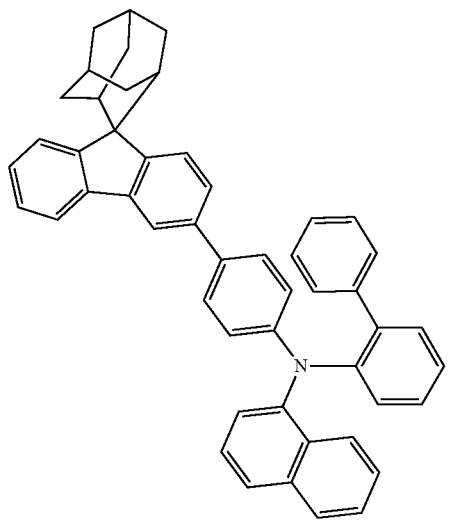
298
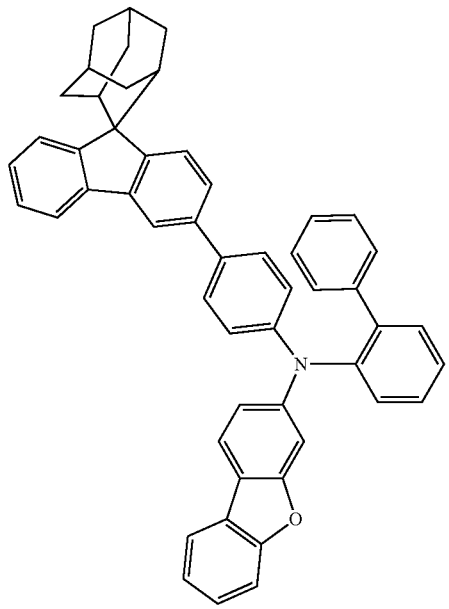

139
-continued
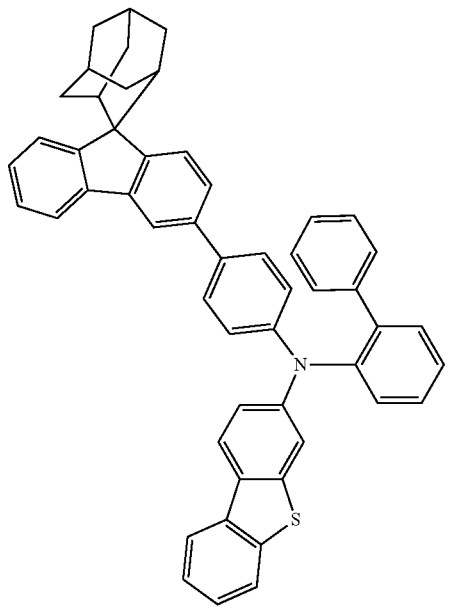
299
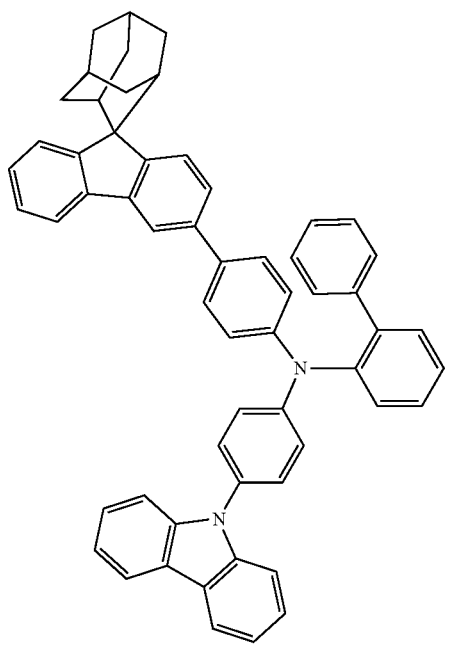
300
140
-continued
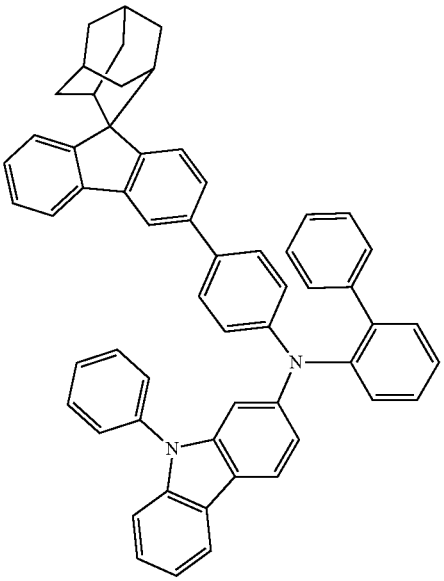
301
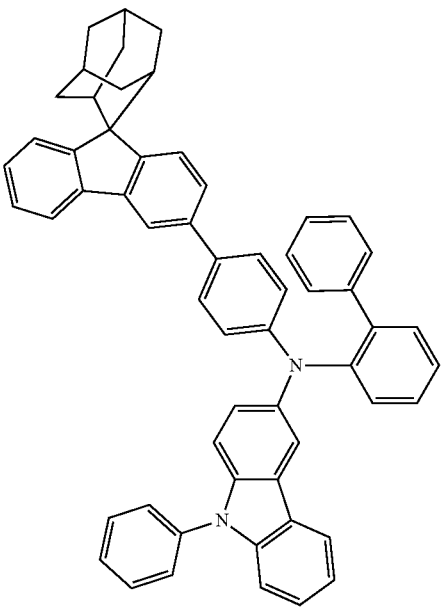
302

141
-continued
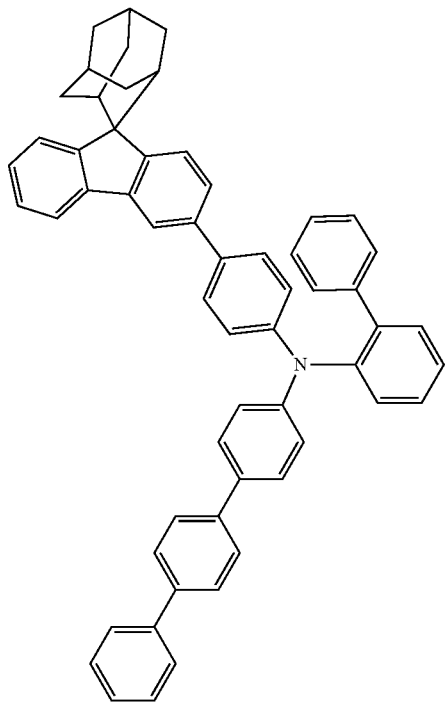
303
142
-continued
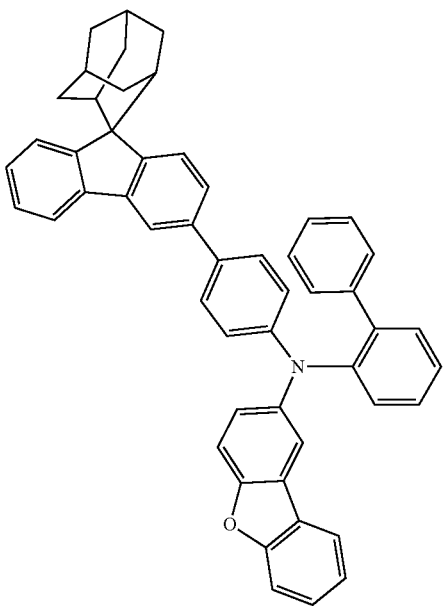
305
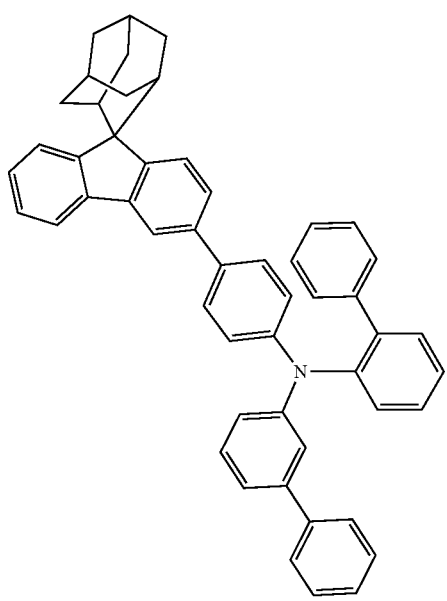
304
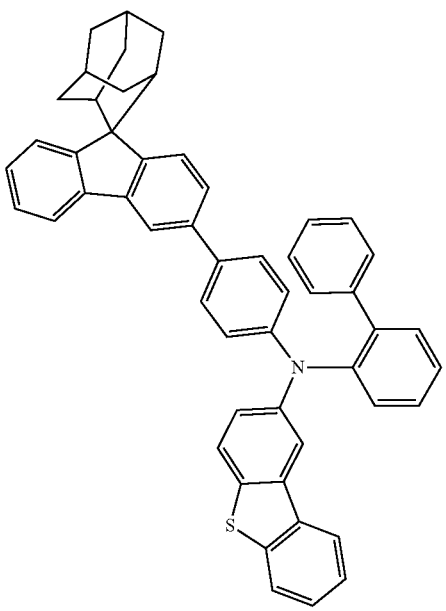
306

307

308

309

310

311

145
-continued
312
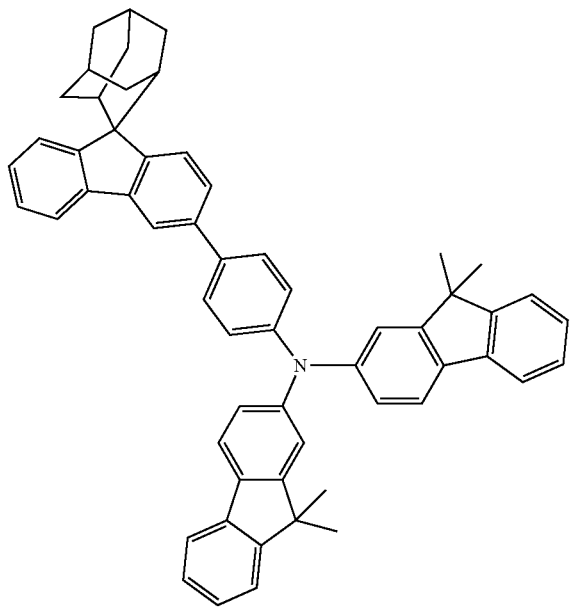
313
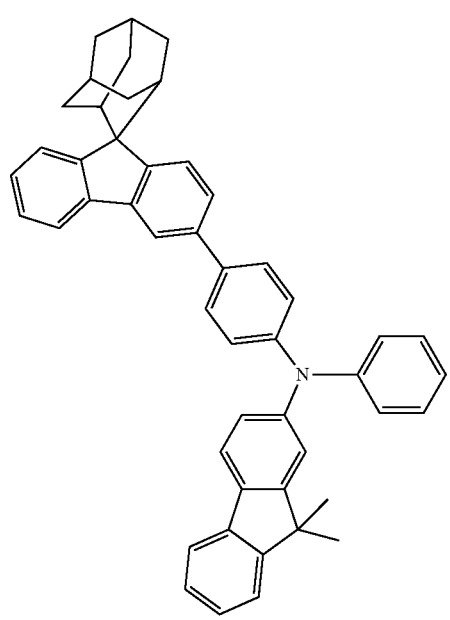
146
-continued
314
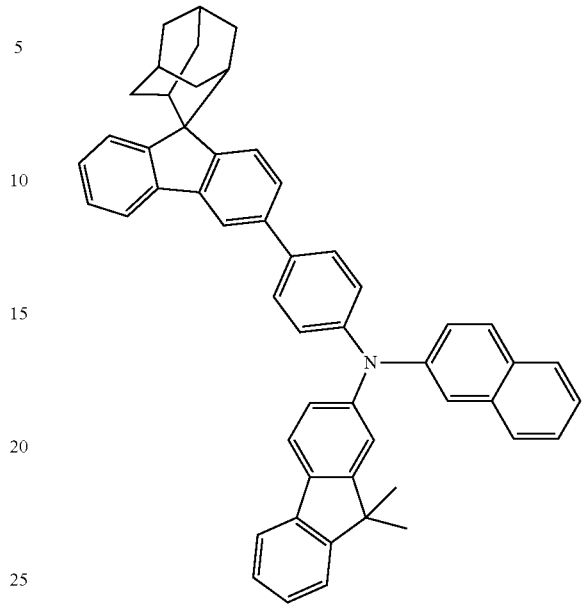
315
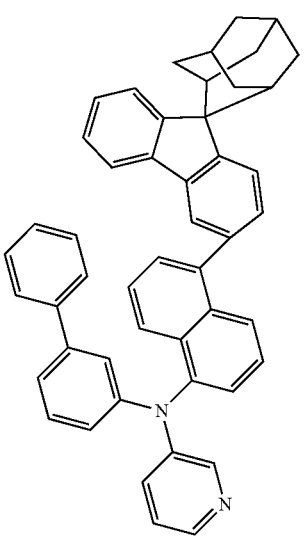

147
-continued
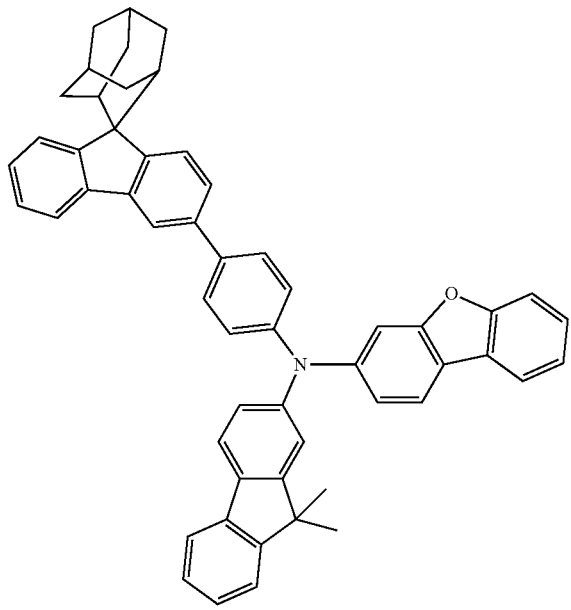
316
148
-continued
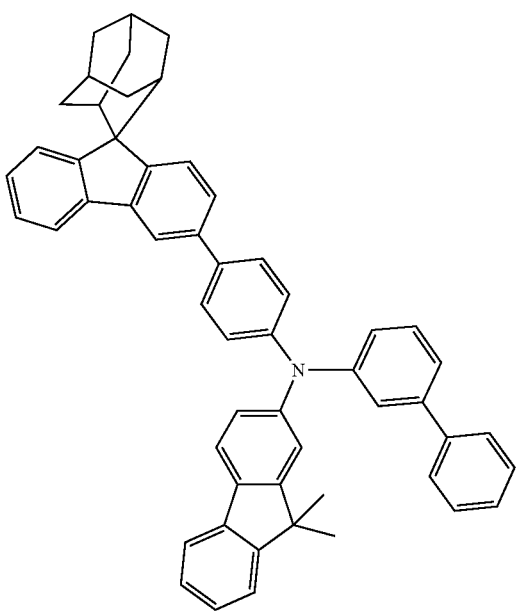
318
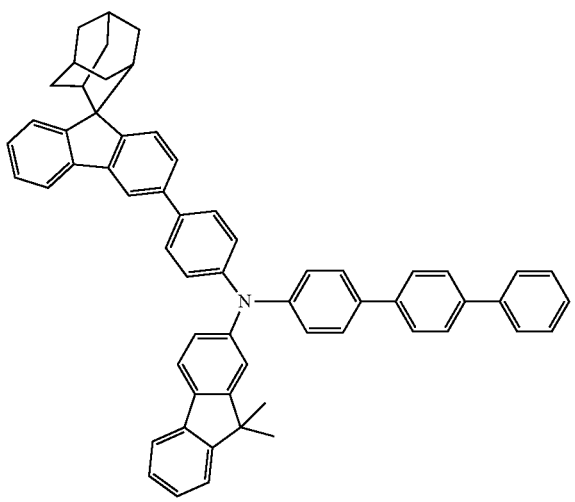
317
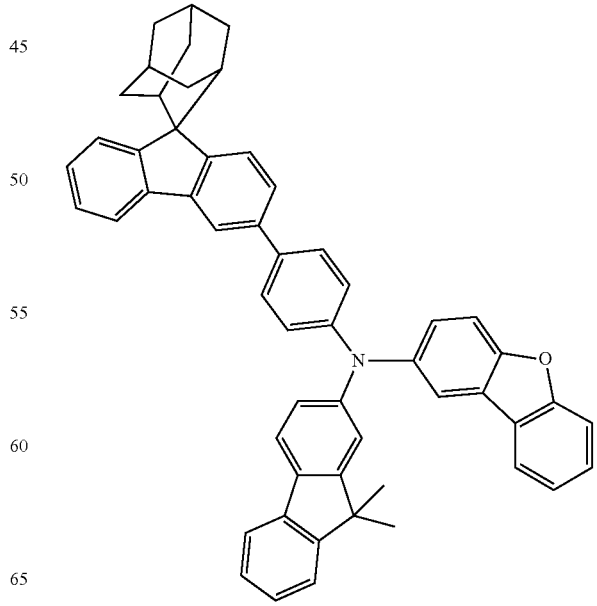
319

149
-continued
320
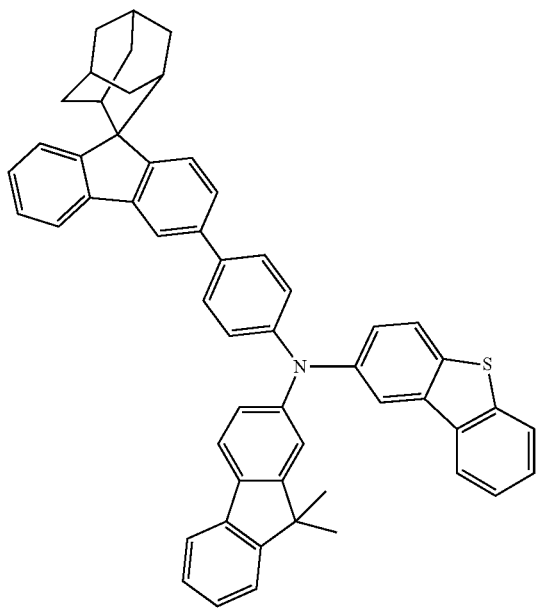
321
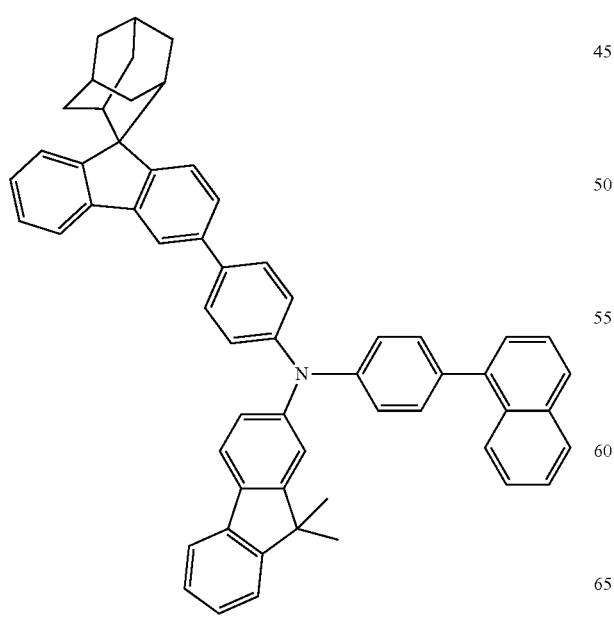
150
-continued
322
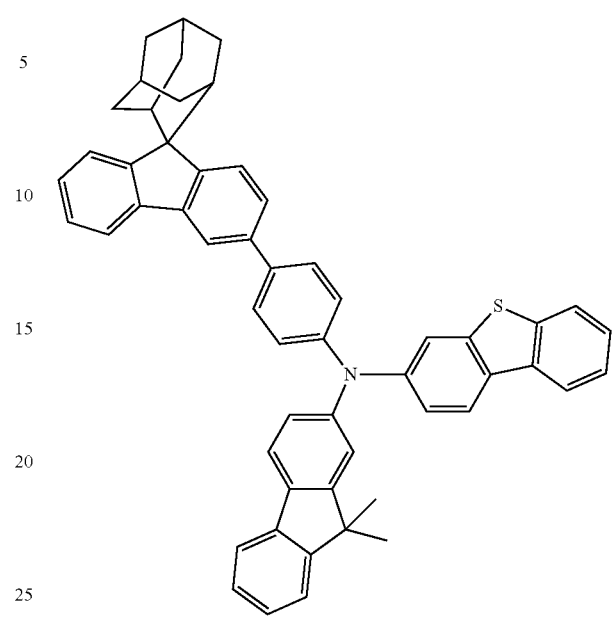
323
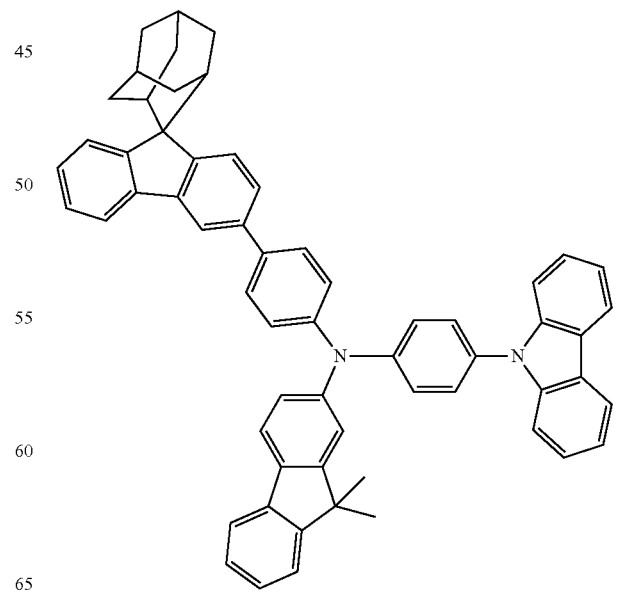

151
-continued
324
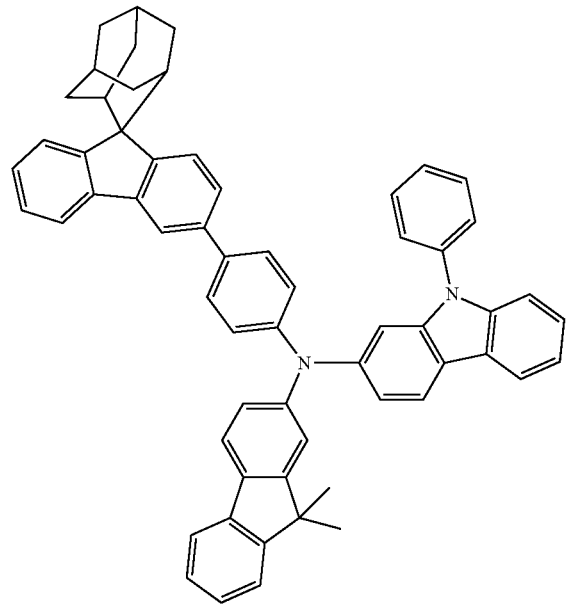
325
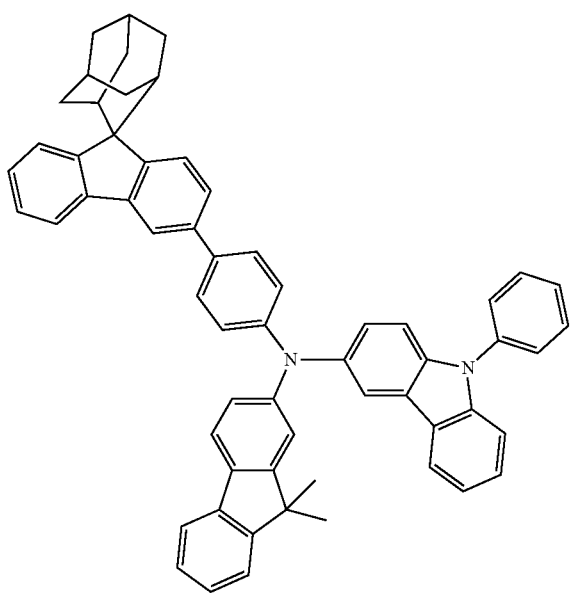
152
-continued
326
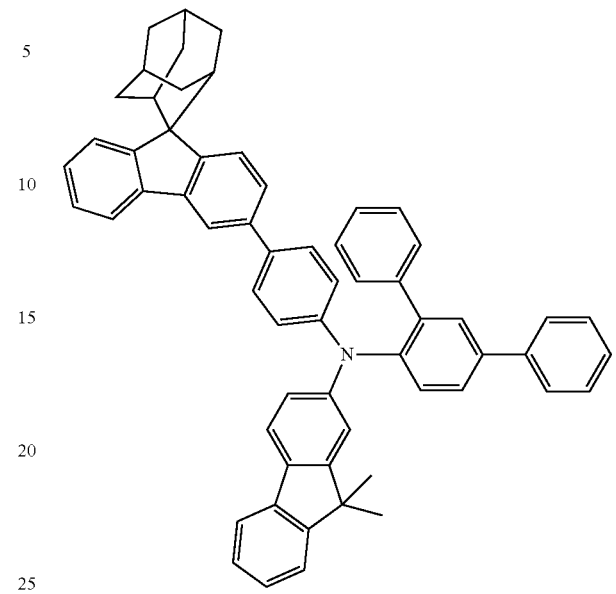
327
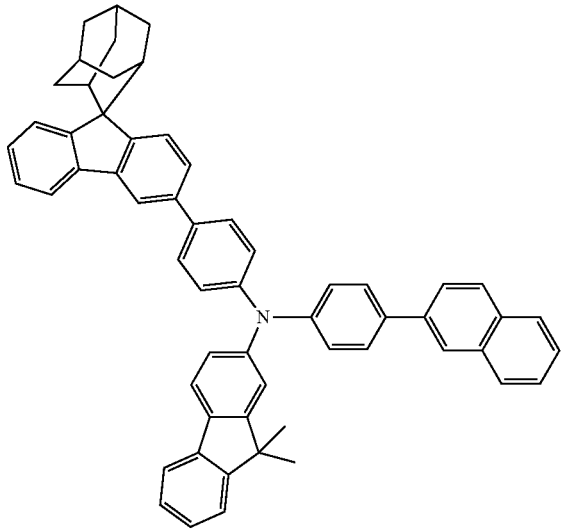

153
-continued
328
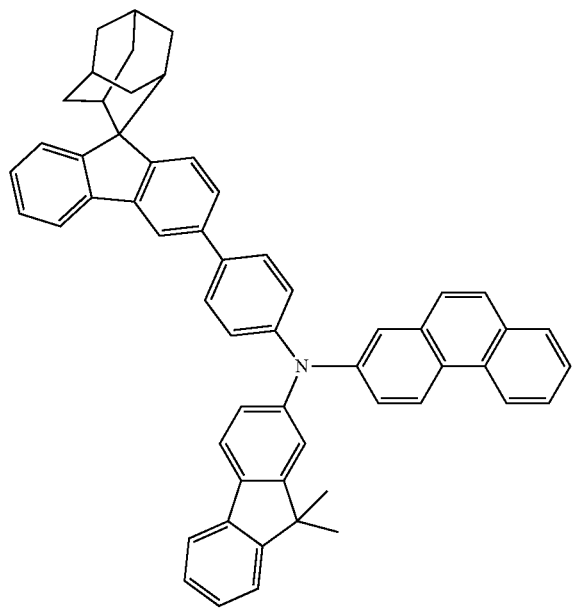
329
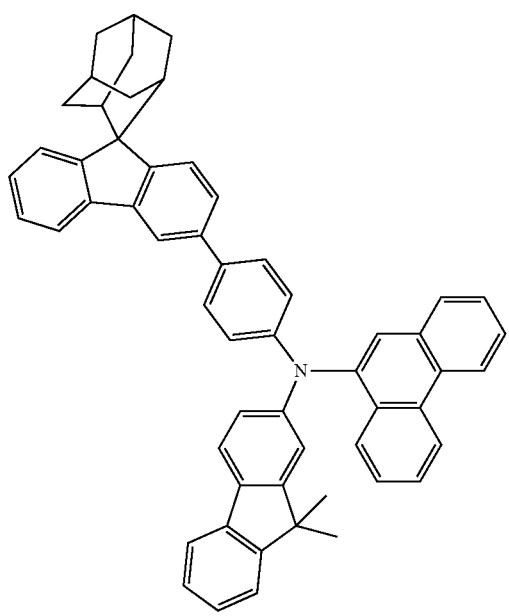
154
-continued
330
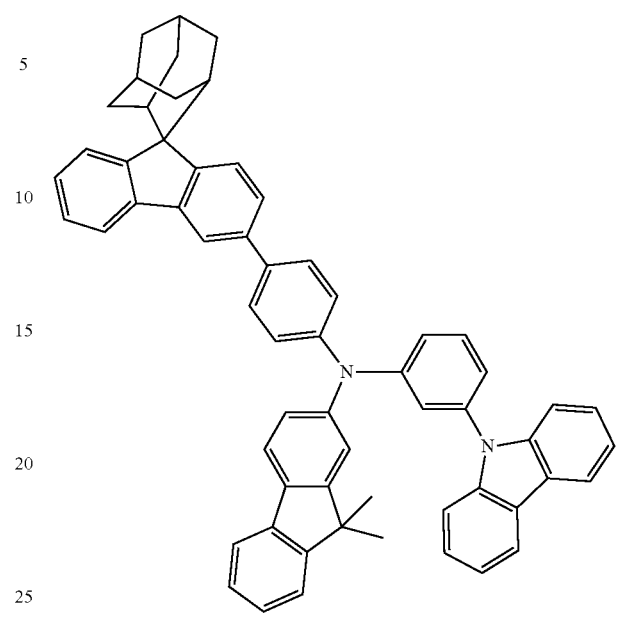
331
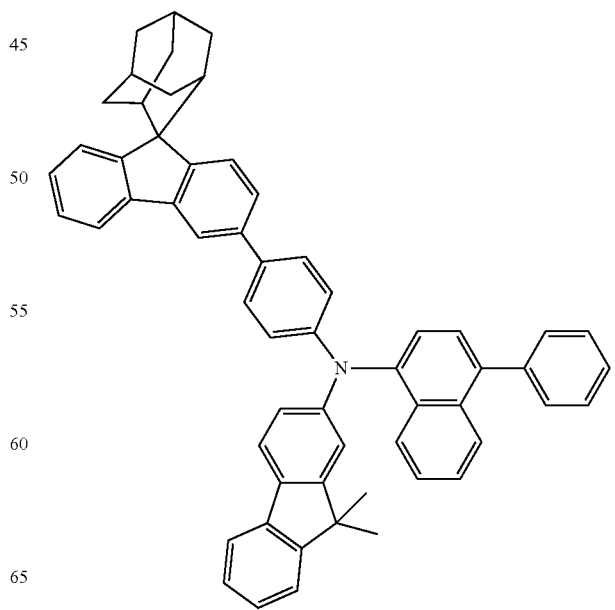

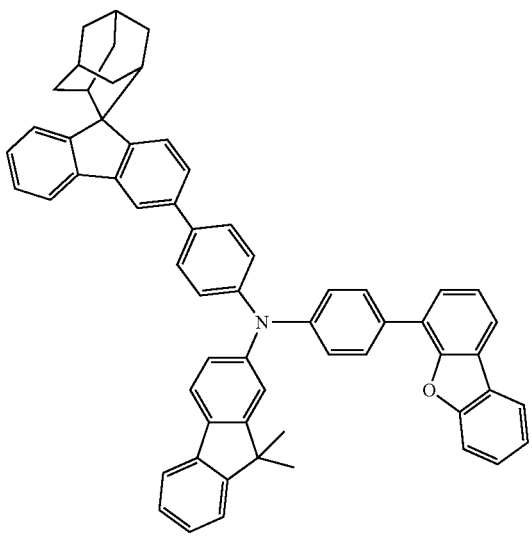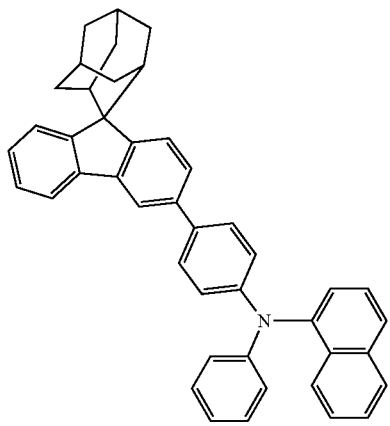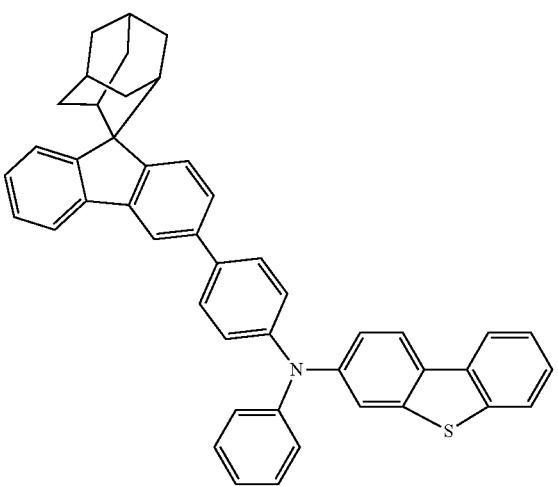

-continued
338
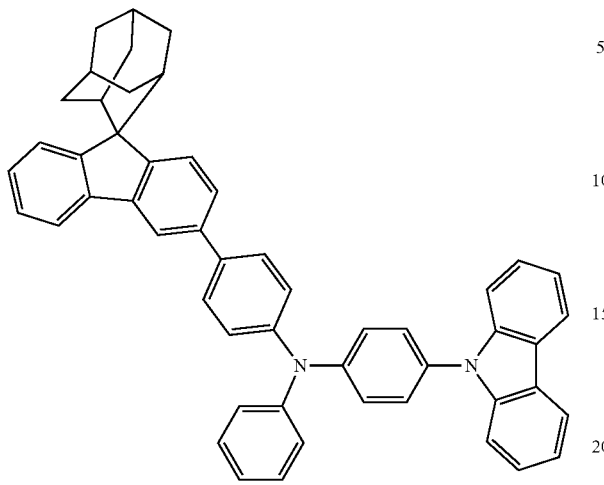
339
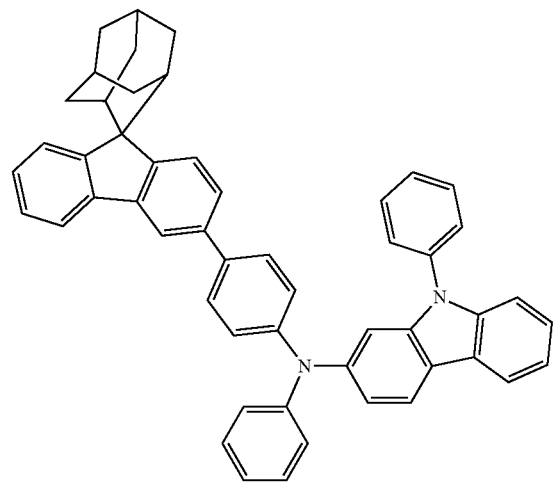
340
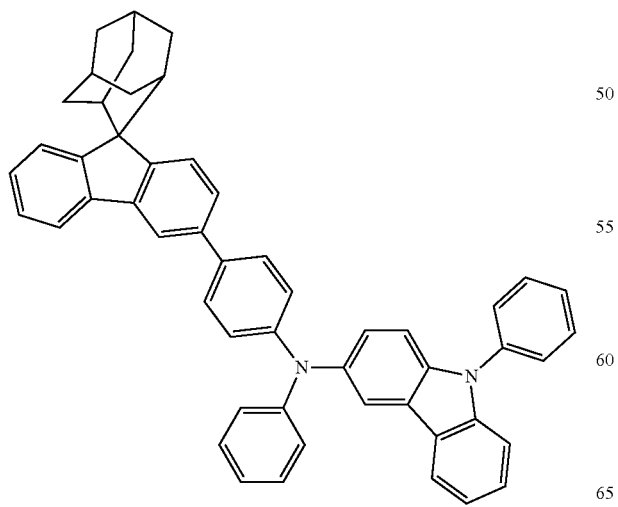
-continued
341
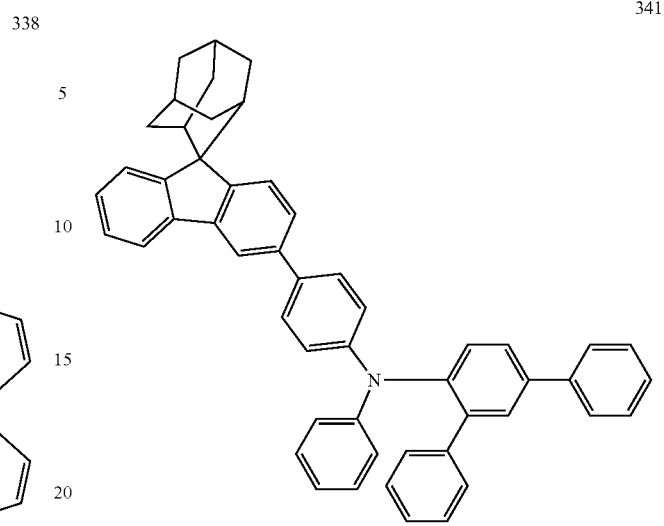
342
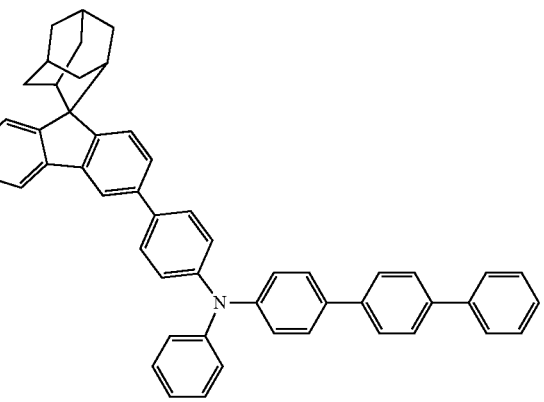
343
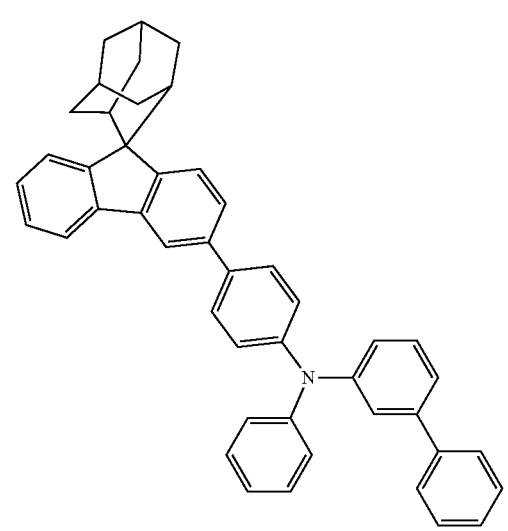

344
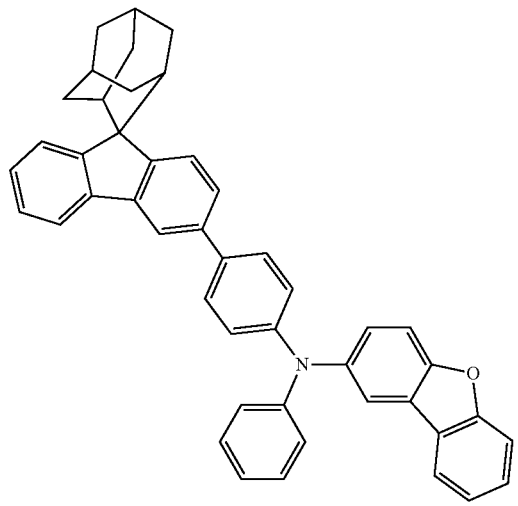
345
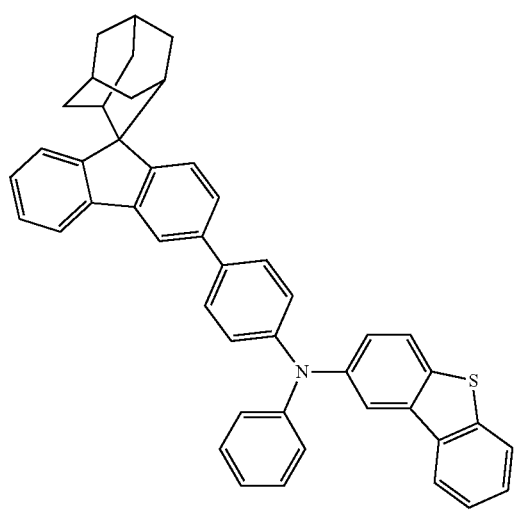
346
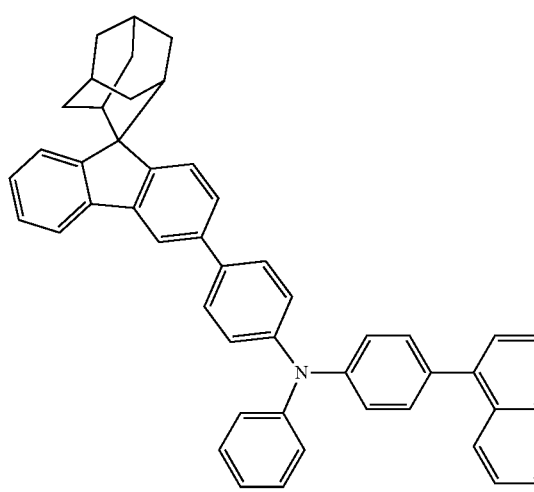
347
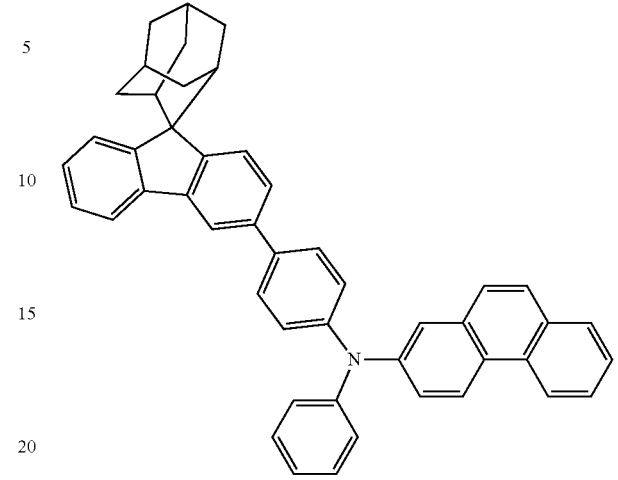
348
349
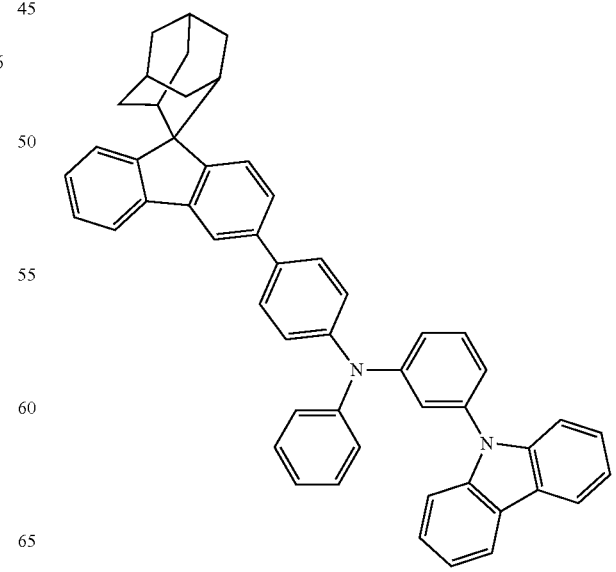

-continued
350
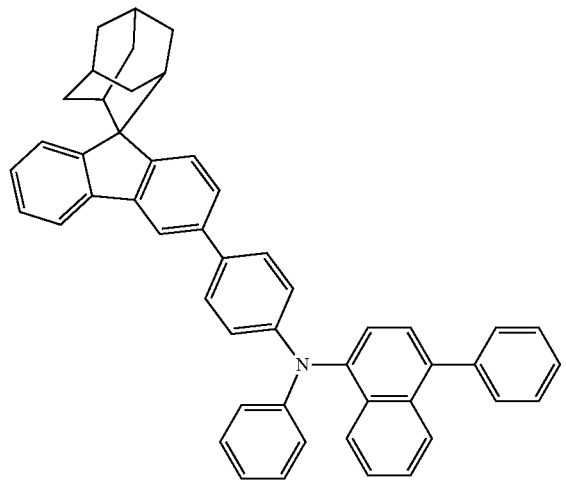
351
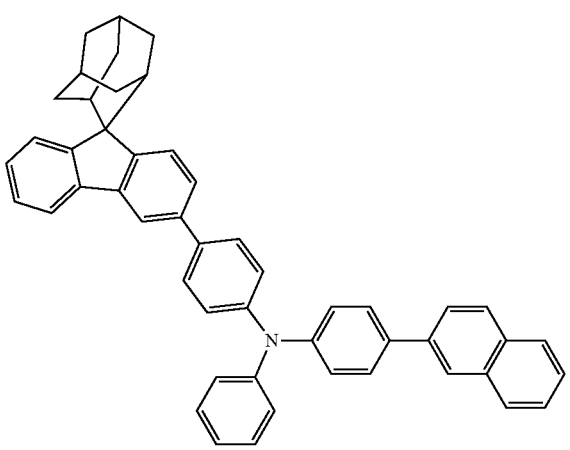
352
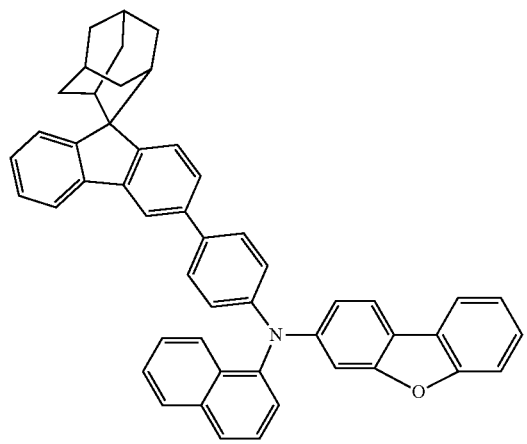
353
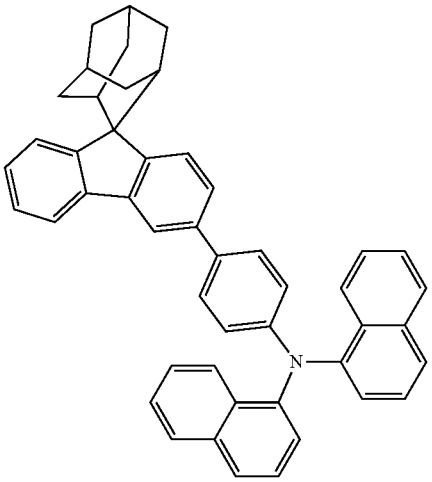
354
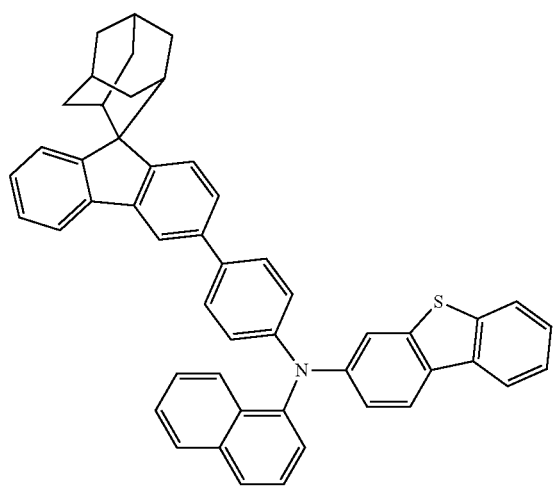
355
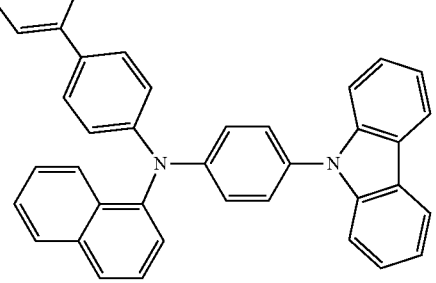

356
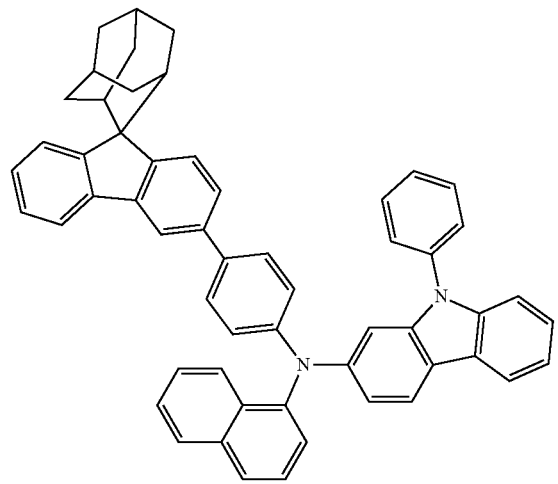
357
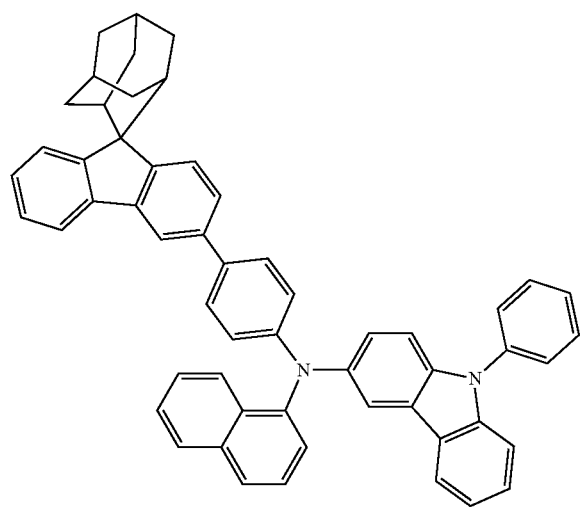
358
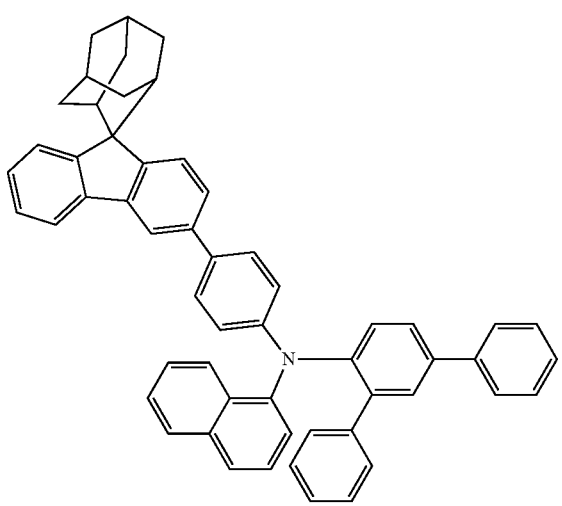
359
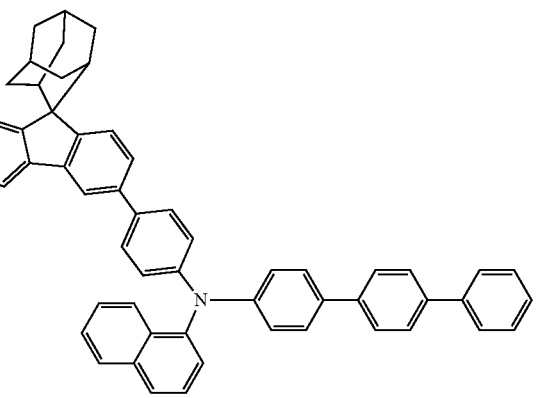
360
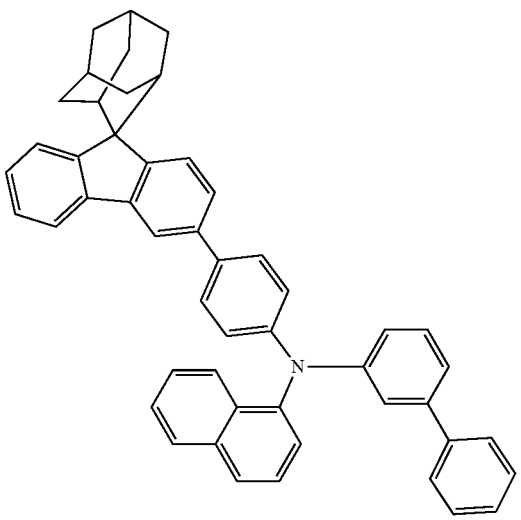
361
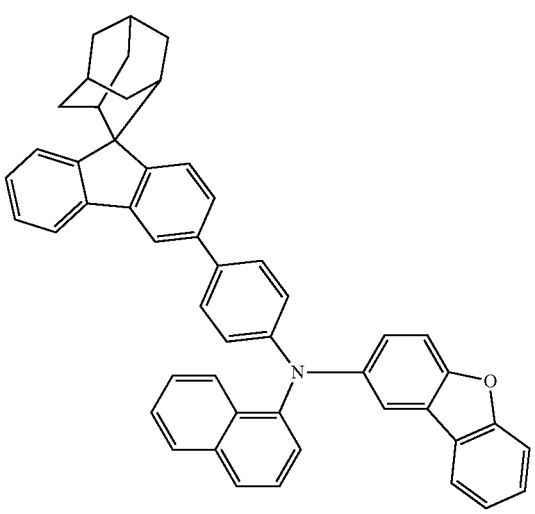

362
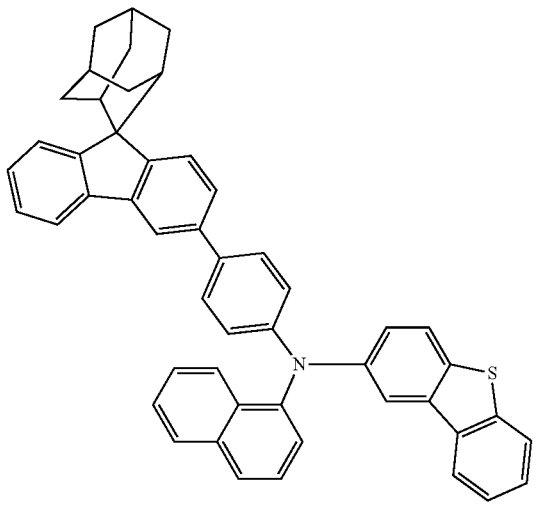
363
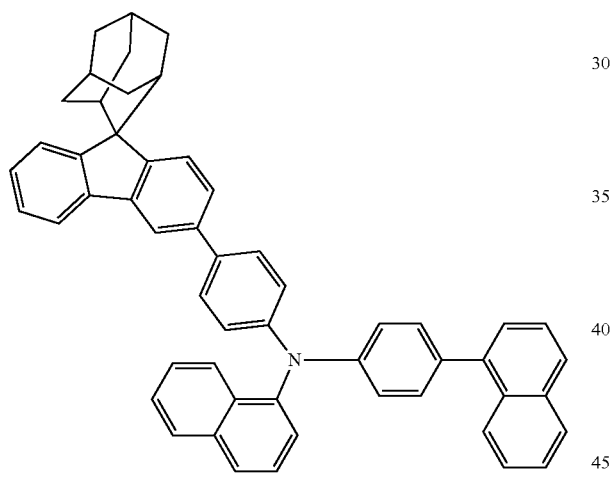
364
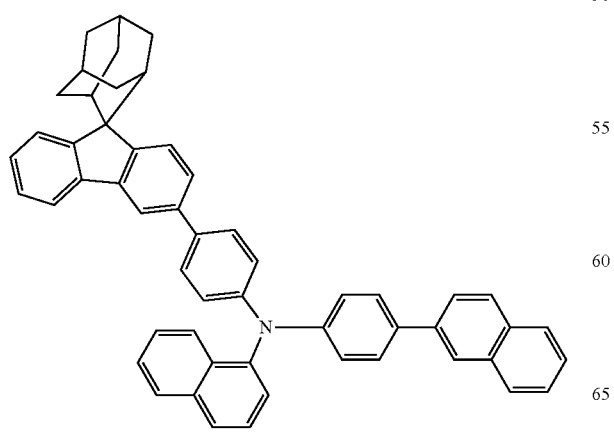
365
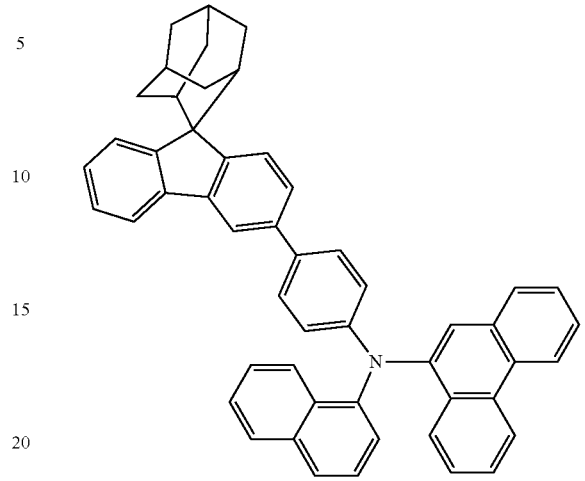
366
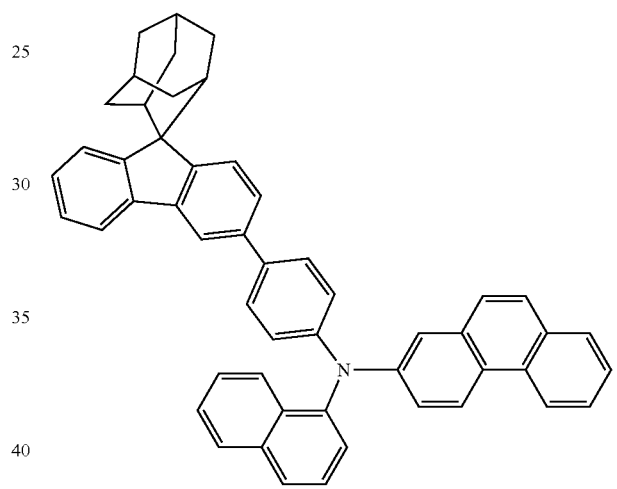
367
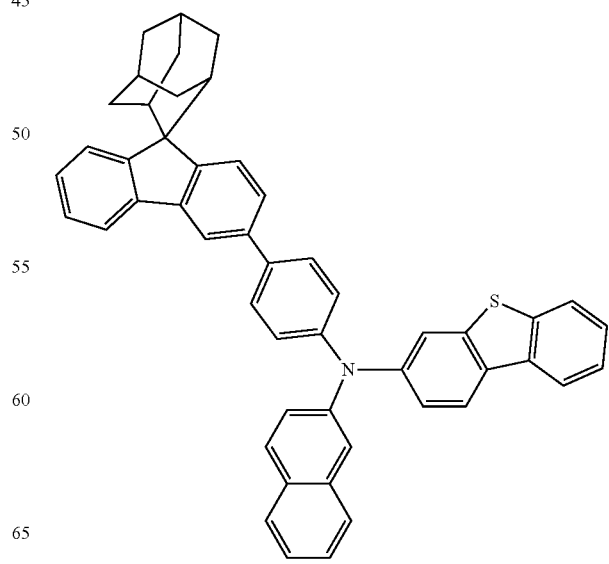

368
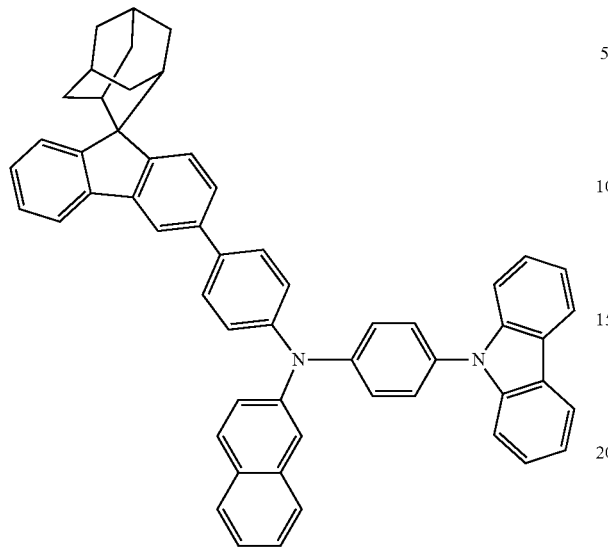
369
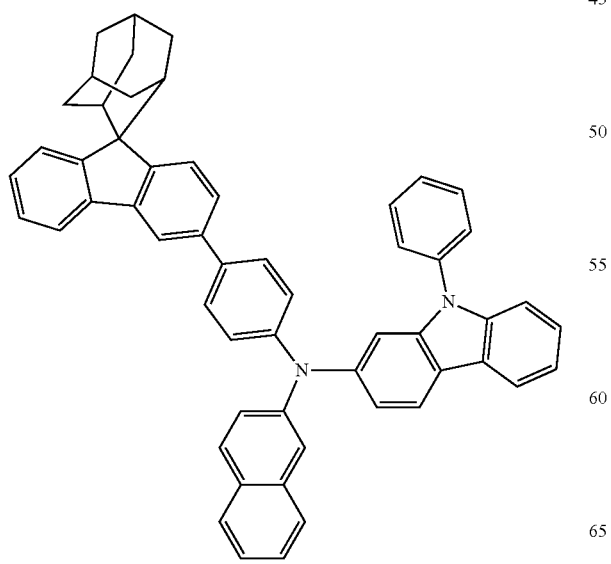
370
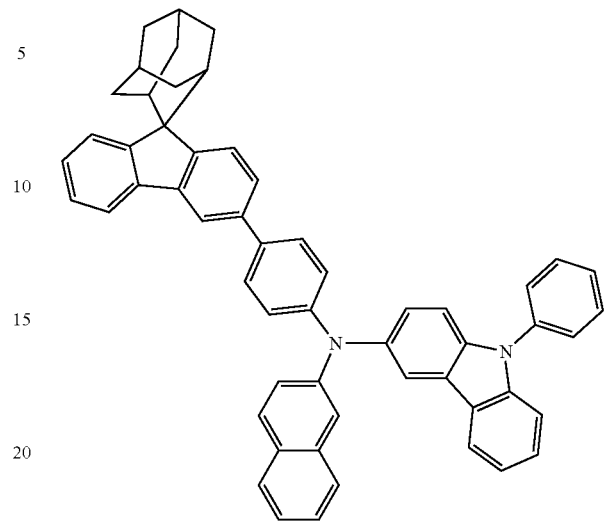
371
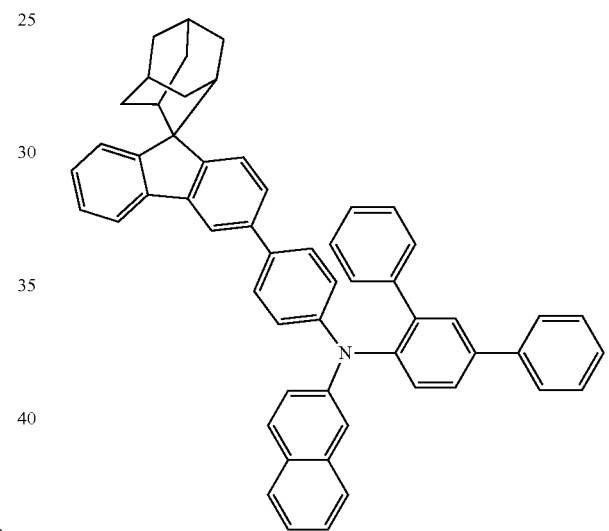
372
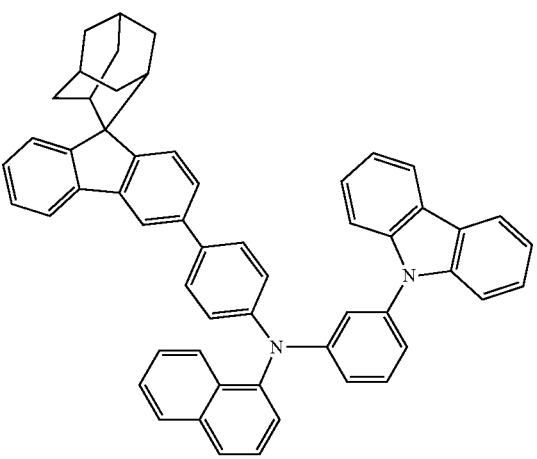

169
-continued
373
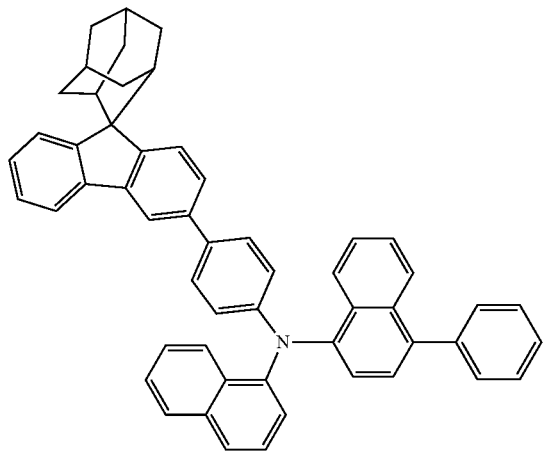
374
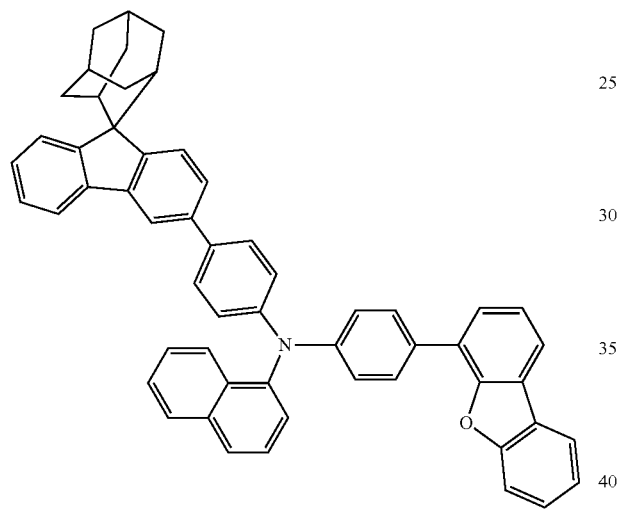
375
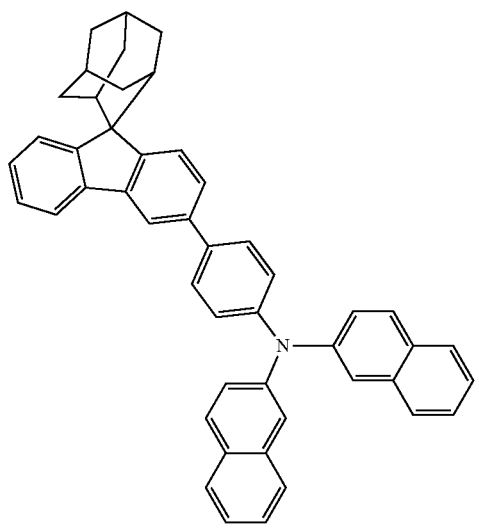
170
-continued
376
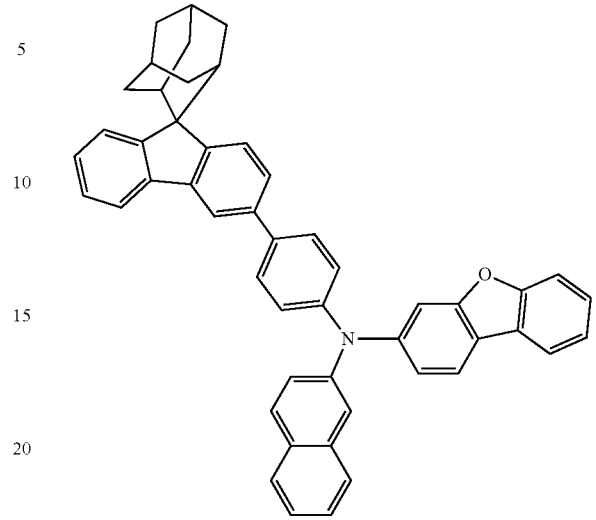
377
378
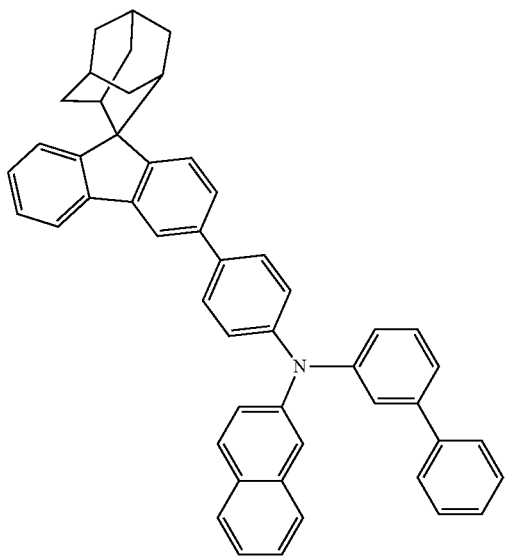

379
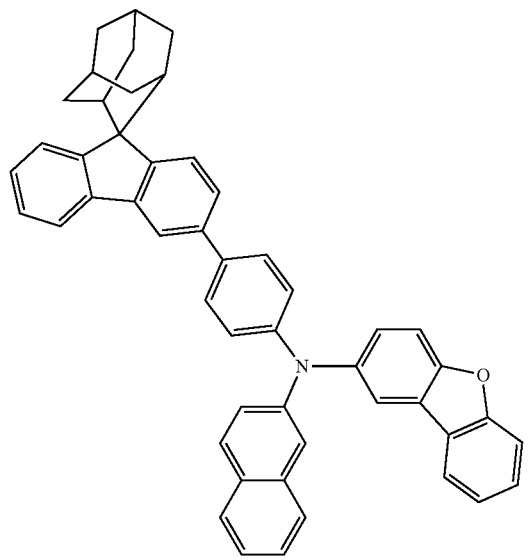
380
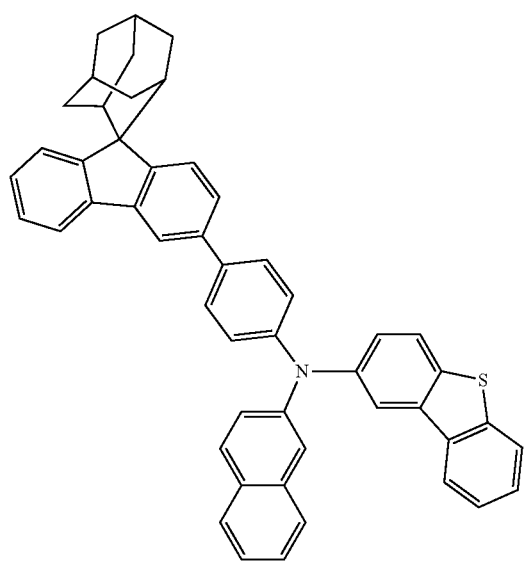
381
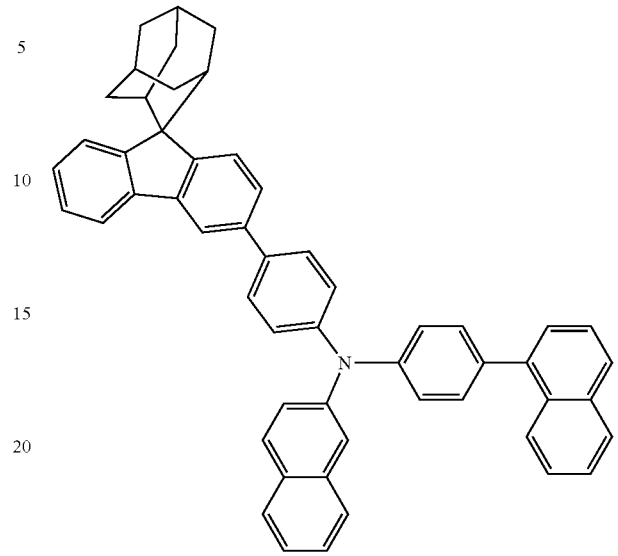
382
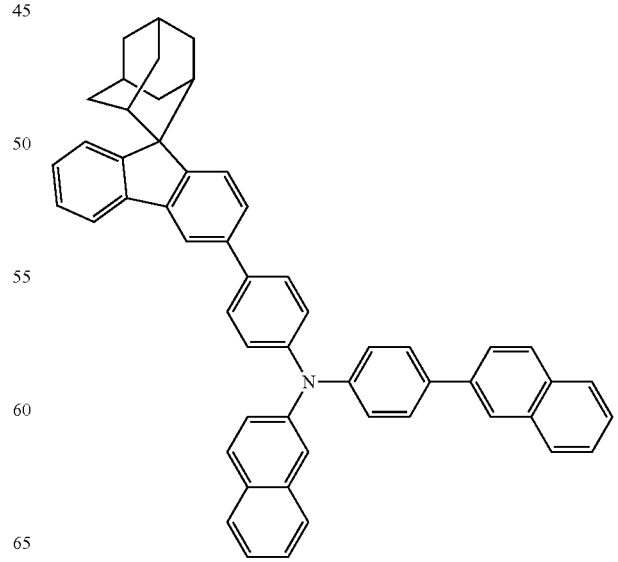

383
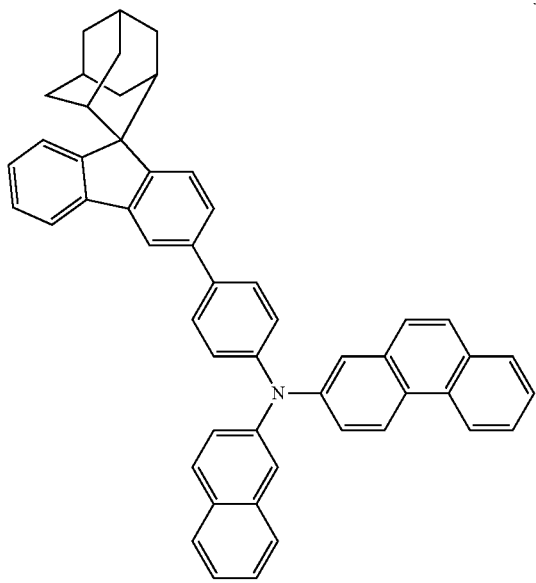
385
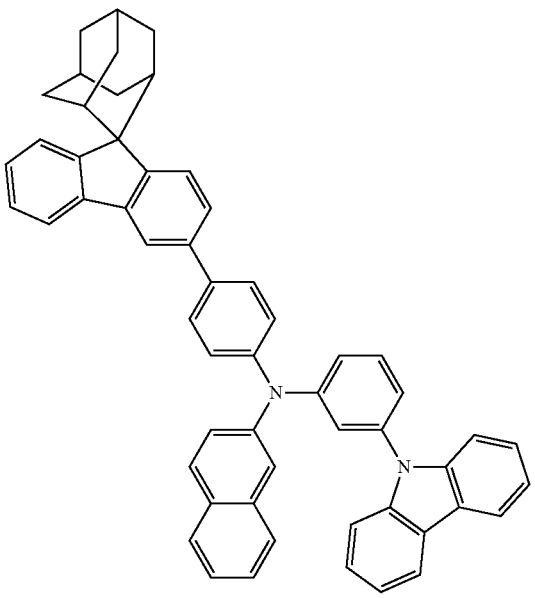
384
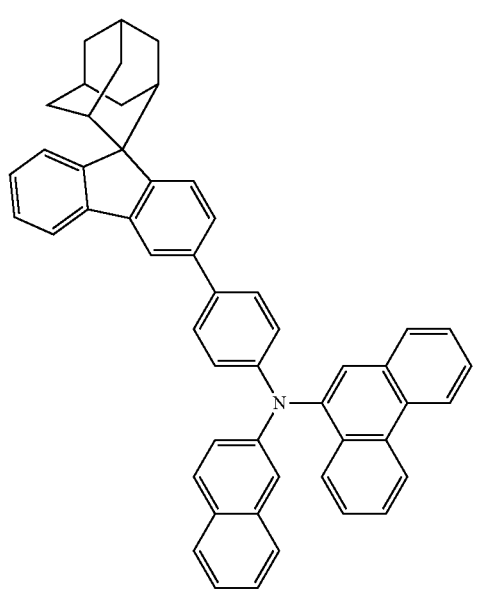
386
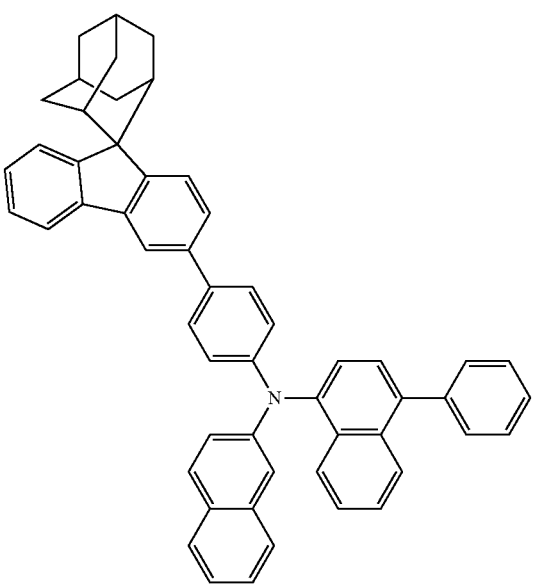

175
-continued
387
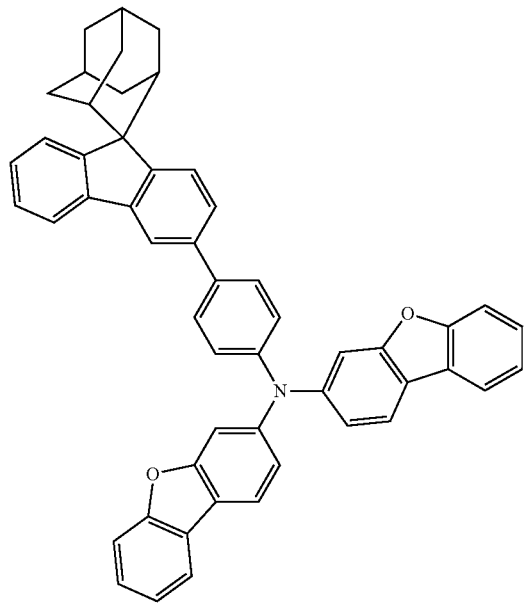
388
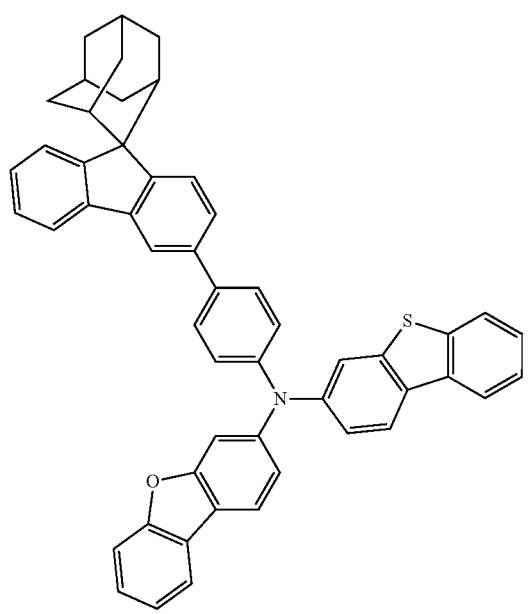
176
-continued
389
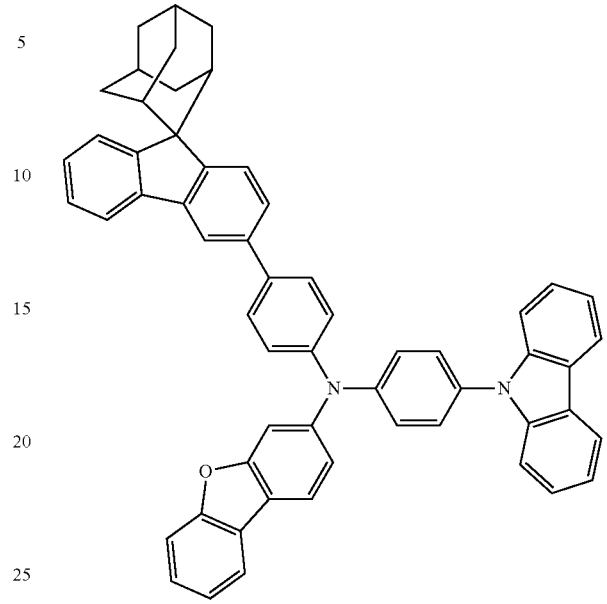
390
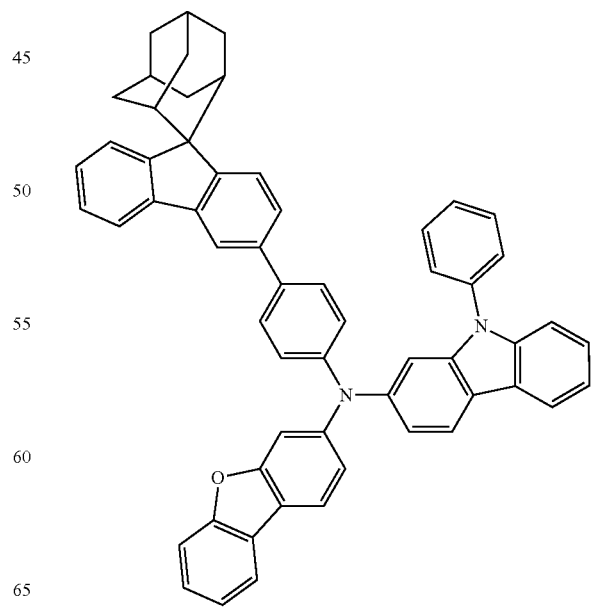

177
391
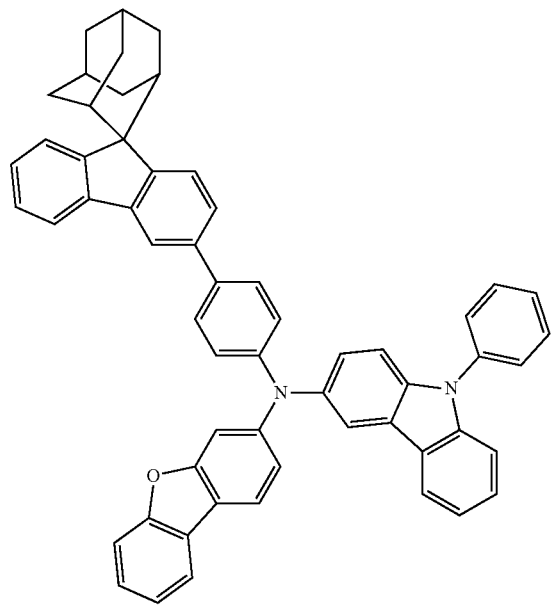
392
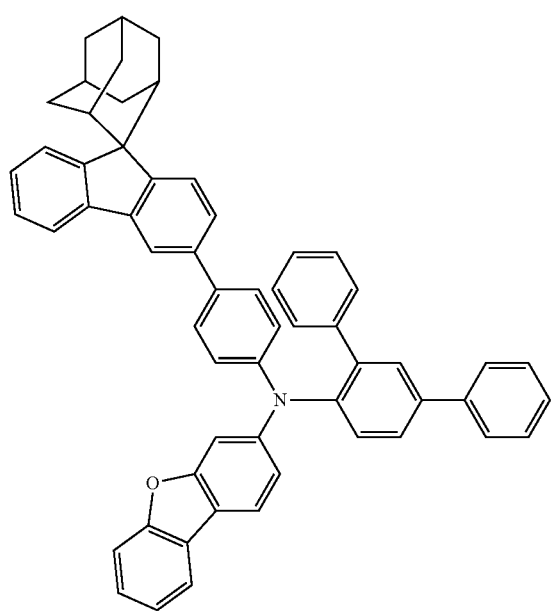
178
393
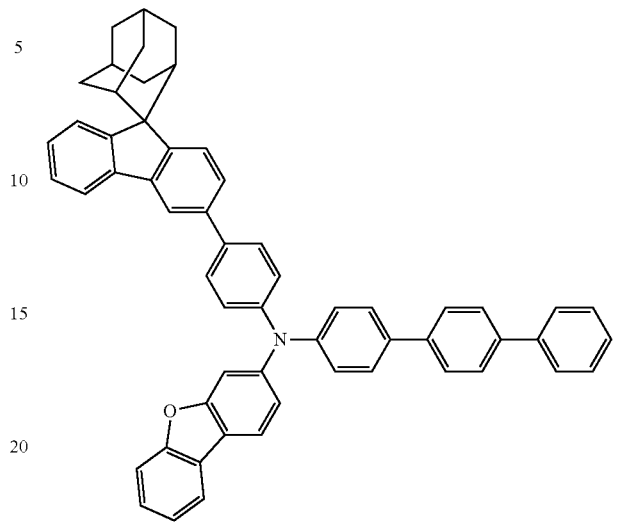
394
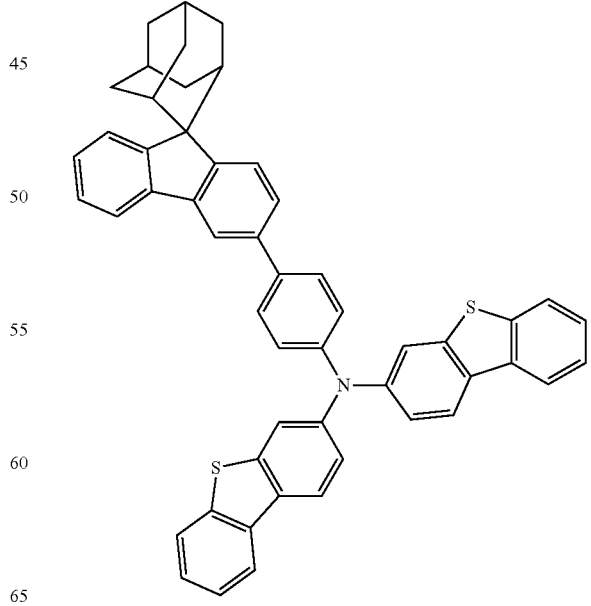

395
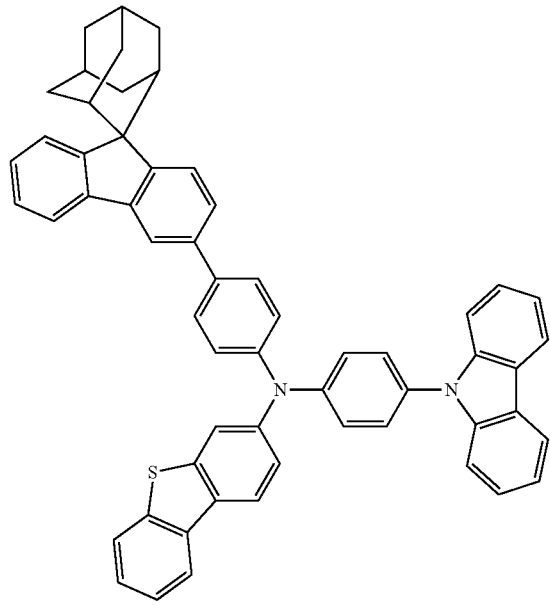
397
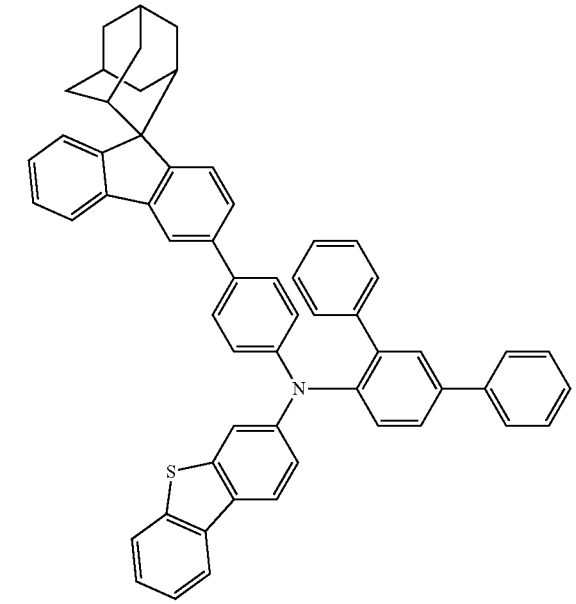
396
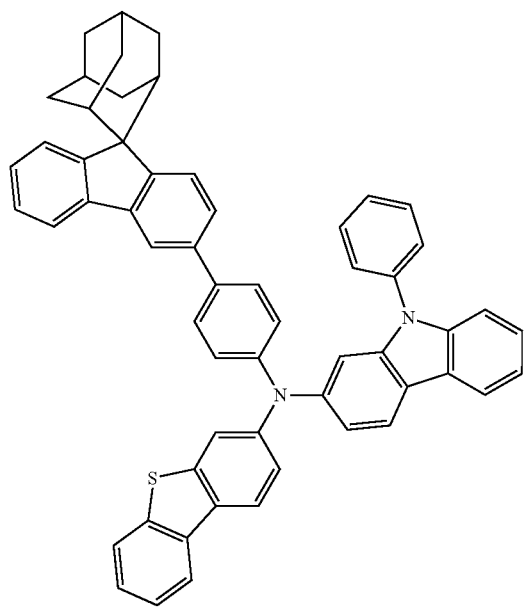
398
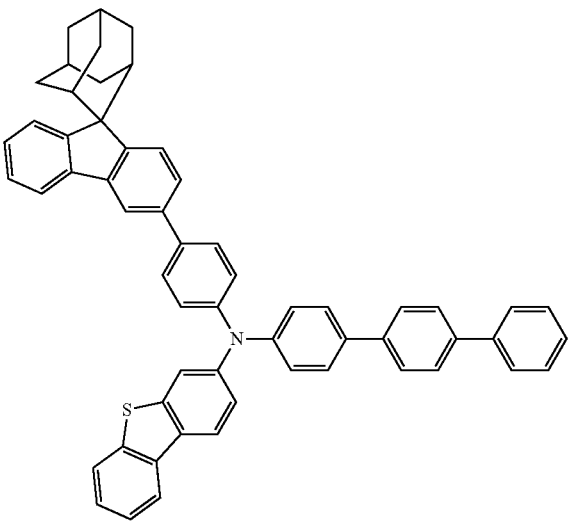

181
-continued
399
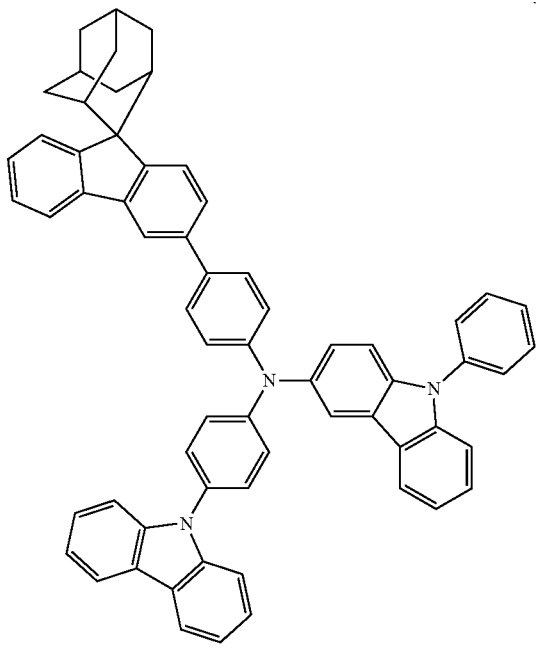
400
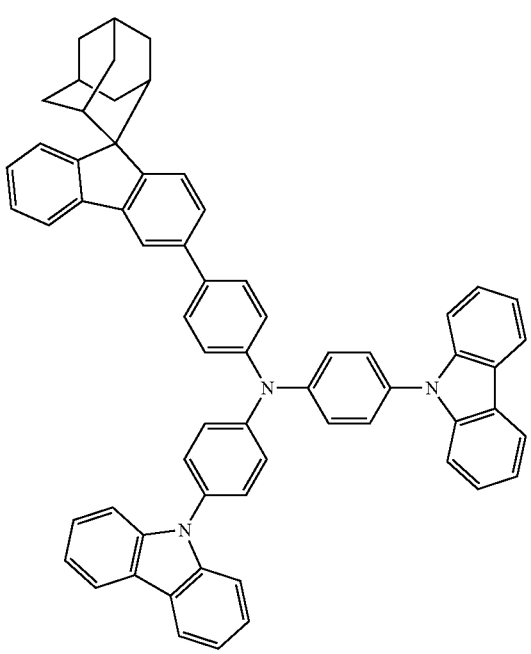
182
-continued
401
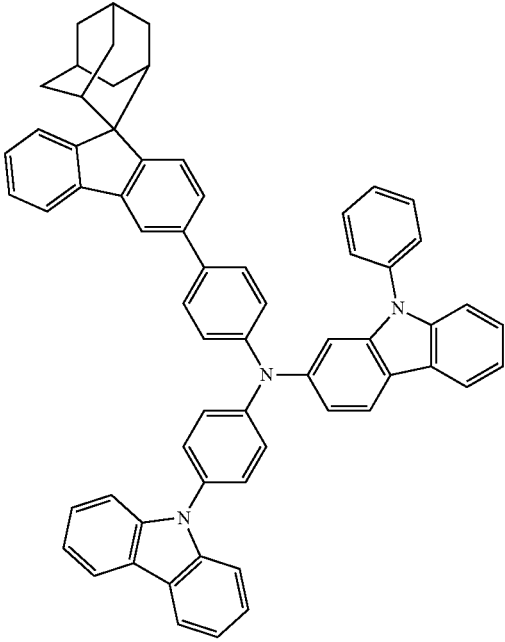
402
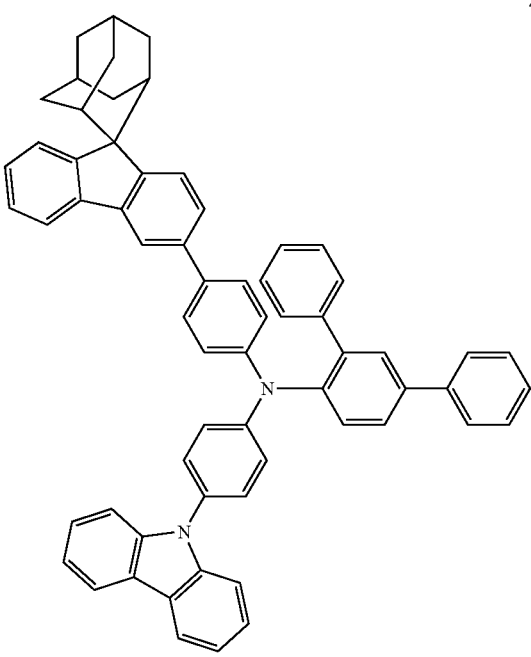

183
-continued
403
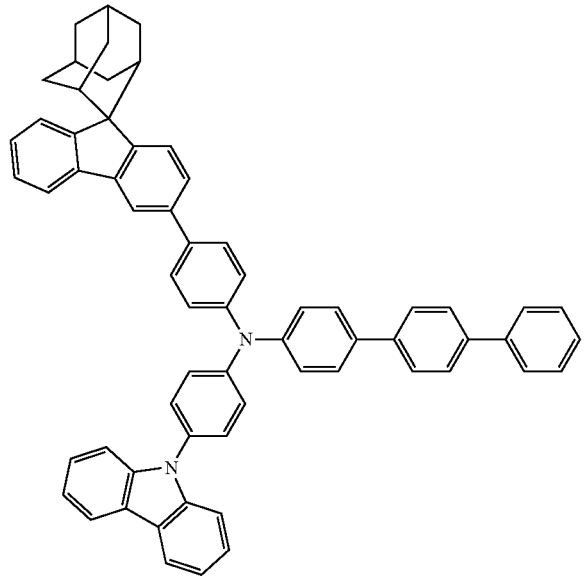
404
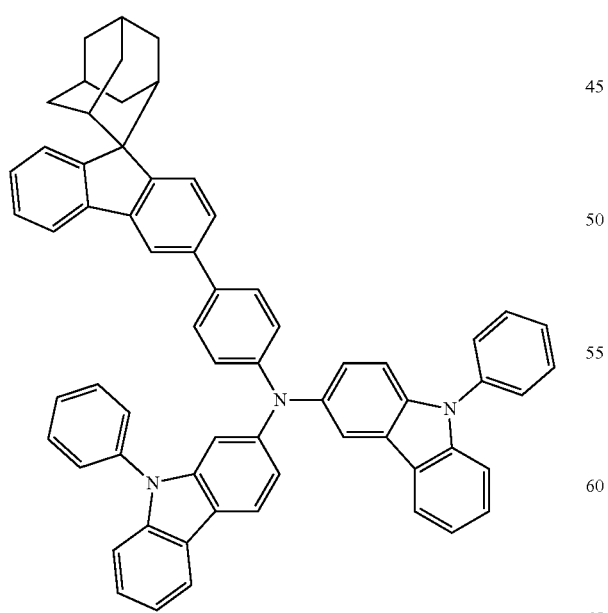
184
-continued
405
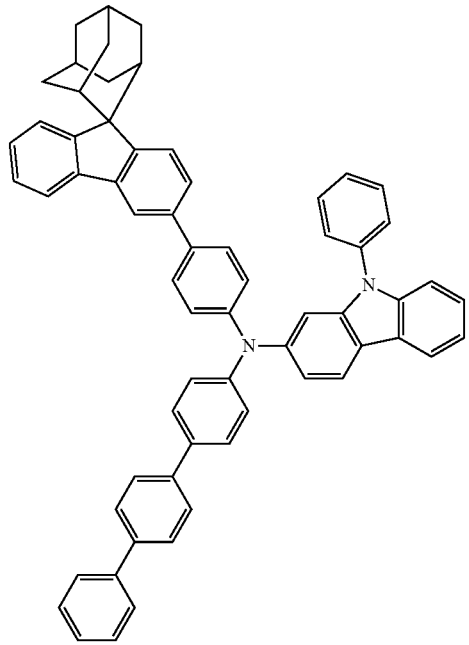
406
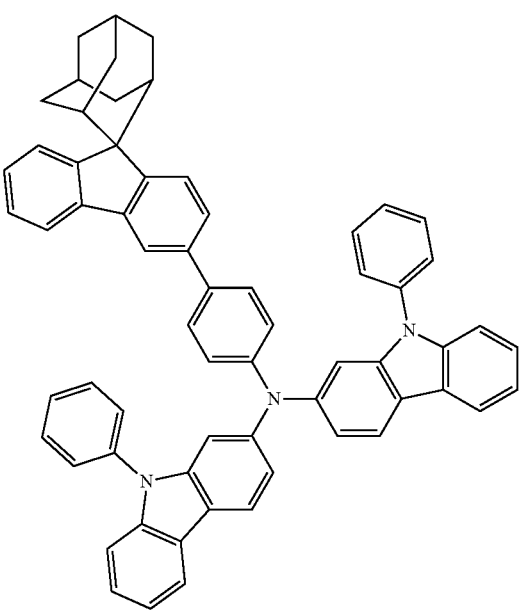

185
-continued
407
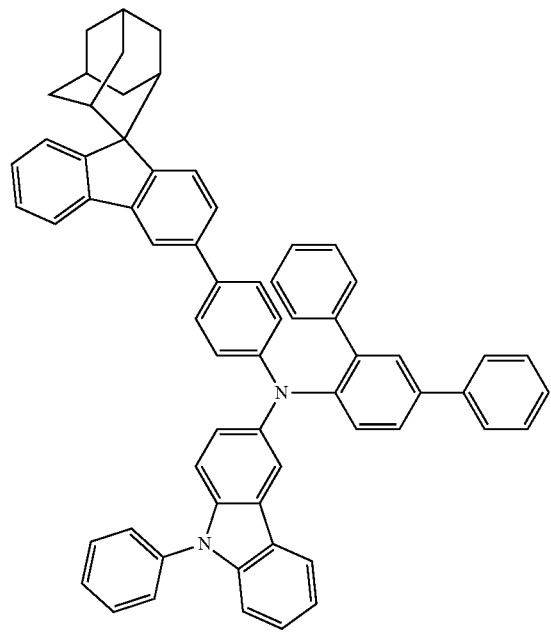
408
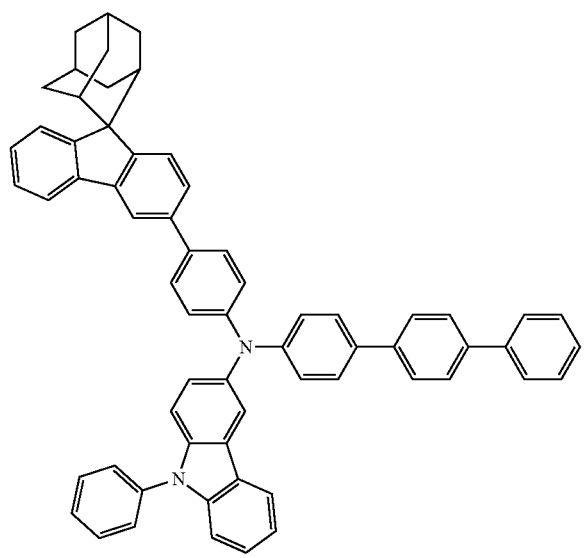
186
-continued
409
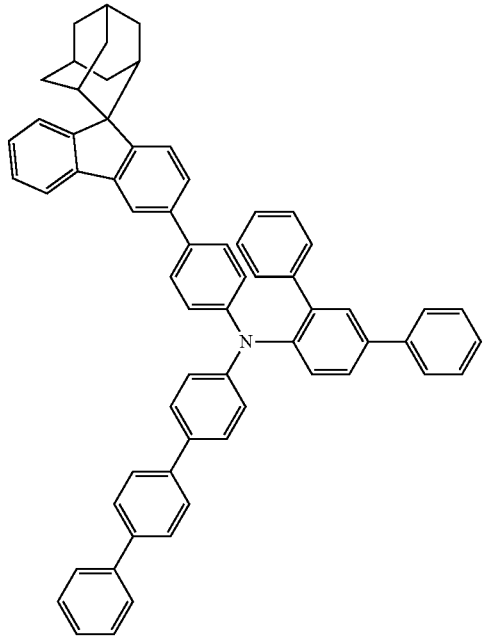
410
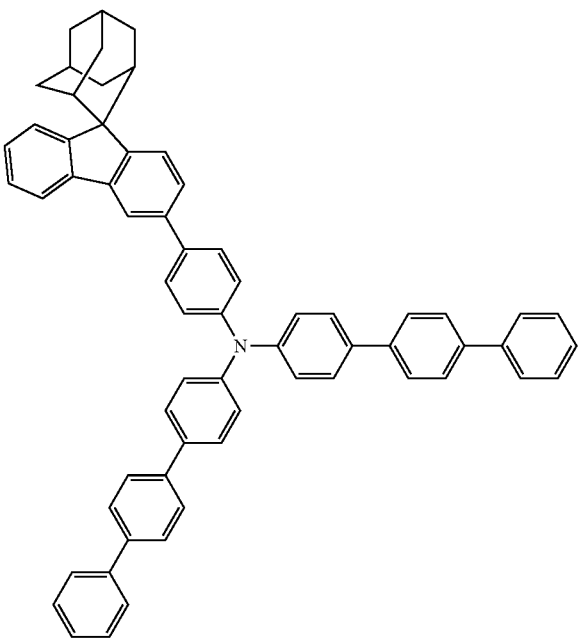

187
-continued
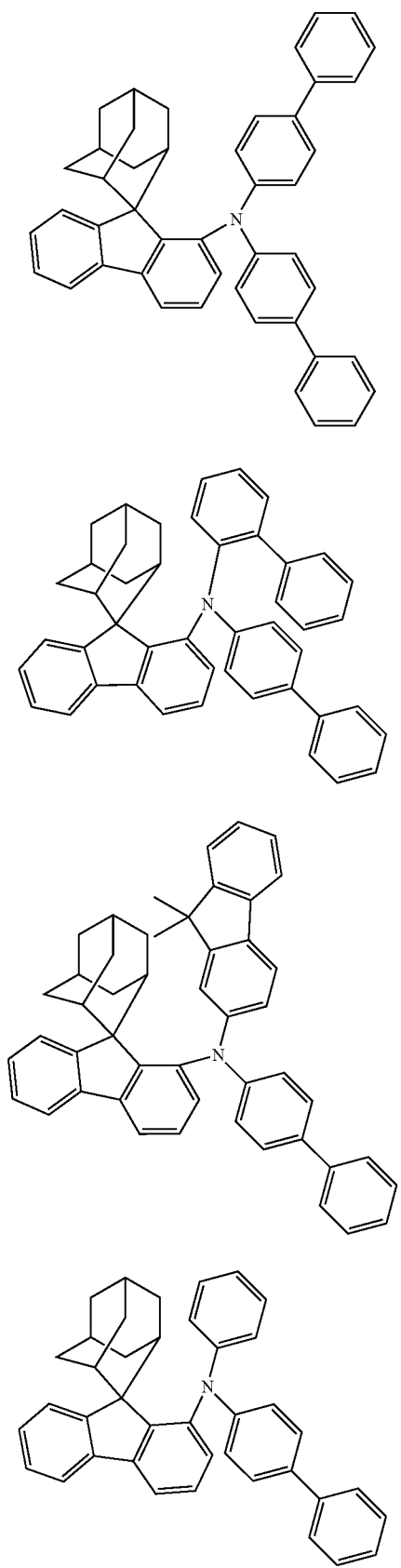
188
-continued
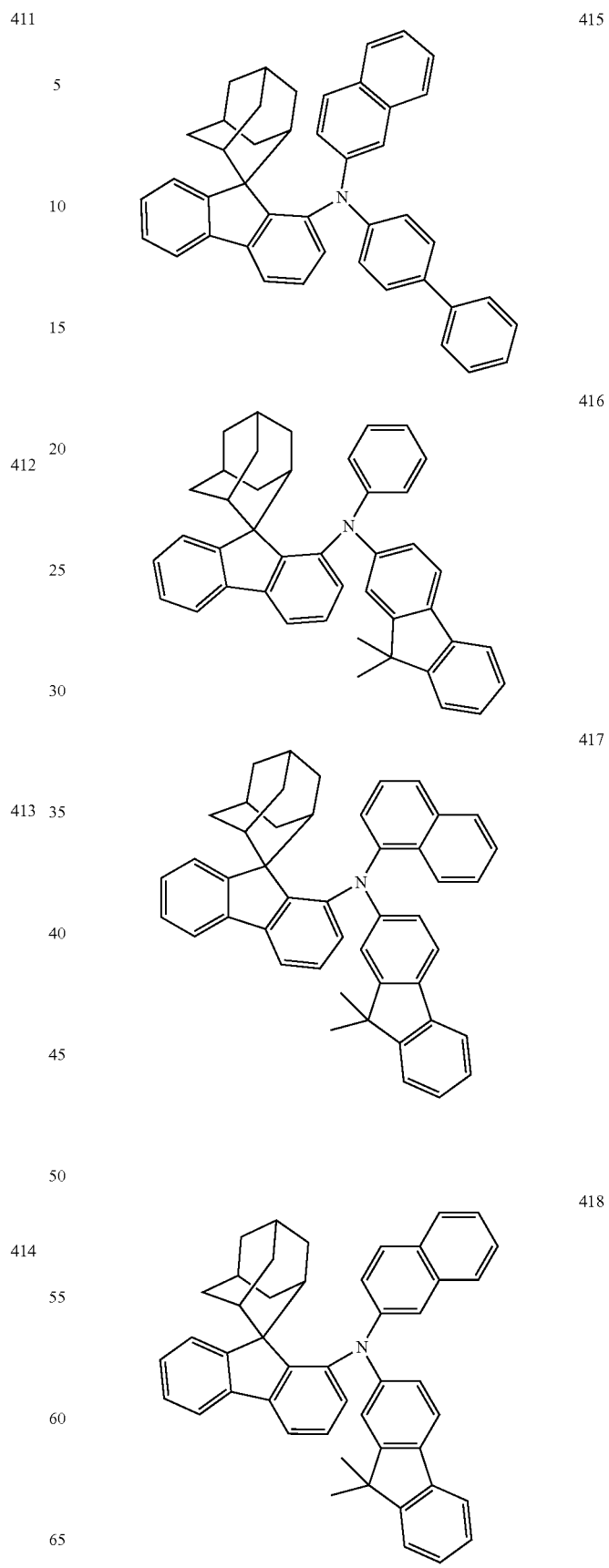

419
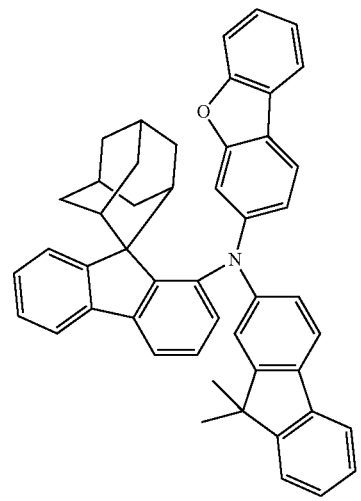
420
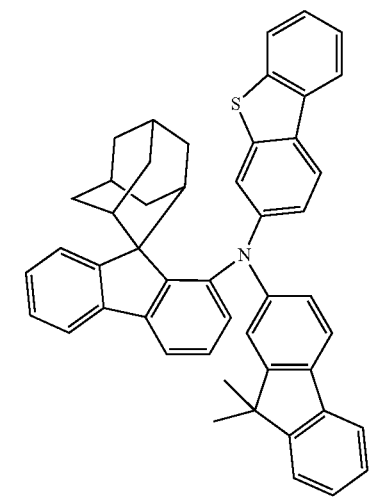
421
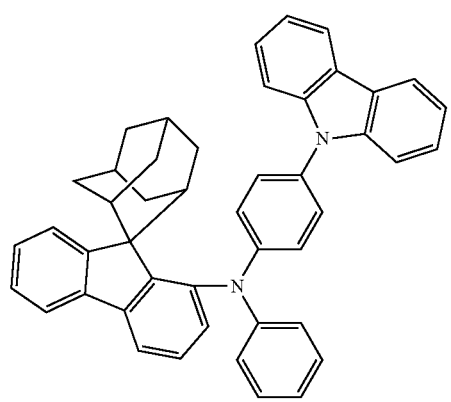
422
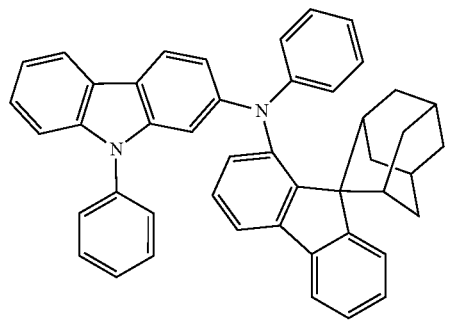
423
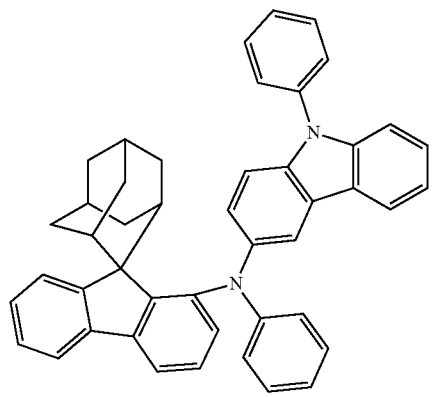
424
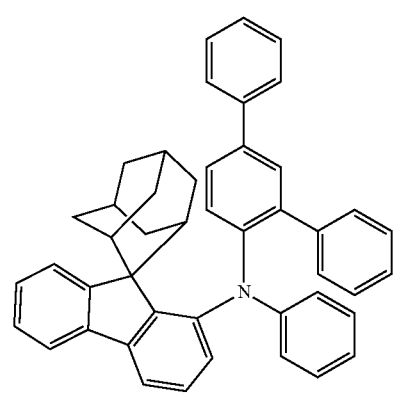
425
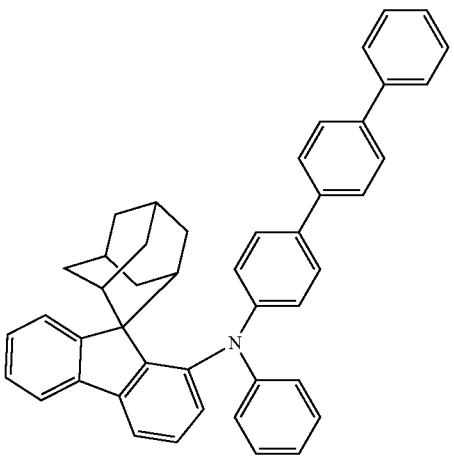

-continued
426
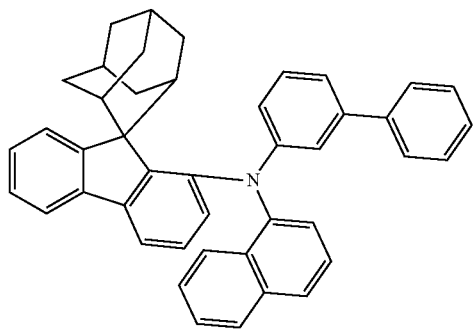
427
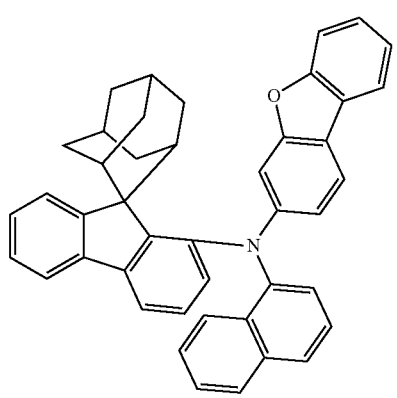
428
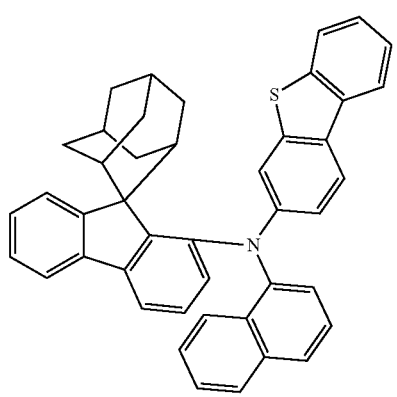
429
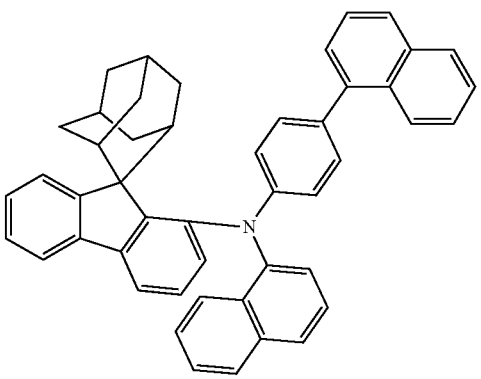
-continued
430
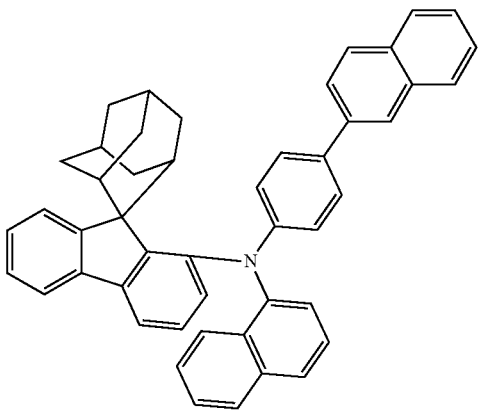
431
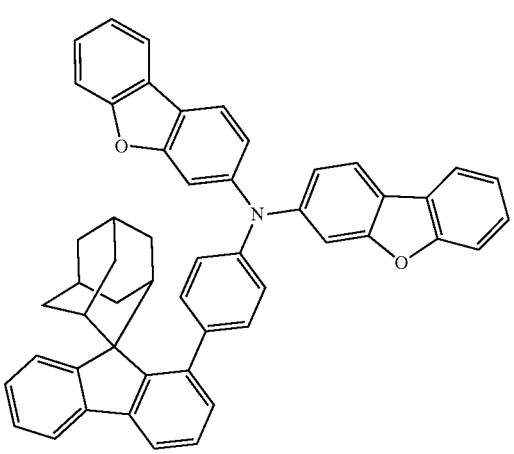
432
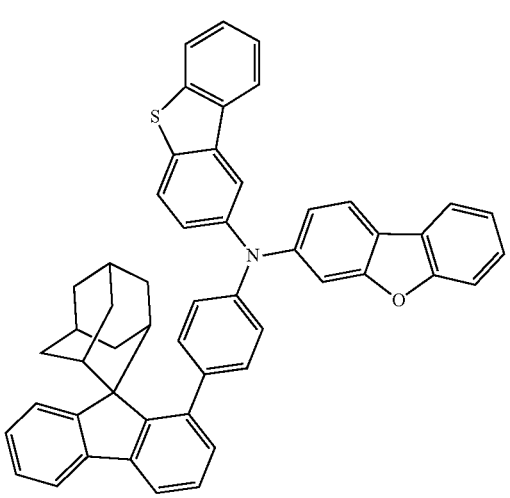

433
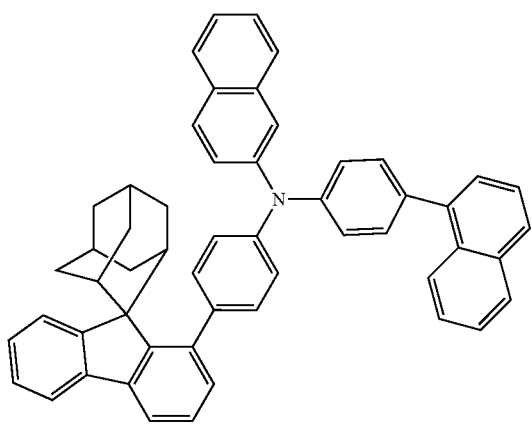
434
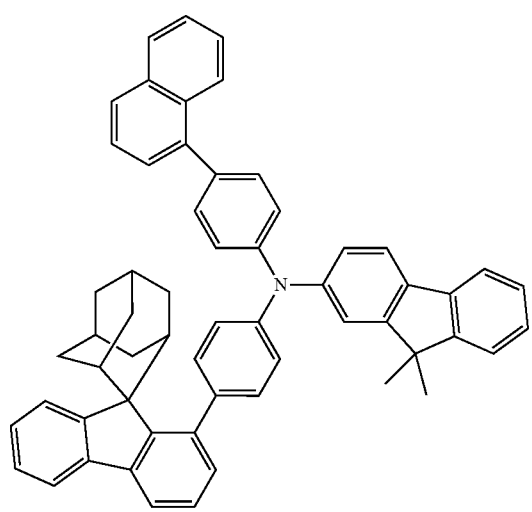
435
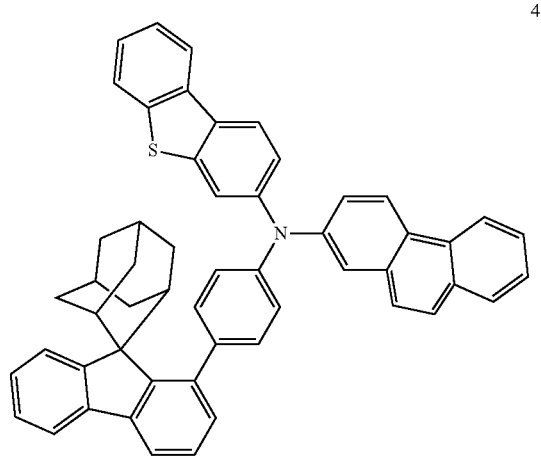
436
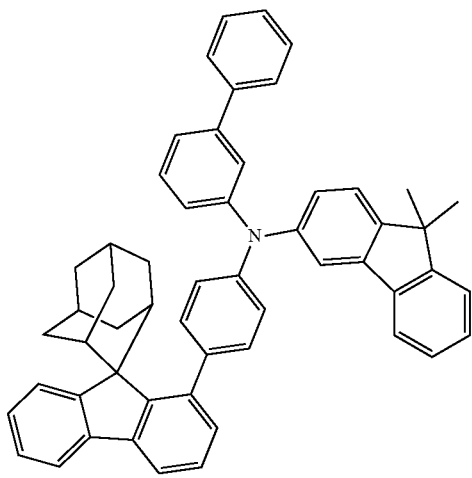
437
438
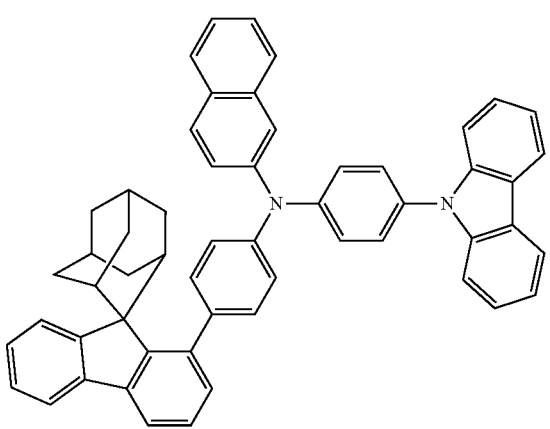

439
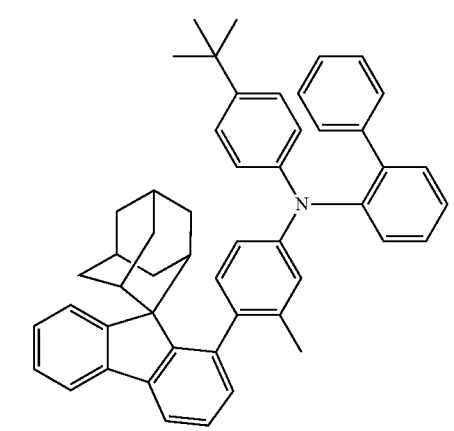
440
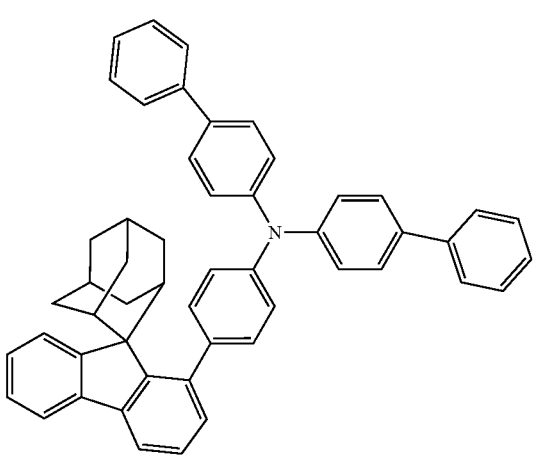
441
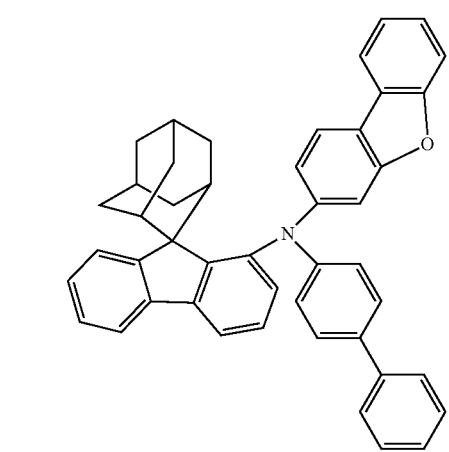
442
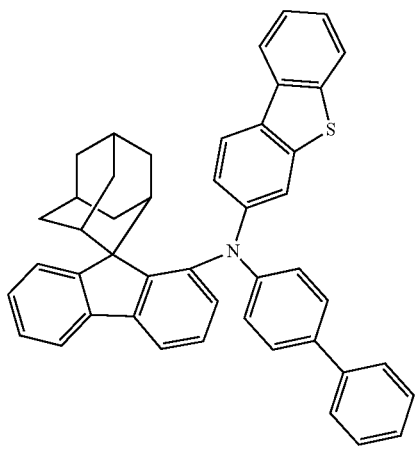
443
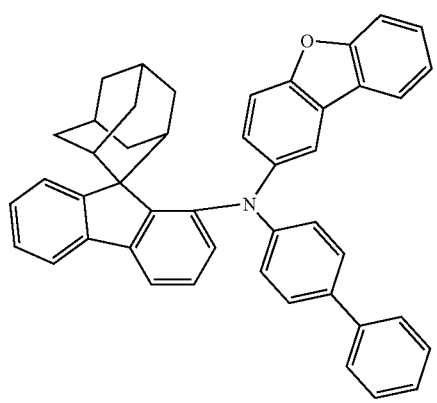
444
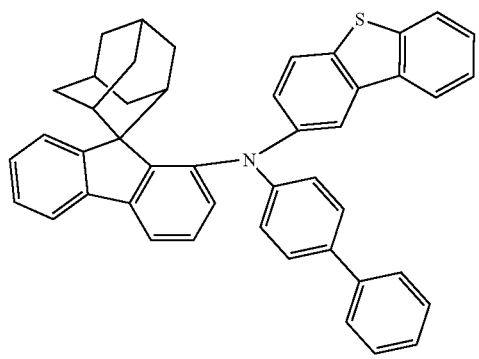
445
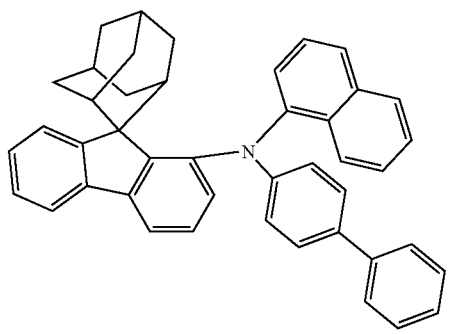

446
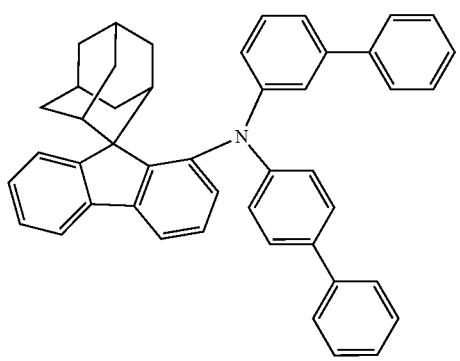
447
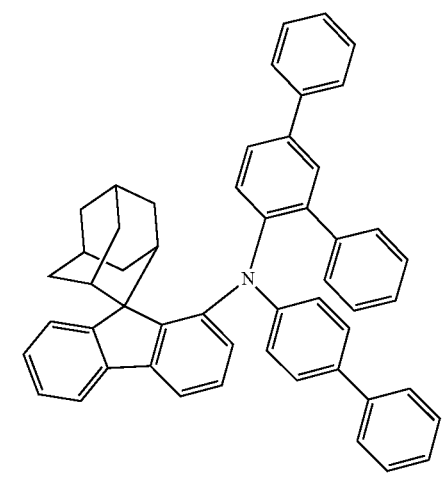
448
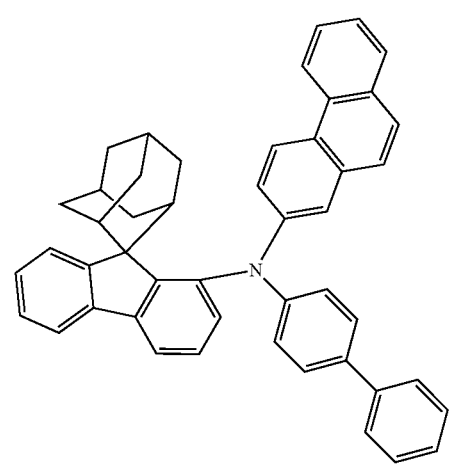
449
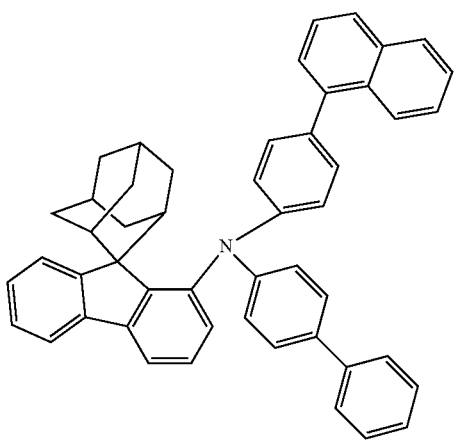
450
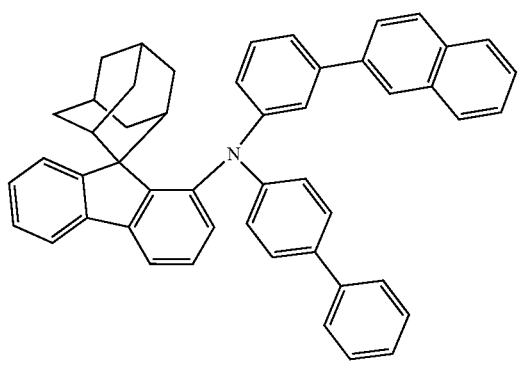
451
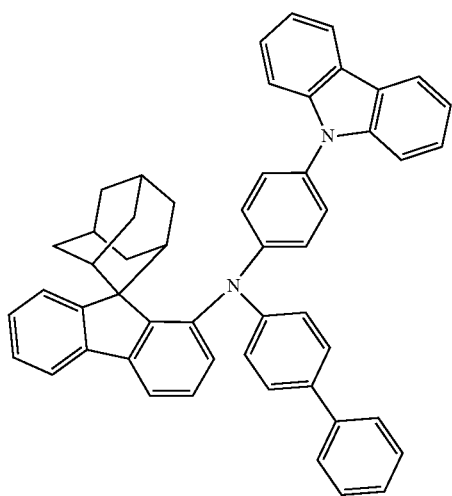

452
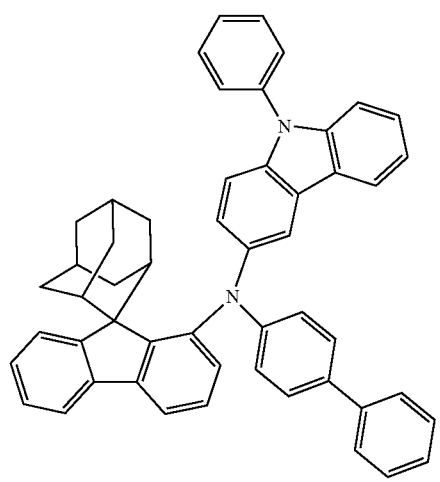
453
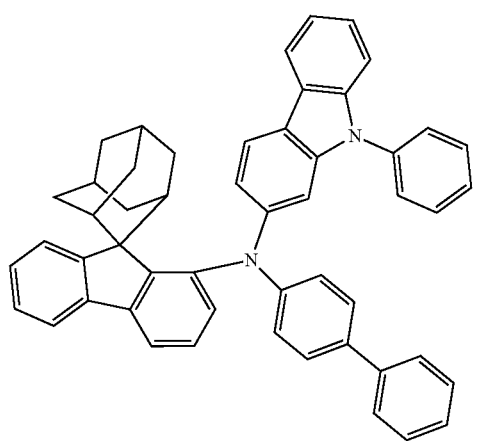
454
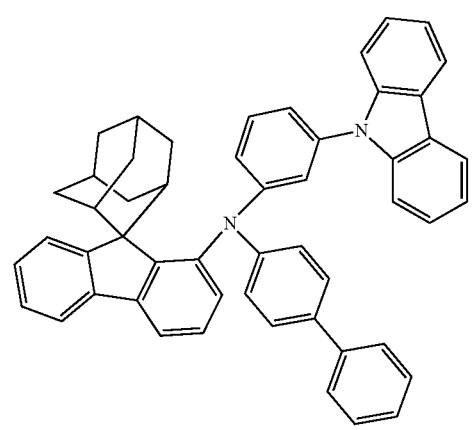
455
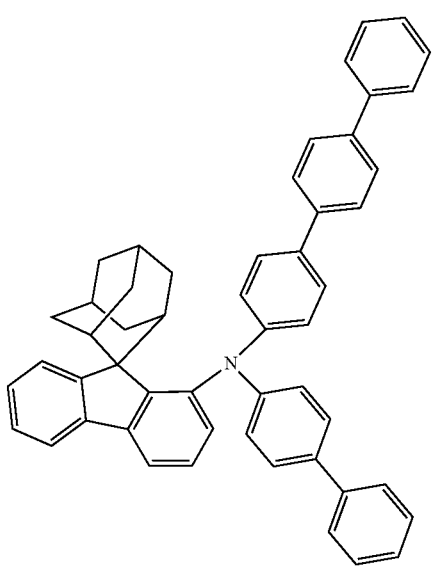
456
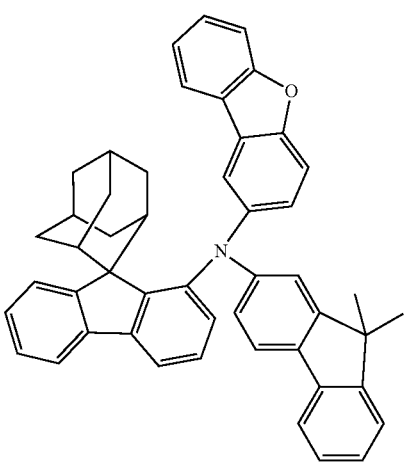
457
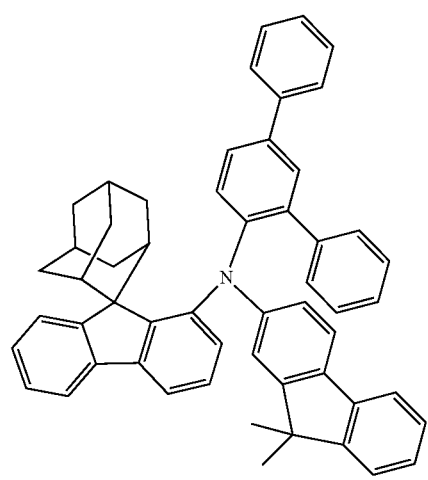

201
-continued
458
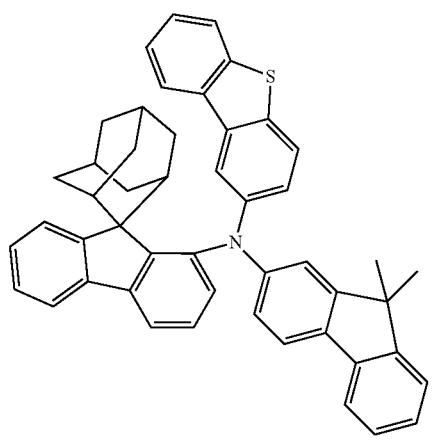
459
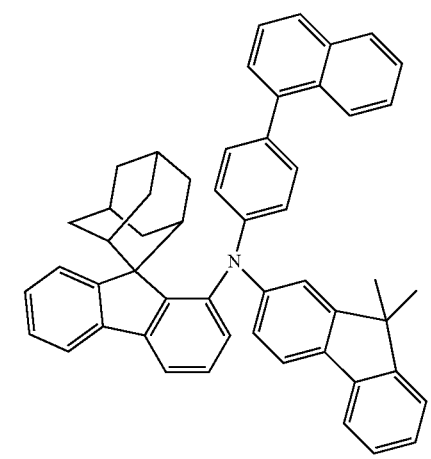
460
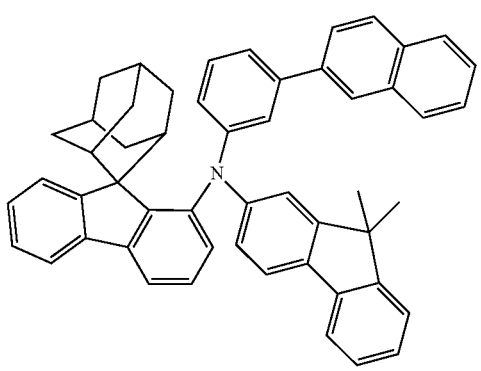
202
-continued
461
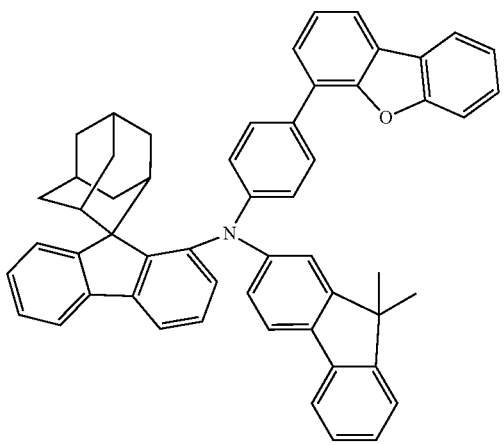
462
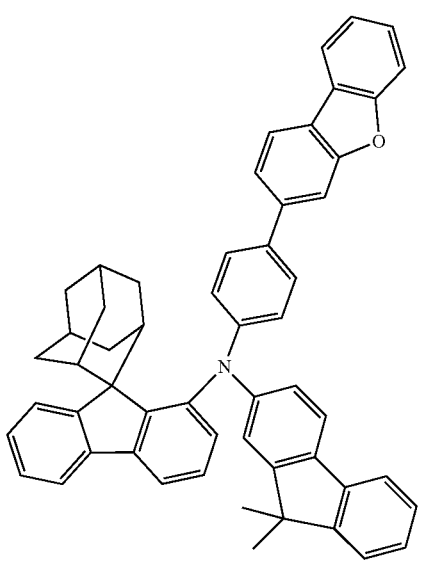
463
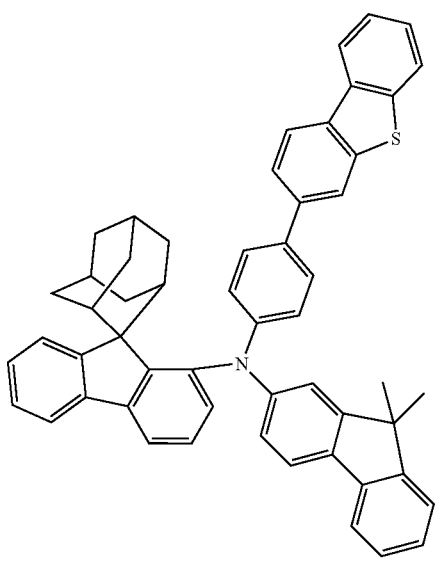

464
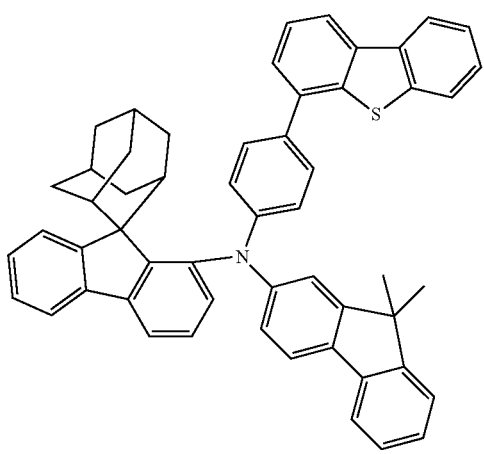
465
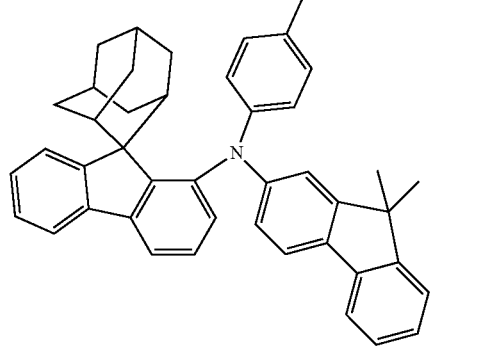
466
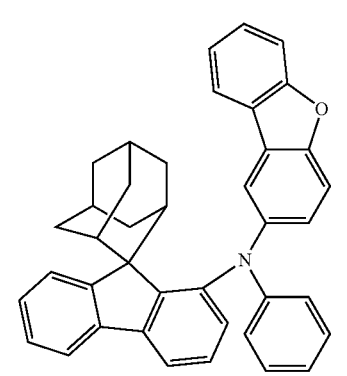
467
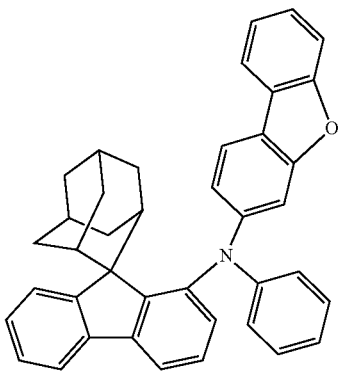
468
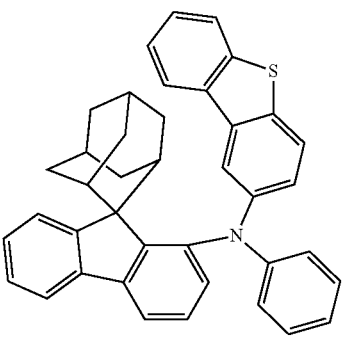
469
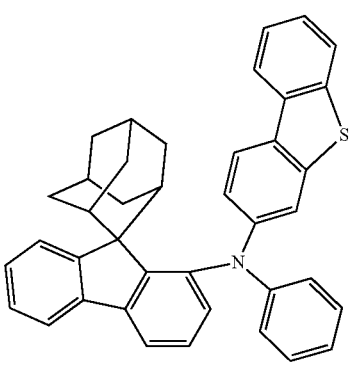
470
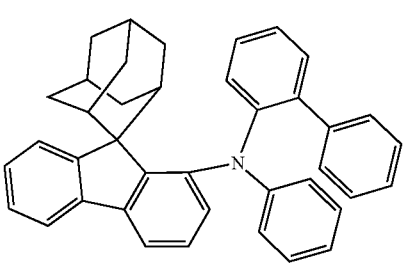

471
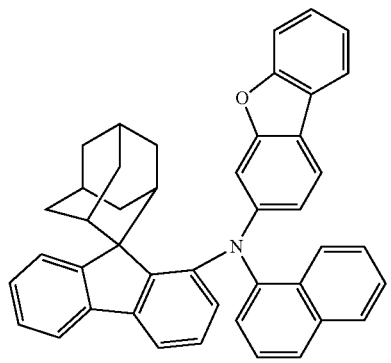
472
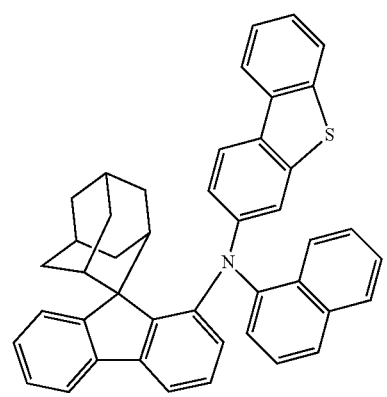
473
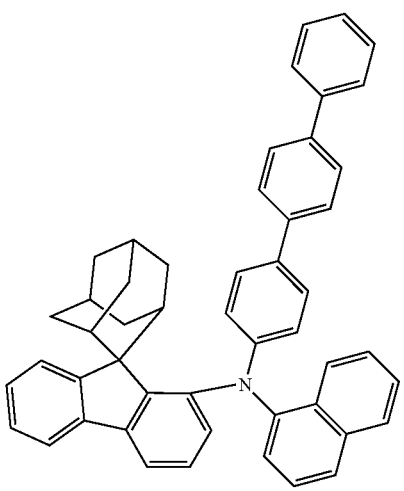
474
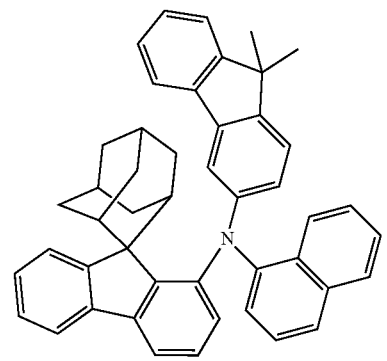
475
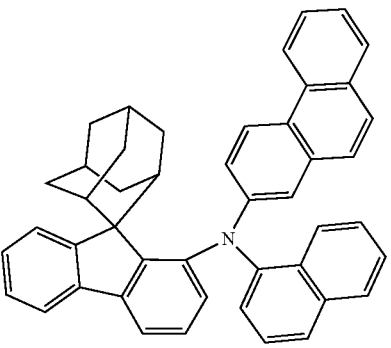
476
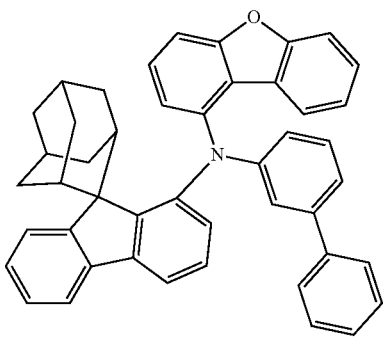
477
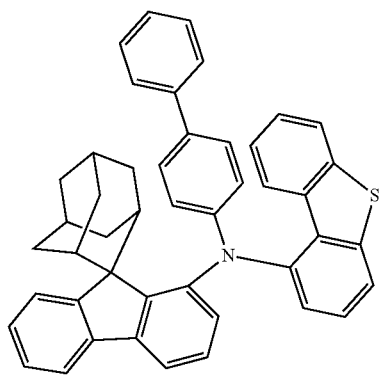
478
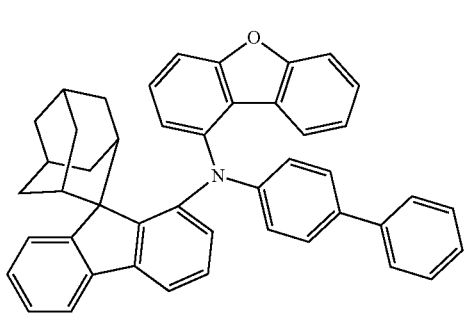

479
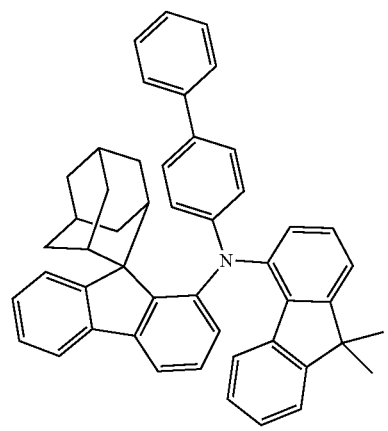
480
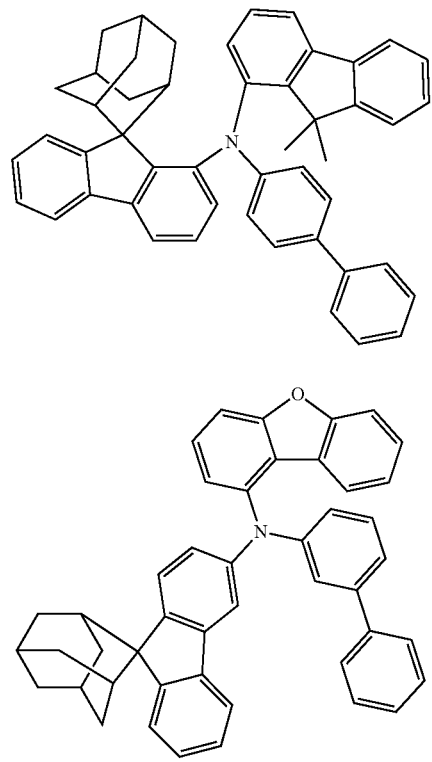
481
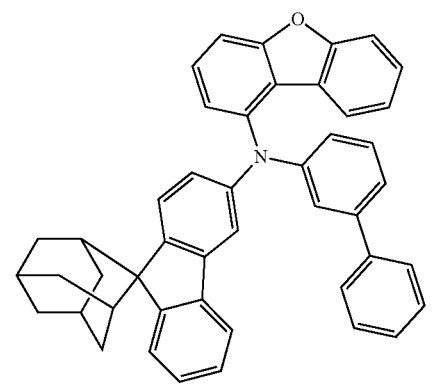
482
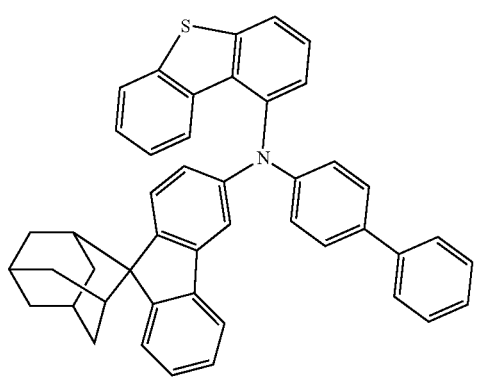
483
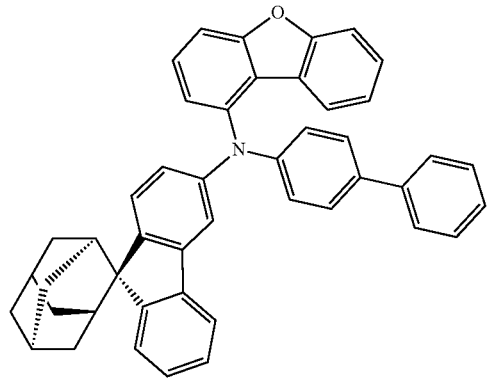
484
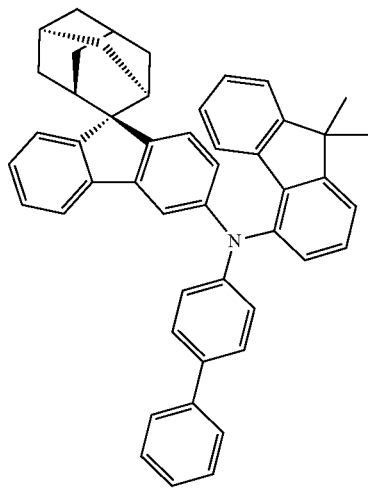
485
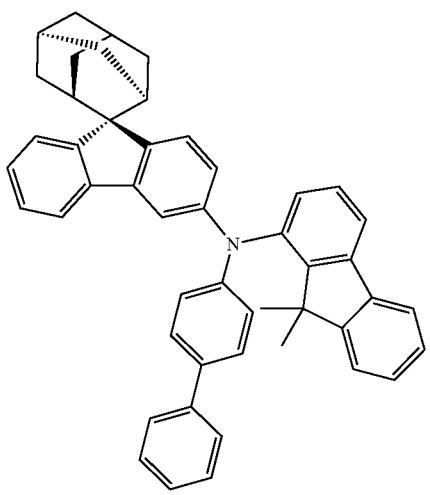

486
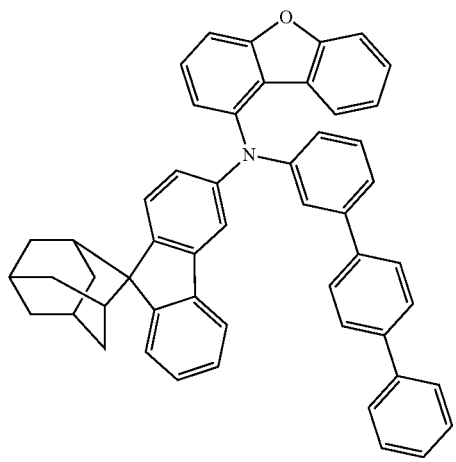
487
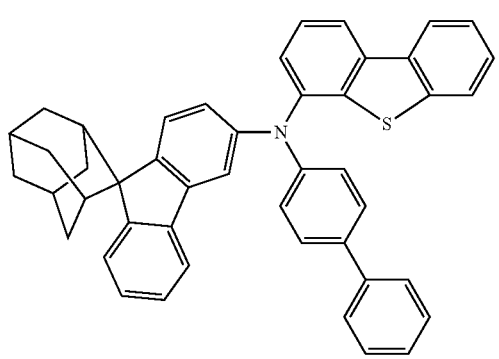
488
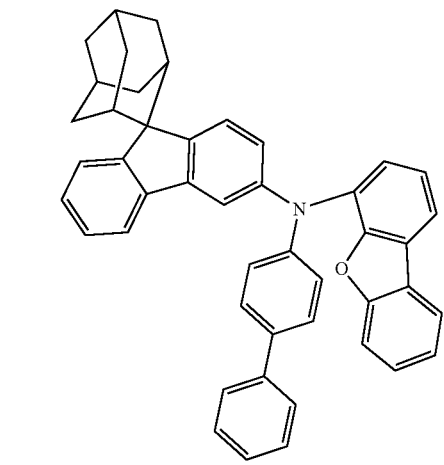
489
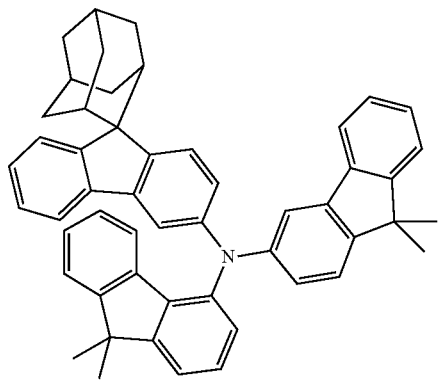
490
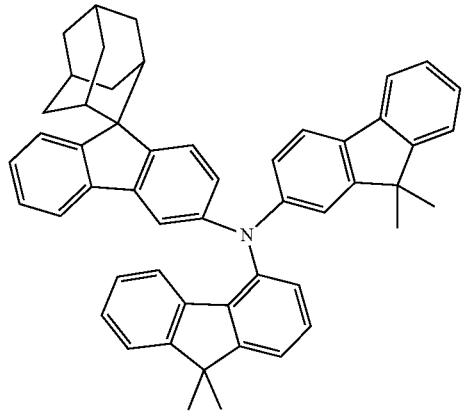
491
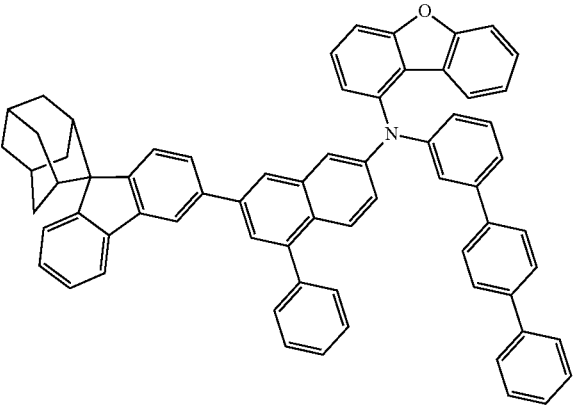
492
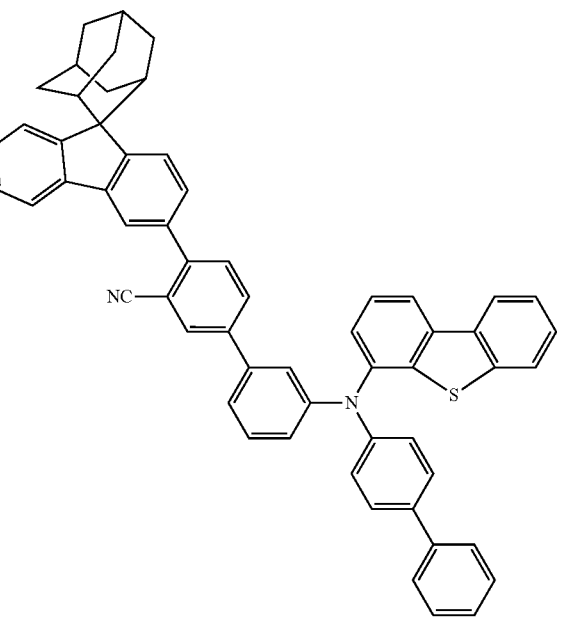

211
-continued
493
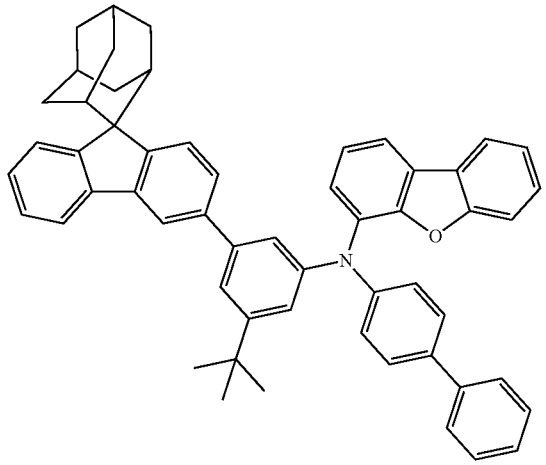
494
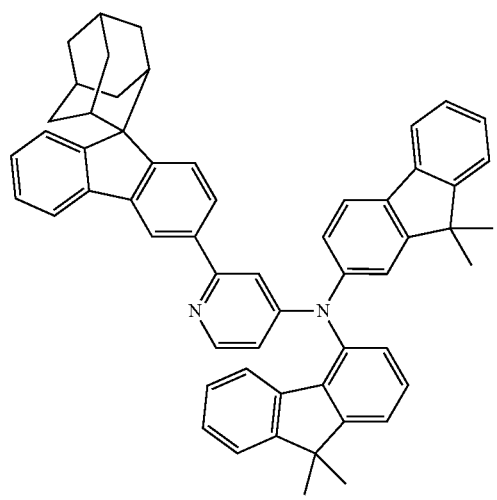
495
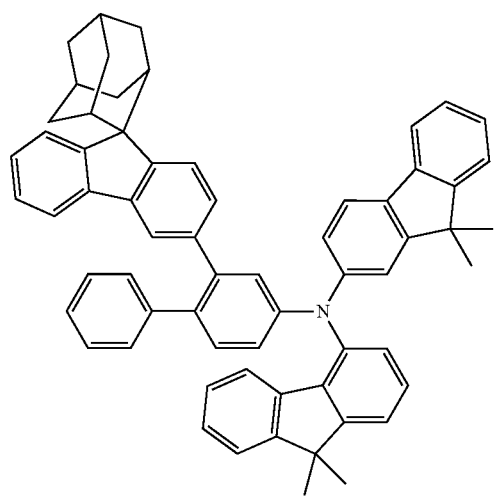
212
-continued
496
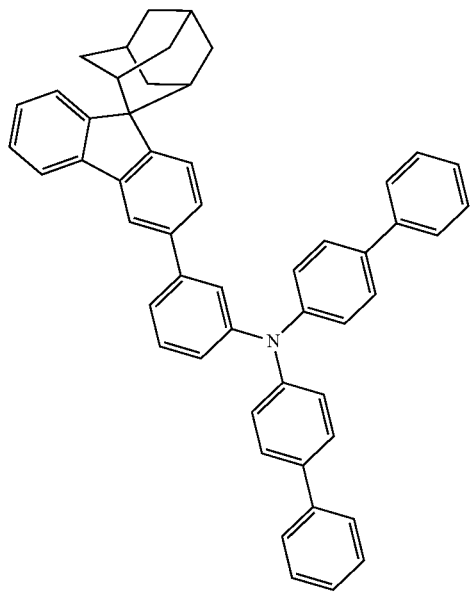
497
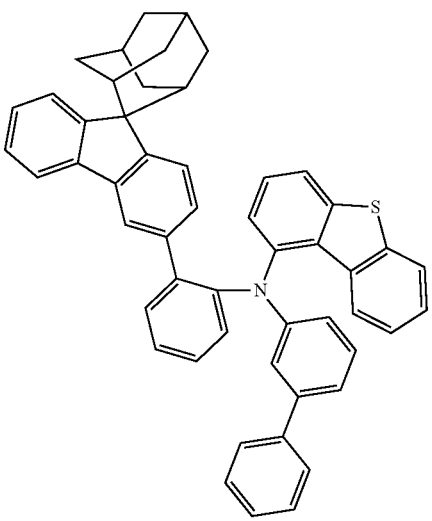
498
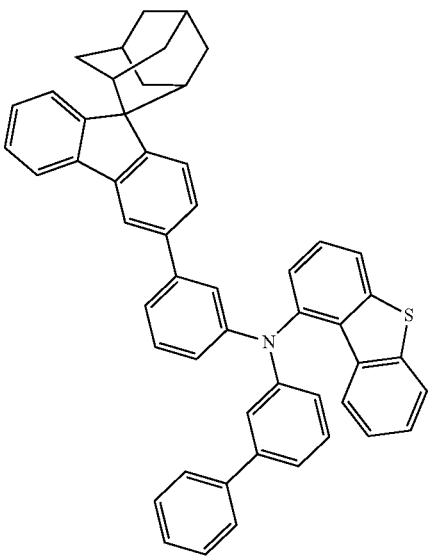

499
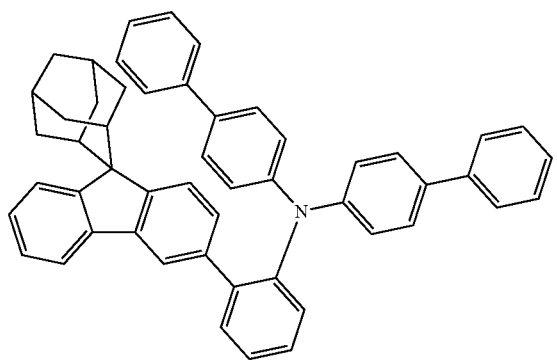
500
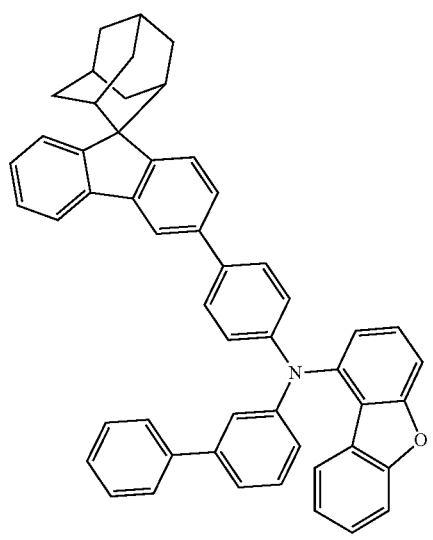
501
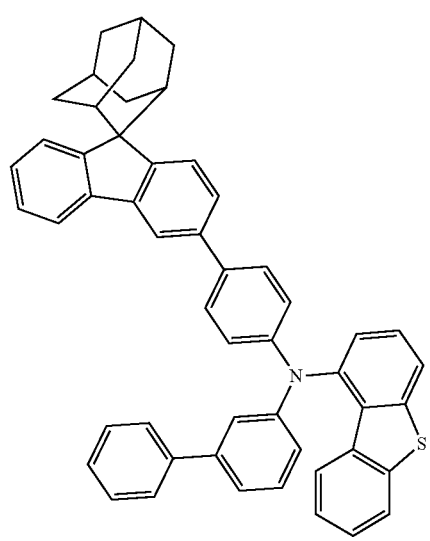
502
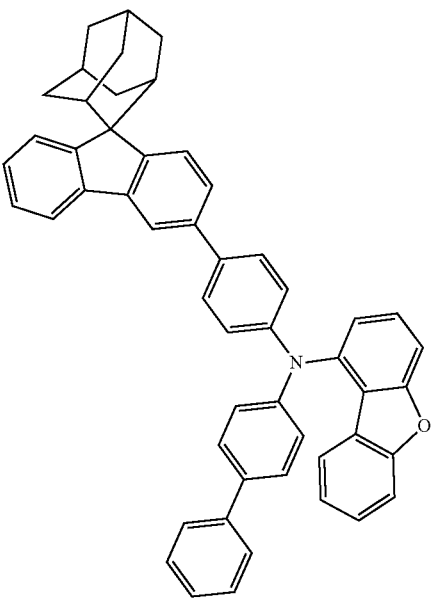
503
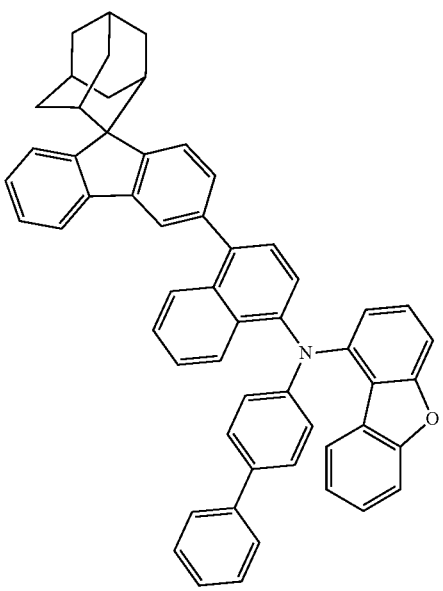

215
-continued
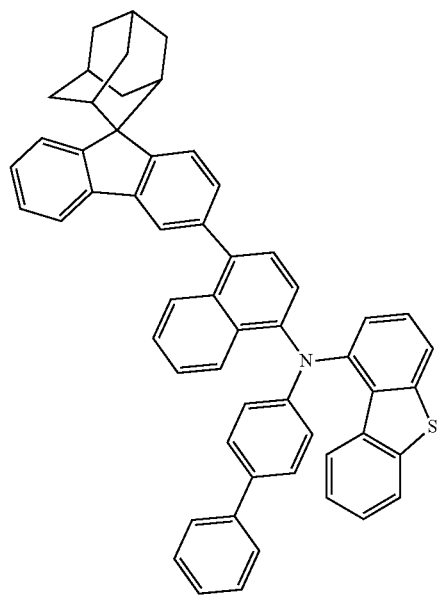
504
216
-continued
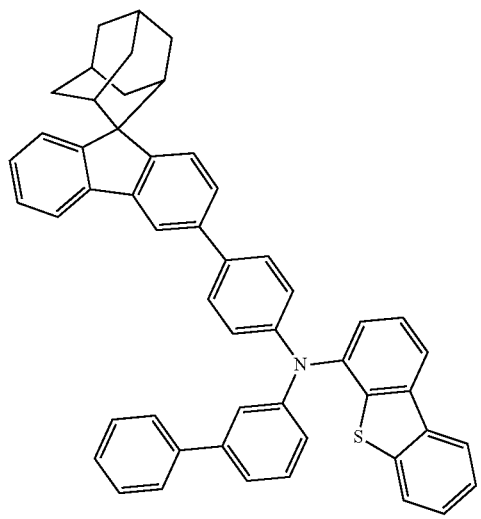
506
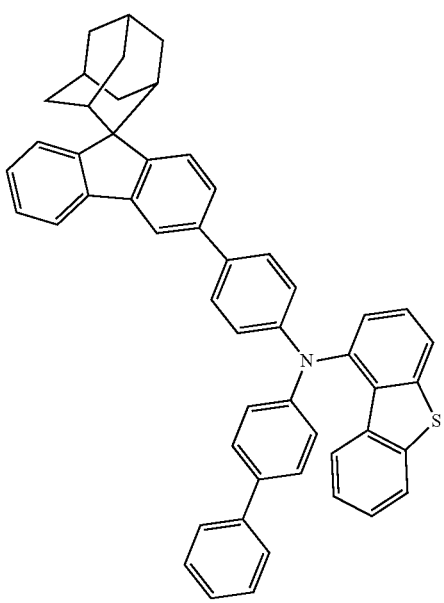
505
507

217
-continued
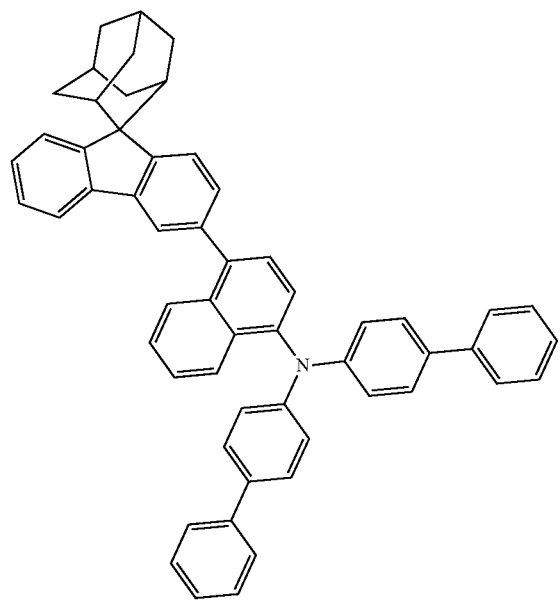
508
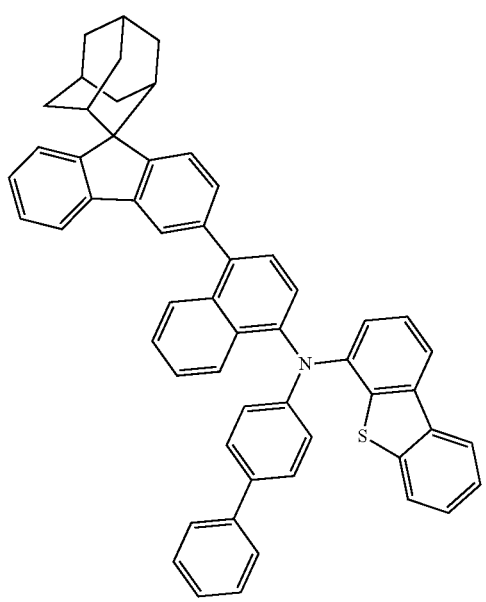
509
218
-continued
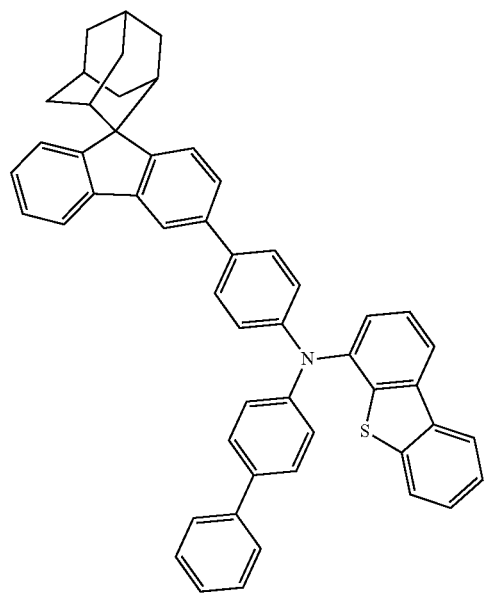
510
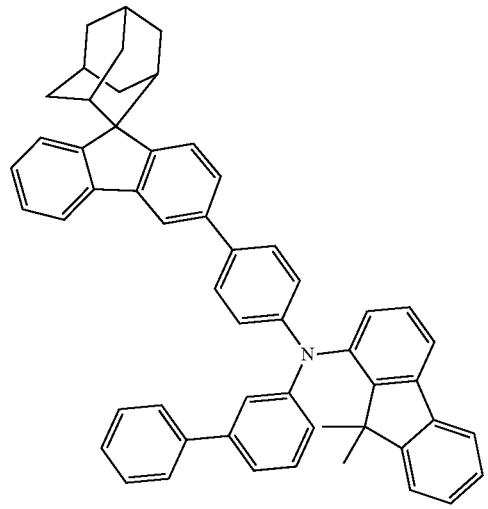
511

219
-continued
512
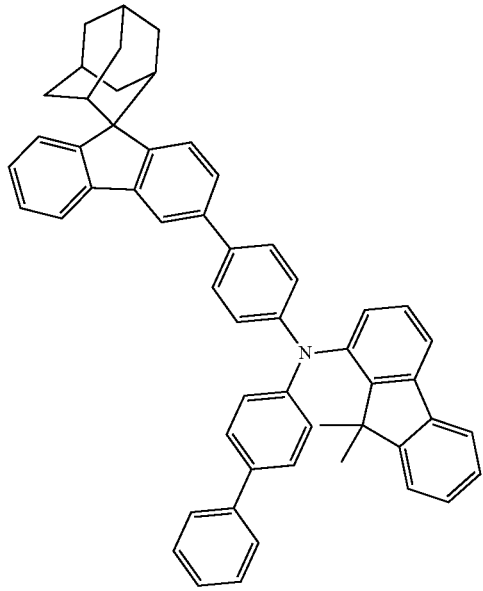
513
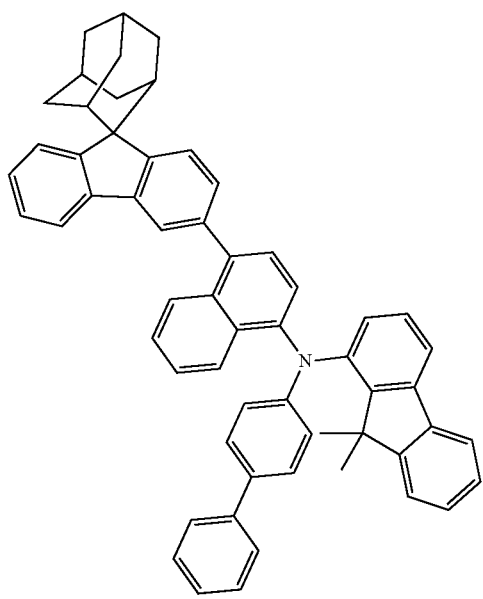
220
-continued
514
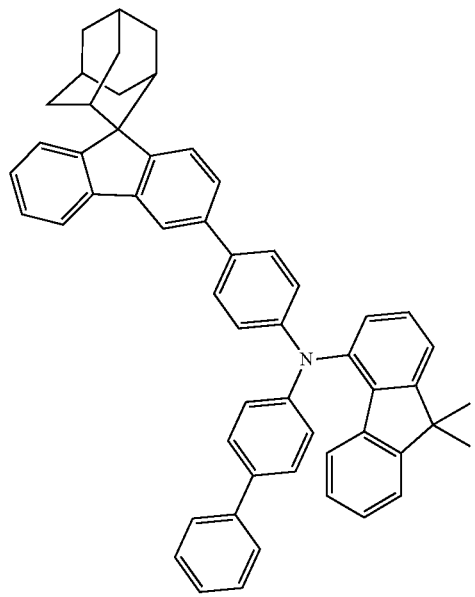
515
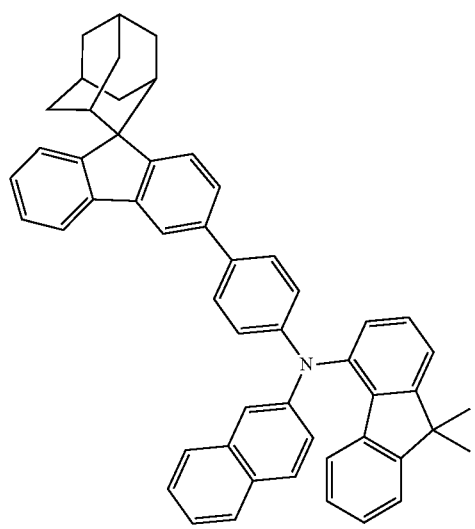
516
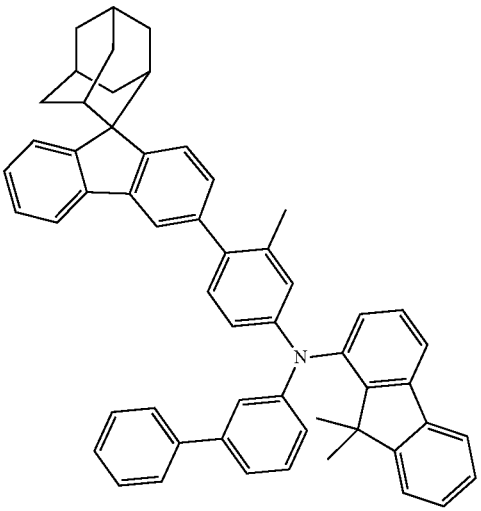

221
-continued
517
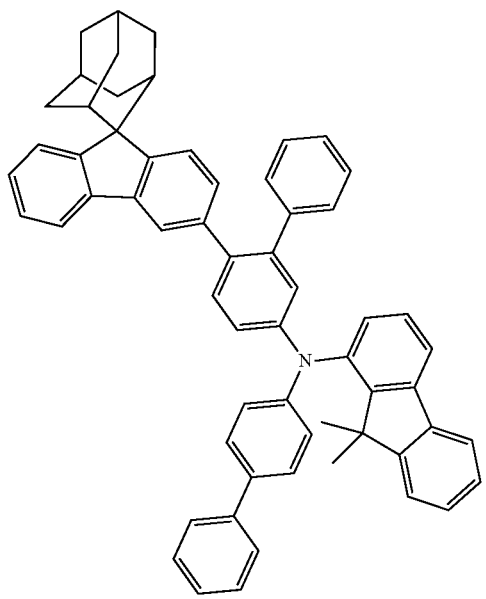
518
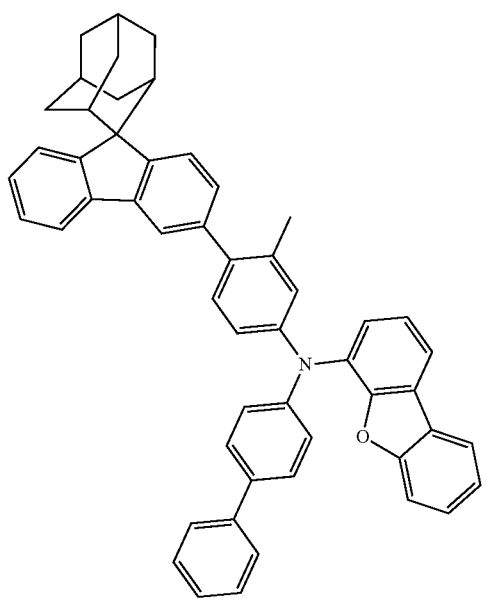
222
-continued
519
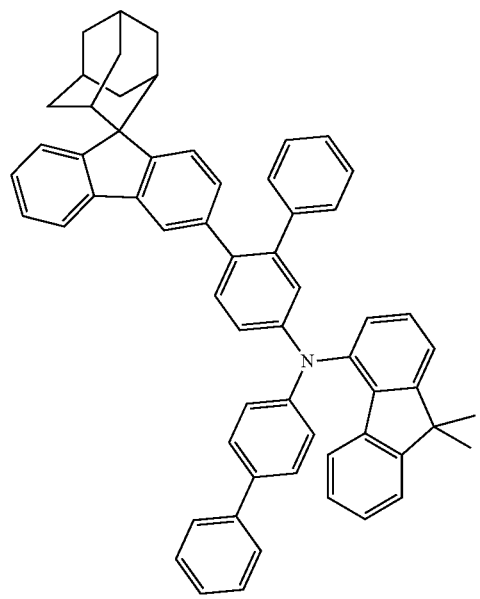
520
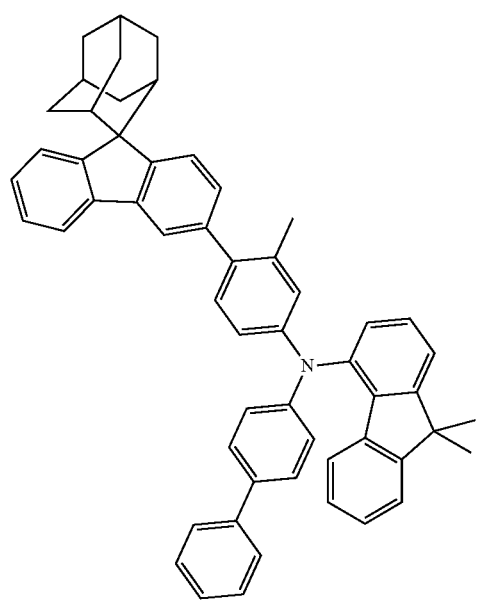

223
-continued
521
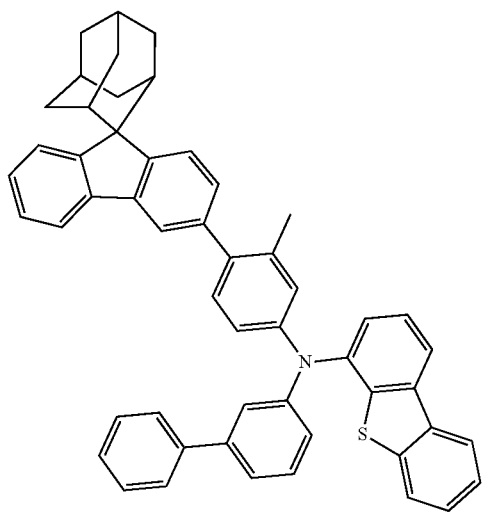
522
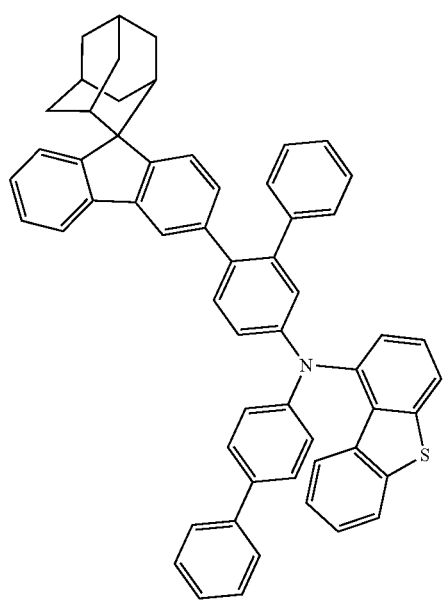
224
-continued
523
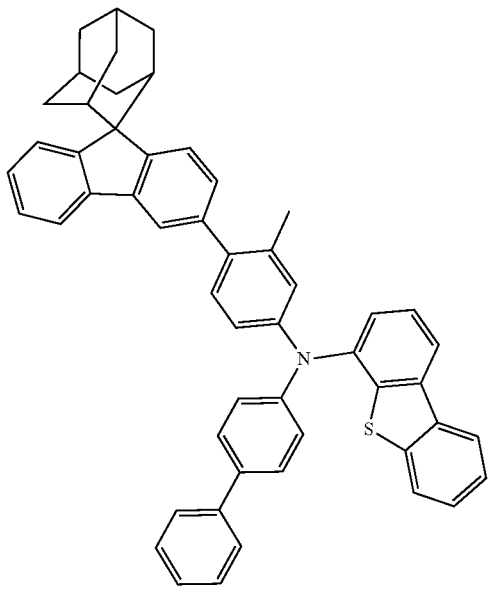
524
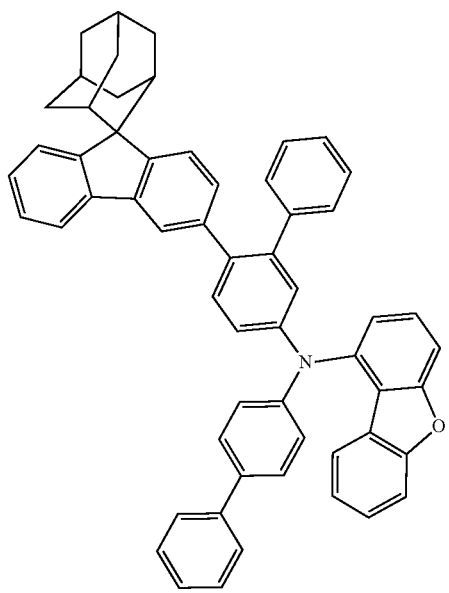

225
-continued
525
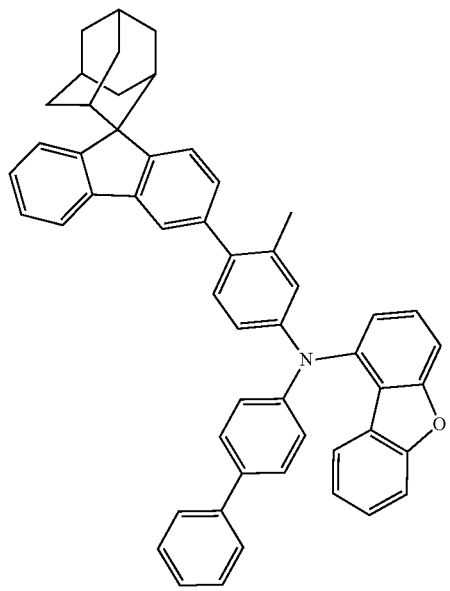
526
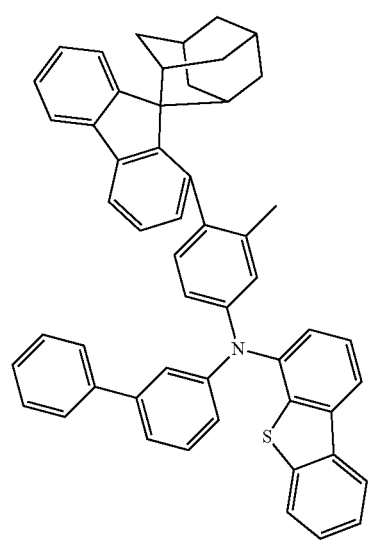
527
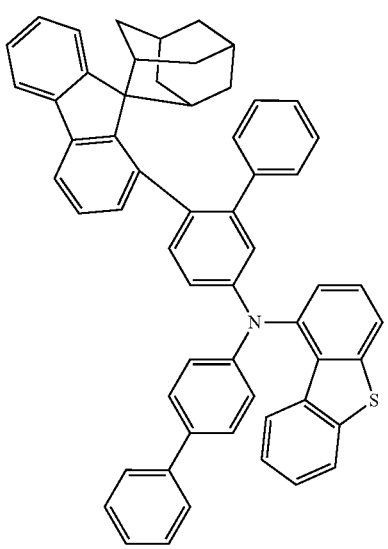
226
-continued
528
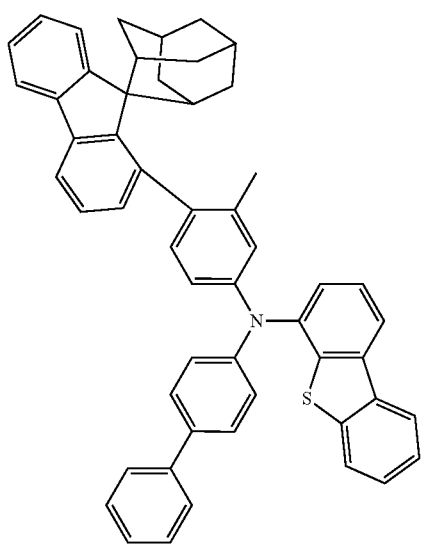
529
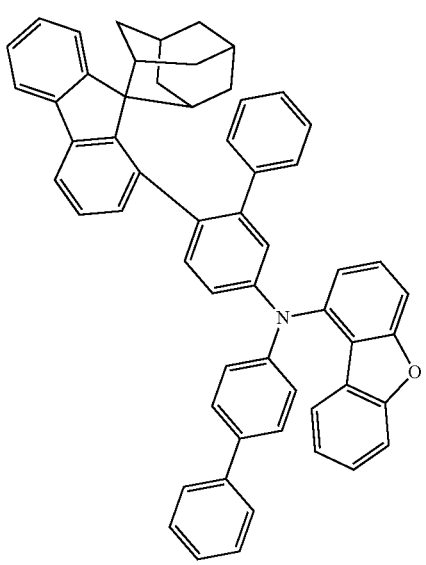
530
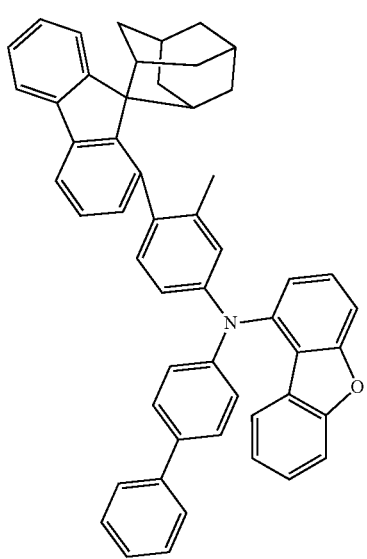

227
-continued
531
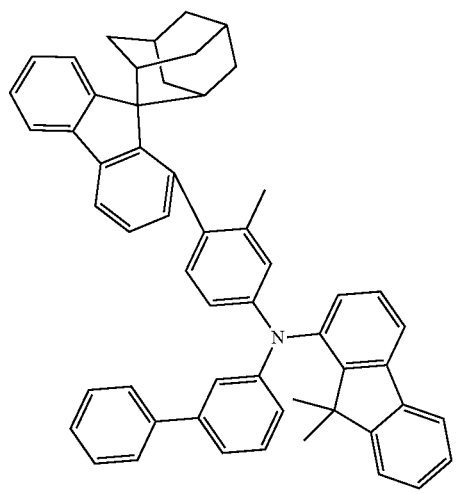
532
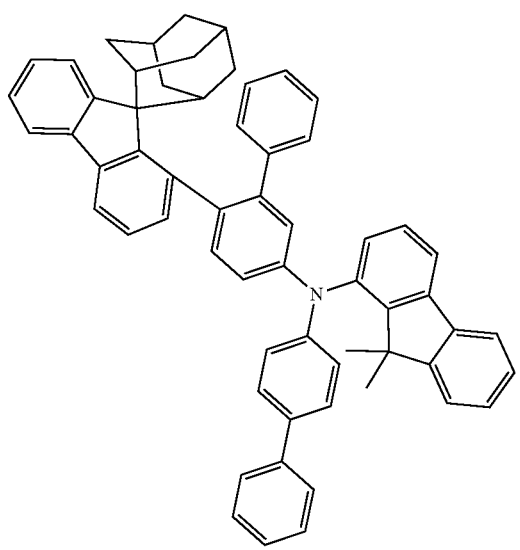
533
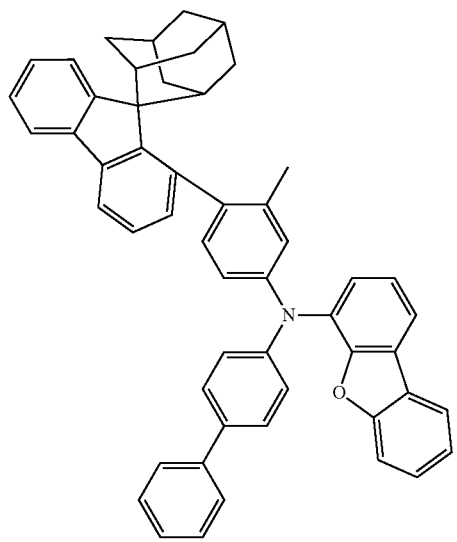
228
-continued
534
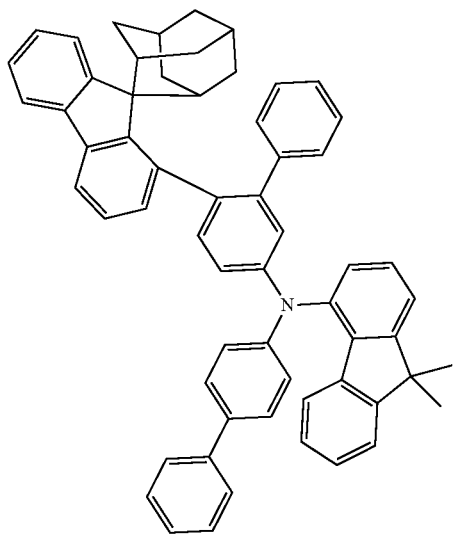
535
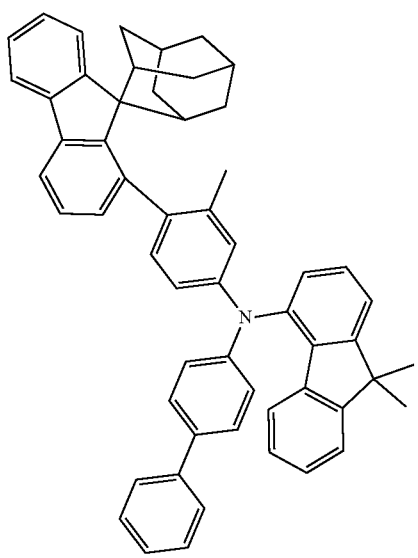
536
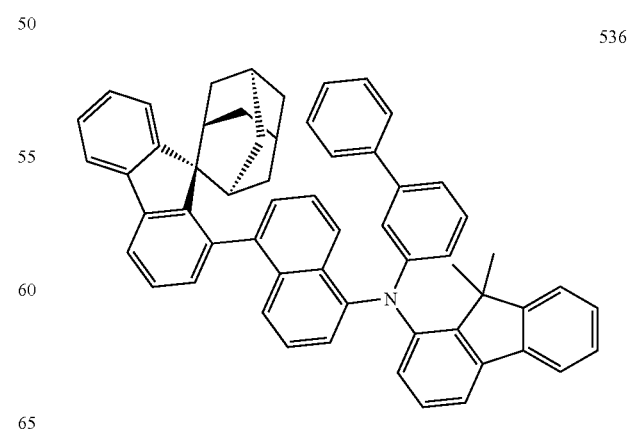

229
-continued
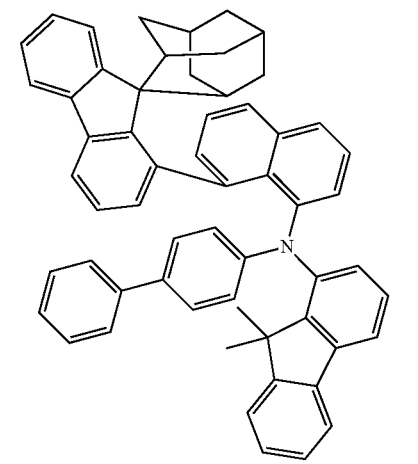
537
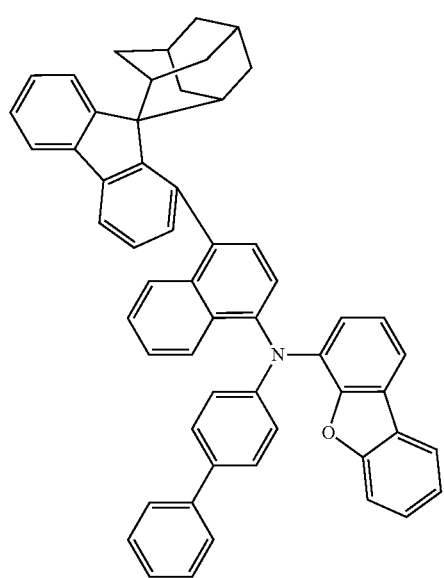
538
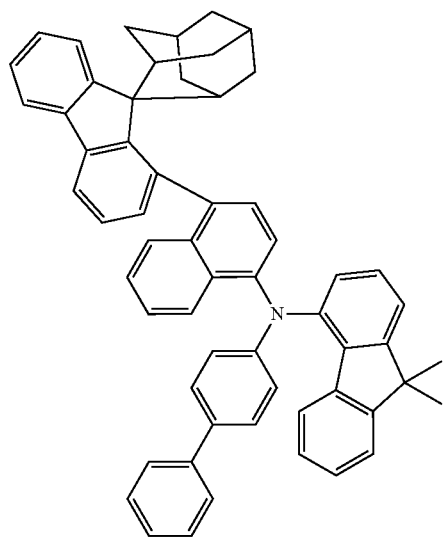
539
230
-continued
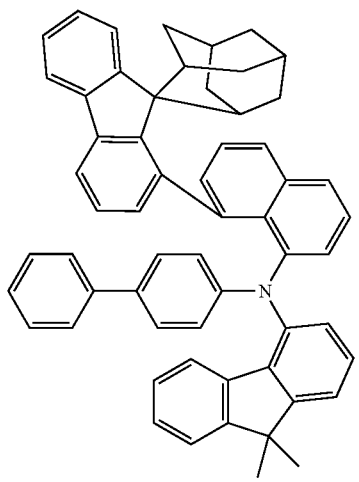
540
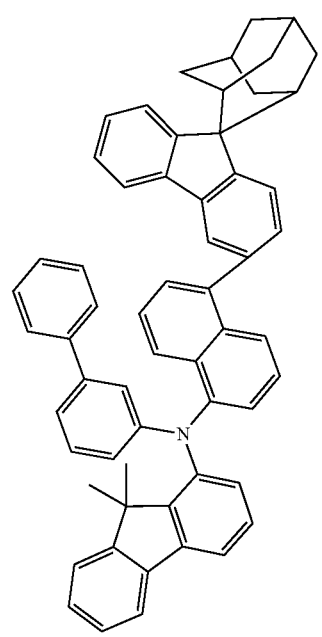
541

542
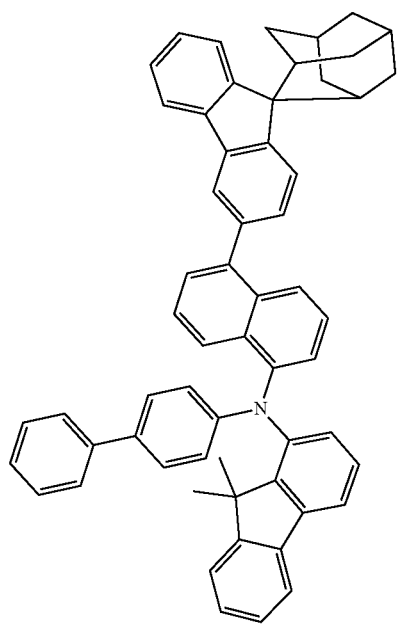
543
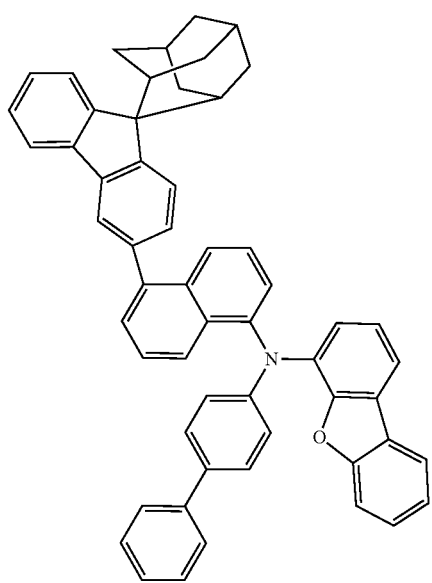
544
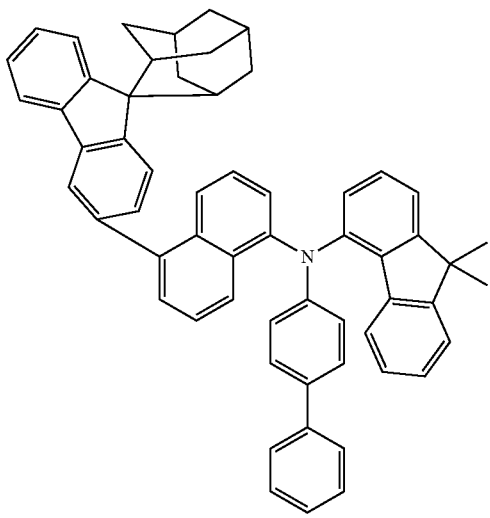
545
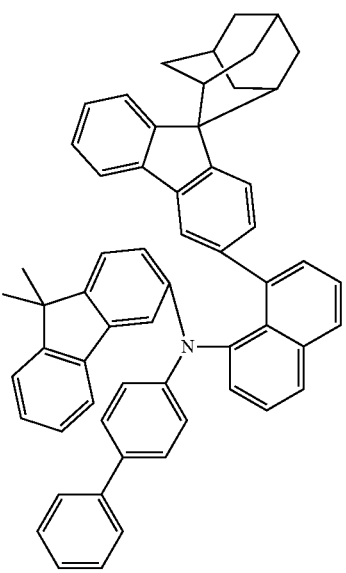

-continued
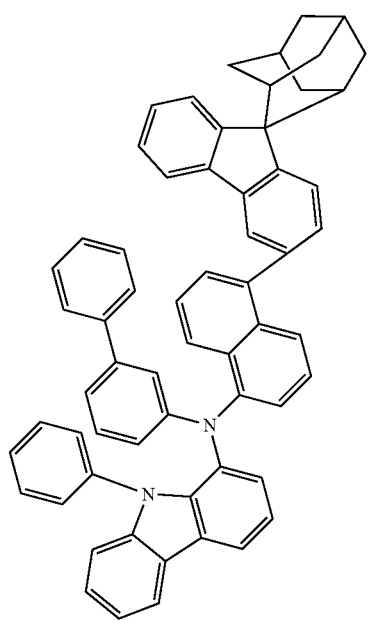
546
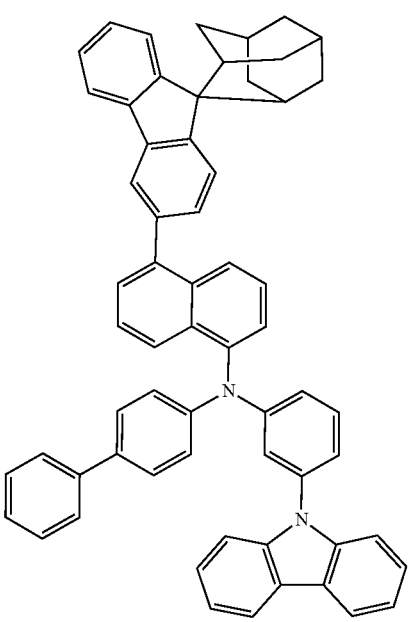
548
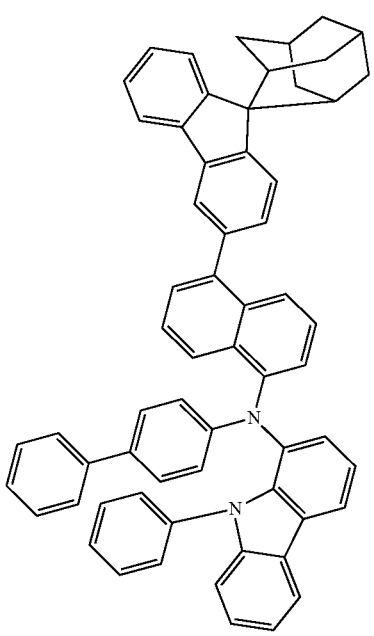
547
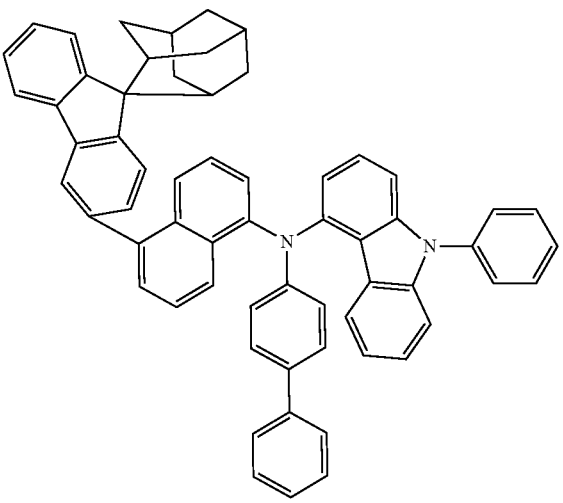
549

235
-continued
550
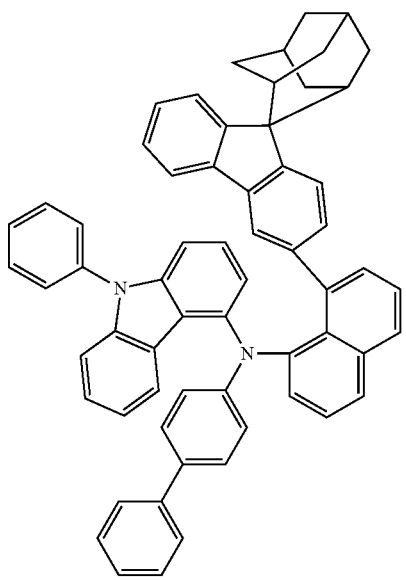
551
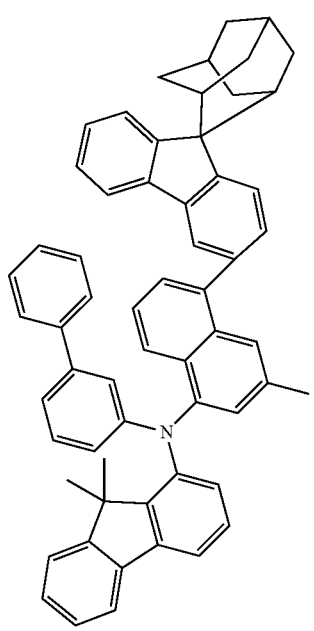
236
-continued
552
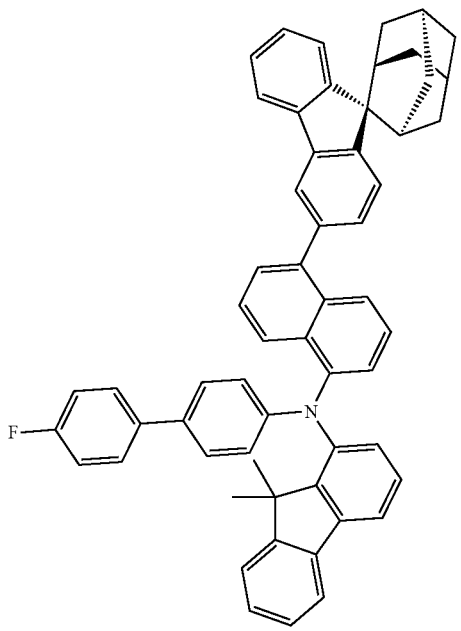
553
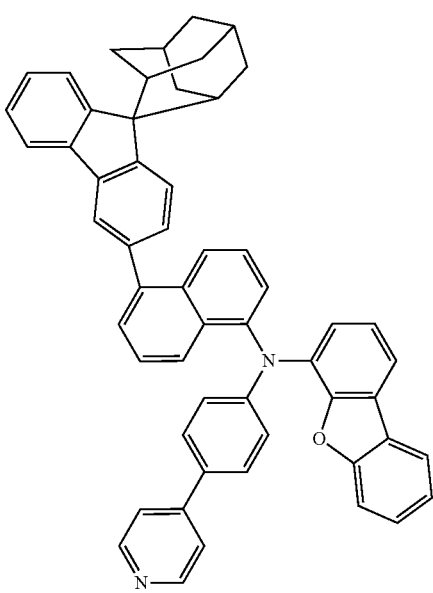

554
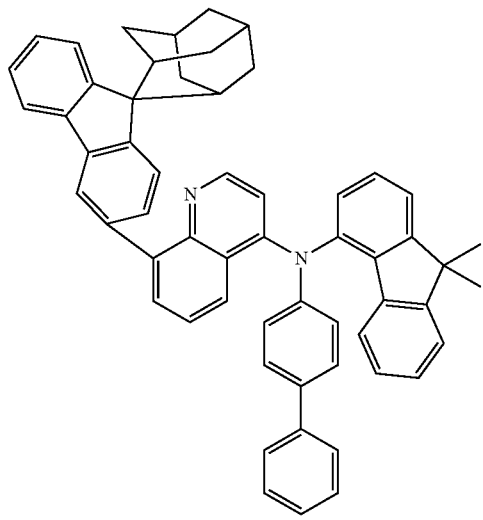
555
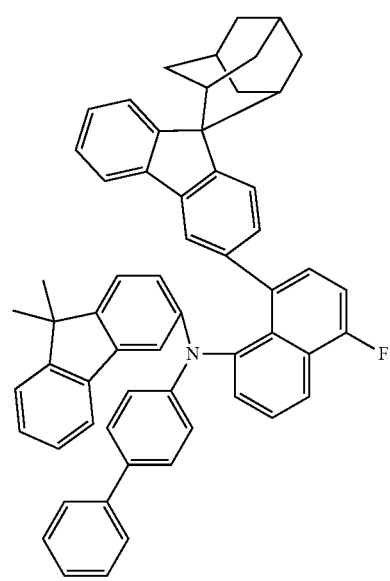
556
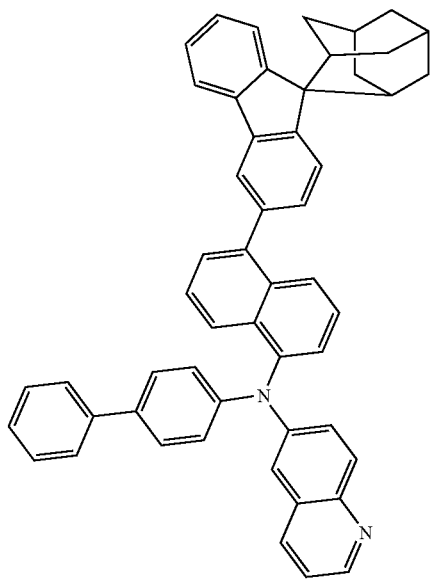
557
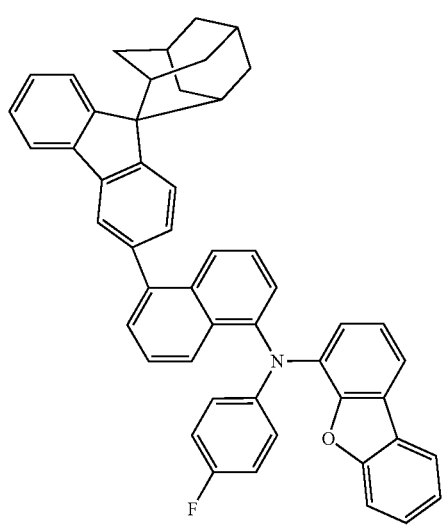
558
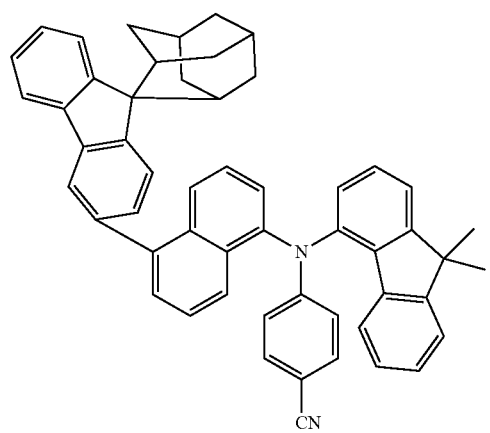
559
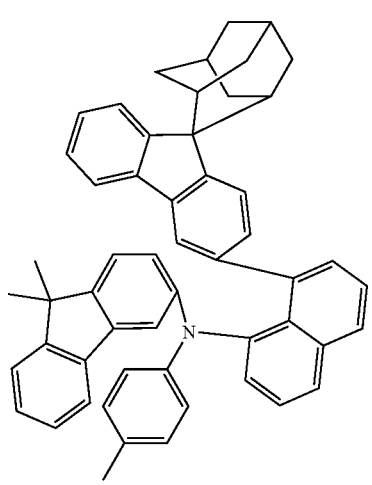

239
-continued
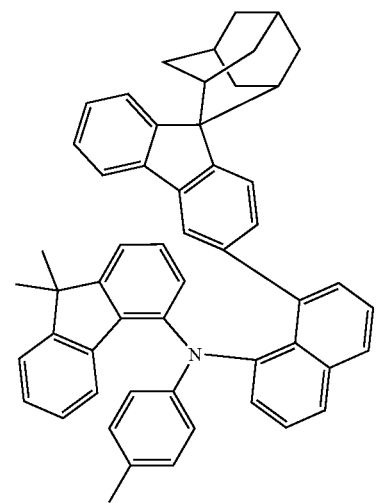
560
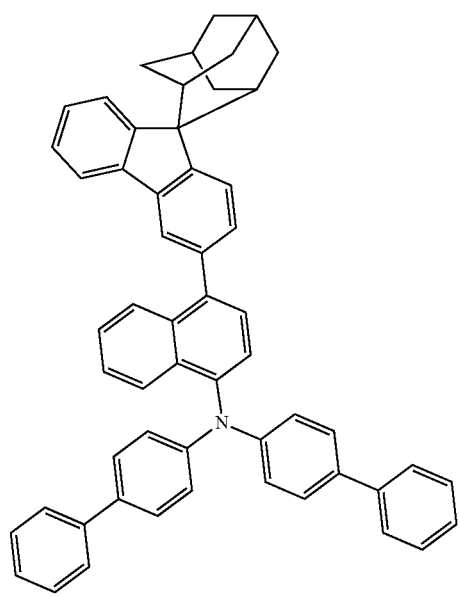
561
240
-continued
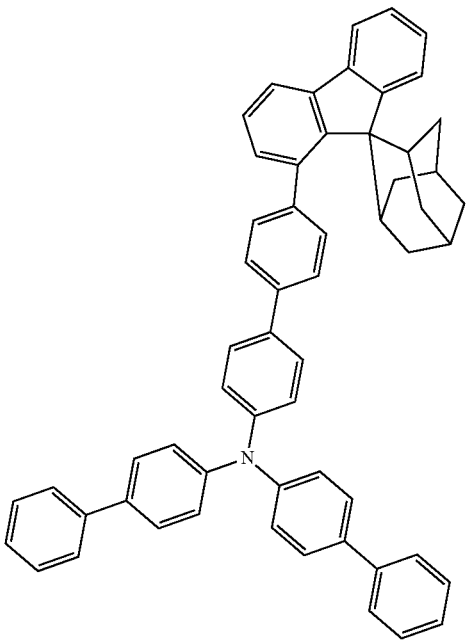
562
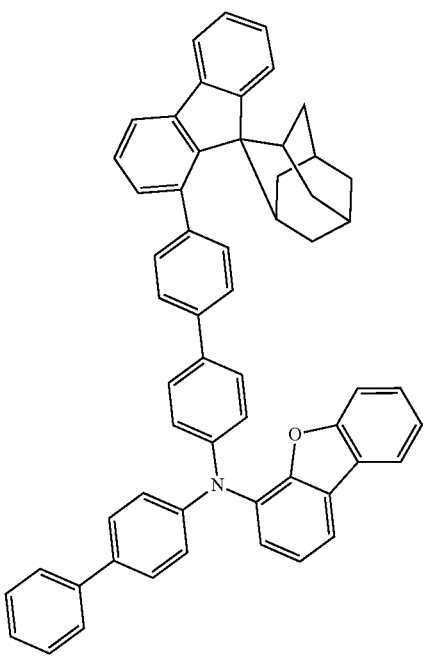
563

564
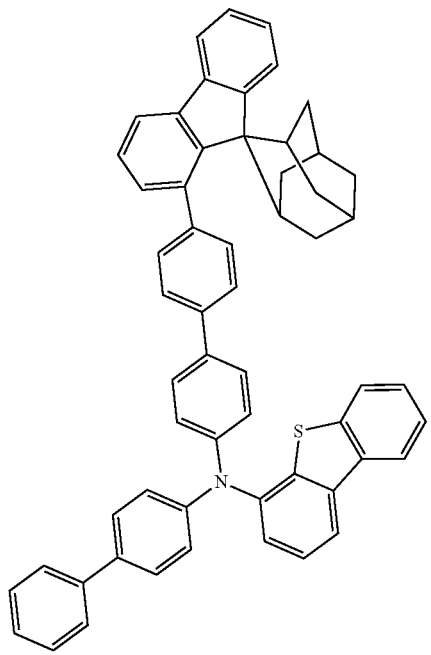
565
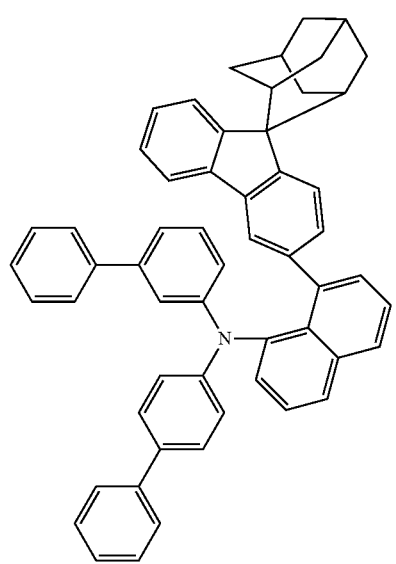
566
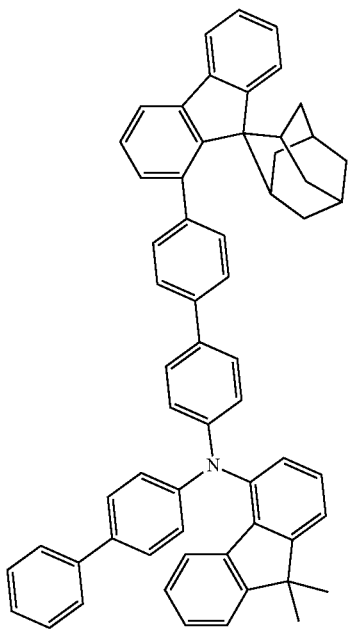
567
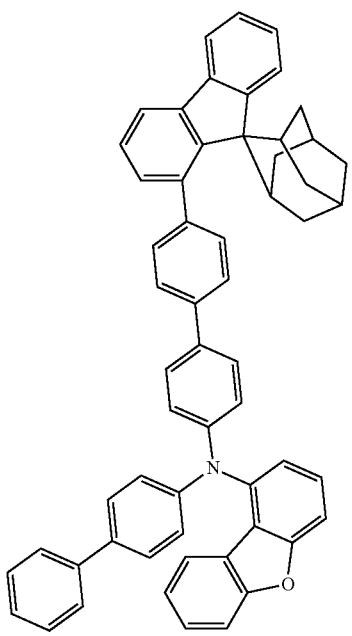

243
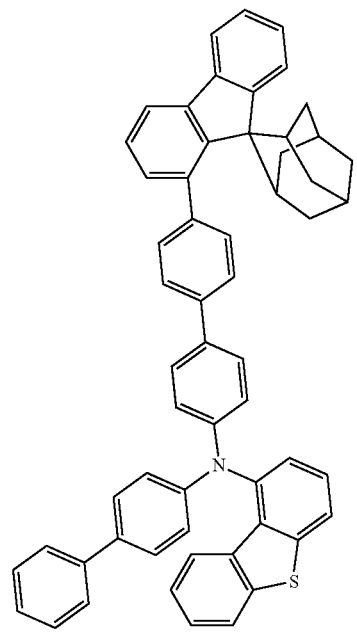
568
244
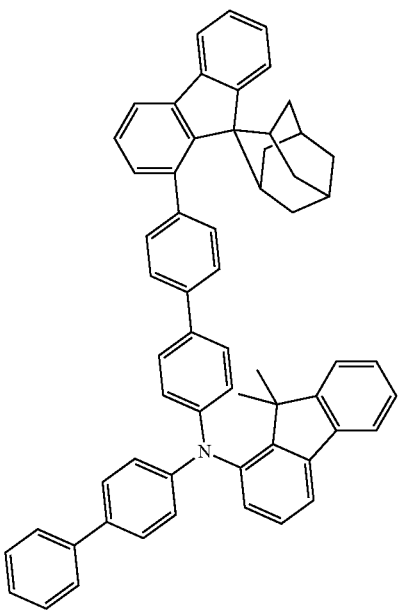
570
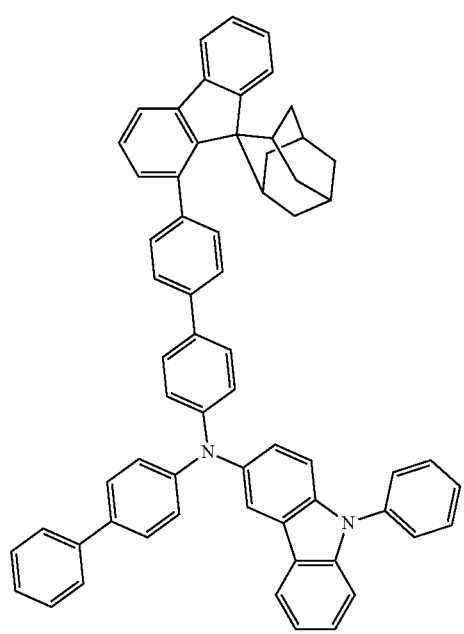
569
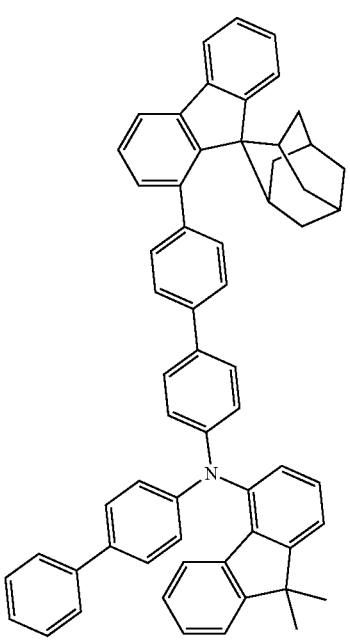
571

245
-continued
572
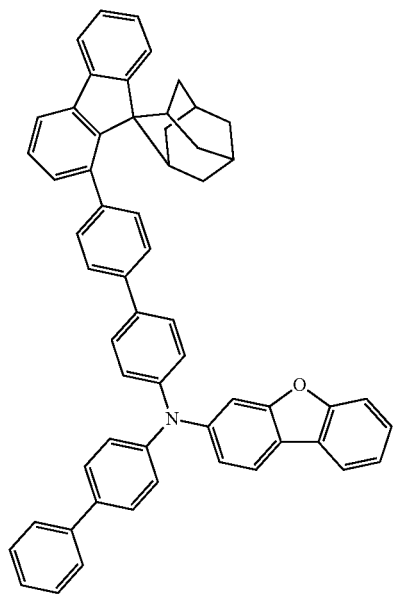
573
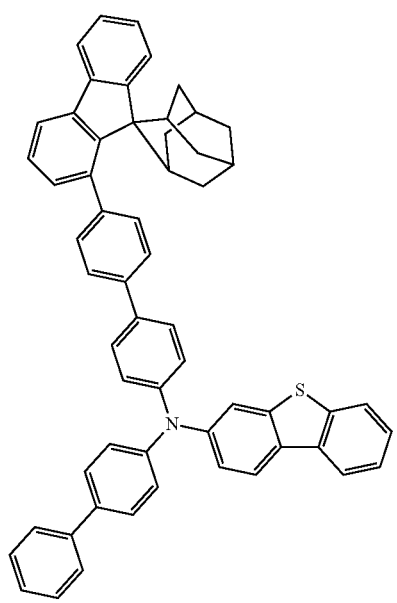
246
-continued
574
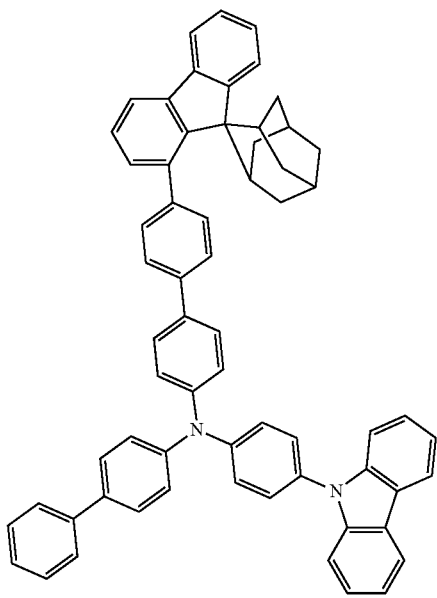
575
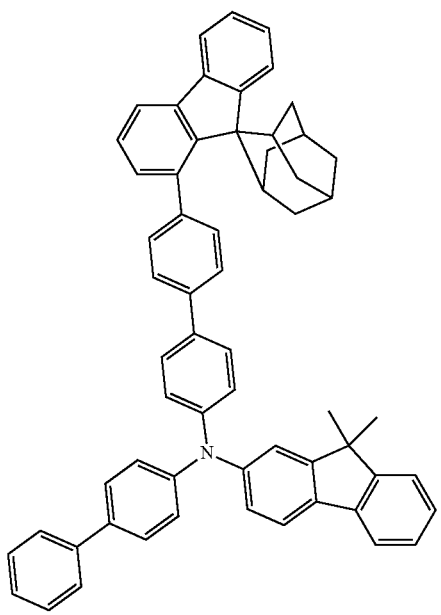

576
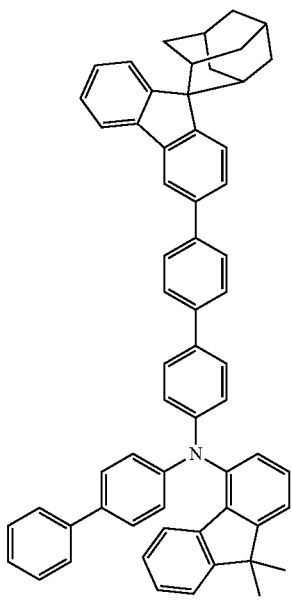
578
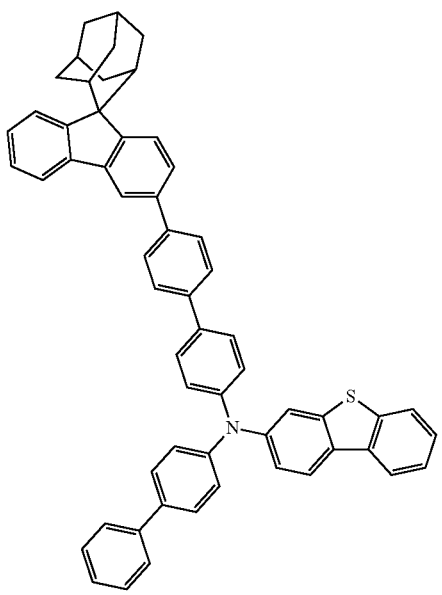
577
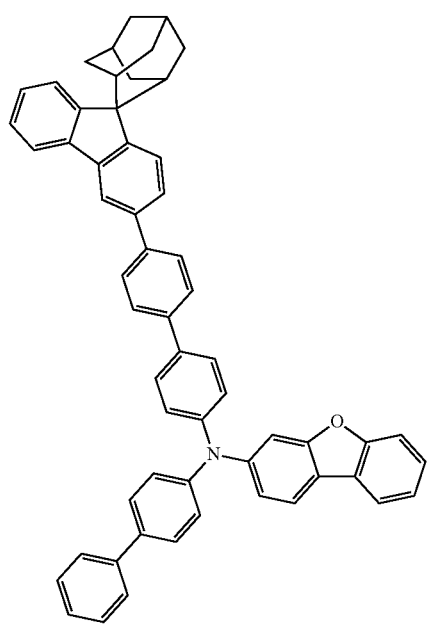
579
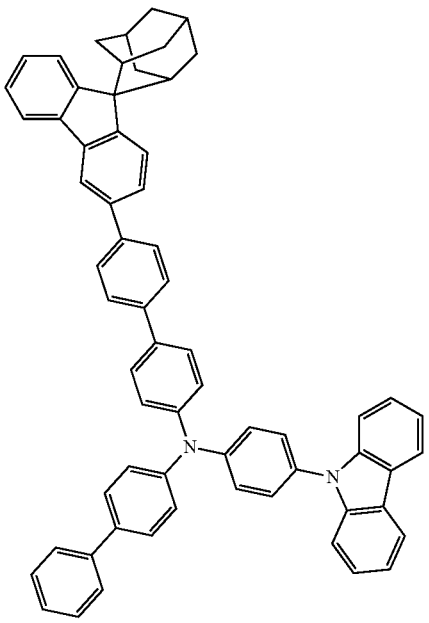

249
-continued
580
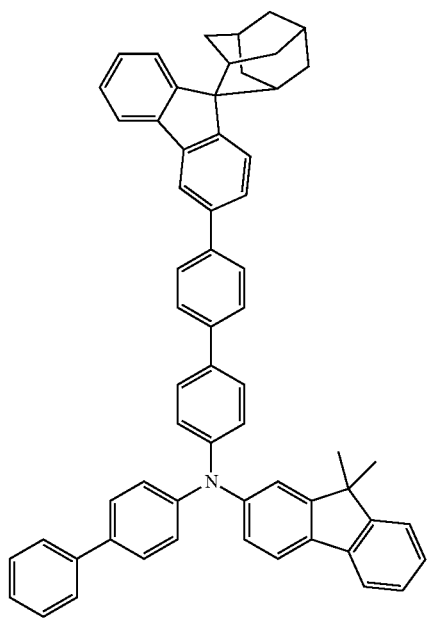
581
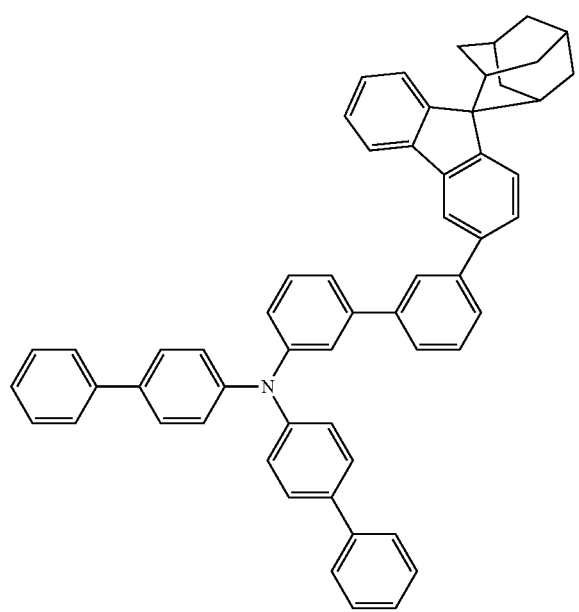
250
-continued
582
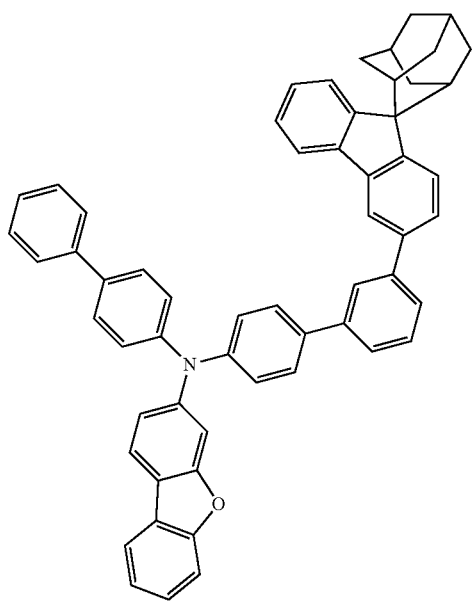
583
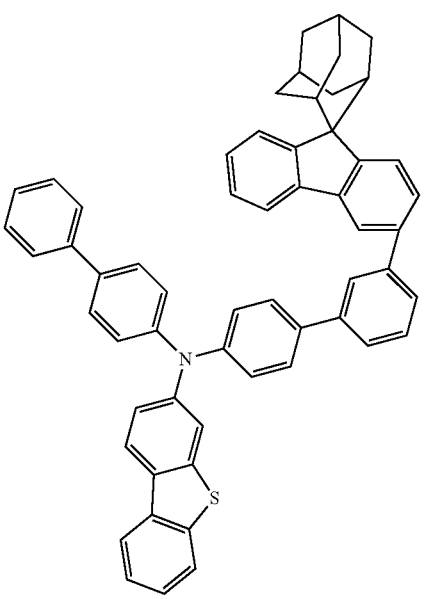

584
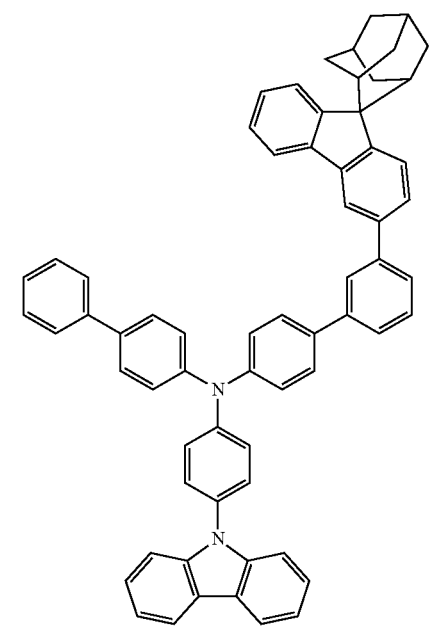
585
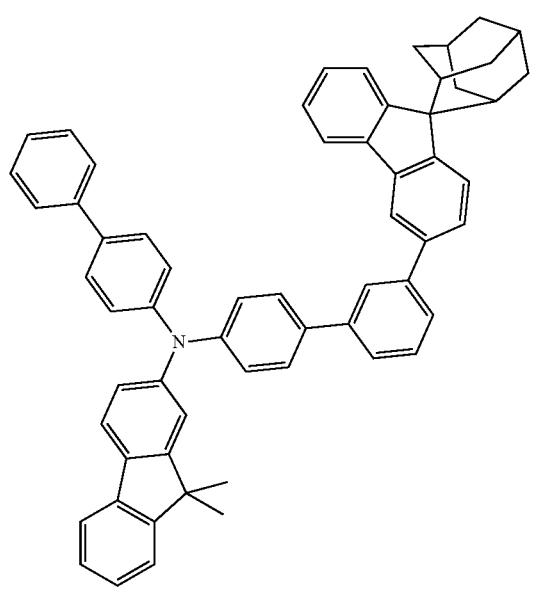
586
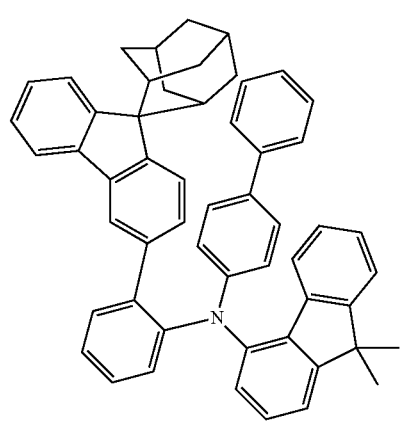
587
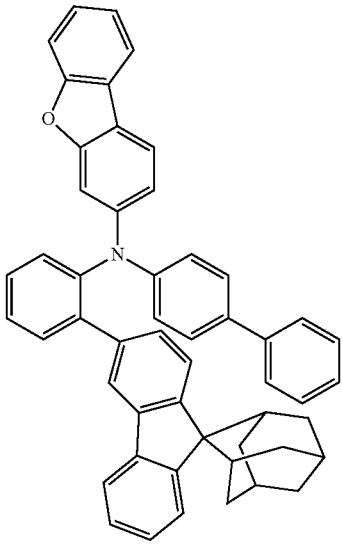
588
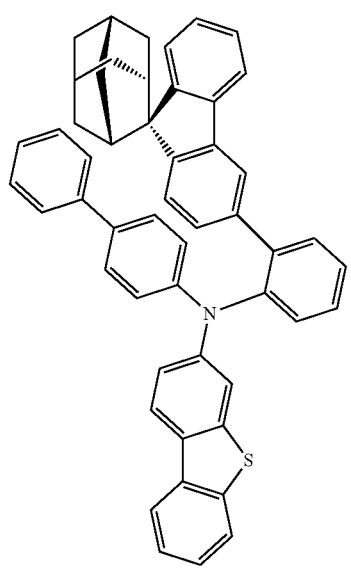
589
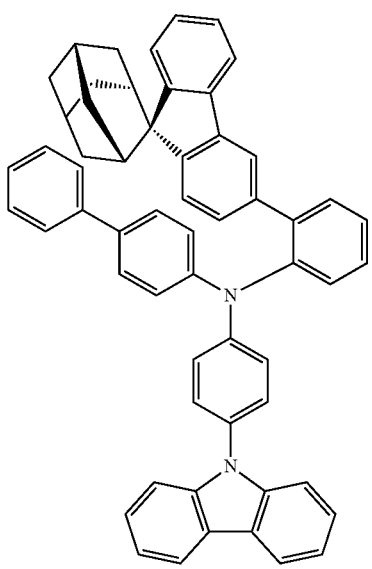

253
-continued
590
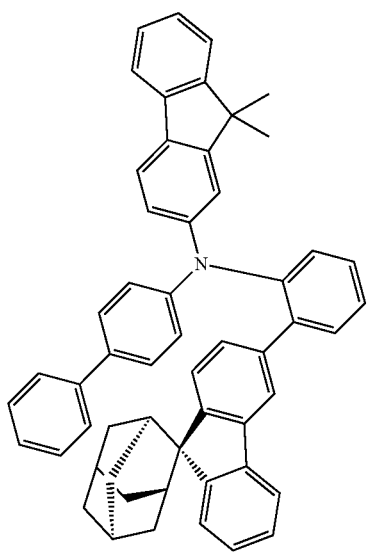
591
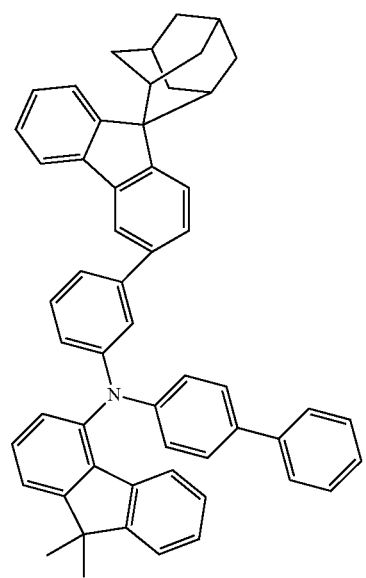
254
-continued
592
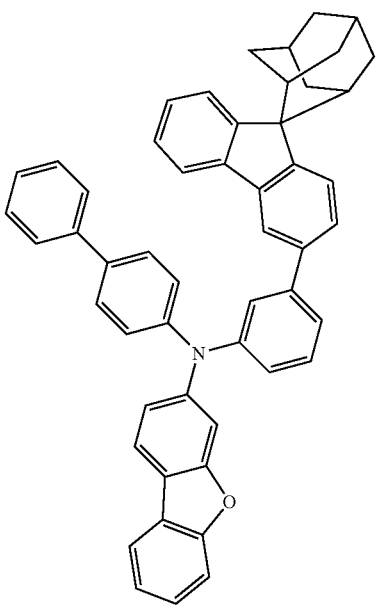
593
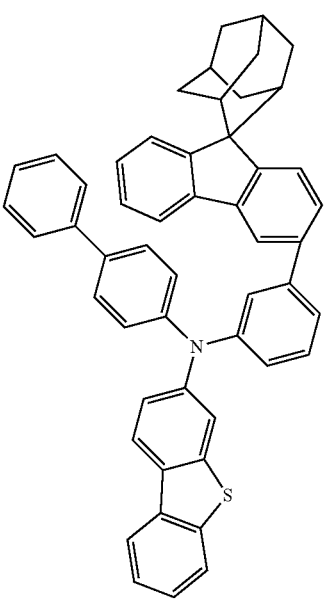

255
-continued
594
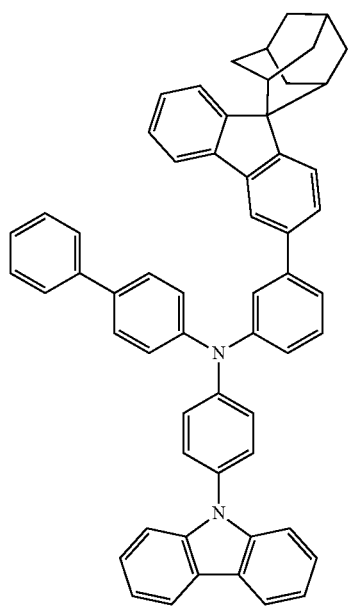
595
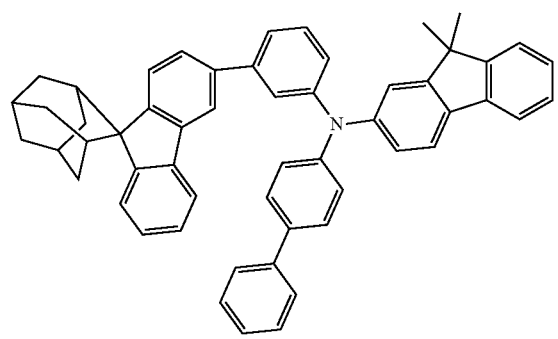
596
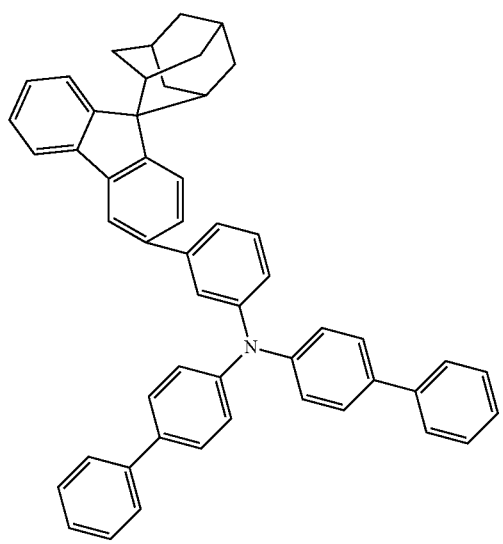
256
-continued
597
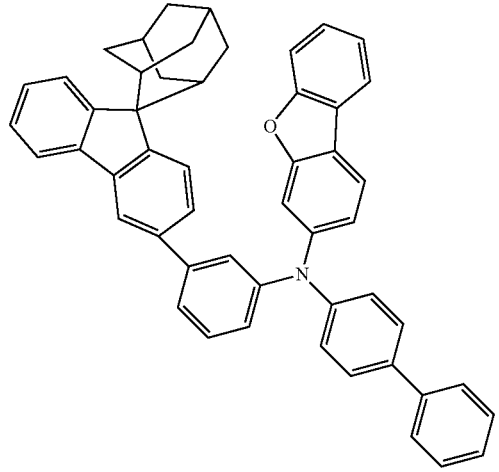
598
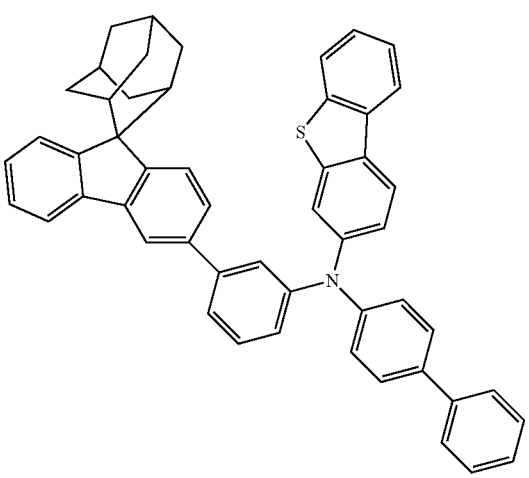
599
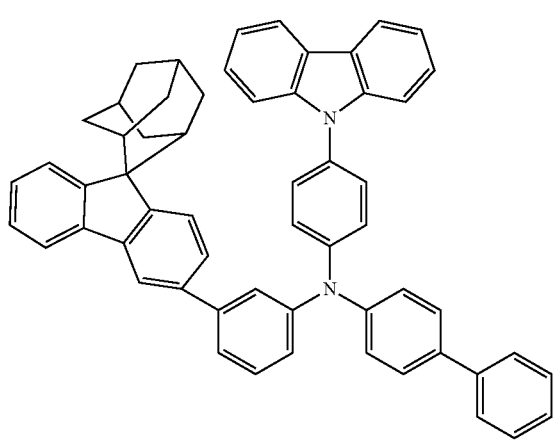

257
-continued
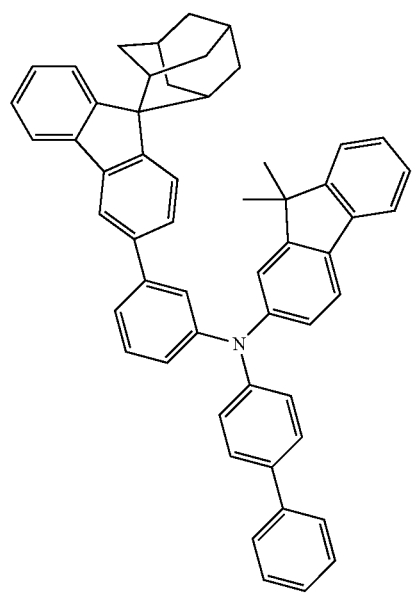
600
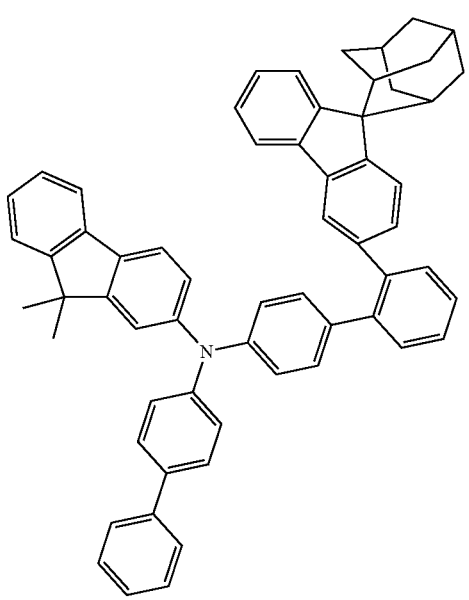
601
258
-continued
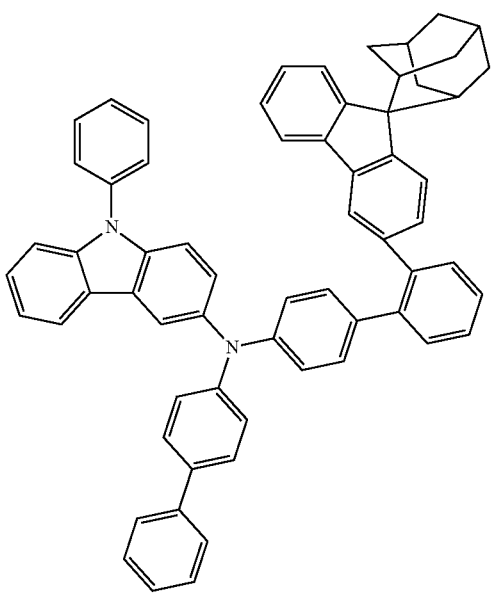
602
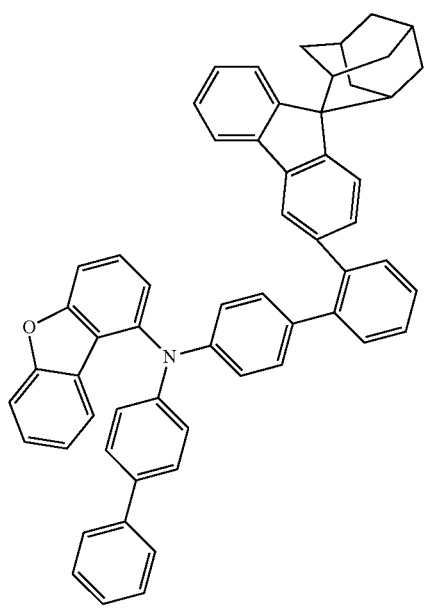
603

259
-continued
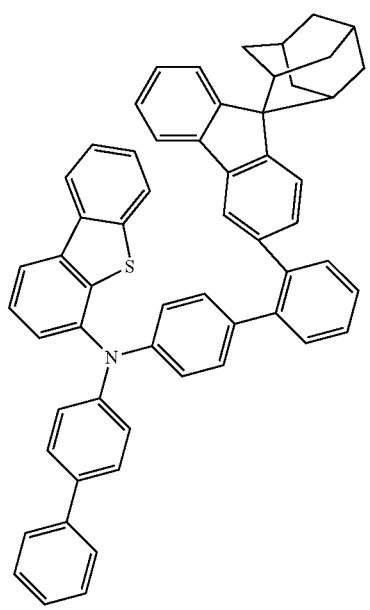
604
260
-continued
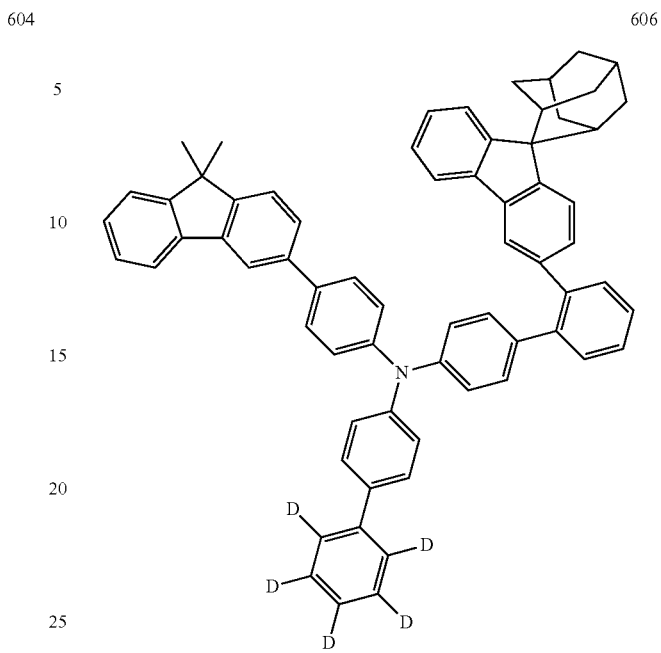
606
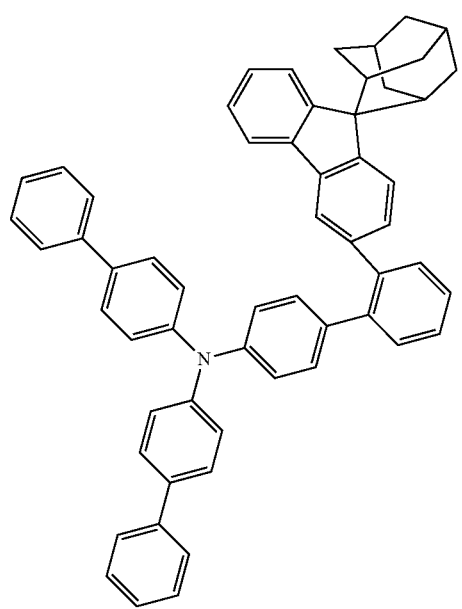
605
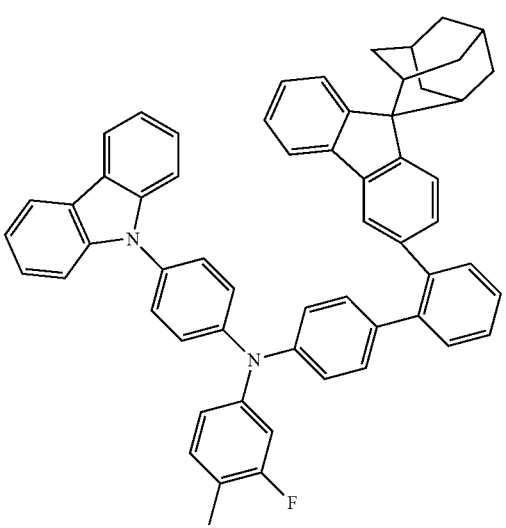
607

608
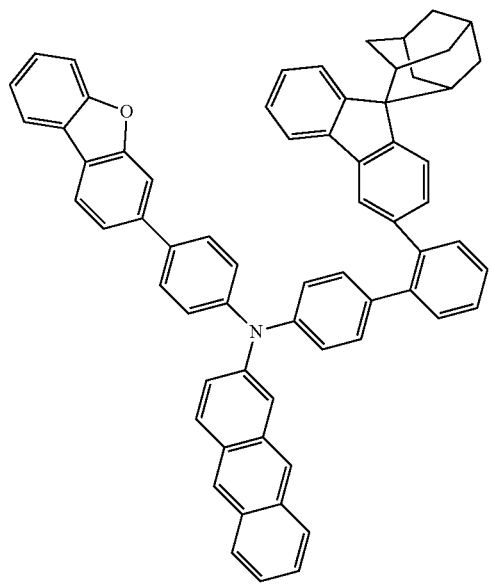
609
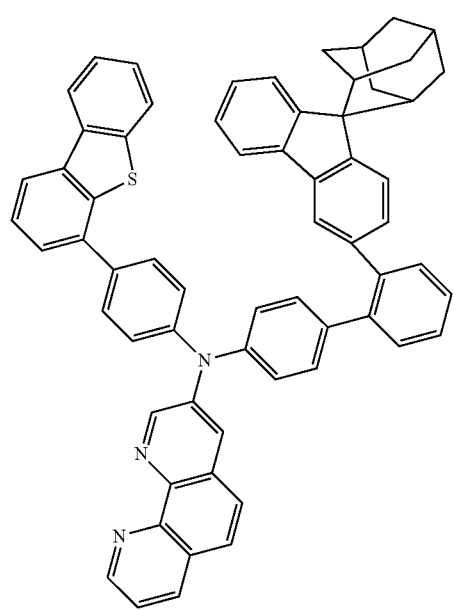
610
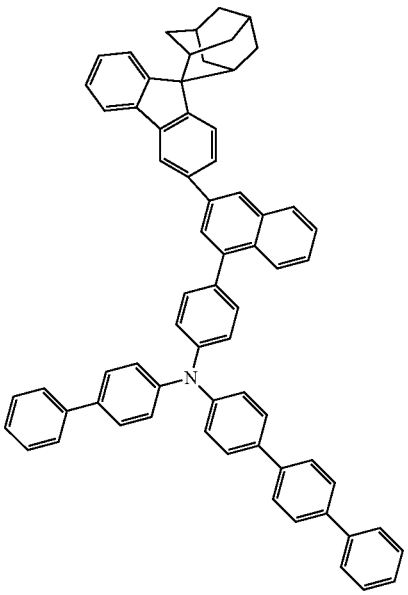
611
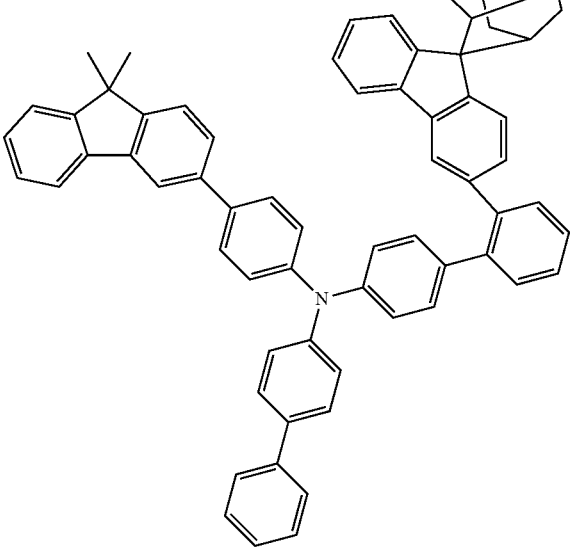

263
-continued
612
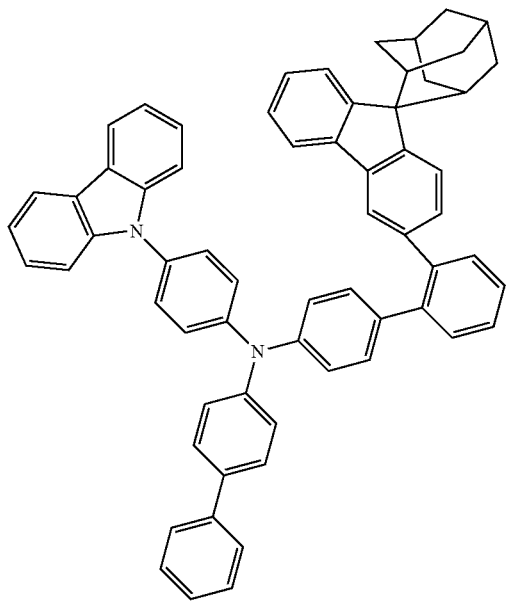
613
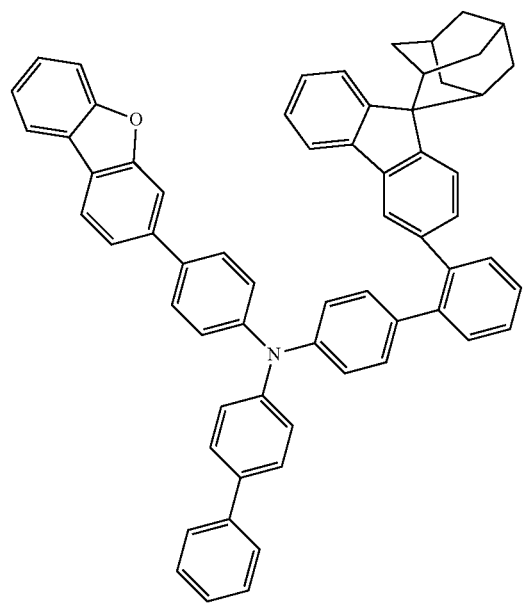
264
-continued
614
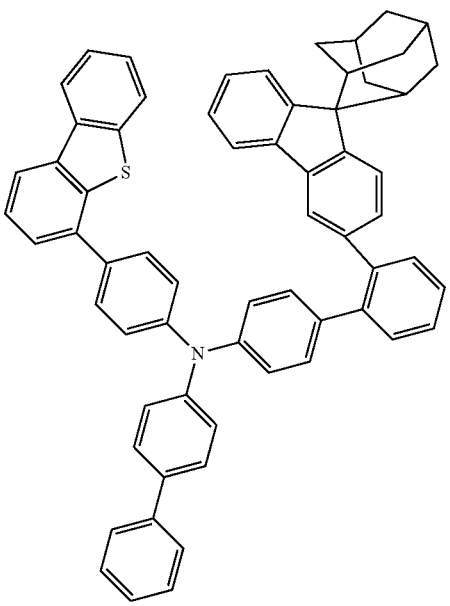
615
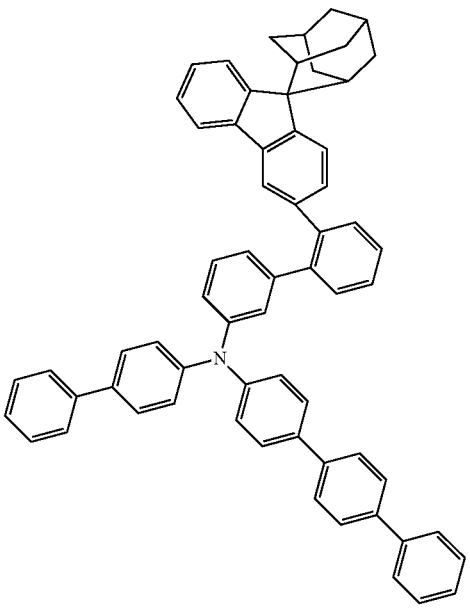

265
-continued
616
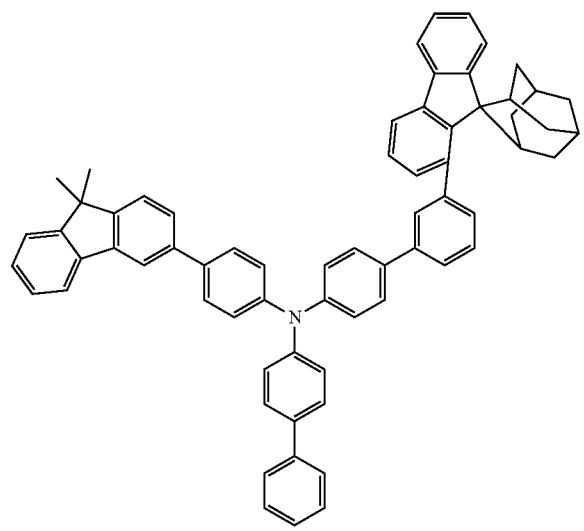
617
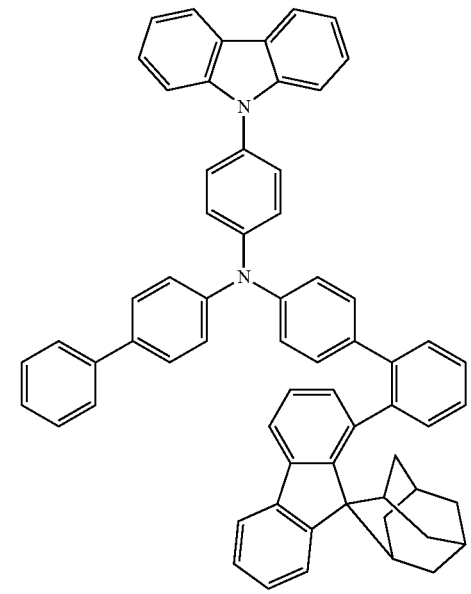
266
-continued
618
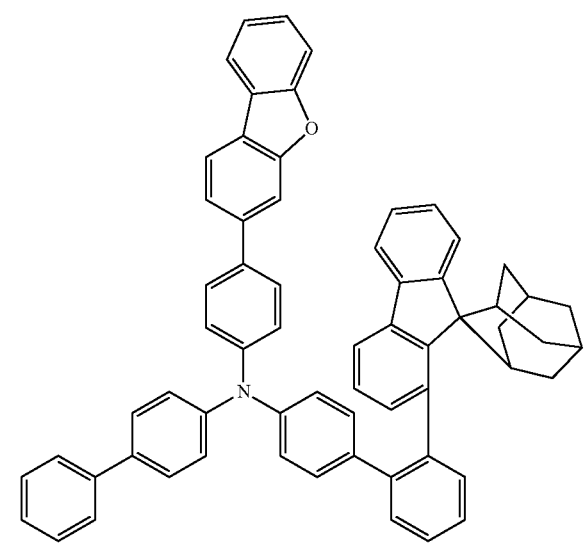
619
620
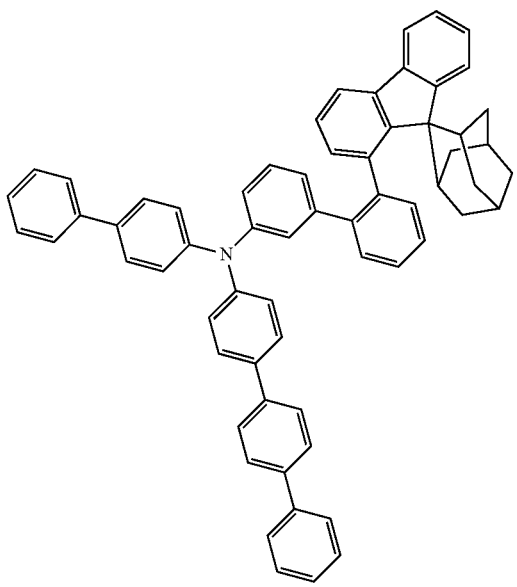

267
-continued
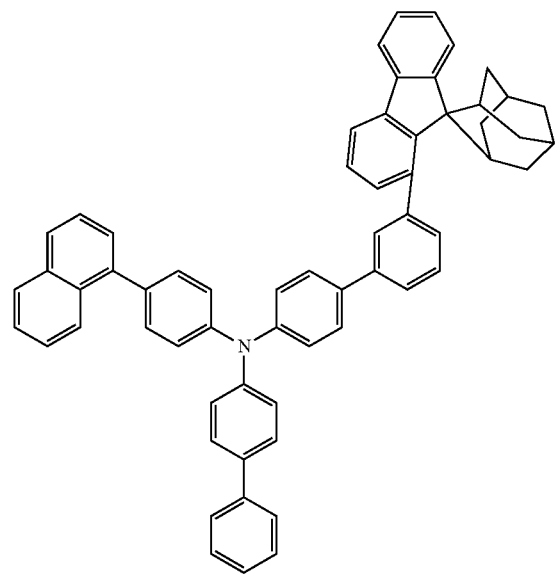
621
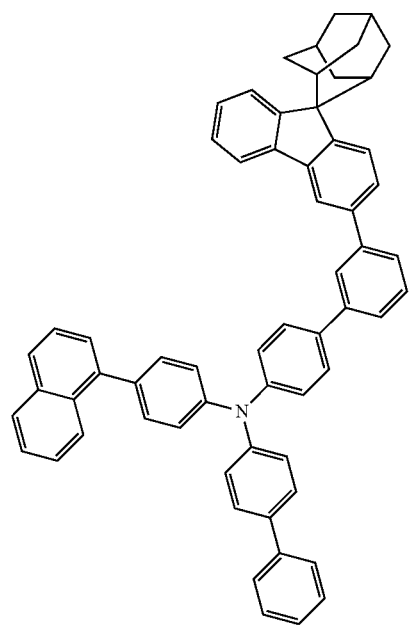
622
268
-continued
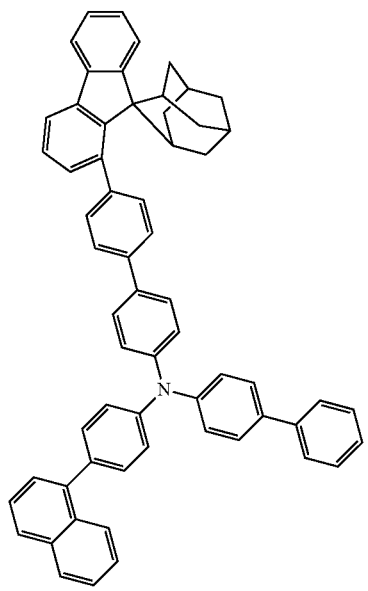
623
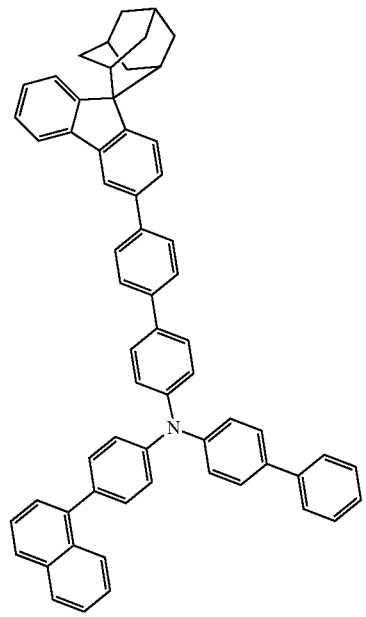
624

269
-continued
270
-continued
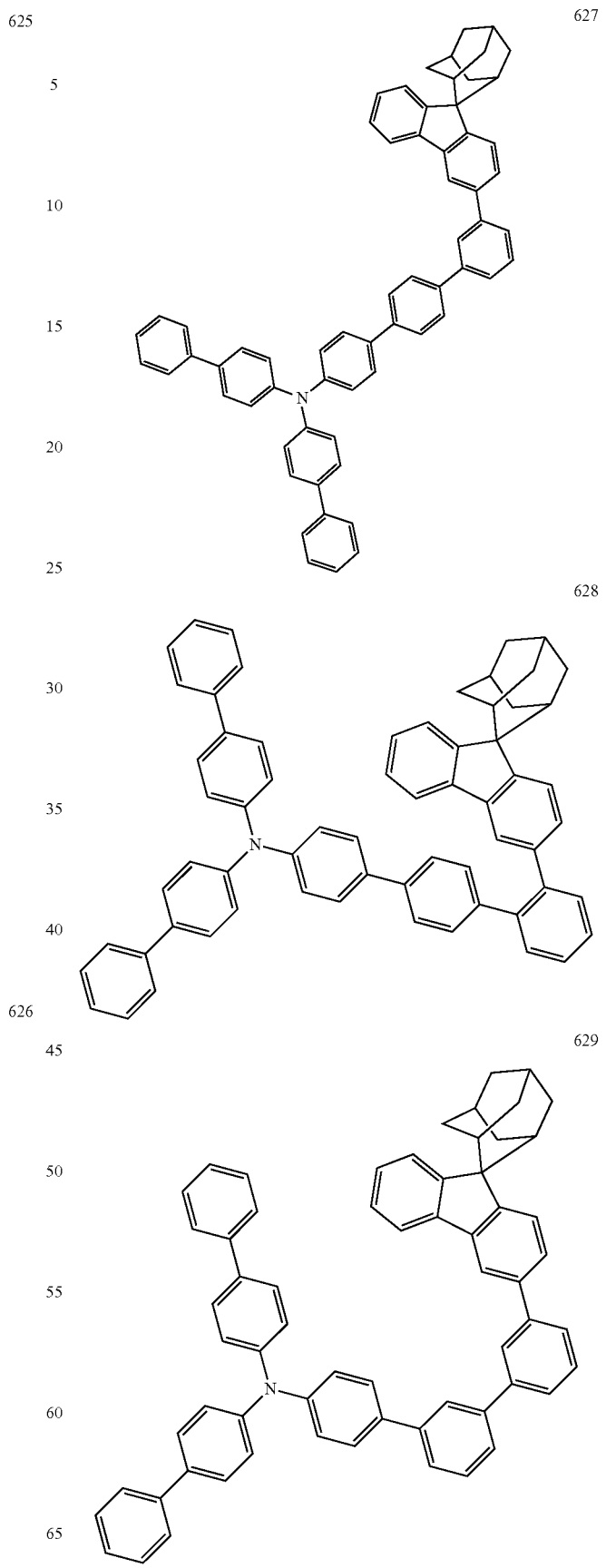

630
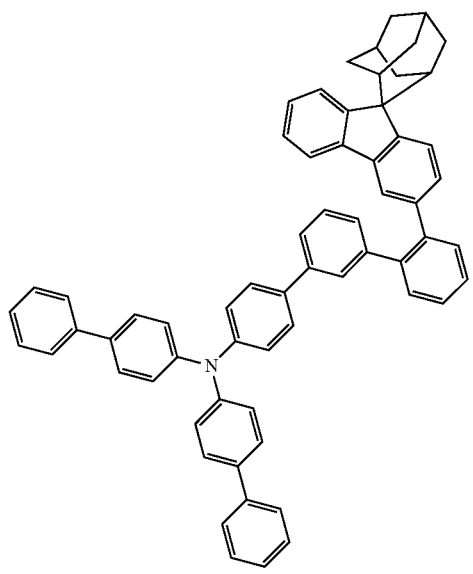
631
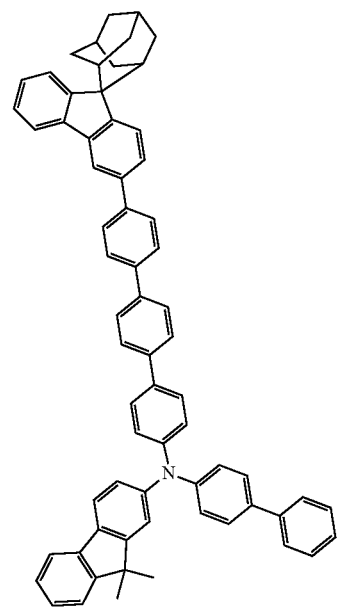
632
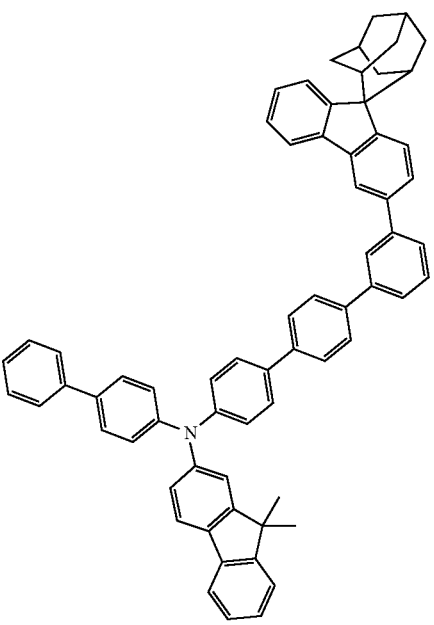
633
634
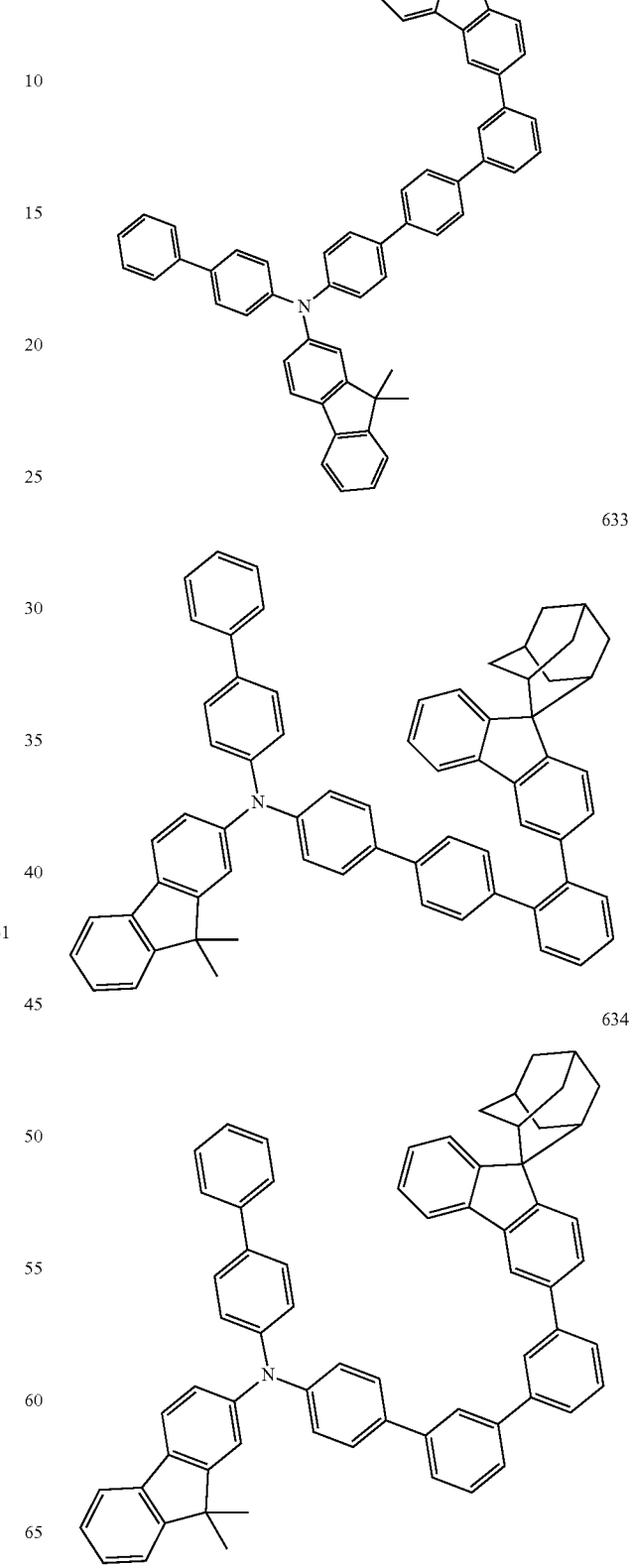

273
-continued
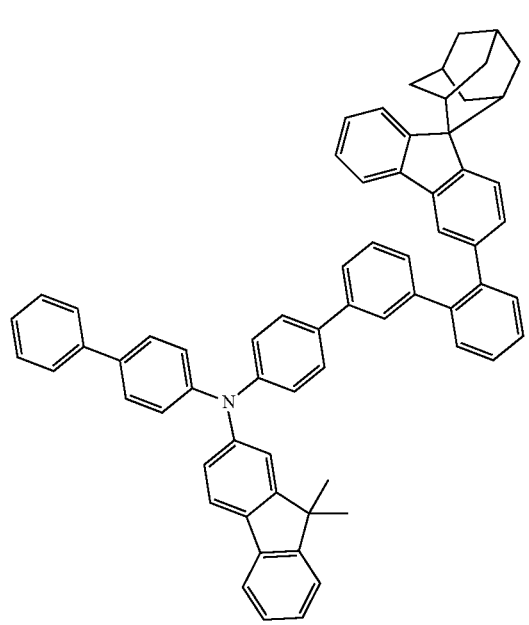
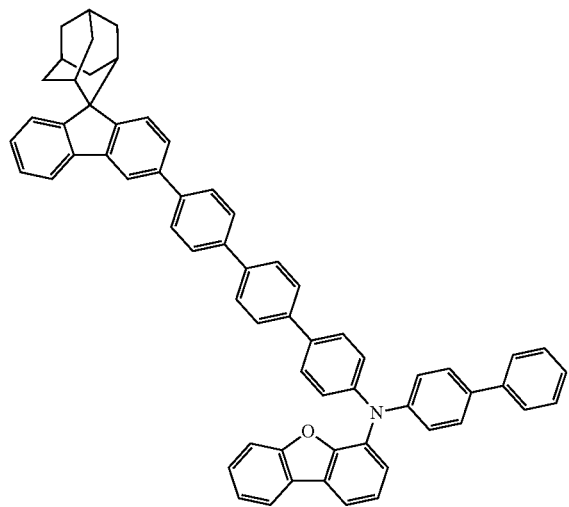
274
-continued
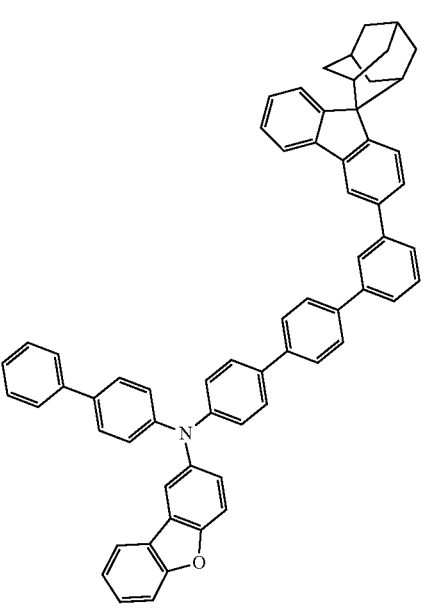
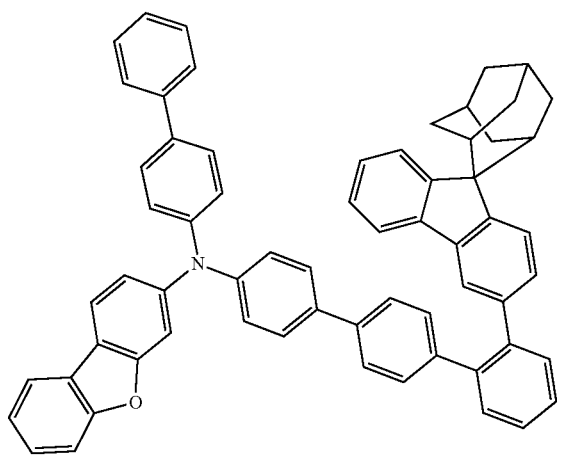
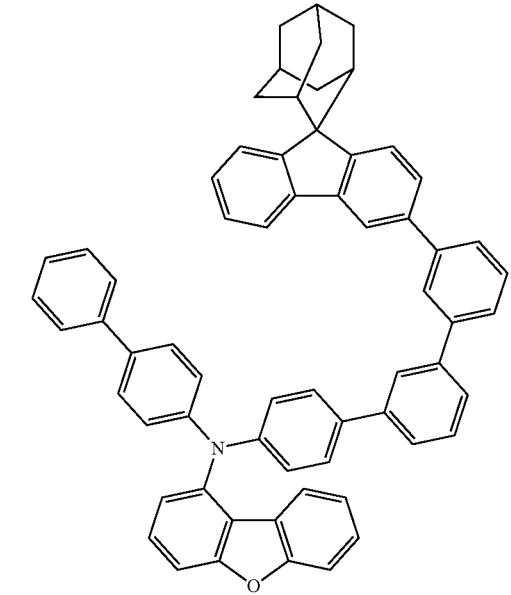

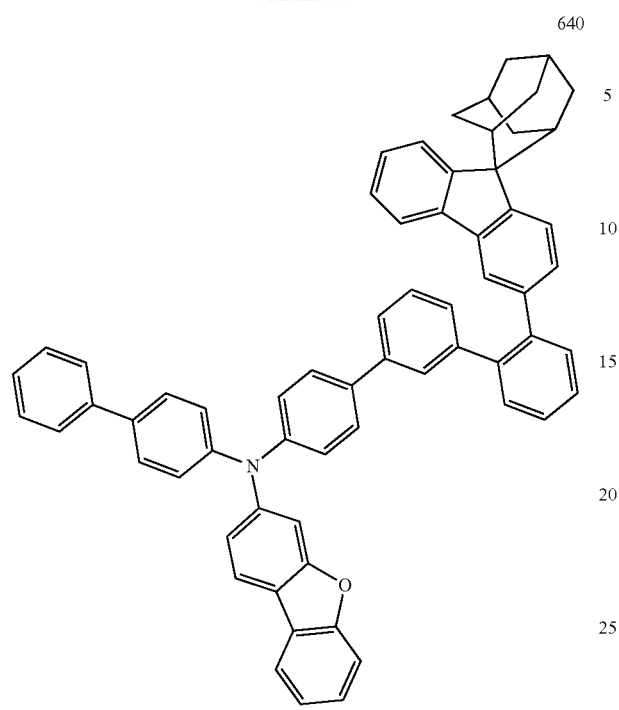
640
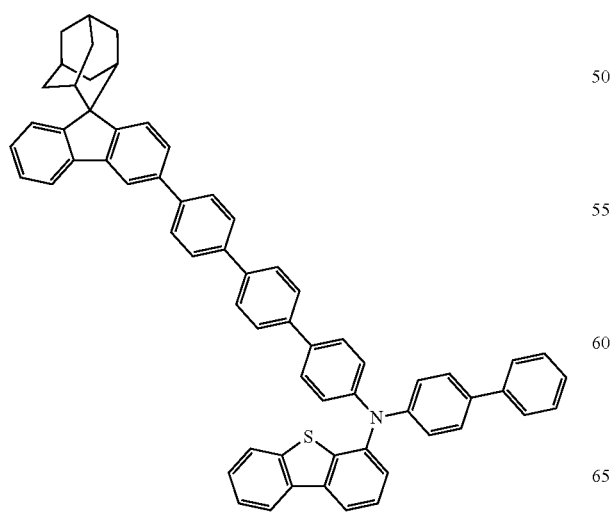
641
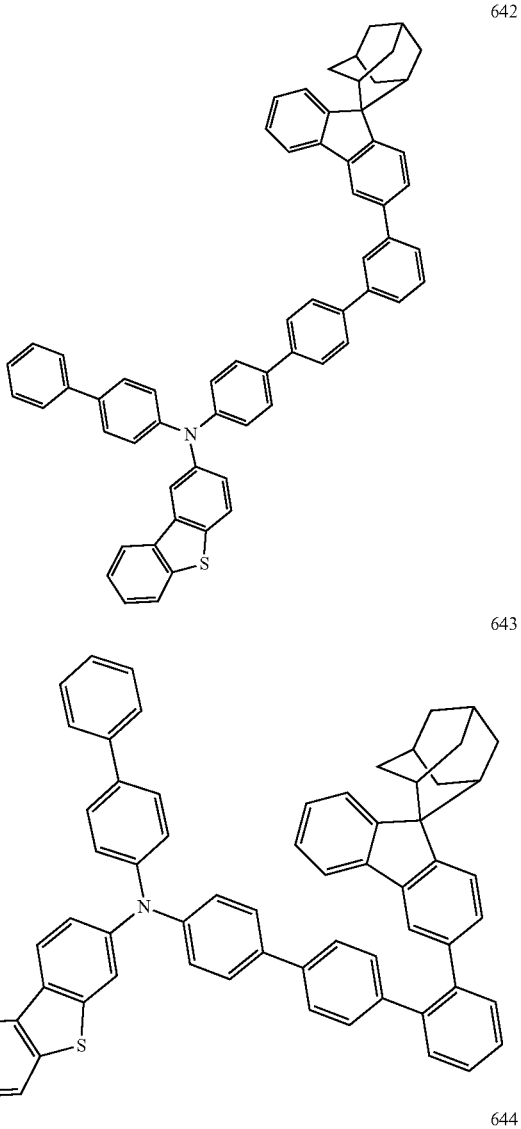
642
643
644

645
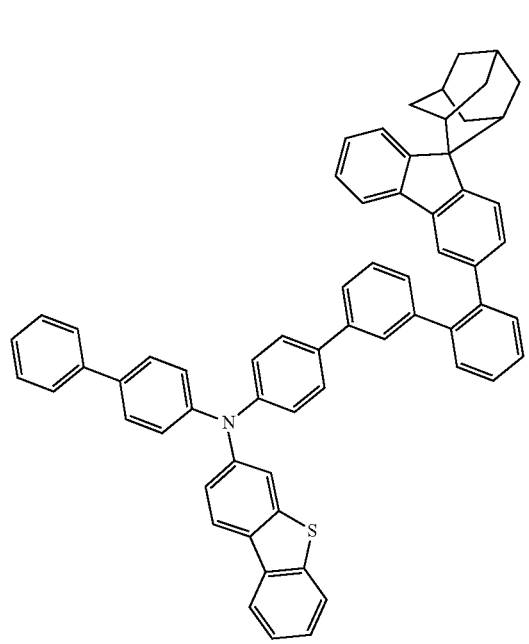
646
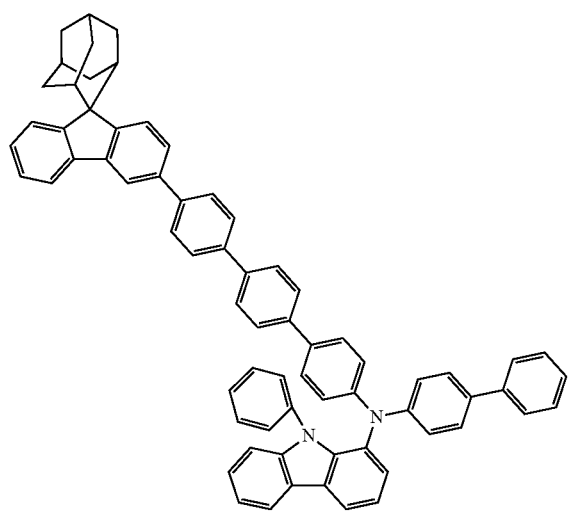
647
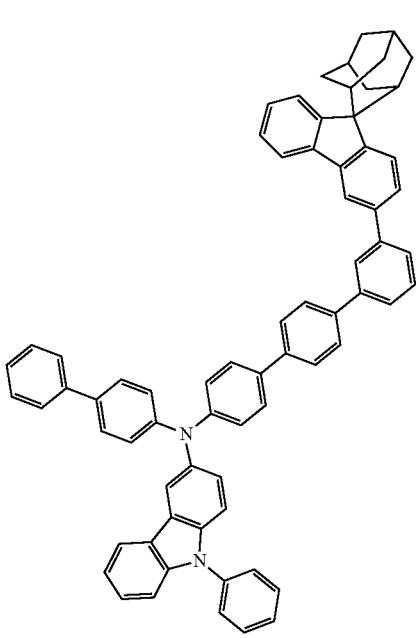
648
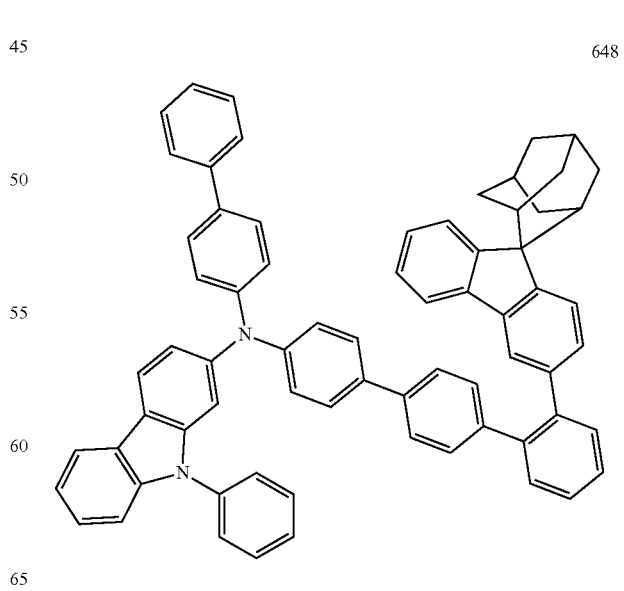

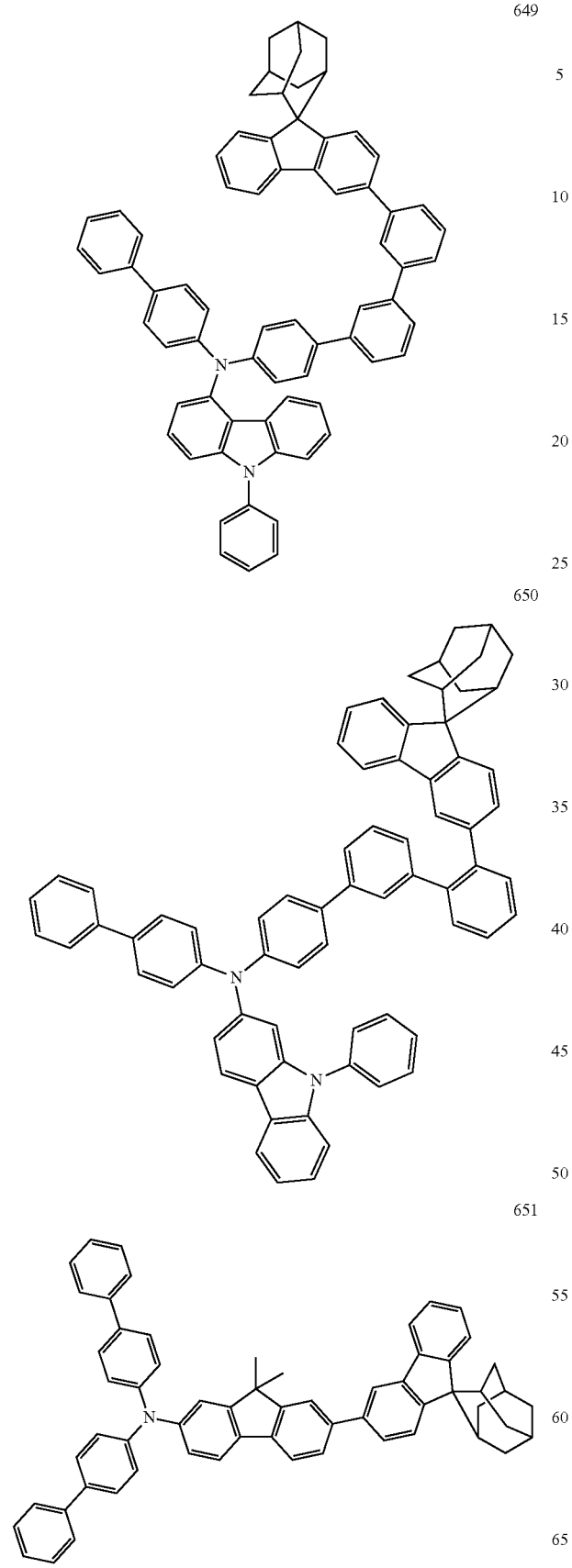
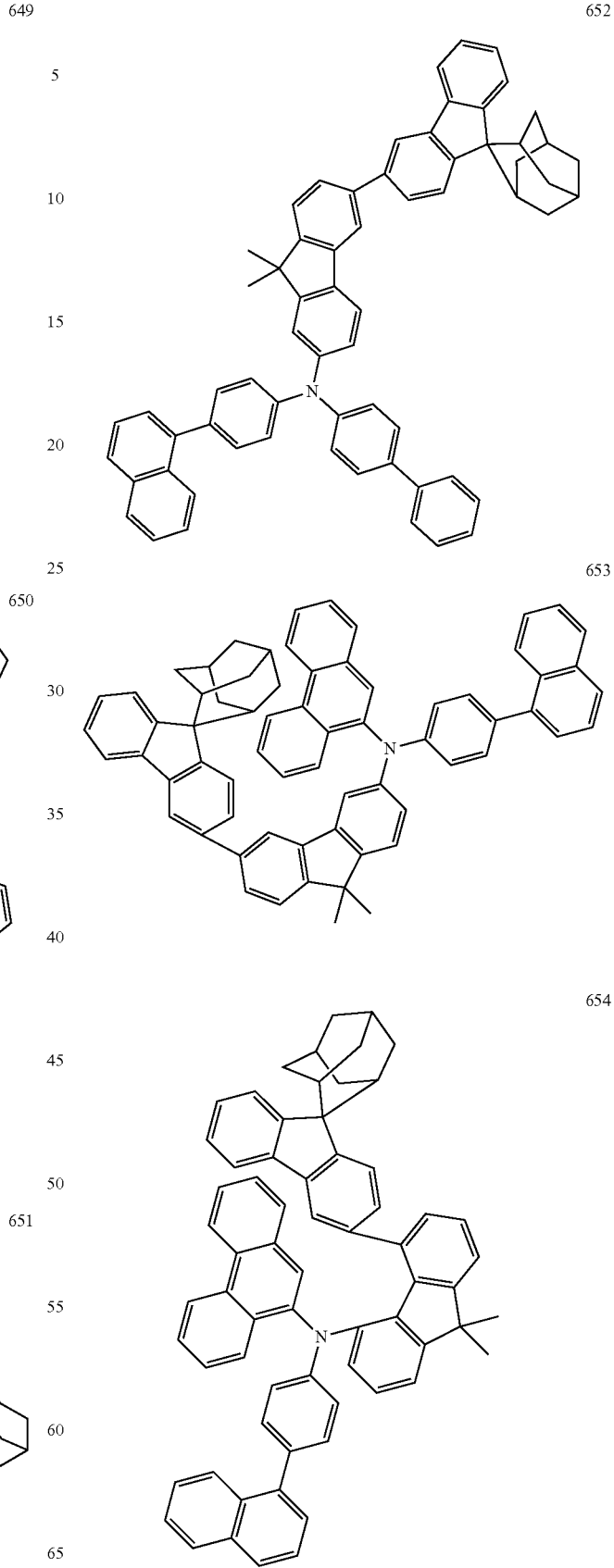

281
-continued
282
-continued
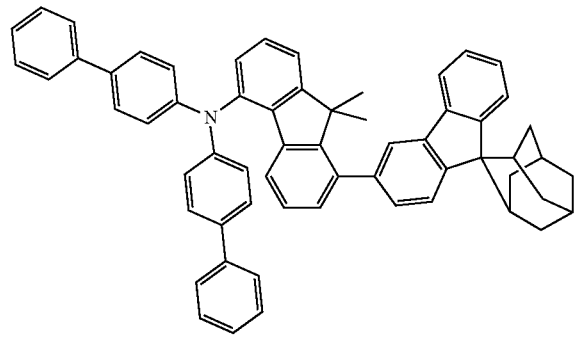
655
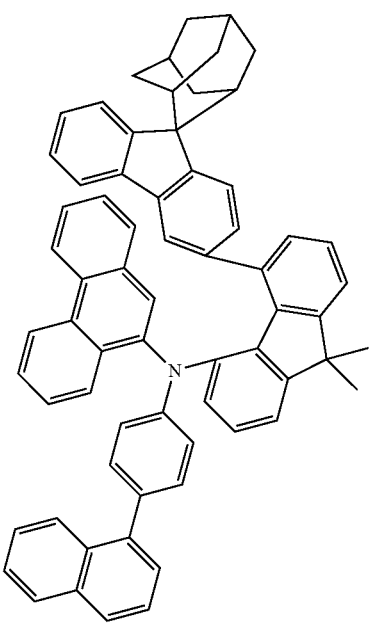
658
656
659
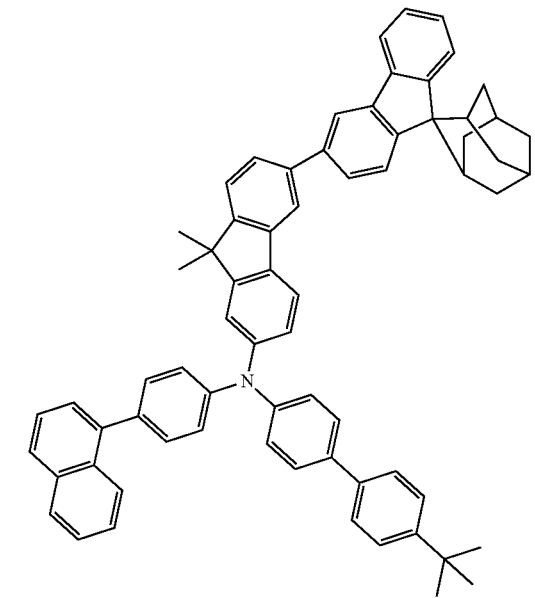
657
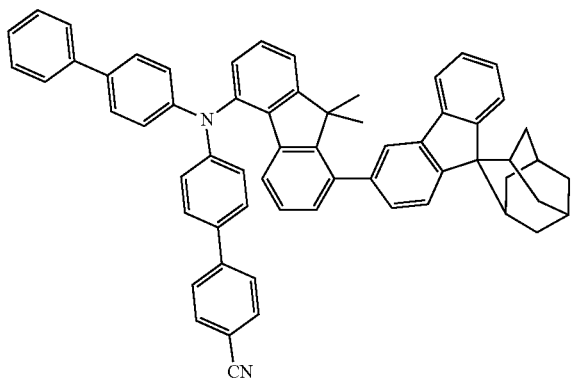
660

283
-continued
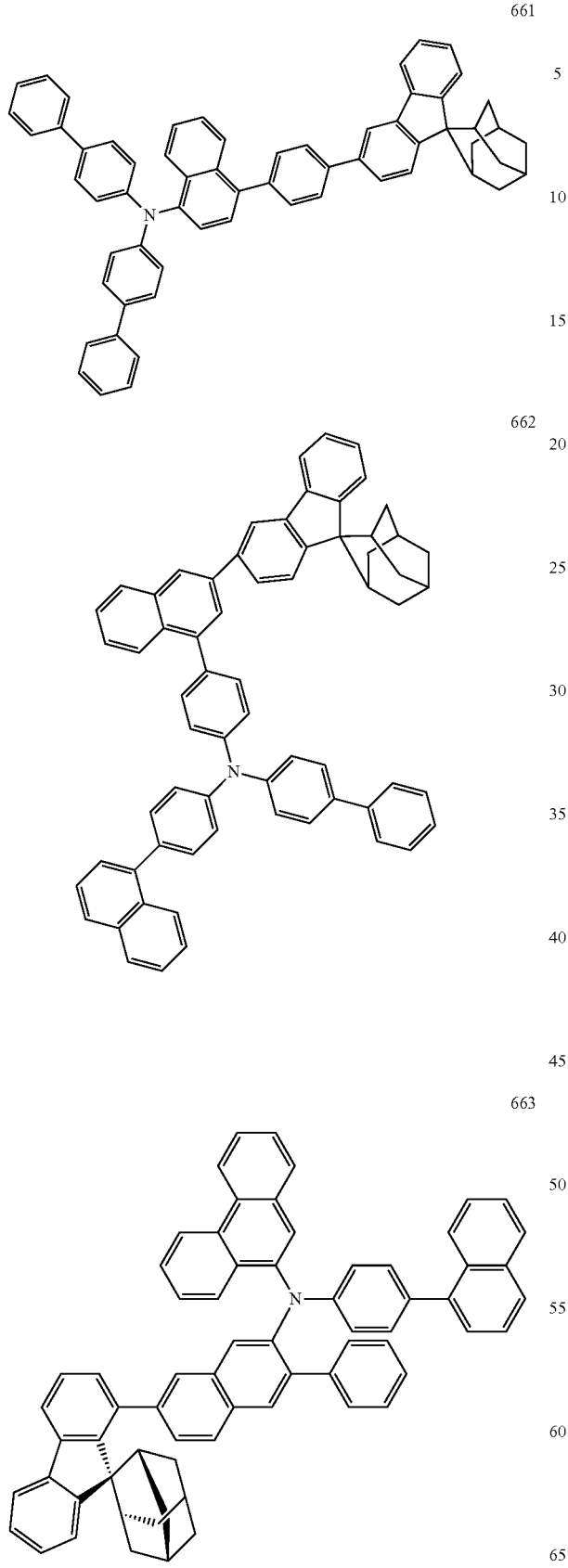
284
-continued
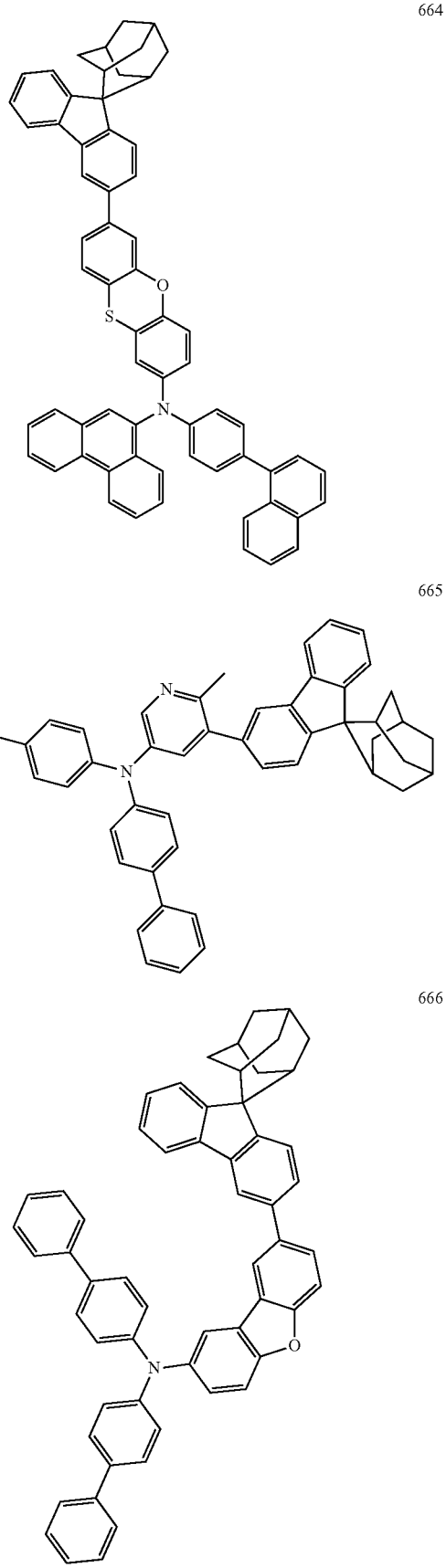

285
-continued
667
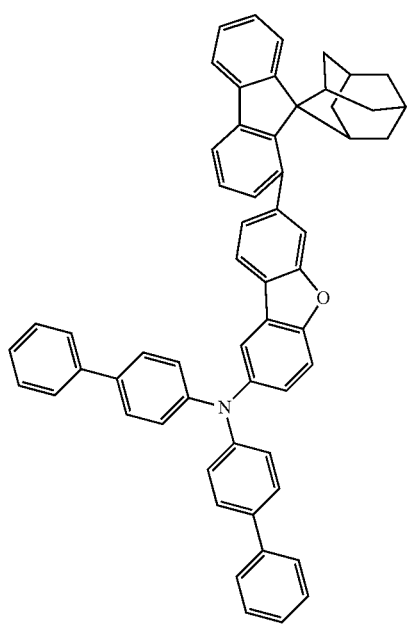
668
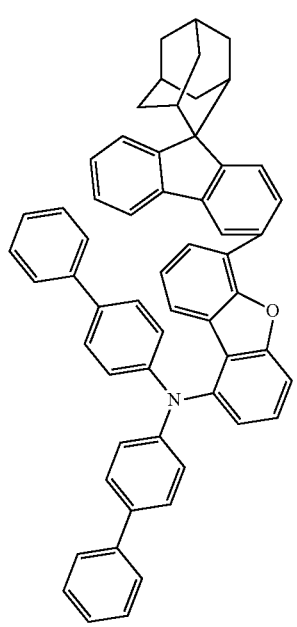
286
-continued
669
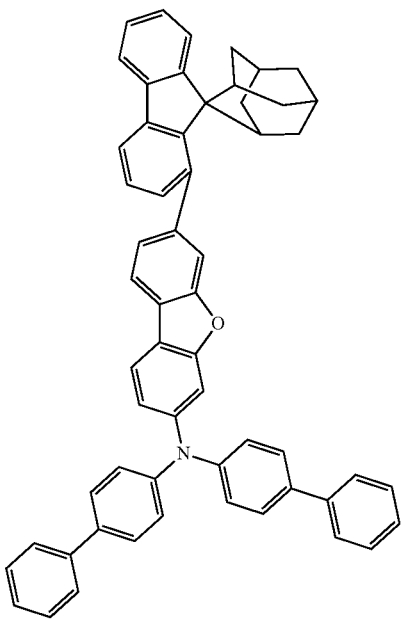
670
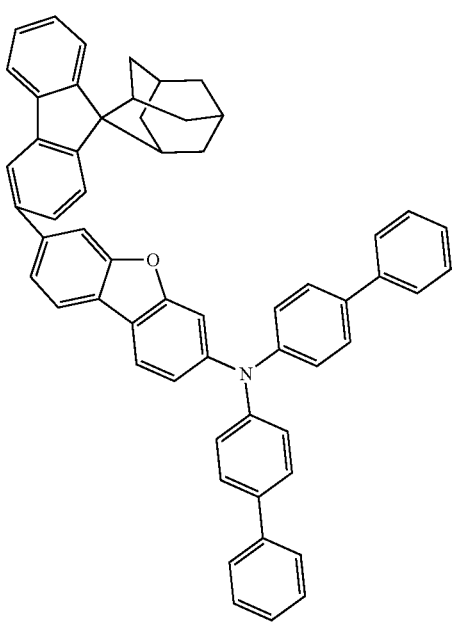

287
-continued
671
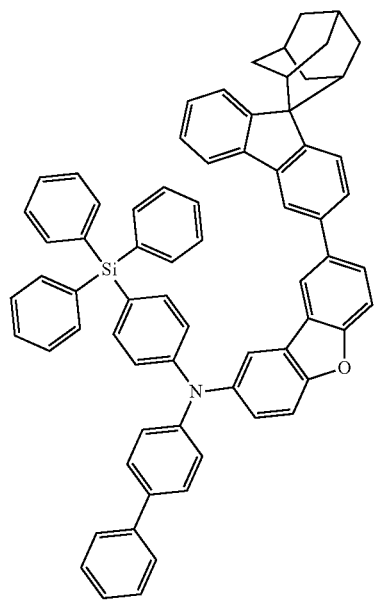
672
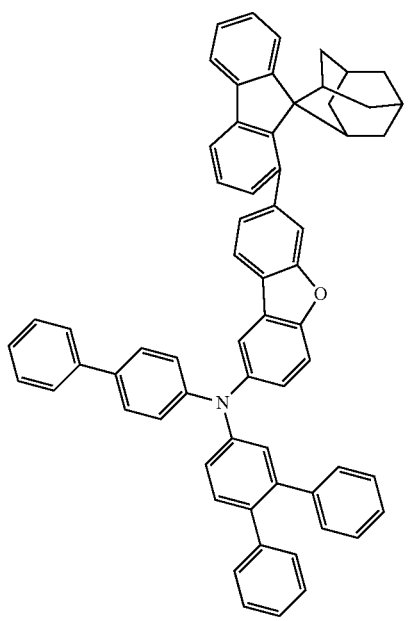
288
-continued
673
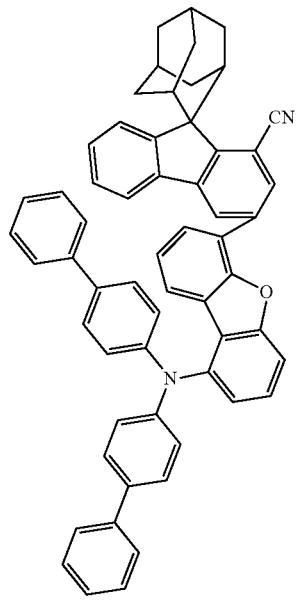
674
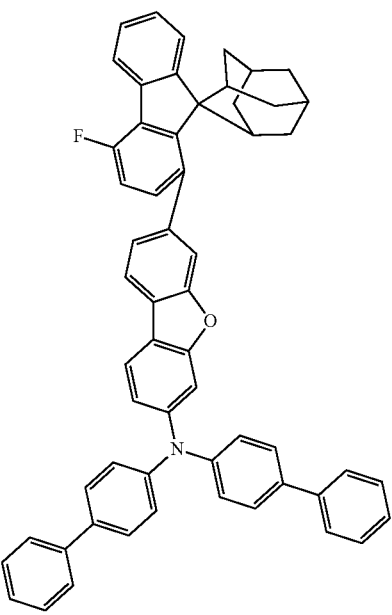

675
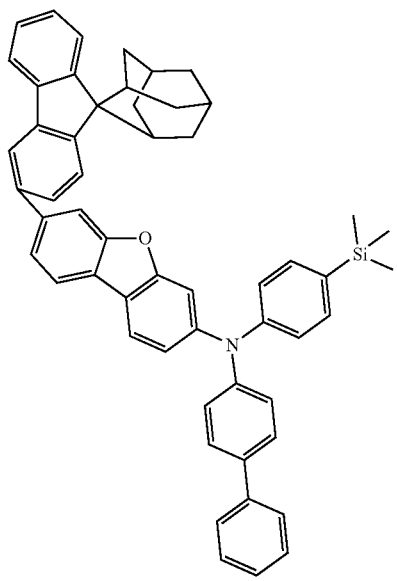
676
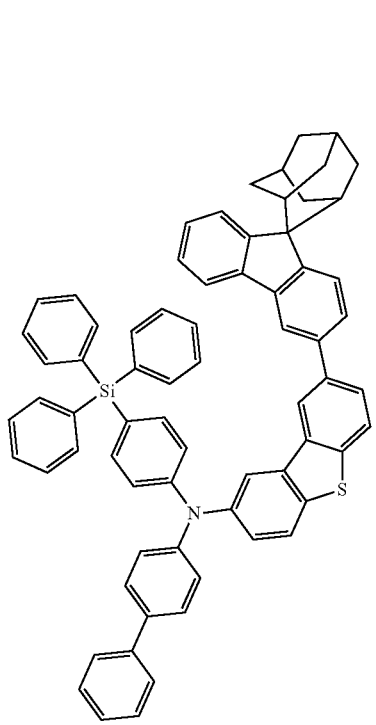
677
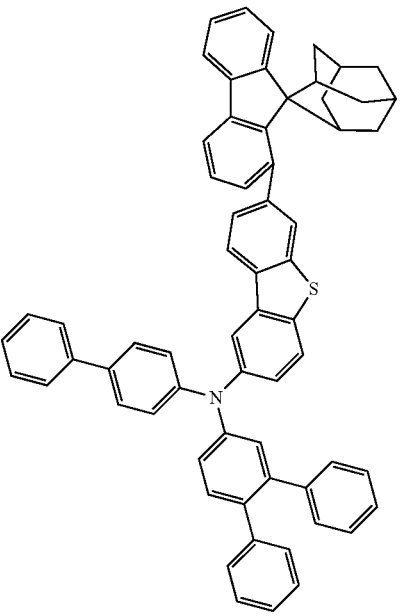
678
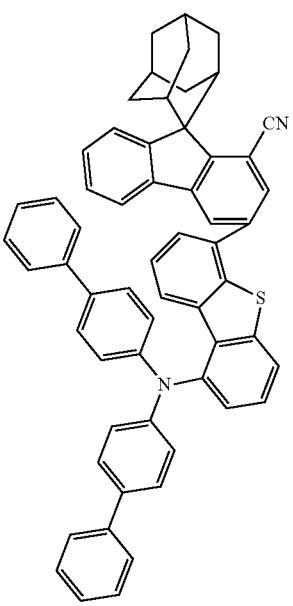

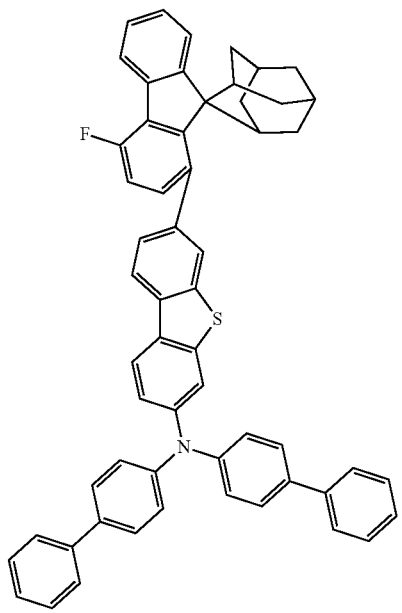
679
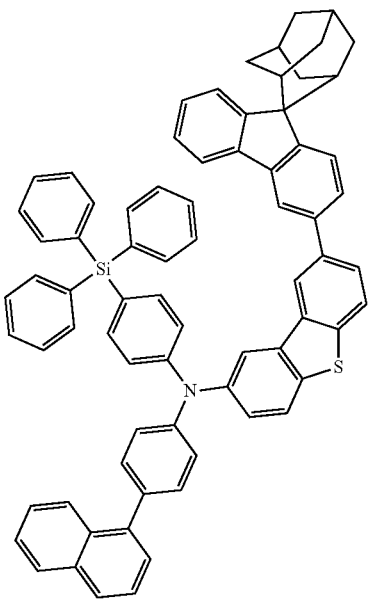
681
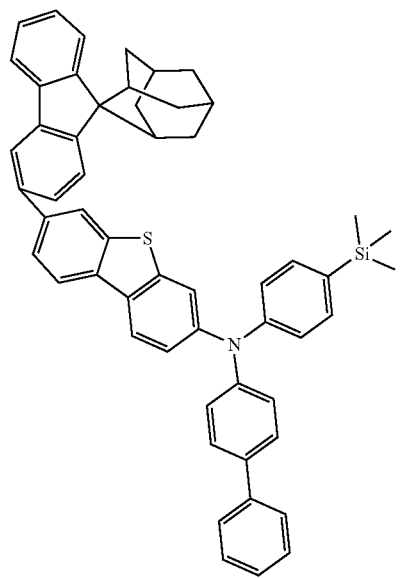
680
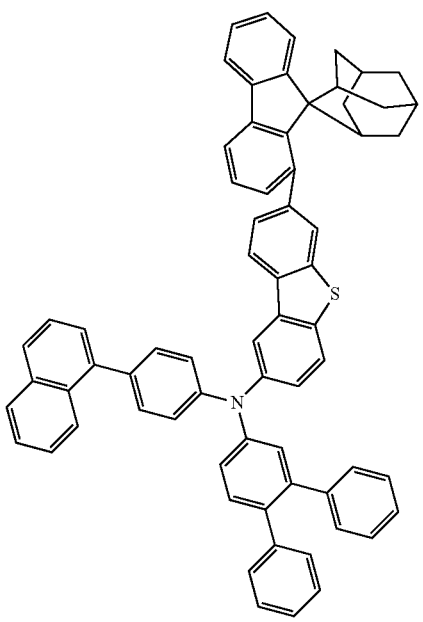
682

293
-continued
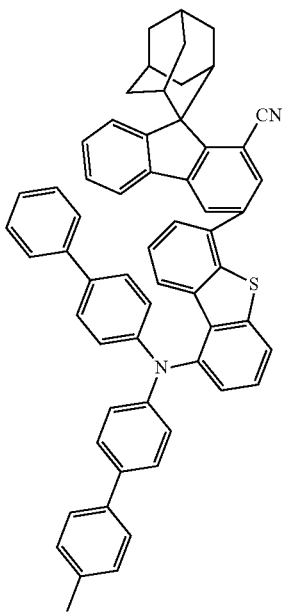
683
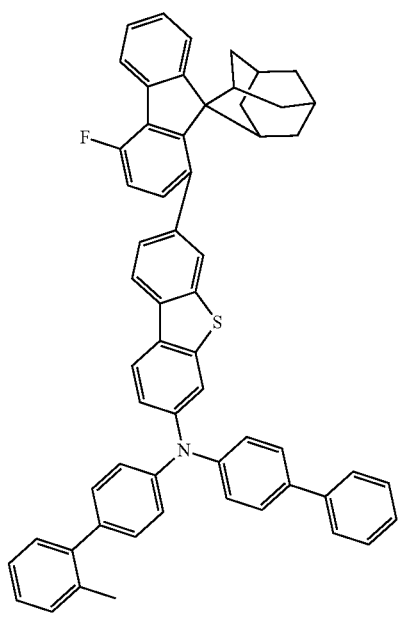
684
294
-continued
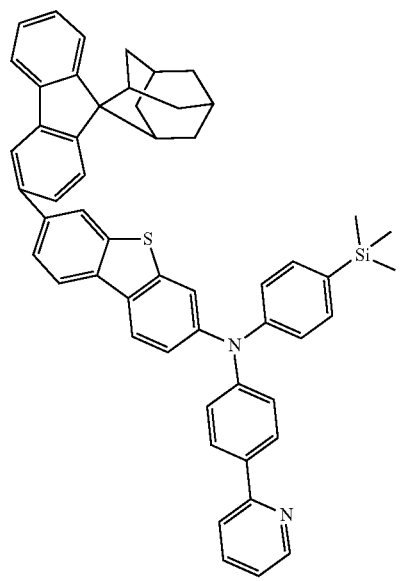
685
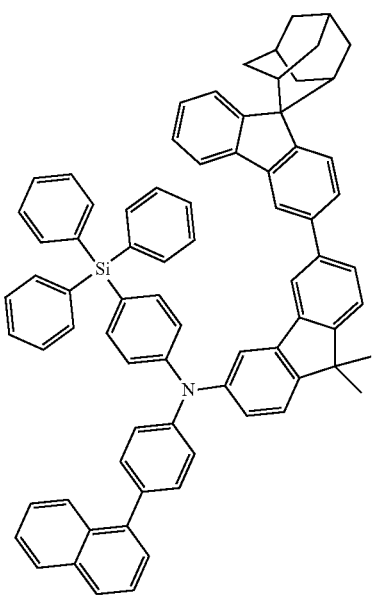
686

687
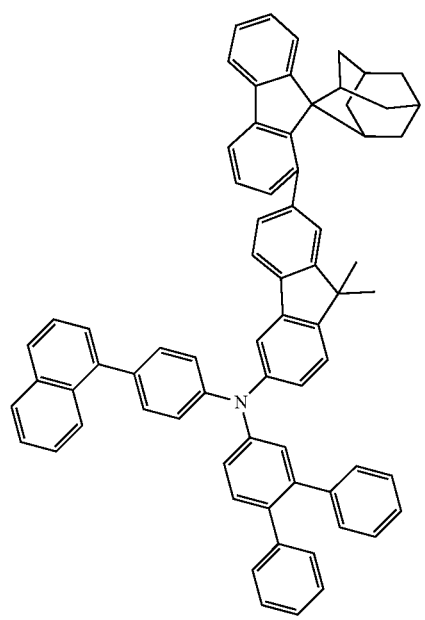
688
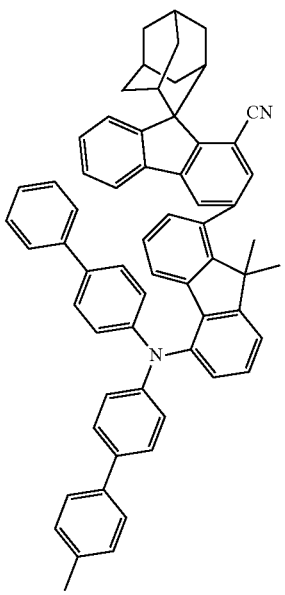
689
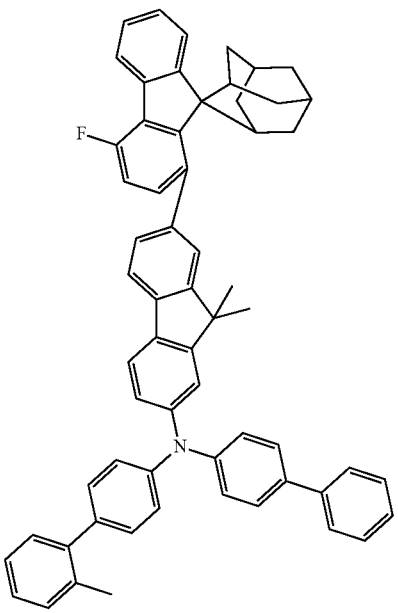
690
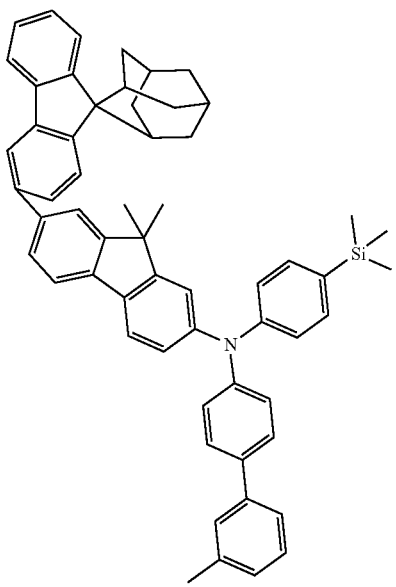

297
-continued
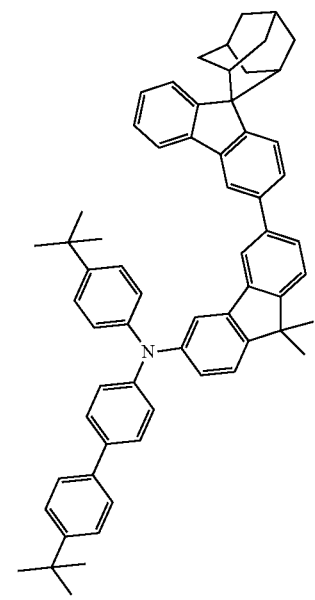
691
298
-continued
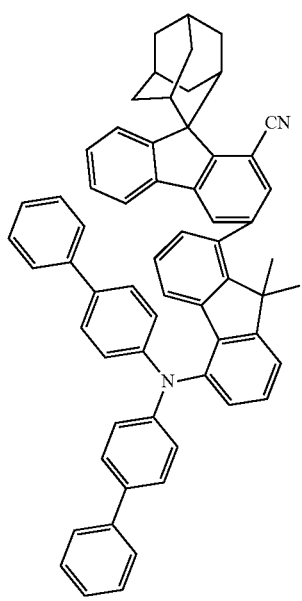
693
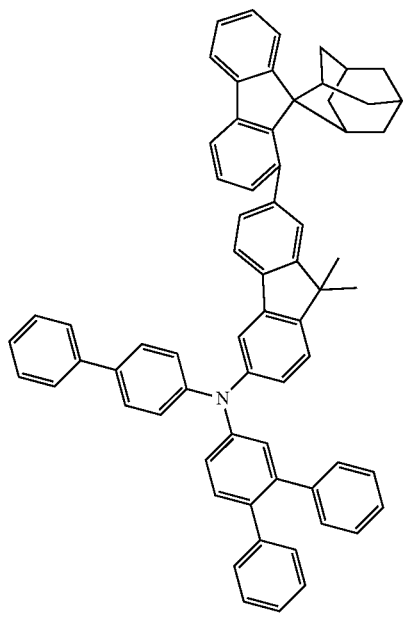
692
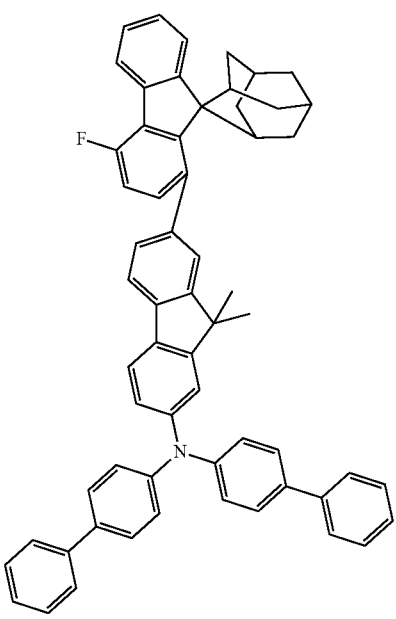
694

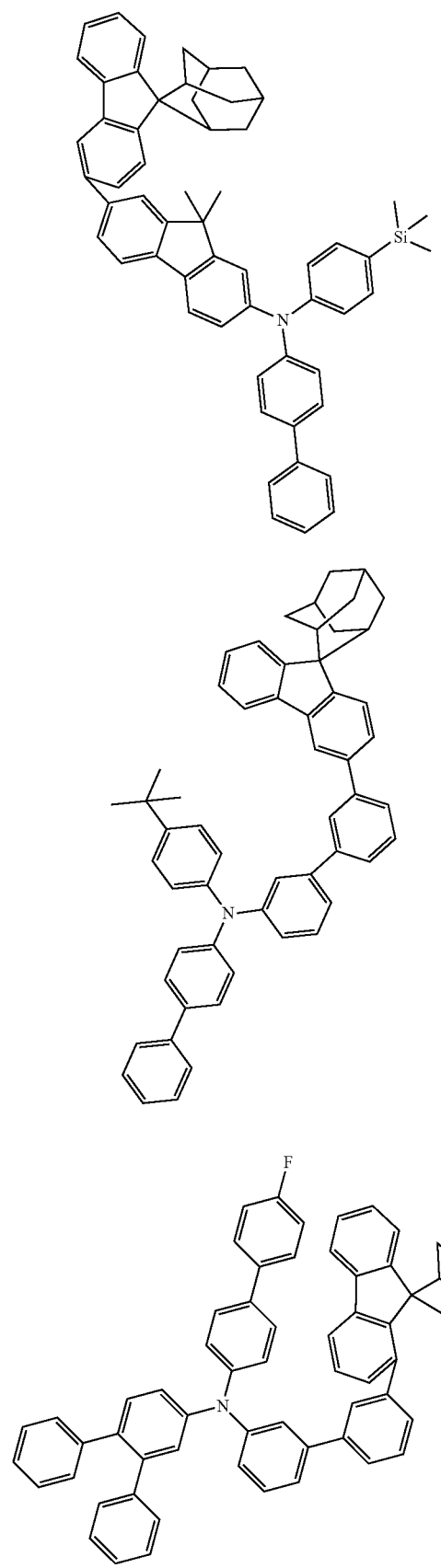

301
-continued
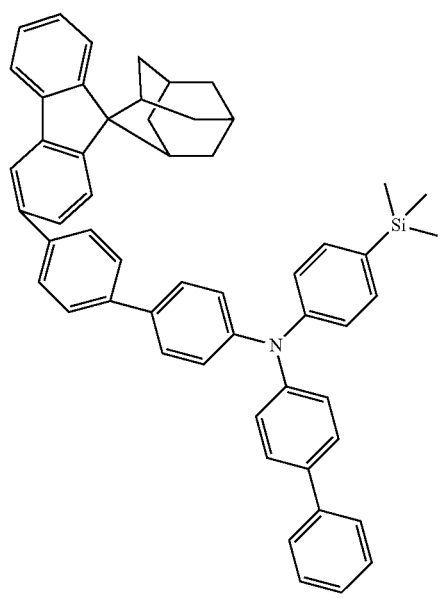
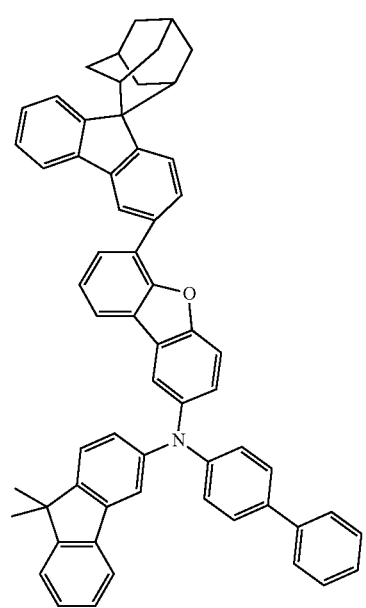
302
-continued
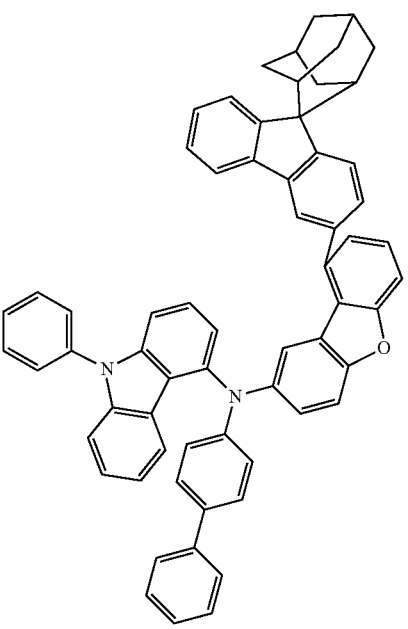
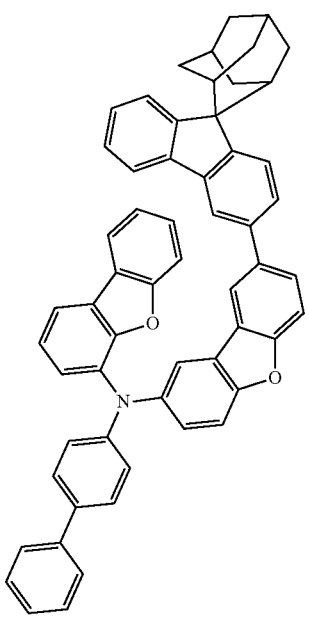

303
-continued
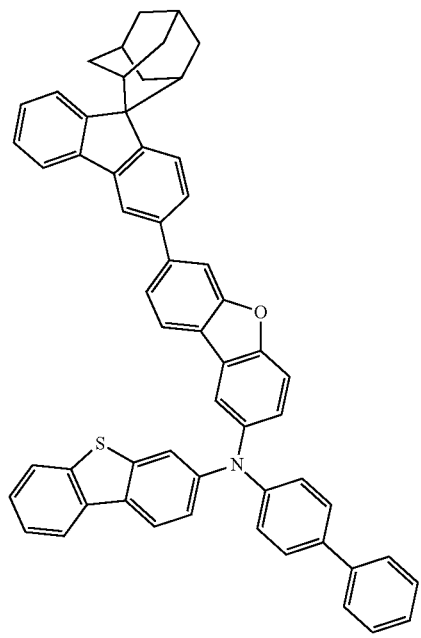
704
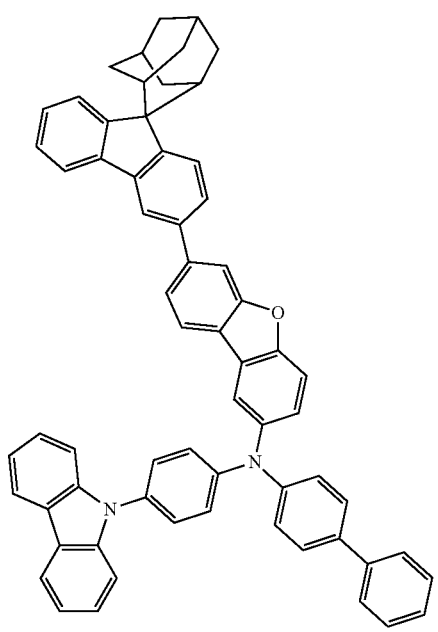
705
304
-continued
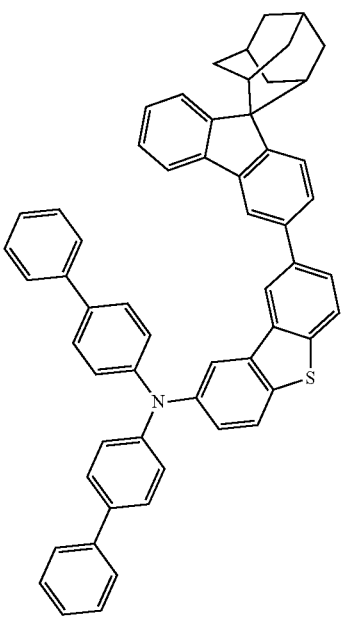
706
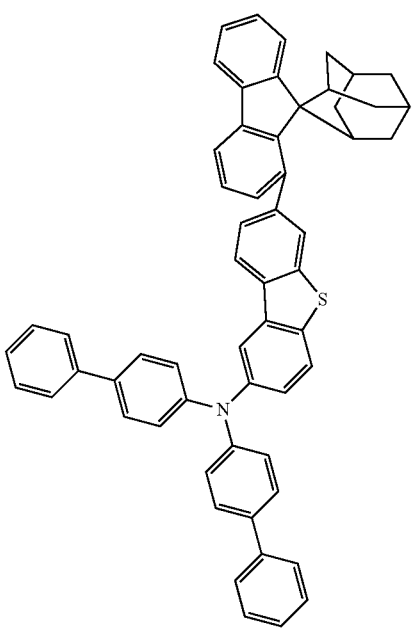
707

305
-continued
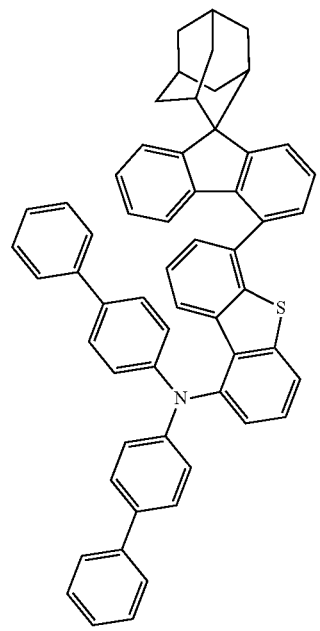
708
306
-continued
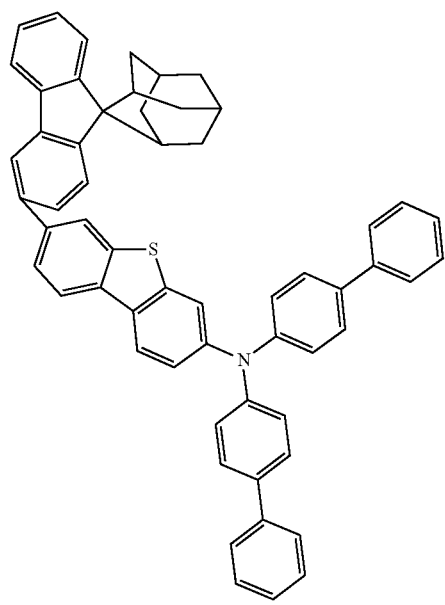
710
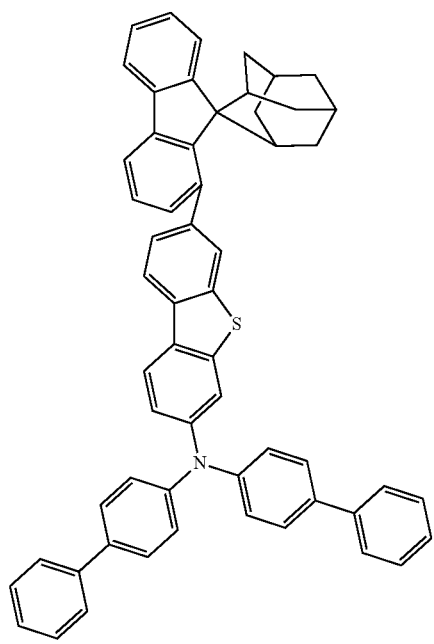
709
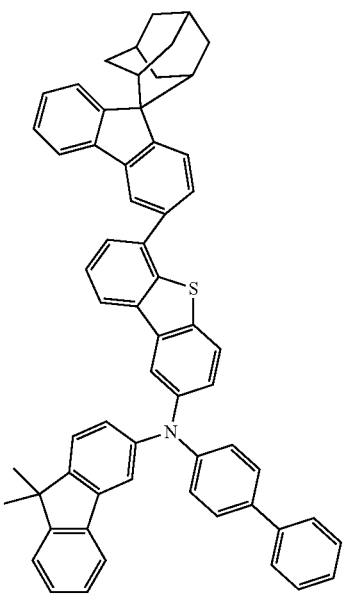
711

307
-continued
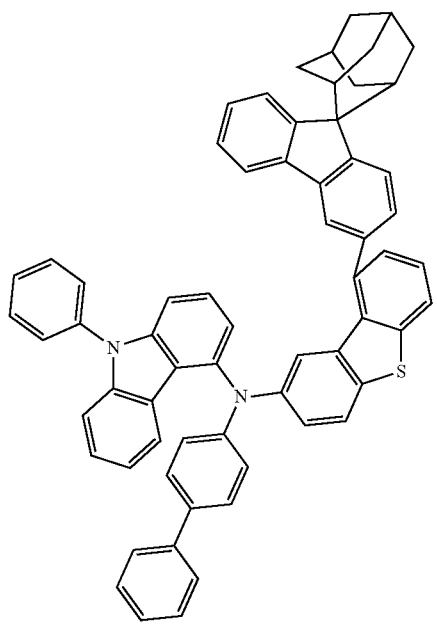
712
308
-continued
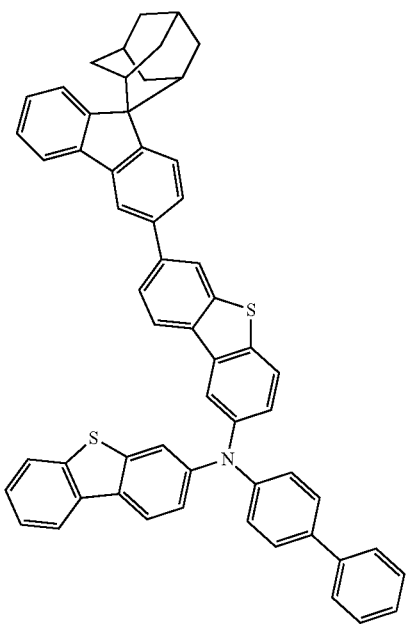
714
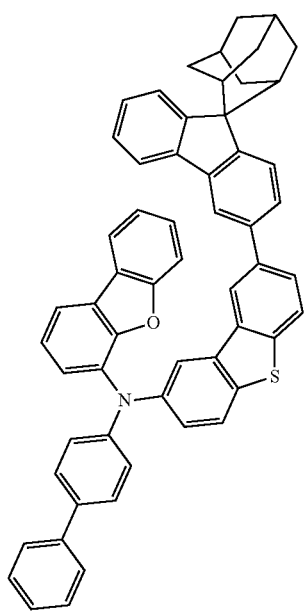
713
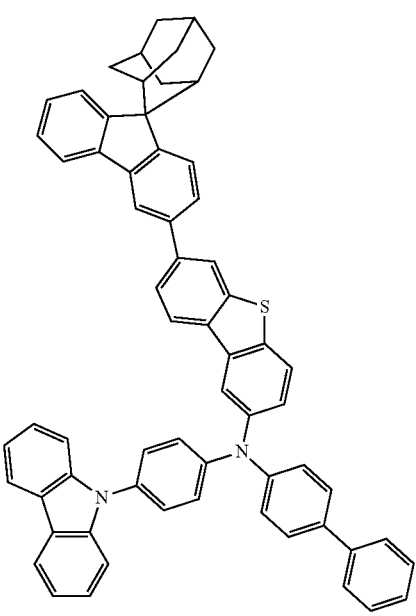
715

309
-continued
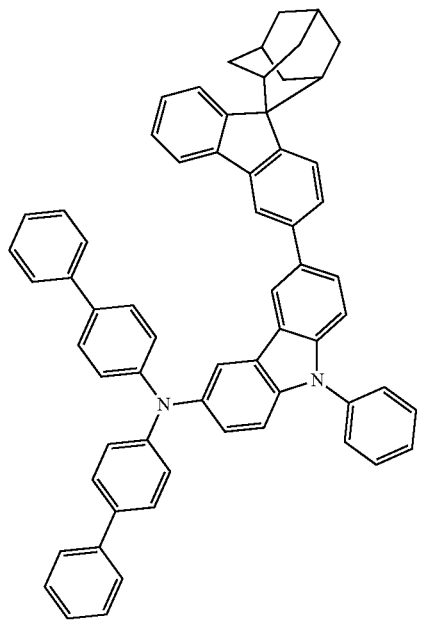
716
310
-continued
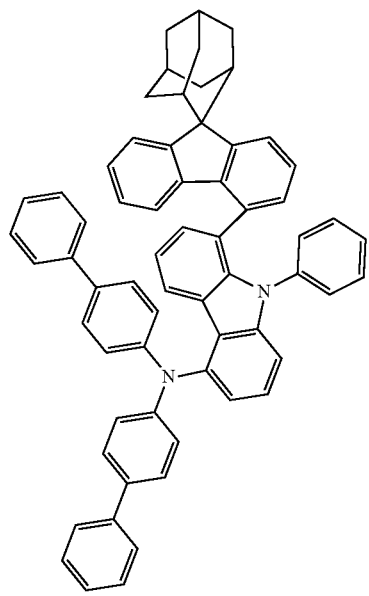
718
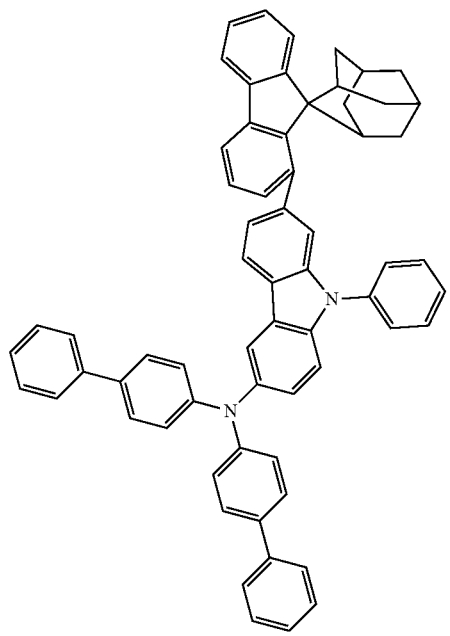
717
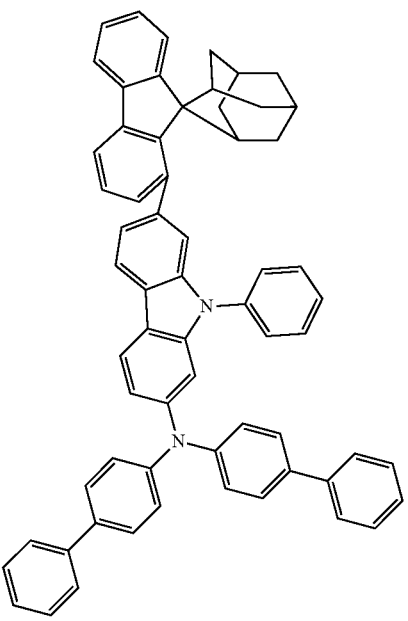
719

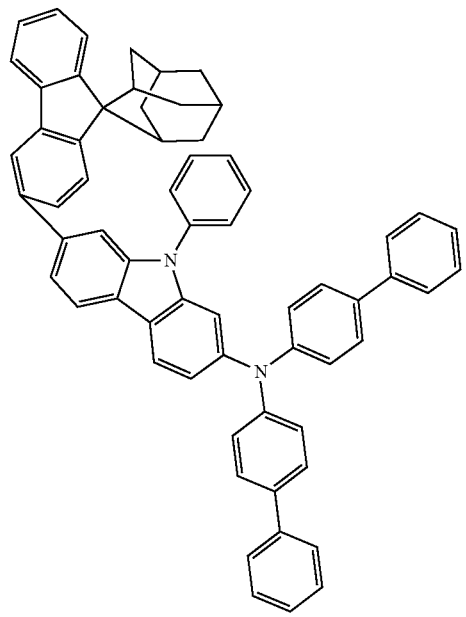
720
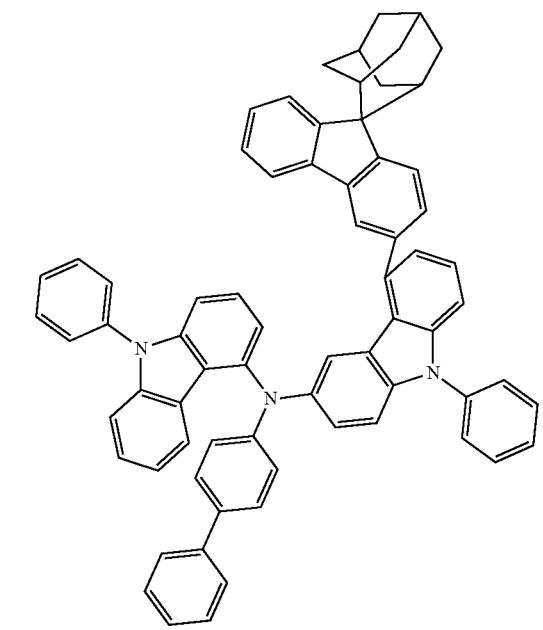
722
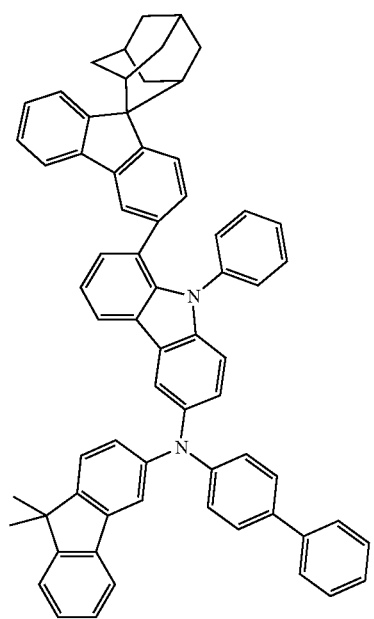
721
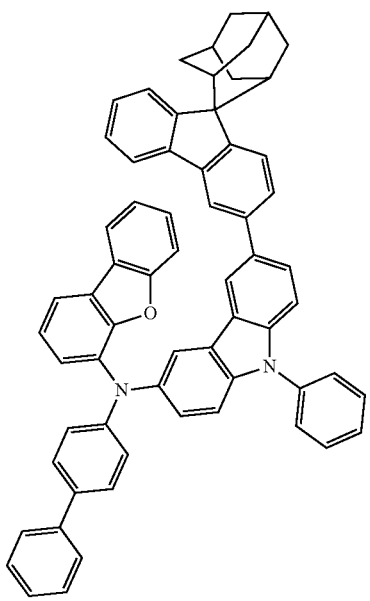
723

313
-continued
724
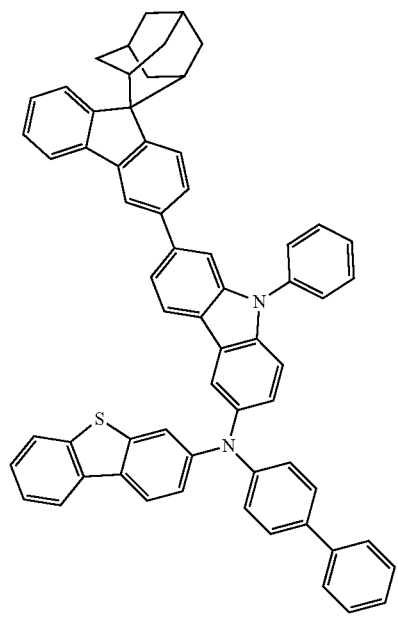
725
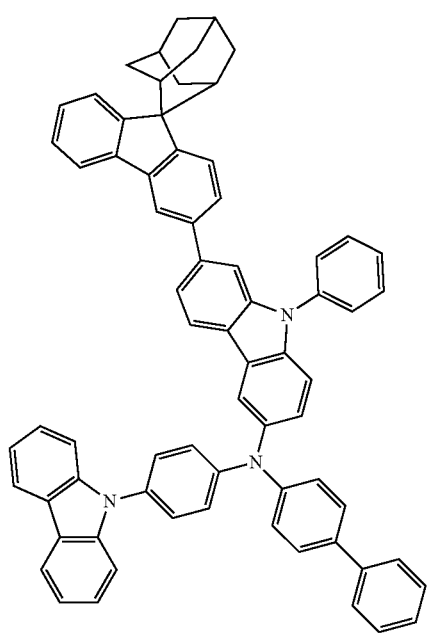
314
-continued
726
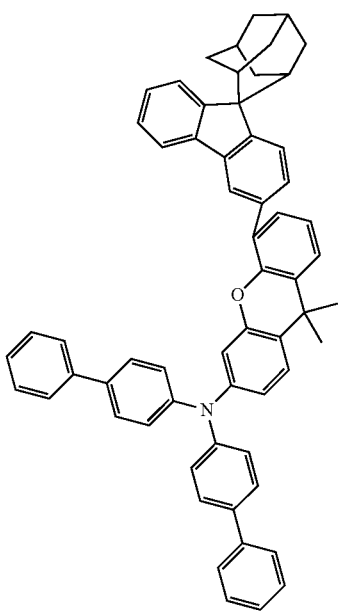
727

315
-continued
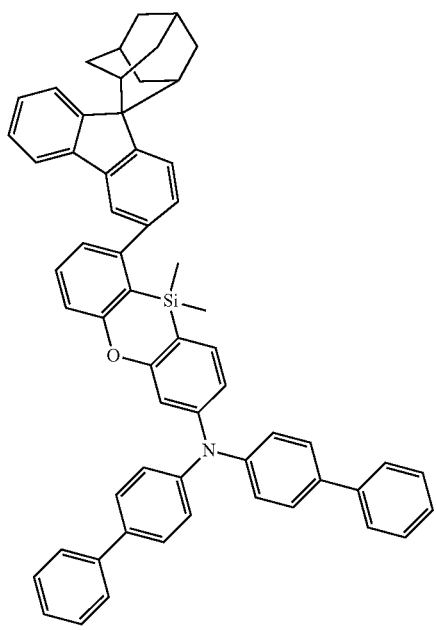
728
729
316
-continued
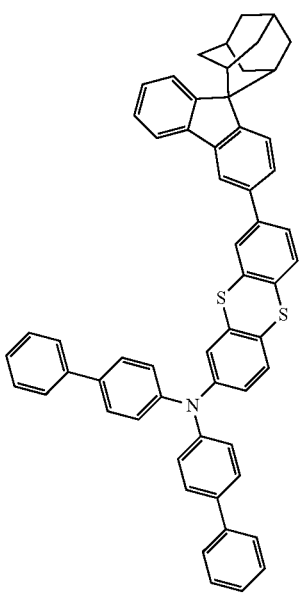
730
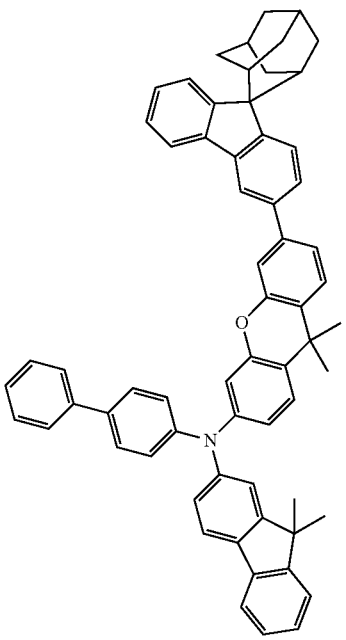
731
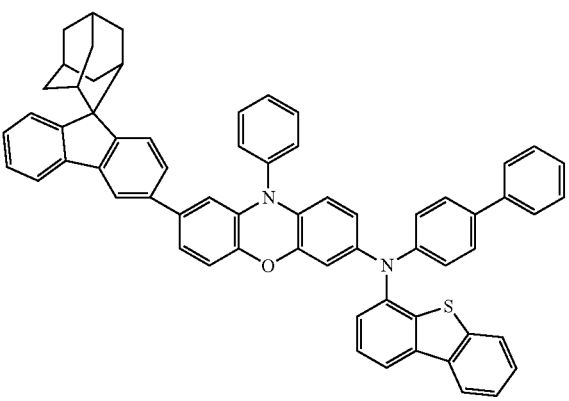
732

317
-continued
733
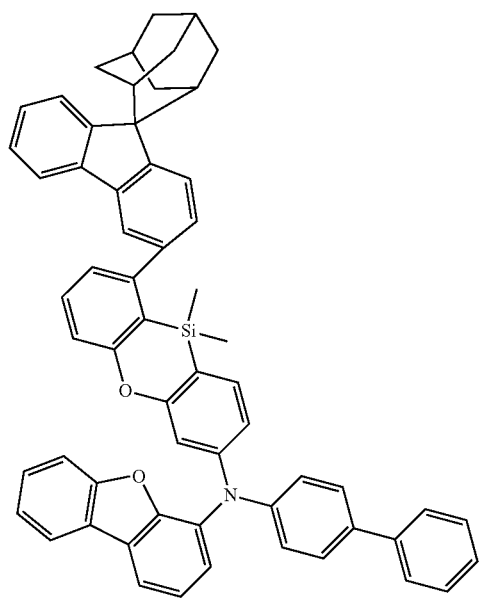
734
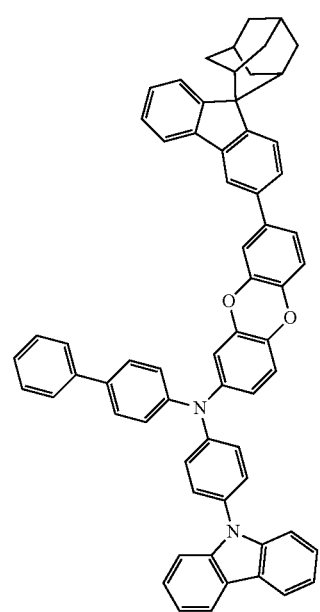
318
-continued
735
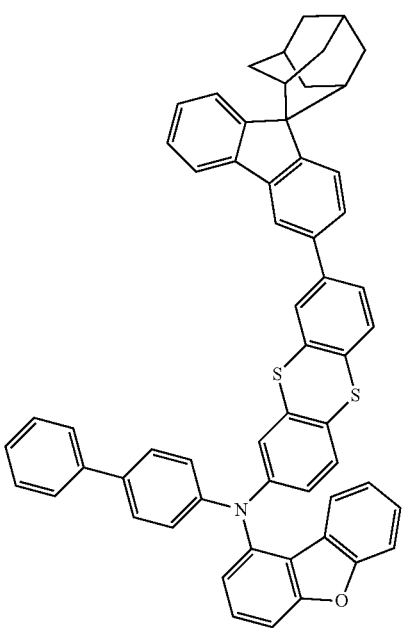
736
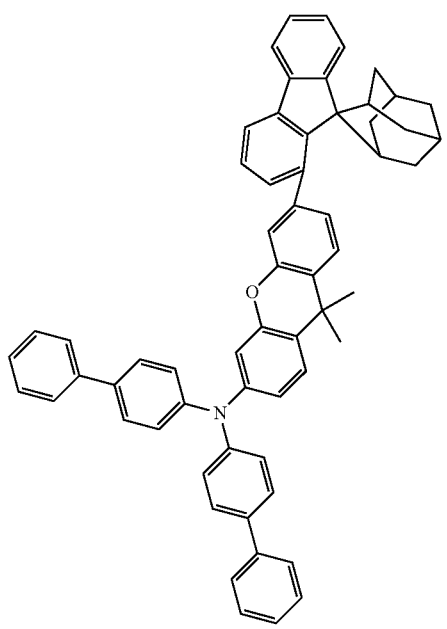

737
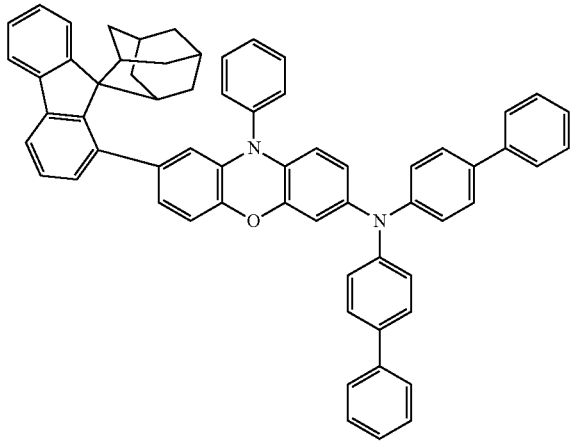
738
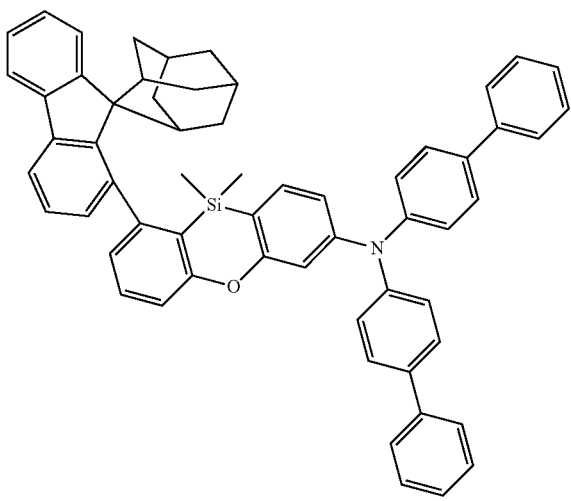
739
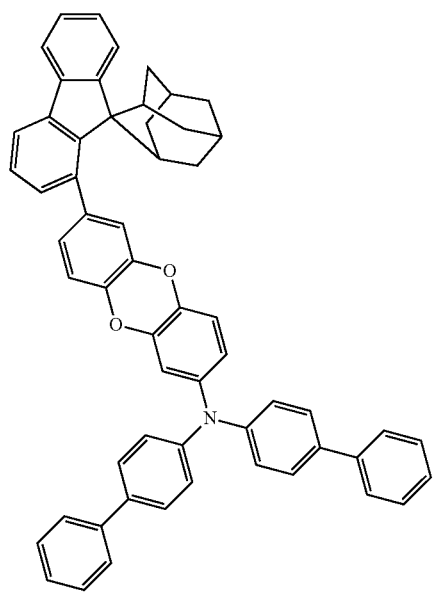
740
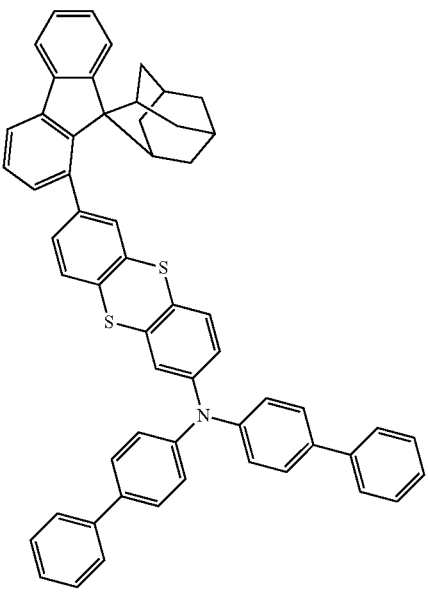
741
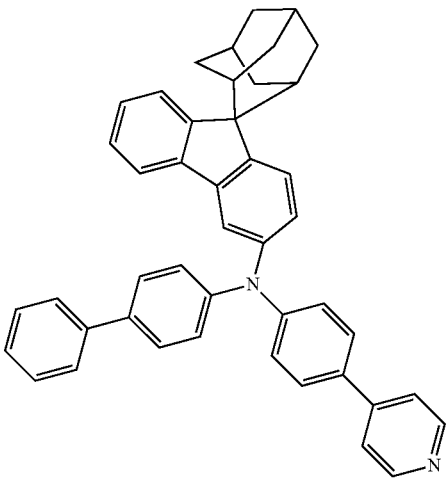
742
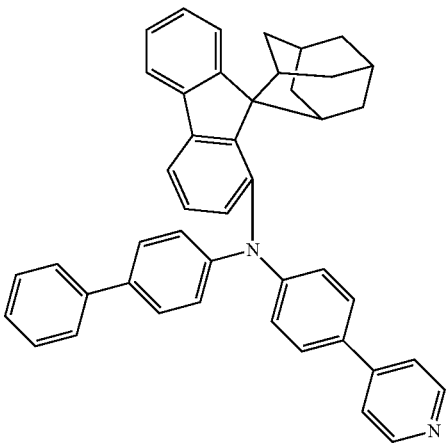

321
-continued
322
-continued
743
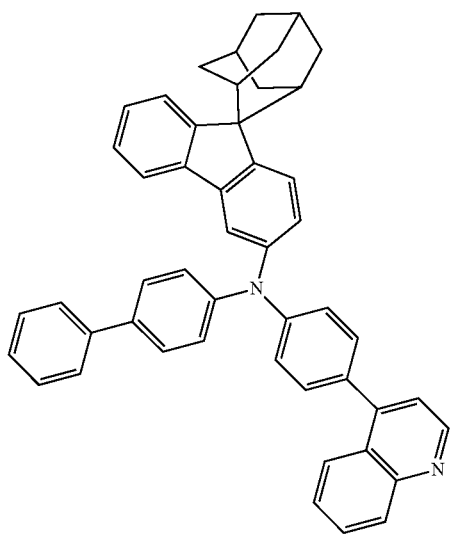
746
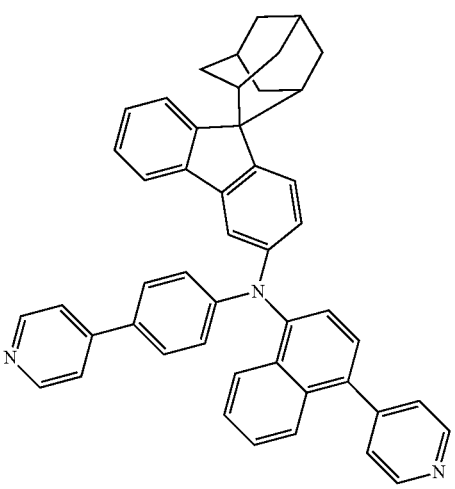
744
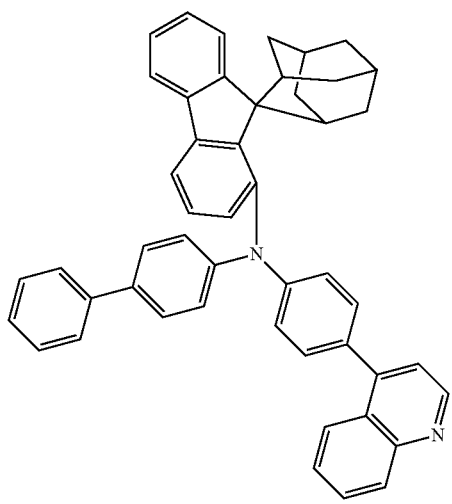
747
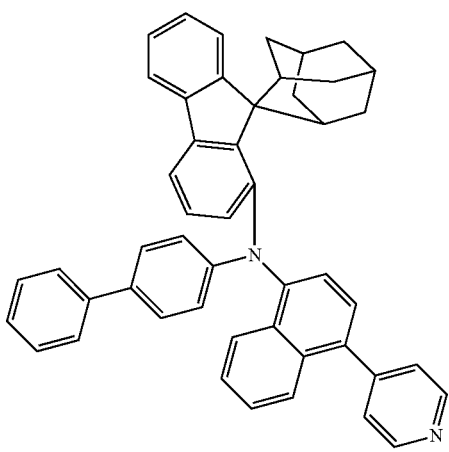
745
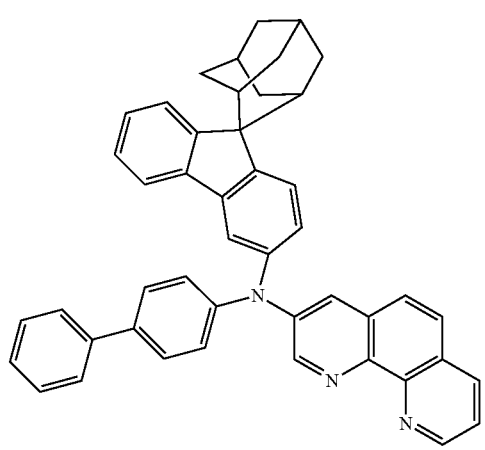
748
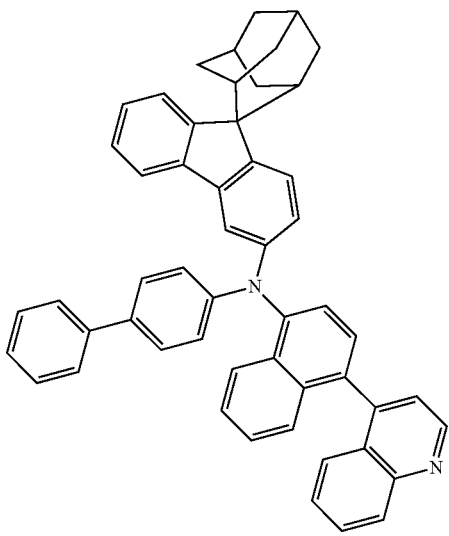

323
-continued
749
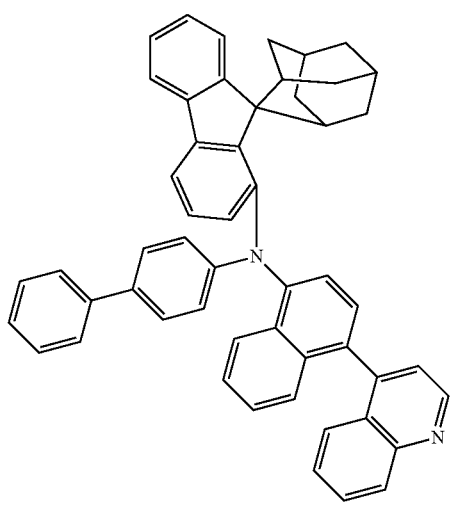
750
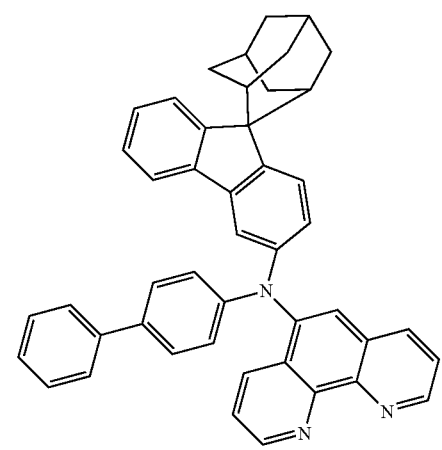
751
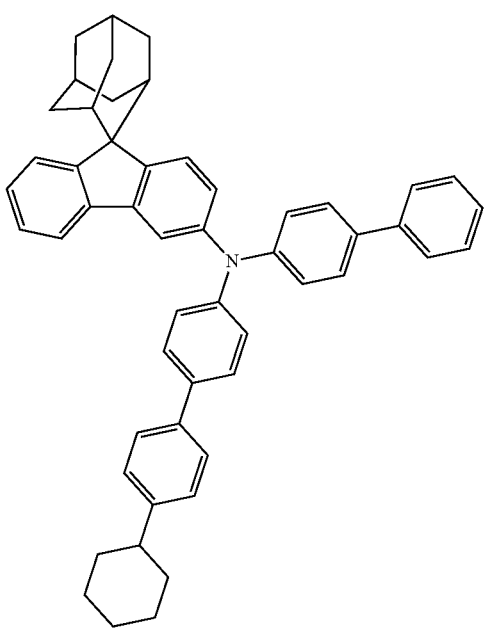
324
-continued
752
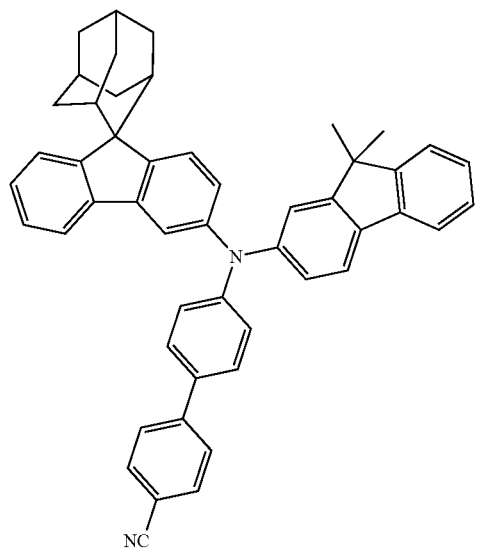
753
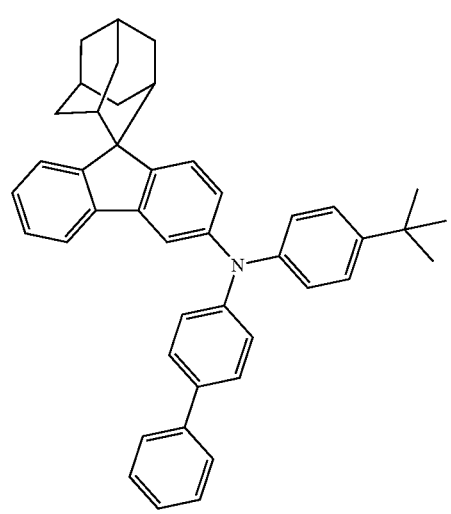
754
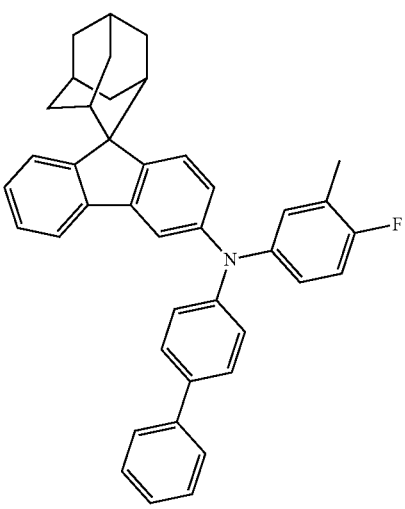

325
-continued
755
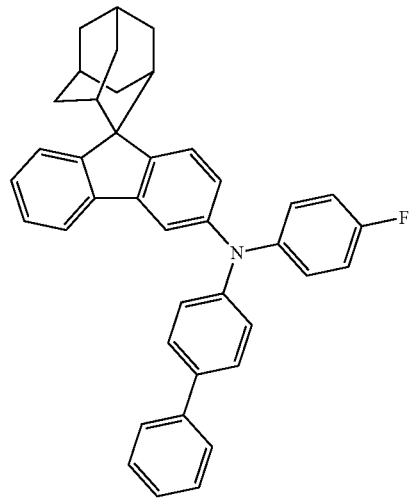
756
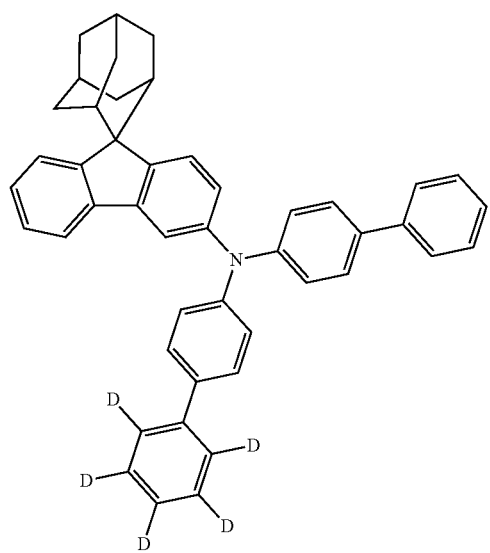
757
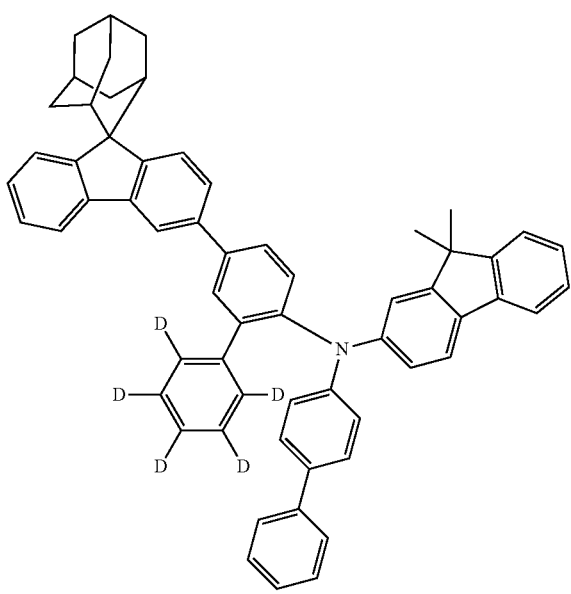
326
-continued
758
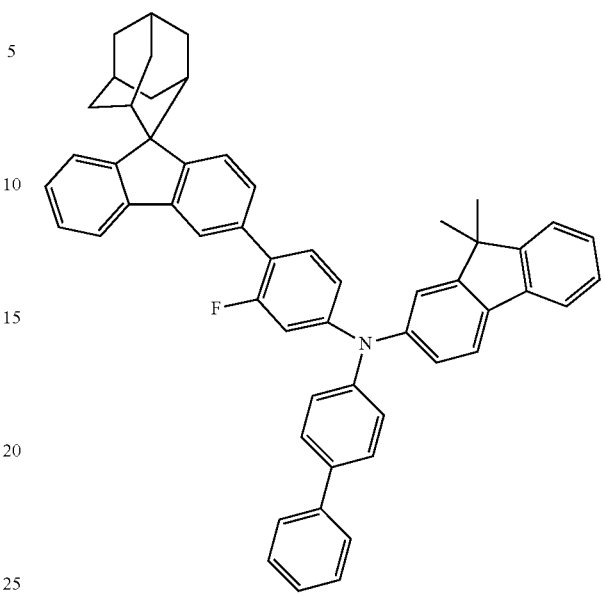
759
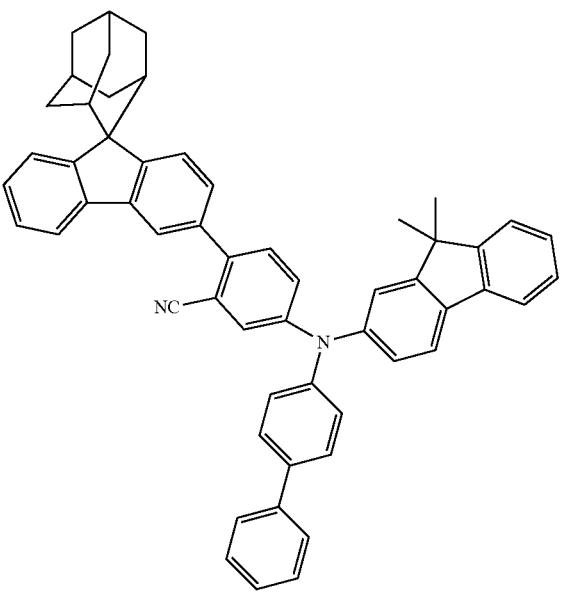

327
-continued
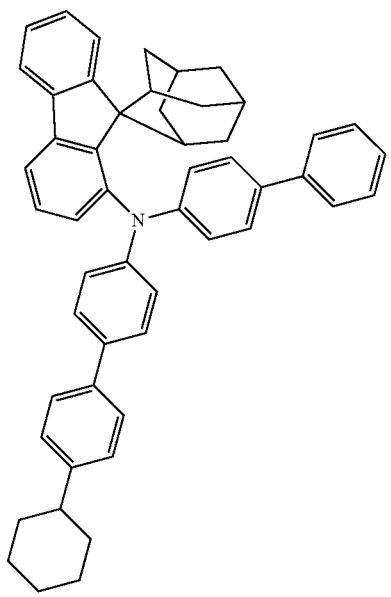
800
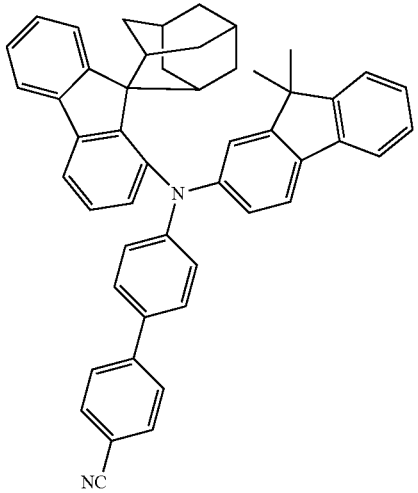
801
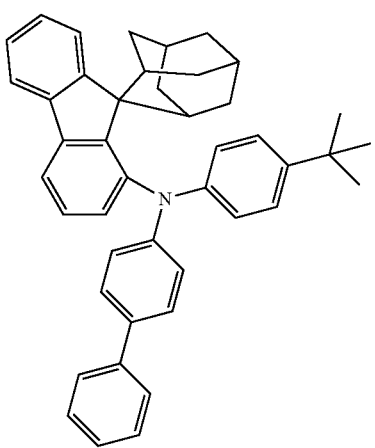
802
328
-continued
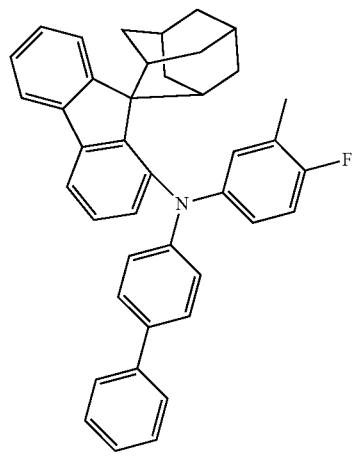
803
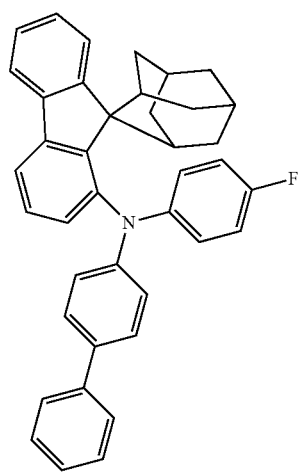
804
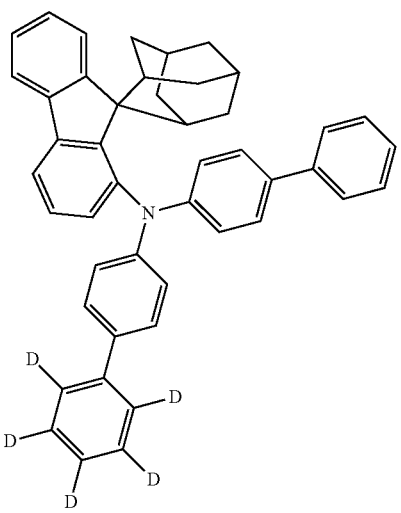
805

806
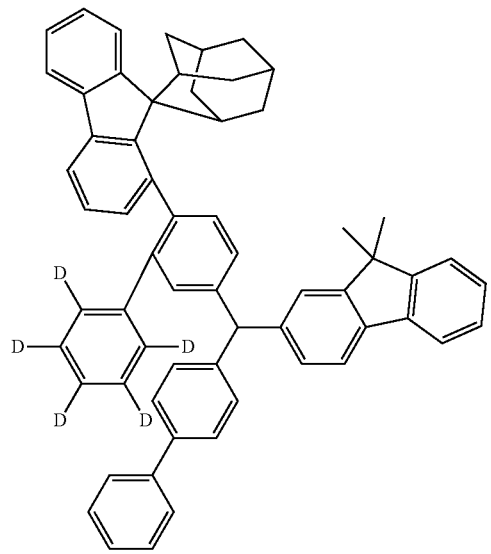
807
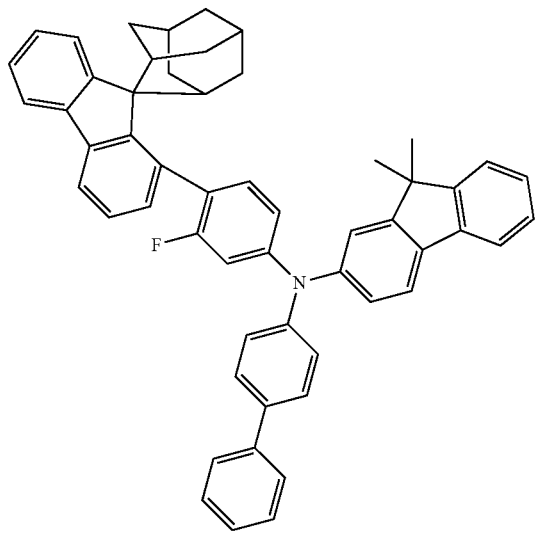
808
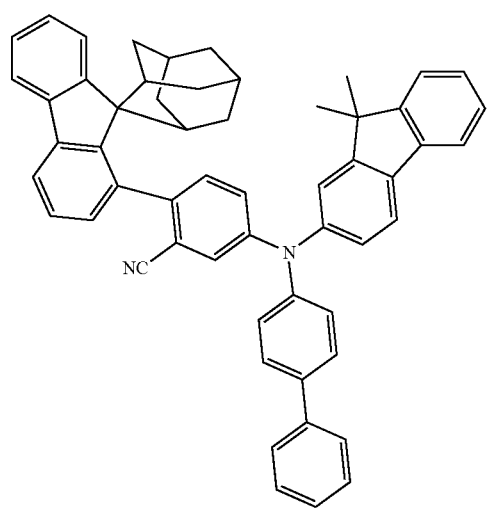
809
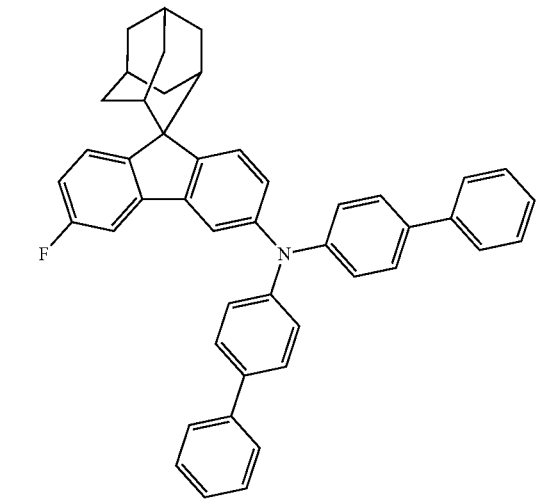
810
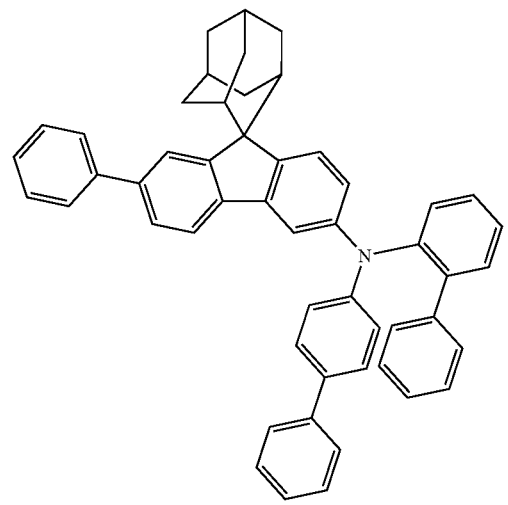
811
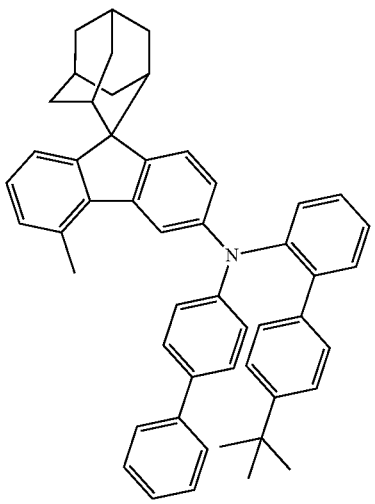

331
-continued
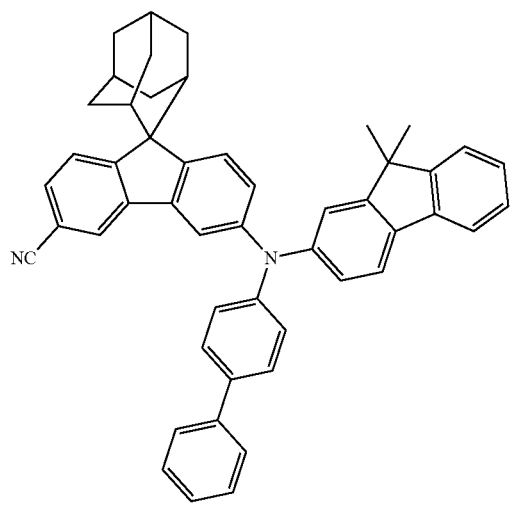
812
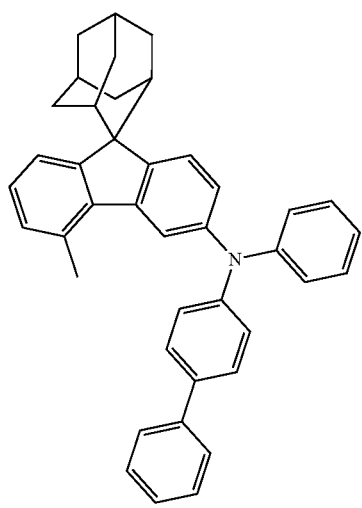
813
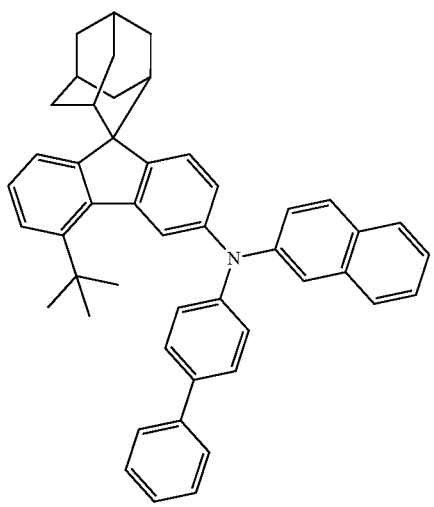
814
332
-continued
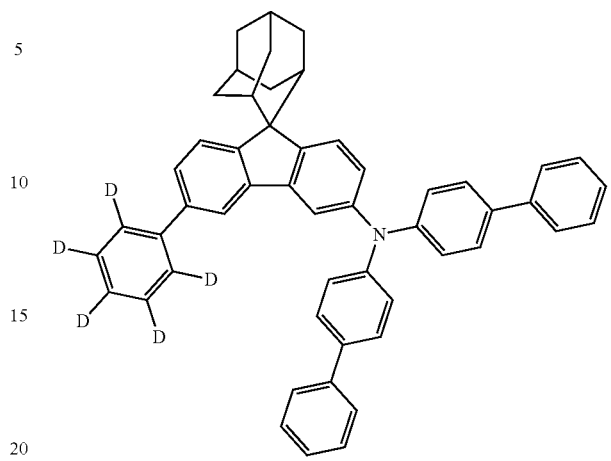
815
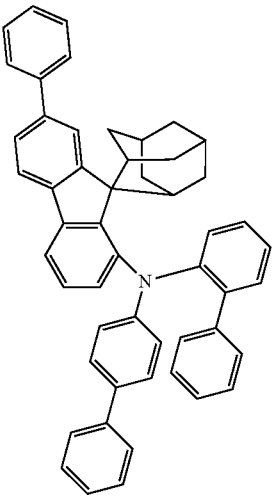
816
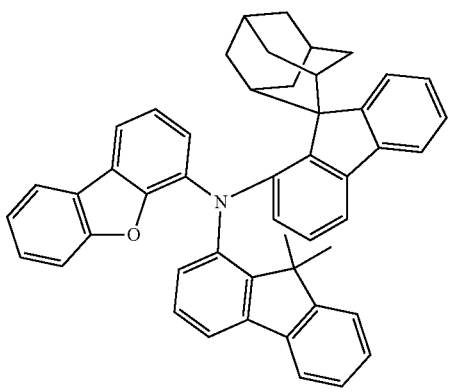
817

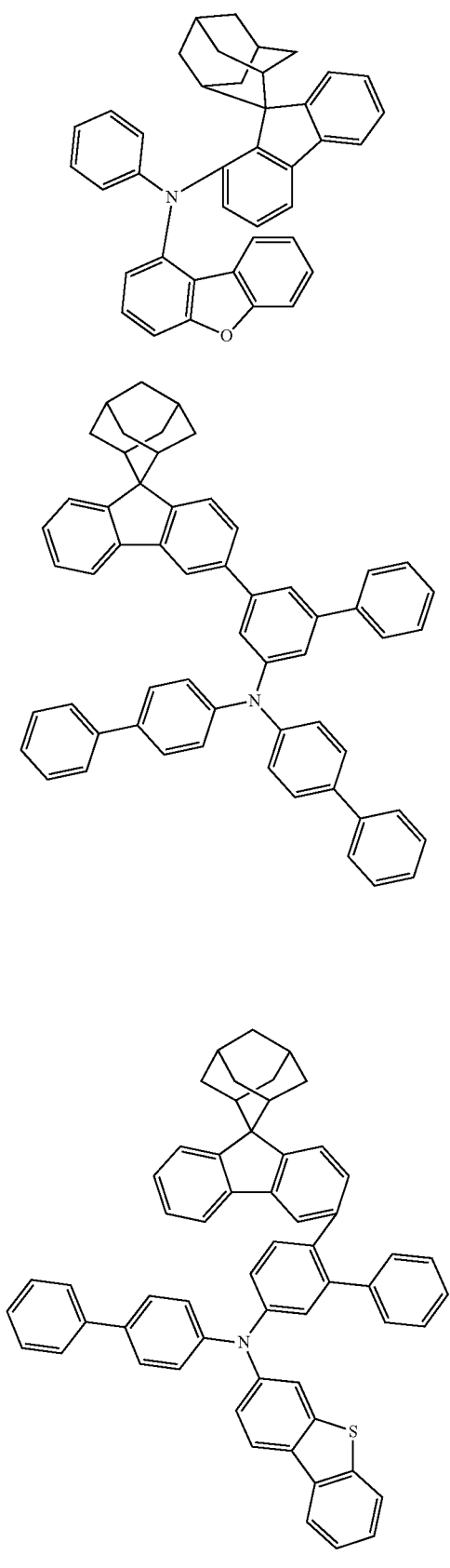
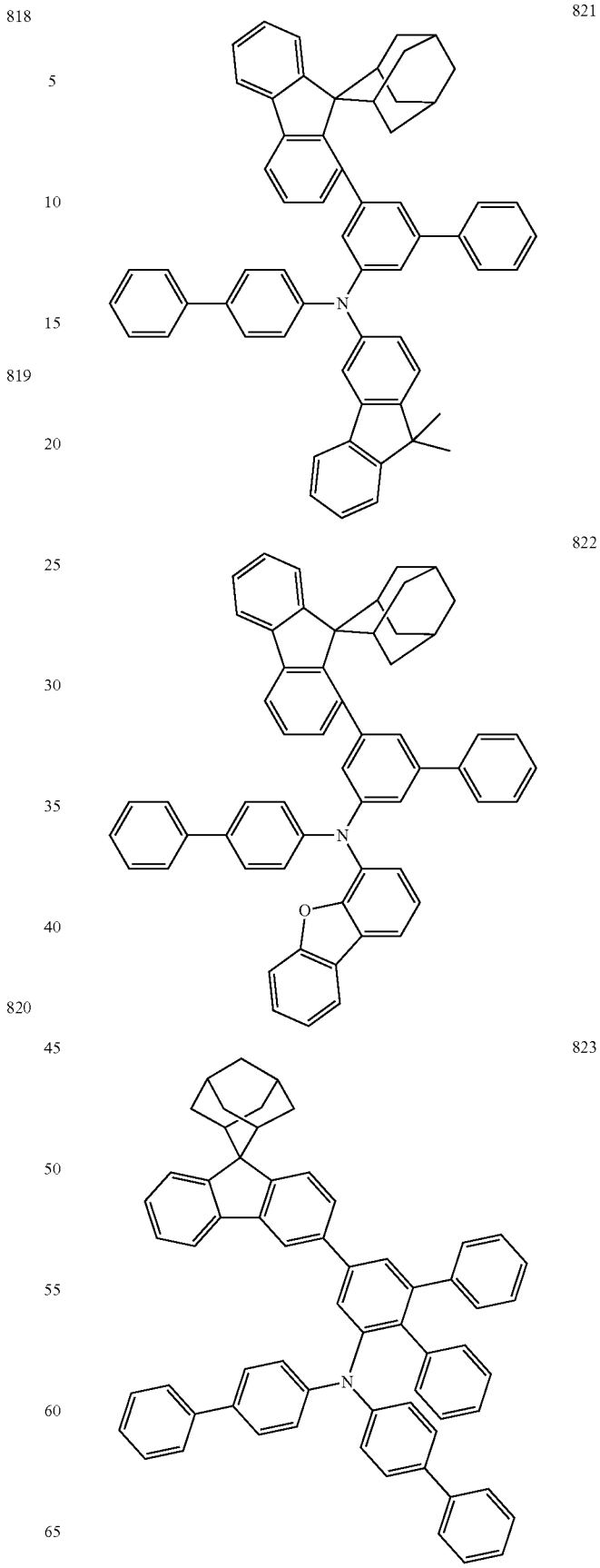

335
-continued
824
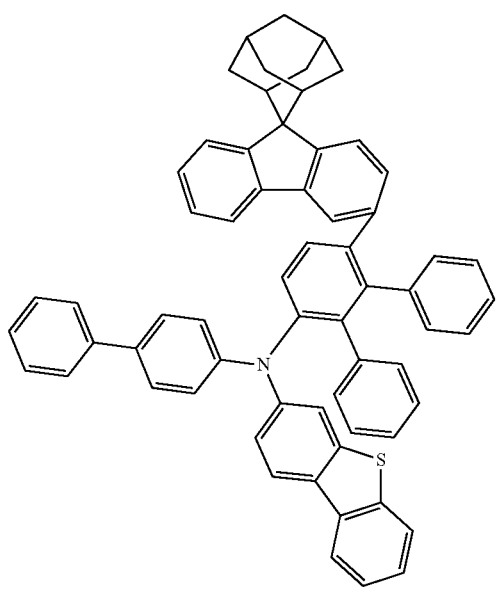
825
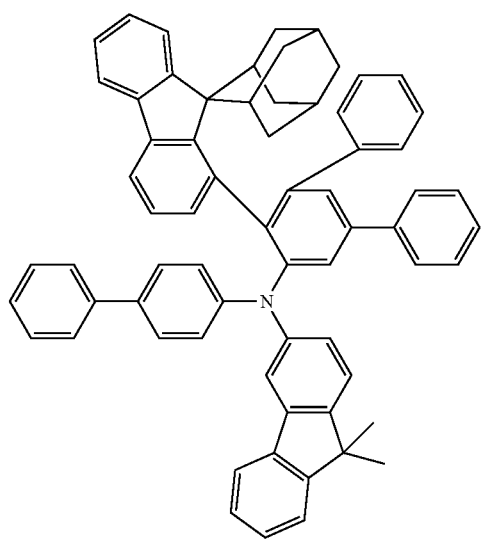
826
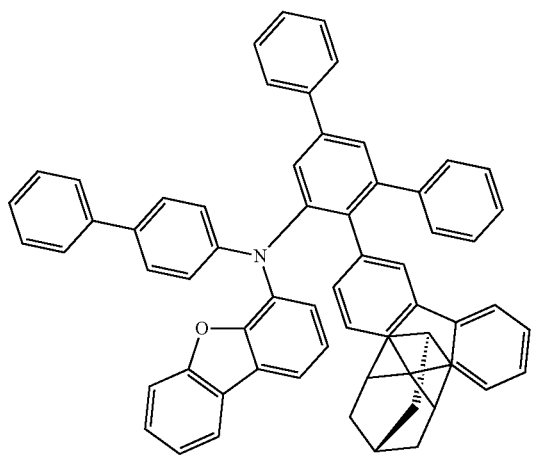
336
-continued
827
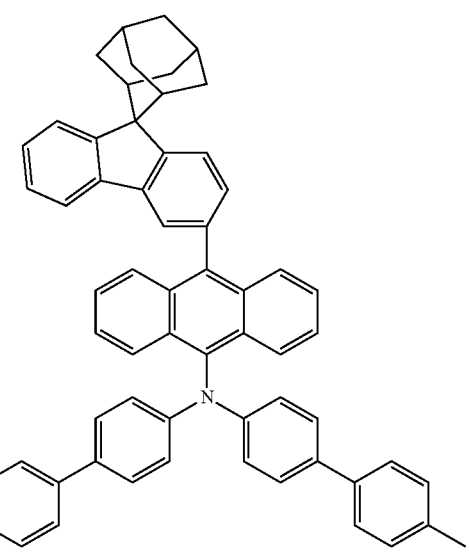
828
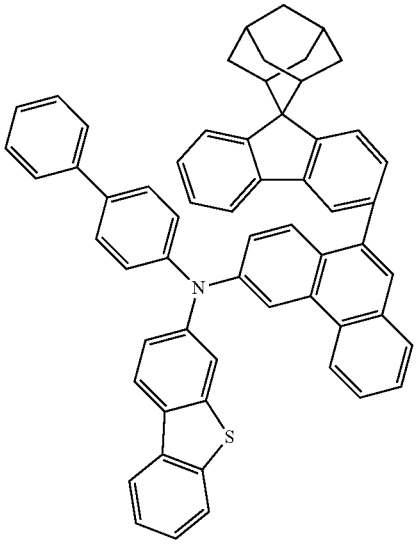
829
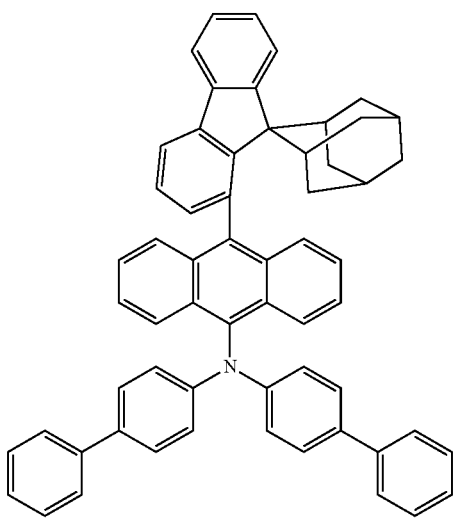

-continued

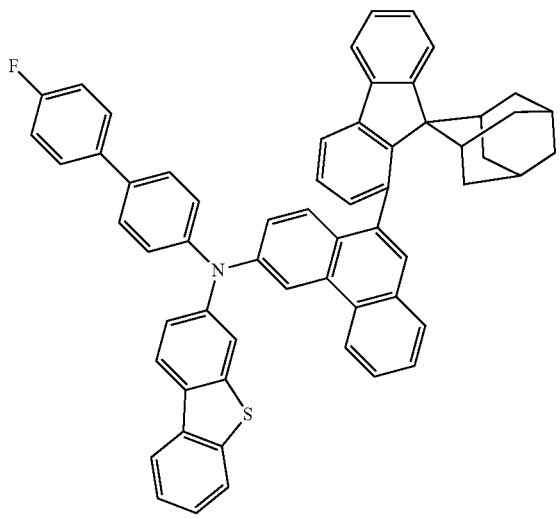

830

The present disclosure also provides an electronic element including an anode and a cathode disposed opposite to each other, and a functional layer disposed between the anode and the cathode; the functional layer contains the nitrogen-containing compound of the present disclosure. The electronic element may be used for implementing photoelectric conversion or electro-optic conversion.

According to an embodiment, the electronic element is an organic electroluminescent device. As shown in FIG. 1, the organic electroluminescent device includes an anode 100 and a cathode 200 disposed opposite to each other, and a functional layer 300 disposed between the anode 100 and the cathode 200; and the functional layer 300 contains the nitrogen-containing compound provided by the present disclosure.

Optionally, the functional layer 300 includes an electron blocking layer 322, and the electron blocking layer 322 contains the nitrogen-containing compound provided by the present disclosure. The electron blocking layer 322 may be composed of the nitrogen-containing compound provided by the present disclosure, or may be composed of the nitrogen-containing compound provided by the present disclosure and other materials.

Optionally, the functional layer 300 includes a hole transporting layer 321 and/or a hole injecting layer 310. The hole transporting layer 321 may contain the nitrogen-containing compound provided by the present disclosure to improve the hole transmission capacity in the electronic element.

In one embodiment of the present disclosure, the organic electroluminescent device may include an anode 100, a hole transporting layer 321, an electron blocking layer 322, an organic electroluminescent layer 330 as the energy conversion layer, an electron transporting layer 350 and cathode 200 that are sequentially stacked. The nitrogen-containing compound provided by the present disclosure may be applied to the electron blocking layer 322, which can effectively improve the luminous efficiency and lifetime of the organic electroluminescent device and reduce the driving voltage of the organic electroluminescent device.

Optionally, the anode 100 includes the anode material. Preferably, it is a material having a large work function that facilitates hole injection into the functional layer. Specific examples of anode materials include: metals such as nickel, platinum, vanadium, chromium, copper, zinc and gold, or their alloys; metal oxides such as zinc oxide, indium oxide, indium tin oxide (ITO) and indium zinc oxide (IZO); combination of metals and oxides such as ZnO:Al or $SnO_2$:Sb, or conductive polymers such as poly(3-methylthiophene), poly[3,4-(ethylene-1,2-dioxy)thiophene] (PEDT), polypyrrole and polyaniline, but not limited thereto. It preferably includes a transparent electrode containing indium tin oxide (ITO) as the anode.

Optionally, the hole transport layer 321 may contain one or more hole transport materials. The hole transporting material may be selected from carbazole polymers, carbazole-linked triarylamine compounds, or other types of compounds, which is not specially limited in the present disclosure. For example, the hole transporting layer 321 is composed of the compound NPB.

Optionally, the organic light-emitting layer 330 may be composed of a single light-emitting material, and may also comprise a host material and a guest material. Alternatively, the organic light-emitting layer 330 is composed of a host material and a guest material. The holes injected into the organic light-emitting layer 330 and the electrons injected into the organic light-emitting layer 330 may combine in the organic light-emitting layer 330 to form excitons, and the excitons transfer energy to the host material, the host material transfers energy to the guest material, which in turn enables the guest material to emit light.

The host material of the organic light-emitting layer 330 may be a metal chelate compound, a bisstyryl derivative, an aromatic amine derivative, a dibenzofuran derivative, or other types of materials, which is not specially limited in the present disclosure. For example, the host material of the organic light-emitting layer 330 may be CBP.

The guest material of the organic light-emitting layer 330 may be a compound having a condensed aryl ring or a derivative thereof, a compound having a heteroaryl ring or a derivative thereof, an aromatic amine derivative or other materials, which is not specially limited in the present disclosure. For example, the guest material of the organic light-emitting layer 330 may be Ir(ppy)$_3$.

The electron transporting layer 350 may have a single layer structure or a multilayer structure, which may comprise one or more electron transporting materials, and the electron transporting materials may be selected from benzimidazole derivatives, oxadiazole derivatives, quinoxaline derivatives or other electron transporting materials, which are not specifically limited in the present disclosure. For example, the electron transporting layer 340 may be composed of ET-1 and LiQ.

Optionally, the cathode 200 includes the cathode material, which is a material having a small work function that facilitates electron injection into the functional layer. Specific examples of cathode materials include: metals such as magnesium, calcium, sodium, potassium, titanium, indium, yttrium, lithium, gadolinium, aluminum, silver, tin and lead, or their alloys; or multilayer materials such as LiF/Al, Liq/Al, $LiO_2$/Al, LiF/Ca, LiF/Al, and $BaF_2$/Ca, but not limited thereto. It is preferable to include a metal electrode containing aluminum as the cathode.

Optionally, as shown in FIG. 1, a hole injecting layer 310 may also be provided between the anode 100 and the hole transporting layer 321 to enhance the ability to inject holes into the hole transporting layer 321. The hole injecting layer 310 may be selected from benzidine derivatives, starburst arylamine compounds, phthalocyanine derivatives, or other materials, which is not specially limited in the present disclosure. For example, the hole injecting layer 310 may be composed of m-MTDATA.

Optionally, as shown in FIG. 1, an electron injecting layer 360 may also be provided between the cathode 200 and the electron transport layer 340 to enhance the ability to inject electrons into the electron transport layer 350. The electron injecting layer 360 may include an inorganic material such as an alkali metal sulfide or an alkali metal halide, or may include a complex compound of an alkali metal and an organic compound. For example, the electron injecting layer 360 may include LiQ.

Optionally, a hole blocking layer 340 may be further provided between the organic electroluminescent layer 330 and the electron transporting layer 350.

Figure 2:
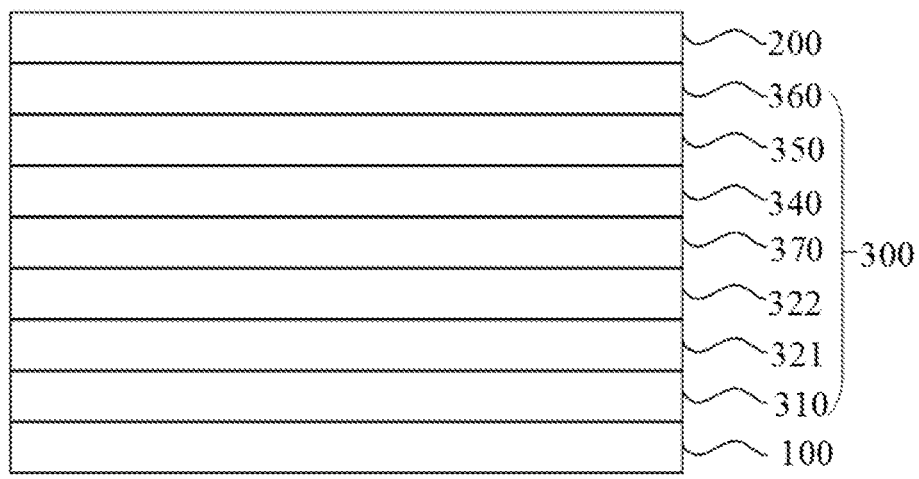
FIG. 2 is a schematic structural diagram of a photoelectric conversion device according to an embodiment of the present disclosure.

According to another embodiment, the electronic element may be a photoelectric conversion device. As shown in FIG. 2, the photoelectric conversion device may include an anode 100 and a cathode 200 disposed opposite to each other, and a functional layer 300 disposed between the anode 100 and the cathode 200; the functional layer 300 contains the nitrogen-containing compound provided in the present disclosure.

Optionally, the functional layer 300 includes an electron blocking layer 322, and the electron blocking layer 322 contains the nitrogen-containing compound provided by the present disclosure. The electron blocking layer 322 may be composed of the nitrogen-containing compound provided by the present disclosure, or may be composed of the nitrogen-containing compound provided by the present disclosure and other materials.

Optionally, as shown in FIG. 2, the photoelectric conversion device may include an anode 100, a hole transporting layer 321, an electron blocking layer 322, a photoelectric conversion layer 370 as the energy conversion layer, an electron transporting layer 350 and a cathode 200 that are sequentially stacked. The nitrogen-containing compound provided in the present disclosure may be applied to the electron blocking layer 322 of the photoelectric conversion device, which can effectively improve the luminous efficiency and lifetime of the photoelectric conversion device and increase the open circuit voltage of the photoelectric conversion device.

Optionally, a hole injecting layer 310 may also be provided between the anode 100 and the hole transporting layer 321.

Optionally, an electron injecting layer 360 may also be provided between the cathode 200 and the electron transporting layer 350.

Optionally, a hole blocking layer 340 may also be provided between the photoelectric conversion layer 370 and the electron transport layer 350.

Optionally, the photoelectric conversion device may be a solar cell, especially an organic thin film solar cell. According to a specific embodiment, the solar cell includes an anode 100, a hole transport layer 321, an electron blocking layer 322, a photoelectric conversion layer 370, an electron transport layer 350 and a cathode 200 that are sequentially stacked, wherein the electron blocking layer 322 contains the nitrogen-containing compound of the present disclosure.

The present disclosure further provides an electronic device including the above-mentioned electronic element. Since the electronic device has the electronic element, it has the same beneficial effects, which will not be repeated here.

Figure 3:
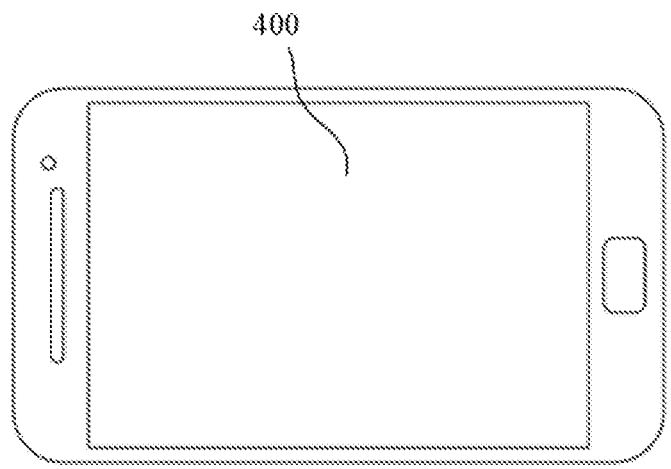
FIG. 3 is a schematic structural diagram of an electronic device according to an embodiment of the present disclosure.

According to an embodiment, as shown in FIG. 3, the electronic device is a first electronic device 400 comprising the above-mentioned organic electroluminescent device.

The first electronic device 400 may be a display device, a lighting device, an optical communication device, or other types of electronic devices. For example, the electronic device 400 may include, but is not limited to, a computer screen, a mobile phone screen, a television, an electronic paper, an emergency lighting lamp and an optical module, etc.

Figure 4:
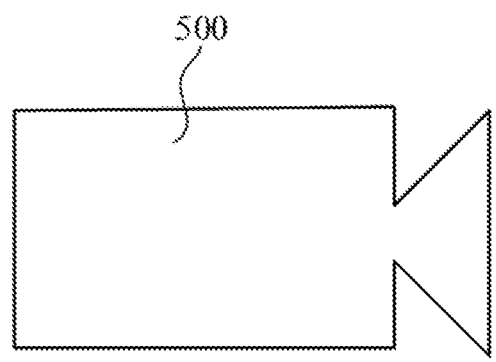
FIG. 4 is a schematic structural diagram of an electronic device according to another embodiment of the present disclosure.

According to another embodiment, as shown in FIG. 4, the electronic device is a second electronic device 500 comprising the above-mentioned photoelectric conversion device. The second electronic device 500 may be a solar power generation device, a light detector, a fingerprint recognition device, an optical module, a CCD camera, or other types of electronic devices.

Hereinafter, the present disclosure will be described in further detail through examples. However, the following examples are merely exemplary of the present disclosure, and do not limit the present disclosure.

Compound Synthesis

The compounds shown in Table 1 were synthesized by the following synthetic route.

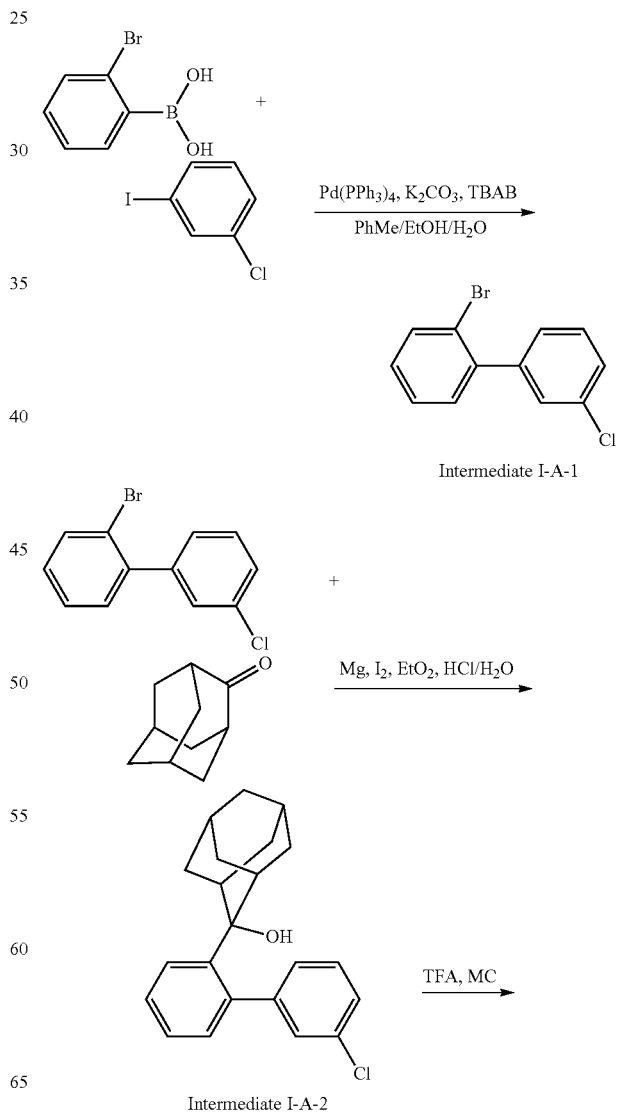

Intermediate I-A-1

Intermediate I-A-2

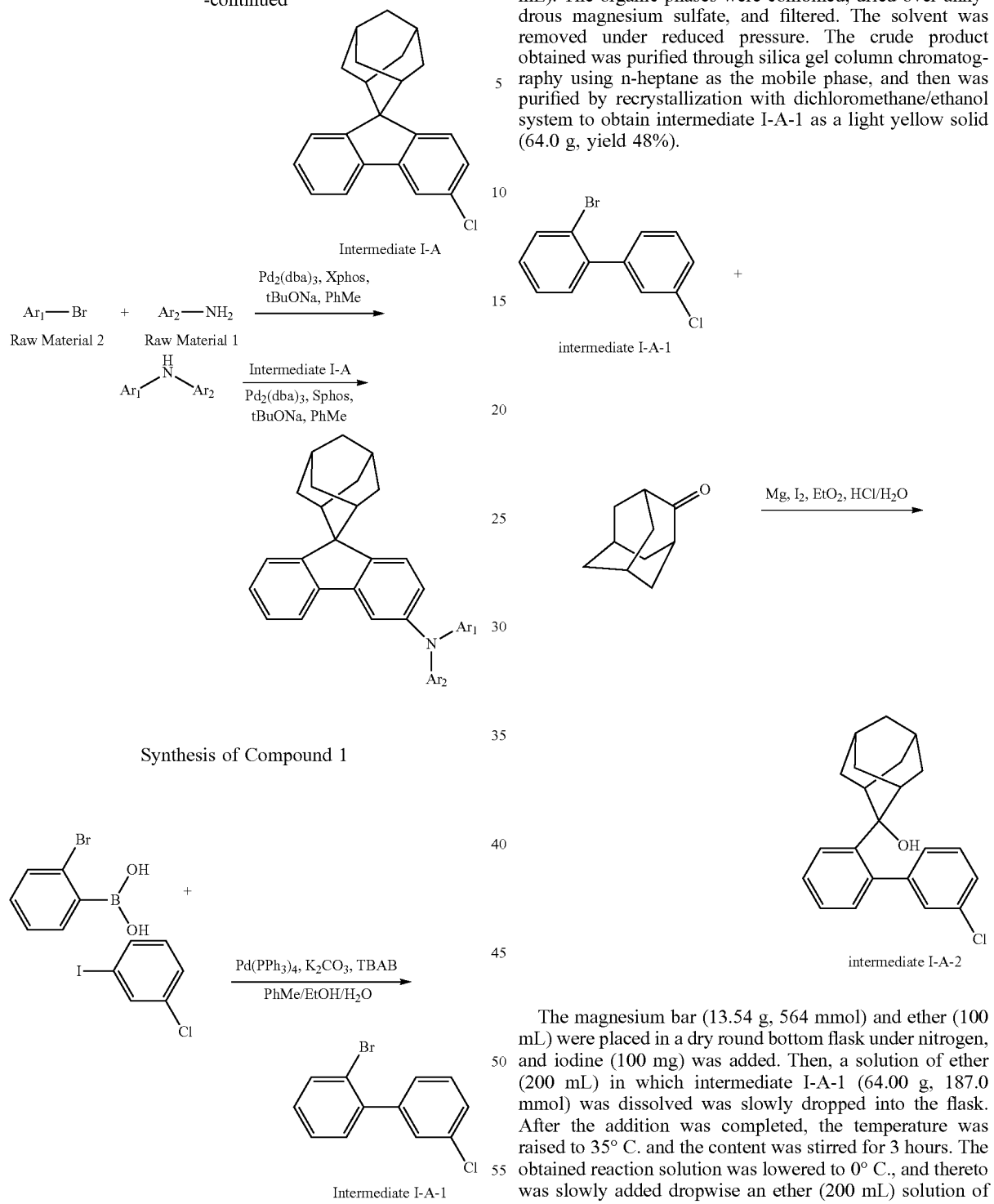

Synthesis of Compound 1

2-bromophenylboronic acid (100.0 g, 500.0 mmol), 1-chloro-3-iodobenzene (142.6 g, 597.6 mmol), tetrakis(triphenylphosphine)palladium (11.5 g, 9.97 mmol), potassium carbonate (102 g 746 mmol), tetrabutylammonium bromide (32.1 g, 99.6 mmol), toluene (800 mL), ethanol (200 mL) and deionized water (200 mL) were added to the round bottom flask, heated to 78° C. under nitrogen, and stirred for 2 hours, then the obtained reaction solution was cooled to room temperature, and extracted with toluene (500 mL). The organic phases were combined, dried over anhydrous magnesium sulfate, and filtered. The solvent was removed under reduced pressure. The crude product obtained was purified through silica gel column chromatography using n-heptane as the mobile phase, and then was purified by recrystallization with dichloromethane/ethanol system to obtain intermediate I-A-1 as a light yellow solid (64.0 g, yield 48%).

The magnesium bar (13.54 g, 564 mmol) and ether (100 mL) were placed in a dry round bottom flask under nitrogen, and iodine (100 mg) was added. Then, a solution of ether (200 mL) in which intermediate I-A-1 (64.00 g, 187.0 mmol) was dissolved was slowly dropped into the flask. After the addition was completed, the temperature was raised to 35° C. and the content was stirred for 3 hours. The obtained reaction solution was lowered to 0° C., and thereto was slowly added dropwise an ether (200 mL) solution of amantadone (22.45 g, 149 mmol) After the dropwise addition, the temperature was raised to 35° C., and stirred for 6 hours. Then, the reaction solution was cooled to room temperature, and 5 wt % hydrochloric acid was added to pH<7. After stirring for 1 hour, ether (200 mL) was added for extraction. The organic phases were combined, dried over anhydrous magnesium sulfate, filtered, and the solvent was removed under reduced pressure. The crude product obtained was purified by silica gel column chromatography using n-heptane as the mobile phase to obtain a solid intermediate I-A-2 (24 g, yield 48%).

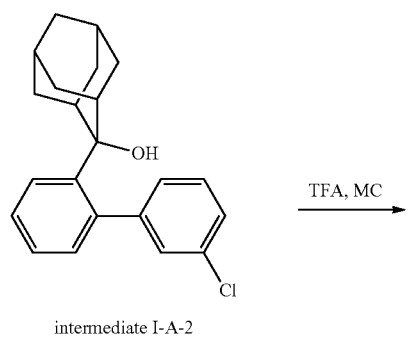

intermediate I-A-2

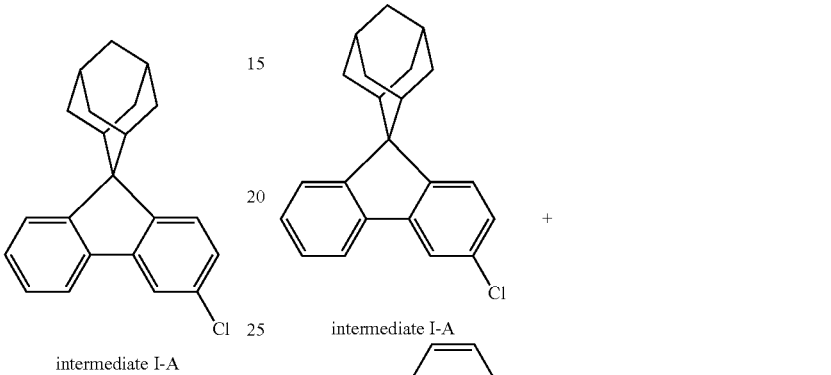

intermediate I-A

Intermediate I-A-2 (24 g, 71.0 mmol), trifluoroacetic acid (40.48 g, 355.0 mmol) and dichloromethane (200 mL) were added to a round bottom flask, and stirred for 2 hours under nitrogen. Then, sodium hydroxide aqueous solution was added to pH=8. After liquid separation, the organic phase was dried over anhydrous magnesium sulfate, filtered, and the solvent was removed under reduced pressure. The crude product obtained was purified by recrystallization using dichloromethane/n-heptane (1:2) to obtain intermediate I-A as a white solid (21 g, yield 92.5%). $^1$HNMR (400 MHz, $CD_2Cl_2$): 8.11 (d, 1H), 8.03 (d, 1H), 7.41-7.63 (m, 2H), 7.37-7.39 (m, 1H), 7.30-7.33 (m, 1H), 7.23-7.24 (m, 1H), 2.88-2.93 (m, 2H), 2.81-2.85 (m, 2H), 2.19 (s, 2H), 1.99 (s, 2H), 1.77-1.83 (m, 4H), 1.54 (s, 2H).

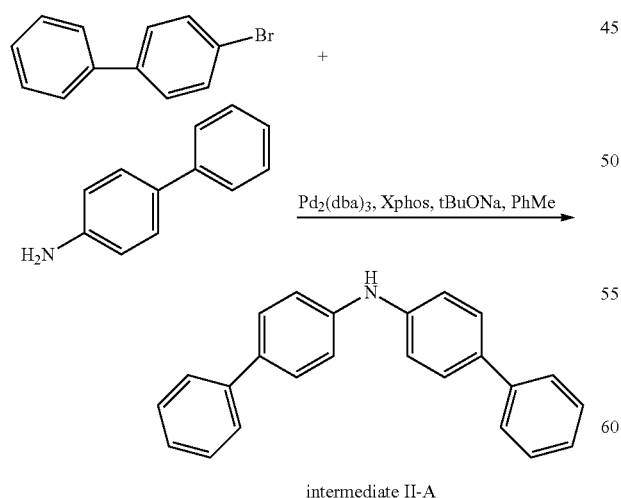

intermediate II-A 4-bromobiphenyl (4.0 g, 17.16 mmol), 4-aminobiphenyl (2.96 g, 17.5 mmol), tris(dibenzylideneacetone)dipalladium (0.16 g, 0.17 mmol), 2-dicyclohexylphosphino-2',4',6'-tri- isopropylbiphenyl (0.16 g, 0.34 mmol) and sodium tert-butoxide (2.47 g, 25.74 mmol) were added to toluene (40 mL) and heated to 108° C. under nitrogen protection, and stirred for 2 h. Then the obtained reaction solution was cooled to room temperature, and washed with water and dried over magnesium sulfate. After filtration, the solvent was removed from the filtrate under reduced pressure. The crude product obtained was purified by recrystallization using dichloromethane/ethyl acetate system to obtain intermediate II-A as a light yellow solid (4.1 g, yield 72.6%).

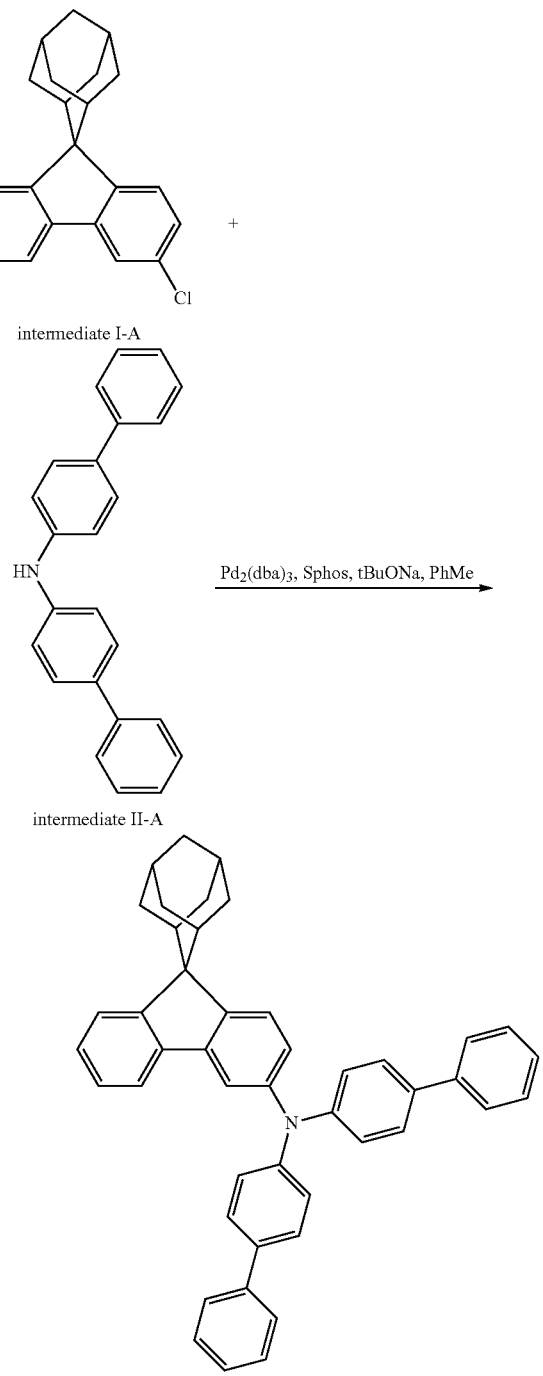

Compound 1

Intermediate I-A (4.1 g, 12.77 mmol), intermediate II-A (4.1 g, 12.77 mmol), tris(dibenzylideneacetone)dipalladium (0.12 g, 0.13 mmol), 2-dicyclohexylphosphino-2',6'-dimethoxybiphenyl (0.10 g, 0.25 mmol) and sodium tert-butoxide (1.84 g, 19.17 mmol) were added to toluene (40 mL), heated to 108° C. under nitrogen protection, and stirred for 1 h. After cooling to room temperature, the obtained reaction solution was washed with water and then dried over magnesium sulfate. After filtration, the solvent was removed from the filtrate under reduced pressure. The crude product obtained was purified by recrystallization using toluene system to obtain Compound 1 as a white solid (4.35 g, yield 56.2%). Mass spectrum (MS): m/z=606.3 [M+H]$^+$. $^1$H NMR (400 MHz, CD$_2$Cl$_2$): 8.11 (d, 1H), 8.02 (d, 1H), 7.64-7.60 (m, 6H), 7.55 (d, 4H), 7.43 (t, 4H), 7.33-7.24 (m, 8H), 7.06 (dd, 1H), 2.91 (m, 4H), 2.19 (m, 2H), 2.00 (s, 2H), 1.82 (d, 4H), 1.61 (s, 2H).

Referring to the synthesis method of Compound 1, and using raw material 2 to replace 4-bromobiphenyl, using raw material 1 to replace 4-aminobiphenyl, the intermediates in the fourth column of Table 1 were synthesized. The intermediates in the fourth column, which were used to replace intermediate II-A, and intermediate I-A were used to prepare other compounds in Table 1. The specific compound number, structure, raw materials, final step synthesis yield, characterization data, etc. are shown in Table 1.

TABLE 1

Compound structure, preparation and characterization data

| Compound No. | Raw material 1 | Raw material 2 | Intermediate | Compound Structure | Yield (%) | MS (m/z) [M + H]$^+$ |
|---|---|---|---|---|---|---|
| 3 | | | | 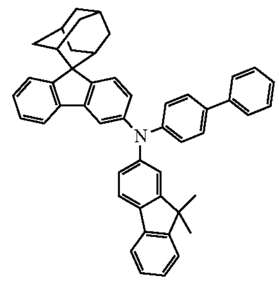 [SMILES: CC1(C)c2ccccc2-c2ccc(N(c3ccc(-c4ccccc4)cc3)c3ccc4c(c3)-c3ccccc3C43C4CC5CC(C4)CC3C5)cc21] | 67 | 646.3 |
| 7 | | | | 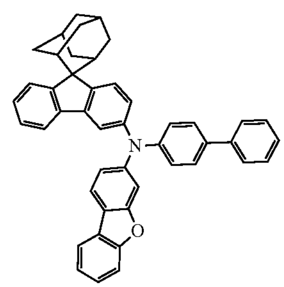 [SMILES: c1ccc(-c2ccc(N(c3ccc4c(c3)-c3ccccc3C43C4CC5CC(C4)CC3C5)c3ccc4c(c3)oc3ccccc34)cc2)cc1] | 69 | 620.3 |
| 15 | | | | 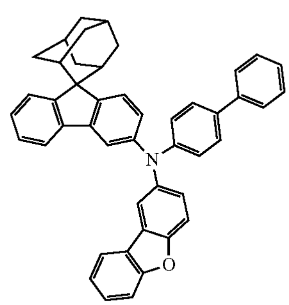 [SMILES: c1ccc(-c2ccc(N(c3ccc4c(c3)-c3ccccc3C43C4CC5CC(C4)CC3C5)c3ccc4oc5ccccc5c4c3)cc2)cc1] | 72 | 620.3 |
| 9 | | | | 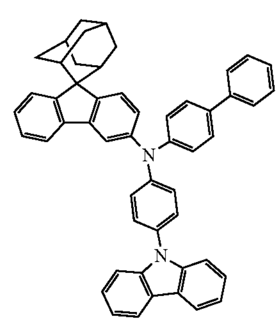 [SMILES: c1ccc(-c2ccc(N(c3ccc(-n4c5ccccc5c5ccccc54)cc3)c3ccc4c(c3)-c3ccccc3C43C4CC5CC(C4)CC3C5)cc2)cc1] | 67 | 695.3 |

TABLE 1-continued

Compound structure, preparation and characterization data

| Compound No. | Raw material 1 | Raw material 2 | Intermediate | Compound Structure | Yield (%) | MS (m/z) [M + H]+ |
|---|---|---|---|---|---|---|
| 23 | | (structure) | (structure) | (structure) | 54 | 696.3 |
| 487 | | (structure) | (structure) | (structure) | 61 | 636.3 |
| 745 | | (structure) | (structure) | (structure) | 53 | 632.3 |
| 36 | (structure) | (structure) | (structure) | (structure) | 55 | 606.3 |
| 31 | | (structure) | (structure) | (structure) | 59 | 695.3 |

TABLE 1-continued
Compound structure, preparation and characterization data
| Compound No. | Raw material 1 | Raw material 2 | Intermediate | Compound Structure | Yield (%) | MS (m/z) [M + H]+ |
|---|---|---|---|---|---|---|
| 54 | 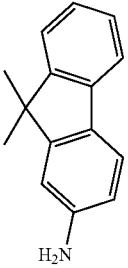 [SMILES: CC1(C)c2ccccc2-c2ccc(N)cc21] | 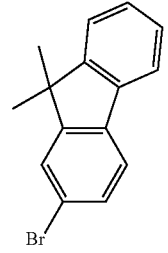 [SMILES: CC1(C)c2ccccc2-c2ccc(Br)cc21] | 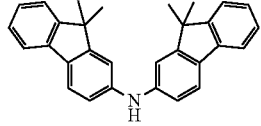 [SMILES: CC1(C)c2ccccc2-c2ccc(Nc3ccc4c(c3)C(C)(C)c3ccccc3-4)cc21] | 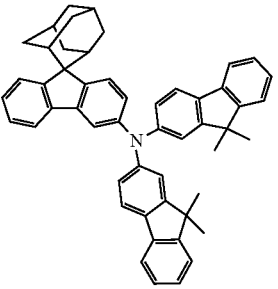 [SMILES: CC1(C)c2ccccc2-c2ccc(N(c3ccc4c(c3)-c3ccccc3C43C4CC5CC(C4)CC3C5)c3ccc4c(c3)C(C)(C)c3ccccc3-4)cc21] | 61 | 686.4 |
| 60 | | 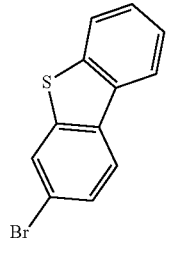 [SMILES: Brc1ccc2c(c1)sc1ccccc12] | 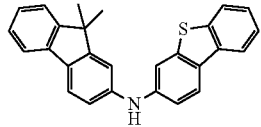 [SMILES: CC1(C)c2ccccc2-c2ccc(Nc3ccc4c(c3)sc3ccccc34)cc21] | 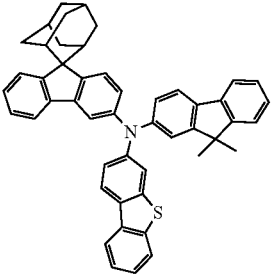 [SMILES: CC1(C)c2ccccc2-c2ccc(N(c3ccc4c(c3)-c3ccccc3C43C4CC5CC(C4)CC3C5)c3ccc4c(c3)sc3ccccc34)cc21] | 62 | 676.3 |
| 66 | |  | 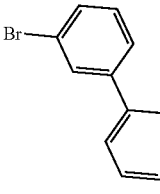 | 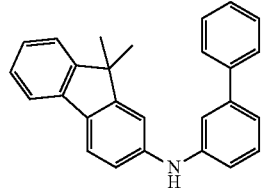 [SMILES: CC1(C)c2ccccc2-c2ccc(Nc3cccc(-c4ccccc4)c3)cc21] | 47 | 646.3 |
| 71 | | 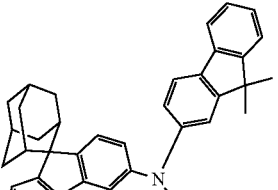 | 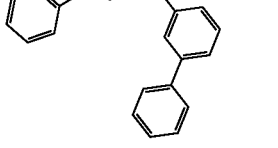 | 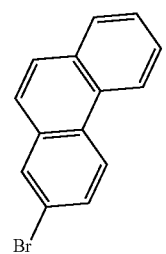 | 49 | 670.3 |

TABLE 1-continued
Compound structure, preparation and characterization data
| Compound No. | Raw material 1 | Raw material 2 | Intermediate | Compound Structure | Yield (%) | MS (m/z) [M + H]+ |
|---|---|---|---|---|---|---|
| 87 |  | 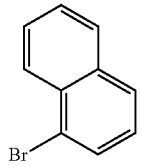 | 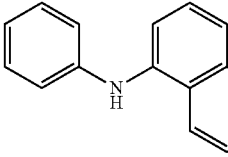 | 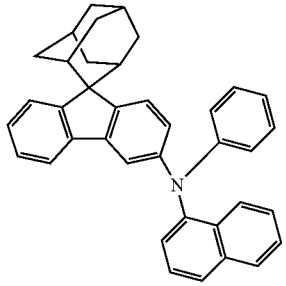 [SMILES: c1ccc(N(c2ccc3c(c2)-c2ccccc2C32C3CC4CC(C3)CC2C4)c2cccc3ccccc23)cc1] | 53 | 504.3 |
| 92 | | 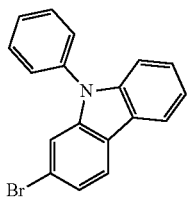 [SMILES: Brc1ccc2c3ccccc3n(-c3ccccc3)c2c1] | 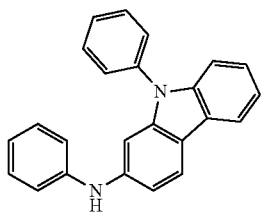 [SMILES: c1ccc(Nc2ccc3c4ccccc4n(-c4ccccc4)c3c2)cc1] | 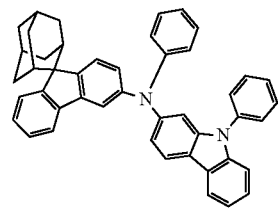 [SMILES: c1ccc(N(c2ccc3c(c2)-c2ccccc2C32C3CC4CC(C3)CC2C4)c2ccc3c4ccccc4n(-c4ccccc4)c3c2)cc1] | 55 | 619.3 |
| 95 | | 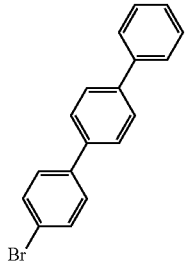 [SMILES: Brc1ccc(-c2ccc(-c3ccccc3)cc2)cc1] | 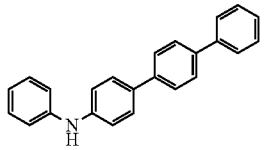 [SMILES: c1ccc(Nc2ccc(-c3ccc(-c4ccccc4)cc3)cc2)cc1] | 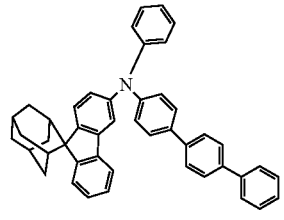 [SMILES: c1ccc(-c2ccc(-c3ccc(N(c4ccccc4)c4ccc5c(c4)-c4ccccc4C54C5CC6CC(C5)CC4C6)cc3)cc2)cc1] | 67 | 606.3 |
| 115 | | 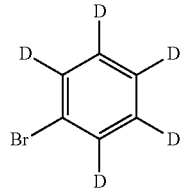 [SMILES: [2H]c1c([2H])c([2H])c(Br)c([2H])c1[2H]] | 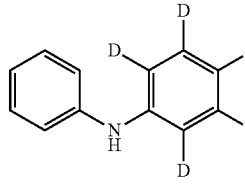 | 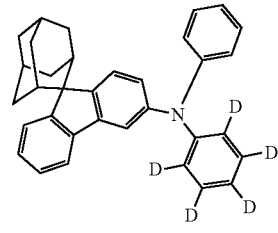 [SMILES: [2H]c1c([2H])c([2H])c(N(c2ccccc2)c2ccc3c(c2)-c2ccccc2C32C3CC4CC(C3)CC2C4)c([2H])c1[2H]] | 69 | 459.3 |
| 116 | 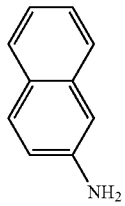 | 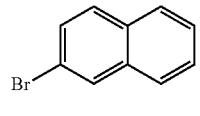 [SMILES: Brc1ccc2ccccc2c1] | 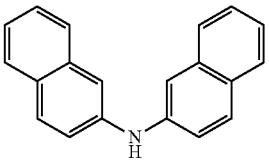 [SMILES: c1ccc2cc(Nc3ccc4ccccc4c3)ccc2c1] | 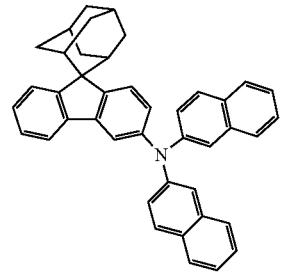 [SMILES: c1ccc2c(c1)-c1cc(N(c3ccc4ccccc4c3)c3ccc4ccccc4c3)ccc1C21C2CC3CC(C2)CC1C3] | 70 | 554.3 |

TABLE 1-continued

Compound structure, preparation and characterization data

| Compound No. | Raw material 1 | Raw material 2 | Intermediate | Compound Structure | Yield (%) | MS (m/z) [M + H]+ |
|---|---|---|---|---|---|---|
| 128 | | | | 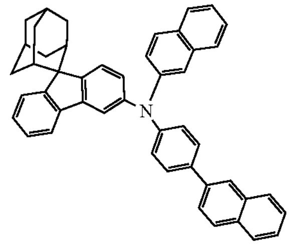 [SMILES: c1ccc2c(c1)-c1cc(N(c3ccc(-c4ccc5ccccc5c4)cc3)c3ccc4ccccc4c3)ccc1C21C2CC3CC(C2)CC1C3] | 50 | 630.3 |
| 127 | | | | 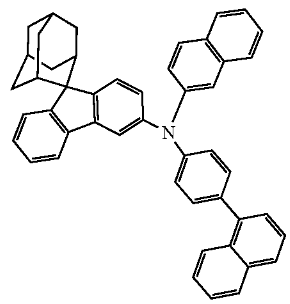 [SMILES: c1ccc2c(c1)-c1cc(N(c3ccc(-c4cccc5ccccc45)cc3)c3ccc4ccccc4c3)ccc1C21C2CC3CC(C2)CC1C3] | 43 | 630.3 |
| 147 | | | | 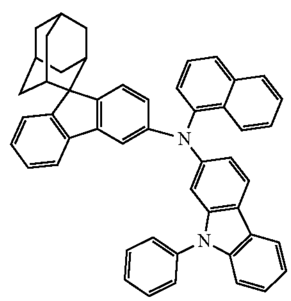 [SMILES: c1ccc(-n2c3ccccc3c3ccc(N(c4ccc5c(c4)-c4ccccc4C54C5CC6CC(C5)CC4C6)c4cccc5ccccc45)cc32)cc1] | 49 | 669.3 |
| 160 | | | | 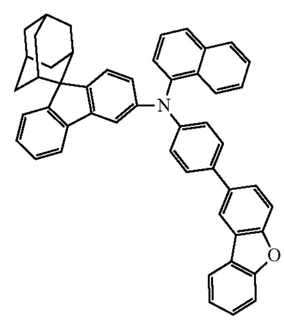 [SMILES: c1ccc2c(c1)-c1cc(N(c3ccc(-c4ccc5oc6ccccc6c5c4)cc3)c3cccc4ccccc34)ccc1C21C2CC3CC(C2)CC1C3] | 48 | 670.3 |
| 195 | | | | 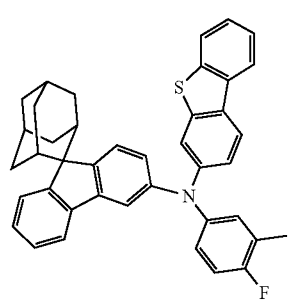 [SMILES: Cc1cc(N(c2ccc3c(c2)-c2ccccc2C32C3CC4CC(C3)CC2C4)c2ccc3c(c2)sc2ccccc23)ccc1F] | 54 | 592.2 |

TABLE 1-continued

Compound structure, preparation and characterization data

| Compound No. | Raw material 1 | Raw material 2 | Intermediate | Compound Structure | Yield (%) | MS (m/z) [M + H]+ |
|---|---|---|---|---|---|---|
| 206 | ![structure] | ![structure] | ![structure] | ![structure] | 58 | 720.3 |

NMR data of Compound 3: $^1$H NMR (CD$_2$Cl$_2$, 400 MHz): 8.10 (d, 1H), 8.00 (d, 1H), 7.67-7.59 (m, 6H), 7.54 (d, 2H), 7.45-7.42 (m, 3H), 7.36-7.25 (m, 8H), 7.12 (br, 1H), 7.06 (br, 1H), 2.92 (t, 4H), 2.19 (d, 2H), 2.00 (s, 2H), 1.82 (d, 4H), 1.61 (s, 2H), 1.44 (s, 6H).

NMR data of Compound 7: $^1$H NMR (CD$_2$Cl$_2$, 400 MHz): 8.11 (d, 1H), 8.03 (d, 1H), 7.91 (d, 1H), 7.85 (d, 1H), 7.62-7.60 (m, 4H), 7.56 (d, 2H), 7.51 (d, 1H), 7.45-7.39 (m, 3H), 7.36-7.26 (m, 7H), 7.21 (d, 1H), 7.07 (d, 1H), 2.92 (t, 4H), 2.19 (d, 2H), 2.00 (s, 2H), 1.82 (d, 4H), 1.62 (s, 2H).

NMR data of Compound 54: $^1$H NMR (400 MHz, CD$_2$Cl$_2$): 8.11 (d, 1H), 7.99 (d, 1H), 7.66 (d, 2H), 7.63-7.62 (m, 3H), 7.58 (d, 1H), 7.41 (d, 2H), 7.35 (s, 2H), 7.32 (t, 2H), 7.28-7.24 (m, 4H), 7.12 (d, 2H), 7.07 (d, 1H), 2.92 (t, 4H), 2.19 (d, 2H), 2.00 (s, 2H), 1.82 (d, 4H), 1.62 (s, 2H), 1.42 (s, 12H).

Synthesis of Compound 295

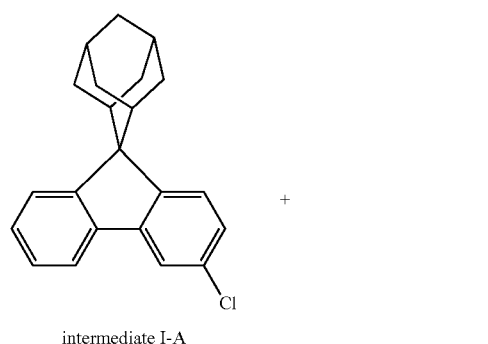

intermediate I-A

+

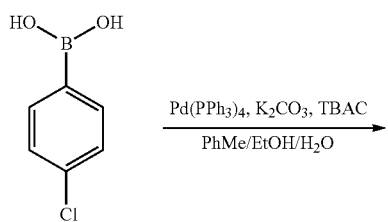

Pd(PPh$_3$)$_4$, K$_2$CO$_3$, TBAC
PhMe/EtOH/H$_2$O

-continued

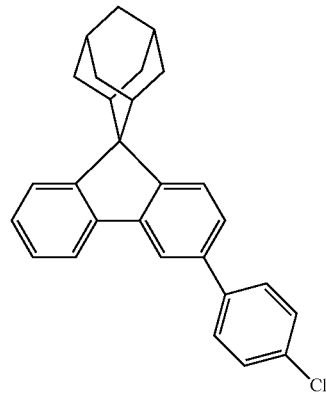

intermediate I-B

Intermediate I-A (10 g, 31.17 mmol), p-chlorophenylboronic acid (3.89 g, 24.93 mmol), tetrakis(triphenylphosphine)palladium (0.72 g, 0.62 mmol), potassium carbonate (6.45 g 46.75 mmol), Tetrabutylammonium chloride (1.73 g, 6.23 mmol), toluene (80 mL), ethanol (20 mL) and deionized water (20 mL) were added to the round-bottom flask, heated to 78° C. under nitrogen protection, and stirred for 6 hours. The obtained reaction solution was cooled to room temperature, and toluene (100 mL) was added for extraction. The organic phases were combined, dried over anhydrous magnesium sulfate, filtered, and the solvent was removed under reduced pressure. The obtained crude product was purified by silica gel column chromatography using n-heptane as the mobile phase, and then was purified by recrystallization using chloromethane/ethyl acetate system to obtain intermediate I-B as a white solid (7.5 g, yield 40.6%).

Referring to the synthesis method of intermediate I-B, the intermediates shown in the third column of Table 2 below were synthesized except that the raw materials 3 in the second column of Table 2 below were used to replace p-chlorophenylboronic acid.

TABLE 2

| Intermediate No. | Raw Material 3 | Intermediate Structure | Yield (%) |
|---|---|---|---|
| Intermediate I-C | 3-chlorophenylboronic acid | (adamantane-spirofluorene)-3-chlorophenyl | 37 |
| Intermediate I-D | 2-chlorophenylboronic acid | (adamantane-spirofluorene)-2-chlorophenyl | 41 |
| Intermediate I-E | 4-chloronaphthalen-1-ylboronic acid | (adamantane-spirofluorene)-(4-chloronaphthalen-1-yl) | 44 |
| Intermediate I-F | 3'-chloro-[1,1'-biphenyl]-3-ylboronic acid | (adamantane-spirofluorene)-(3'-chlorobiphenyl-3-yl) | 39 |

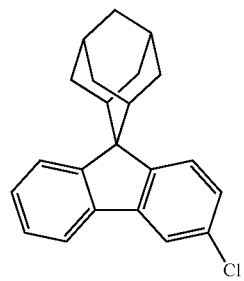

intermediate I-A

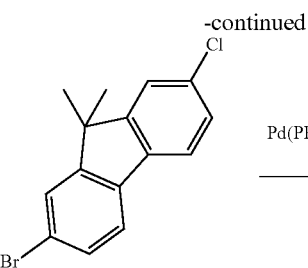

(BPin)₄, Pd₂(dba)₃, XPhos, KOAc
1,4-Dioxane
→

Pd(PPh₃)₄, K₂CO₃, nBu₄NBr
PhMe/EtOH/H₂O
→

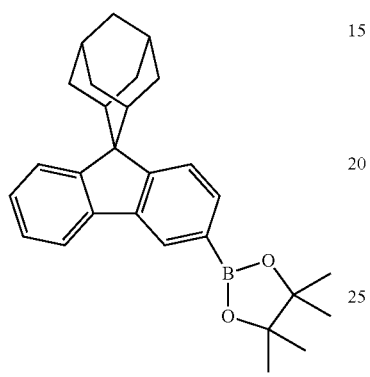

intermediate I-A-1

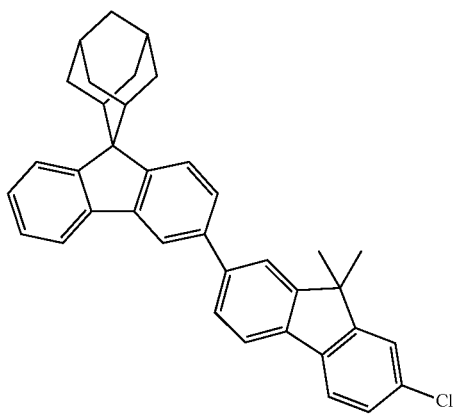

intermediate I-A-2

Intermediate I-A (20.4 g, 63.7 mmol), bis(pinacolato) diboron (19.4 g, 76.5 mmol), tris(dibenzylideneacetone) dipalladium (0.6 g, 0.6 mmol), 2-dicyclohexylphosphino-2', 4',6'-triisopropylbiphenyl (0.6 g; 1.3 mmol), potassium acetate (12.5 g; 127.4 mmol) and 1,4-dioxane (150 mL) were added to the flask, and stirred at 100° C. with reflux for 16 hours under nitrogen. After cooling to room temperature, dichloromethane and water were added into the obtained reaction solution to separate the layers, the resulting organic phase was washed with water and dried over anhydrous magnesium sulfate, and the solvent was removed under reduced pressure to obtain the crude product. The crude product was purified through silica gel column chromatography using dichloromethane/n-heptane system to obtain intermediate I-A-1 as a white solid (13.3 g, yield 51%).

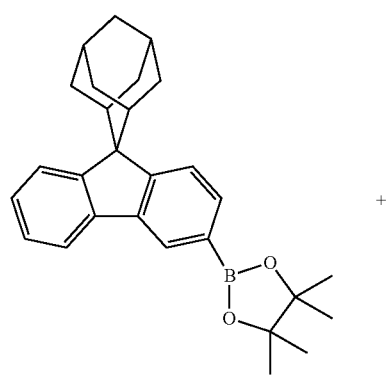

intermediate I-A-1

+

Intermediate I-A-1 (13.3 g, 32.3 mmol), 2-bromo-7-chloro-9,9-dimethylfluorene (7.1 g, 35.5 mmol), tetrakis (triphenylphosphine)palladium (0.7 g, 0.6 mmol), potassium carbonate (11.1 g, 80.7 mmol) and tetrabutylammonium bromide (2.1 g, 6.5 mmol) were added to the flask, and then added a mixed solvent of toluene (80 mL), ethanol (20 mL) and water (20 mL), heated to 80° C. and stirred for 24 hours maintaining the temperature under nitrogen protection. After cooling to room temperature, the stirring was stopped, the resulting reaction solution was washed with water, then the organic phase was separated from it and dried over anhydrous magnesium sulfate, and the solvent was removed under reduced pressure to obtain a crude product. The crude product was purified by silica gel column chromatography using dichloromethane/n-heptane as the mobile phase to obtain product intermediate I-A-2 as a white solid (9.0 g, yield 54.5%).

Referring to the synthesis method of intermediate I-A-2, the intermediates shown in the third column of Table 3 below were synthesized except that the raw material 41 in the second column of Table 3 below were used to replace 2-bromo-7-chloro-9,9-dimethylfluorene.

TABLE 3
Raw materials and intermediates
| Intermediate No. | Raw material 41 | Intermediate structure | Yield (%) |
|---|---|---|---|
| Intermediate I-A-3 | 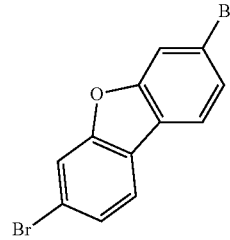 | 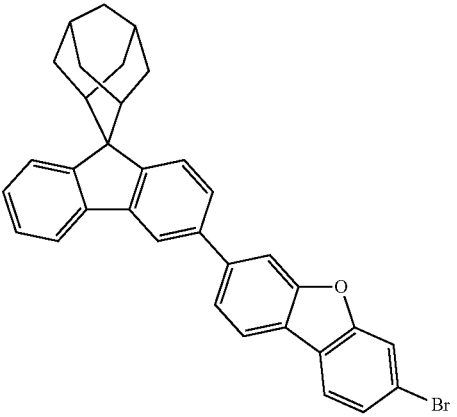 | 59 |
| Intermediate I-A-4 | 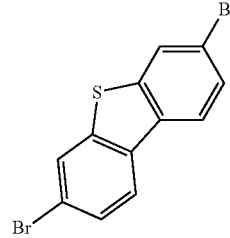 | 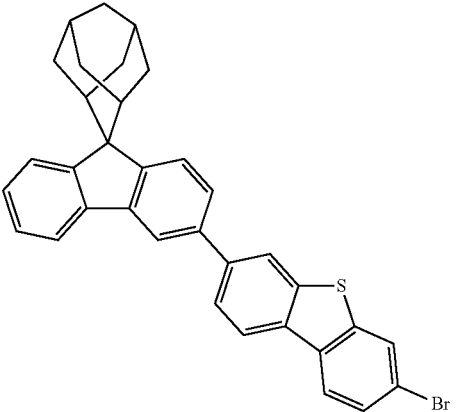 [SMILES: Brc1ccc2c(c1)oc1cc(-c3ccc4c(c3)-c3ccccc3C43C4CC5CC(C4)CC3C5)ccc12] | 62 |
| Intermediate I-A-5 | 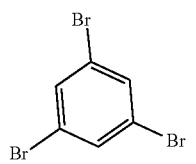 | 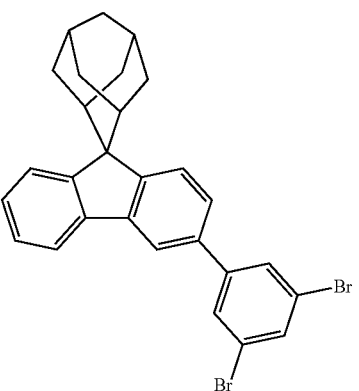 [SMILES: Brc1cc(Br)cc(-c2ccc3c(c2)-c2ccccc2C32C3CC4CC(C3)CC2C4)c1] | 31 |

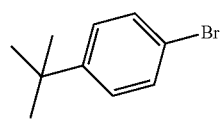

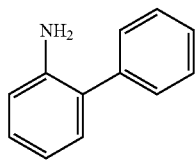

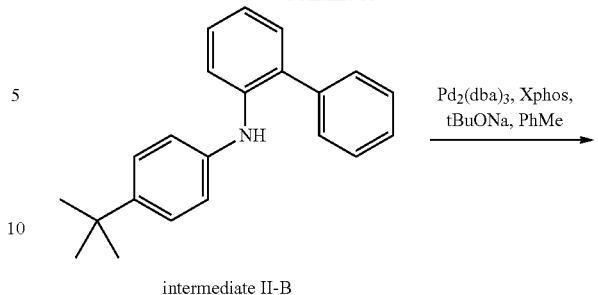

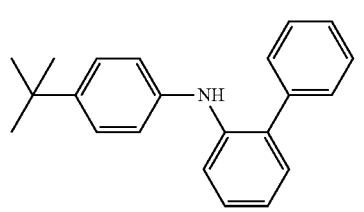

intermediate II-B 4-tert-butylbromobenzene (4.0 g, 25.5 mmol), 2-aminobiphenyl (4.39 g, 25.9 mmol), tris(dibenzylideneacetone)dipalladium (0.23 g, 0.25 mmol), 2-dicyclohexylphosphino-2',4',6'-triisopropylbiphenyl (0.24 g, 0.50 mmol) and sodium tert-butoxide (3.67 g, 38.22 mmol) were added to toluene (40 mL), heated to 108° C. and stirred for 2 h under nitrogen. After cooling to room temperature, the obtained reaction solution was washed with water and dried by adding magnesium sulfate. After filtration, the solvent was removed from the filtrate under reduced pressure. The crude product obtained was purified by recrystallization using dichloromethane/ethyl acetate system to obtain Intermediate II-B as a light yellow solid (3.2 g, yield 56.6%).

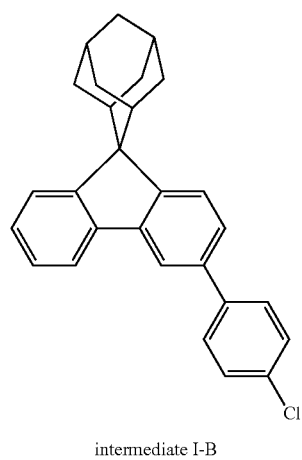

intermediate I-B

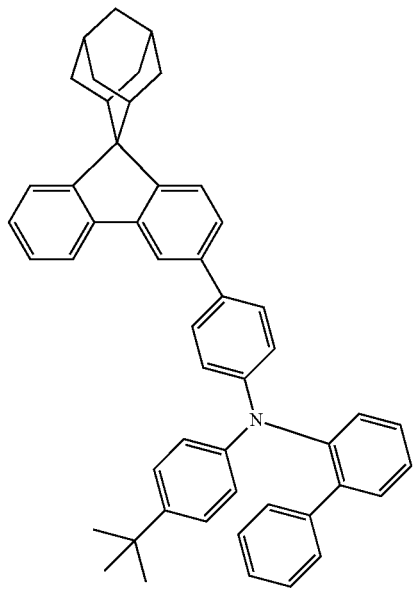

Compound 295

Intermediate I-B (1.50 g, 3.78 mmol), intermediate II-B (0.95 g, 3.85 mmol), tris(dibenzylideneacetone) dipalladium (0.03 g, 0.04 mmol), 2-dicyclohexylphosphinodicyclohexylphosphino-2',6'-dimethoxybiphenyl (0.03 g, 0.07 mmol) and sodium tert-butoxide (0.55 g, 5.67 mmol) were added to toluene (20 mL), heated to 108° C. and stirred for 5 h under nitrogen protection. After cooling to room temperature, the obtained reaction solution was washed with water and dried by adding magnesium sulfate. After filtration, the solvent was removed from the filtrate under reduced pressure. The crude product obtained was purified by recrystallization using toluene system to obtain Compound 295 as a white solid (1.7 g, 74%). Mass spectrum: m/z=662.4 [M+H]$^+$.

Referring to the synthesis method of Compound 295, and using the raw materials 4 to replace 2-aminobiphenyl, and the raw material 5 to replace 4-tert-butylbromobenzene, the intermediates in the fourth column in the following table were synthesized. Other compounds in Table 4 were prepared by replacing the intermediate II-B with the intermediates in the fourth column. The specific compound number, structure, raw materials, synthesis yield of the last step, characterization data, etc. are shown in Table 4.

TABLE 4
Compound number, structure, preparation and characterization data
| Compound No. | Raw material 14 | Raw material 5 | Intermediate | Structure | Yield (%) | MS (m/z) [M + H]+ |
|---|---|---|---|---|---|---|
| 304 | 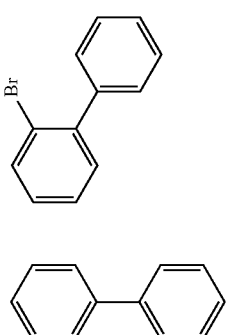 | 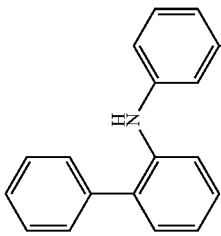 | 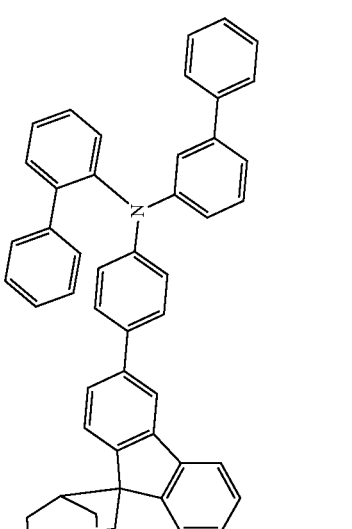 | 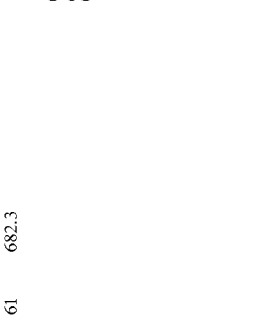 | 61 | 682.3 |
| 316 | 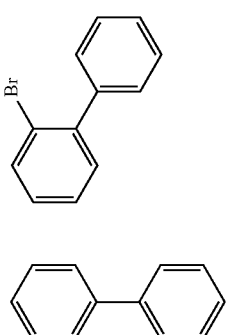 | 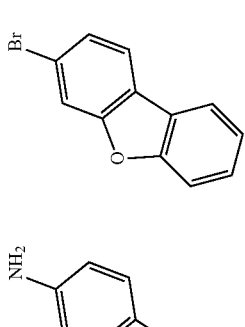 | 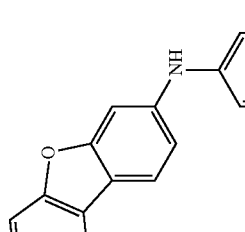 | 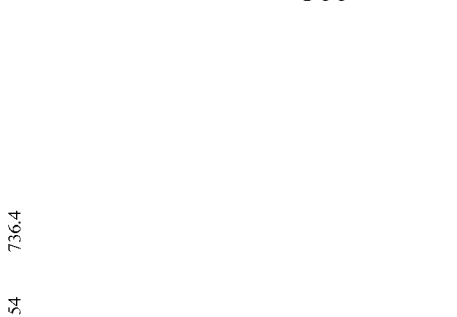 | 54 | 736.4 |

TABLE 4-continued

Compound number, structure, preparation and characterization data

| Compound No. | Raw material 14 | Raw material 5 | Intermediate | Structure | Yield (%) | MS (m/z) [M + H]+ |
|---|---|---|---|---|---|---|
| 341 | | | | 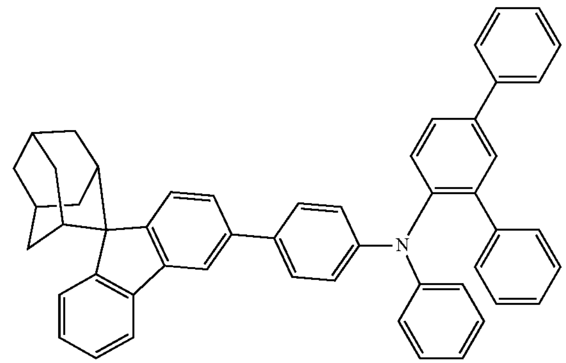 [SMILES: c1ccc(-c2ccc(N(c3ccccc3)c3ccc(-c4ccc5c(c4)-c4ccccc4C54C5CC6CC(C5)CC4C6)cc3)c(-c3ccccc3)c2)cc1] | 59 | 682.3 |
| 351 | | | | 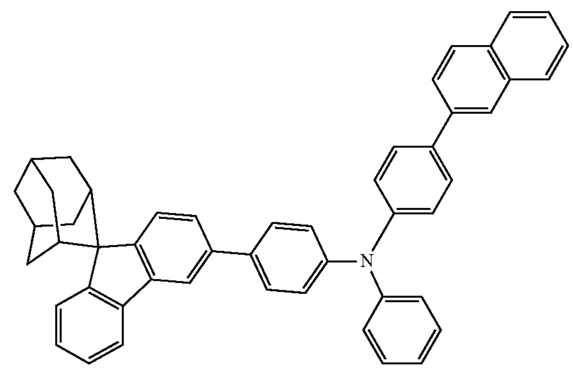 [SMILES: c1ccc(N(c2ccc(-c3ccc4c(c3)-c3ccccc3C43C4CC5CC(C4)CC3C5)cc2)c2ccc(-c3ccc4ccccc4c3)cc2)cc1] | 63 | 656.3 |

TABLE 4-continued
Compound number, structure, preparation and characterization data
| Compound No. | Raw material 14 | Raw material 5 | Intermediate | Structure | Yield (%) | MS (m/z) [M + H]+ |
|---|---|---|---|---|---|---|
| 384 | 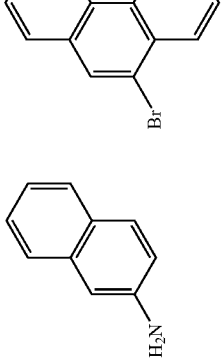 | 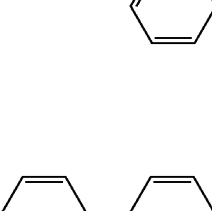 | 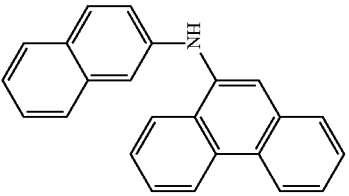 | 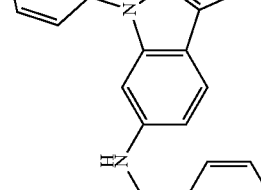 | 66 | 680.3 |
| 369 | 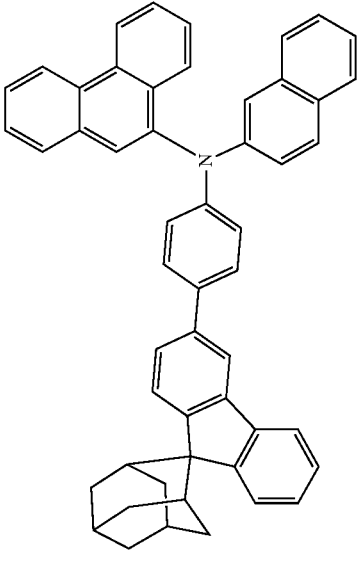 |  | 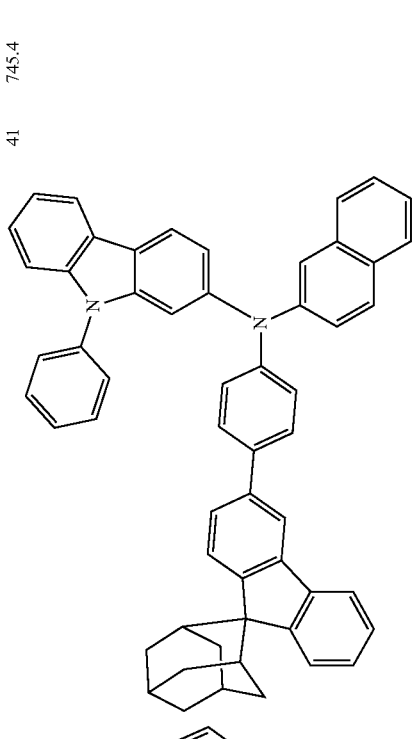 | 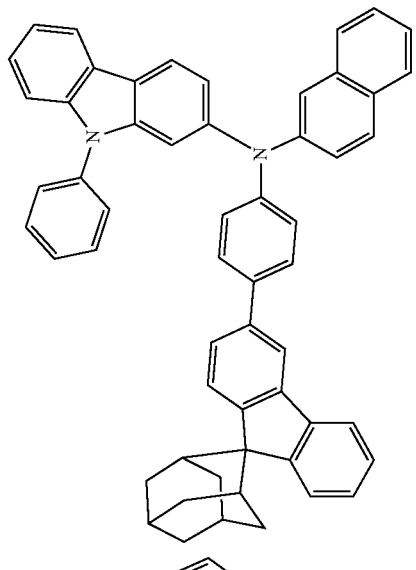 | 41 | 745.4 |

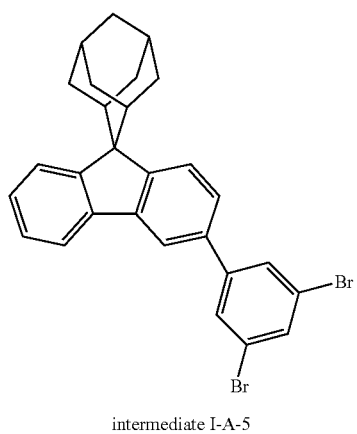

intermediate I-A-5

+

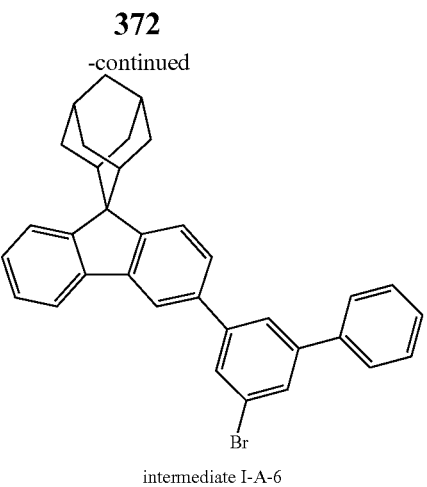

intermediate I-A-6

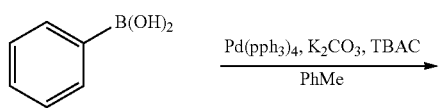

Intermediate I-A-6 was prepared according to the synthesis method of intermediate I-B, except that intermediate I-A was replaced by intermediate I-A-5, and p-chlorophenylboronic acid was replaced by phenylboronic acid to obtain intermediate I-A-6.

Referring to the synthesis method of Compound 1, the compounds shown in the fourth column of Table 5 below were prepared, except that the intermediate shown in the third column of Table 5 below replaces the intermediate I-A to react with the intermediate II-A. The specific compound number, structure, raw materials, the synthetic yield of last step and characterization data are shown in Table 5.

TABLE 5
Compound number, structure, preparation and characterization data
| Compound No. | Intermediate No. | Intermediate Structure | Compound Structure | Yield (%) | MS (m/z) [M + H]+ |
|---|---|---|---|---|---|
| 496 | Intermediate I-C | 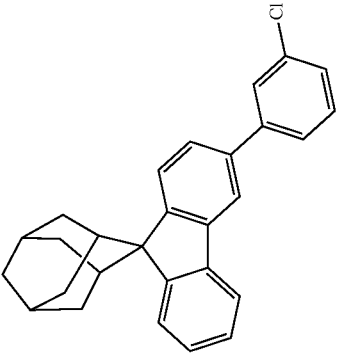 | 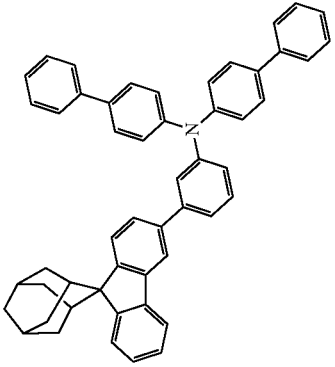 | 61 | 682.3 |
| 499 | Intermediate I-D | 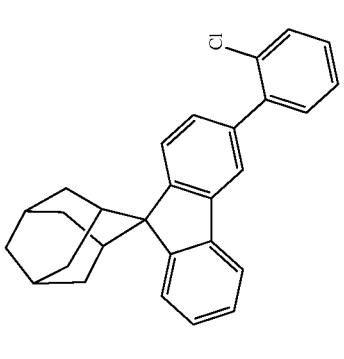 | 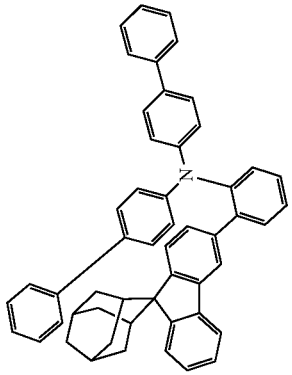 | 57 | 682.3 |

TABLE 5-continued

Compound number, structure, preparation and characterization data

| Compound No. | Intermediate No. | Intermediate Structure | Compound Structure | Yield (%) | MS (m/z) [M + H]+ |
|---|---|---|---|---|---|
| 508 | Intermediate I-E | | 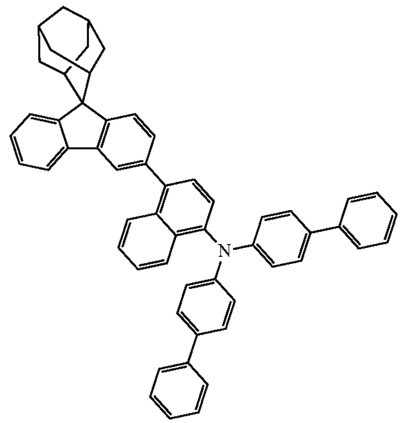 [SMILES: c1ccc(-c2ccc(N(c3ccc(-c4ccccc4)cc3)c3ccc(-c4ccc5c(c4)-c4ccccc4C54C5CC6CC(C5)CC4C6)c4ccccc34)cc2)cc1] | 69 | 732.4 |
| 581 | Intermediate I-F | | 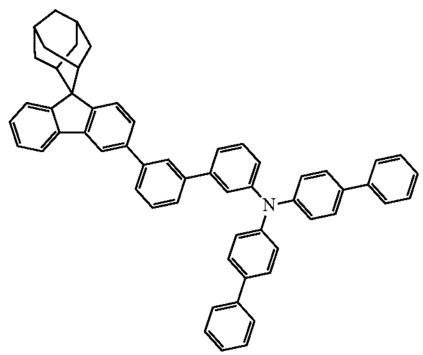 [SMILES: c1ccc(-c2ccc(N(c3ccc(-c4ccccc4)cc3)c3cccc(-c4cccc(-c5ccc6c(c5)-c5ccccc5C65C6CC7CC(C6)CC5C7)c4)c3)cc2)cc1] | 54 | 758.4 |

TABLE 5-continued

Compound number, structure, preparation and characterization data

| Compound No. | Intermediate No. | Intermediate Structure | Compound Structure | Yield (%) | MS (m/z) [M + H]$^+$ |
|---|---|---|---|---|---|
| 651 | Intermediate I-A-2 | | 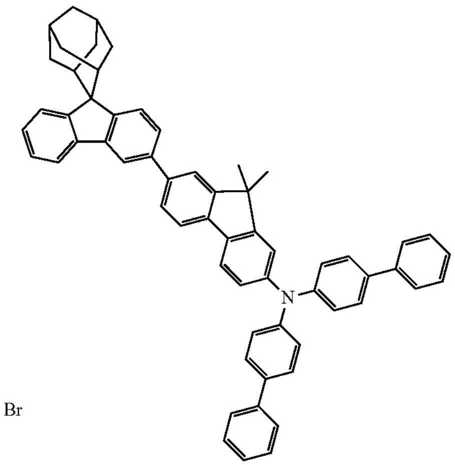 | 49 | 798.4 |
| 670 | Intermediate I-A-3 | | 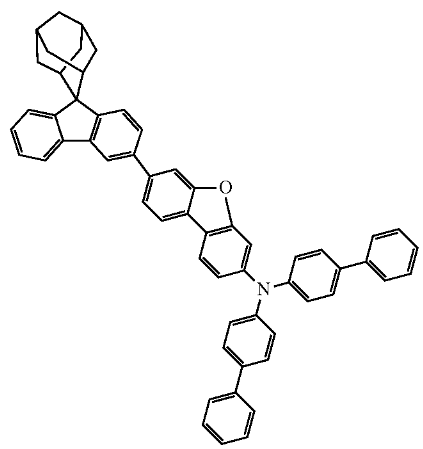 [SMILES: c1ccc(-c2ccc(N(c3ccc(-c4ccccc4)cc3)c3ccc4c(c3)oc3cc(-c5ccc6c(c5)-c5ccccc5C65C6CC7CC(C6)CC5C7)ccc34)cc2)cc1] | 44 | 772.4 |

TABLE 5-continued

Compound number, structure, preparation and characterization data

| Compound No. | Intermediate No. | Intermediate Structure | Compound Structure | Yield (%) | MS (m/z) [M + H]+ |
|---|---|---|---|---|---|
| 710 | Intermediate I-A-4 | | 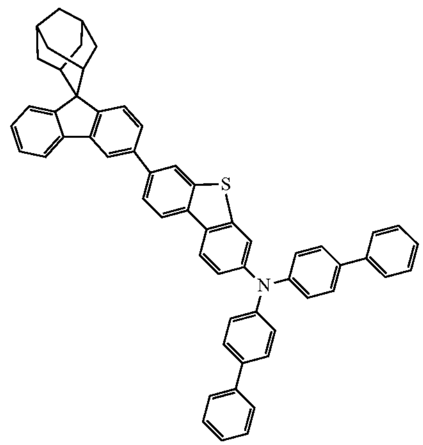 [SMILES: c1ccc(-c2ccc(N(c3ccc(-c4ccccc4)cc3)c3ccc4c(c3)sc3cc(-c5ccc6c(c5)-c5ccccc5C65C6CC7CC(C6)CC5C7)ccc34)cc2)cc1] | 51 | 788.3 |
| 819 | Intermediate I-A-6 | | 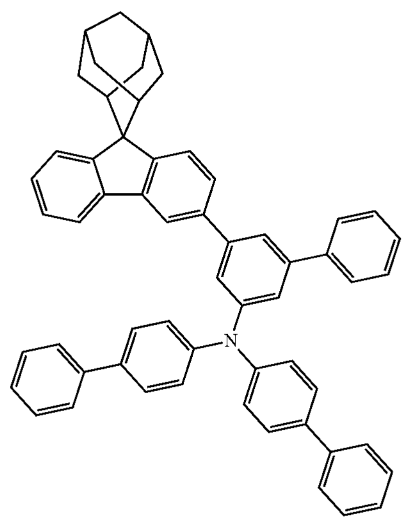 [SMILES: c1ccc(-c2ccc(N(c3ccc(-c4ccccc4)cc3)c3cc(-c4ccccc4)cc(-c4ccc5c(c4)-c4ccccc4C54C5CC6CC(C5)CC4C6)c3)cc2)cc1] | 49 | 758.4 |

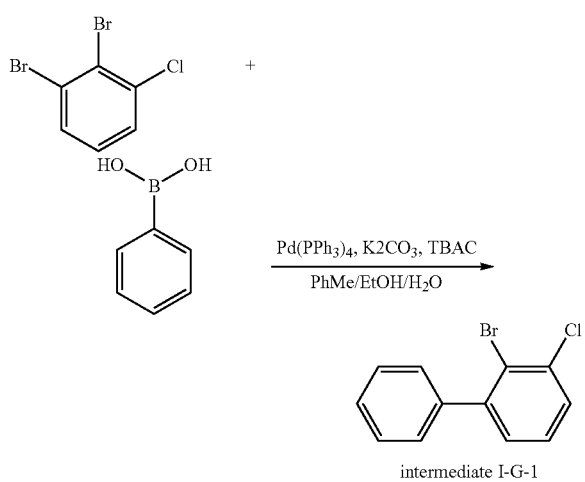

intermediate I-G-1

1,2-dibromo-3-chlorobenzene (80.0 g, 298.7 mmol), phenylboronic acid (36.5 g, 298.7 mmol), tetrakis(triphenylphosphine)palladium (6.9 g, 6.0 mmol), potassium carbonate (103.2 g, 746.7 mmol), and tetrabutylammonium bromide (19.2 g; 59.7 mmol) were added to the flask, and then added a mixed solvent of toluene (600 mL), ethanol (150 mL) and water (150 mL), heated to 80° C. and stirred for 18 hours maintaining the temperature under nitrogen protection. After cooling to room temperature, stopped stirring, the resulting reaction liquid was washed with water, then the organic phase was separated from it and dried over anhydrous magnesium sulfate, and the solvent was removed under reduced pressure to obtain a crude product. The crude product was purified by silica gel column chromatography using dichloromethane/n-heptane as the mobile phase to obtain product intermediate I-G-1 as a white solid (42.0 g, yield 53%).

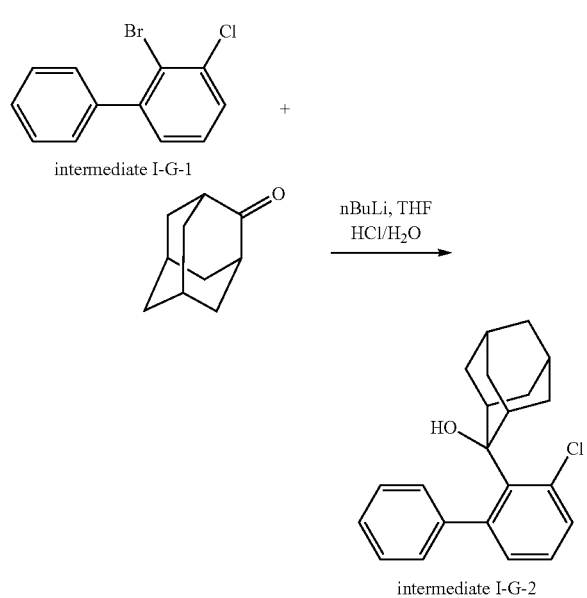

intermediate I-G-2

Intermediate I-G-1 (42.0 g, 157.9 mmol) and tetrahydrofuran (300 mL) were added to the flask, cooled down −78° C. under nitrogen protection, and a solution of n-butyllithium in tetrahydrofuran (2.5M) (95 mL, 236.9 mmol) was added dropwise under stirring. The stirring was maintained for 1 hour after the dropwise addition. Keeping at −78° C., adamantanone-(19.0 g, 126.3 mmol) solution in tetrahydrofuran (100 mL) was added dropwise. After the addition, the temperature was maintained for 1 hour, and then warmed up to room temperature and stirred for 24 hours. A solution of hydrochloric acid (12M) (26.3 mL, 315.8 mmol) in water (100 mL) was added to the resulting reaction solution and stirred for 1 hour. Separating the liquid, the obtained organic phase was washed to neutrality with water, and anhydrous magnesium sulfate was added for drying. The solvent was removed under reduced pressure to obtain a crude product. The crude product was purified by silica gel column chromatography using ethyl acetate/n-heptane system to obtain product intermediate I-G-2 as a white solid (25.8 g, yield 48%).

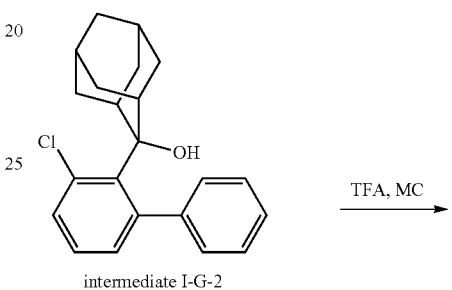

intermediate I-G

Intermediate I-G was synthesized referring to the synthesis method of intermediate I-A, except that intermediate I-G-2 was used to replace intermediate I-A-2.

Referring to the synthesis method of Compound 1, the compounds shown in the fifth column of Table 6 were prepared in which intermediate I-A was replaced by intermediate I-G, 4-aminobiphenyl was replaced by raw material 6 in the second column in the following table, 4-bromobiphenyl was replaced by raw material 7 in the third column, and intermediate II-A was replaced by the intermediates in the fourth column synthesized by raw material 6 and raw material 7. The specific compound number, structure, final step synthesis yield, characterization data, etc. are shown in Table 6.

TABLE 6

Compound number, structure, preparation and characterization data

| Compound No. | Raw material 6 | Raw material 7 | Intermediate | Compound Structure | Yield (%) | MS (m/z) [M + H]+ |
|---|---|---|---|---|---|---|
| 817 | 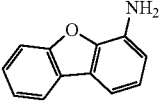 [SMILES: Nc1cccc2c1oc1ccccc12] | 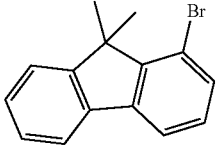 [SMILES: CC1(C)c2ccccc2-c2cccc(Br)c21] | 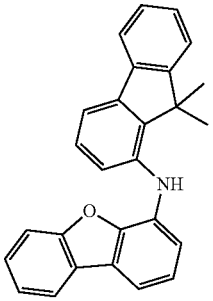 [SMILES: CC1(C)c2ccccc2-c2cccc(Nc3cccc4c3oc3ccccc34)c21] | 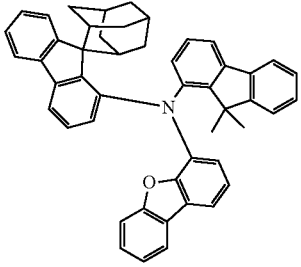 [SMILES: CC1(C)c2ccccc2-c2cccc(N(c3cccc4c3C3(c5ccccc5-4)C4CC5CC(C4)CC3C5)c3cccc4c3oc3ccccc34)c21] | 43 | 660.3 |
| 818 | 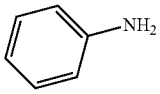 | 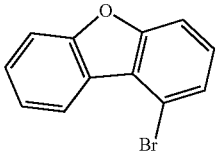 [SMILES: Brc1cccc2oc3ccccc3c12] | 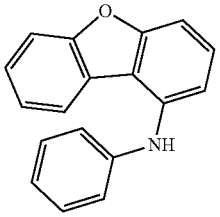 [SMILES: c1ccc(Nc2cccc3oc4ccccc4c23)cc1] | 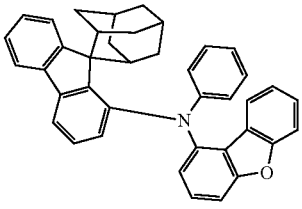 [SMILES: c1ccc(N(c2cccc3c2C2(c4ccccc4-3)C3CC4CC(C3)CC2C4)c2cccc3oc4ccccc4c23)cc1] | 51 | 544.3 |

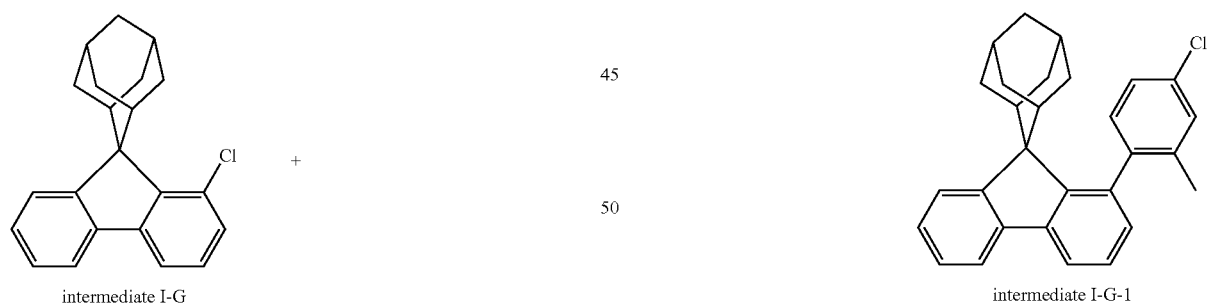

-continued

Intermediate I-G-1 was synthesized referring to the synthesis method of intermediate I-B, except that intermediate I-G was used to replace intermediate I-A.

Compound 439 was synthesized referring to the synthesis method of Compound 295, except that intermediate I-G-1 was used to replace intermediate I-B. The specific compound number, structure, final step synthesis yield, characterization data, etc. are shown in Table 7.

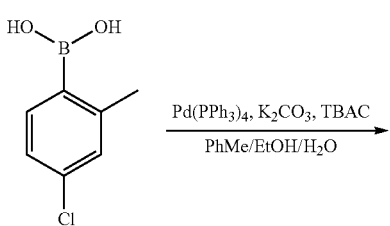

TABLE 7

Compound number, structure, preparation and characterization data

| Compound No. | Compound Structure | yield (%) | Mass (m/z) [M + H]+ |
|---|---|---|---|
| 439 | (structure) | 37 | 676.4 |

Preparation and Evaluation of Organic Electroluminescent Devices

Example 1

The green organic electroluminescent device was manufactured by the following method.

The ITO substrate (made by Corning) with an ITO thickness of 1500 Å was cut into a size of 40 mm (length)× 40 mm (width)×0.7 mm (thickness), then making it into an experimental substrate with cathode, anode and insulating layer patterns by the photolithography process. The experimental substrate was treated with ultraviolet ozone and $O_2:N_2$ plasma to increase the work function of the anode (experimental substrate) and remove scum.

m-MTDATA was vacuum-evaporated on the experimental substrate (anode) to form a hole injecting layer (HIL) with a thickness of 100 Å, and NPB was vacuum-evaporated on the hole injecting layer to form a first hole transporting layer with a thickness of 1000 Å.

Compound 1 was evaporated on the first hole transporting layer to form a second hole transporting layer with a thickness of 350 Å.

CBP as the host material was doped with Ir(ppy)$_3$ at a film thickness ratio of 100:5 simultaneously to form a light-emitting layer (EML) with a thickness of 380 Å.

ET-1 and LiQ were mixed in a weight ratio of 1:1 and evaporated to form an electron transporting layer (ETL) with a thickness of 300 Å. LiQ was vapor-deposited on the electron transporting layer to form an electron injecting layer (EIL) with a thickness of 10 Å. Magnesium (Mg) and silver (Ag) were then mixed and vacuum-evaporated at a vapor deposition rate of 1:9 on the electron injecting layer to form a cathode with a thickness of 120 Å.

In addition, CP-1 was vapor-deposited on the cathode with a thickness of 650 Å, thereby completing the manufacture of the organic light-emitting device.

The chemical structures of some materials used during the manufacture of the above electroluminescent device are shown as follows:

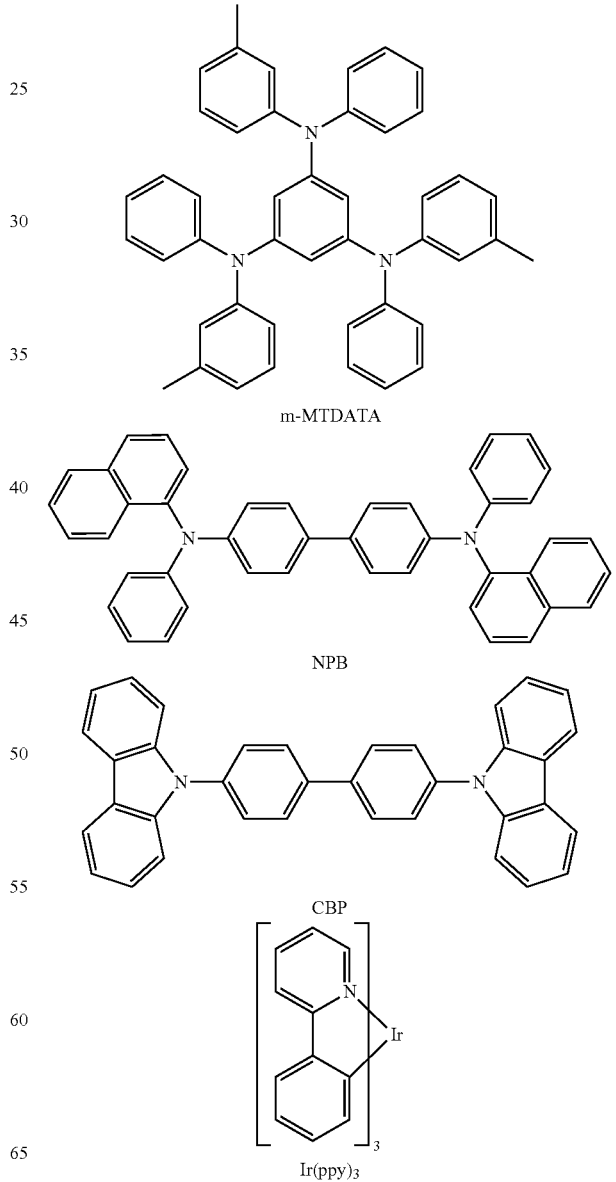

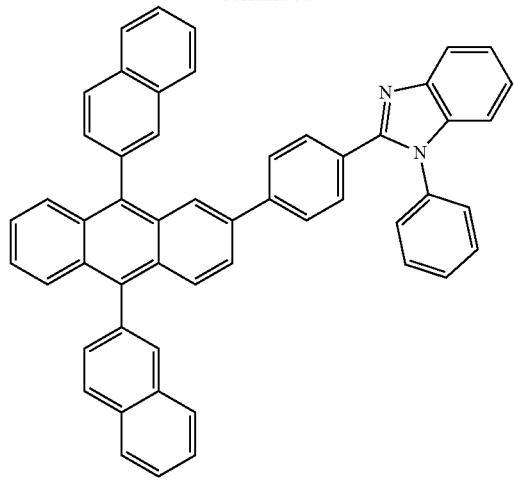

ET-1

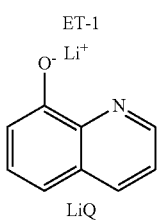

LiQ

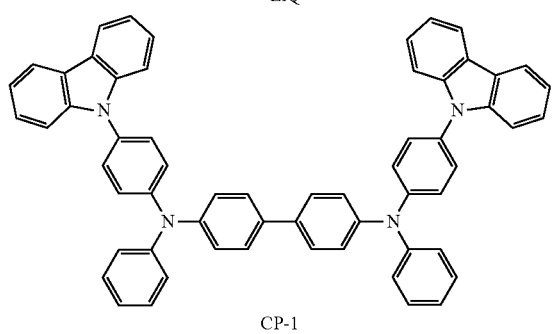

CP-1

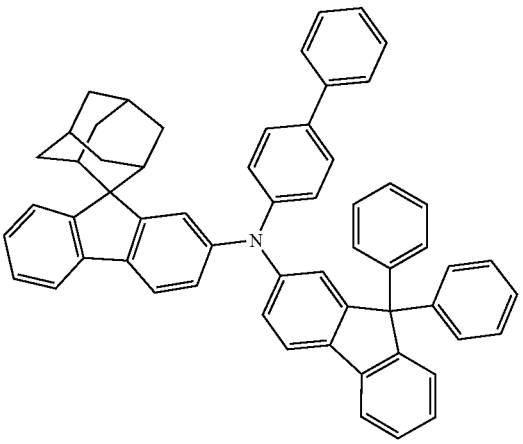

Compound A

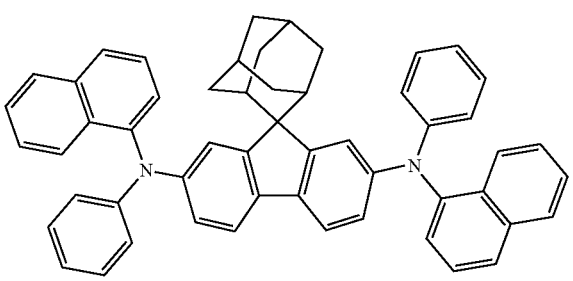

Compound B

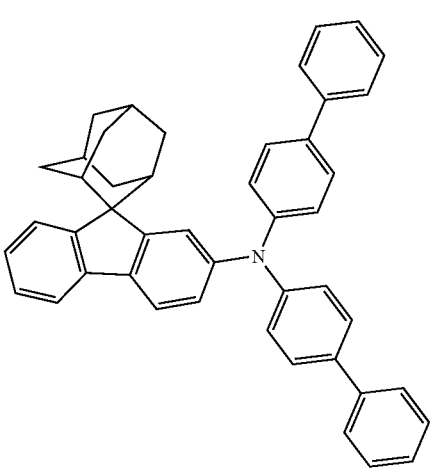

Compound C

Example 2 to Example 43

The devices of Examples 2 to 43 were manufactured by referring to the method of Example 1, except that the compounds synthesized shown in Table 8 below were used to replace Compound 1, respectively, to form the second hole transporting layer with a thickness of 350 Å, thereby completing the manufacture of corresponding green organic electroluminescent devices.

Comparative Example 1 to Comparative Example 7

The devices of Comparative Example 1 to Comparative Example 7 were manufactured by referring to the method of Example 1, except that Compound A, Compound B, Compound C, Compound D, Compound E, Compound F and Compound G were used to replace Compound 1, respectively, thereby completing the manufacture of corresponding green organic electroluminescent devices.

The chemical structures of Compound A, Compound B, Compound C, Compound D, Compound E, Compound F and Compound G are shown as follows:

Compound D

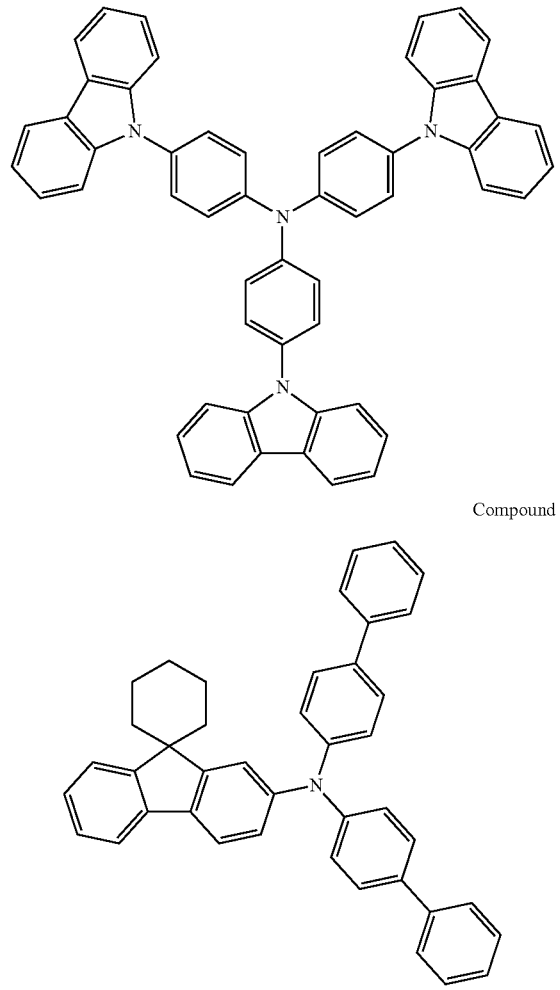

Compound E

Compound F

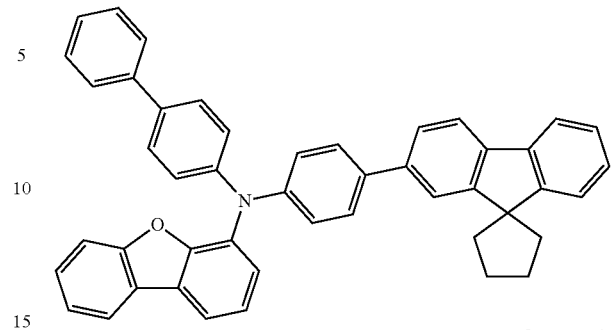

Compound G

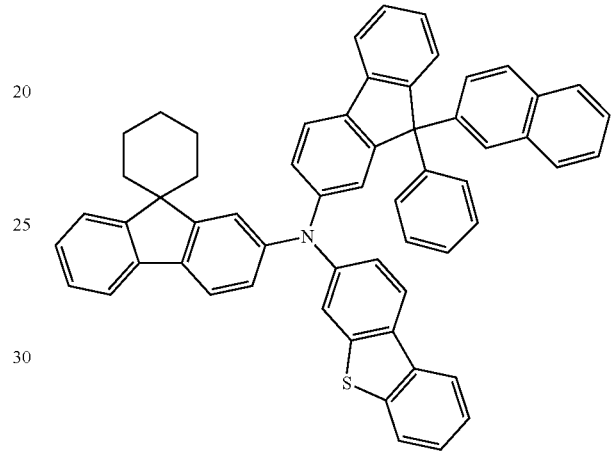

The green organic electroluminescent devices manufactured in Examples 1 to 43 and Comparative Examples 1 to 7 were tested for performance. Specifically, the IVL performance of the devices was tested under the condition of 10 mA/cm², and the T95 lifetime of the devices was tested under the initial brightness of 17,000 nit. The test results are shown in Table 8.

TABLE 8

Performance test results of green organic electroluminescent devices

| Examples | Second hole transporting layer material | Driving voltage (V) | Current efficiency (Cd/A) | Color coordinate CIEx, CIEy | External quantum efficiency EQE (%) | T95 lifetime (h) |
|---|---|---|---|---|---|---|
| Example 1 | Compound 1 | 4.11 | 86.92 | 0.266, 0.700 | 32.7 | 160 |
| Example 2 | Compound 3 | 4.14 | 86.84 | 0.266, 0.701 | 32.5 | 158 |
| Example 3 | Compound 7 | 4.10 | 87.01 | 0.265, 0.700 | 33.1 | 161 |
| Example 4 | Compound 9 | 4.13 | 86.96 | 0.262, 0.702 | 32.9 | 155 |
| Example 5 | Compound 15 | 4.12 | 86.92 | 0.262, 0.702 | 32.9 | 160 |
| Example 6 | Compound 23 | 4.14 | 86.78 | 0.261, 0.704 | 32.5 | 158 |
| Example 7 | Compound 36 | 4.09 | 87.01 | 0.266, 0.700 | 33.1 | 161 |
| Example 8 | Compound 31 | 4.07 | 86.93 | 0.266, 0.700 | 32.5 | 162 |
| Example 9 | Compound 54 | 4.09 | 86.80 | 0.266, 0.701 | 32.5 | 158 |
| Example 10 | Compound 60 | 4.08 | 87.01 | 0.265, 0.700 | 33.1 | 162 |
| Example 11 | Compound 66 | 4.12 | 86.95 | 0.262, 0.702 | 32.8 | 156 |
| Example 12 | Compound 71 | 4.15 | 86.92 | 0.262, 0.702 | 32.9 | 160 |
| Example 13 | Compound 87 | 4.14 | 86.78 | 0.261, 0.704 | 32.5 | 158 |
| Example 14 | Compound 92 | 4.18 | 87.04 | 0.266, 0.700 | 32.9 | 163 |
| Example 15 | Compound 95 | 4.07 | 86.92 | 0.266, 0.700 | 32.7 | 160 |
| Example 16 | Compound 115 | 4.09 | 86.84 | 0.266, 0.701 | 32.5 | 158 |
| Example 17 | Compound 116 | 4.12 | 87.02 | 0.265, 0.700 | 33.0 | 160 |
| Example 18 | Compound 128 | 4.14 | 86.94 | 0.262, 0.702 | 32.9 | 155 |
| Example 19 | Compound 127 | 4.09 | 86.92 | 0.262, 0.702 | 32.9 | 160 |
| Example 20 | Compound 147 | 4.11 | 86.79 | 0.261, 0.704 | 32.4 | 158 |

TABLE 8-continued

Performance test results of green organic electroluminescent devices

| Examples | Second hole transporting layer material | Driving voltage (V) | Current efficiency (Cd/A) | Color coordinate CIEx, CIEy | External quantum efficiency EQE (%) | T95 lifetime (h) |
|---|---|---|---|---|---|---|
| Example 21 | Compound 162 | 4.15 | 87.01 | 0.266, 0.700 | 33.1 | 161 |
| Example 22 | Compound 195 | 4.12 | 86.78 | 0.261, 0.704 | 32.5 | 158 |
| Example 23 | Compound 206 | 4.11 | 87.00 | 0.266, 0.700 | 33.3 | 165 |
| Example 24 | Compound 295 | 4.08 | 86.89 | 0.262, 0.702 | 32.9 | 155 |
| Example 25 | Compound 304 | 4.14 | 86.92 | 0.263, 0.702 | 33.0 | 160 |
| Example 26 | Compound 316 | 4.17 | 86.80 | 0.261, 0.704 | 32.4 | 158 |
| Example 27 | Compound 341 | 4.15 | 87.12 | 0.266, 0.700 | 33.1 | 161 |
| Example 28 | Compound 351 | 4.18 | 87.12 | 0.266, 0.700 | 33.1 | 161 |
| Example 29 | Compound 384 | 4.12 | 86.83 | 0.262, 0.703 | 32.8 | 155 |
| Example 30 | Compound 369 | 4.10 | 86.90 | 0.262, 0.703 | 32.9 | 160 |
| Example 31 | Compound 439 | 4.15 | 84.90 | 0.263, 0.703 | 32.8 | 155 |
| Example 32 | Compound 487 | 4.15 | 84.73 | 0.262, 0.703 | 31.8 | 161 |
| Example 33 | Compound 496 | 4.06 | 83.17 | 0.262, 0.700 | 32.9 | 160 |
| Example 34 | Compound 499 | 4.09 | 85.44 | 0.262, 0.704 | 30.2 | 159 |
| Example 35 | Compound 508 | 4.18 | 86.32 | 0.266, 0.701 | 31.5 | 160 |
| Example 36 | Compound 581 | 4.11 | 83.69 | 0.263, 0.703 | 32.8 | 155 |
| Example 37 | Compound 651 | 4.17 | 82.7 | 0.262, 0.702 | 31.9 | 159 |
| Example 38 | Compound 670 | 4.10 | 83.62 | 0.262, 0.702 | 30.2 | 157 |
| Example 39 | Compound 710 | 4.09 | 85.17 | 0.263, 0.703 | 32.5 | 155 |
| Example 40 | Compound 745 | 4.17 | 82.69 | 0.263, 0.703 | 31.5 | 154 |
| Example 41 | Compound 817 | 4.11 | 85.74 | 0.262, 0.702 | 30.9 | 160 |
| Example 42 | Compound 818 | 4.07 | 87.19 | 0.261, 0.704 | 32.2 | 159 |
| Example 43 | Compound 819 | 4.14 | 86.81 | 0.261, 0.704 | 32.2 | 159 |
| Comparative Example 1 | Compound A | 4.67 | 86.89 | 0.262, 0.702 | 25.8 | 149 |
| Comparative Example 2 | Compound B | 4.73 | 85.04 | 0.262, 0.702 | 24.2 | 145 |
| Comparative Example 3 | Compound C | 4.62 | 85.54 | 0.263, 0.703 | 24.4 | 155 |
| Comparative Example 4 | Compound D | 4.66 | 82.69 | 0.263, 0.703 | 24.5 | 154 |
| Comparative Example 5 | Compound E | 4.65 | 85.04 | 0.262, 0.702 | 24.2 | 140 |
| Comparative Example 6 | Compound F | 4.68 | 85.64 | 0.263, 0.703 | 24.4 | 143 |
| Comparative Example 7 | Compound G | 4.72 | 84.54 | 0.263, 0.703 | 24.4 | 150 |

According to the above table, the luminous efficiency (Cd/A) and lifetime of the organic electroluminescent devices manufactured in Examples 1 to 43 are comparable to those of Comparative Examples 1 to 7 in the case of little difference in the color coordinates, while the overall device voltages of Comparative Examples 1 to 7 are relatively high. As shown in the table above, the driving voltages of Examples 1 to 43 are reduced by at least 0.45V compared to those of Comparative Examples 1 to 7. Therefore, an organic electroluminescent device with a lower operating voltage can be produced by using the nitrogen-containing compound of the present disclosure in the second hole transporting layer.

The nitrogen-containing compound of the present disclosure introduces an adamantane structure at the fluorene to enhance the electron density of the fluorene ring and the conjugate system of the entire compound through the hyperconjugation effect, which can enhance the hole conductivity and electron tolerance of the nitrogen-containing compound. In addition, the introduction of adamantyl can also increase the molecular weight of the nitrogen-containing compound and reduce the molecular symmetry, can increase the glass transition temperature and evaporation temperature of the compound of the present disclosure, control the crystallinity of the nitrogen-containing compound, makes the nitrogen-containing compound has higher physical and thermal stability when being mass-produced, which is convenient for mass production stability of organic electroluminescent devices and photoelectric conversion devices. Compared with Comparative Examples 1, 2 and 3, connecting amine to fluorene at positions 1 and 3 can increase the steric hindrance of the arylamine structure to a certain extent, and increase the twist angles of the fluorene plane and the arylamine plane (especially the triarylamine plane), which reduces the conjugation degree of the nitrogen-containing compound. When the nitrogen-containing compound is used as the second hole transporting layer (also known as the electron blocking layer), it may better match the HOMO energy level of the adjacent layer, thereby reducing the operating voltage of the organic electroluminescent device.

The organic electroluminescent devices manufactured in Example 1 were divided into two groups, and one group of devices was directly subjected to performance tests without heat treatment, and the test results are shown in Table 9. The other group was subjected to heat-treated (placed at 110° C. for 1 hour) before performance tests. The test results for performance are shown in Table 10. Referring to the aforementioned method, the performance parameters without heat treatment and performance parameters after heat treatment were also obtained for the organic electroluminescent devices manufactured in Example 14, Example 21, Example 32, Example 35, Example 38, Example 41, and Comparative Examples 1 to 7.

TABLE 9

Performance parameters of organic electroluminescent devices without heat treatment

| Example | Compound | Operating voltage (V) | Current efficiency (Cd/A) | External quantum efficiency EQE (%) | Color coordinate CIEx, CIEy | T95 lifetime (hr) |
|---|---|---|---|---|---|---|
| Example 1 | Compound 1 | 4.11 | 86.92 | 32.7 | 0.266, 0.700 | 160 |
| Example 14 | Compound 92 | 4.18 | 87.04 | 32.9 | 0.266, 0.700 | 163 |
| Example 21 | Compound 162 | 4.17 | 87.01 | 33.1 | 0.266.0.700 | 161 |
| Example 31 | Compound 439 | 4.15 | 84.90 | 32.8 | 0.263, 0.703 | 155 |
| Example 35 | Compound 508 | 4.18 | 86.32 | 31.5 | 0.266, 0.701 | 160 |
| Example 38 | Compound 670 | 4.10 | 83.62 | 30.2 | 0.262, 0.702 | 157 |
| Example 41 | Compound 817 | 4.11 | 85.74 | 30.9 | 0.262, 0.702 | 160 |
| Comparative Example 1 | Compound A | 4.67 | 86.89 | 25.8 | 0.262, 0.702 | 149 |
| Comparative Example 2 | Compound B | 4.73 | 85.04 | 24.2 | 0.262, 0.702 | 145 |
| Comparative Example 3 | Compound C | 4.62 | 85.54 | 24.4 | 0.263, 0.703 | 155 |
| Comparative Example 4 | Compound D | 4.66 | 82.69 | 24.5 | 0.263, 0.703 | 154 |
| Comparative Example 5 | Compound E | 4.65 | 85.04 | 24.2 | 0.262, 0.702 | 140 |
| Comparative Example 6 | Compound F | 4.68 | 85.64 | 24.4 | 0.263, 0.703 | 143 |
| Comparative Example 7 | Compound G | 4.72 | 84.54 | 24.4 | 0.263, 0.703 | 150 |

TABLE 10

Performance parameters of organic electroluminescent devices after heat treatment

| Example | Compound | Operating voltage (V) | Current efficiency (Cd/A) | External quantum efficiency EQE (%) | Color coordinate CIEx, CIEy | T95 lifetime (h) |
|---|---|---|---|---|---|---|
| Example 1 | Compound 1 | 4.05 | 83.25 | 32.7 | 0.263, 0.703 | 160 |
| Example 14 | Compound 92 | 4.07 | 86.84 | 32.9 | 0.266, 0.700 | 154 |
| Example 21 | Compound 162 | 4.13 | 86.72 | 33.1 | 0.266.0.700 | 167 |
| Example 31 | Compound 439 | 4.08 | 87.01 | 31.5 | 0.263, 0.703 | 164 |
| Example 35 | Compound 508 | 4.10 | 86.32 | 31.5 | 0.266, 0.701 | 160 |
| Example 38 | Compound 670 | 4.06 | 84.62 | 30.2 | 0.262, 0.702 | 157 |
| Example 41 | Compound 817 | 4.03 | 85.94 | 30.9 | 0.262, 0.702 | 160 |
| Comparative Example 1 | Compound A | 4.66 | 66.89 | 16.7 | 0.262, 0.702 | 134 |
| Comparative Example 2 | Compound B | 4.75 | 65.04 | 16.0 | 0.262, 0.702 | 130 |
| Comparative Example 3 | Compound C | 4.65 | 80.54 | 20.4 | 0.263, 0.703 | 145 |
| Comparative Example 4 | Compound D | 4.68 | 62.69 | 16.1 | 0.263, 0.703 | 134 |
| Comparative Example 5 | Compound E | 4.67 | 65.04 | 16.8 | 0.262, 0.702 | 127 |
| Comparative Example 6 | Compound F | 4.68 | 62.64 | 16.0 | 0.263, 0.703 | 123 |
| Comparative Example 7 | Compound G | 4.73 | 64.54 | 15.6 | 0.263, 0.703 | 125 |

From the results in Table 9 and Table 10, it can be seen that for the organic electroluminescent devices of Comparative Examples 1, Comparative Examples 2, and Comparative Examples 4 to 7, compared with those without heat treatment, the luminous efficiency and external quantum efficiency are reduced by more than 23% after heat treatment, and the lifetimes are reduced by more than 10% after heat treatment. Compared with that without heat treatment, the efficiency and lifetime of the organic electroluminescent device of Comparative Example 3 after heat treatment are reduced by 5.8%, and the lifetime is reduced by 6.5%. However, for the organic electroluminescent devices of Example 1, Example 14, Example 21, Example 35, Example 38 and Example 41 after heat treatment, they maintained the comparable efficiency and lifetime as those without heat treatment.

From the device results in Table 8 to Table 10, it can be seen that the voltages of the devices using the compounds of the present disclosure are reduced, comparing those of the devices using the compounds of Comparative Example 1 and Comparative Example 3. The reason may be that the compounds of the present disclosure in which the aromatic amine is connected at the 1st or 3rd positions of adamantane fluorene have a deeper HOMO than the compounds in which the aromatic amine is connected at the 2nd position of adamantane fluorene, so as to make the injection of holes into the light-emitting layer smoother. Compared with the compounds of Comparative Example 5, Comparative Example 6 and Comparative Example 7, the application of the compounds of the present disclosure can reduce the voltage and improve the thermal stability for the device. The reason may be that the cycloalkyl group formed on the 9,9-dimethylfluorene of the present disclosure is the rigid and large-volume adamantyl group, which has a stronger ability to reduce the molecular stacking, compared with the single ring structure. The material can achieve a more stable film state.

It can be seen that, according to Table 8 to Table 10 for the results of the organic electroluminescent device of the examples, when the arylamine compound with adamantane-fluorene as the core is used as the second hole transporting layer material of the green light device, it can produce organic electroluminescent devices with excellent characteristics in terms of driving voltage, luminous efficiency, external quantum efficiency and thermal stability, etc. For example, it can produce an organic electroluminescent device with high-efficiency, high heat-resistance and long lifetime.

It should be understood that the present disclosure should not be limited to the detailed structure and arrangement of the components proposed in this specification. The present disclosure can have other embodiments, and can be implemented and executed in various ways. The aforementioned modified forms and modified forms fall within the scope of the present disclosure. It should be understood that the disclosed and defined in this specification of the disclosure extends to all alternative combinations of two or more individual features which are mentioned or obvious in the text and/or drawings. All of these different combinations constitute multiple alternative aspects of the present disclosure. The embodiments described in this specification illustrate the best ways known to implement the present disclosure, and will enable those skilled in the art to utilize the present disclosure.

What is claimed is:

1. An electronic element comprising:
a hole transporting layer; and
an electronic blocking layer, wherein the electron blocking layer contains a nitrogen-containing compound having a structure shown in Chemical Formula 1:

Chemical Formula 1

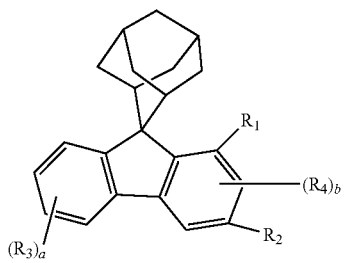

Chemical Formula 1-1

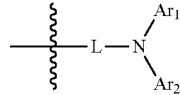

wherein

represents a chemical bond;

$R_1$ and $R_2$ are each independently selected from hydrogen or a group represented by Chemical Formula 1-1, and one and only one of $R_1$ and $R_2$ has the group represented by Chemical Formula 1-1; when $R_1$ or $R_2$ is selected from hydrogen, $R_1$ or $R_2$ selected from hydrogen may be substituted by $R_4$;

$R_3$, $R_4$ are each independently selected from the group consisting of halogen, cyano, an aryl having 6 to 20 carbon atoms, and an alkyl having 1 to 10 carbon atoms;

a is selected from 0, 1, 2, 3, or 4; when a is greater than or equal to 2, any two $R_3$ are the same or different;

b is selected from 0, 1, 2, or 3, when b is greater than or equal to 2, any two $R_4$ are the same or different;

L is single bond or selected from the group consisting of the following groups:

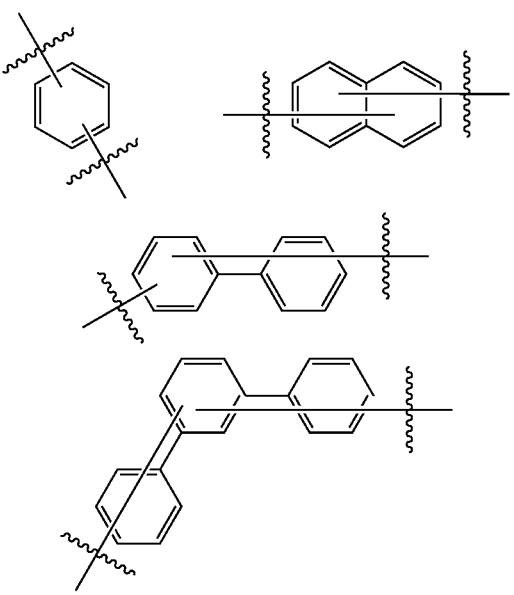

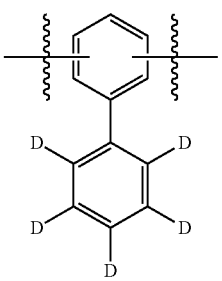

-continued
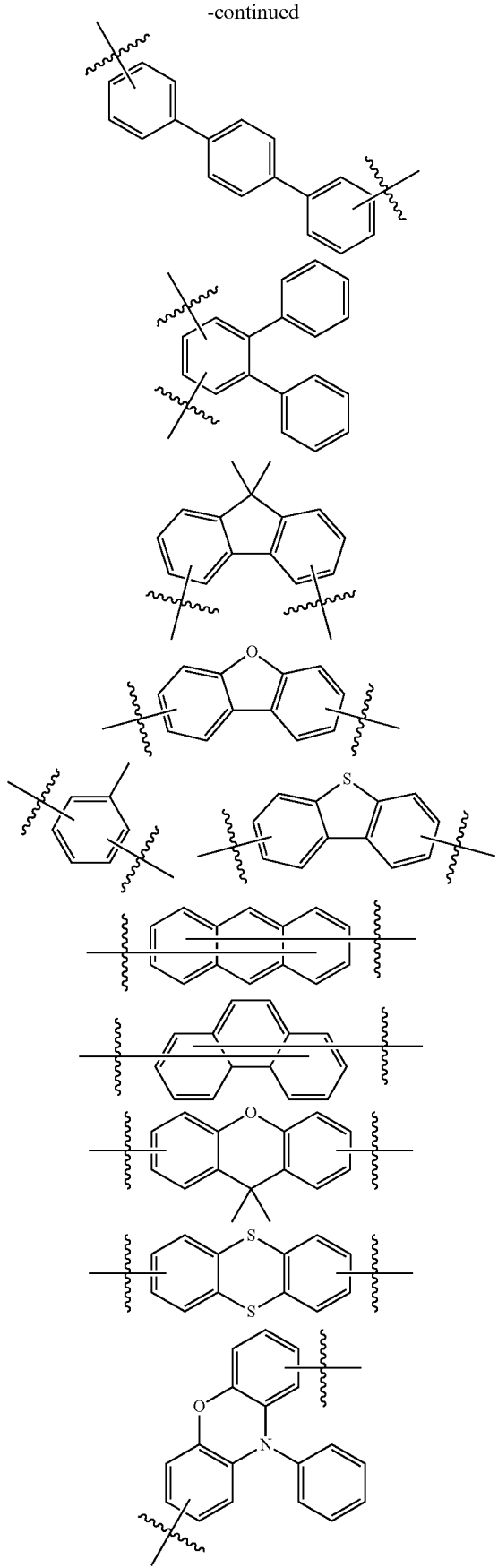
-continued
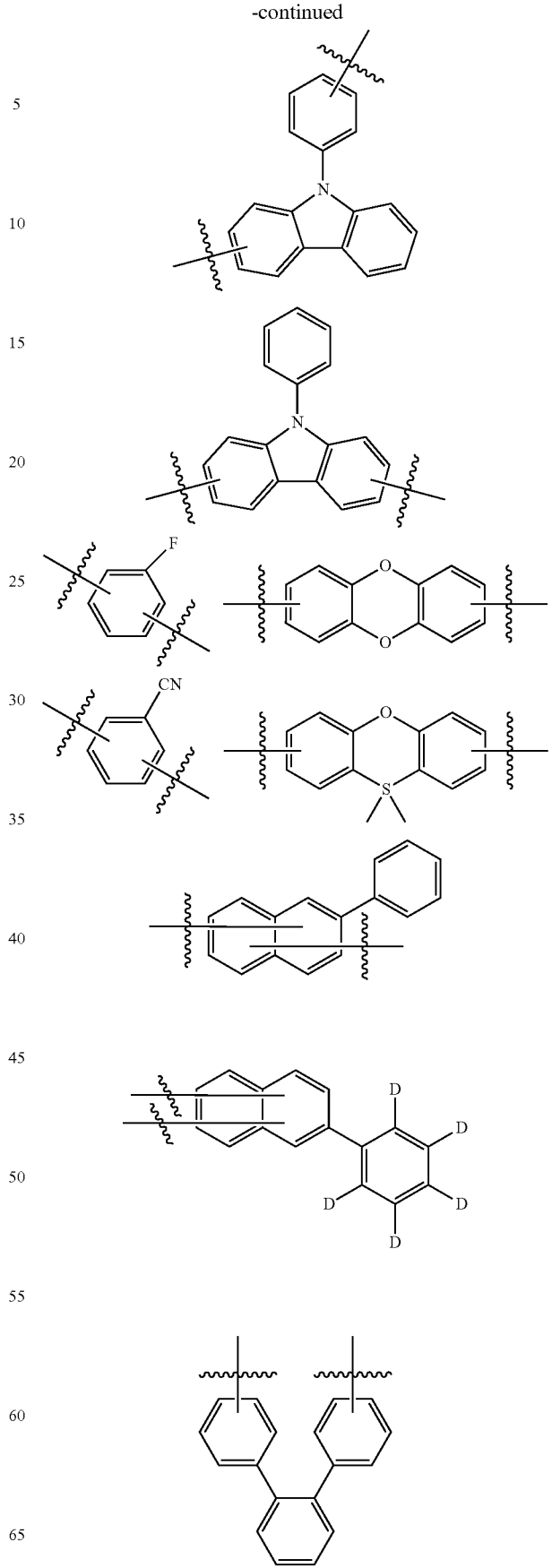

399
-continued
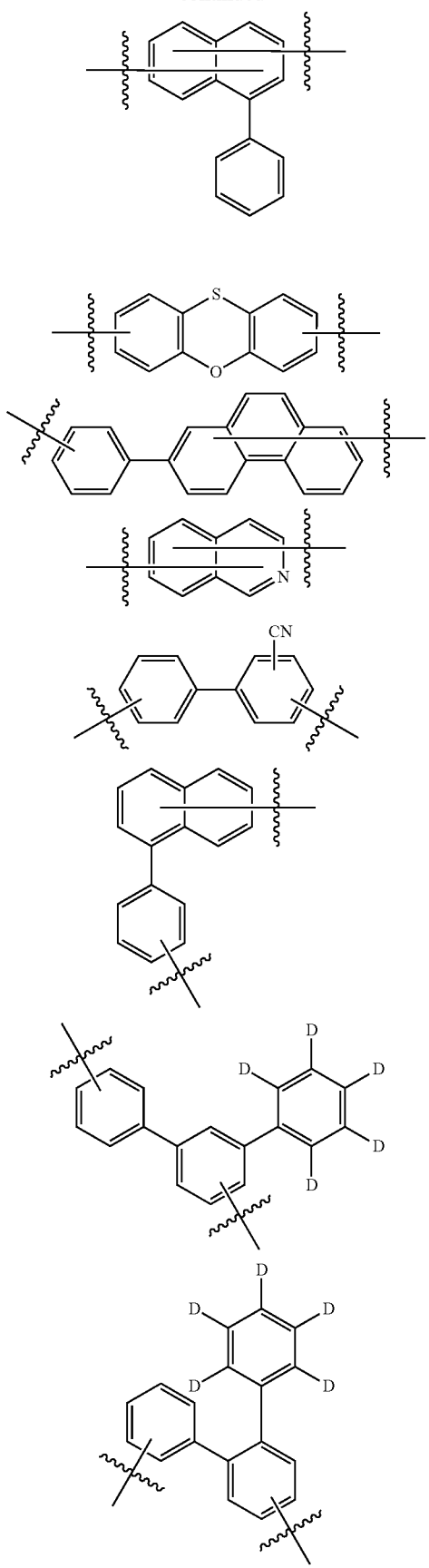
400
-continued
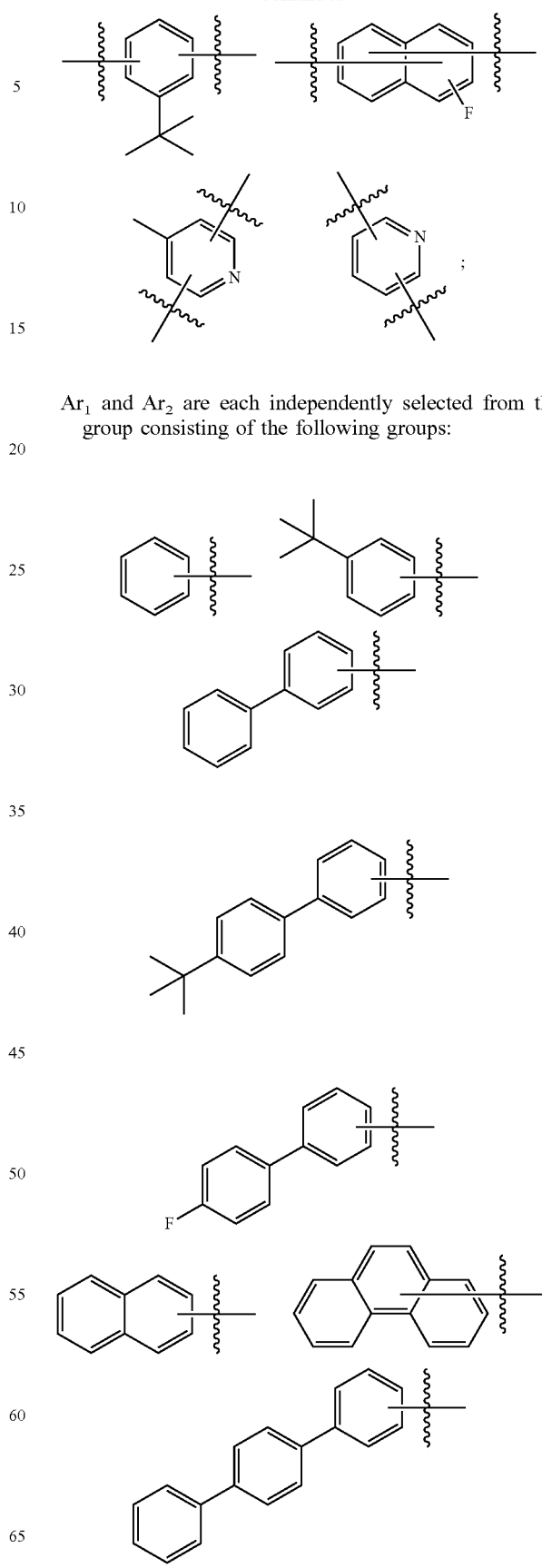
Ar$_1$ and Ar$_2$ are each independently selected from the group consisting of the following groups:

401
-continued
402
-continued
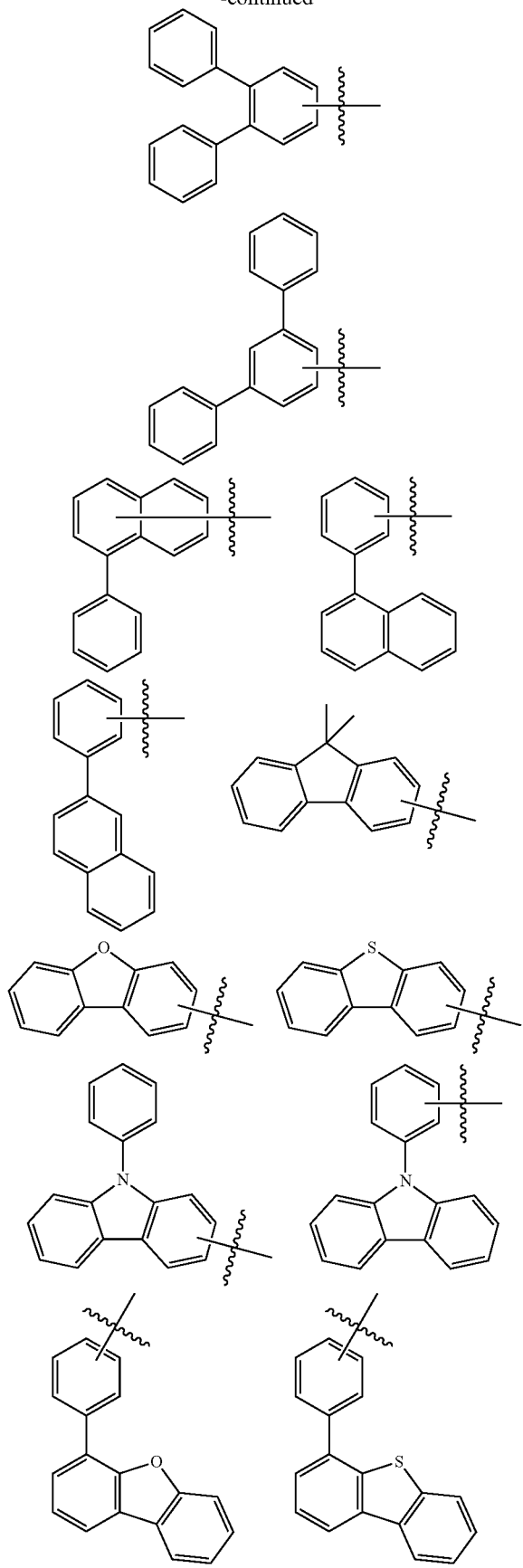
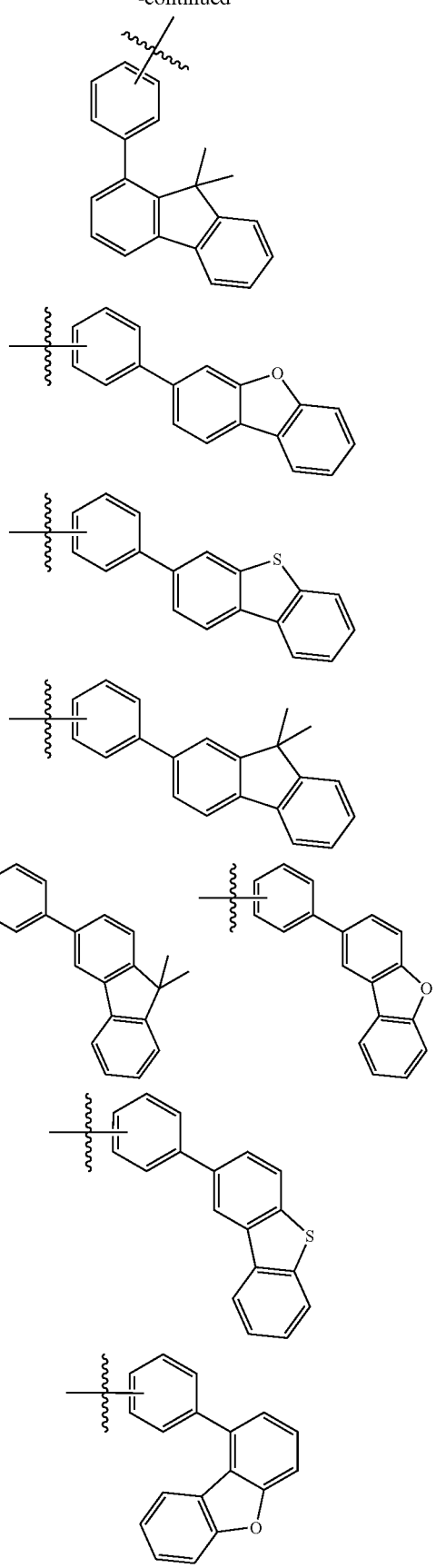

403
-continued

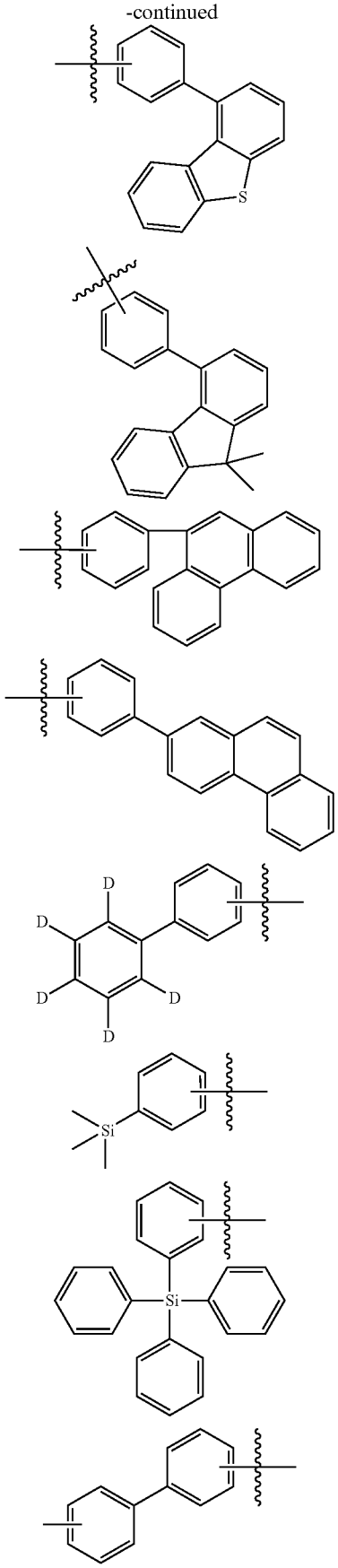

404
-continued

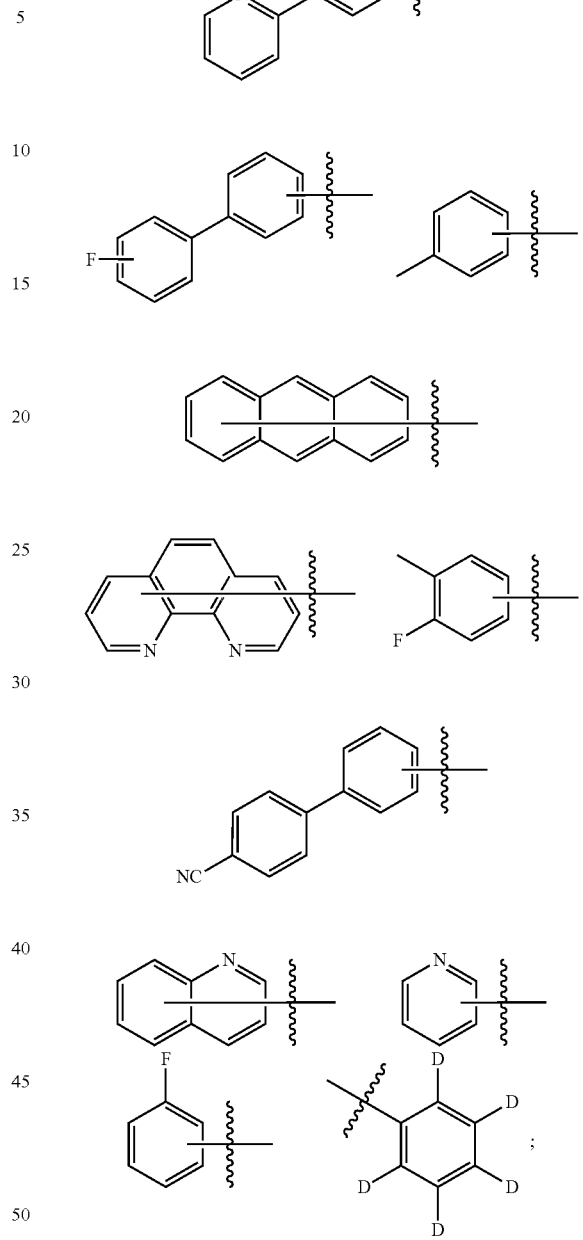

and wherein the electronic element is an organic electroluminescence device and is a green light device.

2. The electronic element of claim 1, wherein $R_3$ and $R_4$ are each independently selected from the group consisting of fluorine, cyano, an aryl having 6 to 18 carbon atoms, and an alkyl having 1 to 6 carbon atoms.

3. An electronic element comprising:

a hole transporting layer; and an electronic blocking layer, wherein the electron blocking layer contains a nitrogen-containing compound selected from the group consisting of the following compounds:

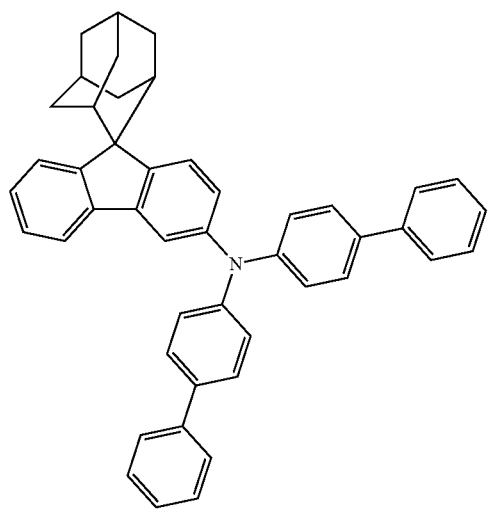
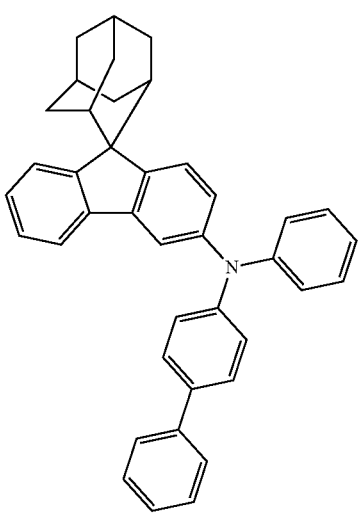
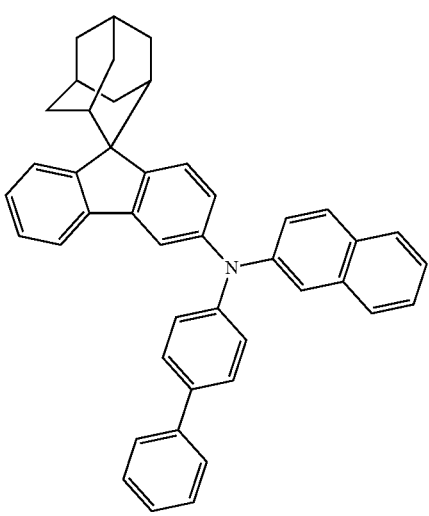
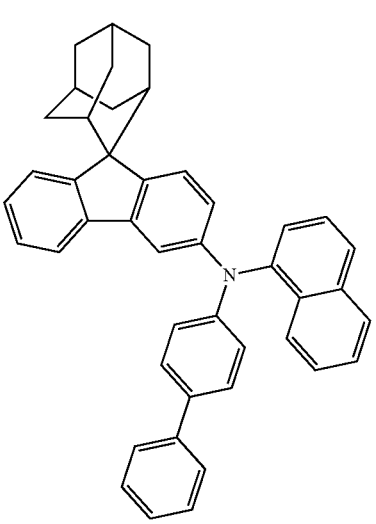

407
-continued
408
-continued
7
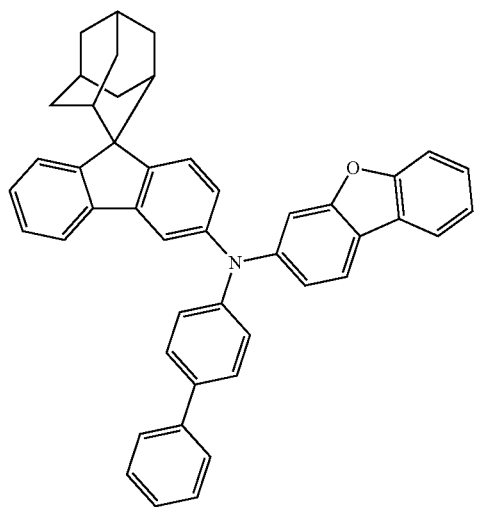
10
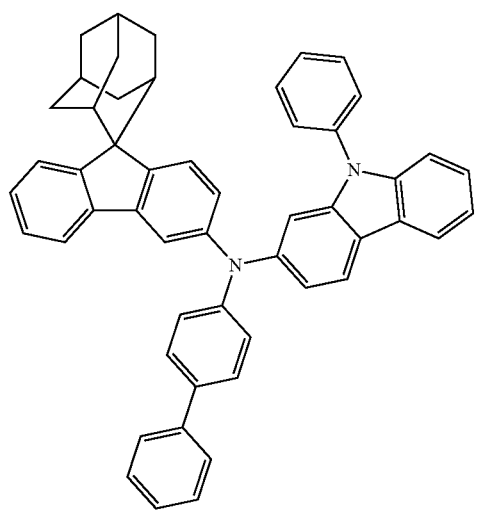
8
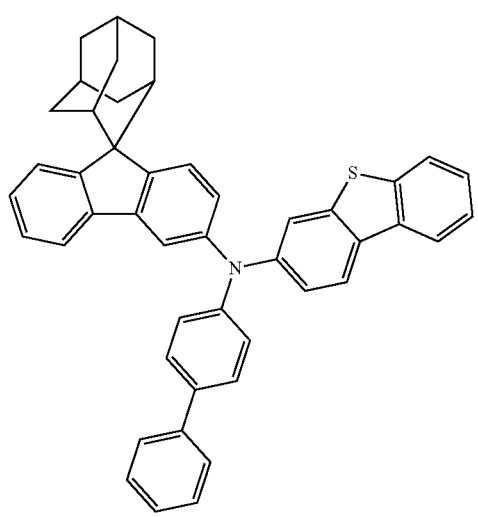
11
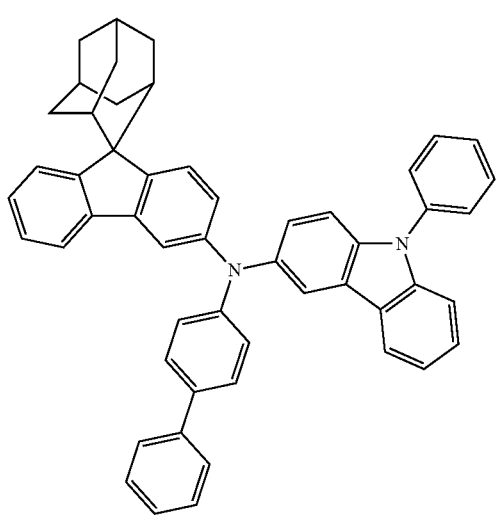
9
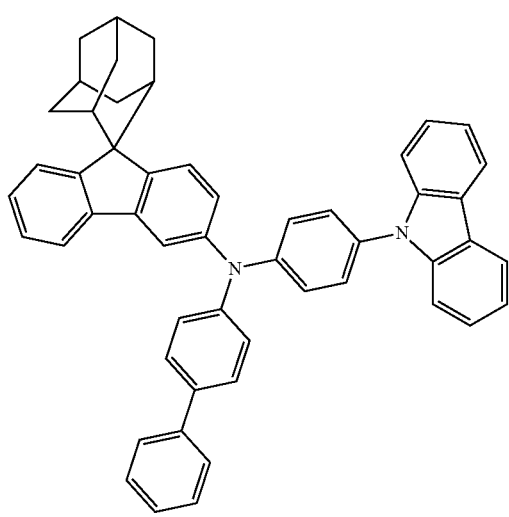
12
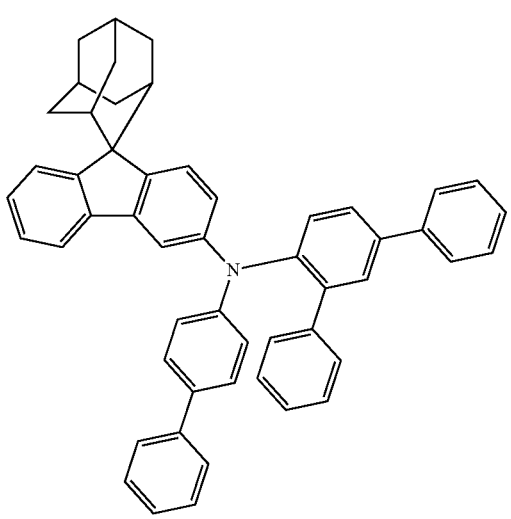

13
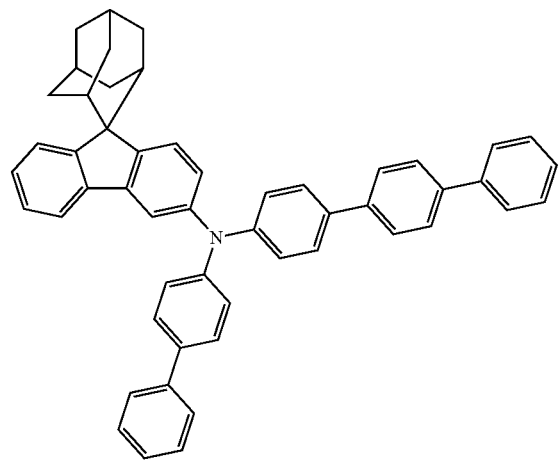
16
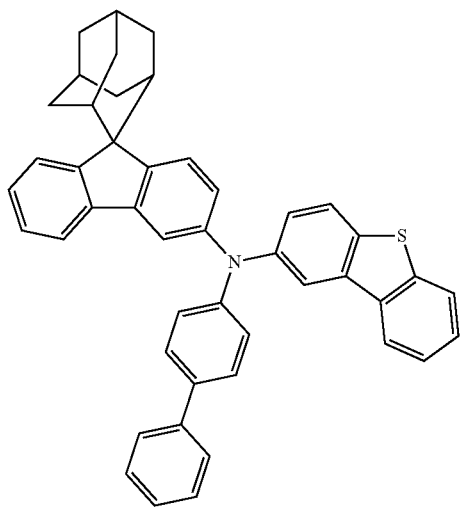
14
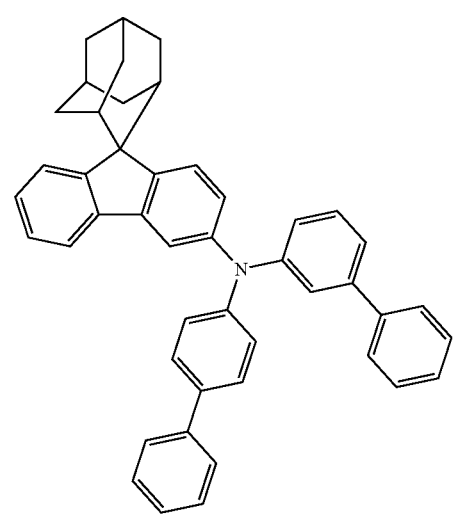
17
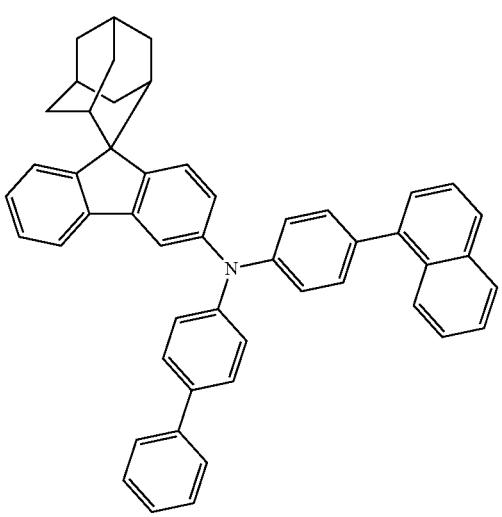
15
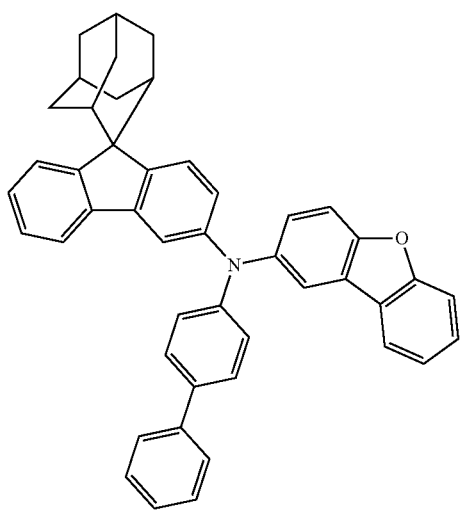
18
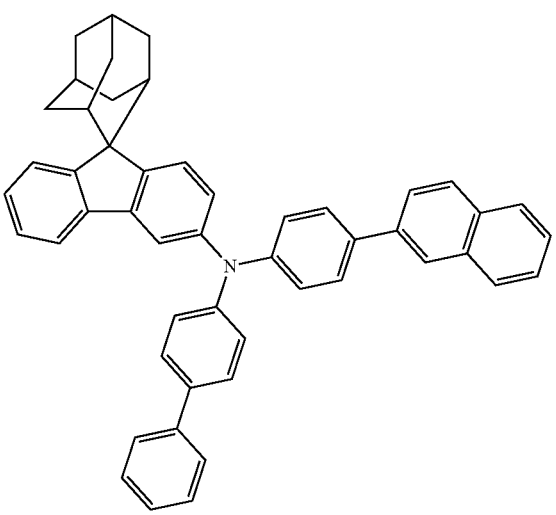

411
-continued
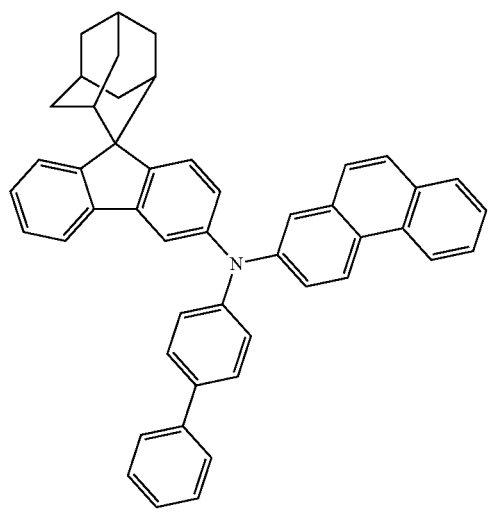
19
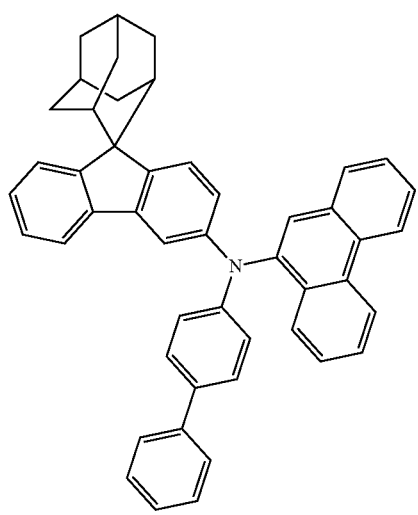
20
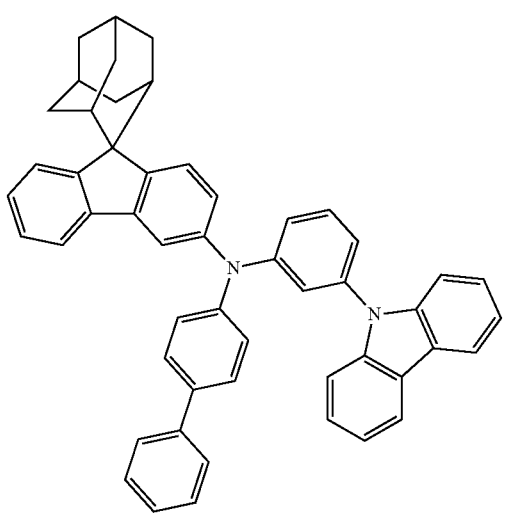
21
412
-continued
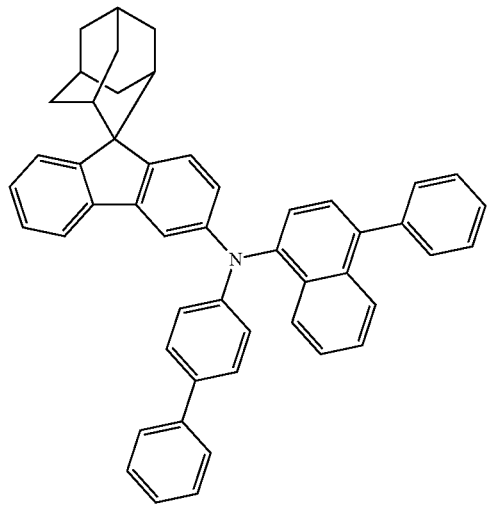
22
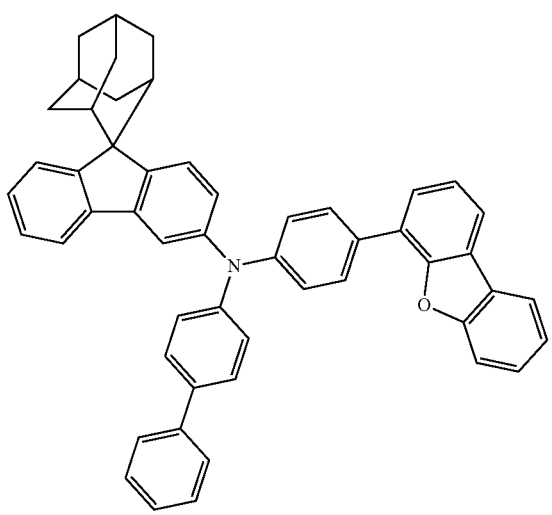
23
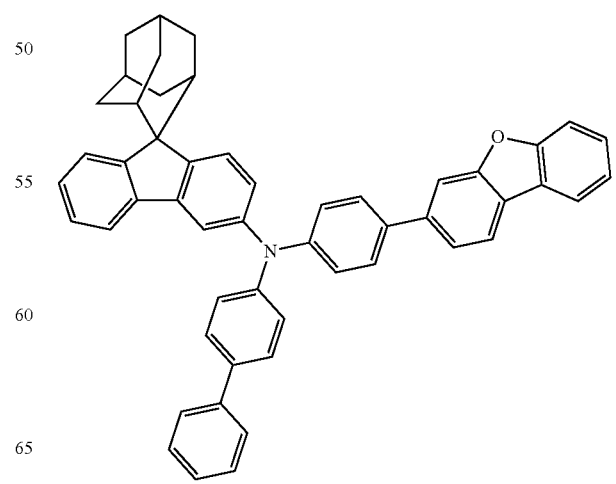
24

413
-continued
25
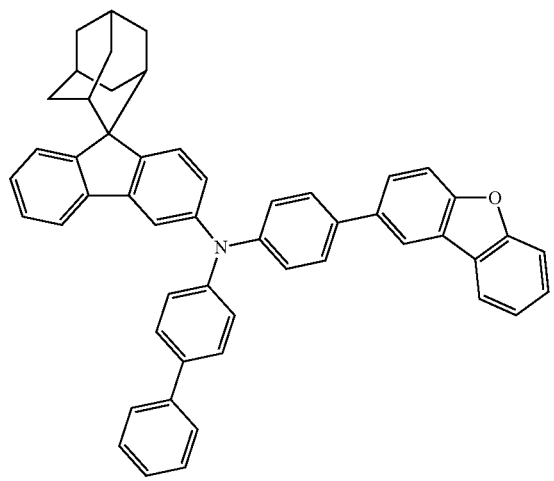
26
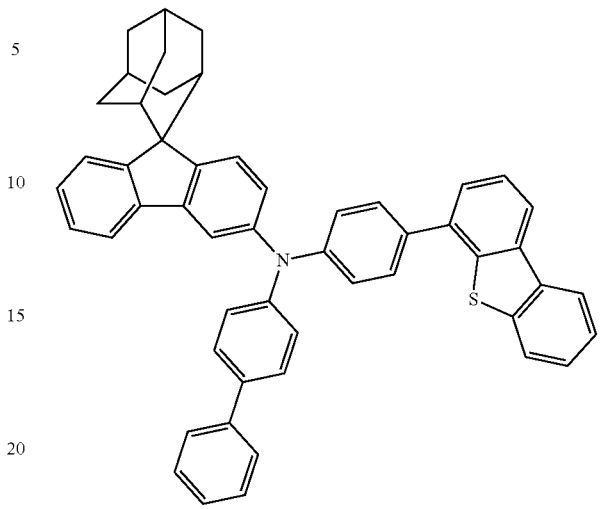
27
414
-continued
28
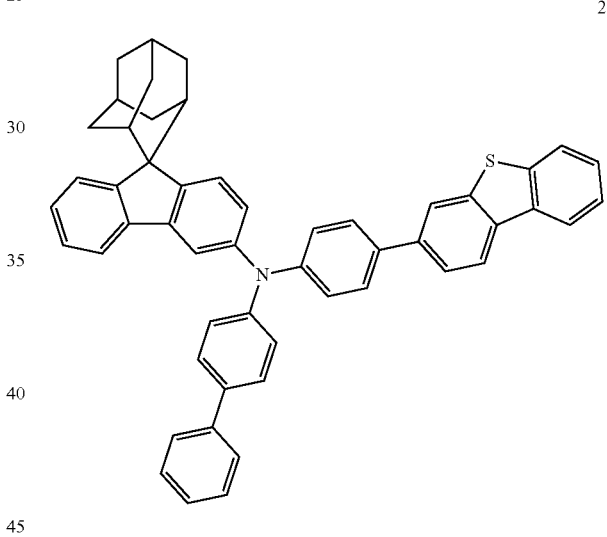
29
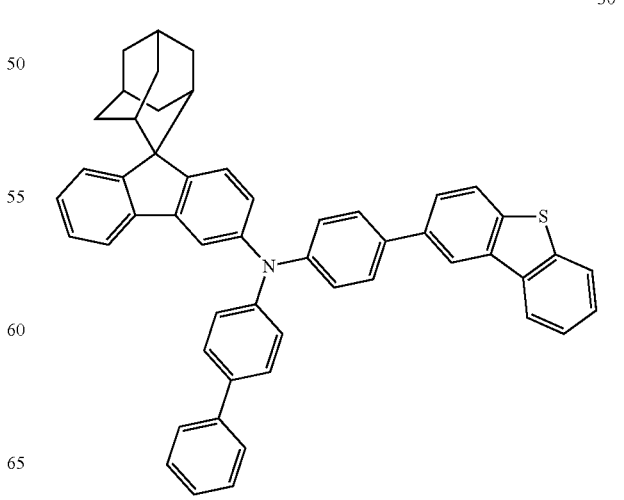
30

31
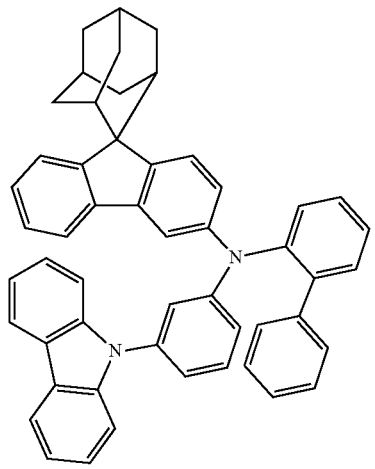
32
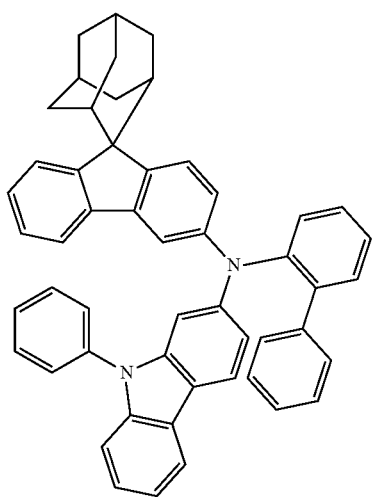
33
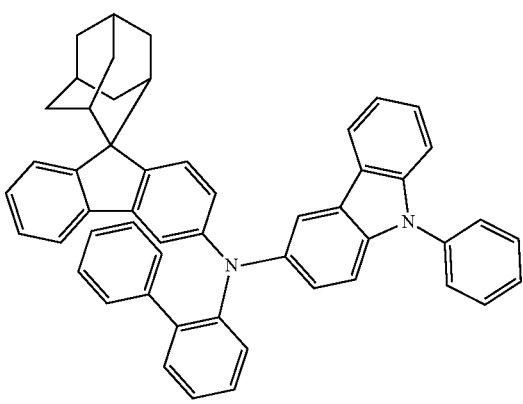
34
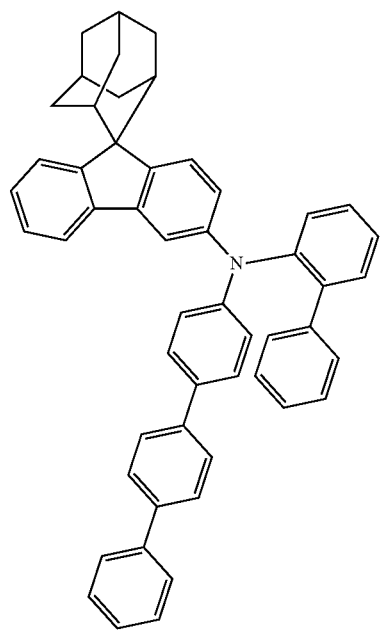
35
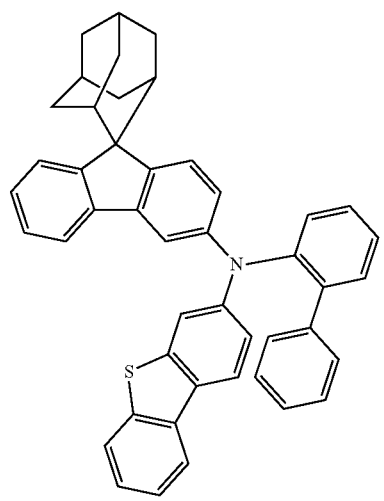
36
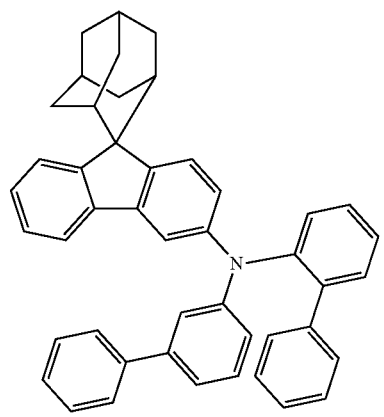

-continued
37
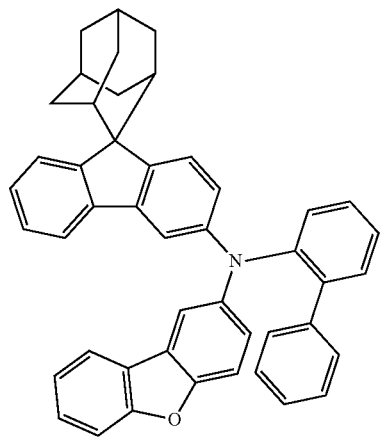
38
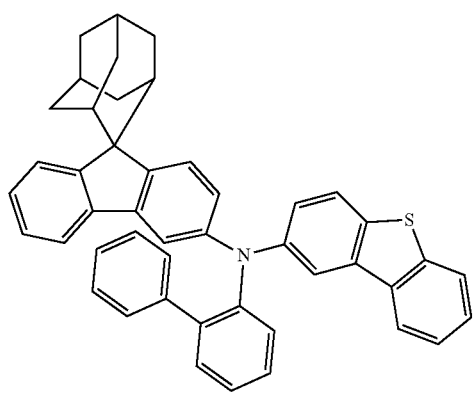
39
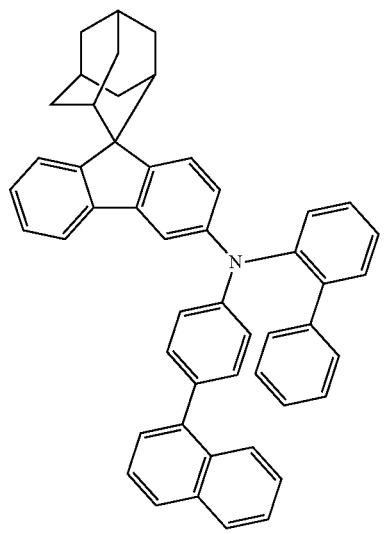
-continued
40
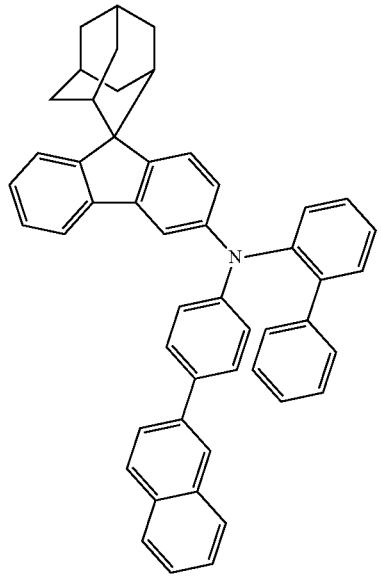
41
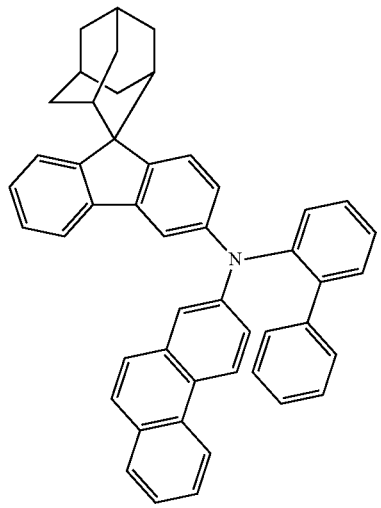
42
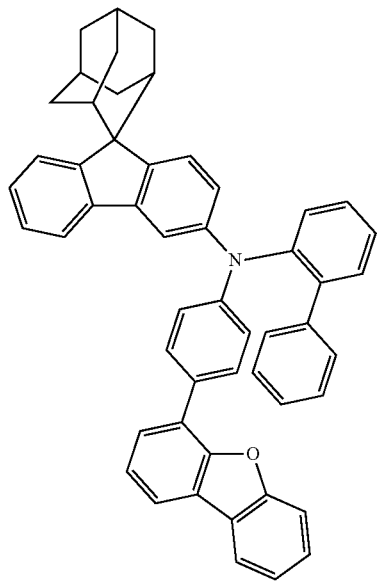

419
-continued
43
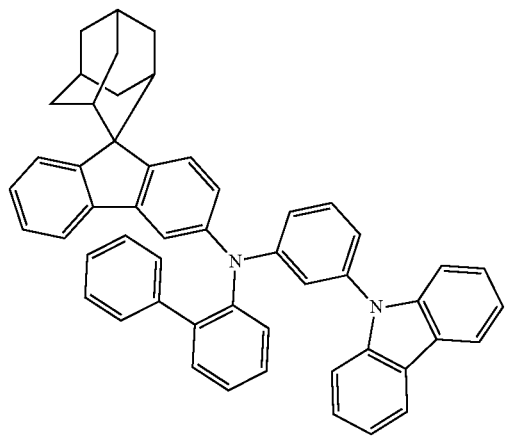
44
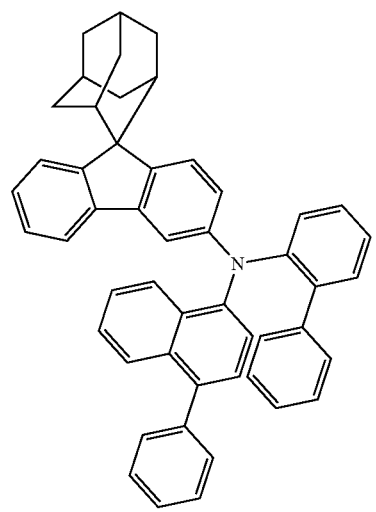
45
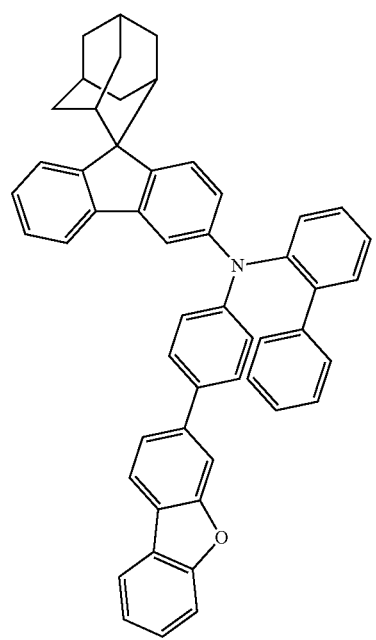
420
-continued
46
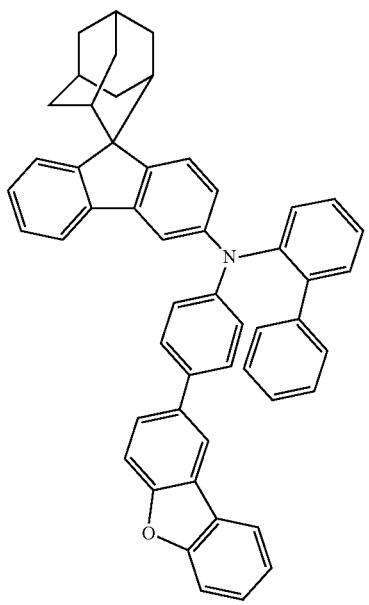
47
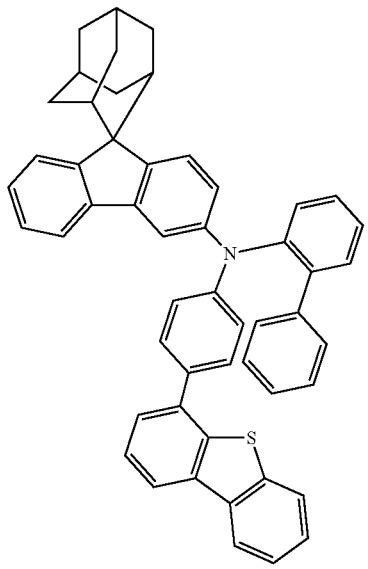
48
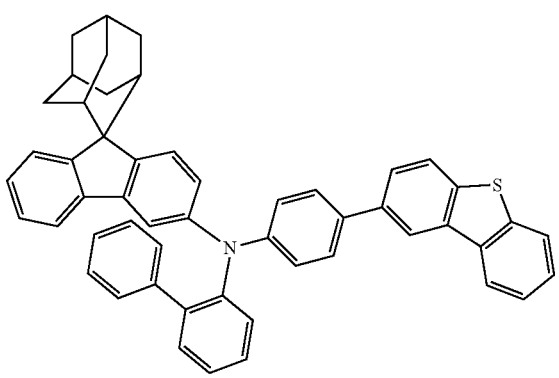

421
-continued
49
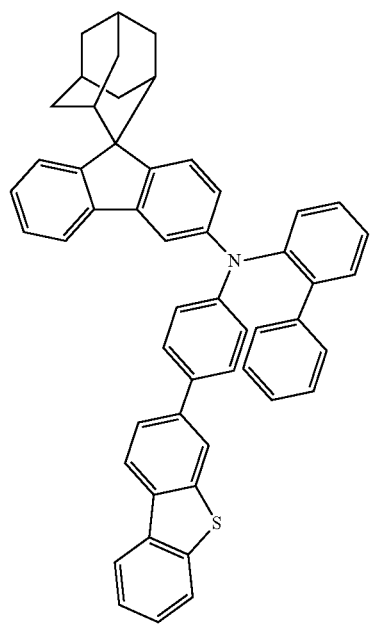
50
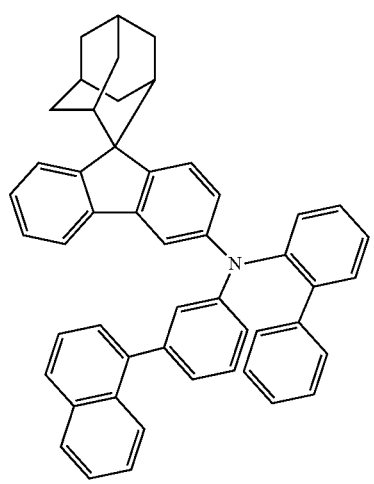
51
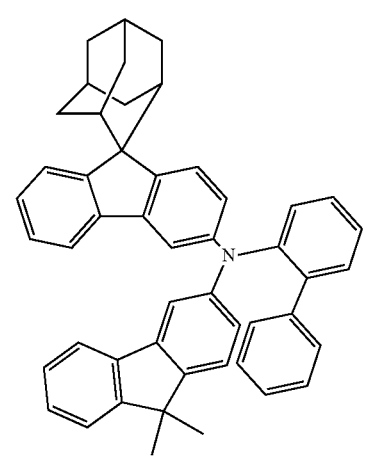
422
-continued
52
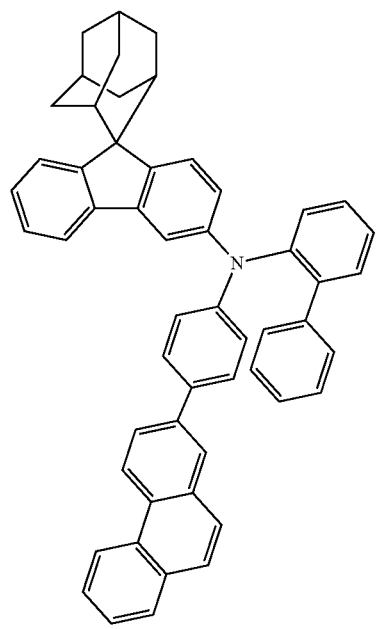
53
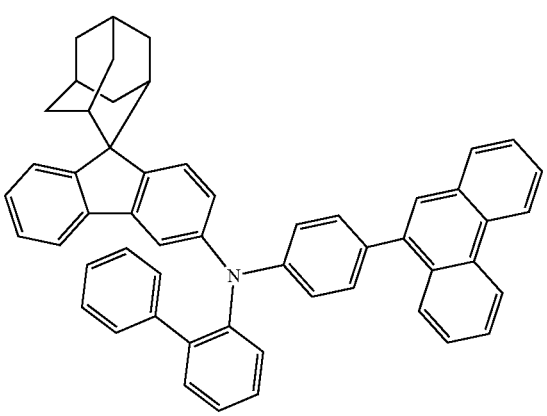
54
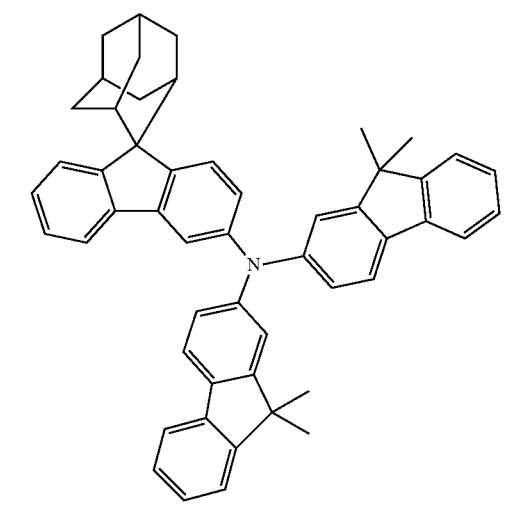

423
-continued
424
-continued
55
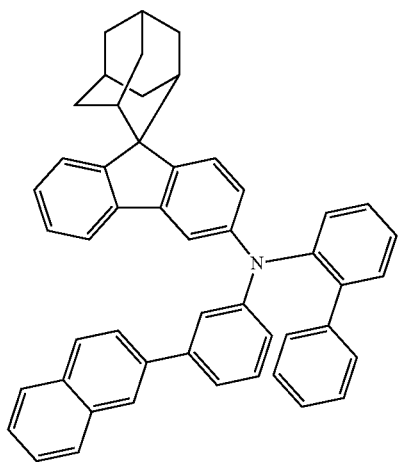
58
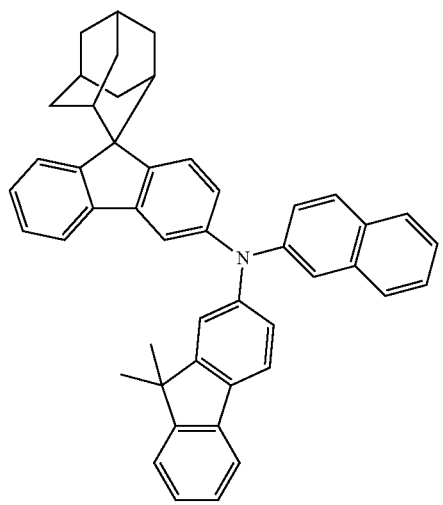
56
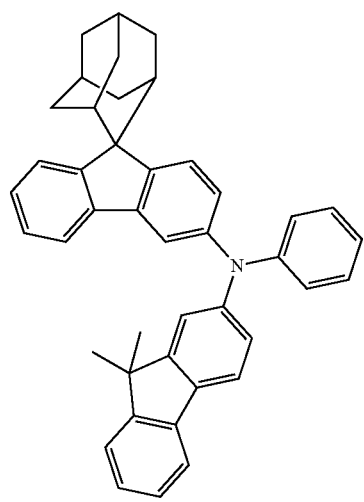
59
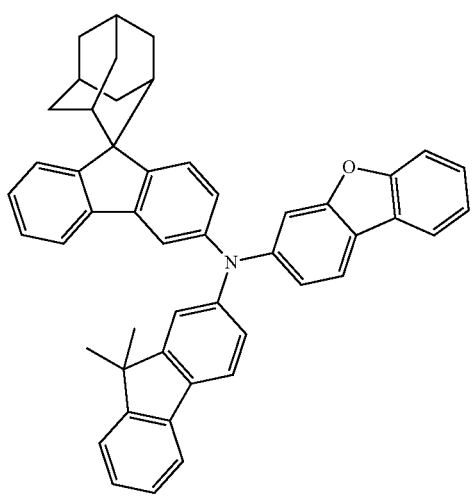
57
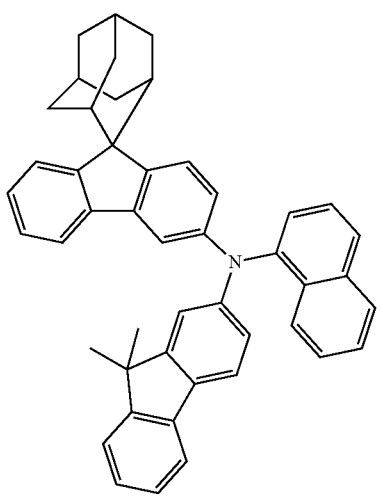
60
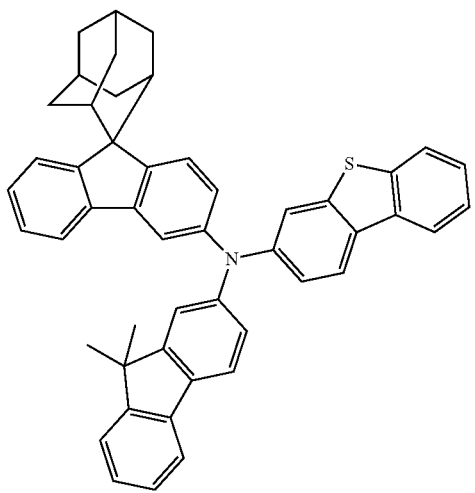

425
-continued
426
-continued
61
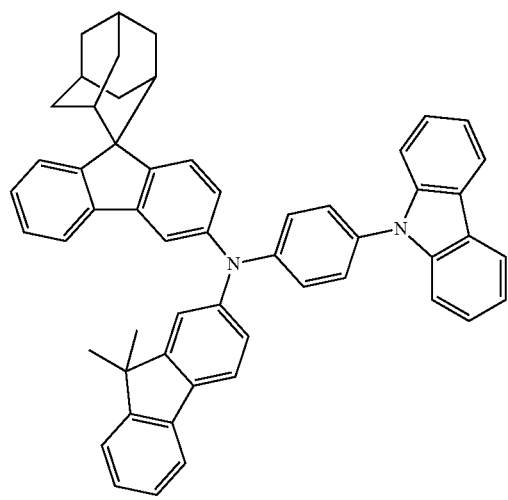
64
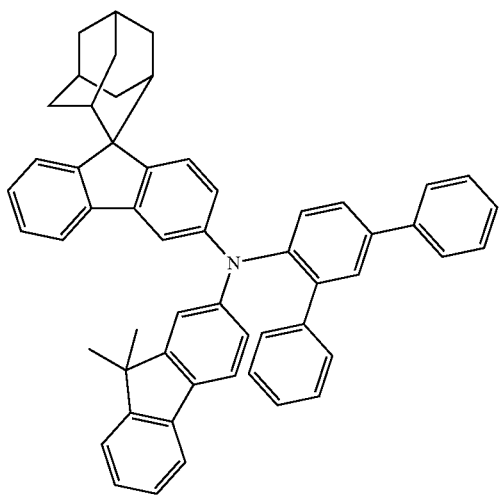
62
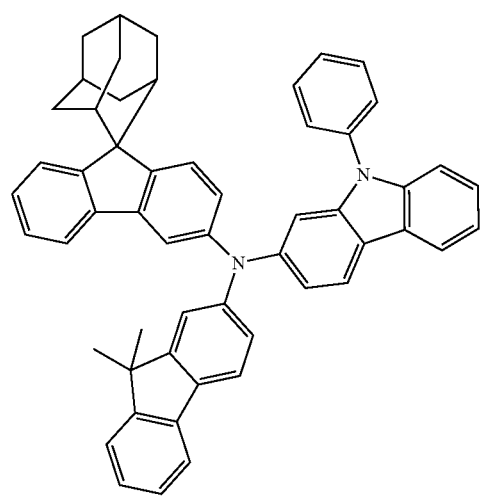
65
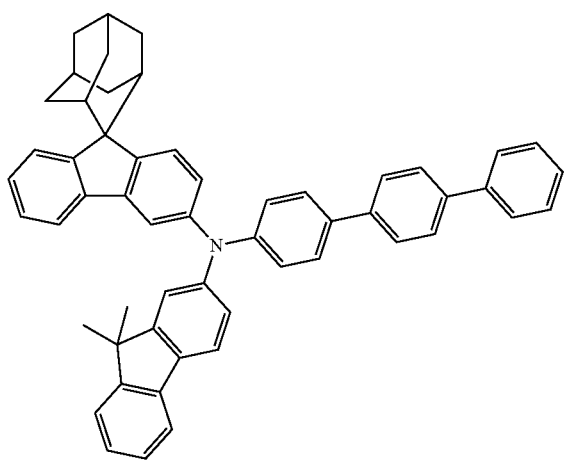
63
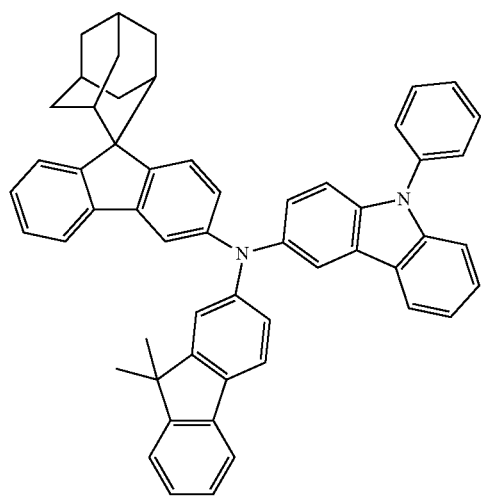
66
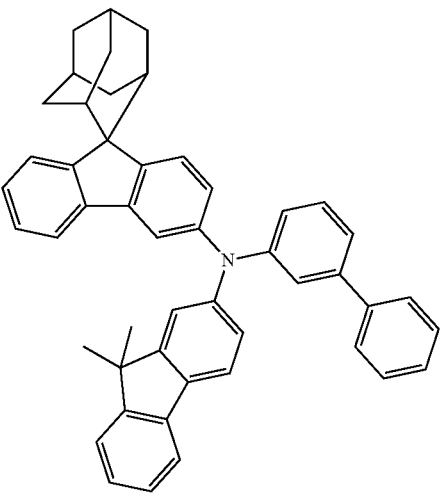

427
-continued
67
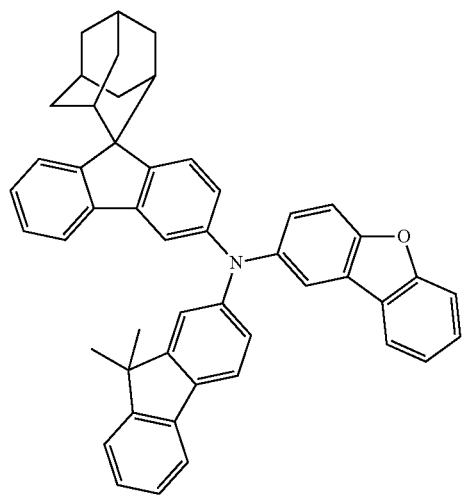
68
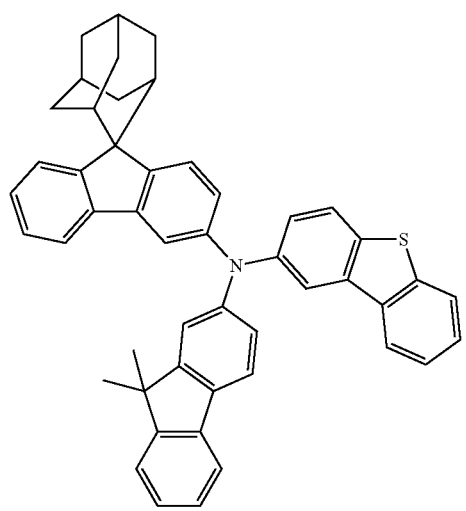
69
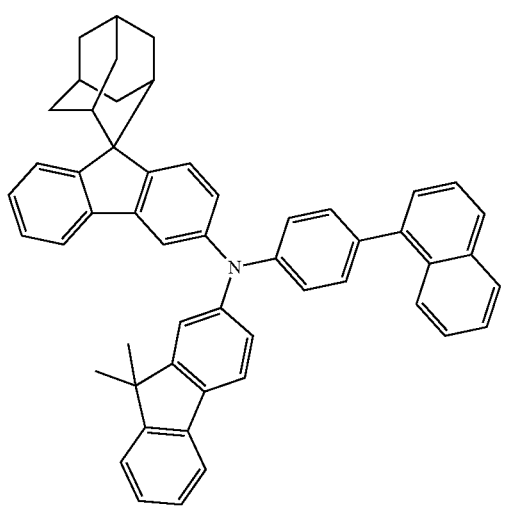
428
-continued
70
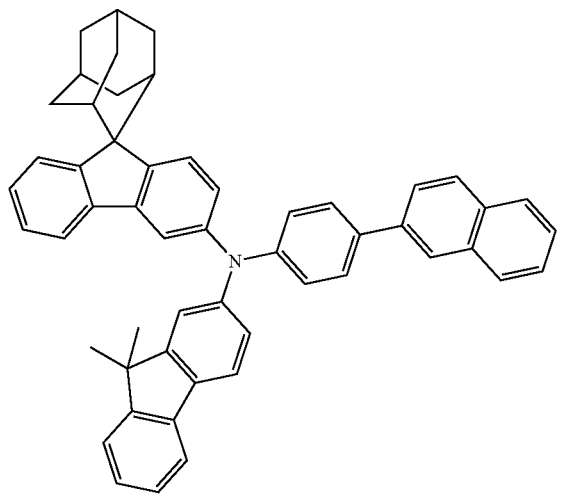
71
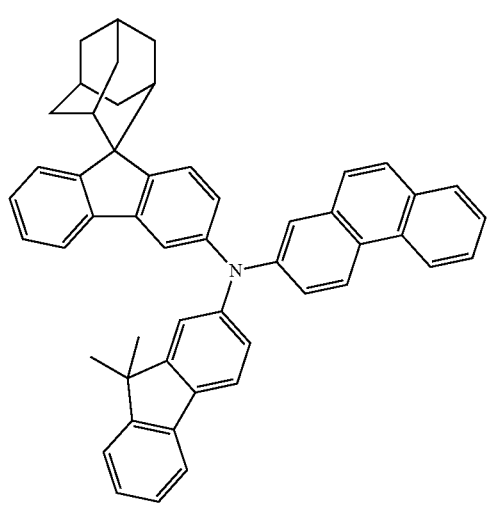
72
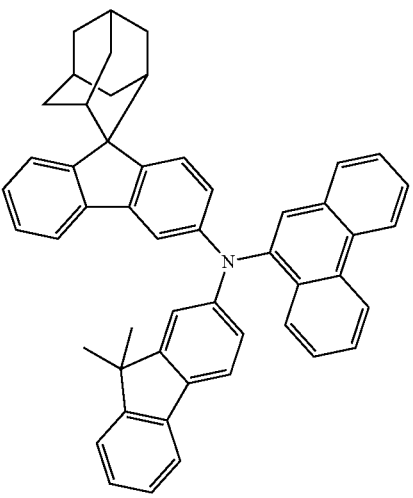

429
-continued
73
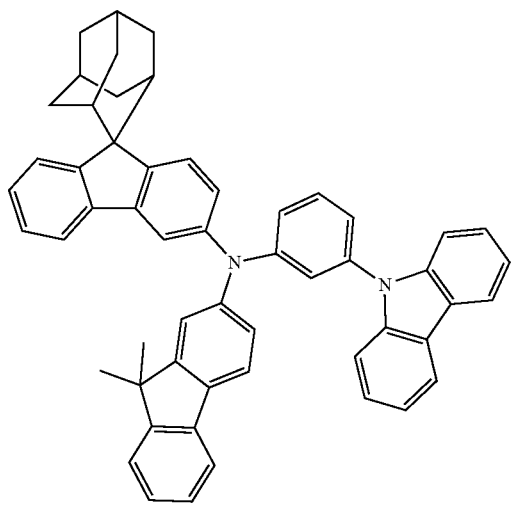
74
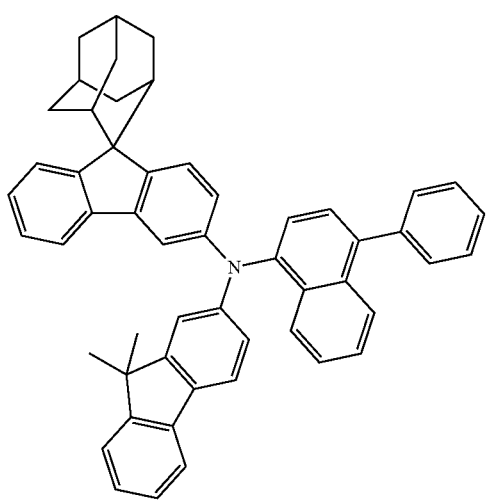
75
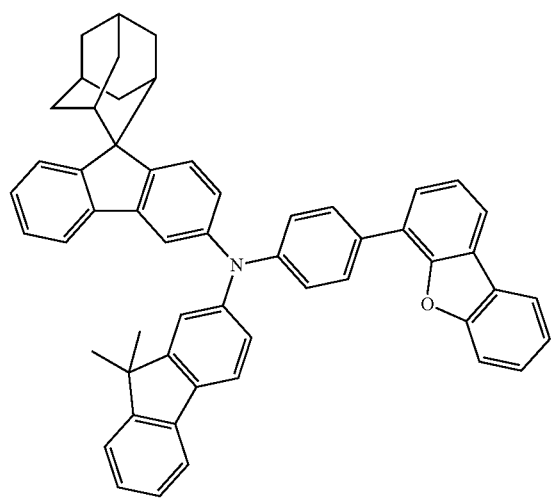
430
-continued
76
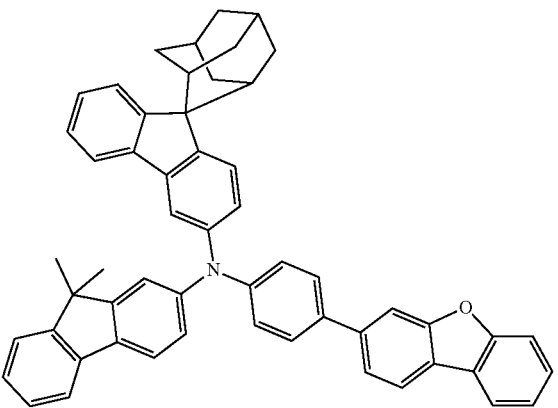
77
78
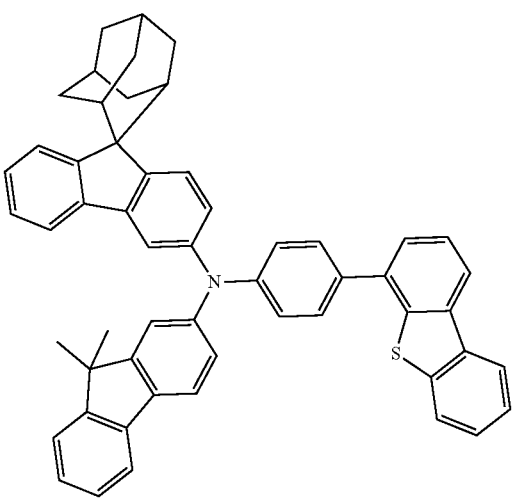

431
-continued
79
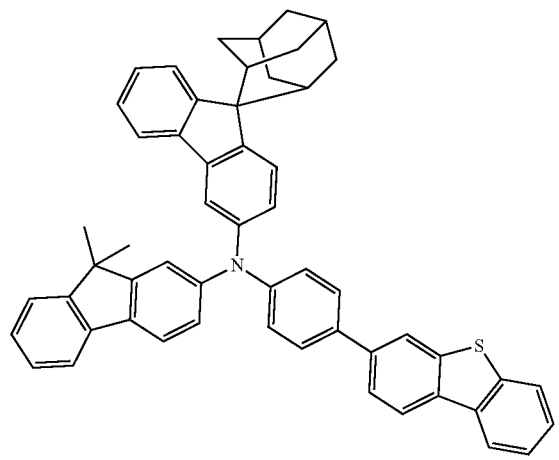
80
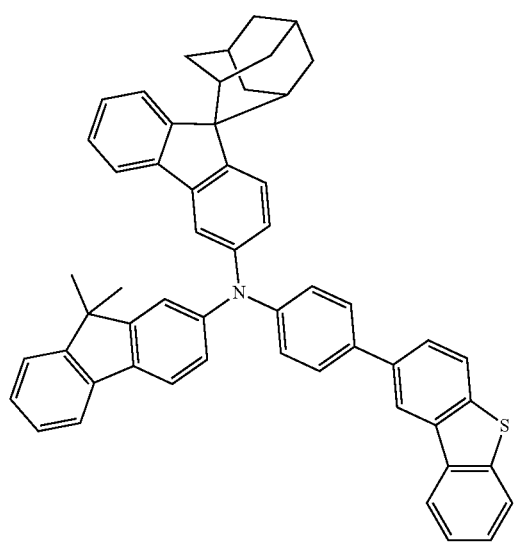
81
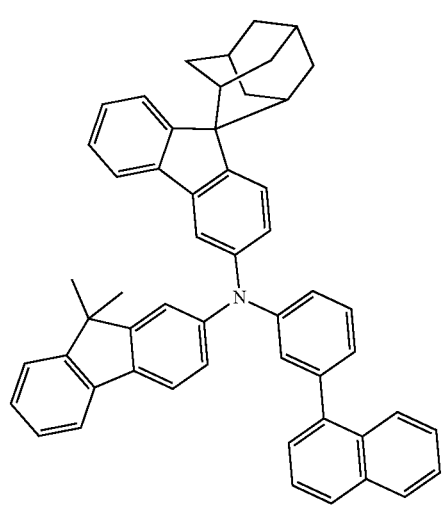
432
-continued
82
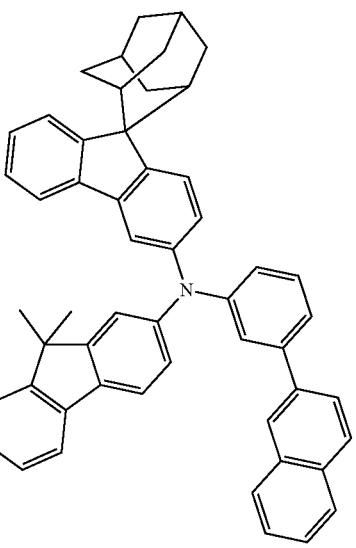
83
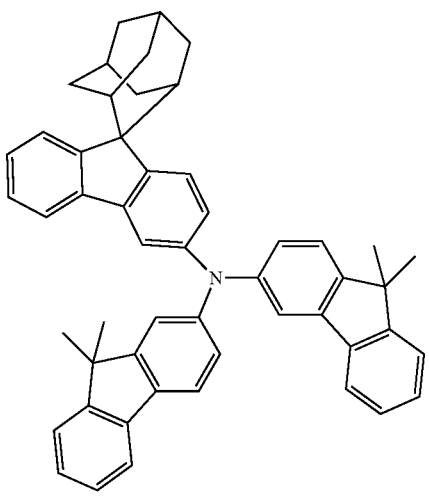
84
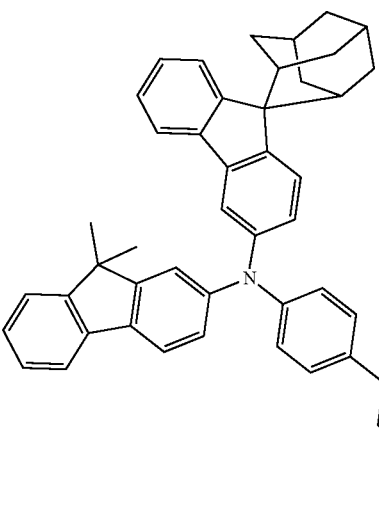

85
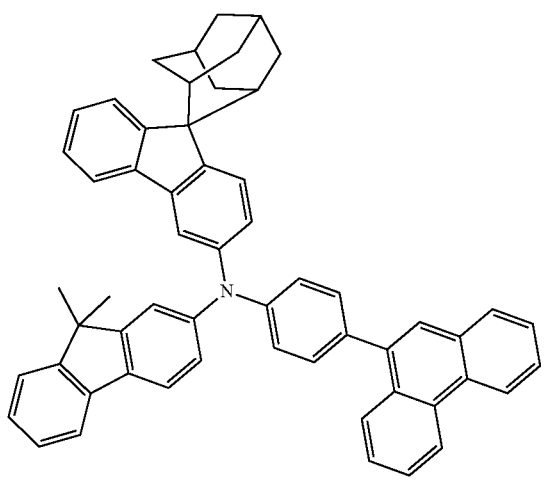
86
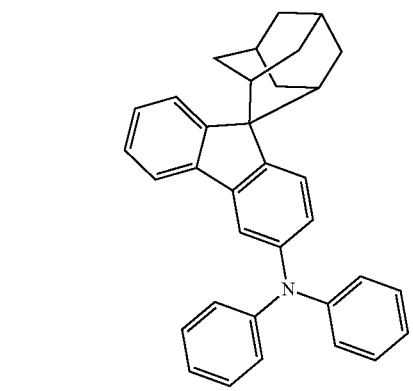
87
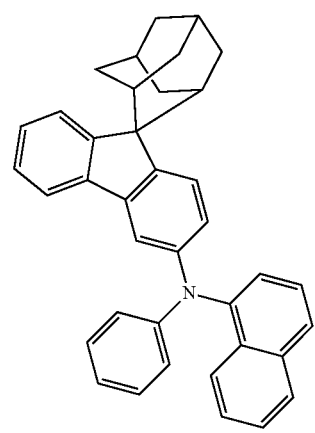
88
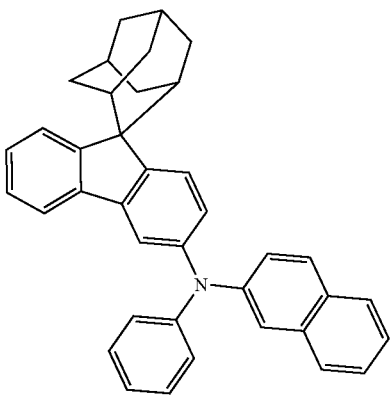
89
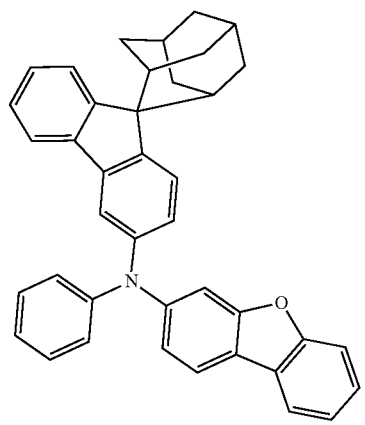
90
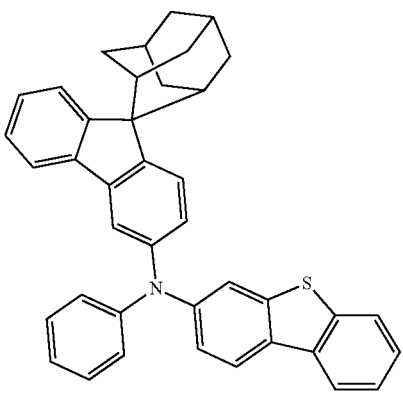

435
-continued
91
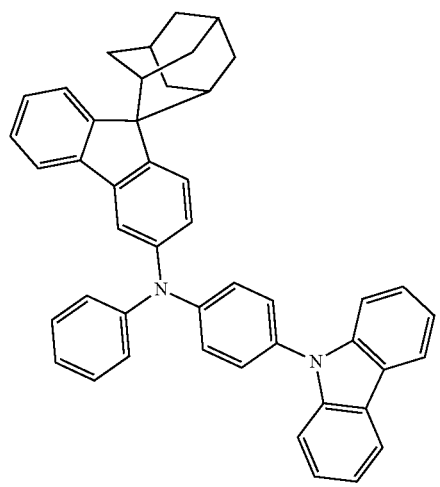
92
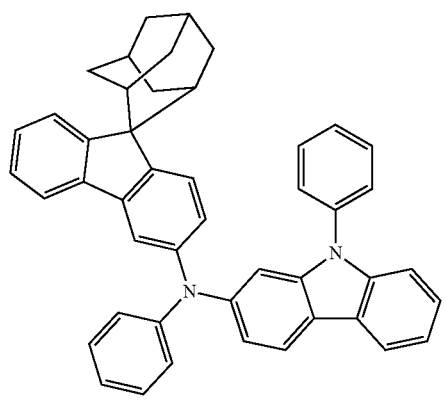
93
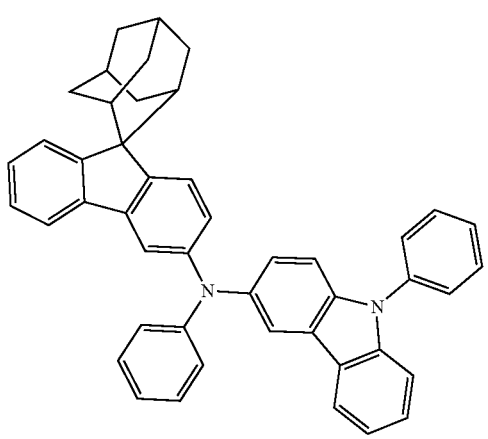
436
-continued
94
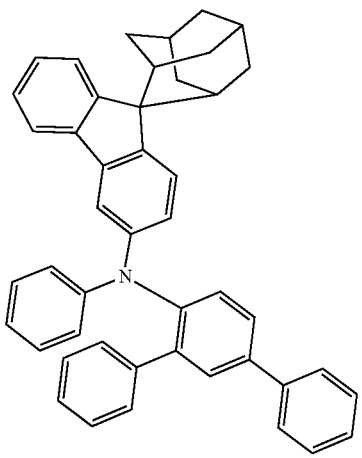
95
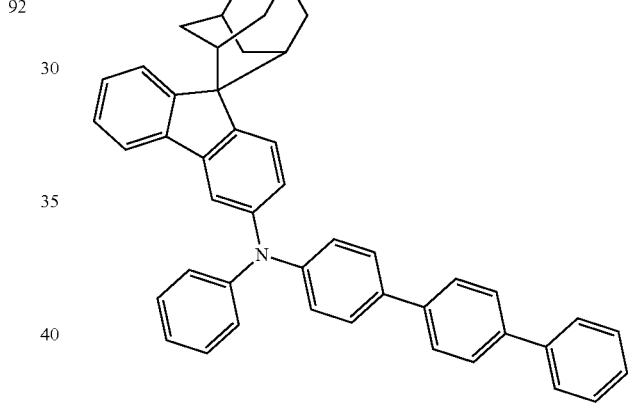
96
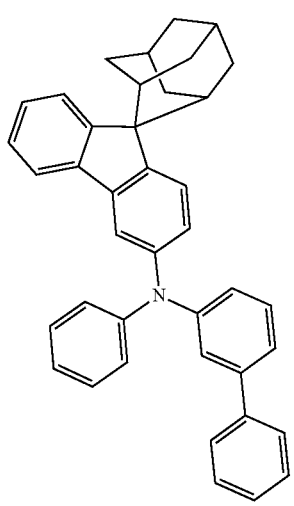

-continued
97
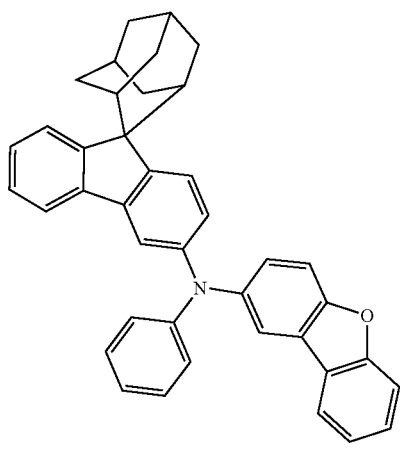
98
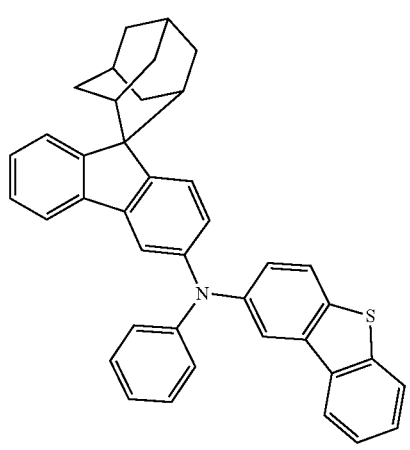
99
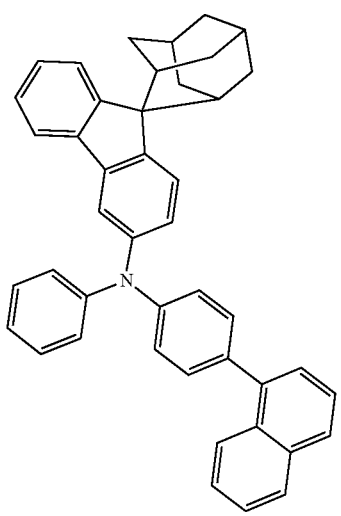
-continued
100
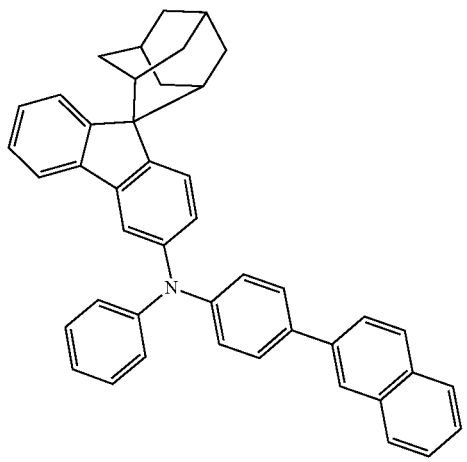
101
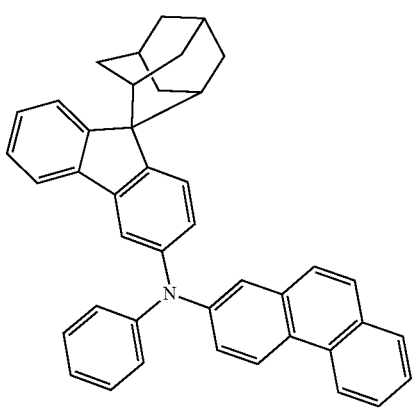
102
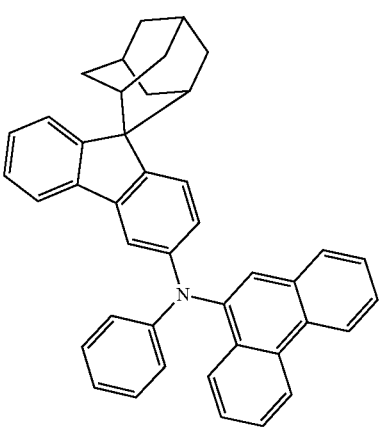

103
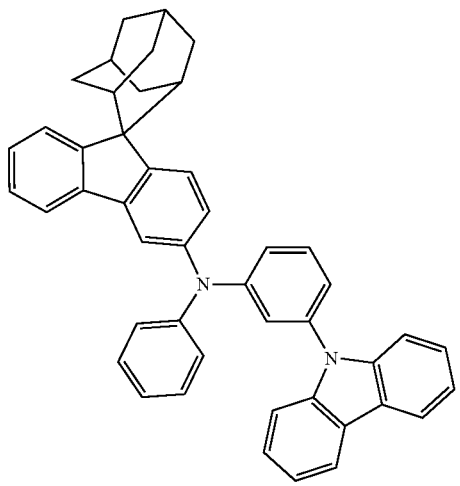
104
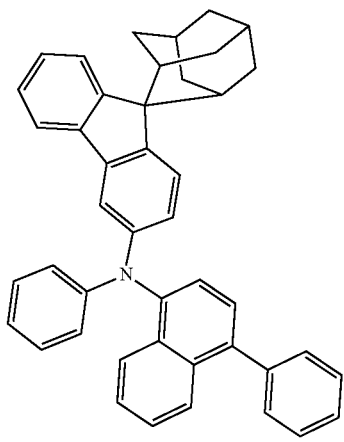
105
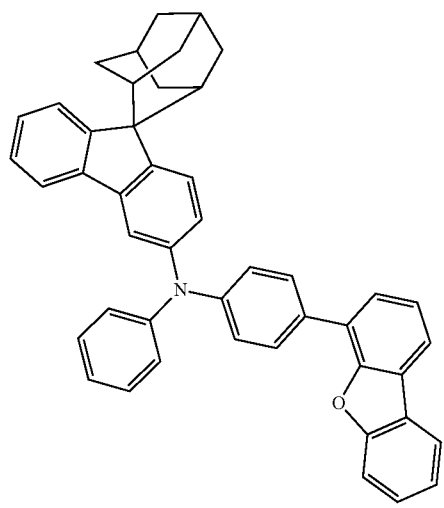
106
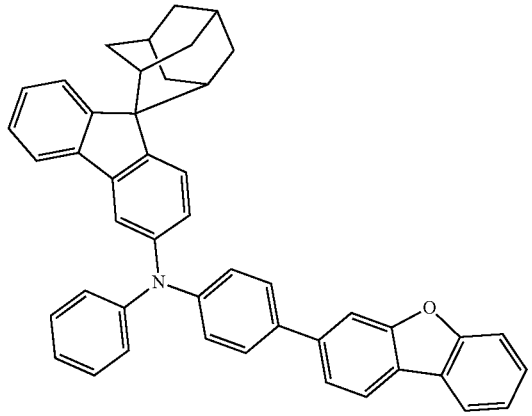
107
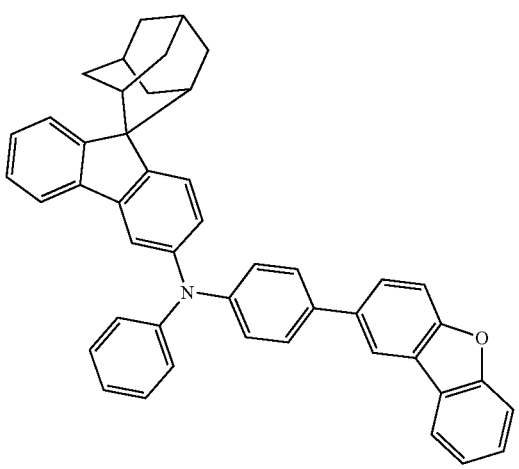
108
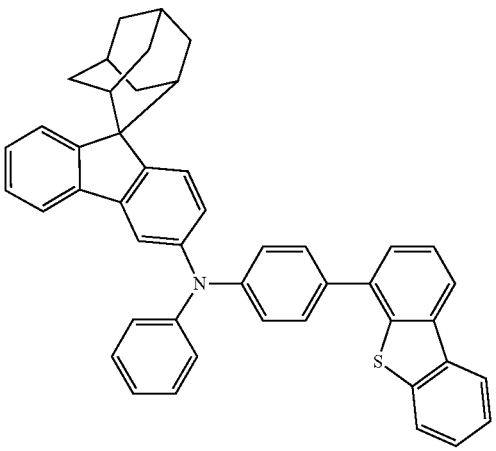

109
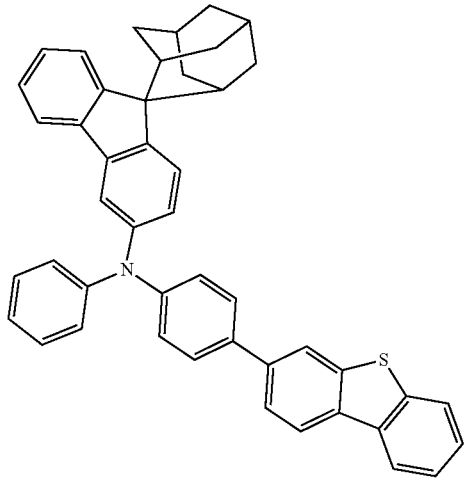
110
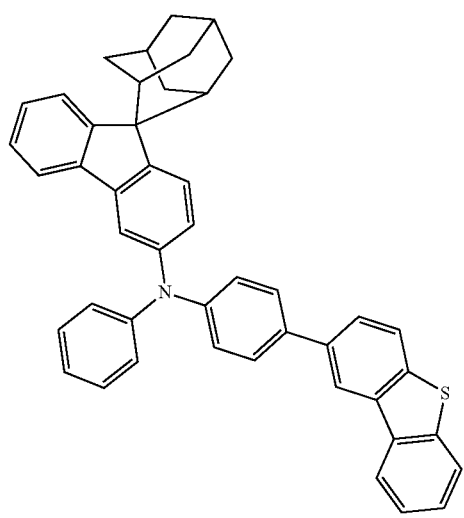
111
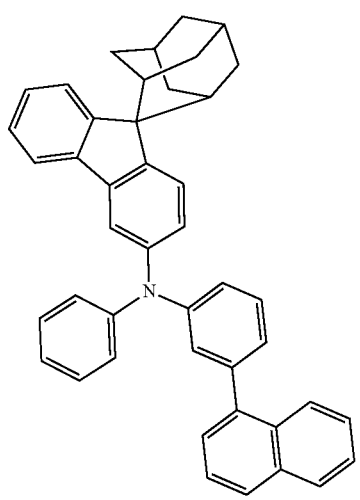
112
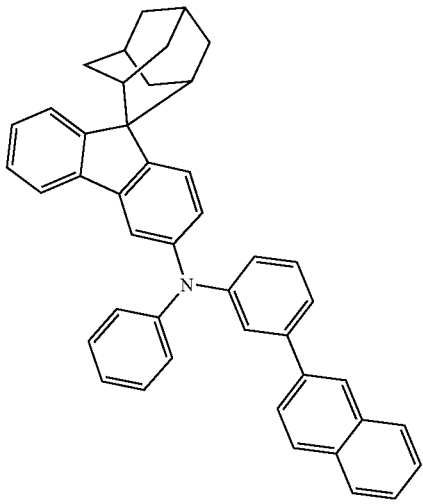
113
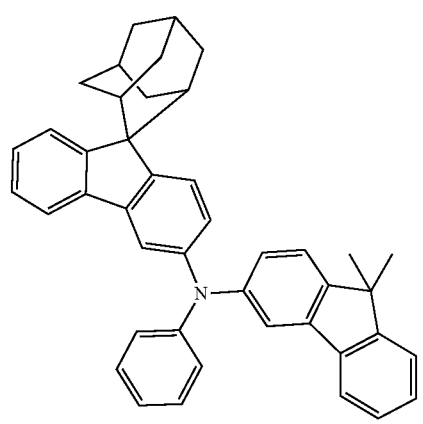
114
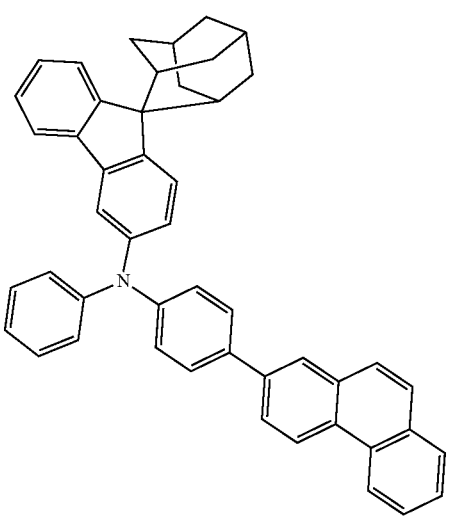

-continued
| 115 | 118 |
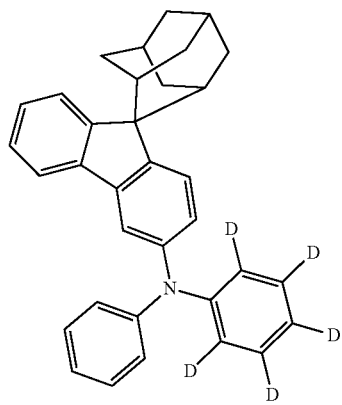
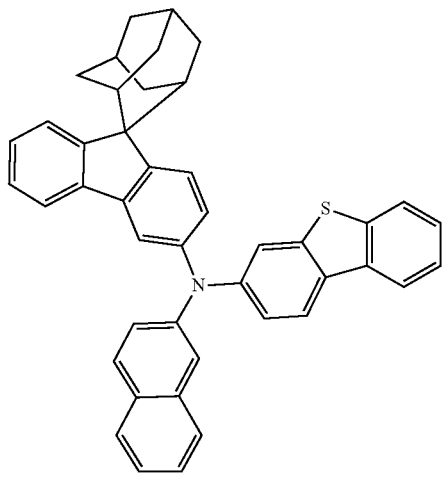
| 116 | 119 |
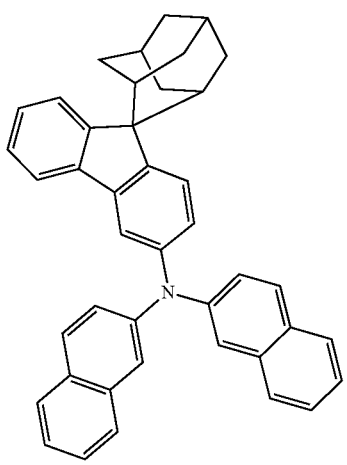
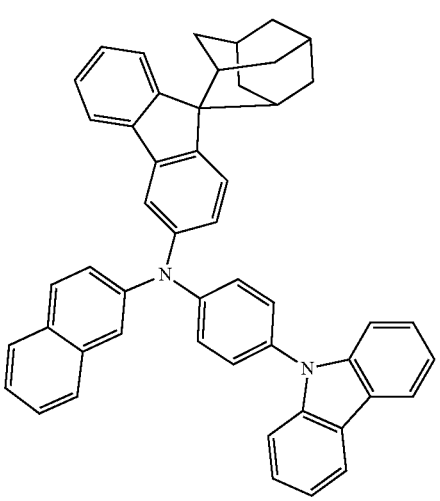
| 117 | 120 |
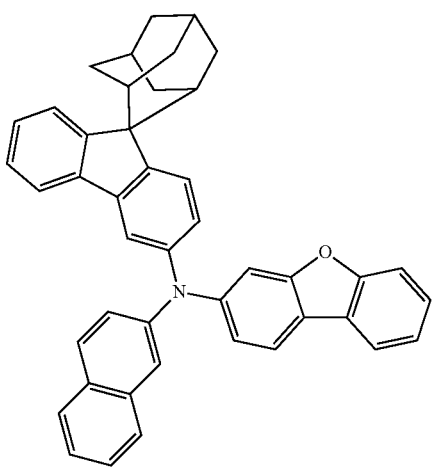
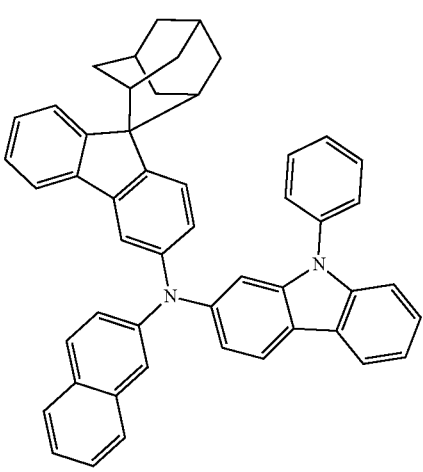

121
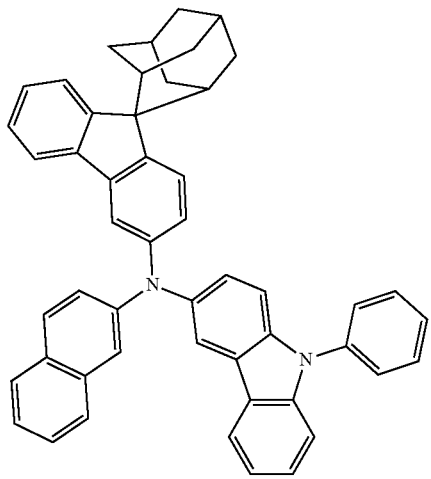
122
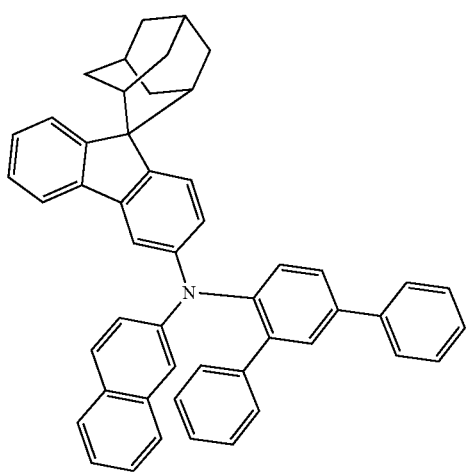
123
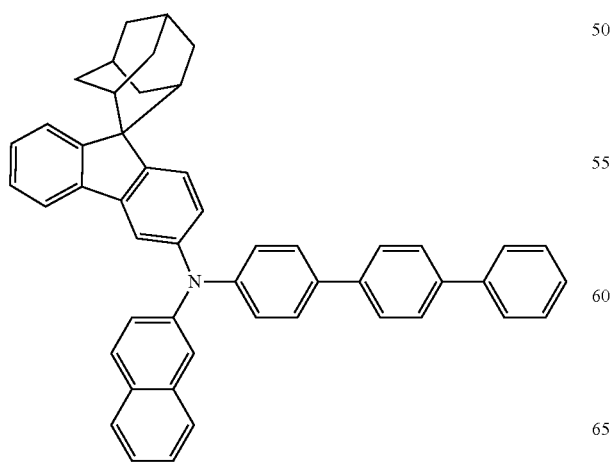
124
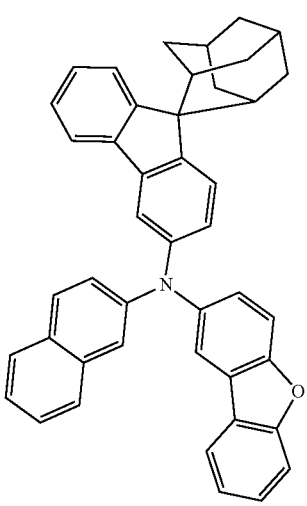
125
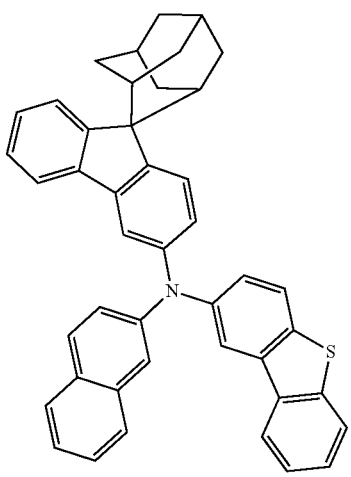
126
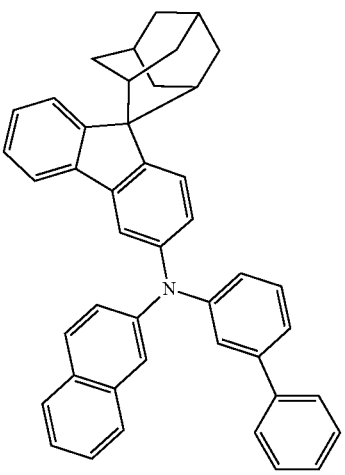

127
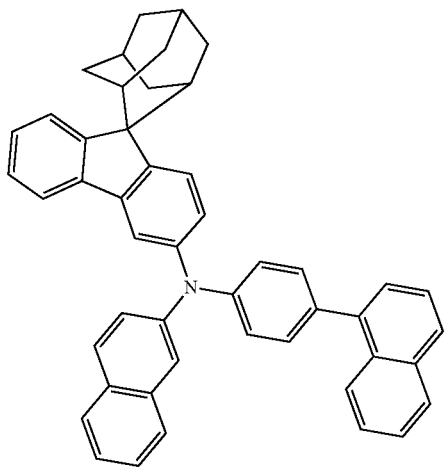
128
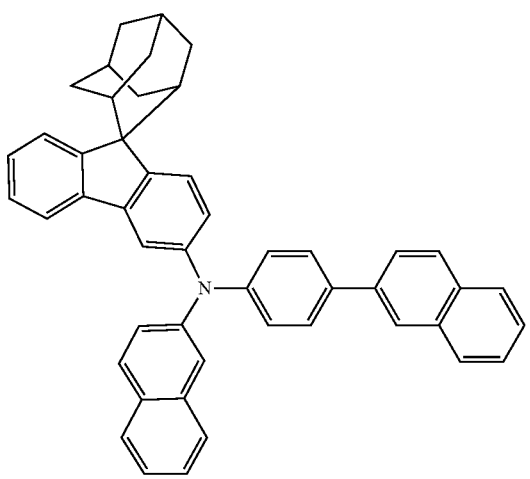
129
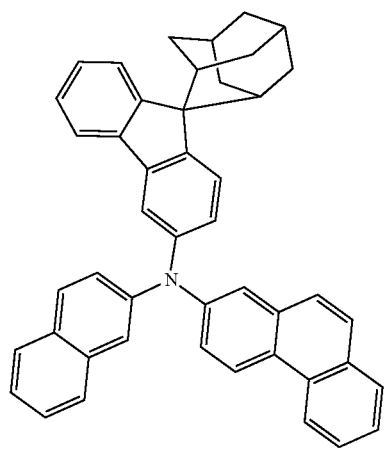
130
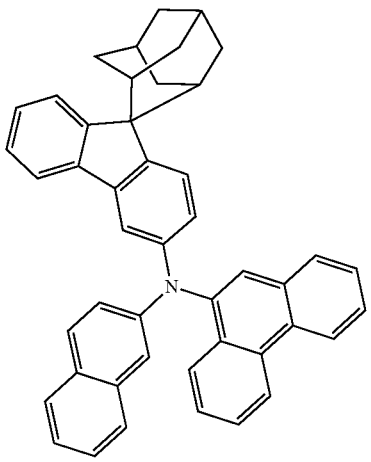
131
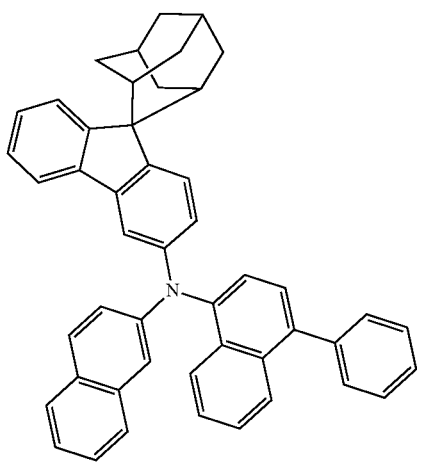
132
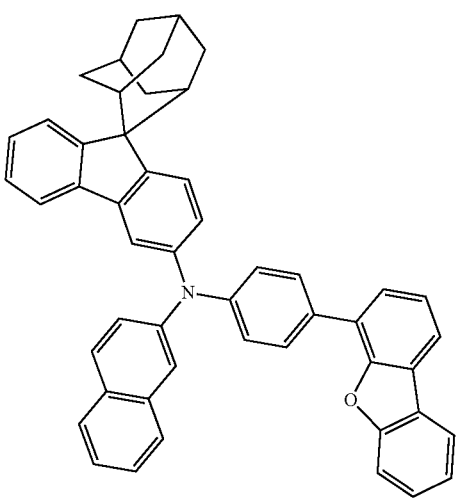

133
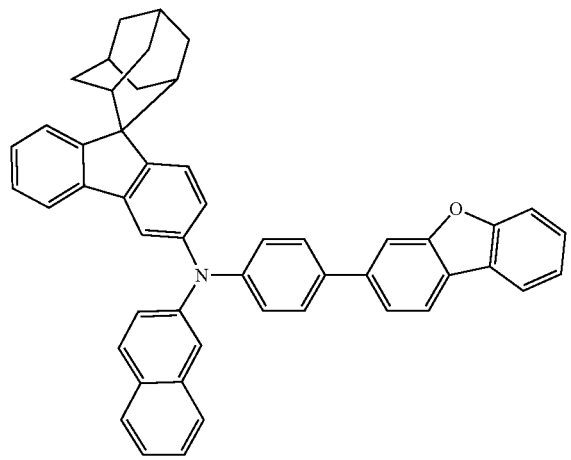
134
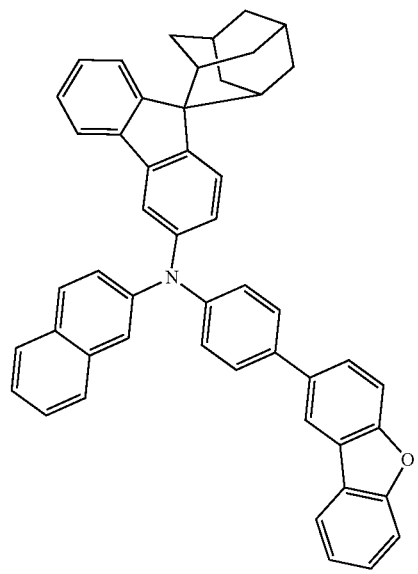
135
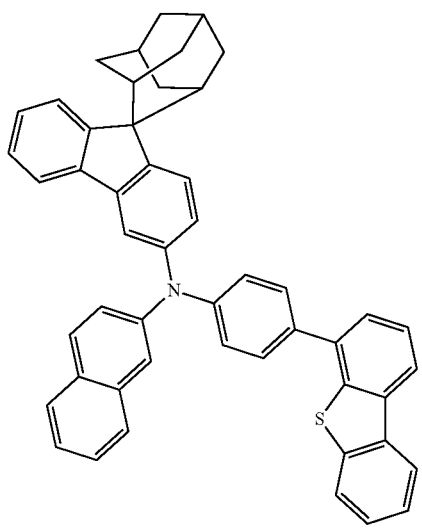
136
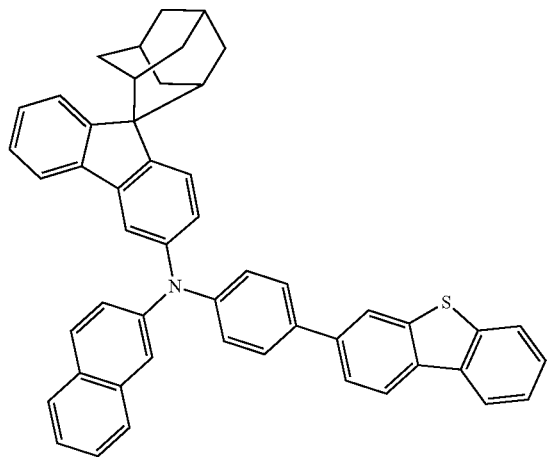
137
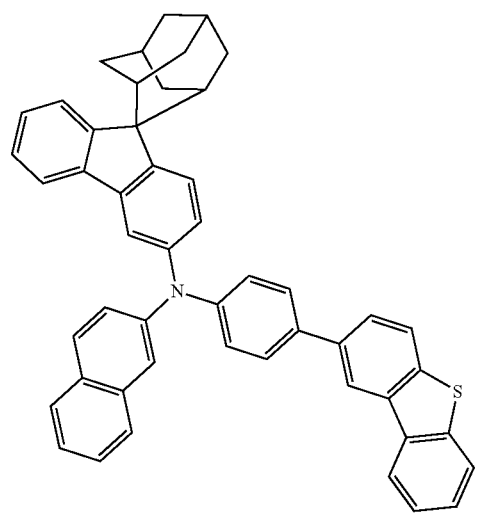
138
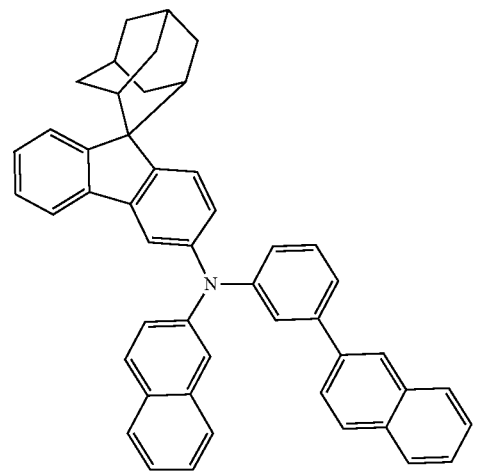

-continued
139
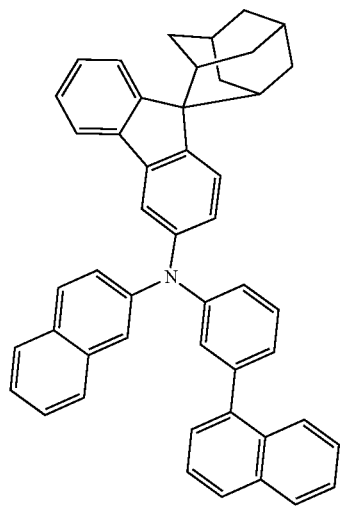
140
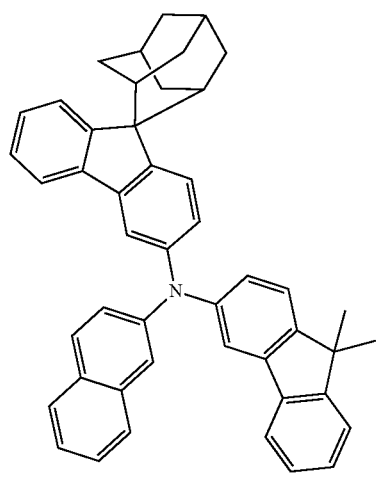
141
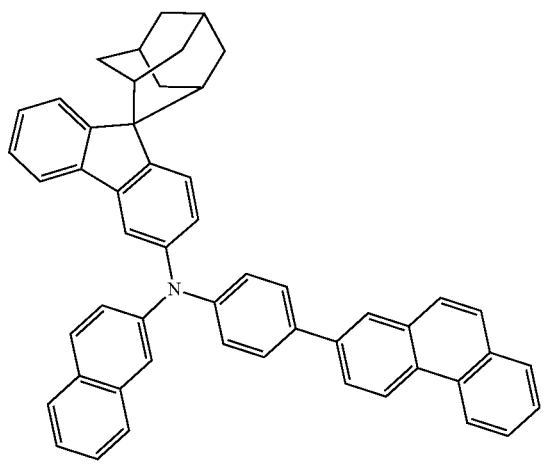
-continued
142
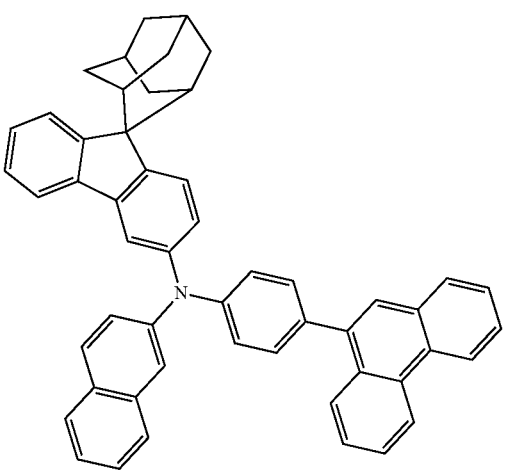
143
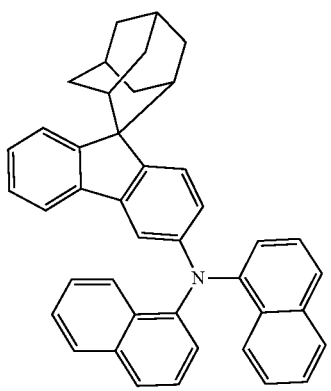
144
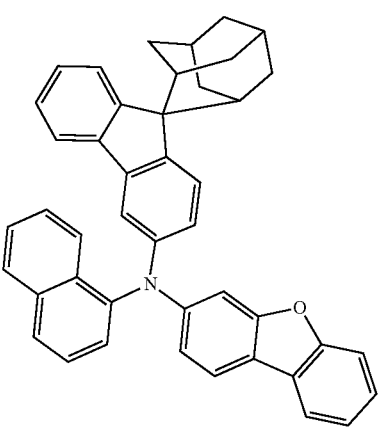

453
-continued
145
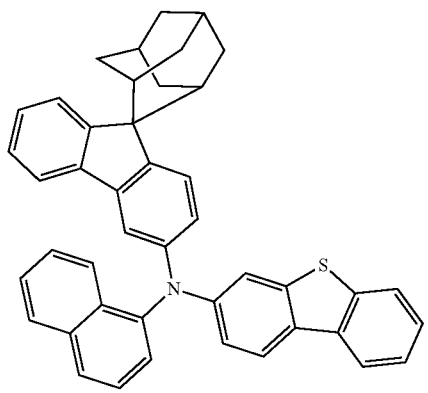
146
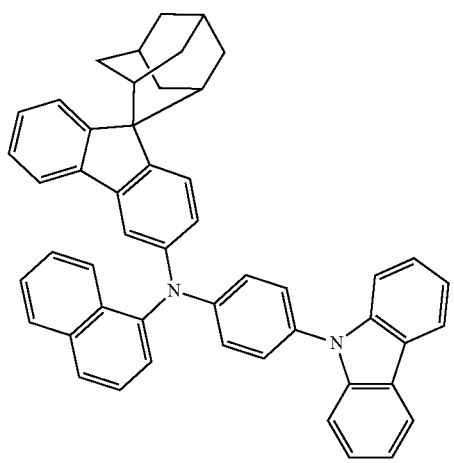
147
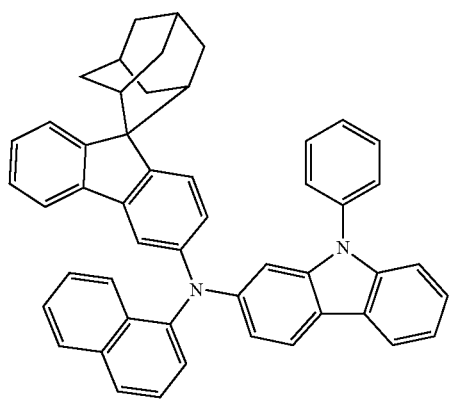
454
-continued
148
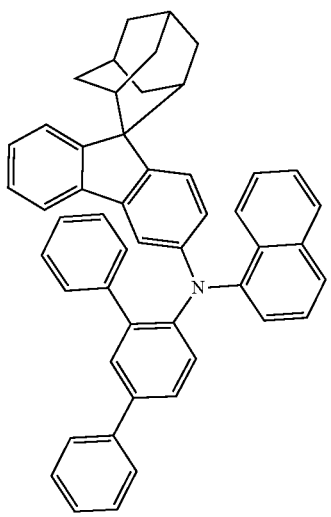
149
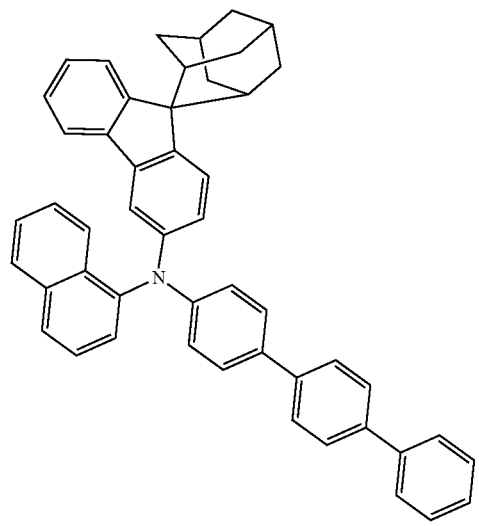
150
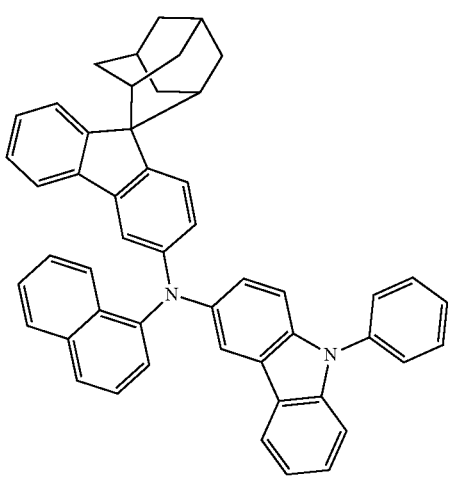

455
-continued
456
-continued
151
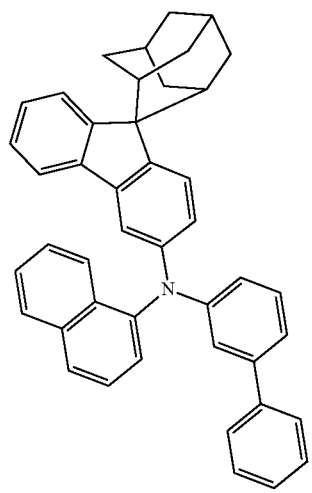
154
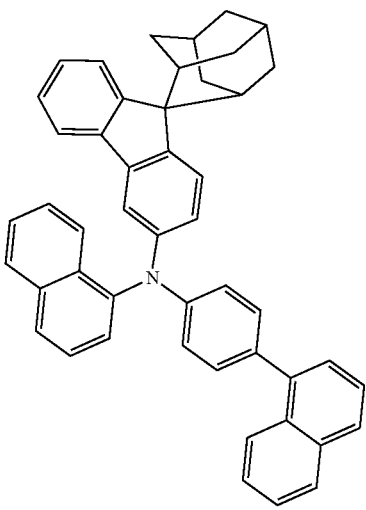
152
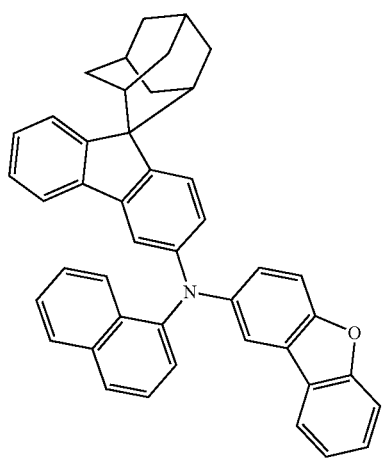
155
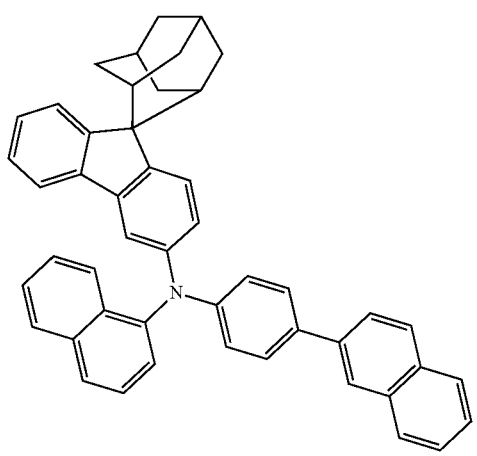
153
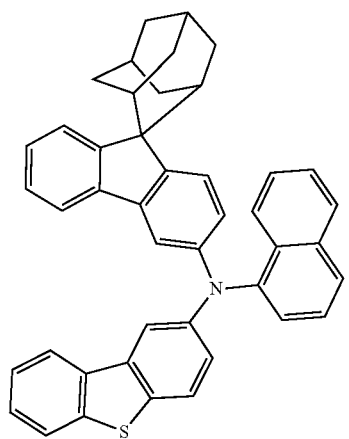
156
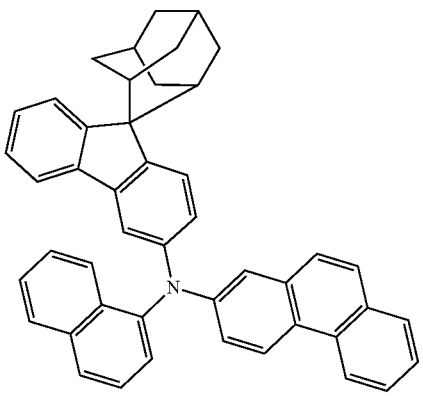

157 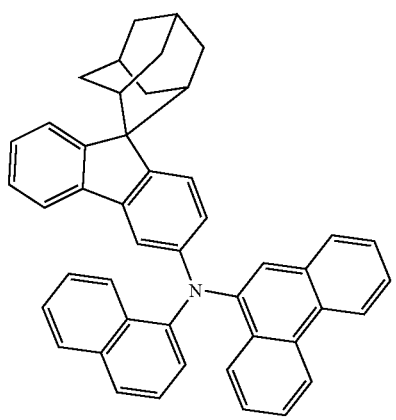
158 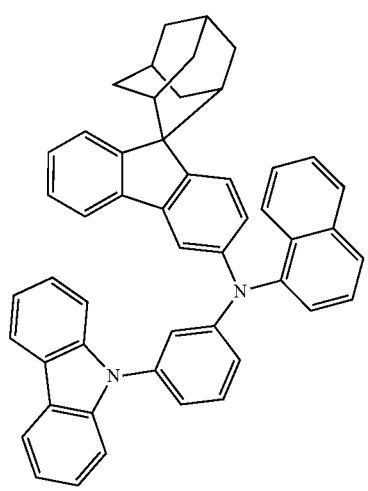
159 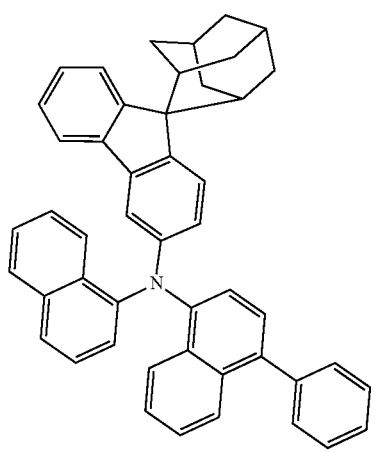
160 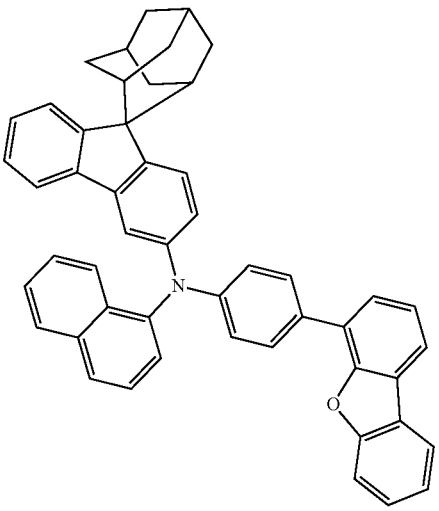
161 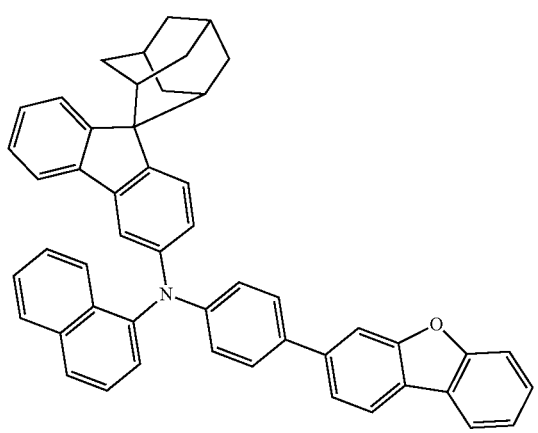
162 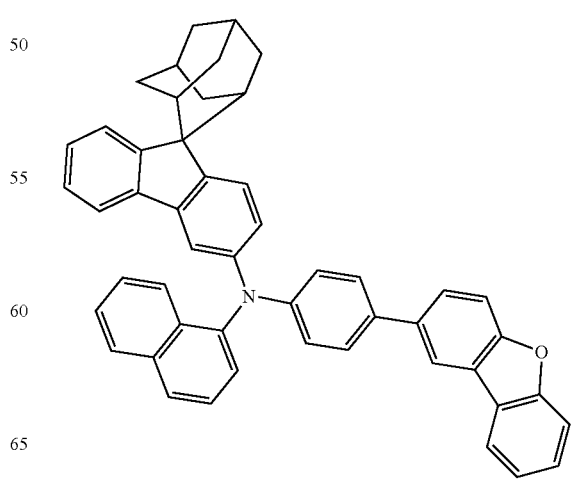

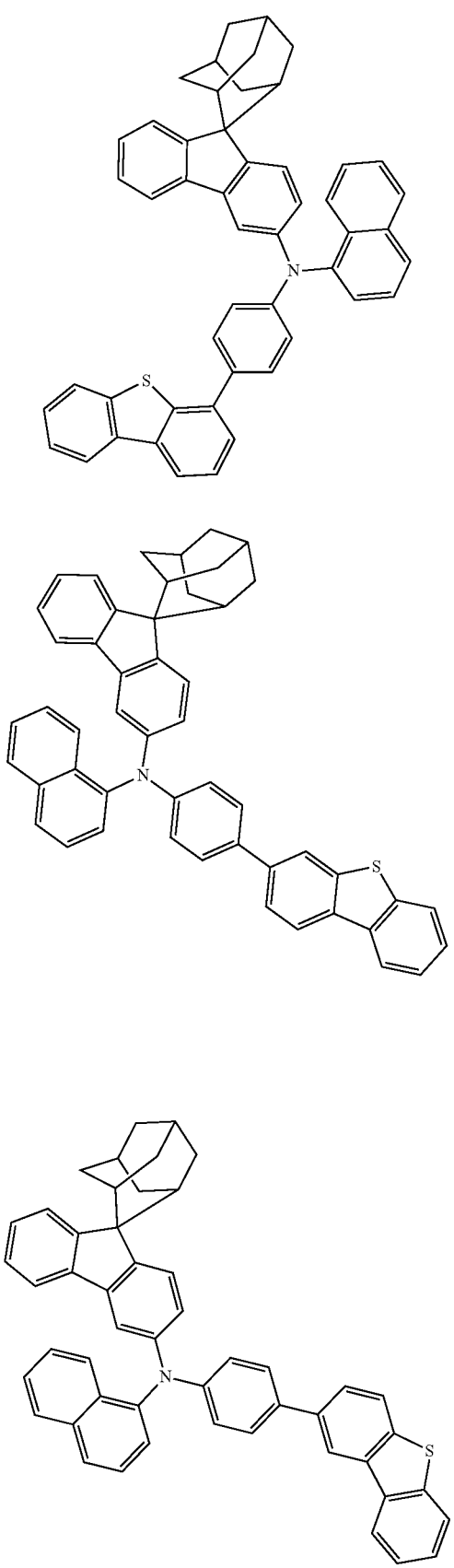
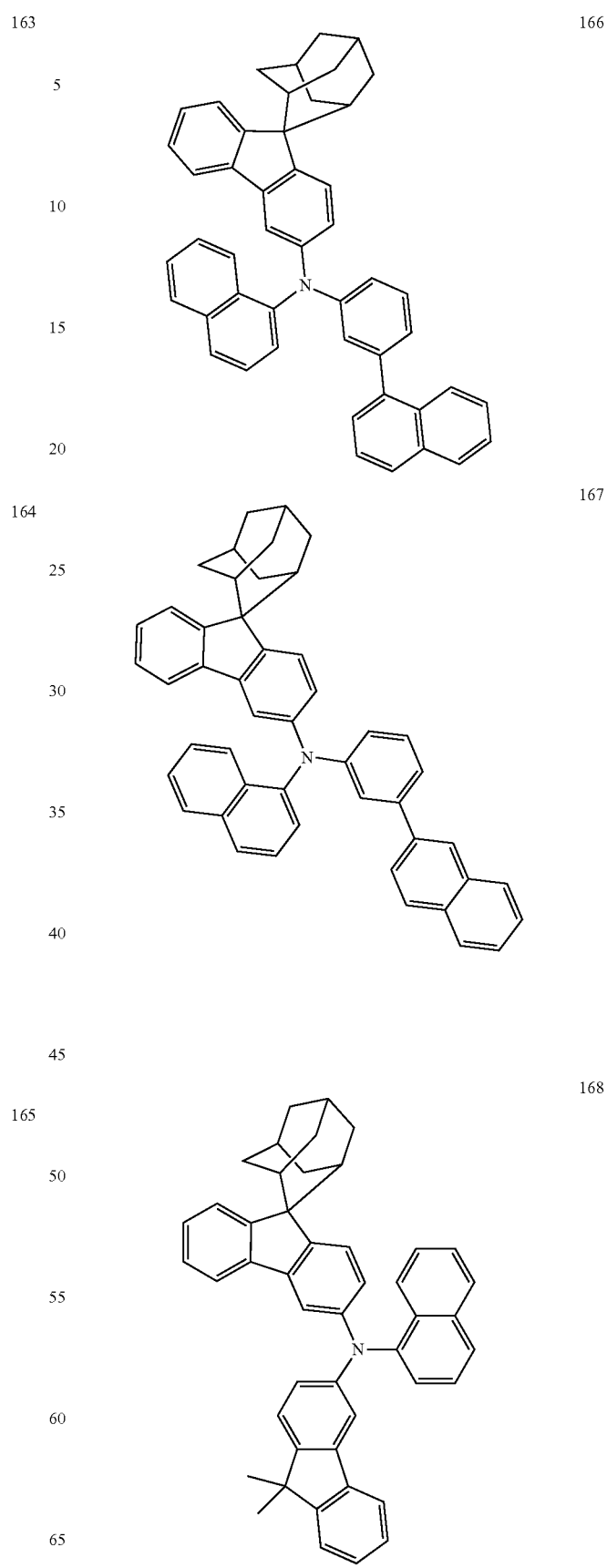

-continued
169
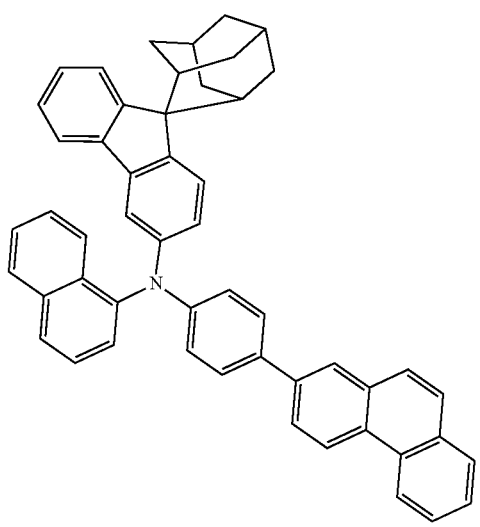
170
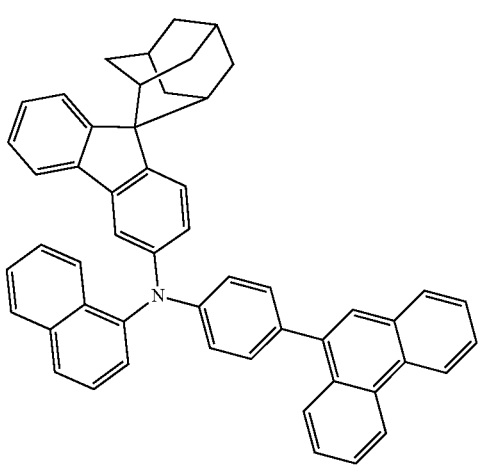
171
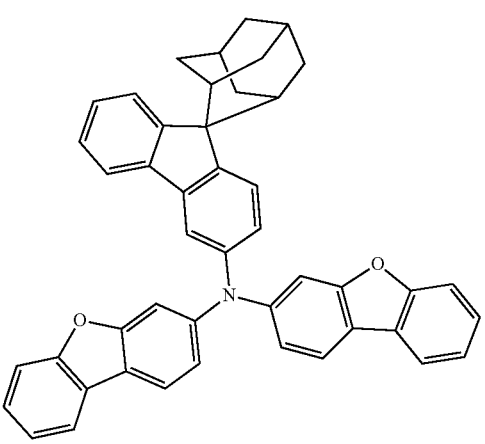
-continued
172
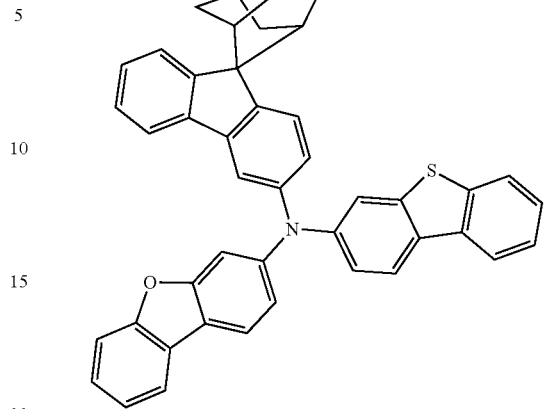
173
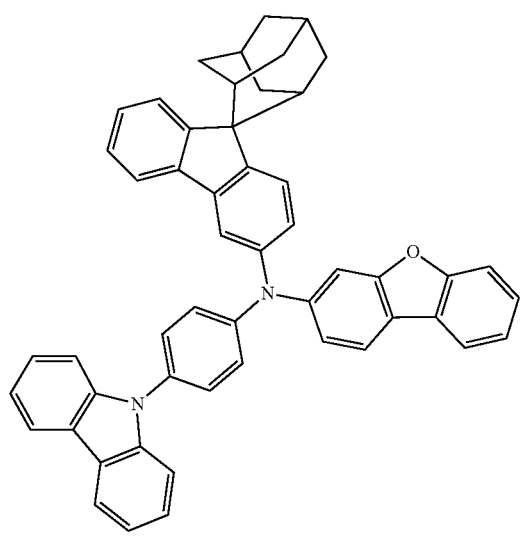
174
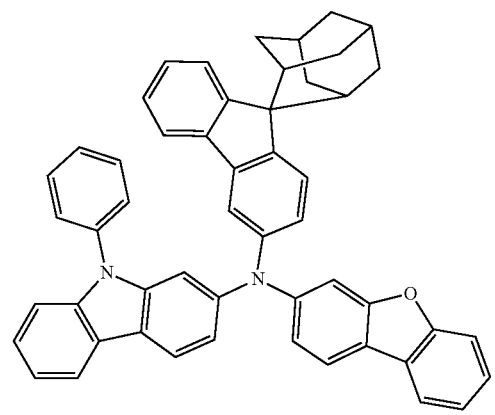

175
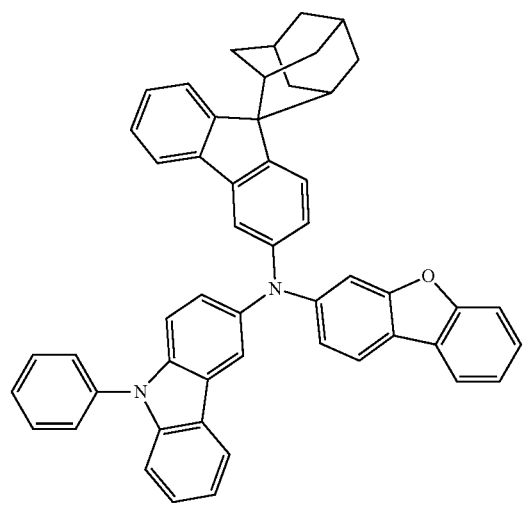
176
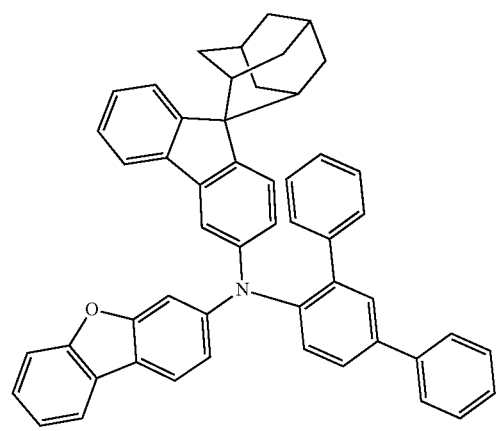
177
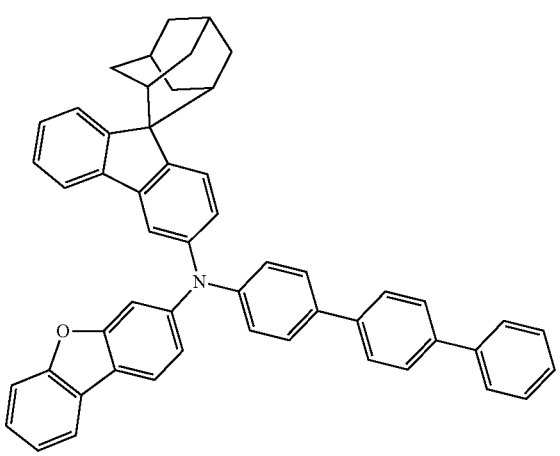
178
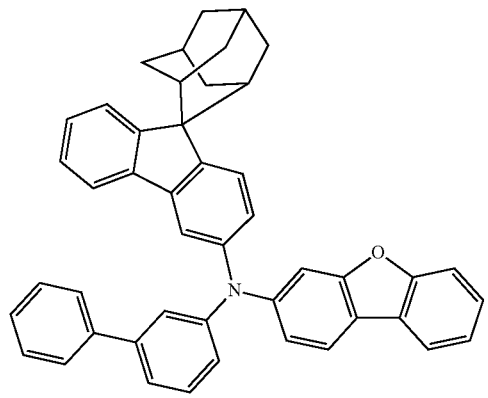
179
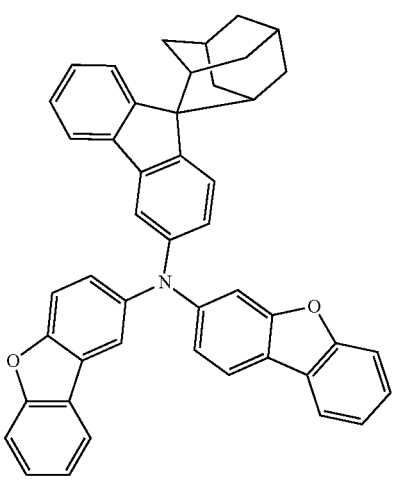
180
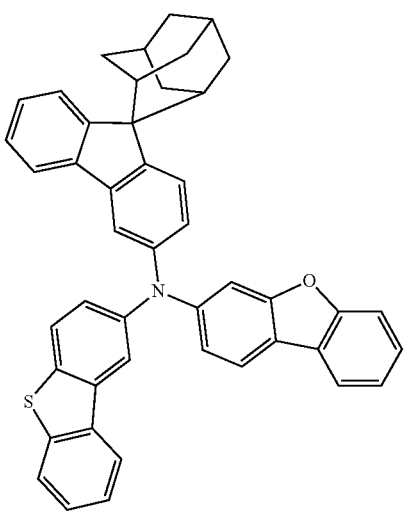

181
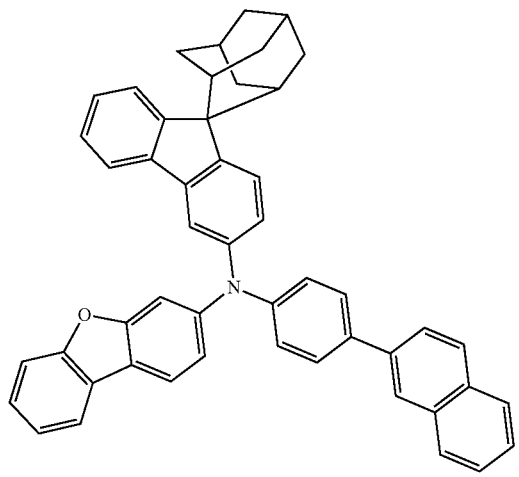
182
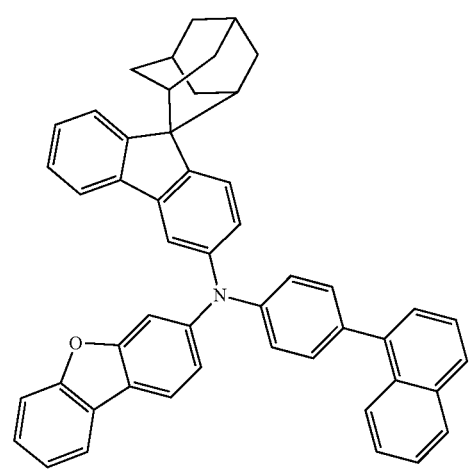
183
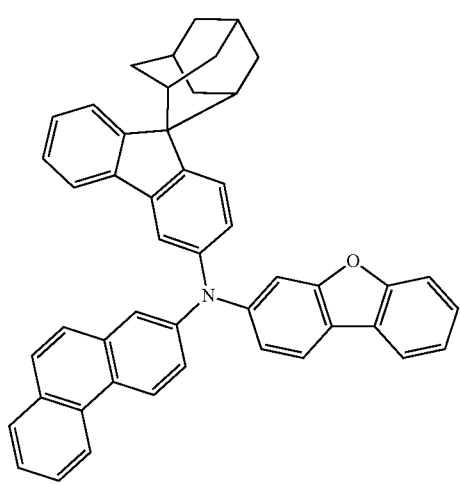
184
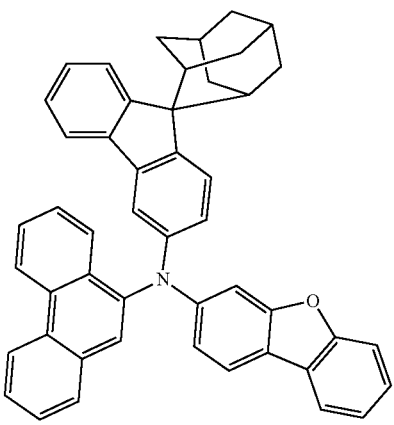
185
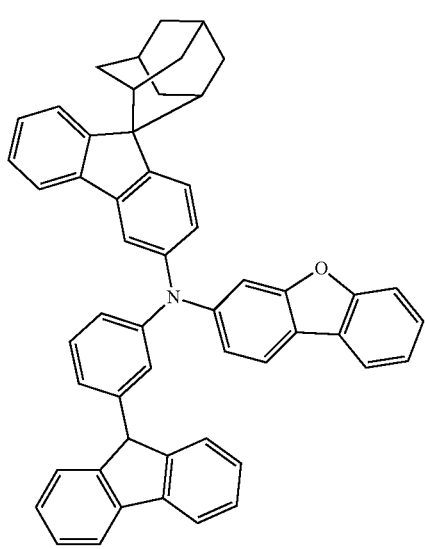
186
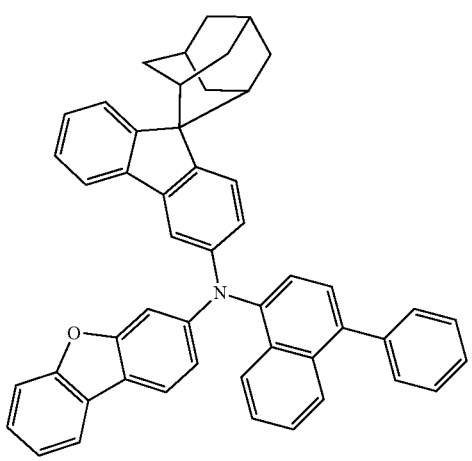

187
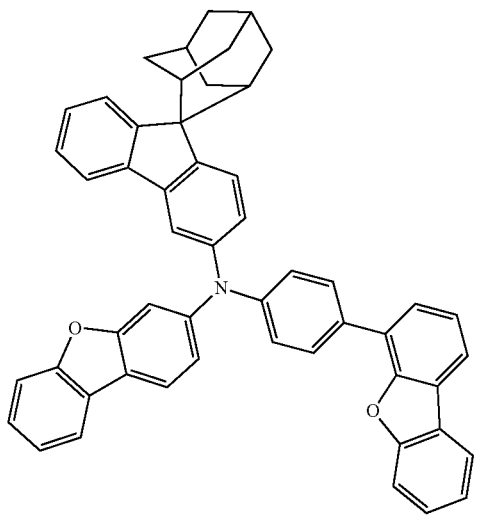
190
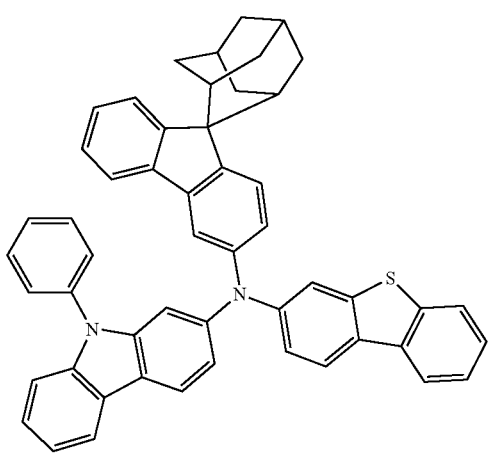
188
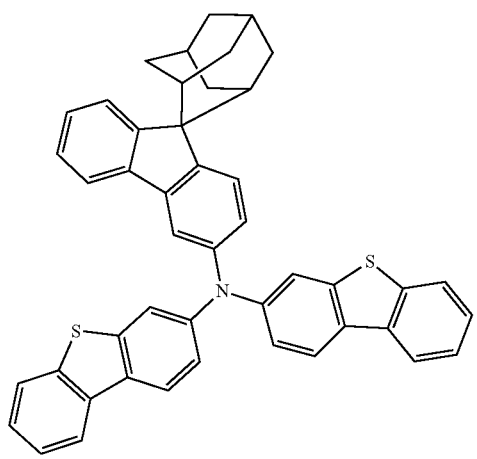
191
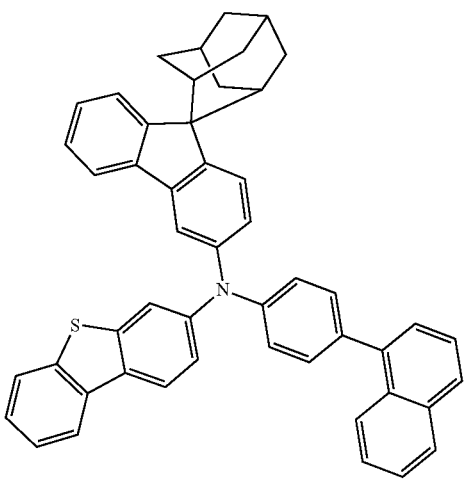
189
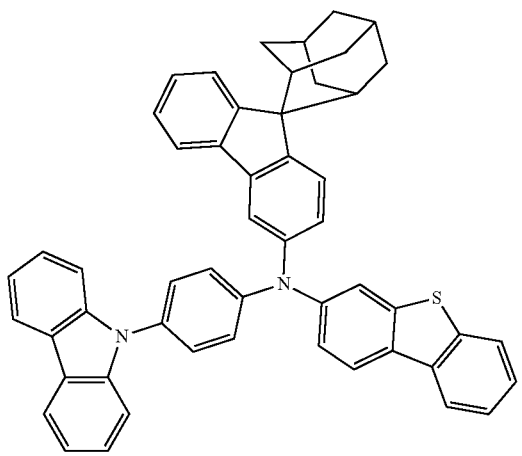
192
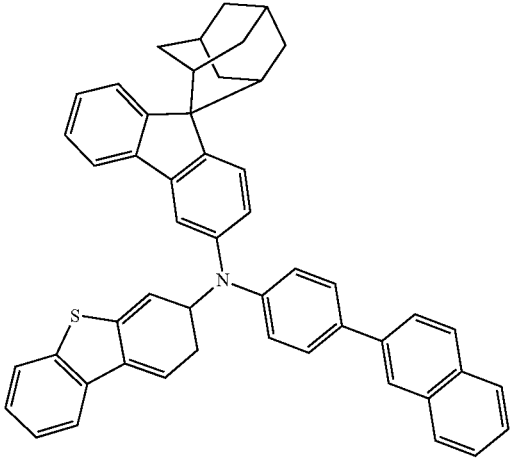

193
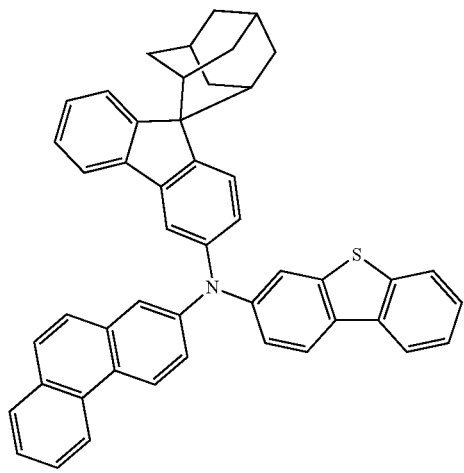
194
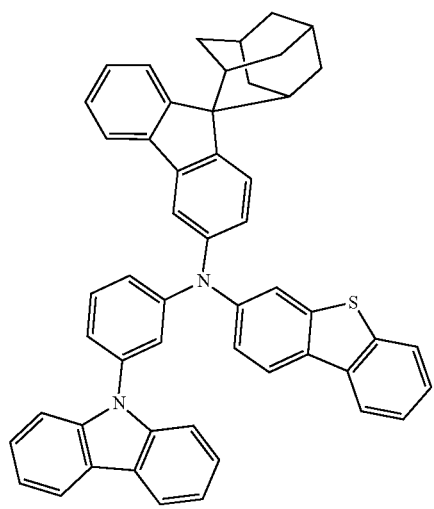
195
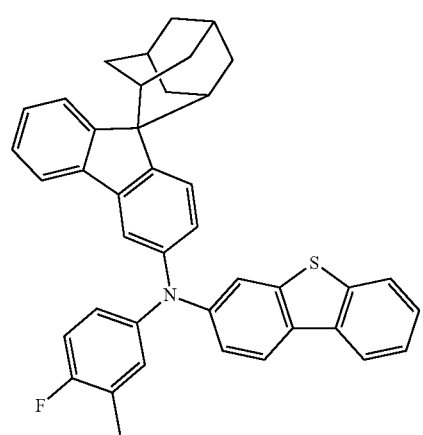
196
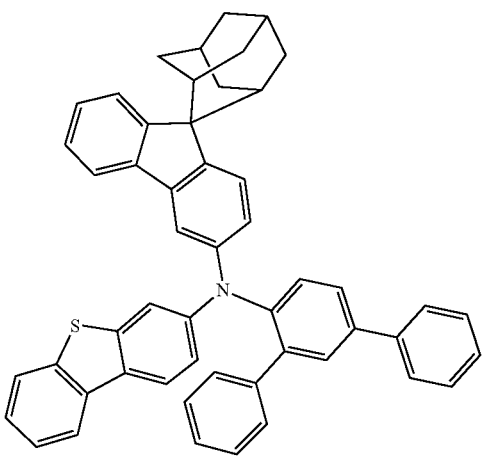
197
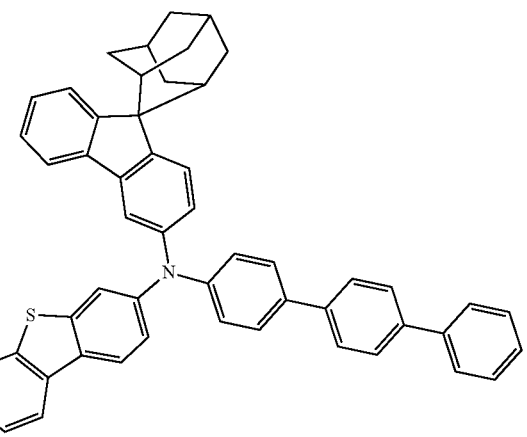
198
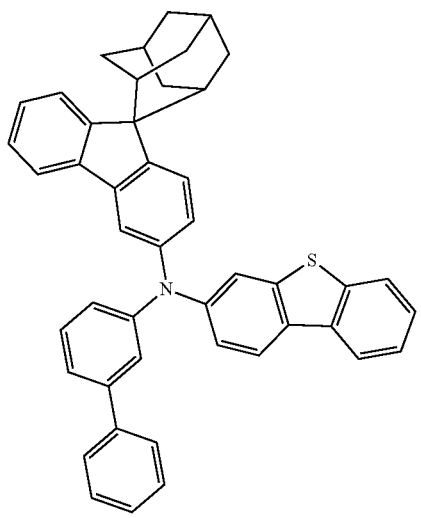

US 11,203,584 B2
471
-continued
199
472
-continued
202
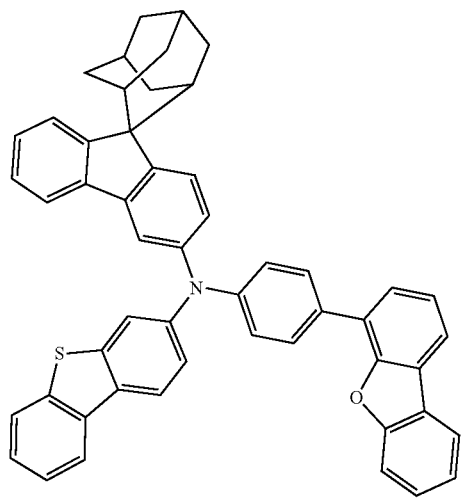
200
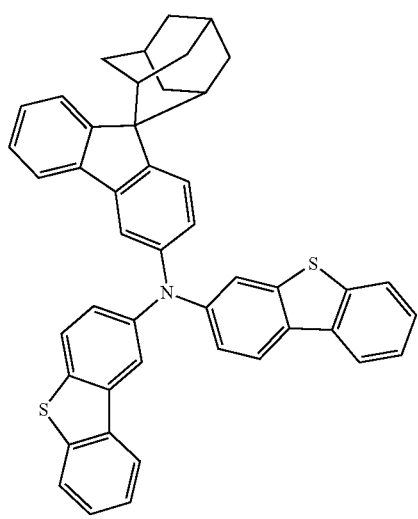
203
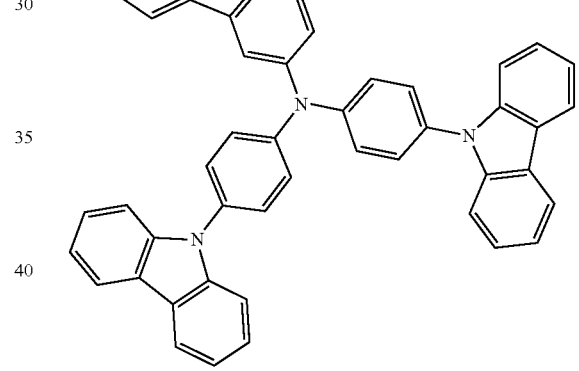
201
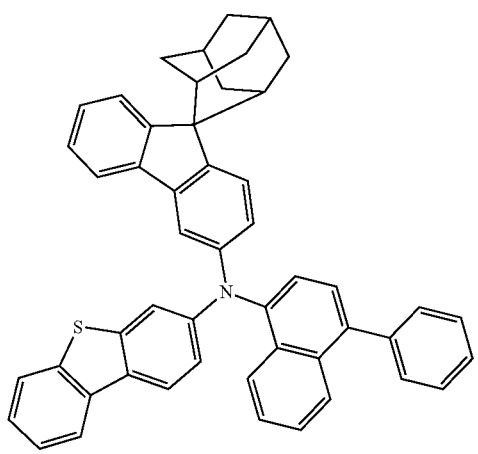
204
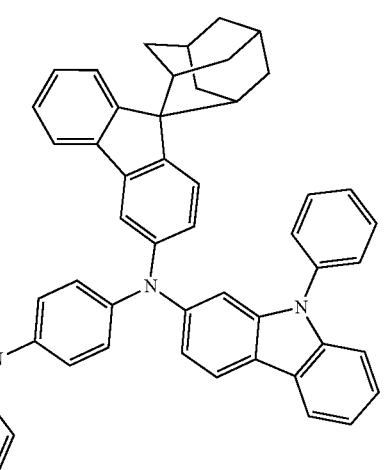

205
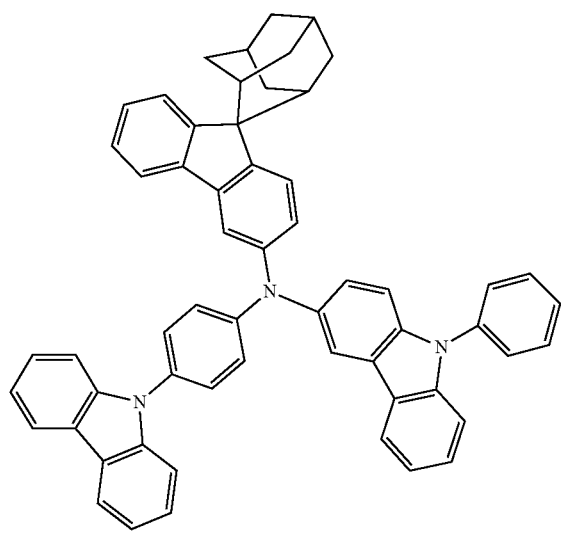
206
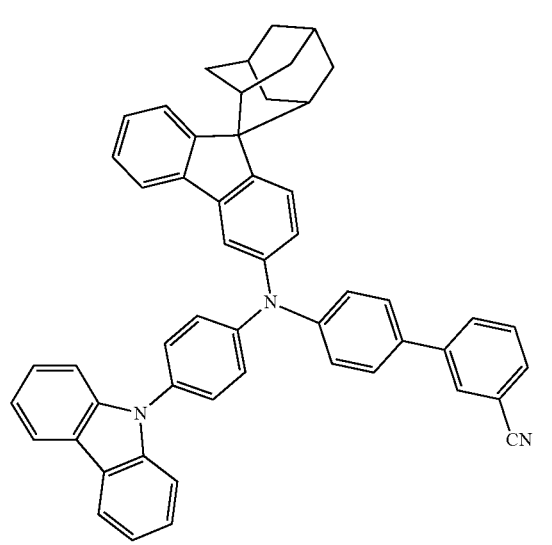
207
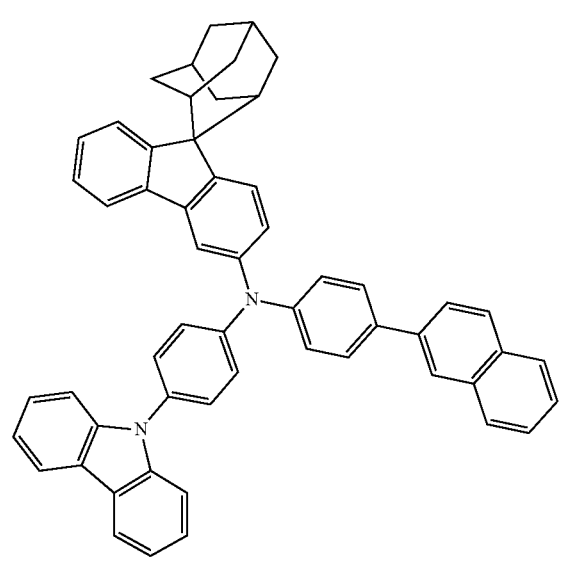
208
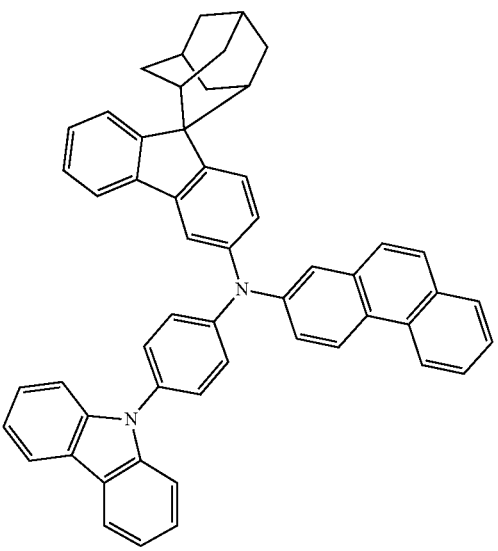
209
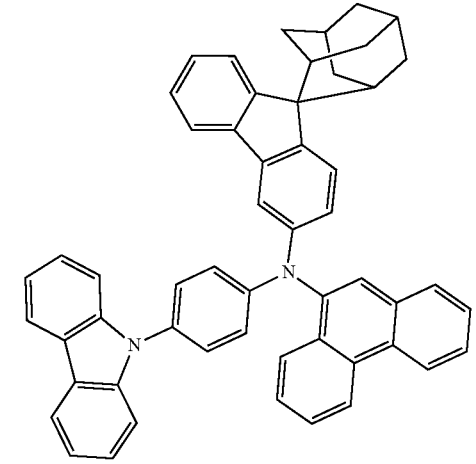
210
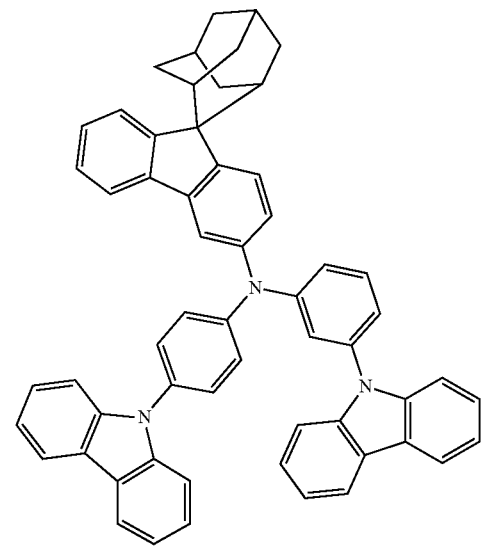

211
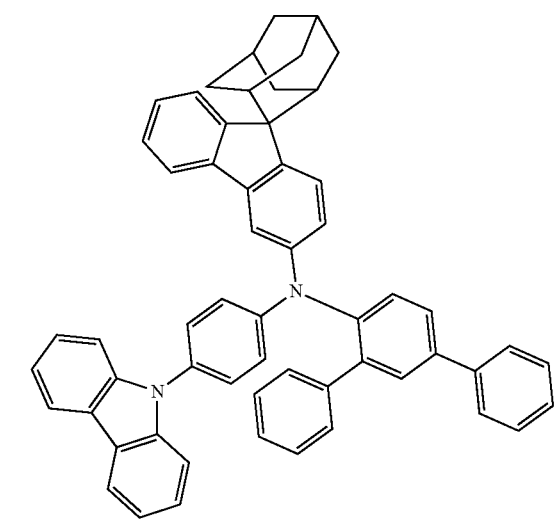
212
213
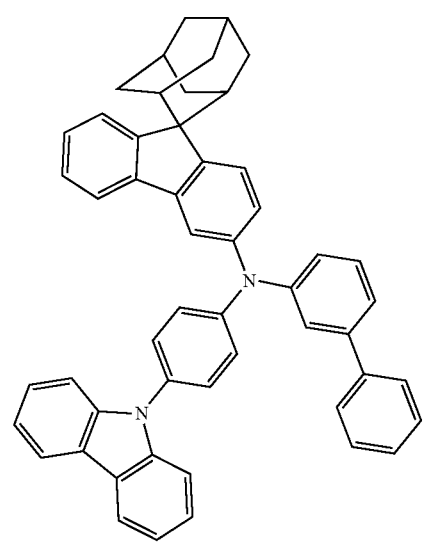
-continued
214
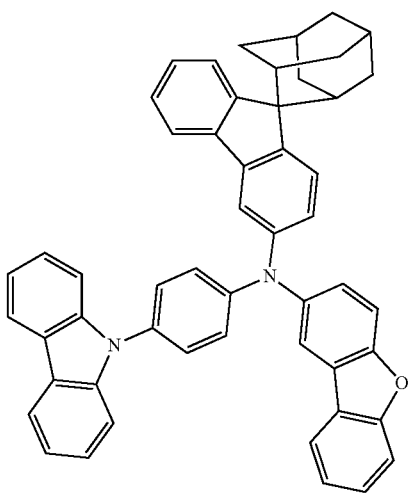
215
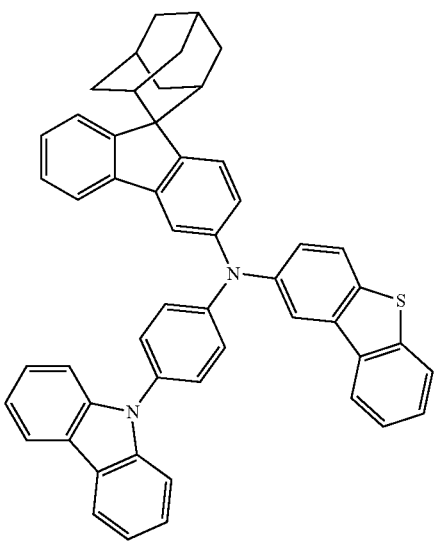
216

477
-continued
217
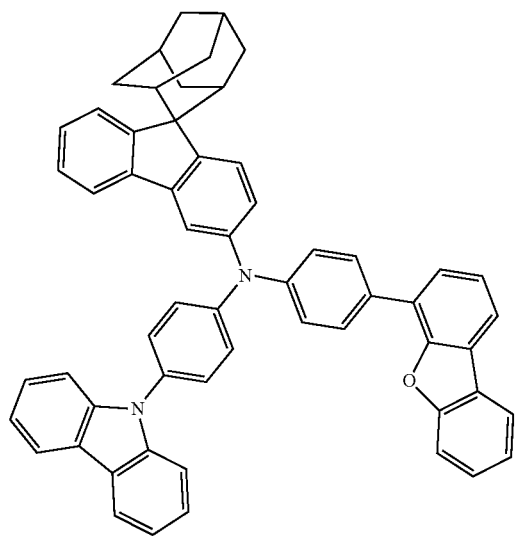
218
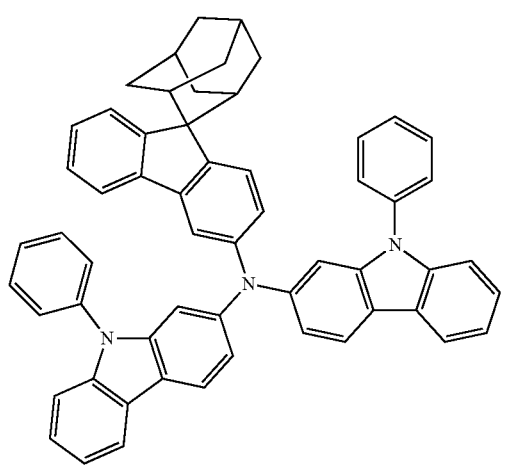
219
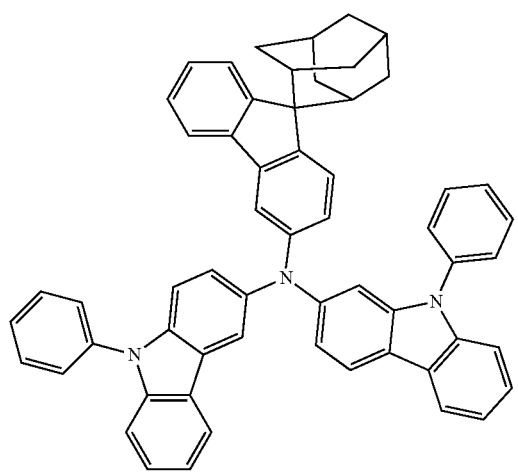
478
-continued
220
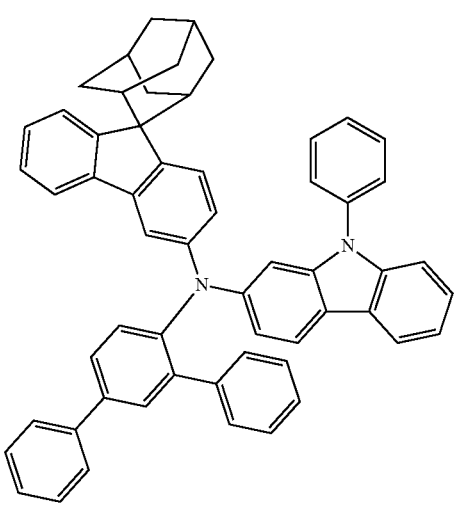
221
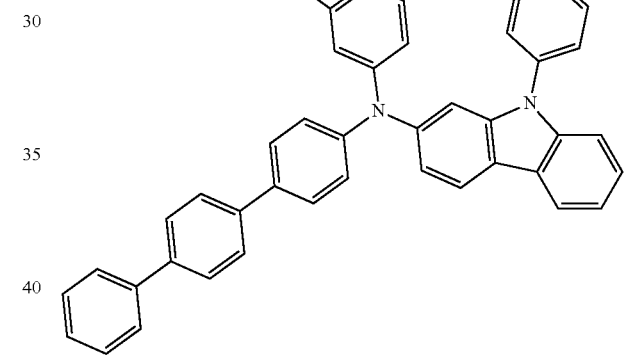
222
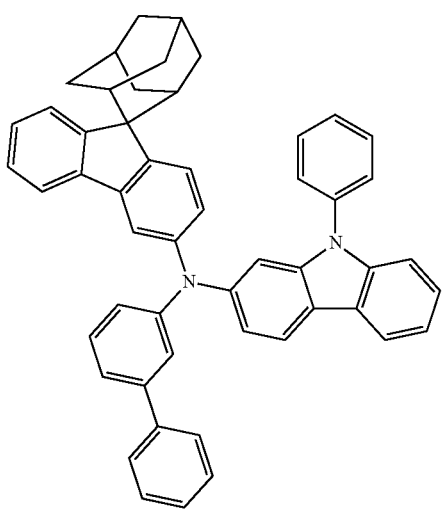

479
-continued
480
-continued
223
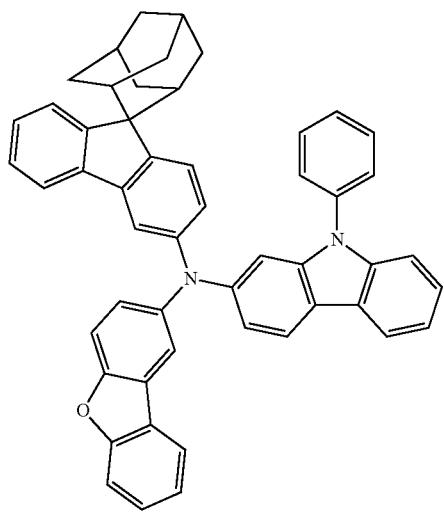
224
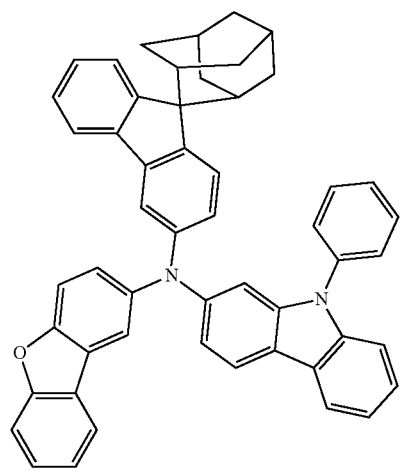
225
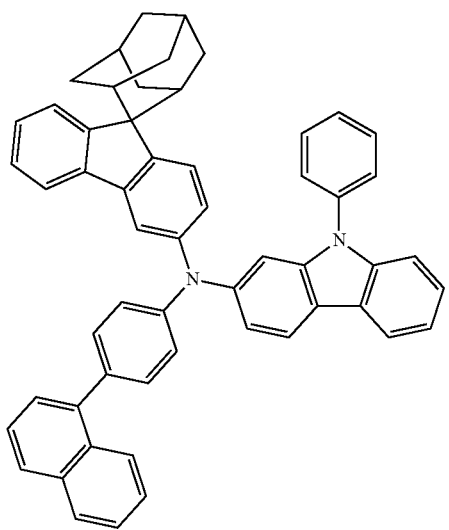
226
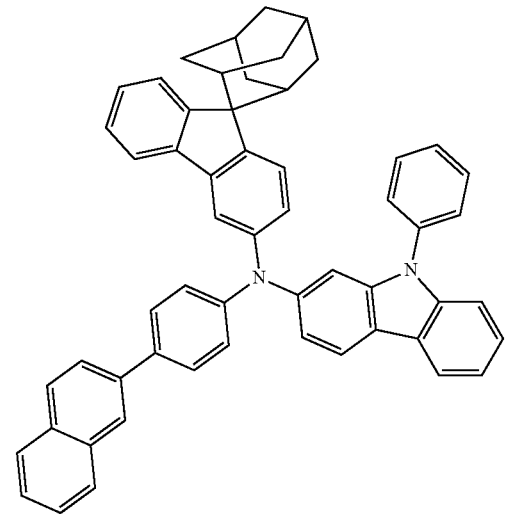
227
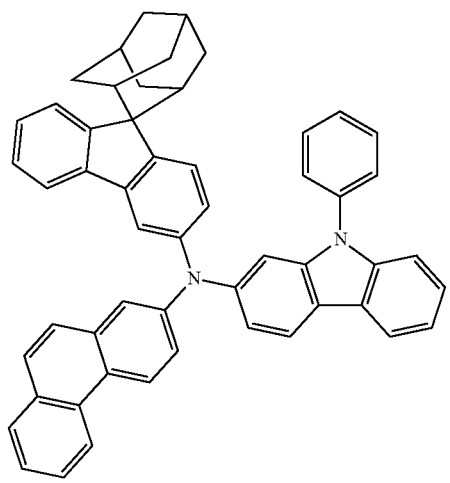
228
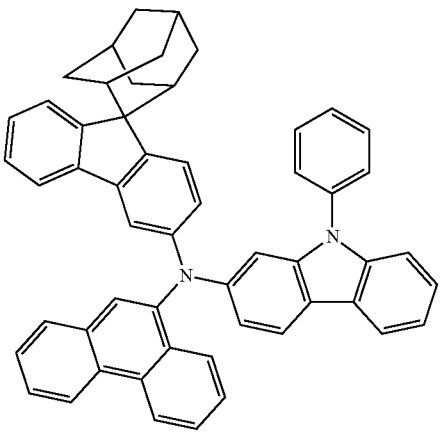

229
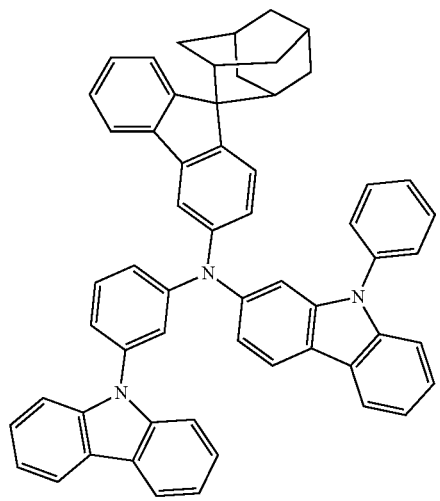
230
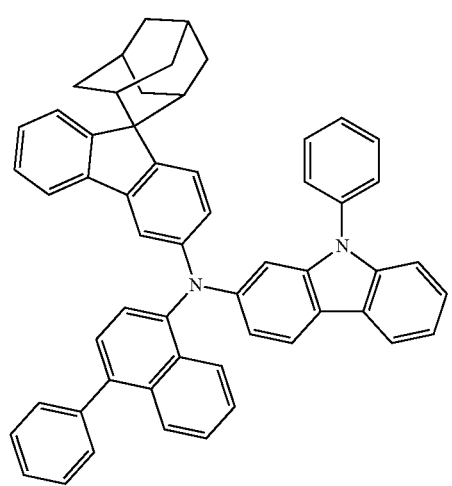
231
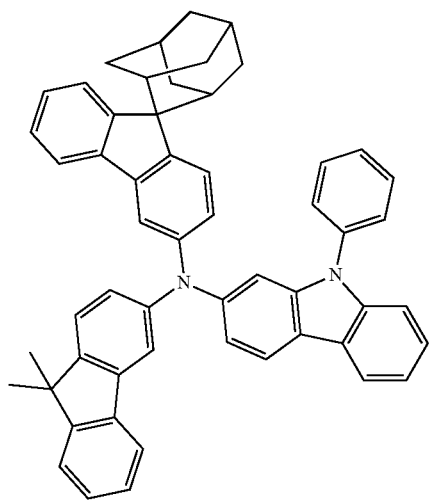
232
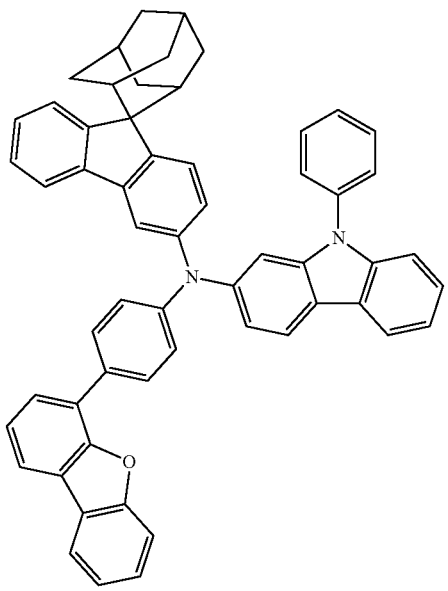
233
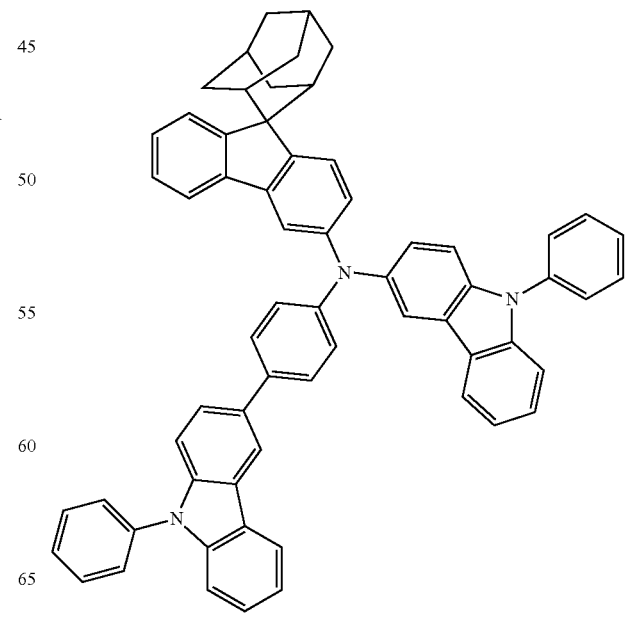

234
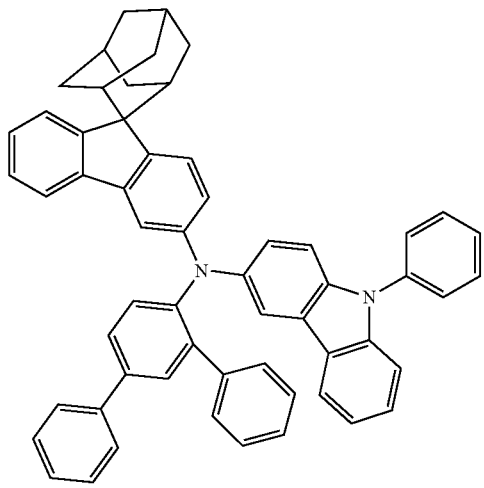
235
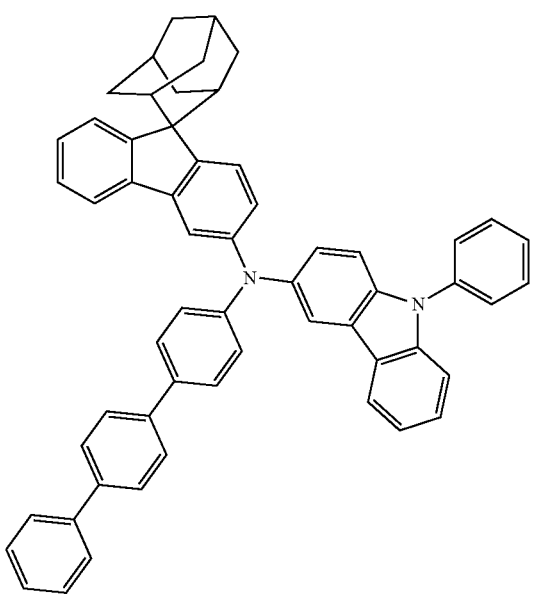
236
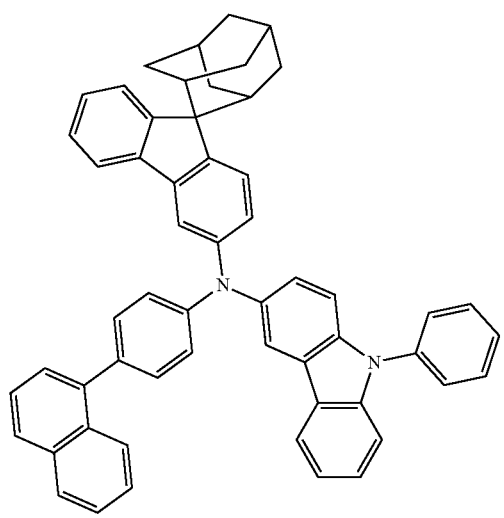
237
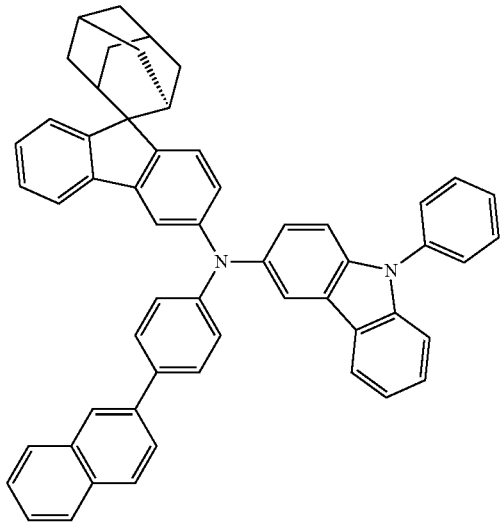
238
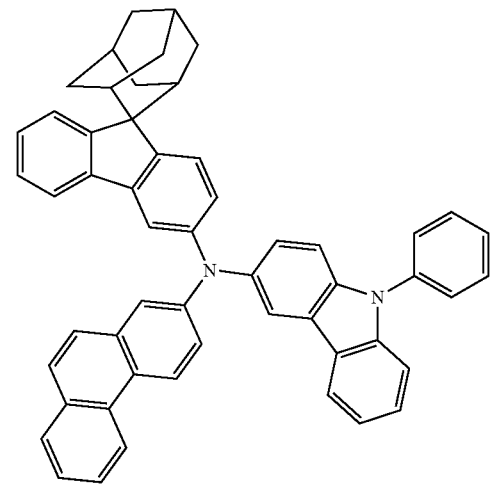
239
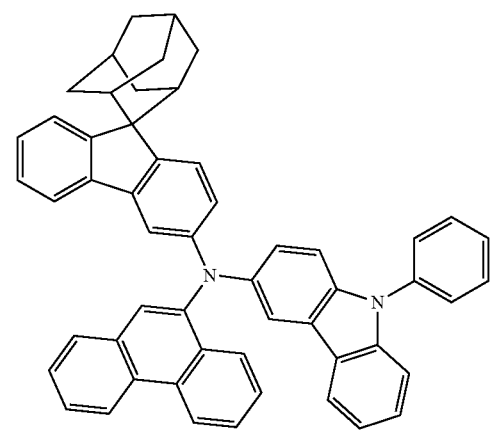

240
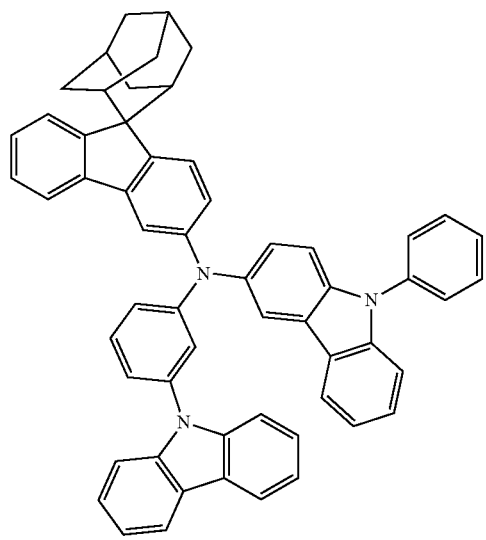
241
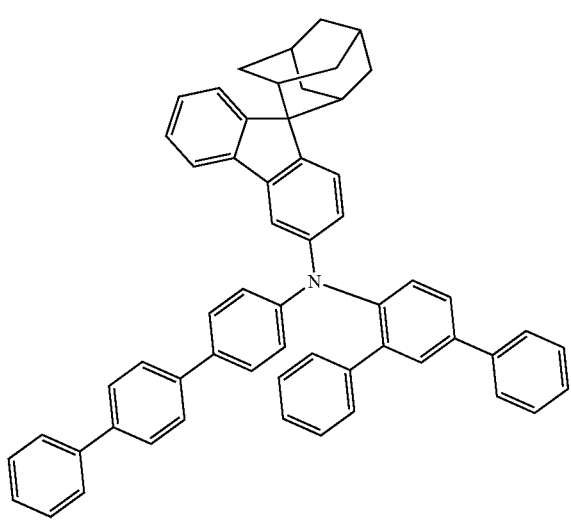
242
243
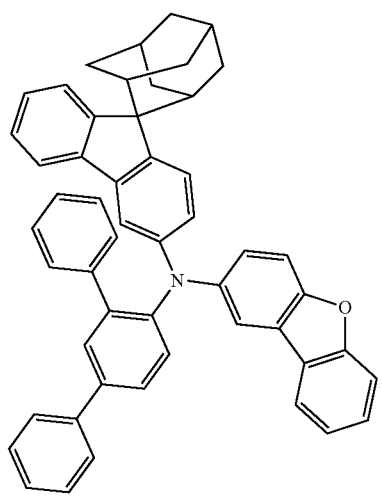
244
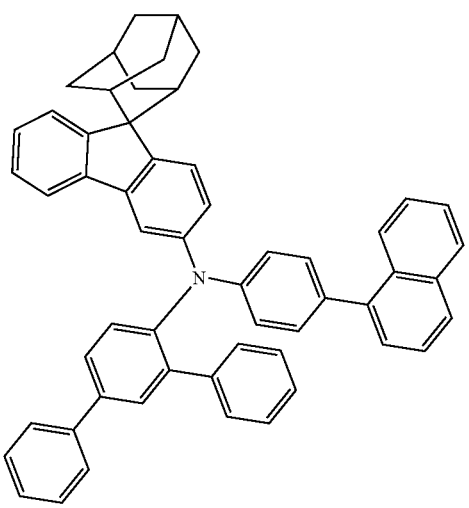
245
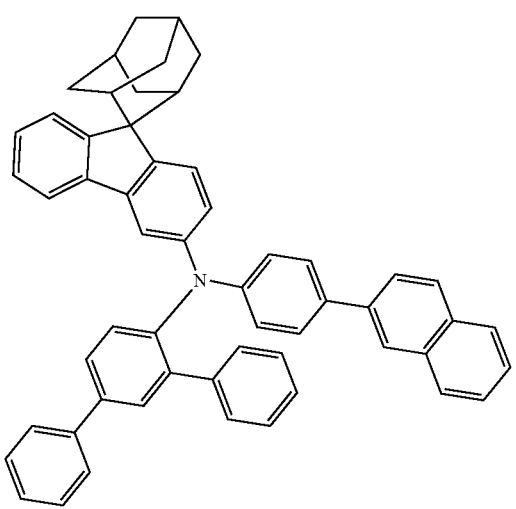

| 487 | 488 |
|---|---|
| 246 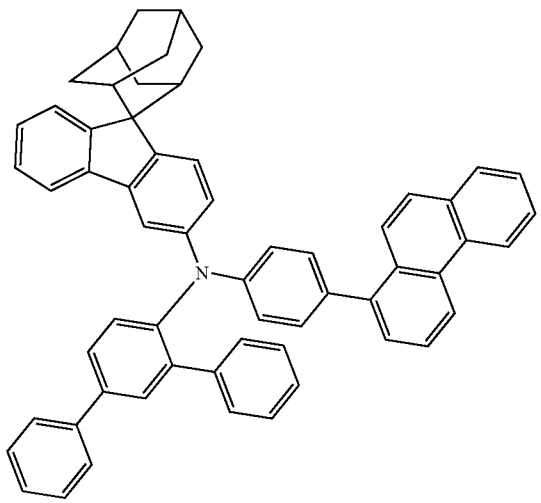 | 249 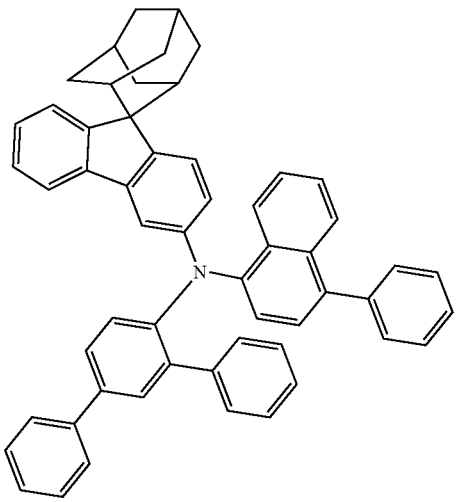 |
| 247 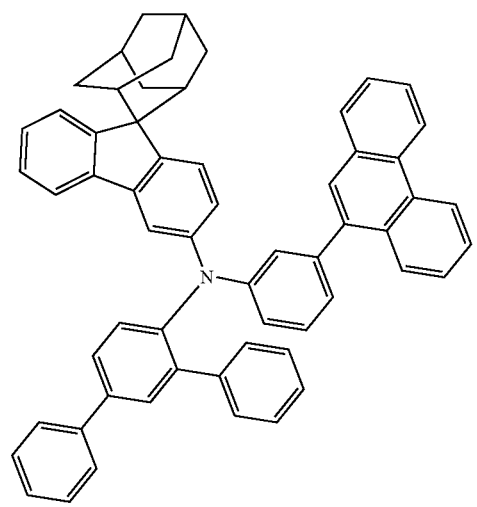 | 250 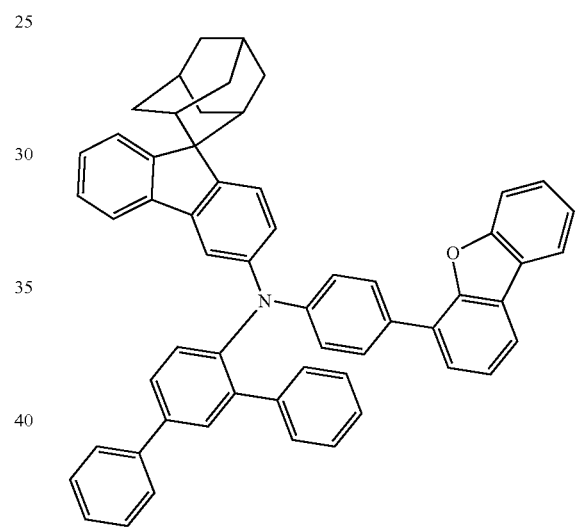 |
| 248 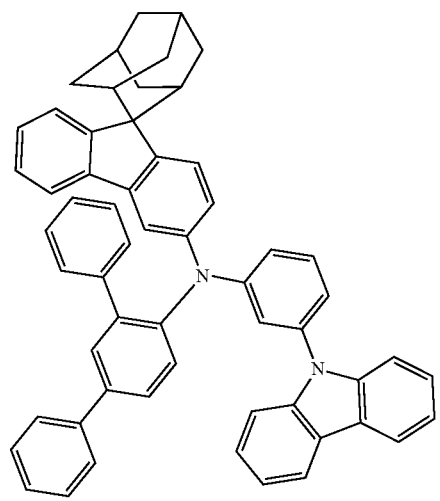 | 251 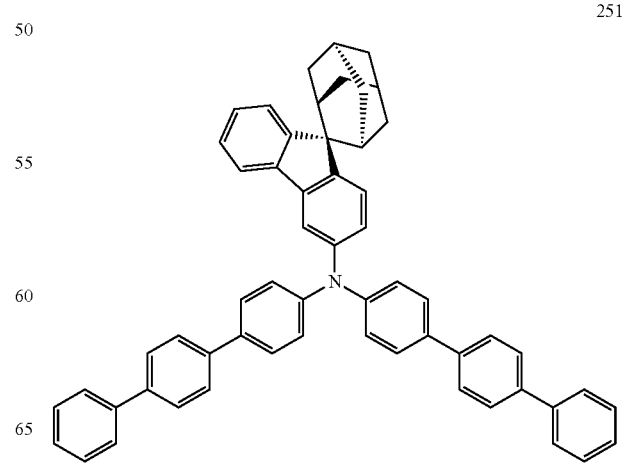 |

489
-continued
252
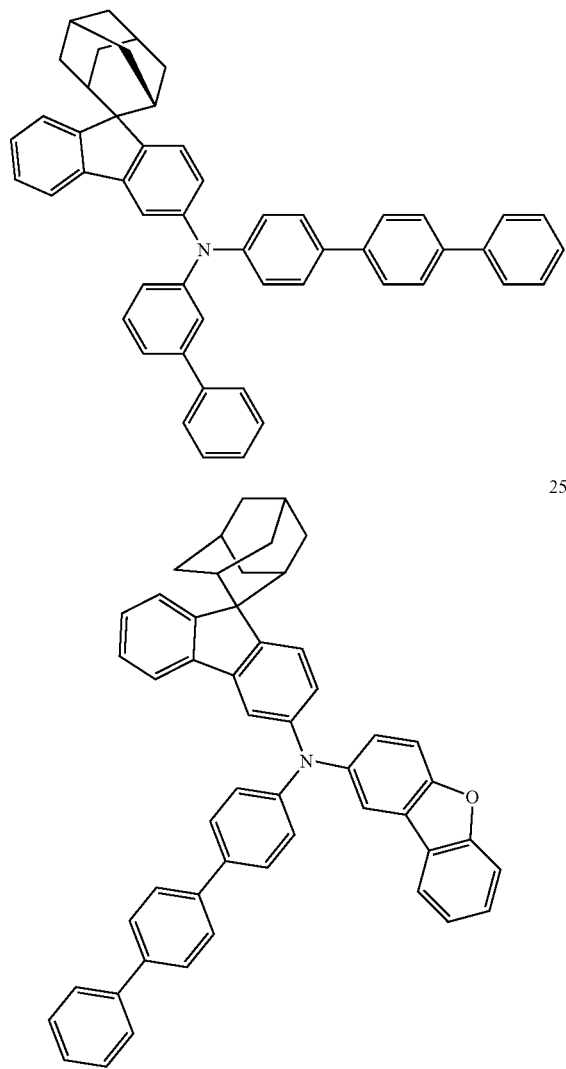
253
490
-continued
255
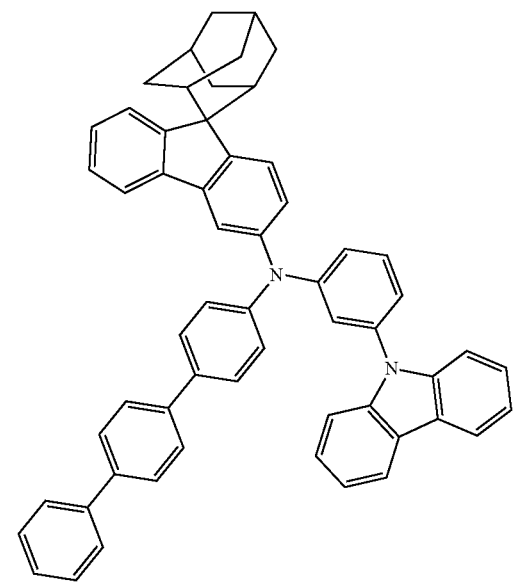
254
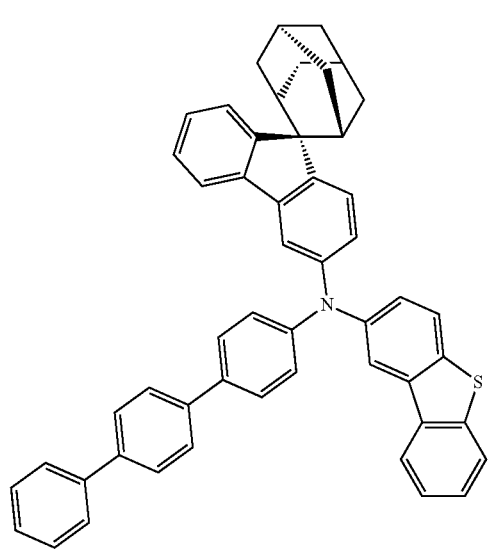
256
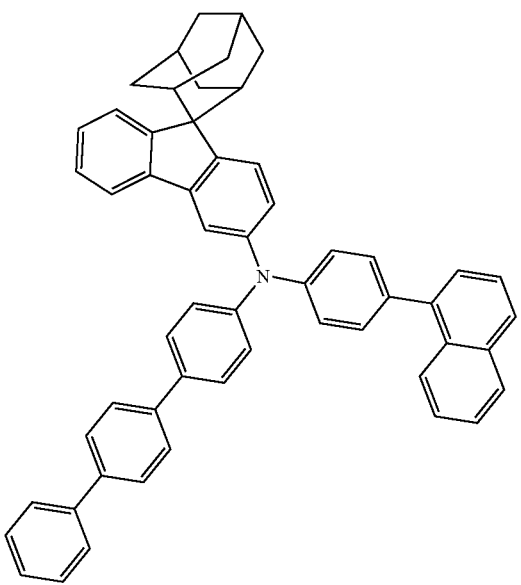

491
-continued
257
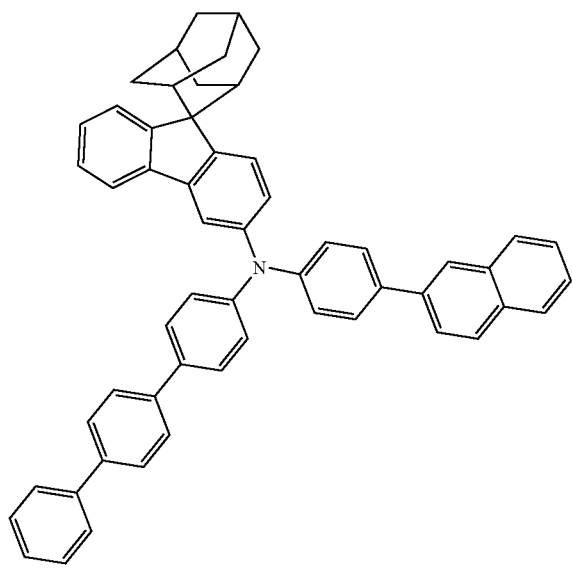
258
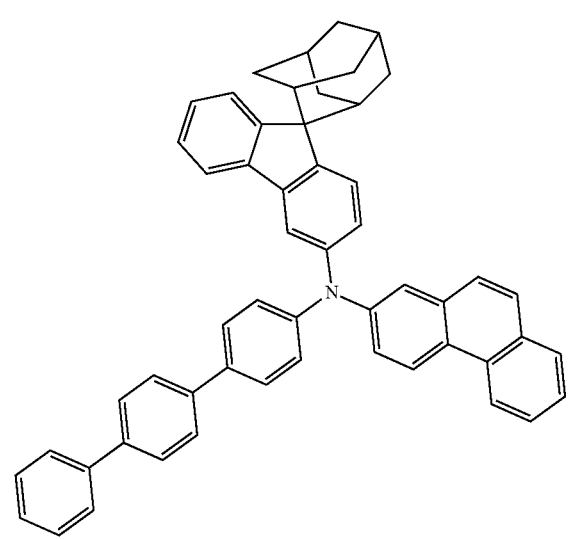
492
-continued
259
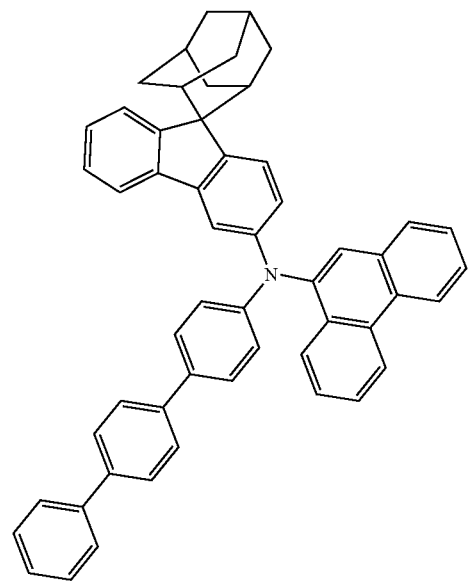
260
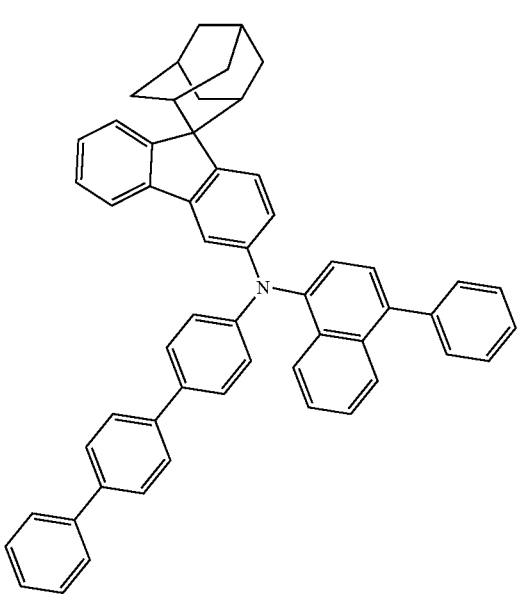

493
-continued
261
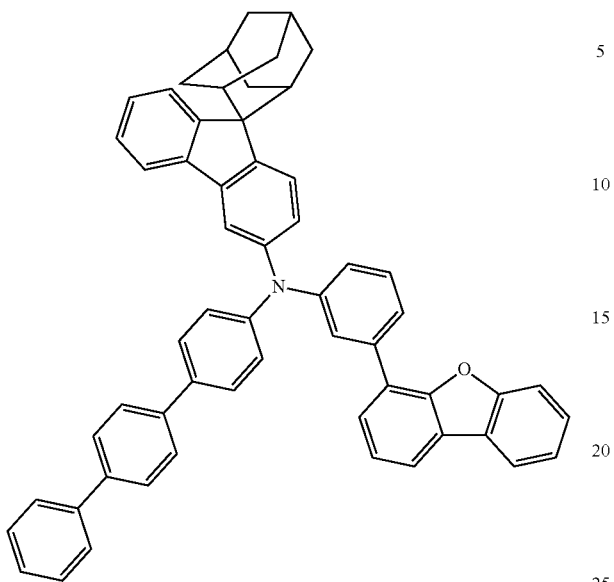
262
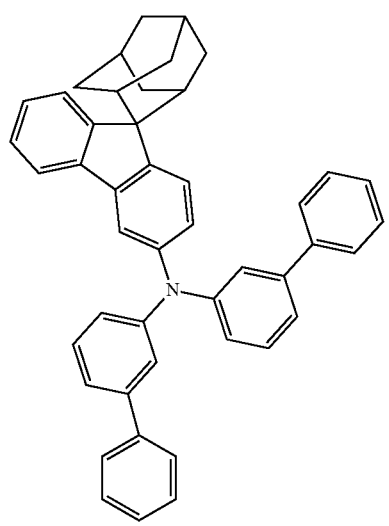
263
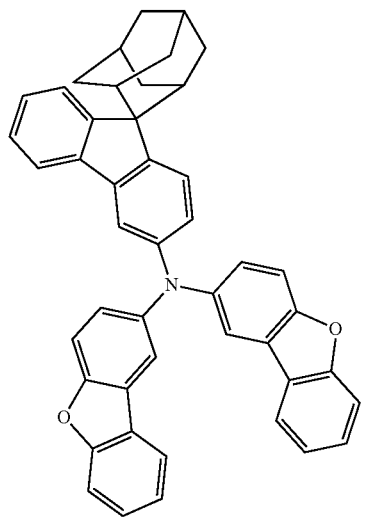
494
-continued
264
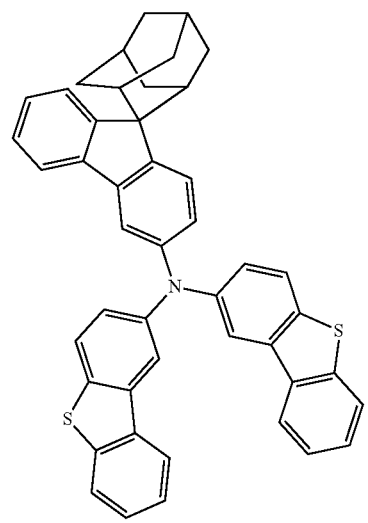
265
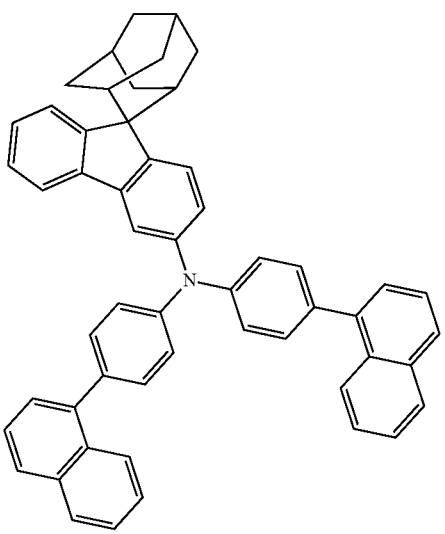
266
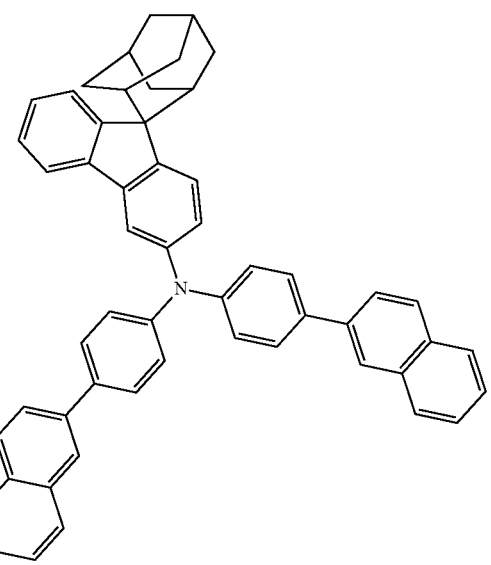

495
-continued
267
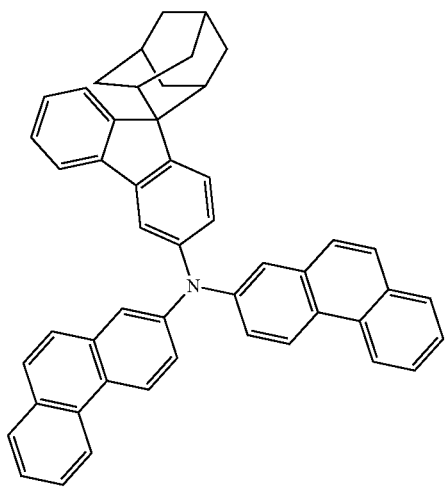
268
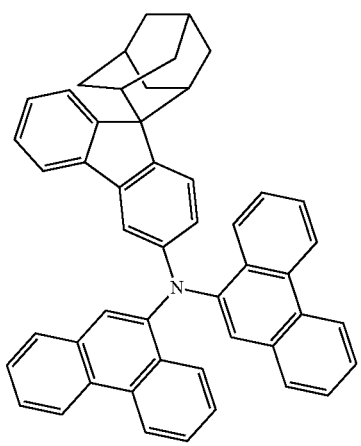
269
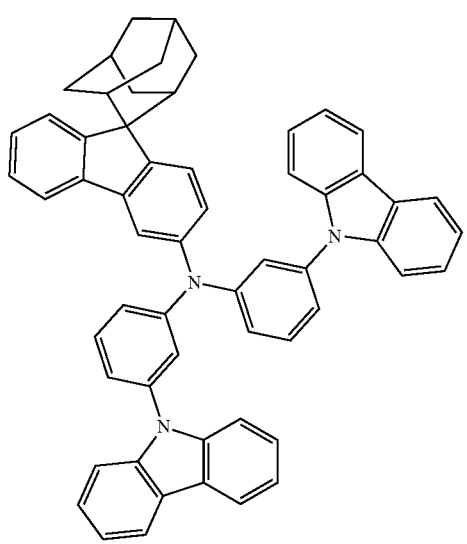
496
-continued
270
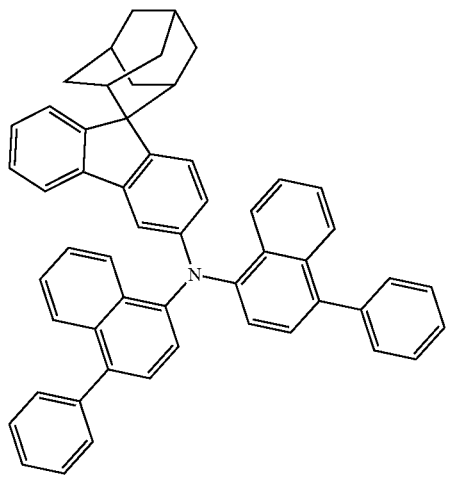
271
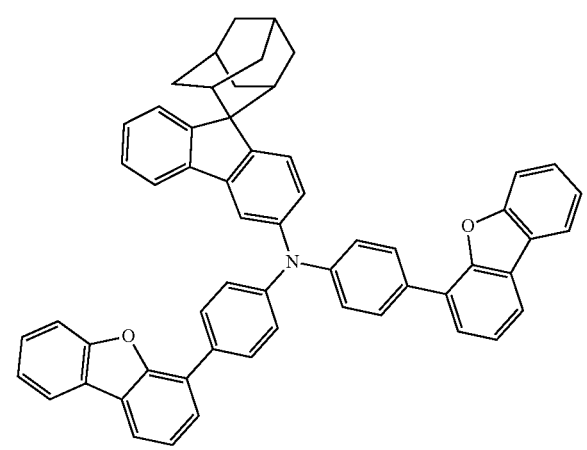
272
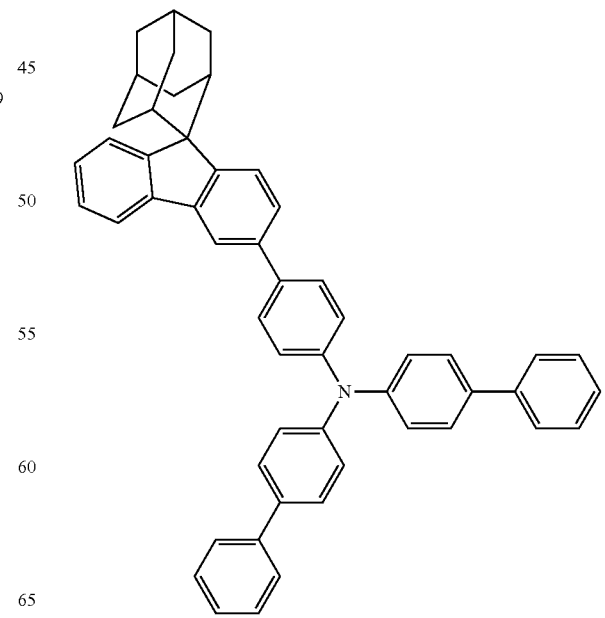

497
-continued
273
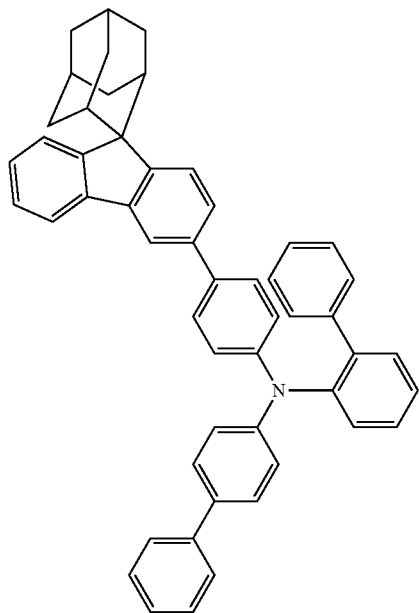
274
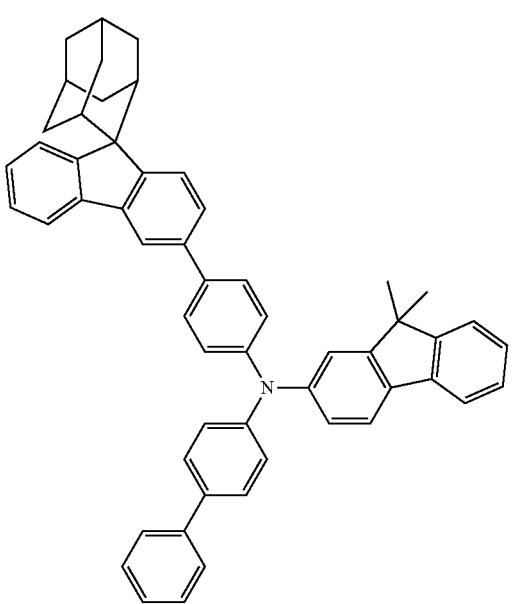
498
-continued
275
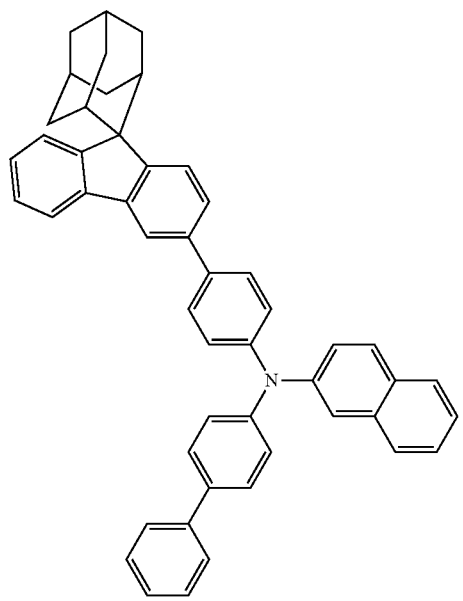
276
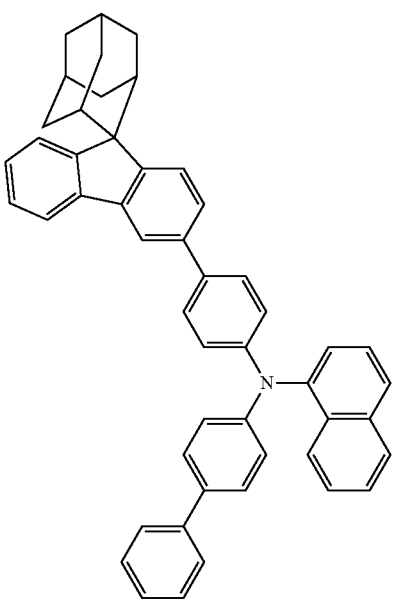

499
-continued
277
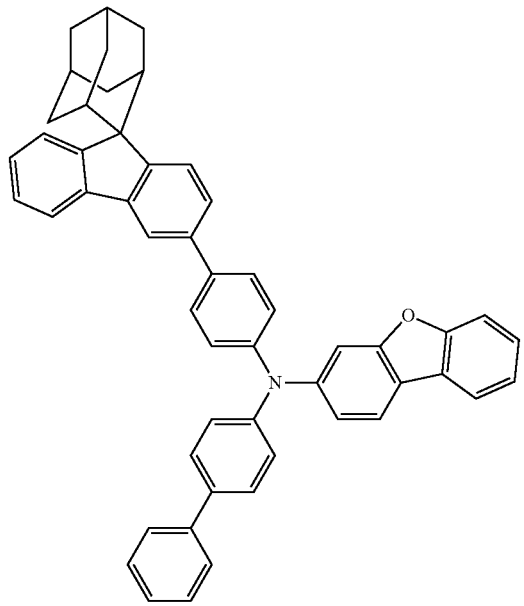
278
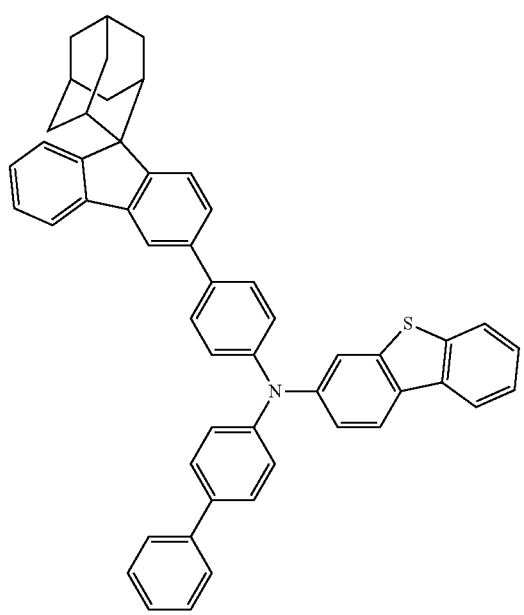
500
-continued
279
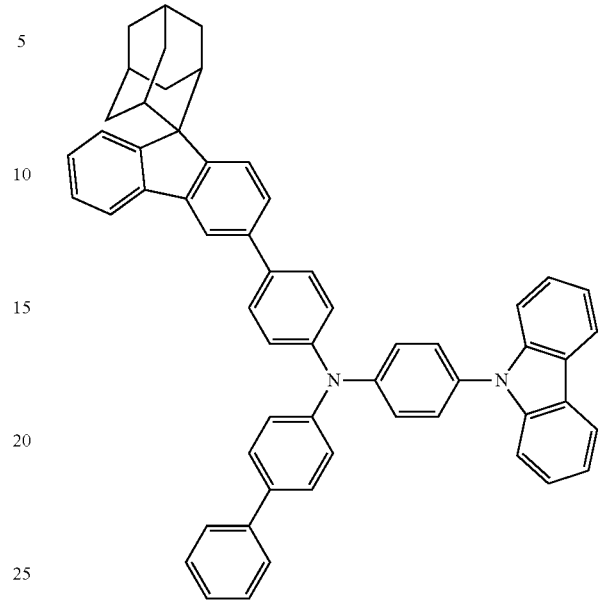
280
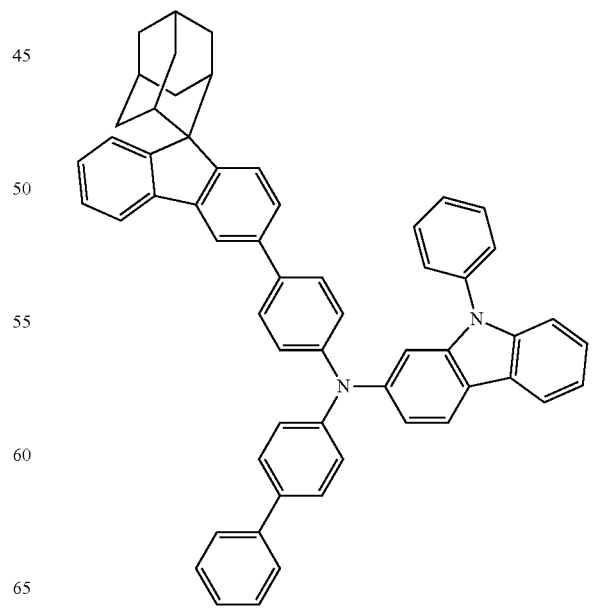

501
-continued
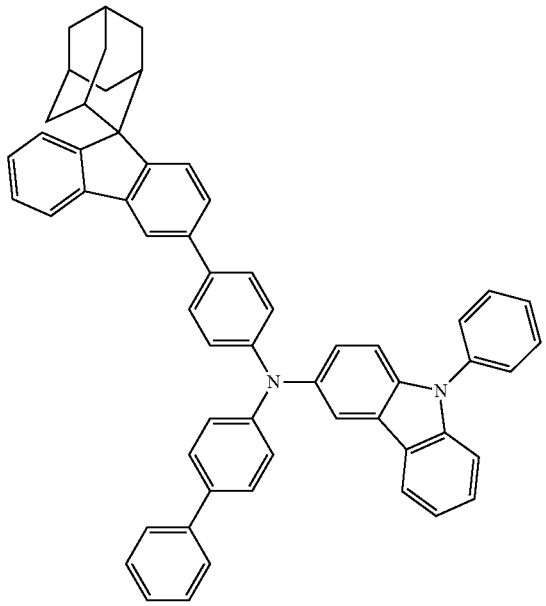
281
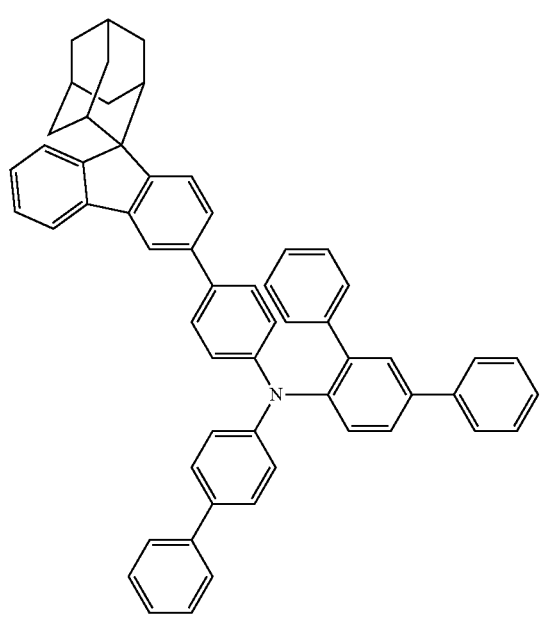
282
502
-continued
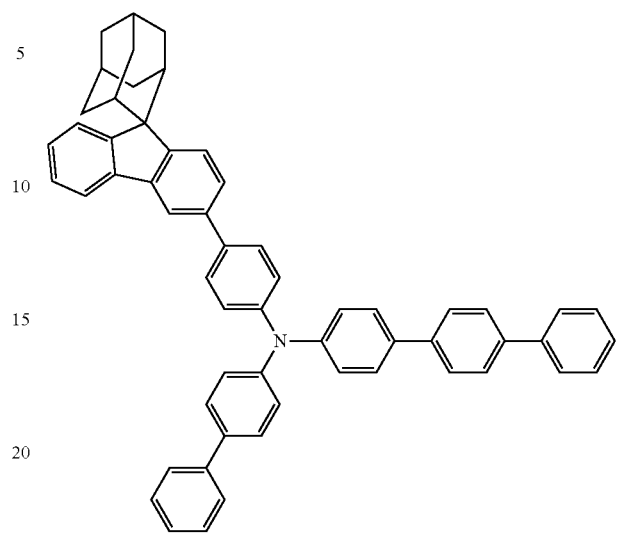
283
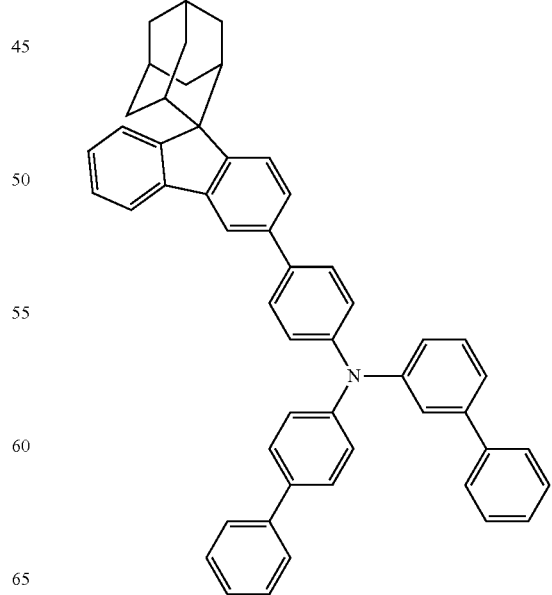
284

503
-continued
285
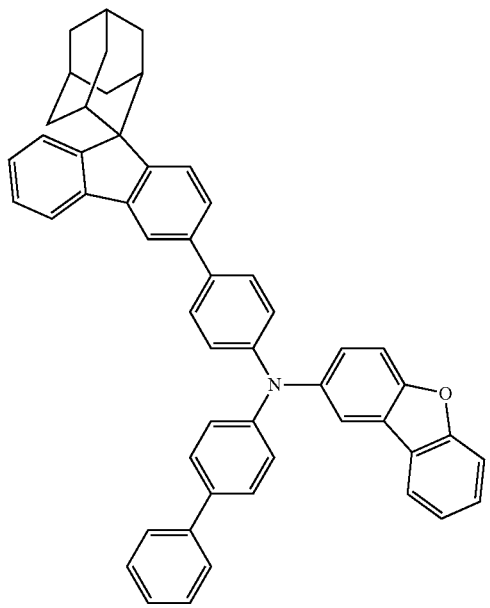
286
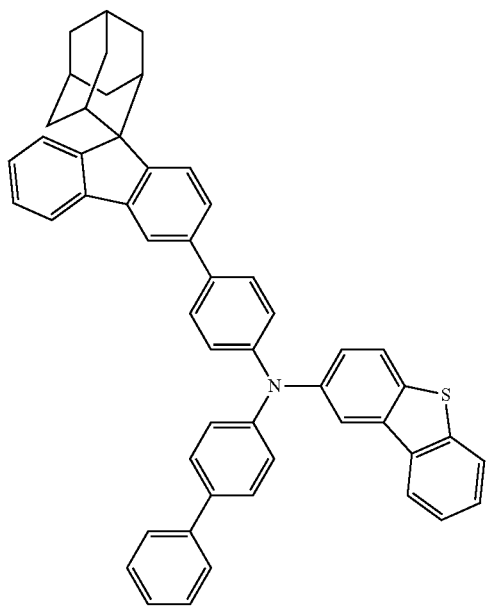
504
-continued
287
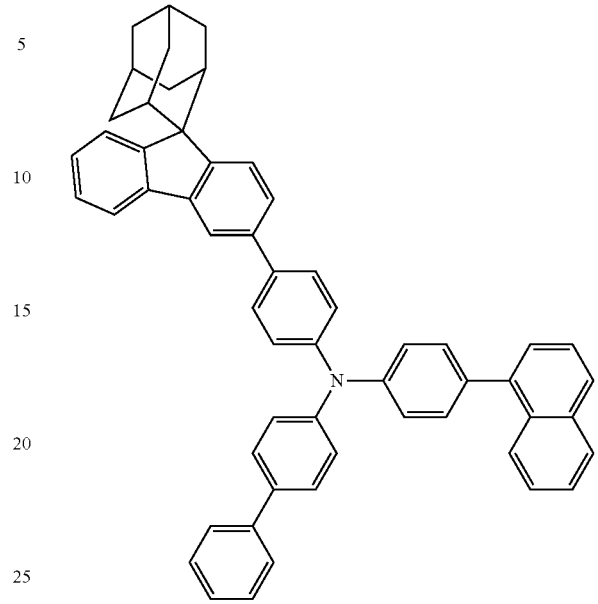
288
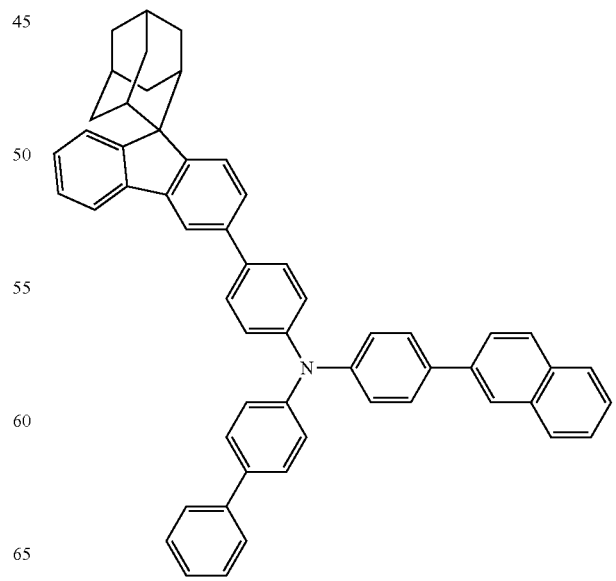

505
-continued
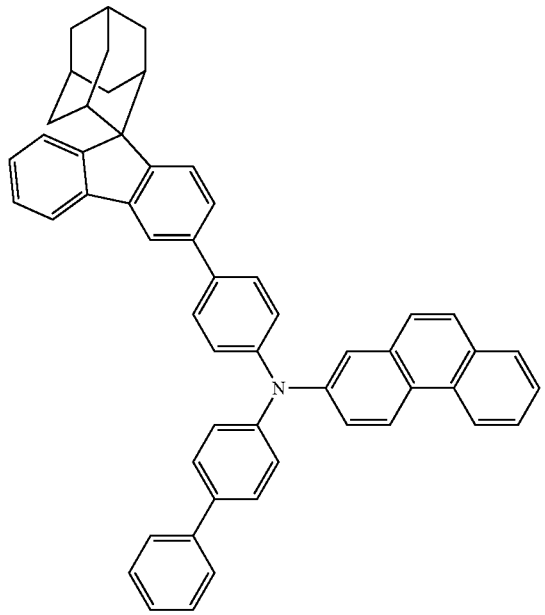
289
506
-continued
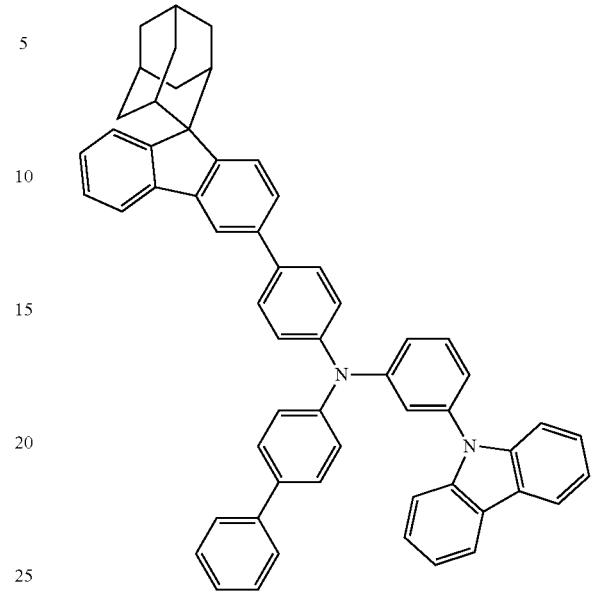
291
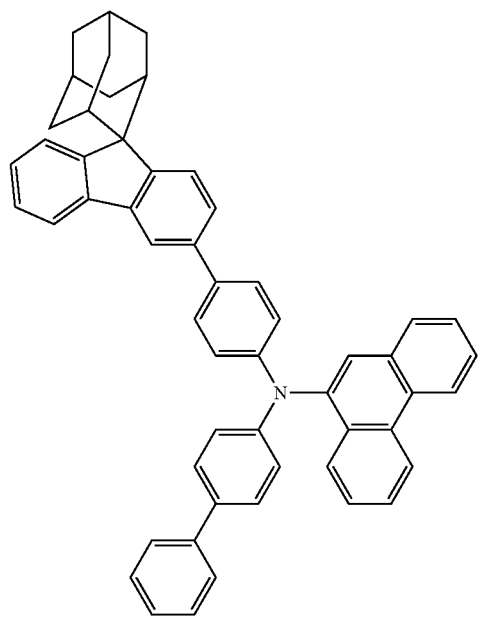
290
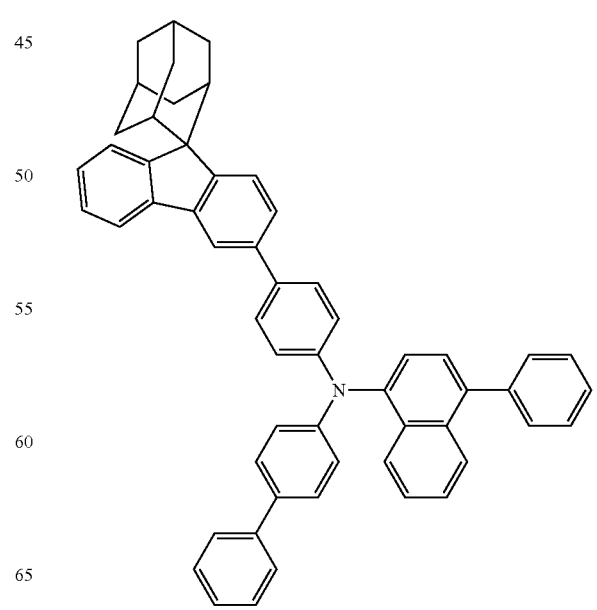
292

507
-continued
293
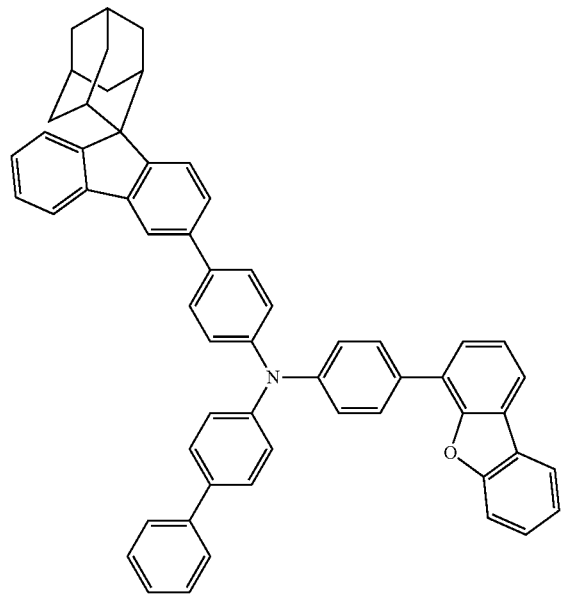
294
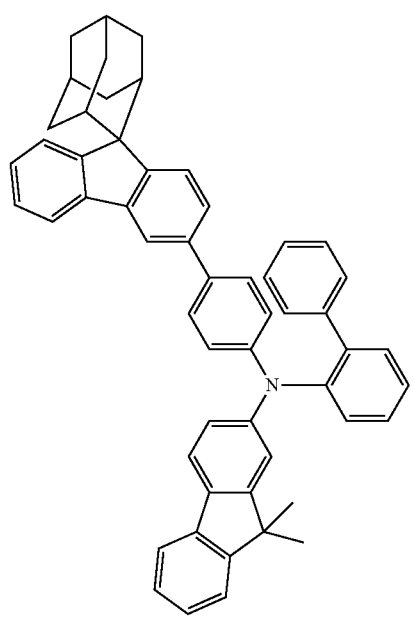
508
-continued
295
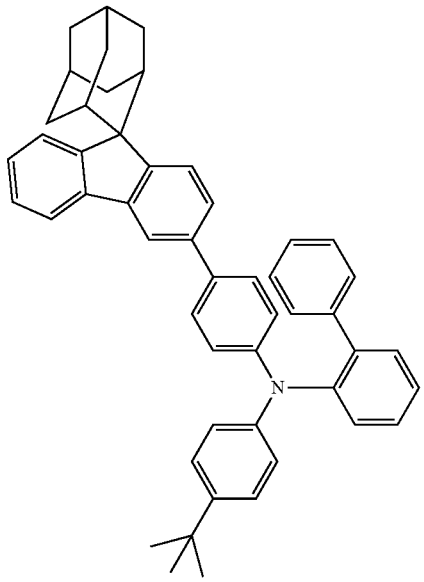
296
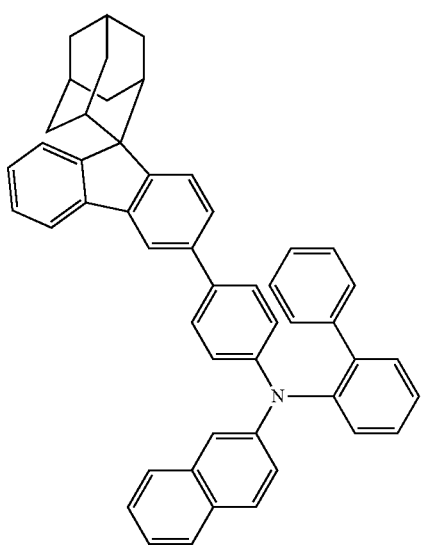
297
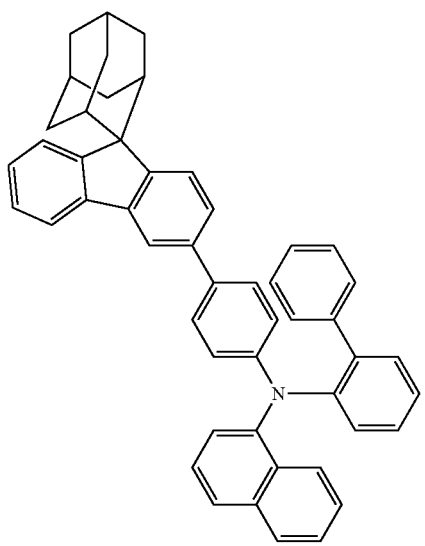

509
-continued
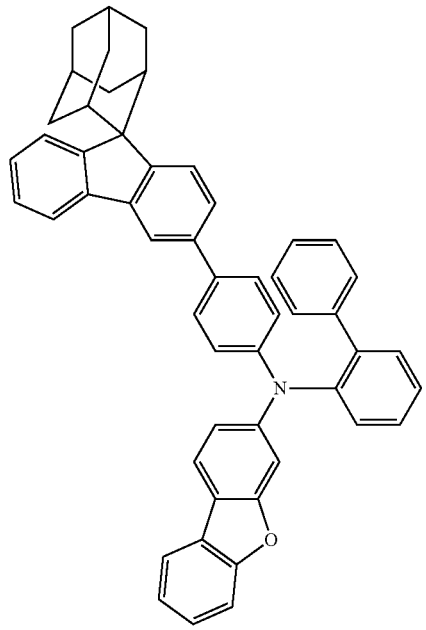
298
510
-continued
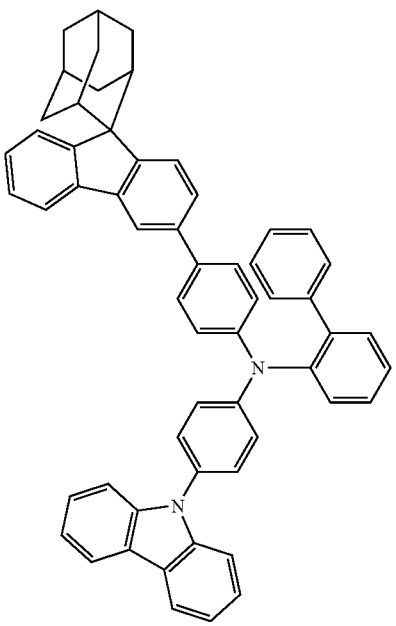
300
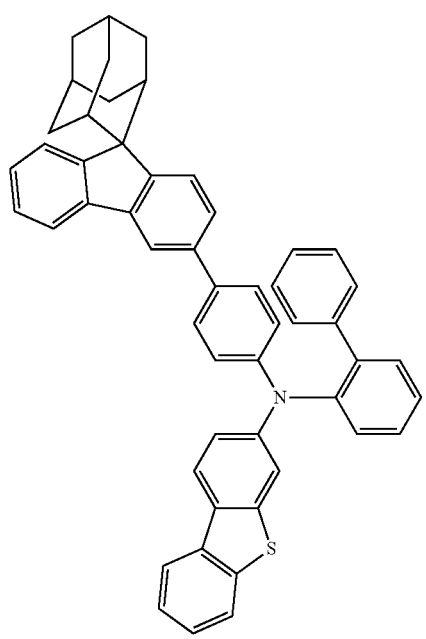
299
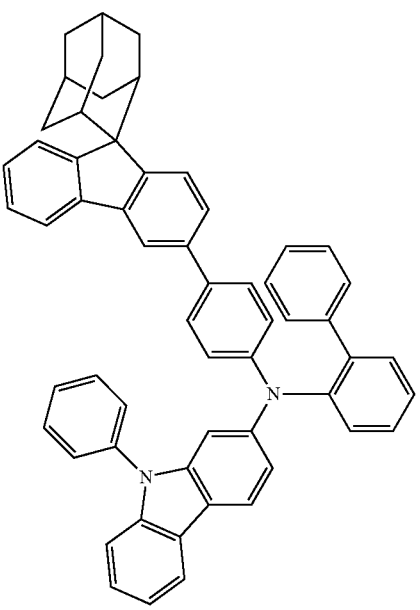
301

511
-continued
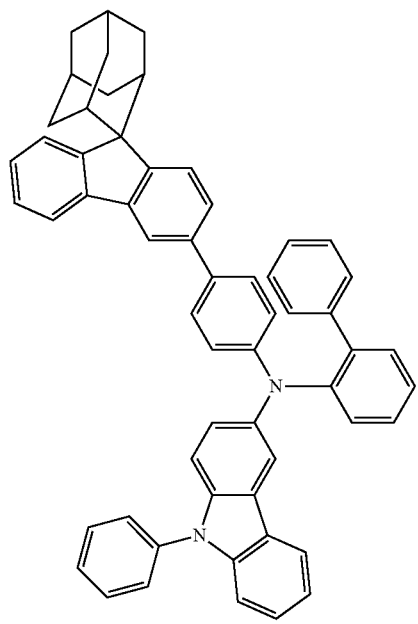
302
512
-continued
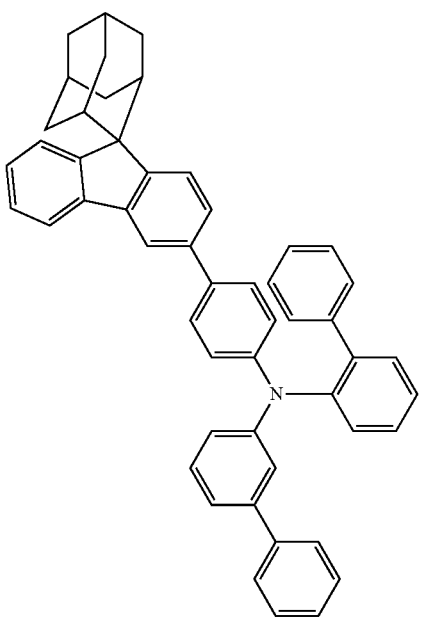
304
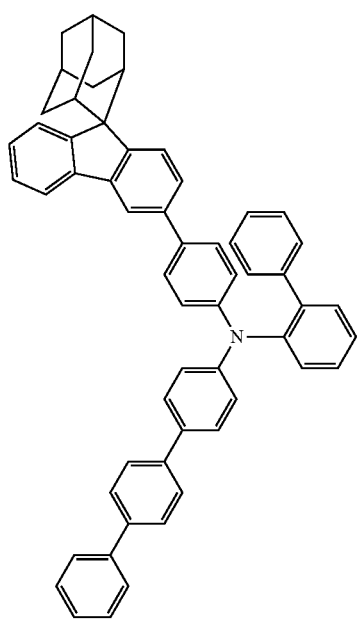
303
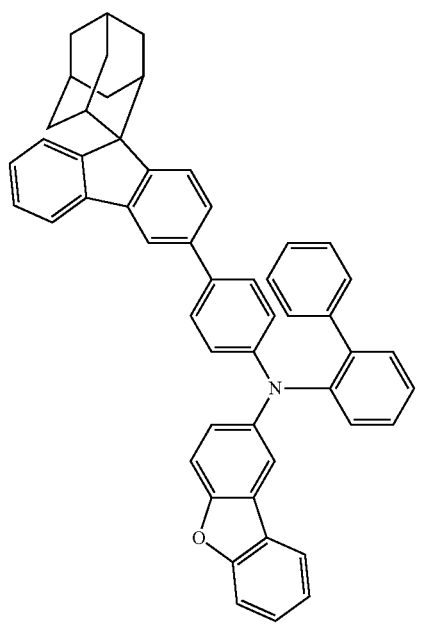
305

513
-continued
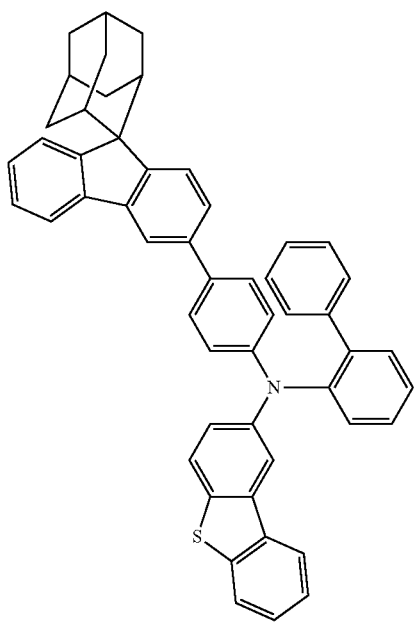
306
514
-continued
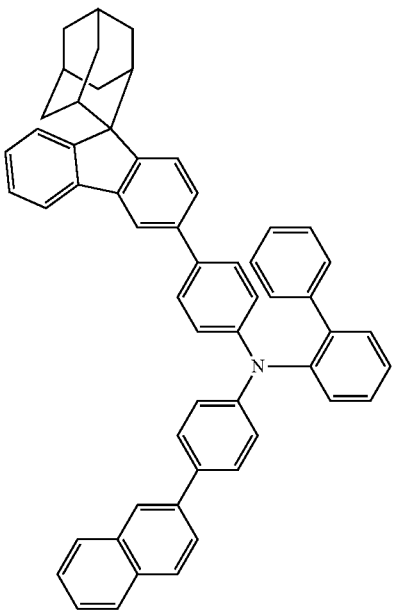
308
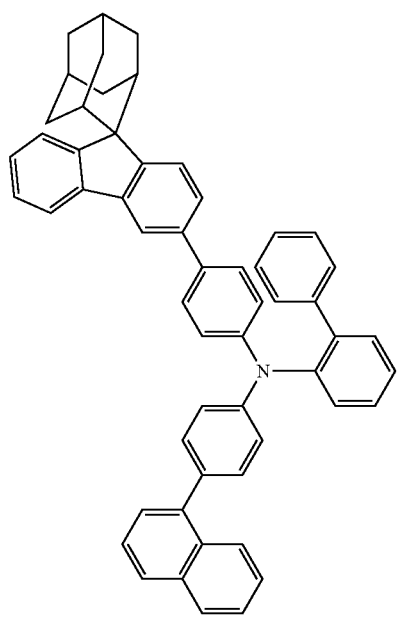
307
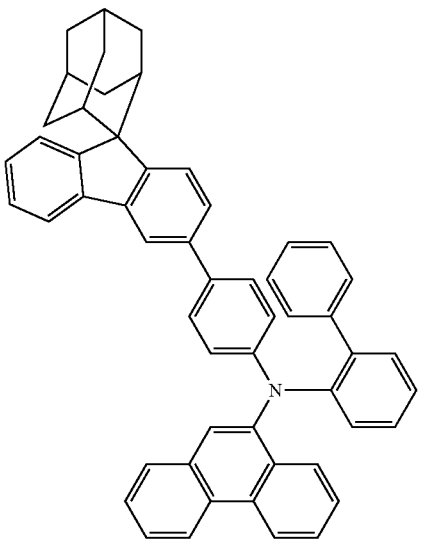
310

515
-continued
311
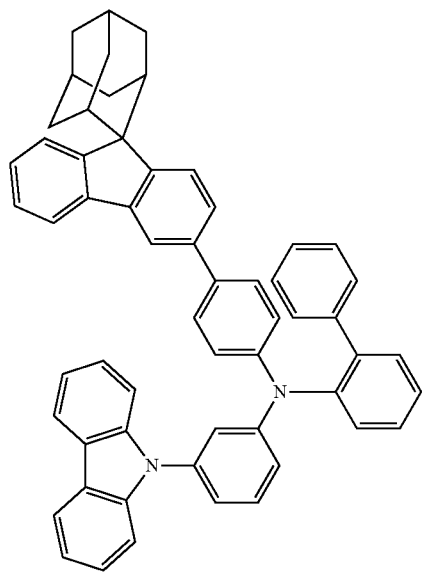
312
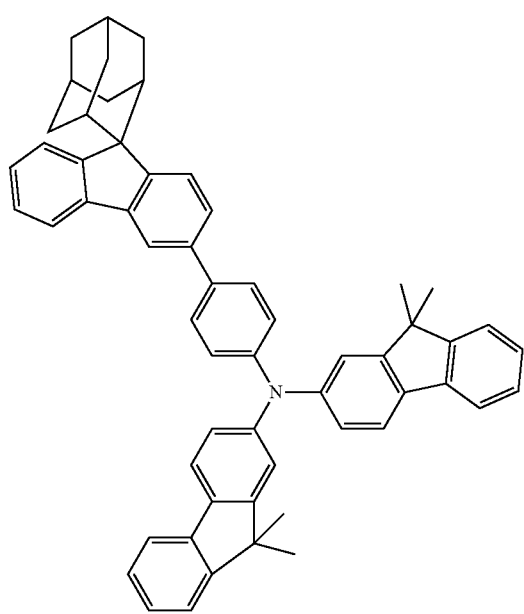
516
-continued
313
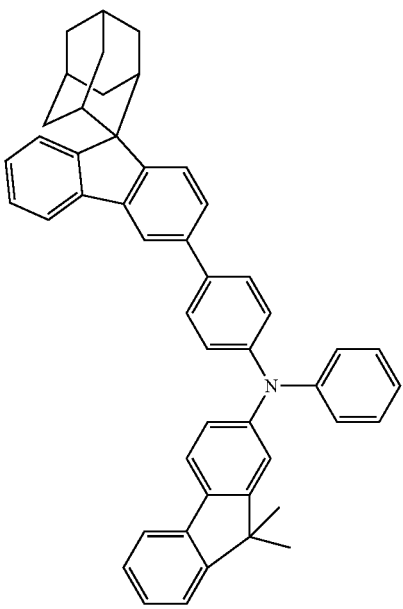
314
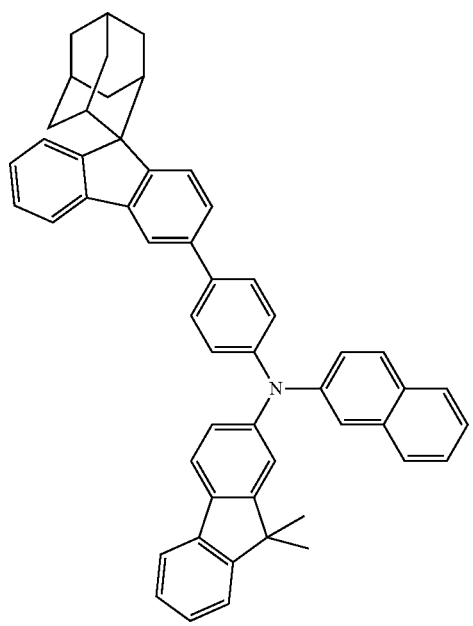

517
-continued
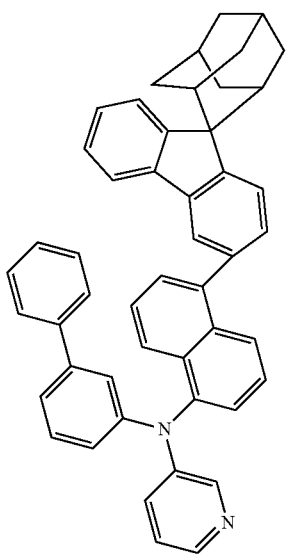
315
518
-continued
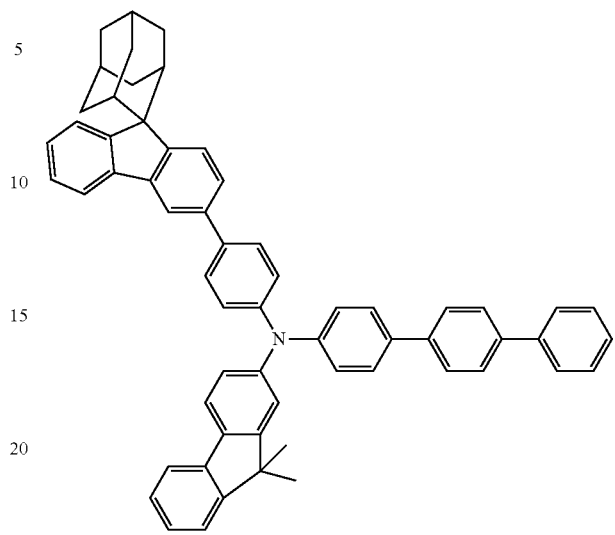
317
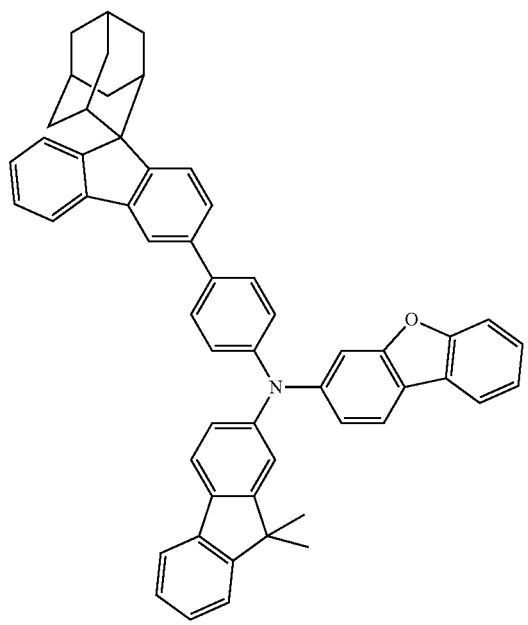
316
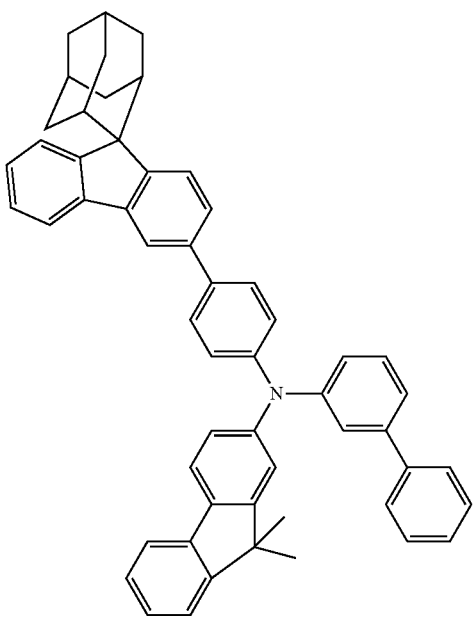
318

519
-continued
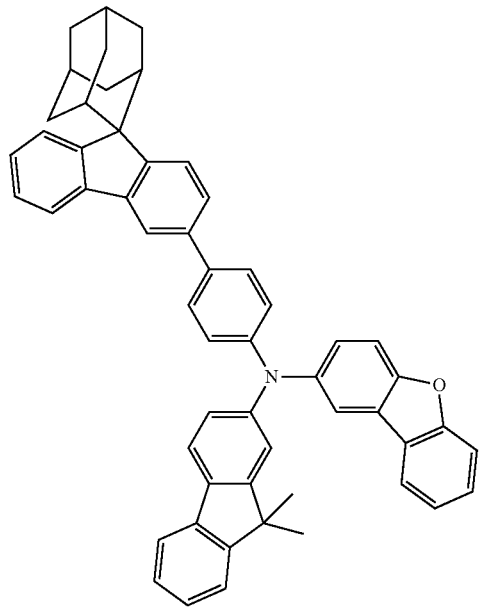
319
520
-continued
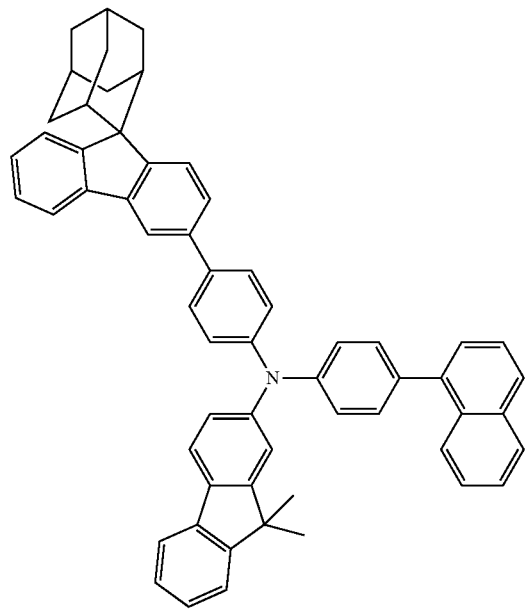
321
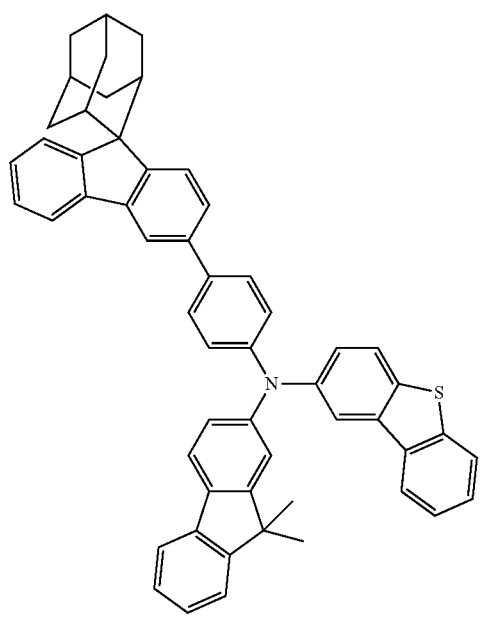
320
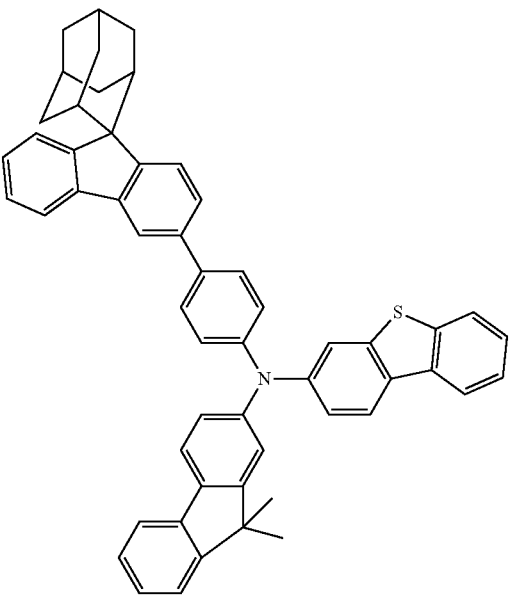
322

521
-continued
323
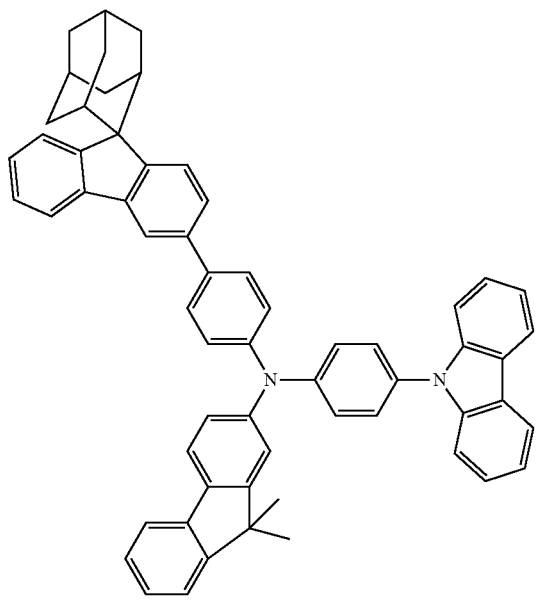
324
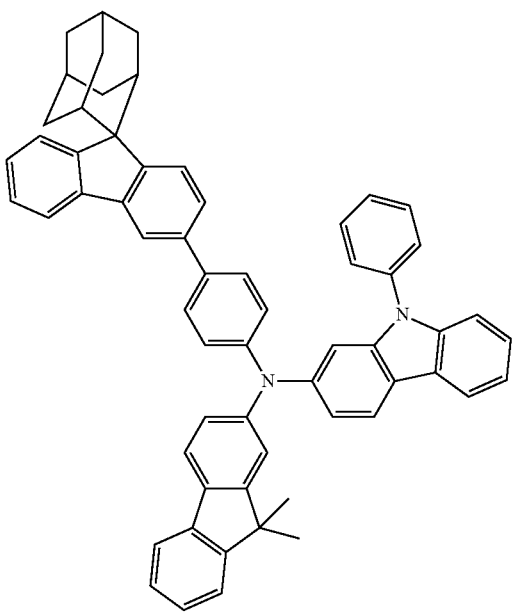
522
-continued
325
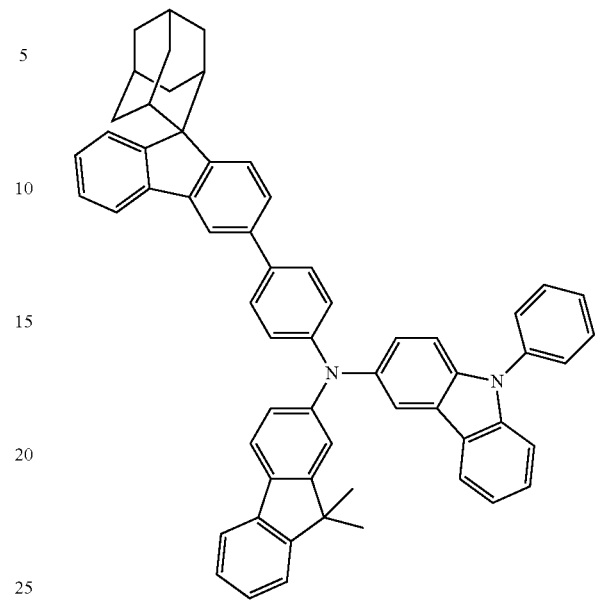
326
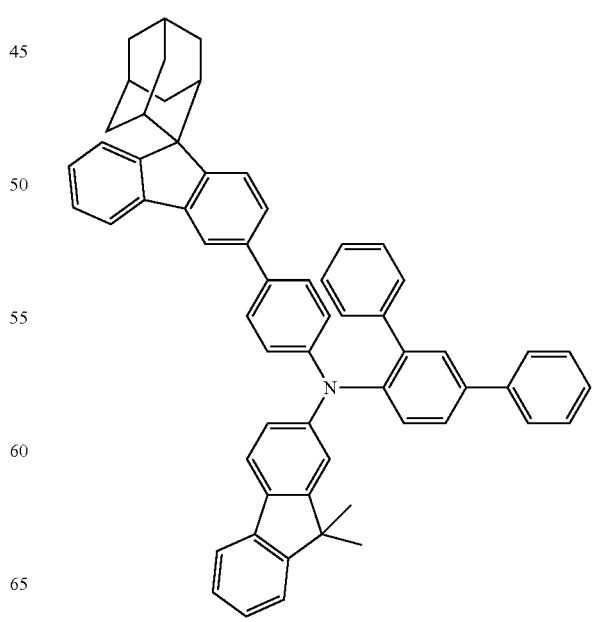

523
-continued
327
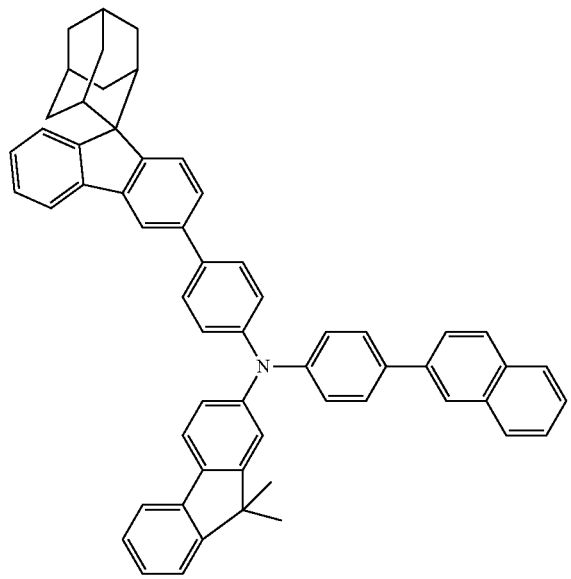
328
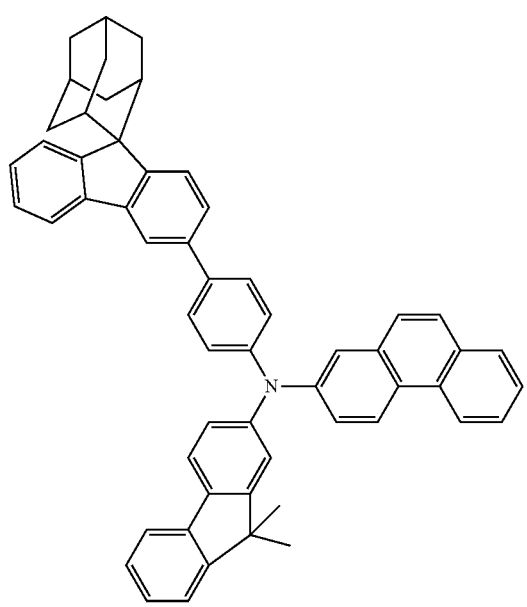
524
-continued
329
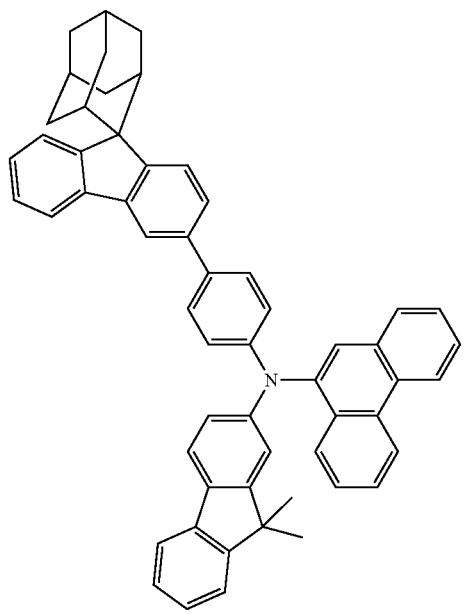
330
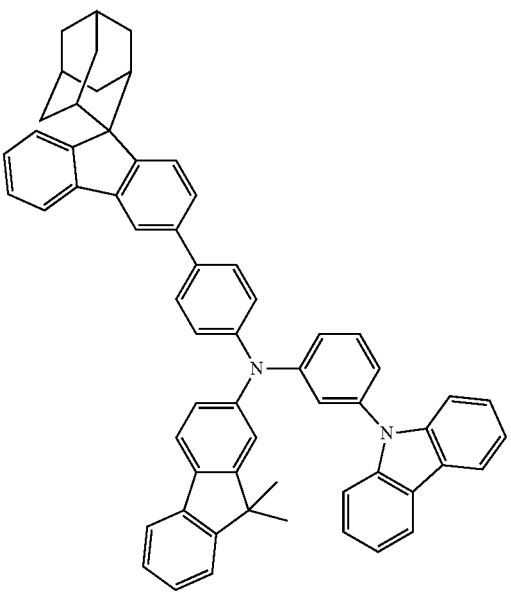

525
-continued
526
-continued
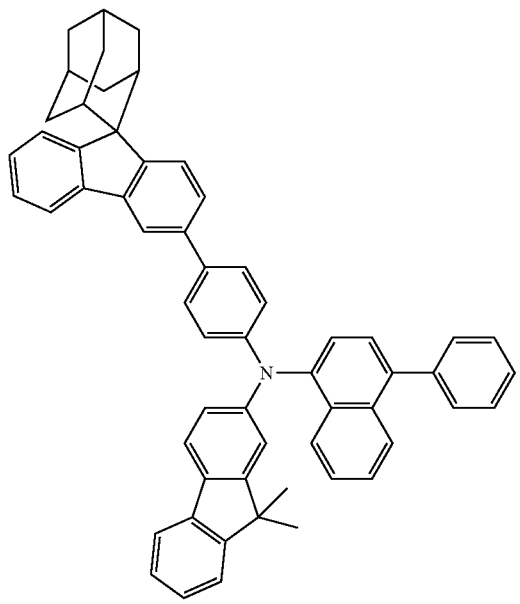
331
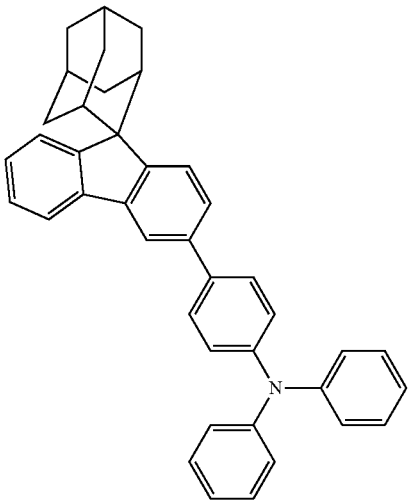
333
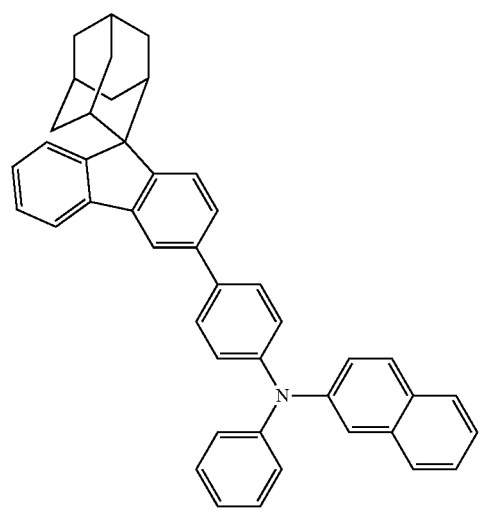
334
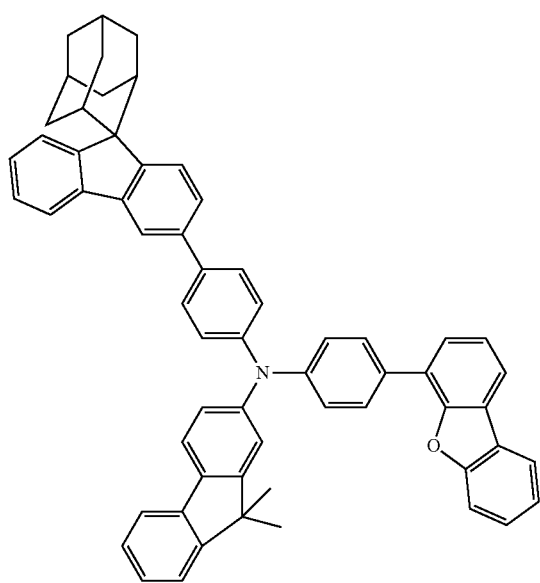
332
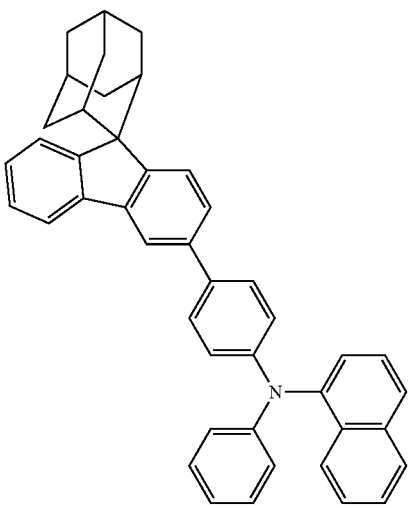
335

| 336 | 339 |
|---|---|
| 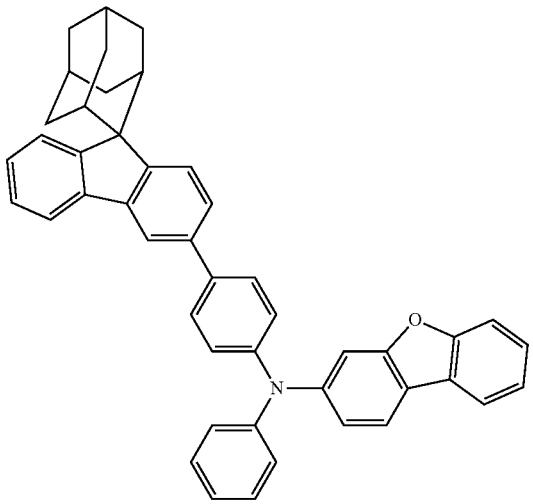 | 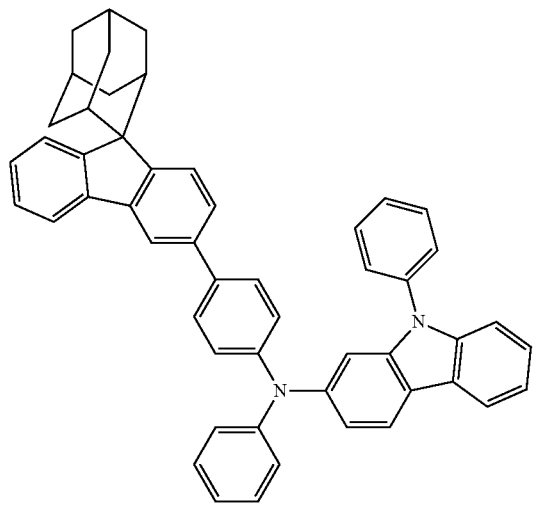 |
| 337 | 340 |
| 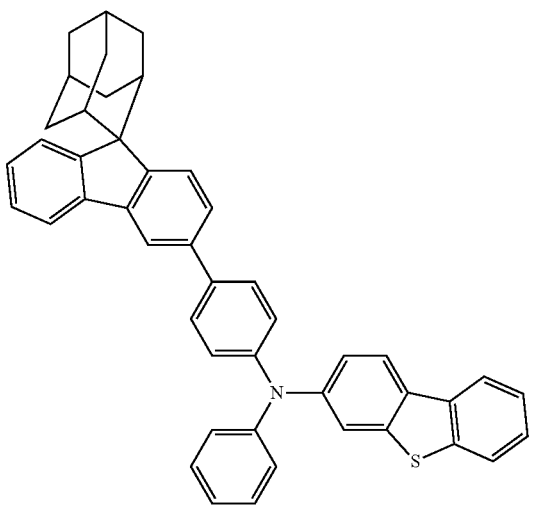 | 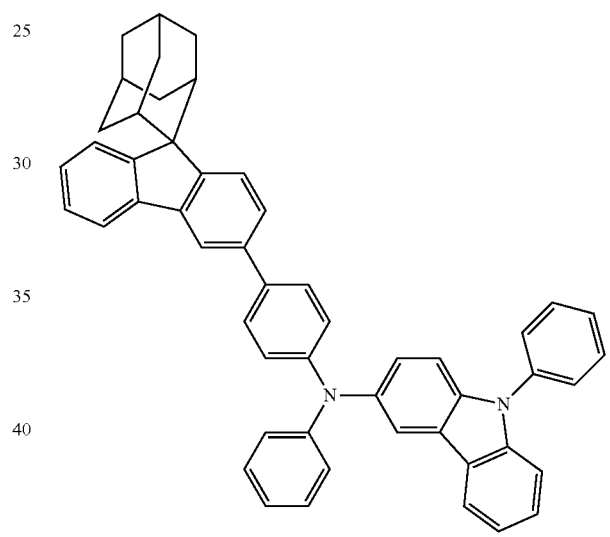 |
| 338 | 341 |
| 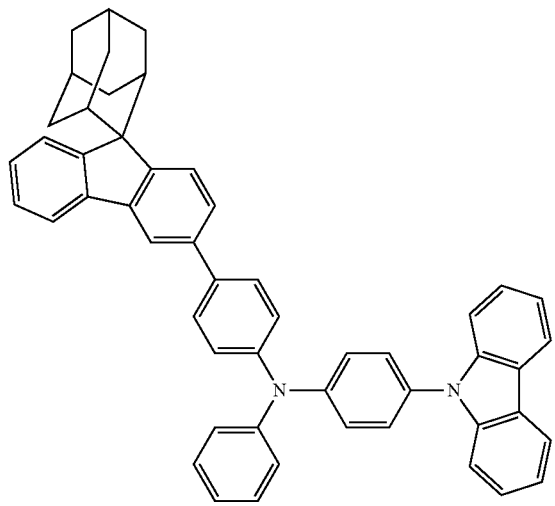 | 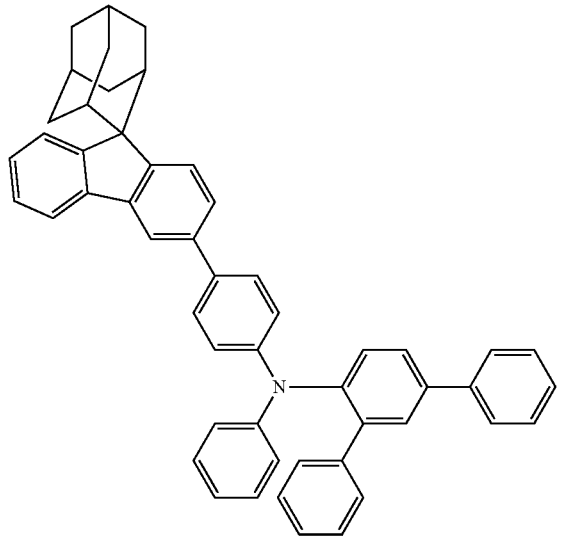 |

529
-continued
342
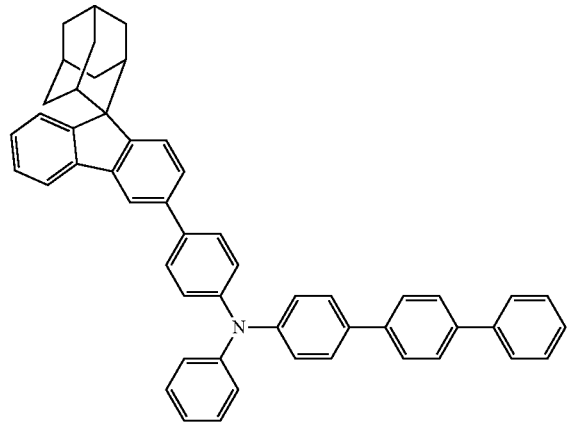
343
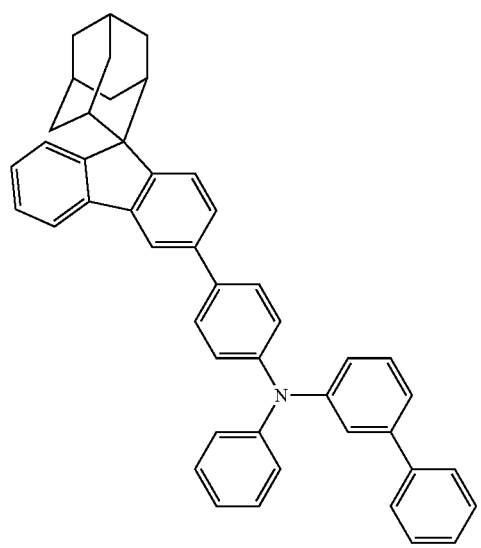
344
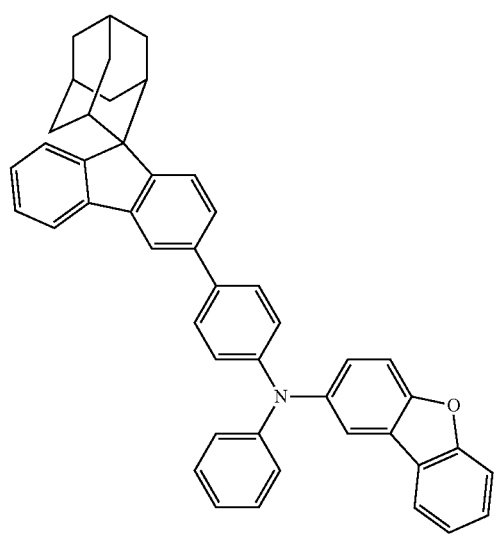
530
-continued
345
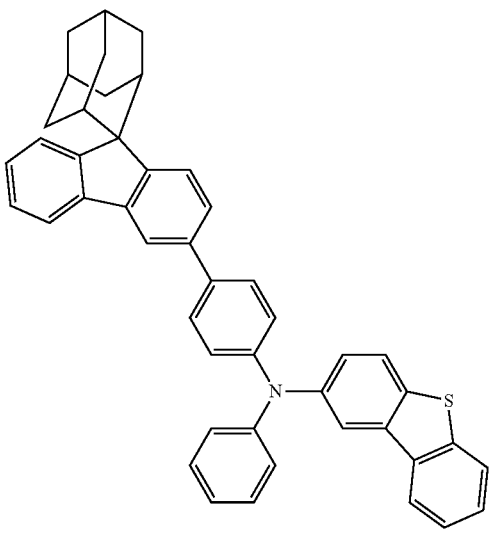
346
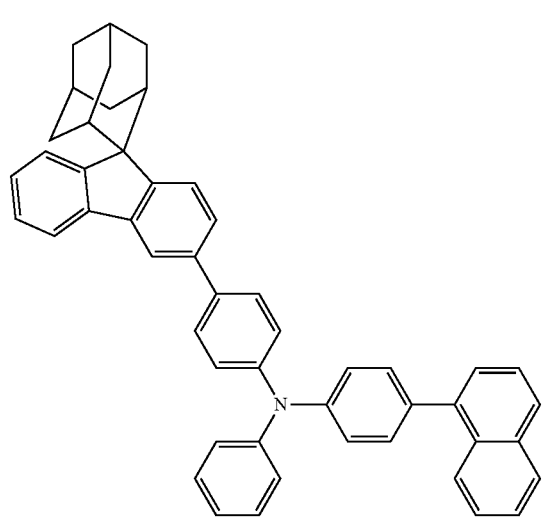
347
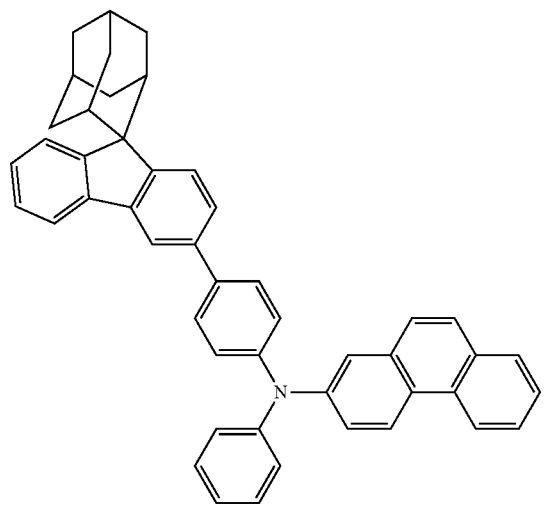

531
-continued
532
-continued
348
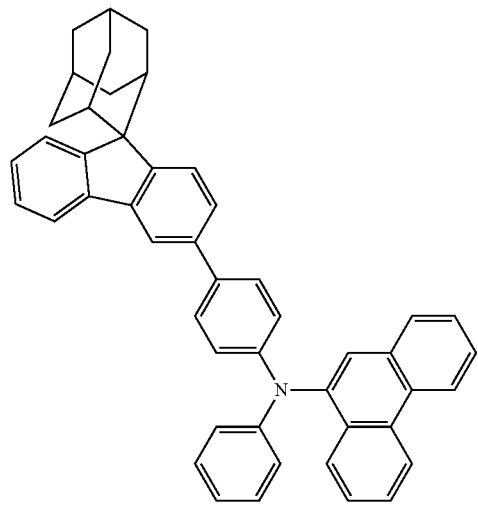
351
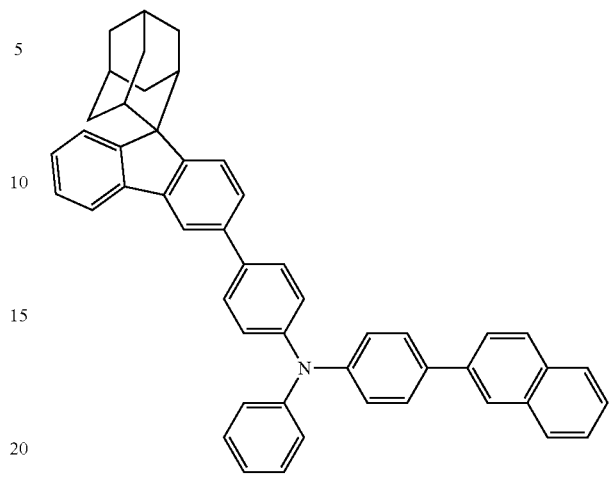
349
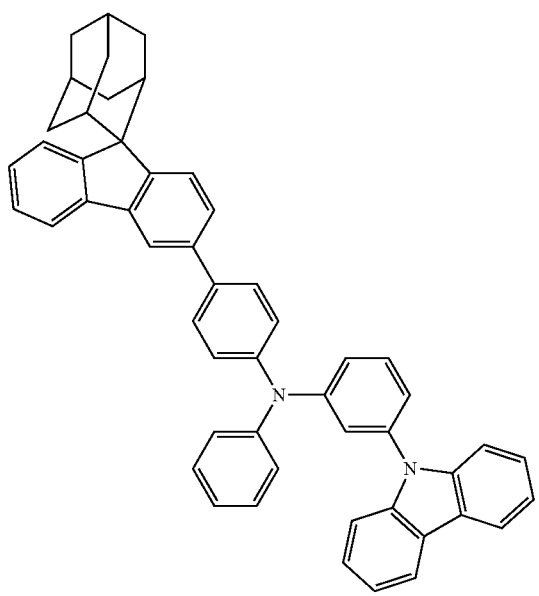
352
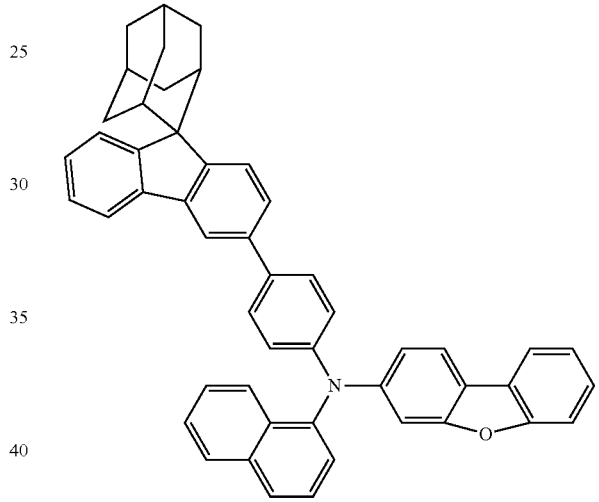
350
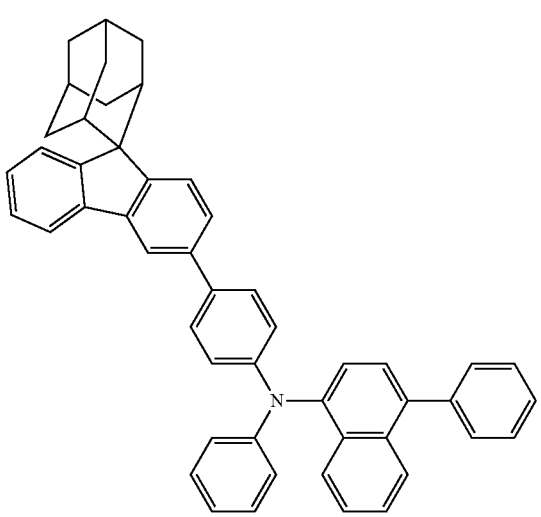
353
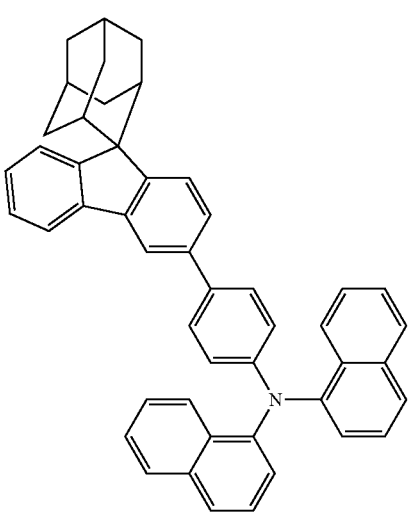

354
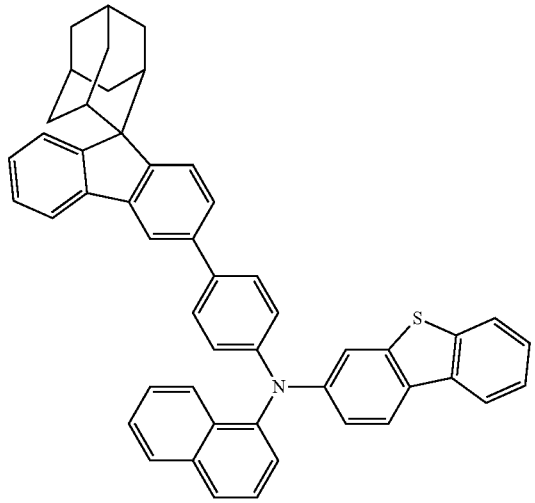
355
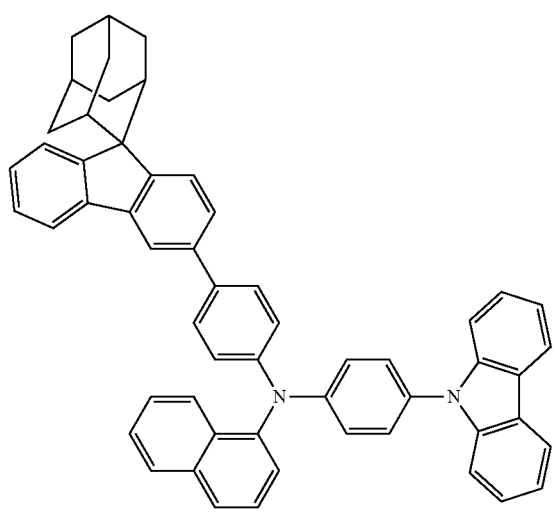
356
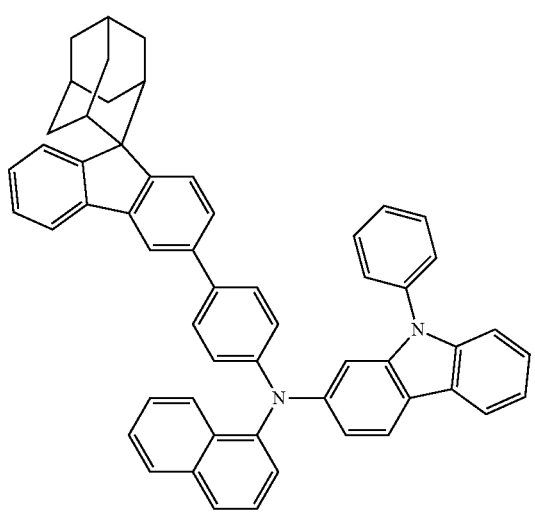
357
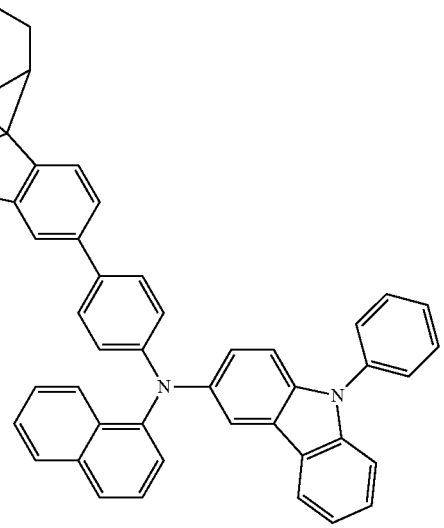
358
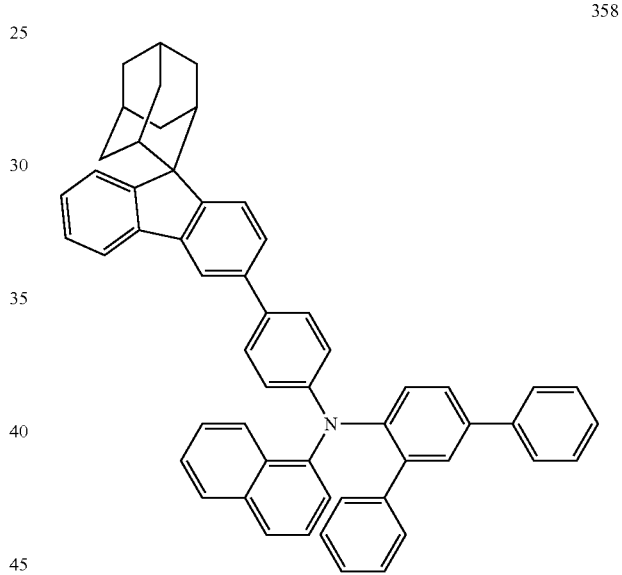
359
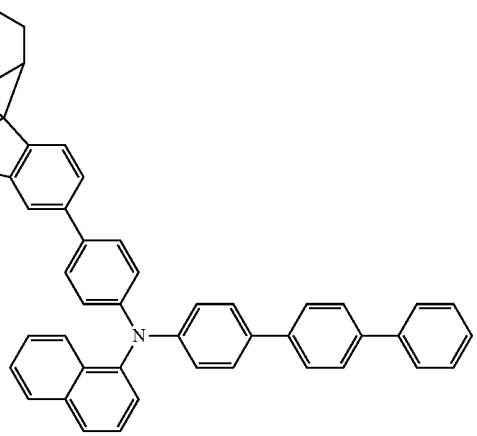

535
-continued
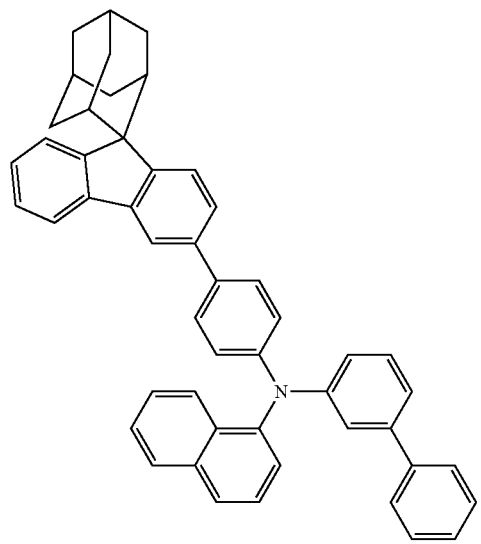
360
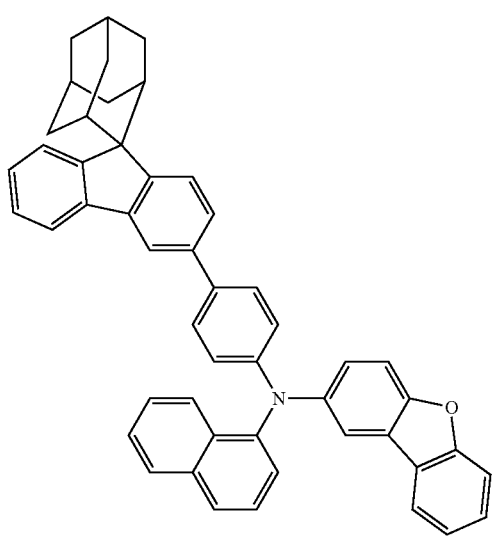
361
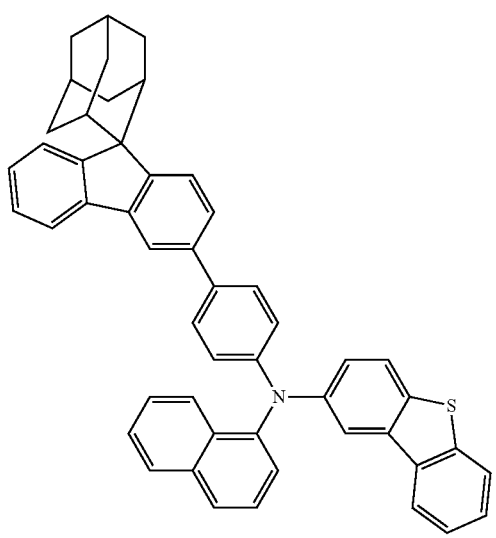
362
536
-continued
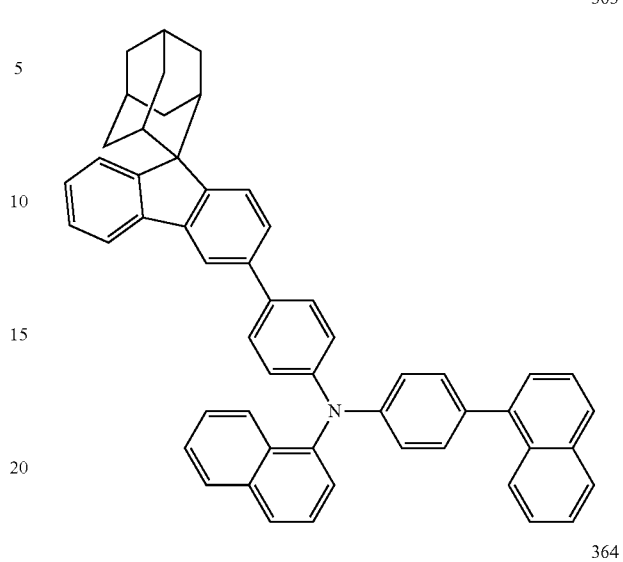
363
364
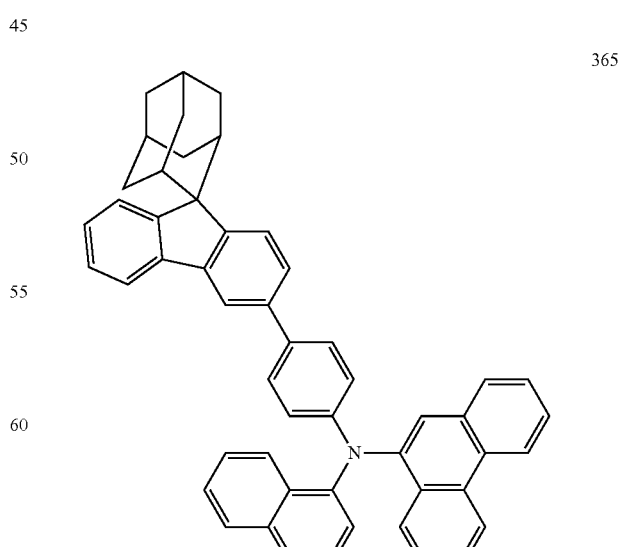
365

537 538
366 368
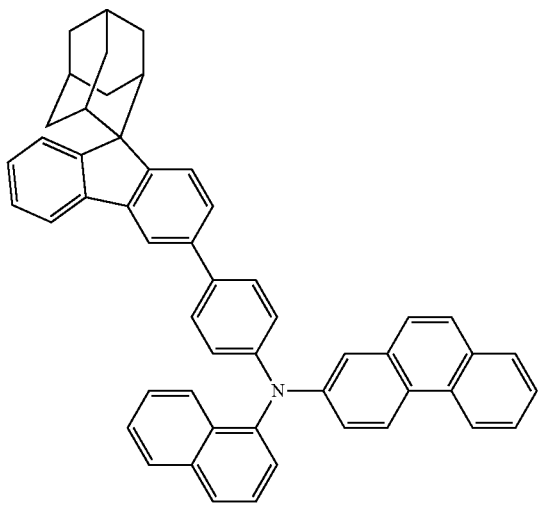
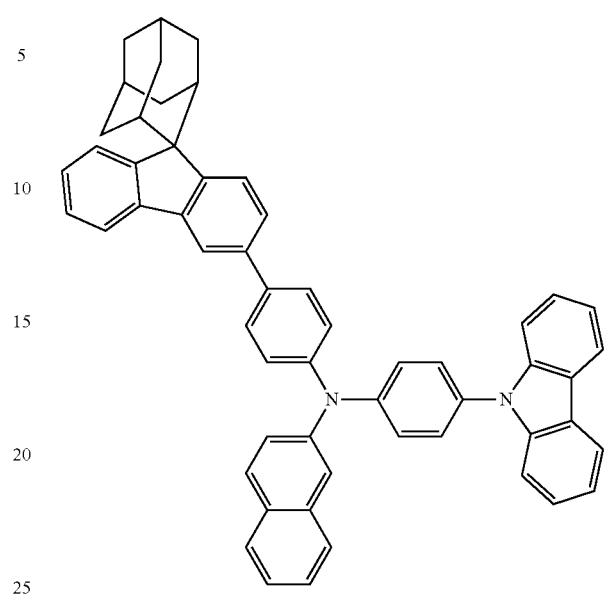
367 369
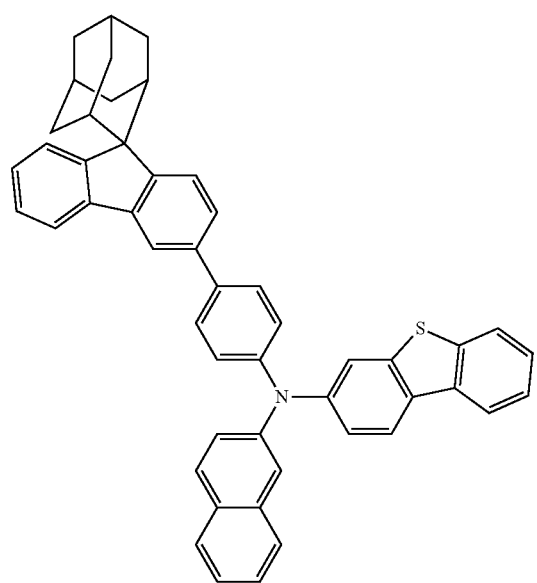
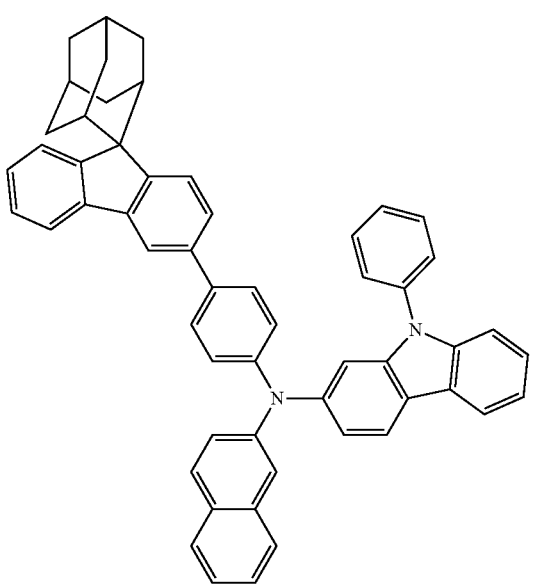

539 540
-continued -continued
370
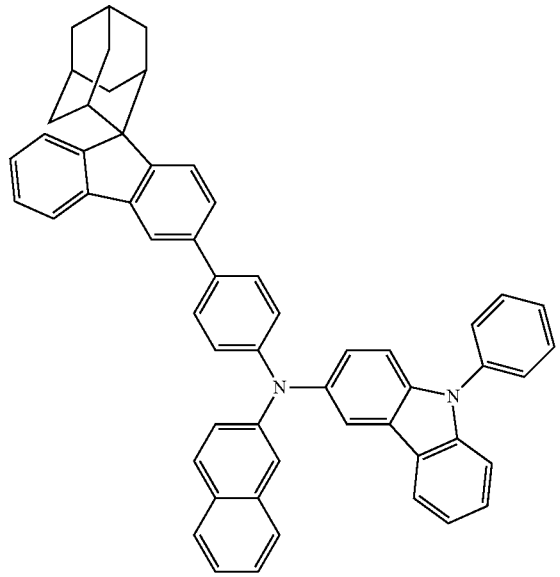
372
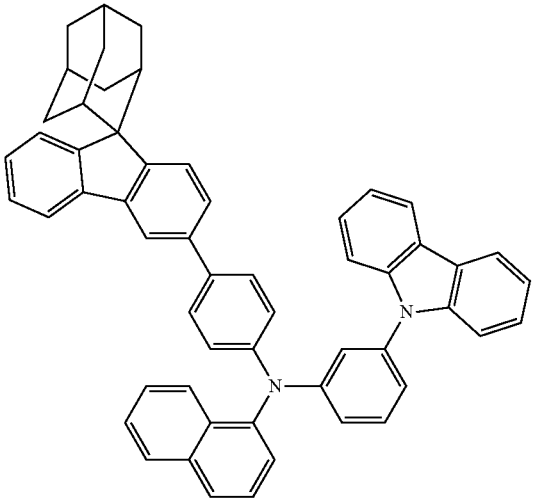
373
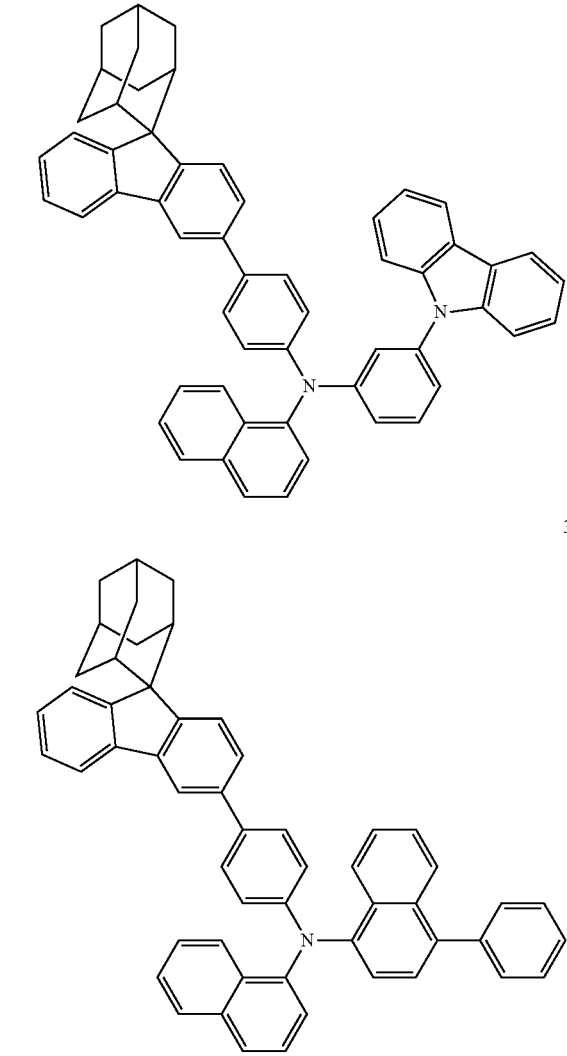
371
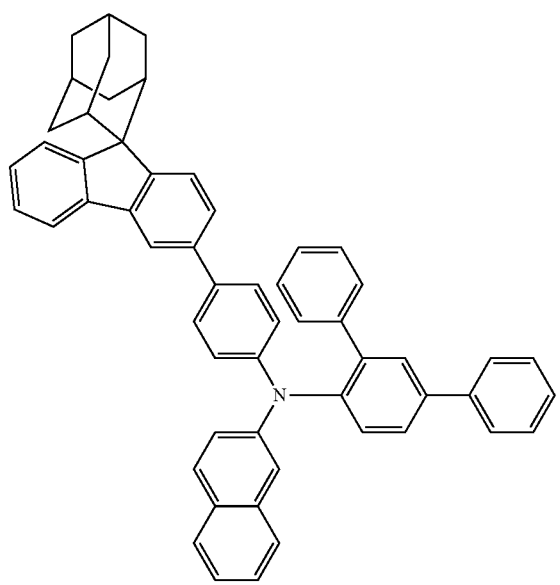
374
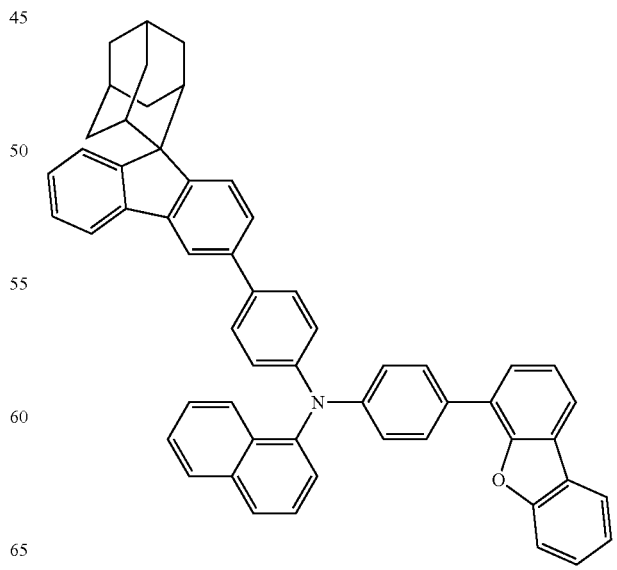

541
-continued
375
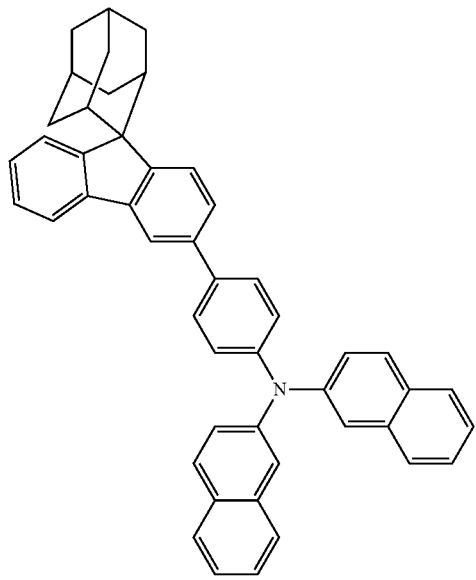
376
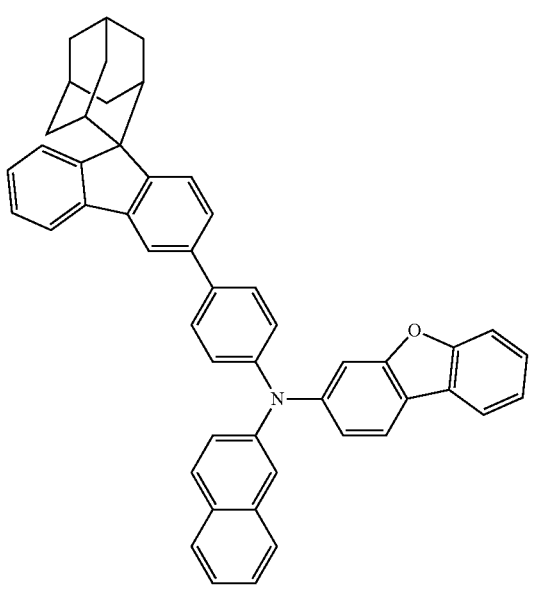
542
-continued
377
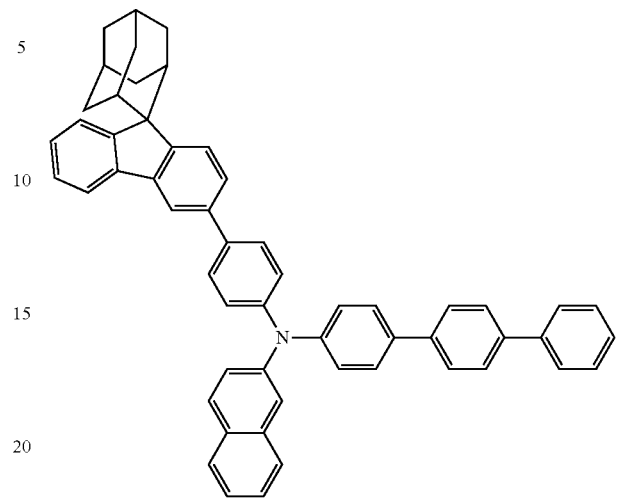
378
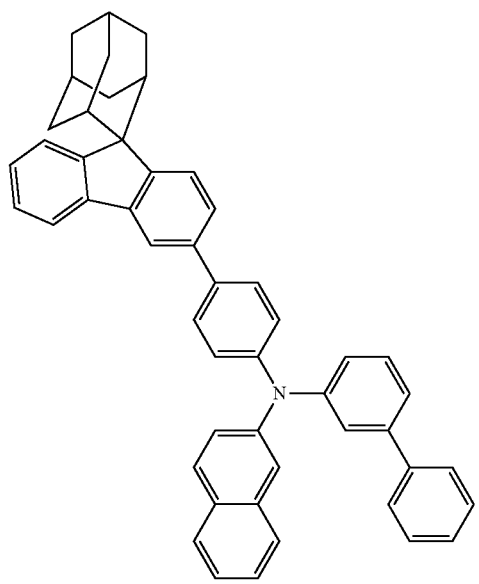

543
-continued
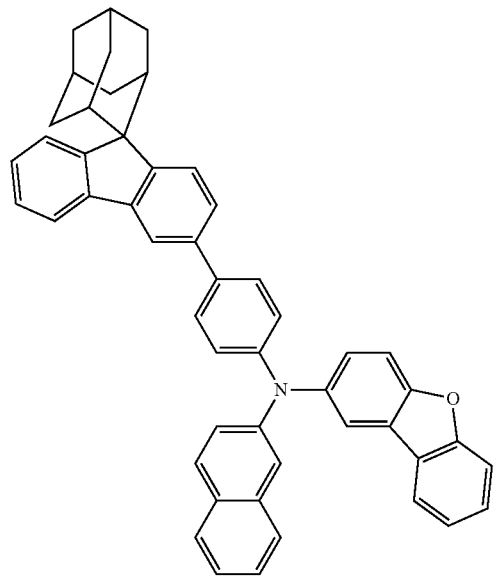
379
544
-continued
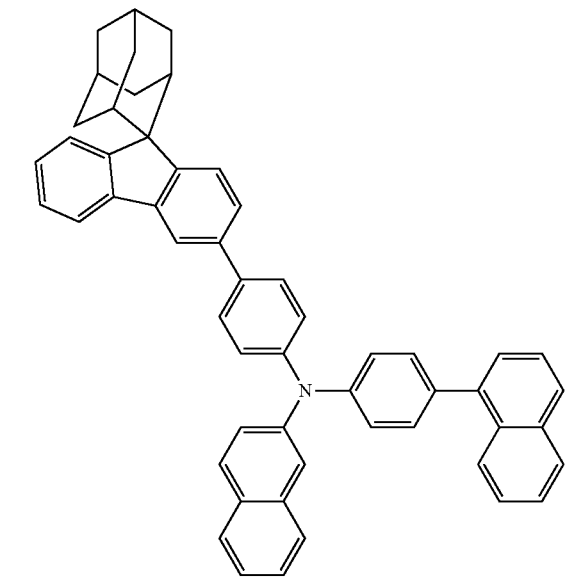
381
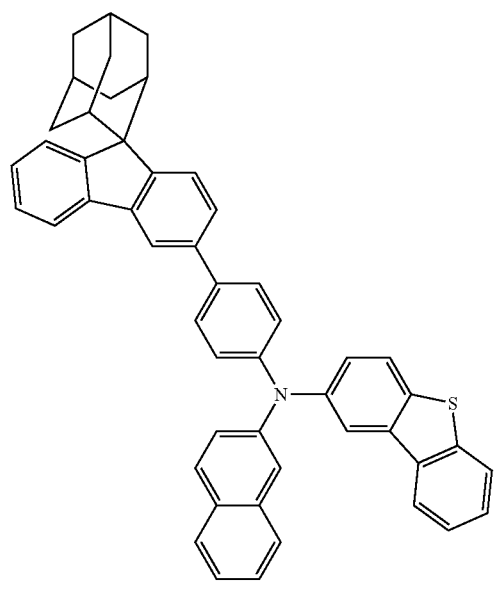
380
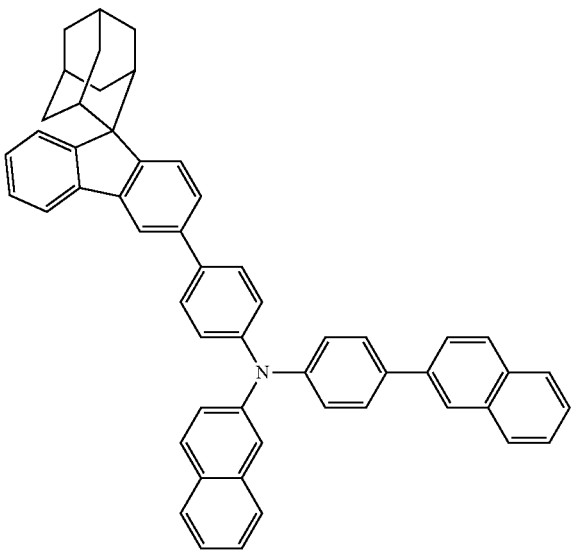
382

545
-continued
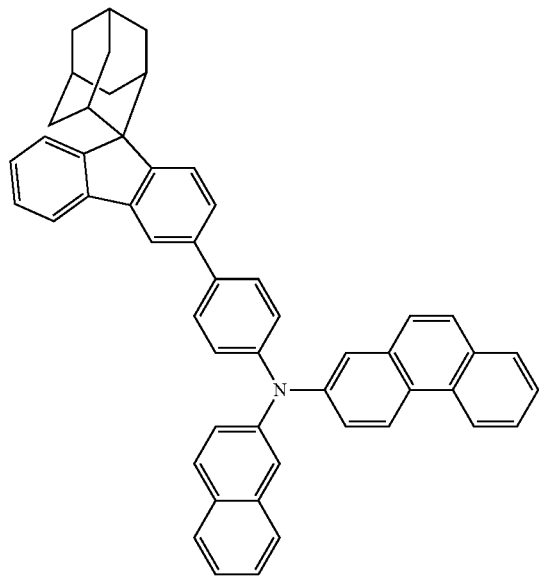
546
-continued
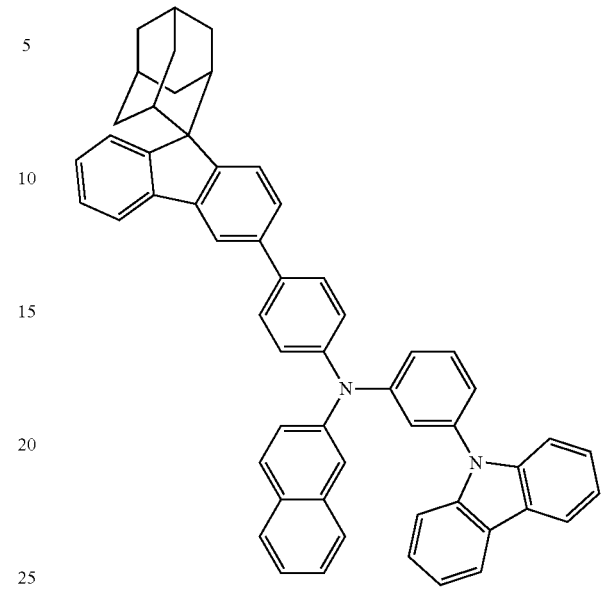
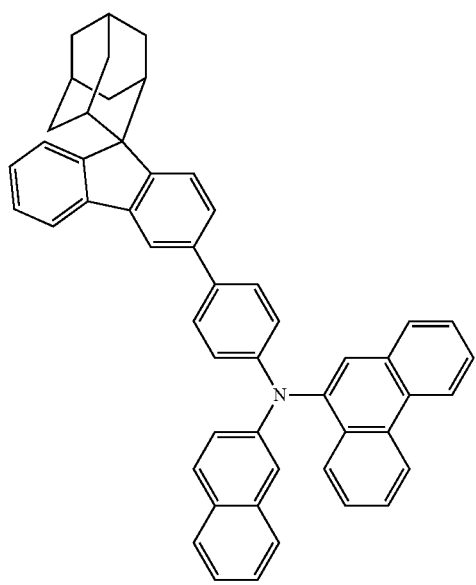
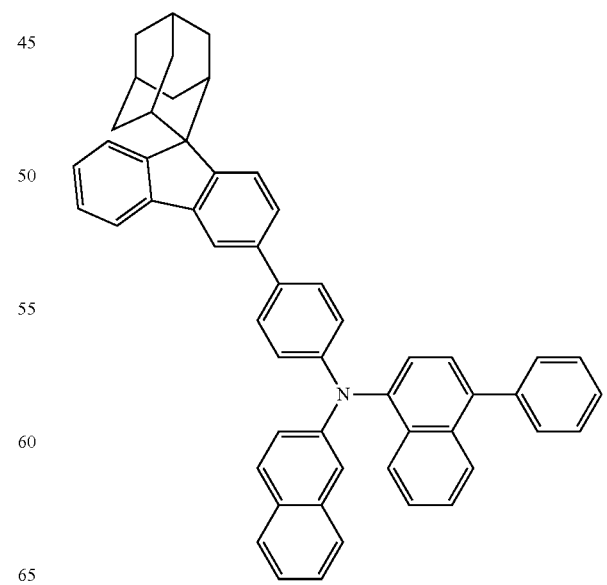

387
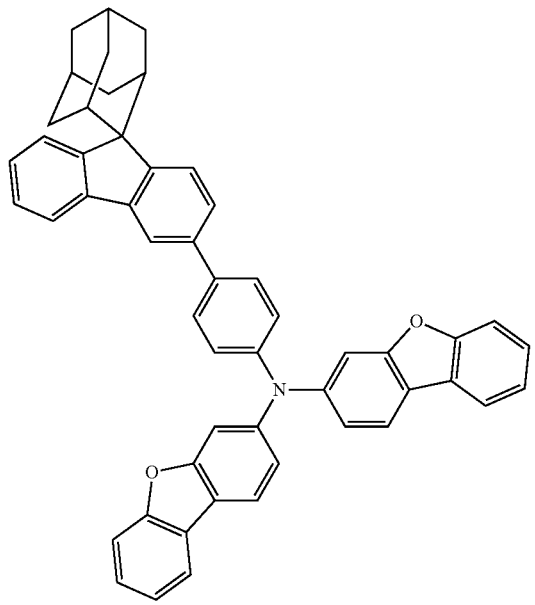
389
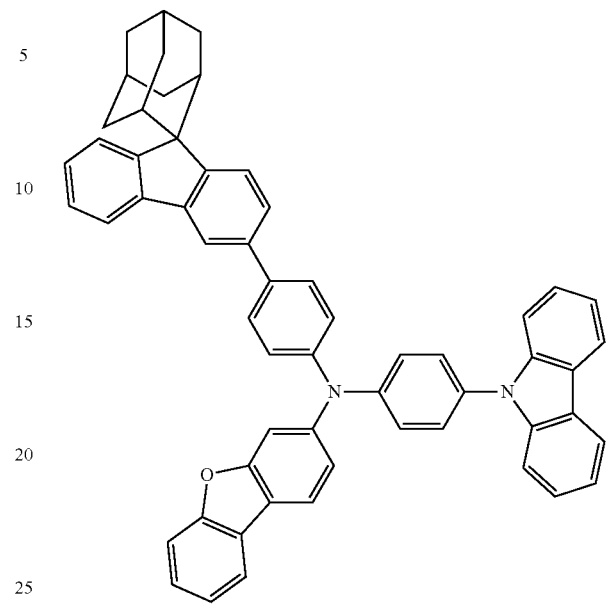
388
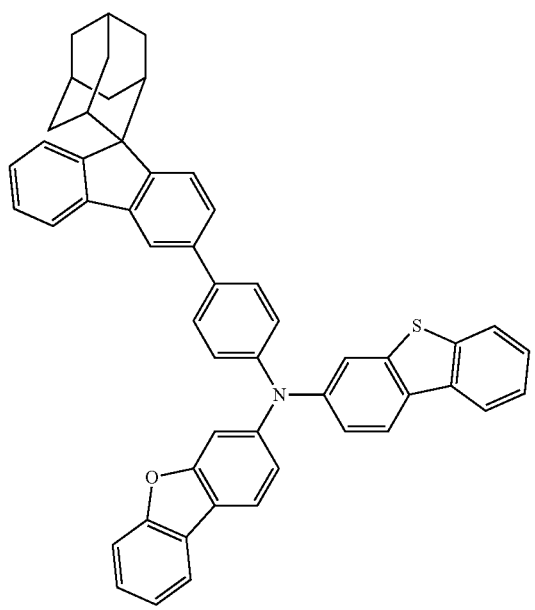
390
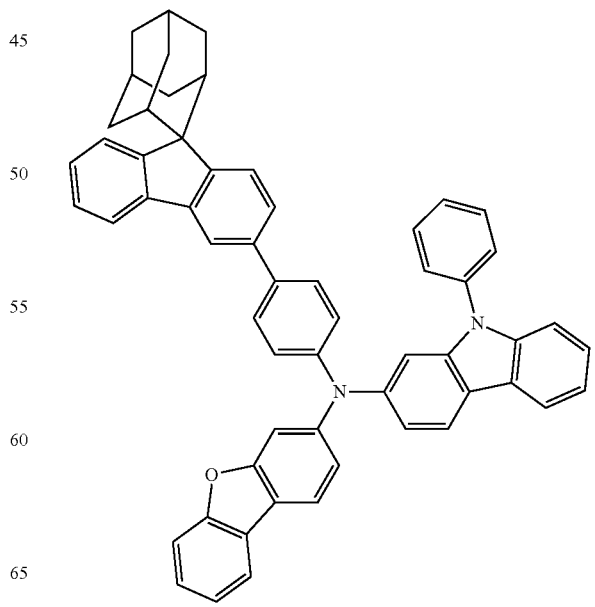

549
-continued
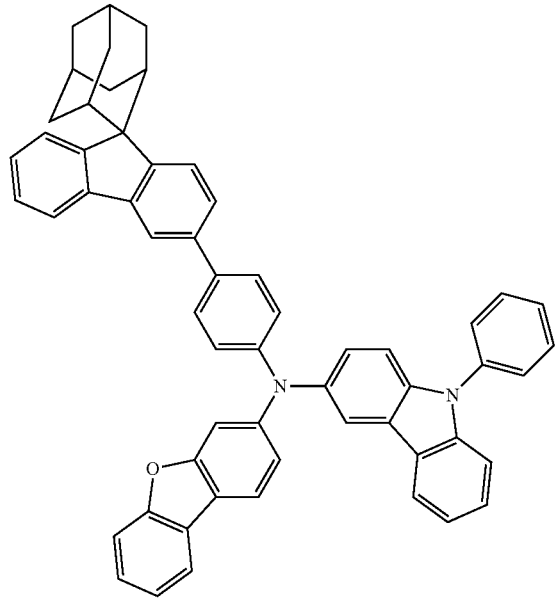
550
-continued
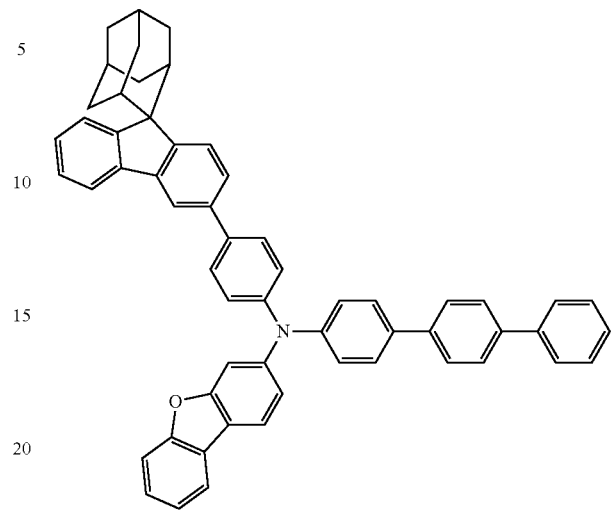
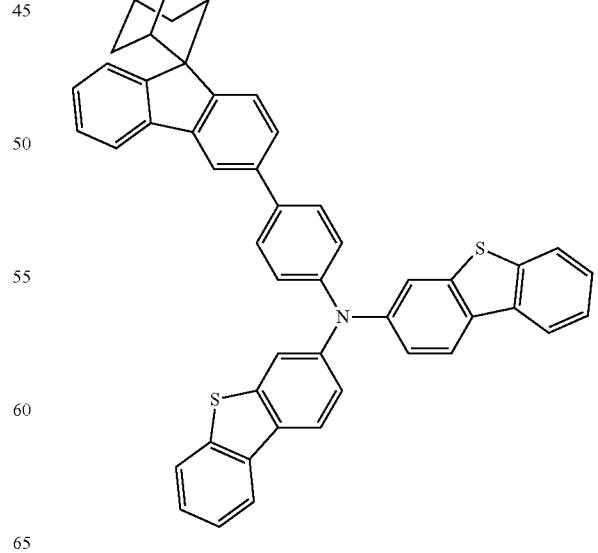

| 551 | 552 |
|---|---|
| 395 | 397 |
| 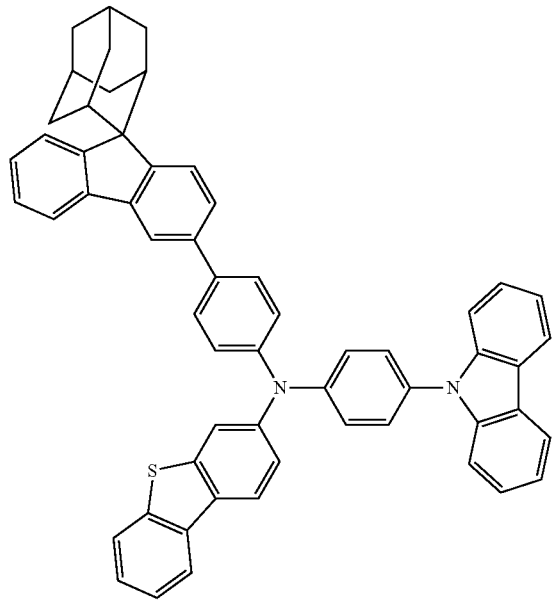 | 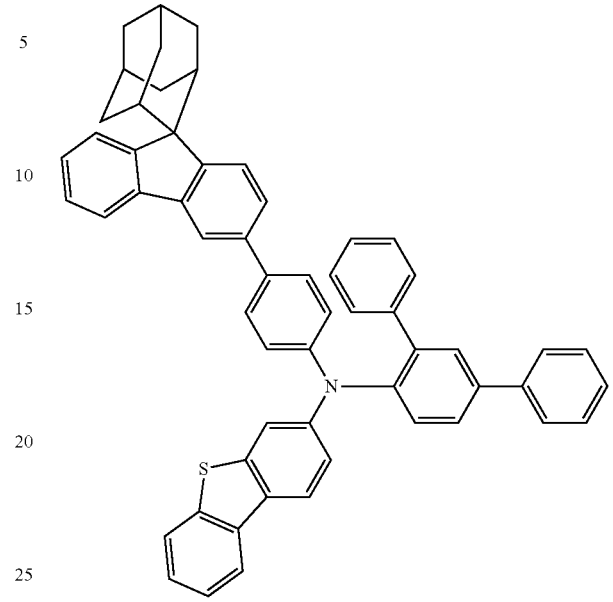 |
| 396 | 398 |
| 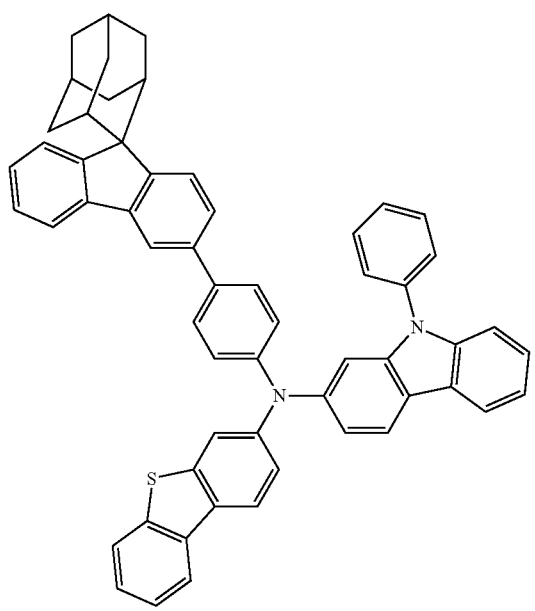 | 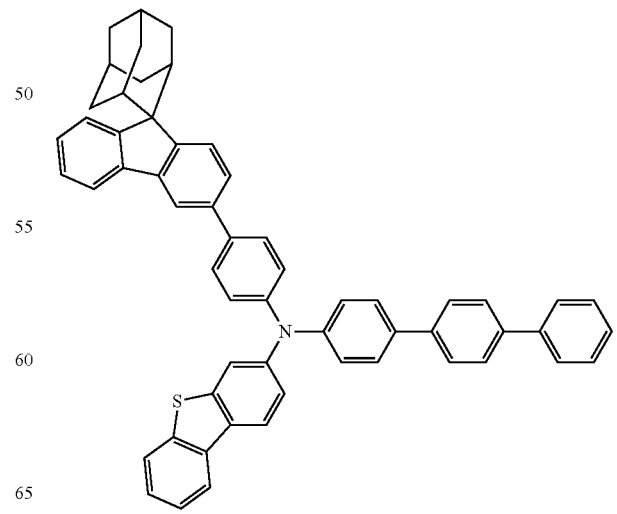 |

553
-continued
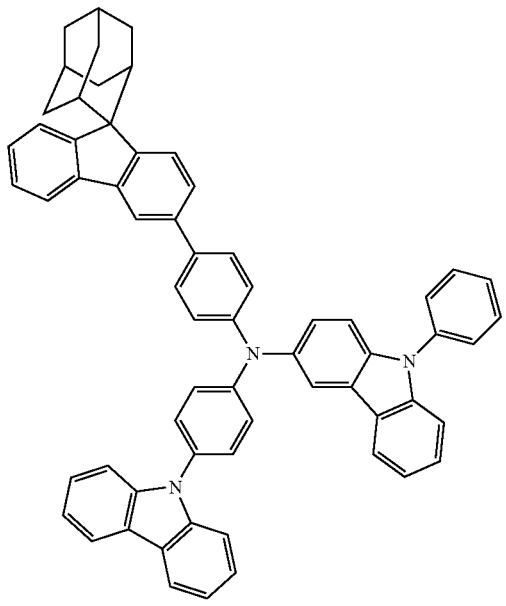
399
554
-continued
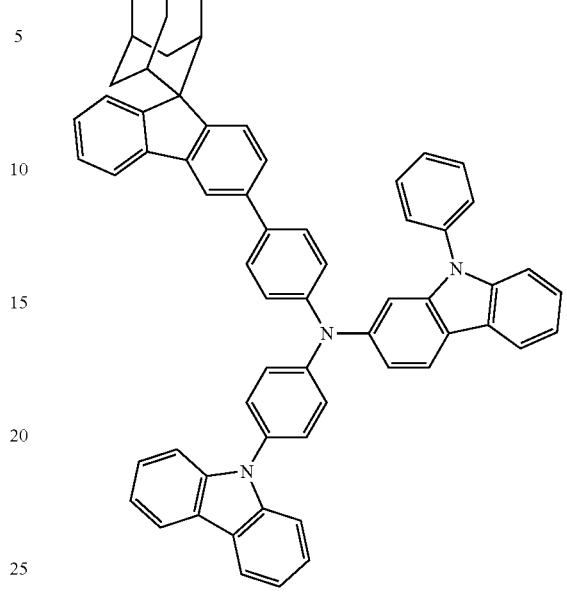
401
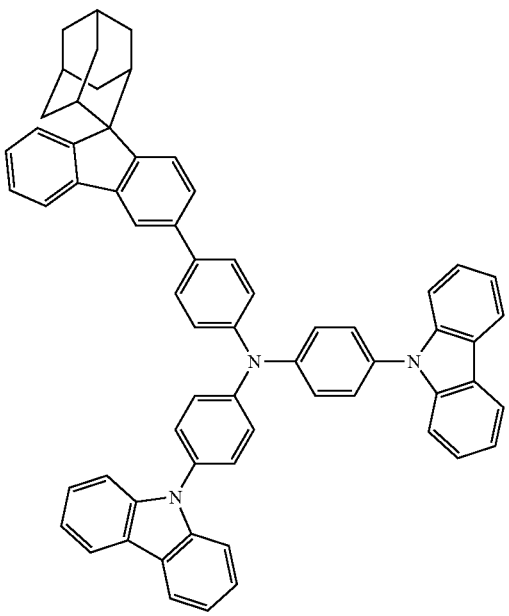
400
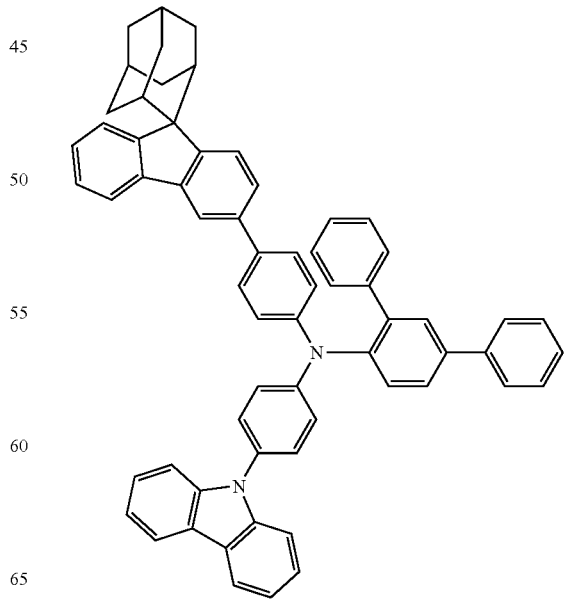
402

555
-continued
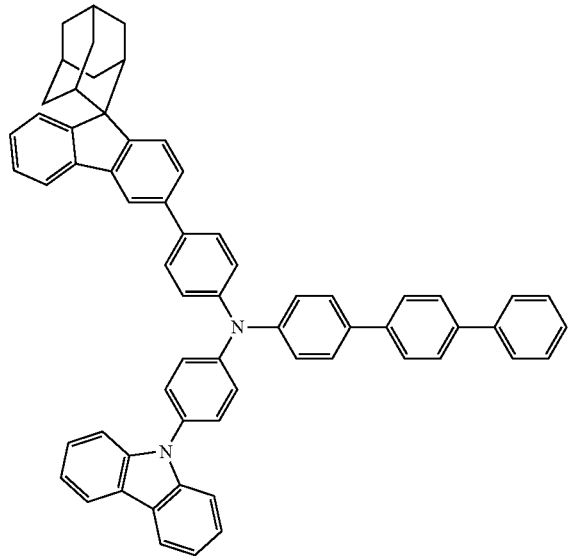
403
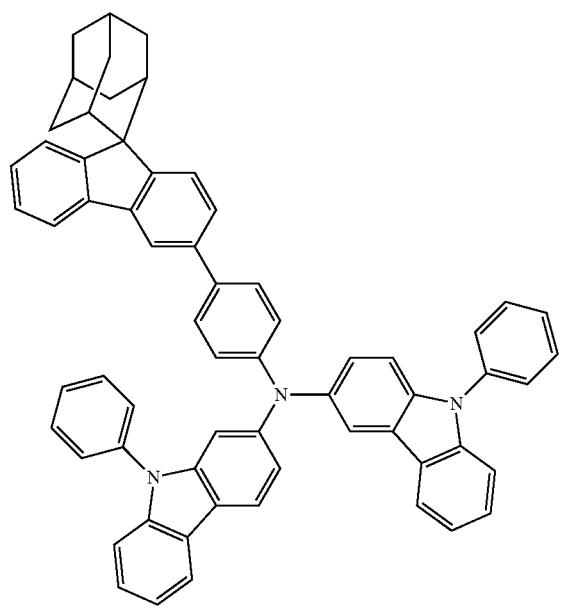
404
556
-continued
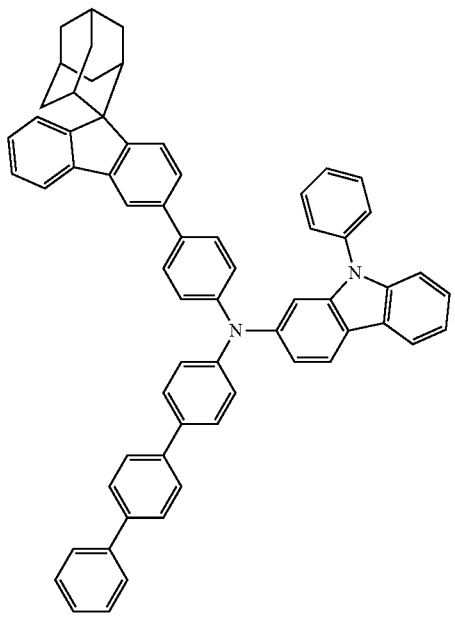
405
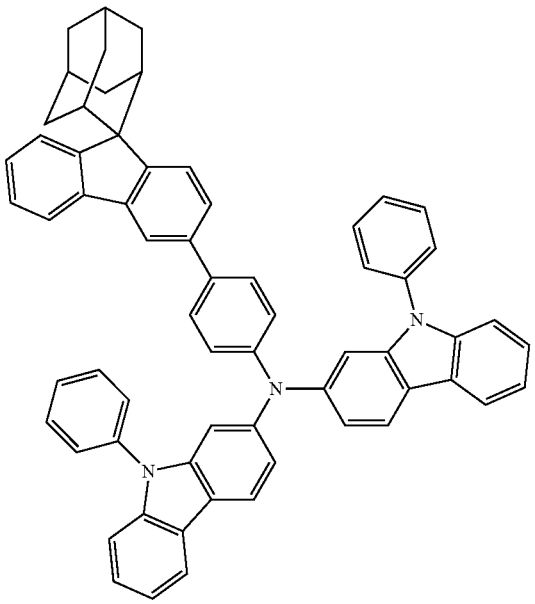
406

557
-continued
407
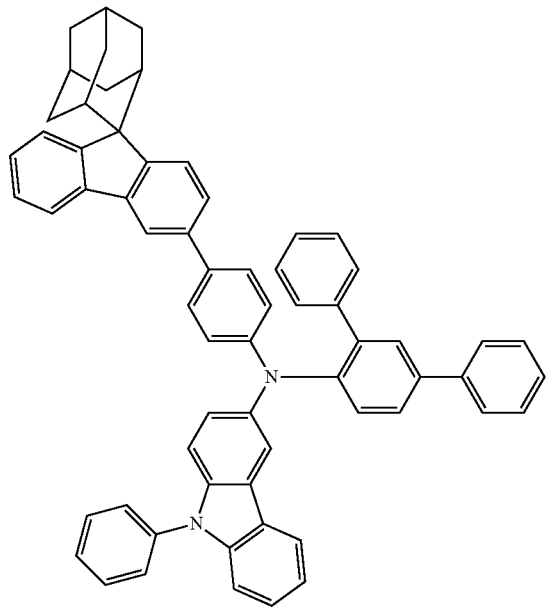
408
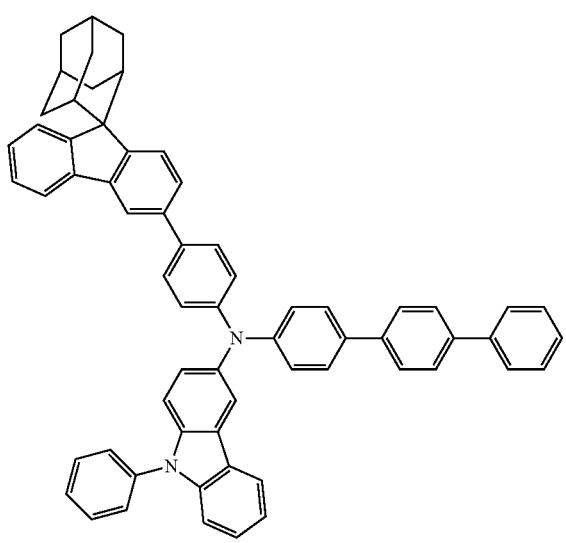
558
-continued
409
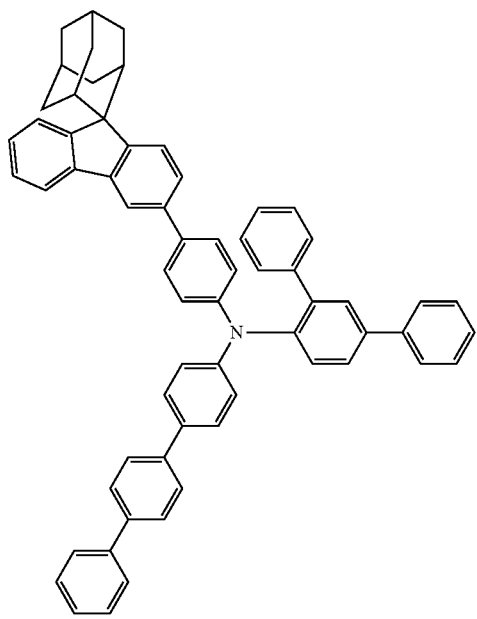
410
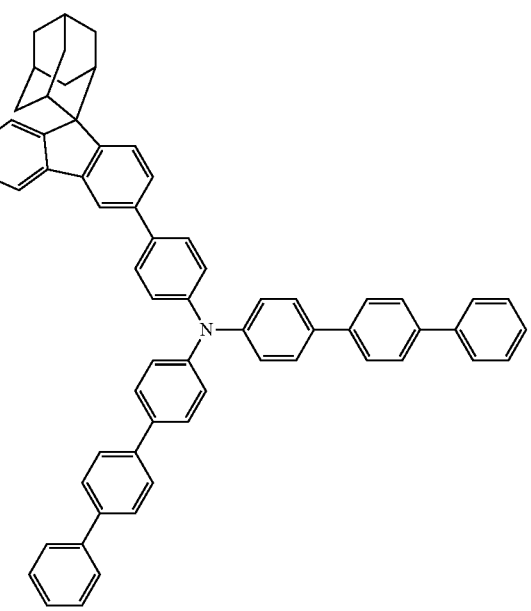

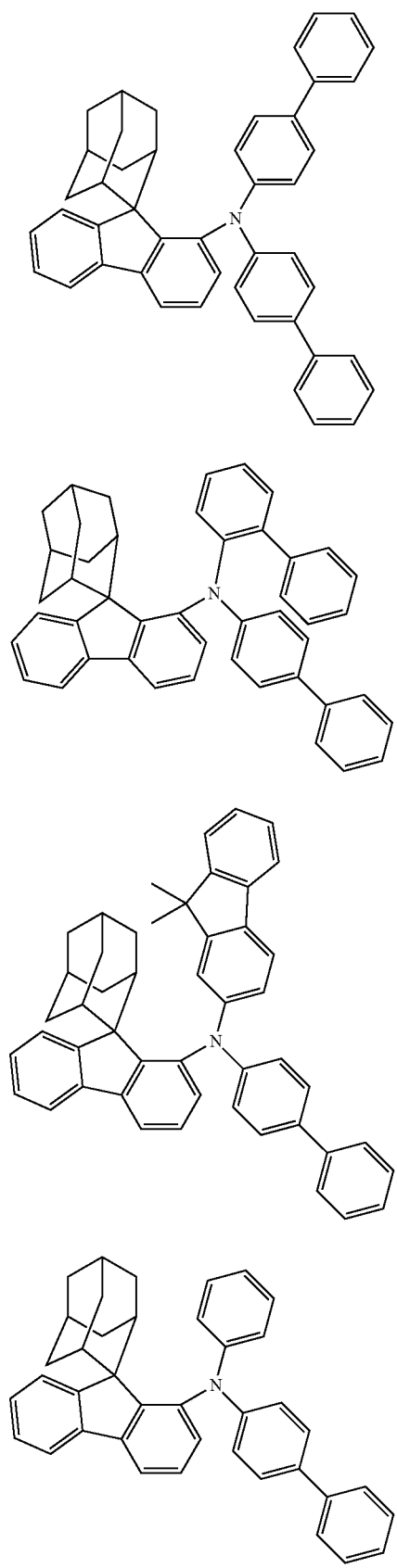
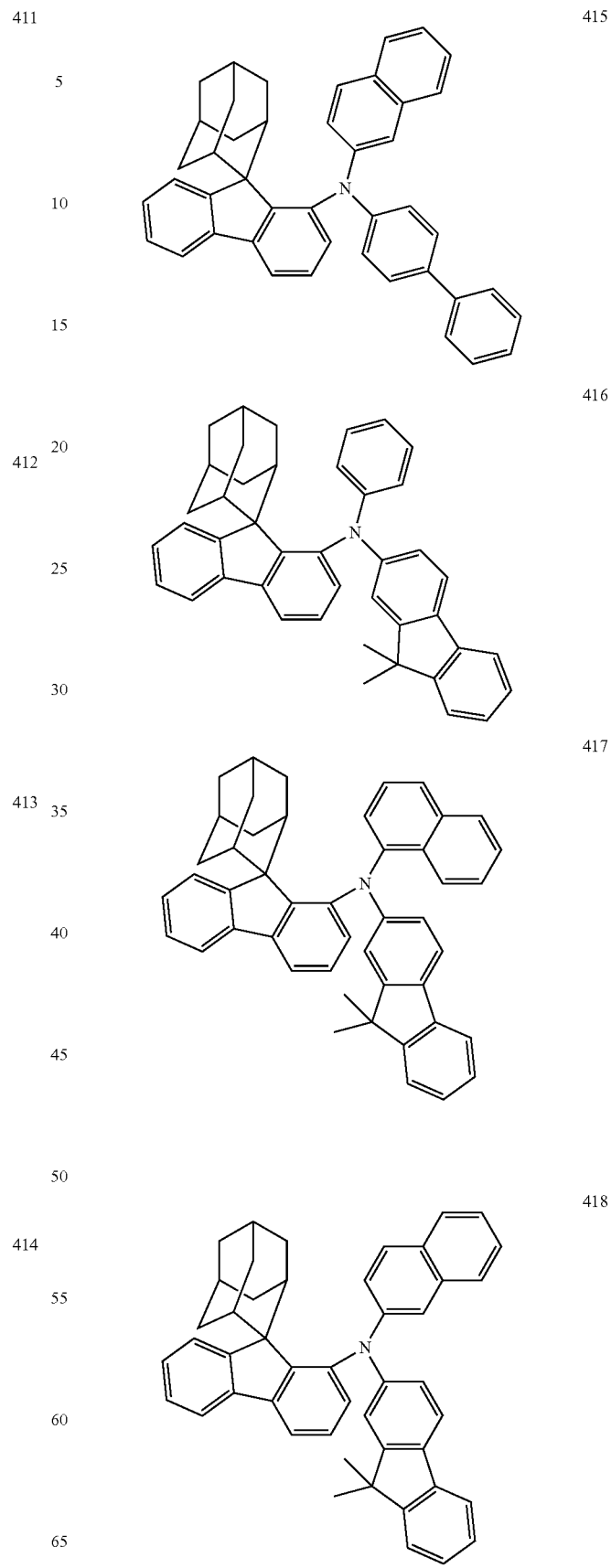

419
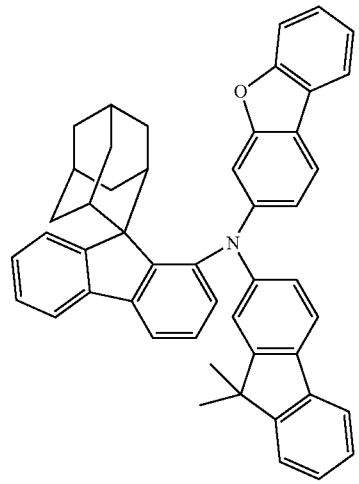
420
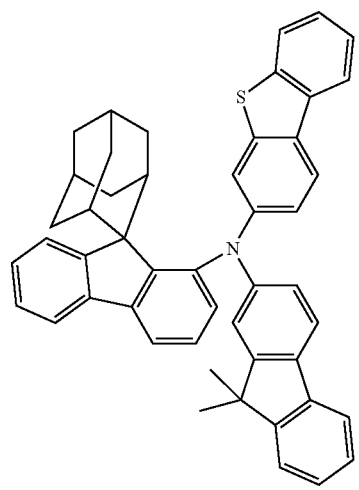
421
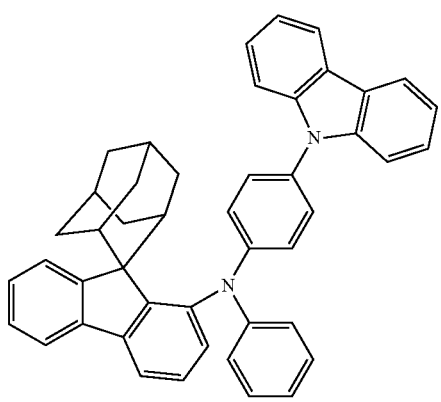
422
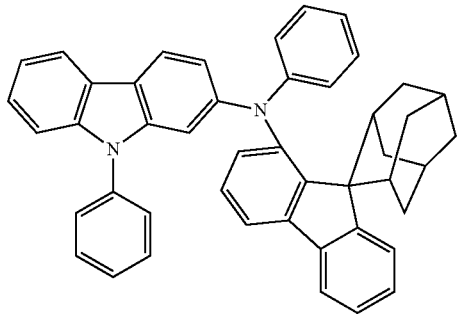
423
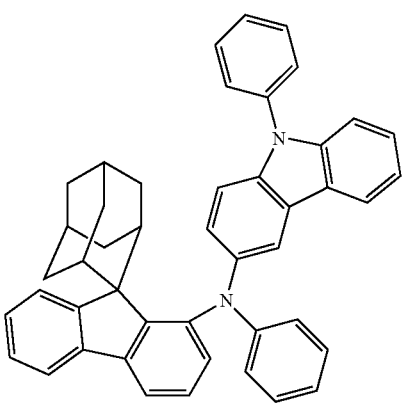
424
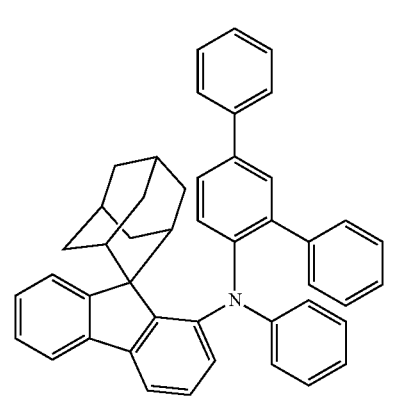
425
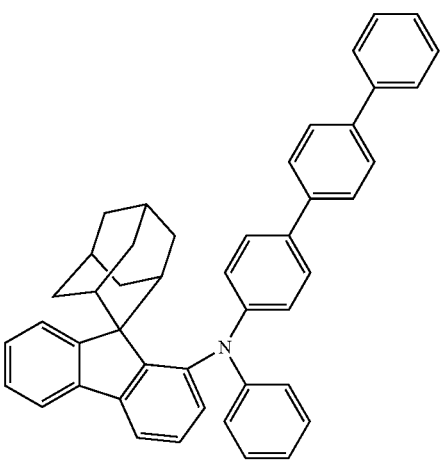

563
-continued
426
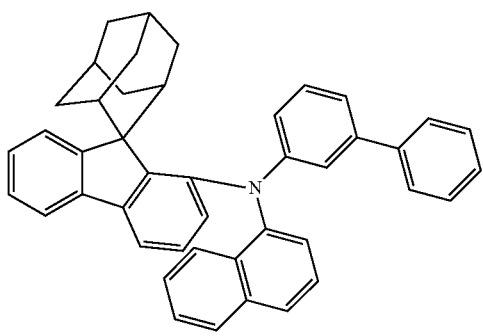
427
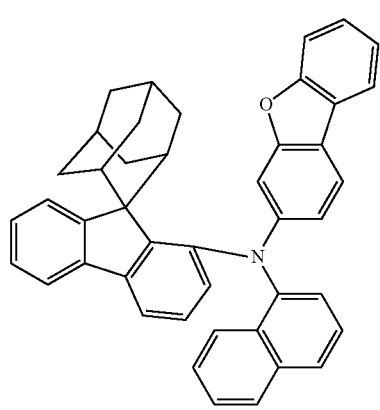
428
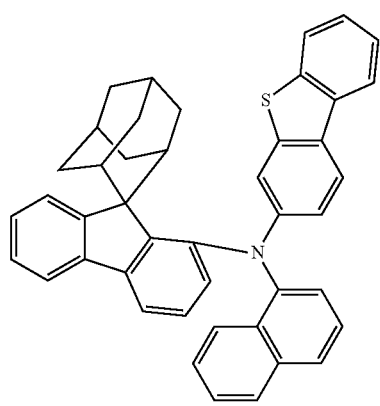
429
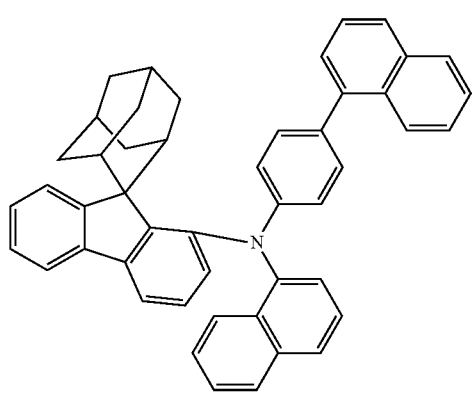
564
-continued
430
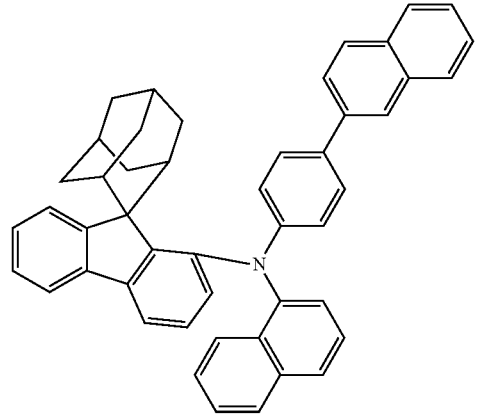
431
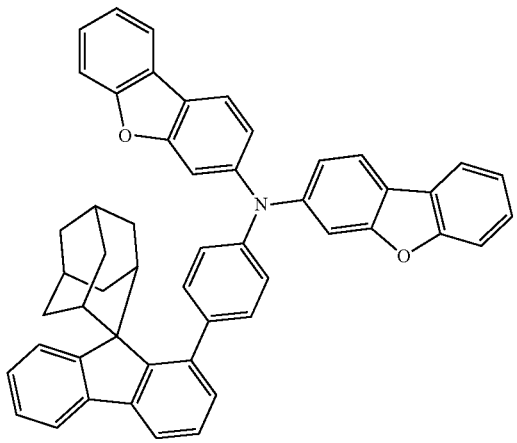
432
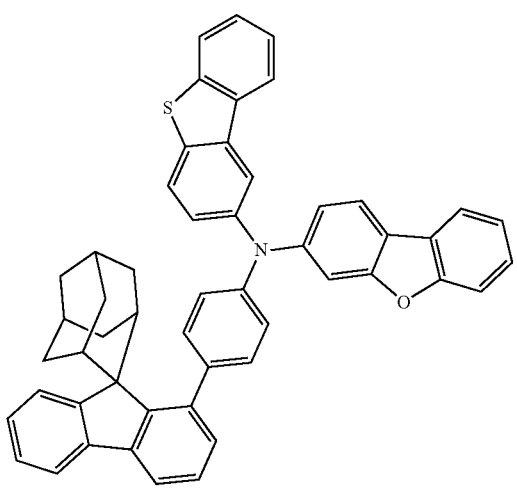

433
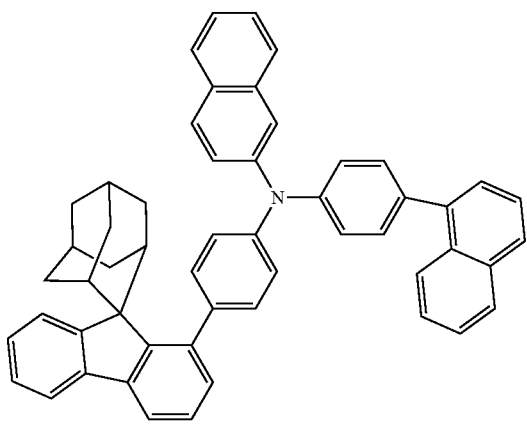
434
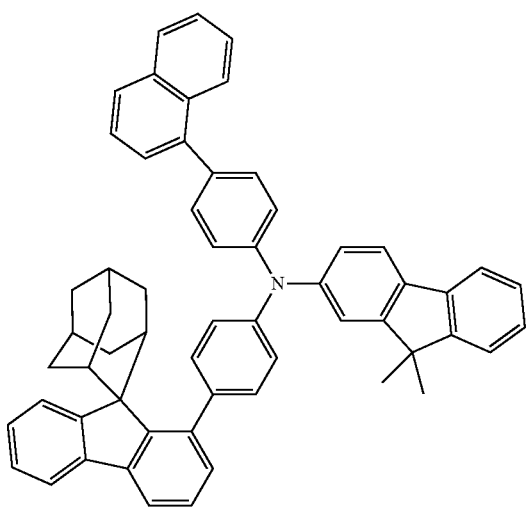
435
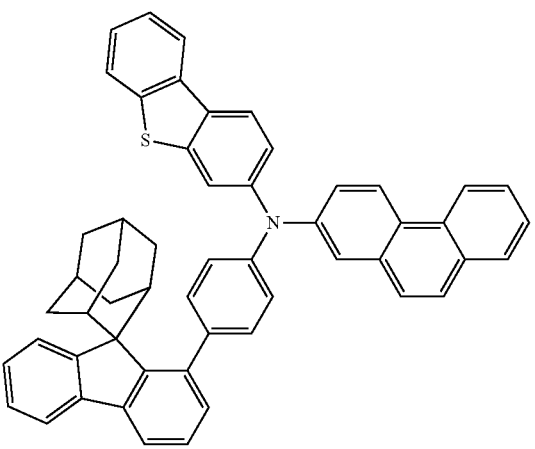
436
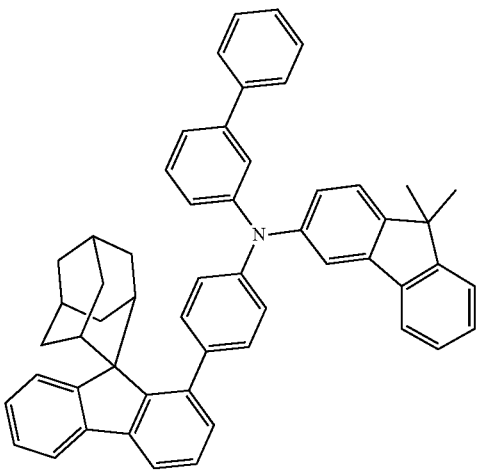
437
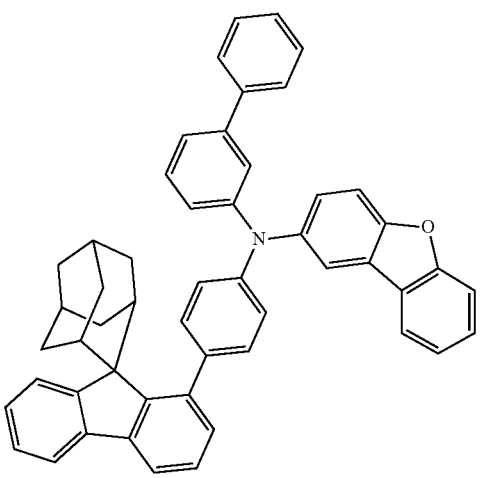
438
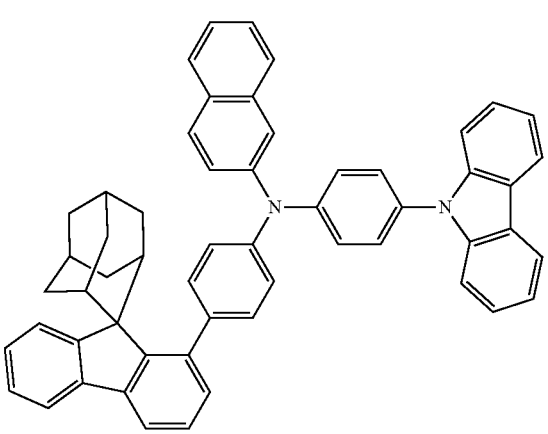

439
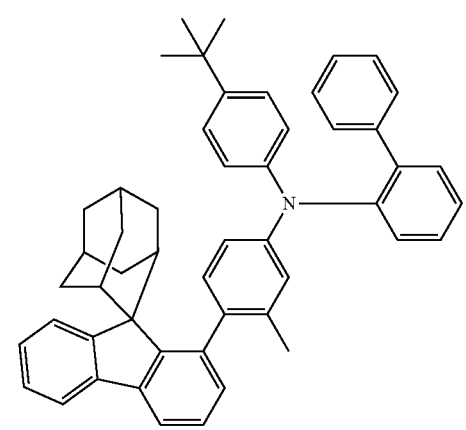
440
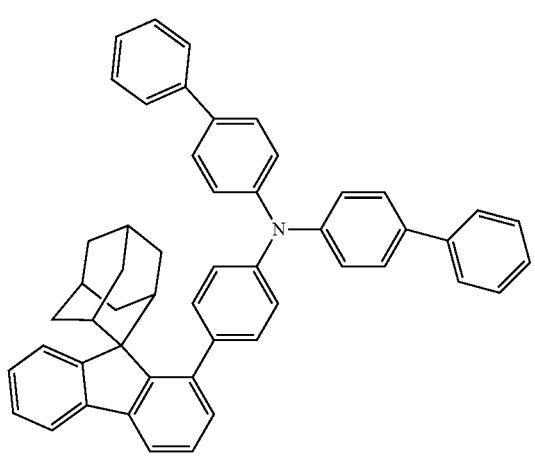
441
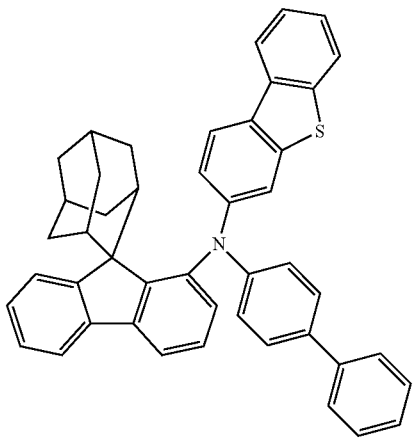
442
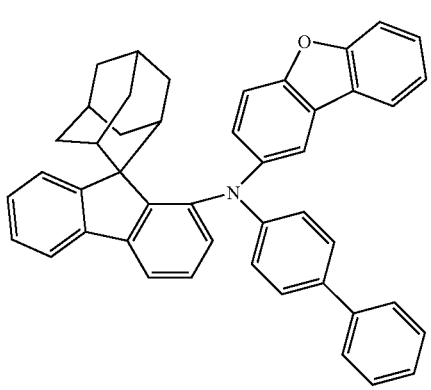
443
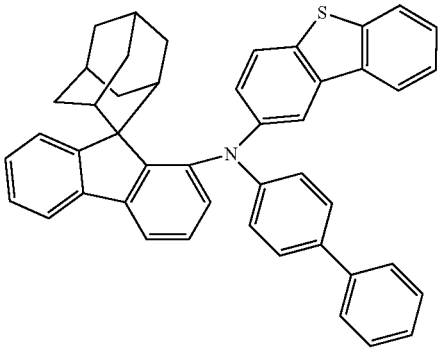
444
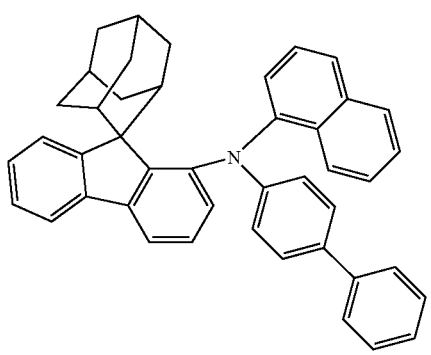
445

569 -continued
446
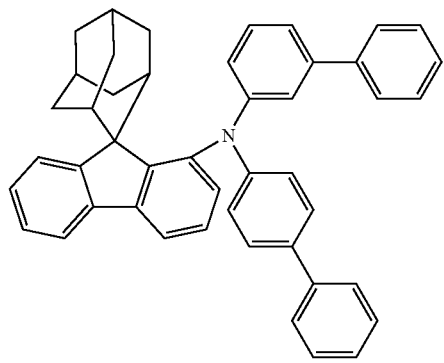
447
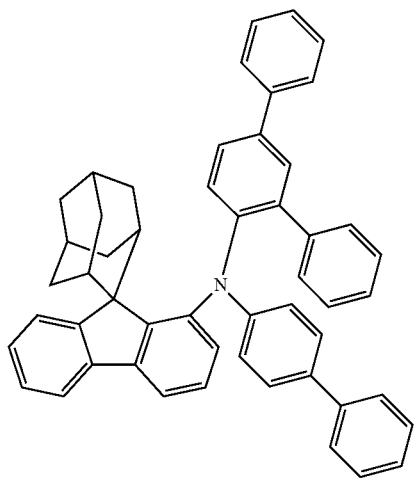
448
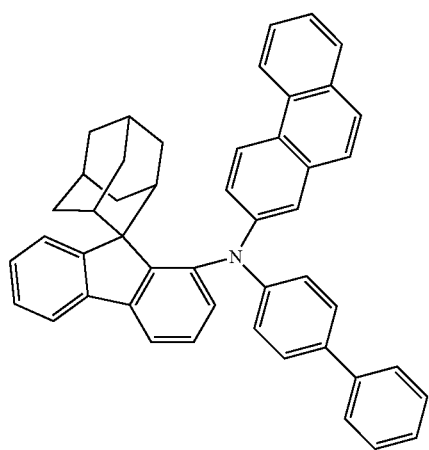
570 -continued
449
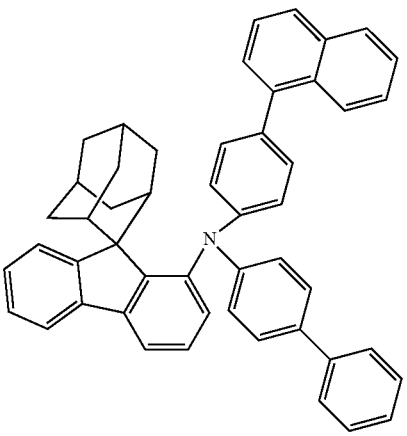
450
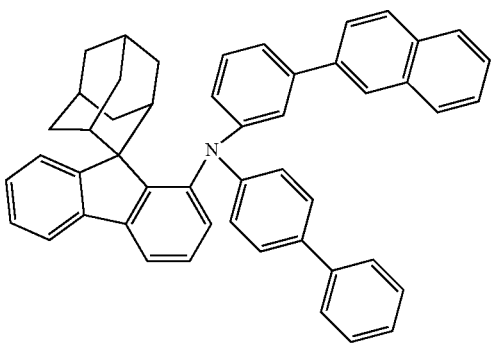
451
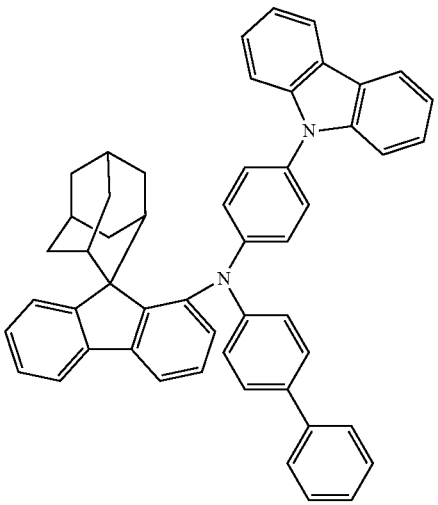

| 452 | 455 |
|---|---|
| 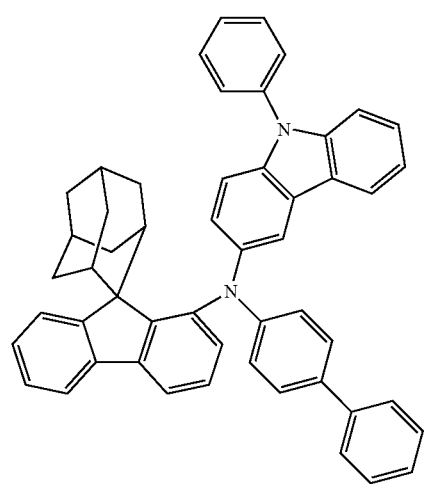 | 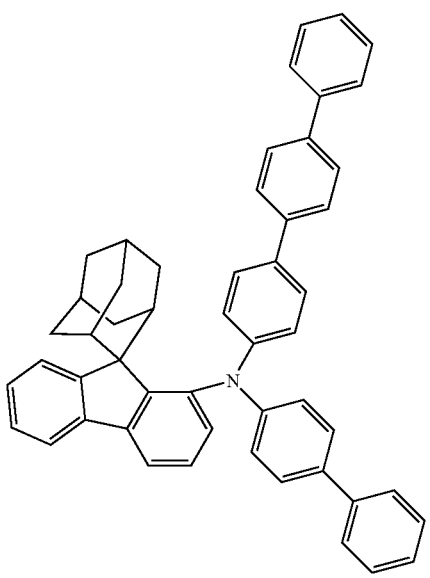 |
| 453 | 456 |
| 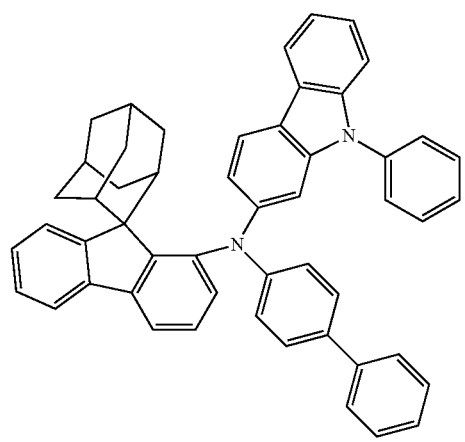 | 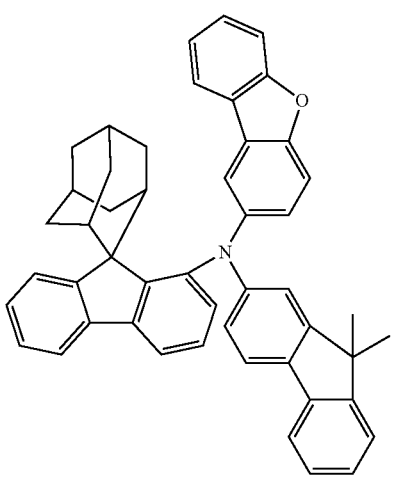 |
| 454 | 457 |
| 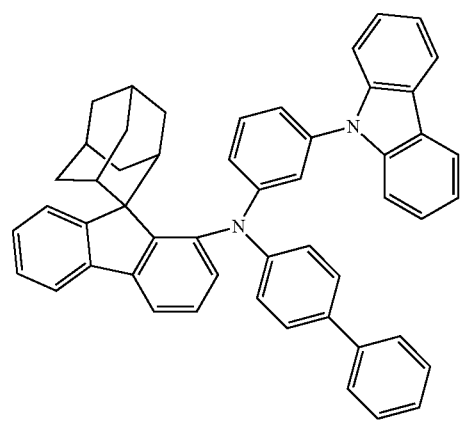 | 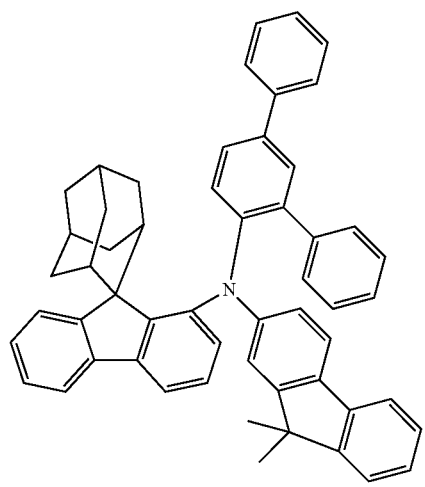 |

| 573 -continued | 574 -continued |
|---|---|
| 458 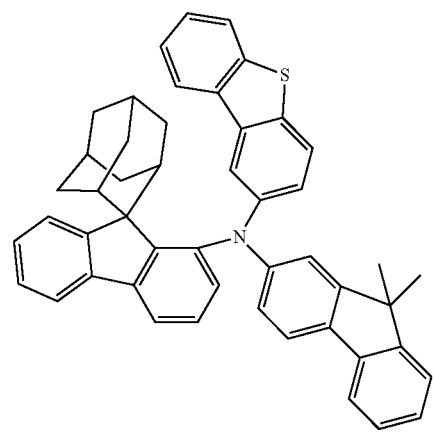 | 461 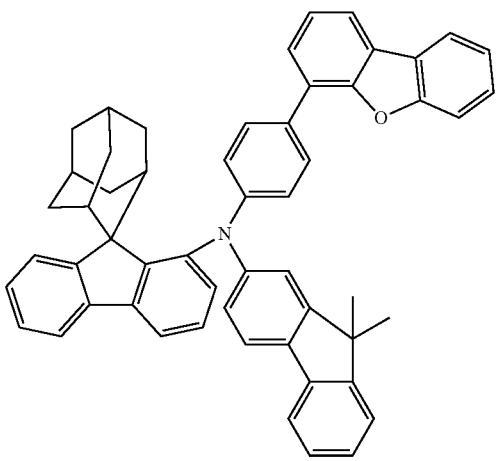 |
| 459 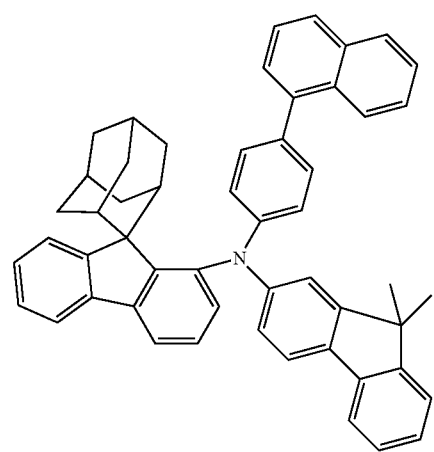 | 462 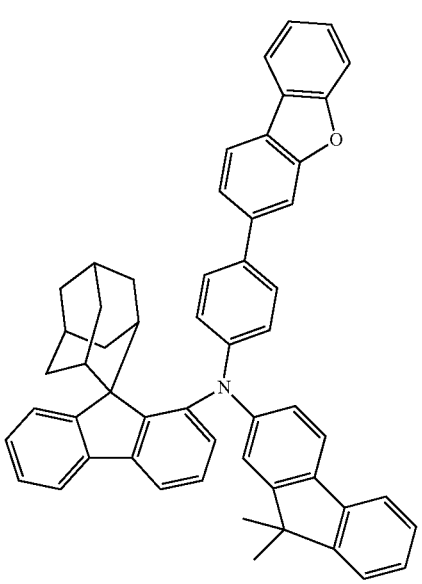 |
| 460 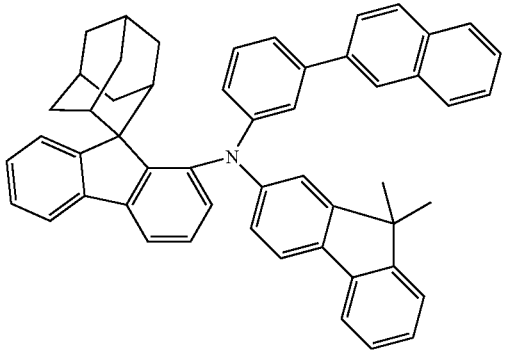 | 463 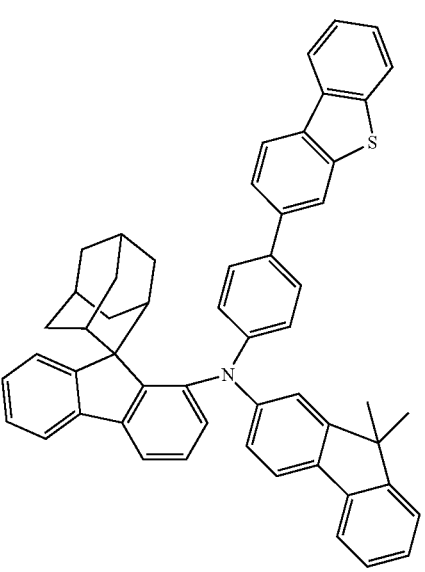 |

464
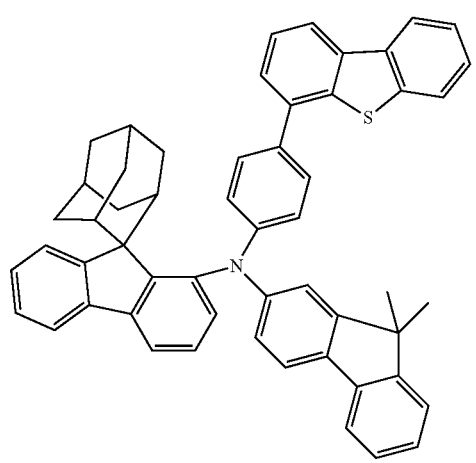
465
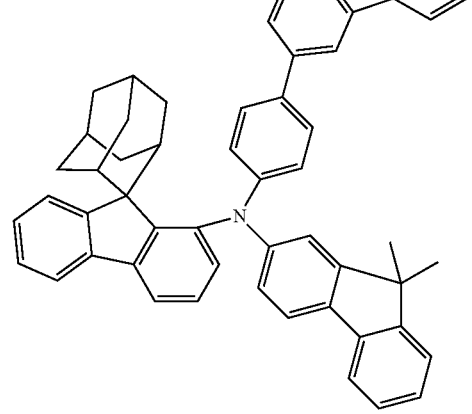
466
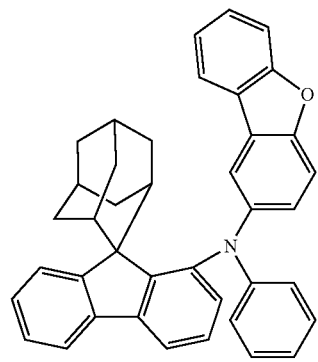
467
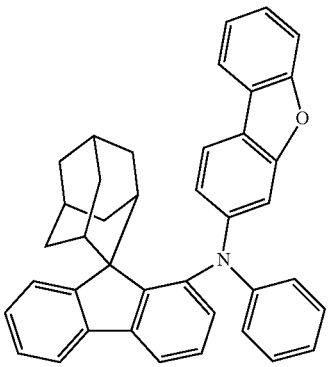
468
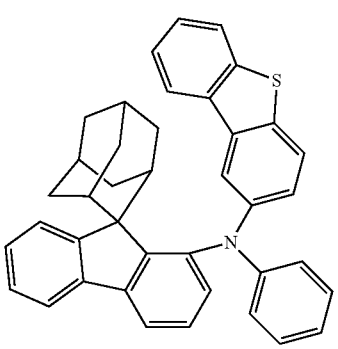
469
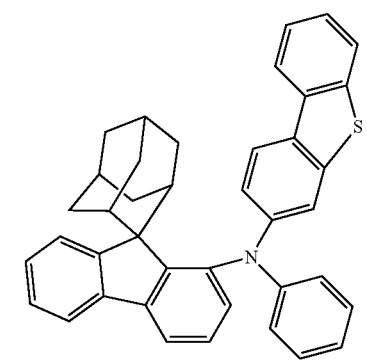
470
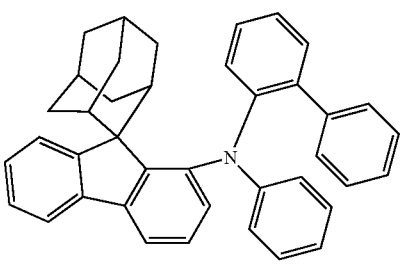

471
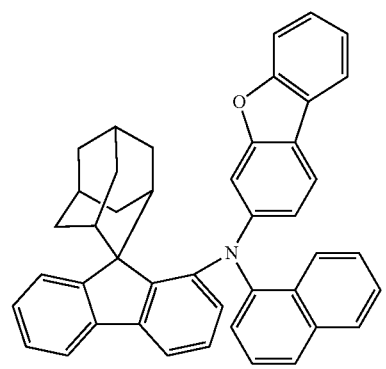
472
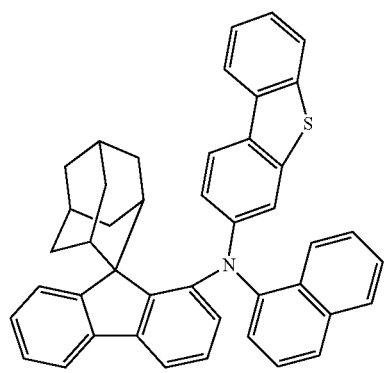
473
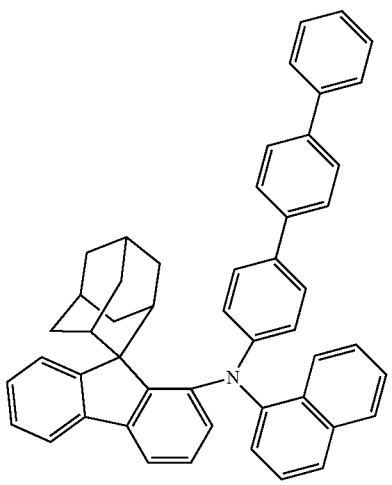
474
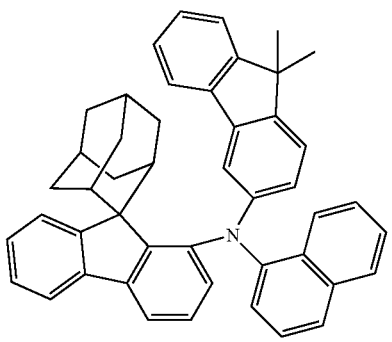
475
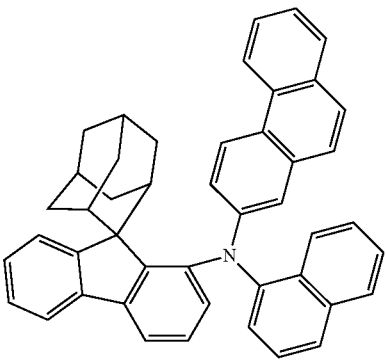
476
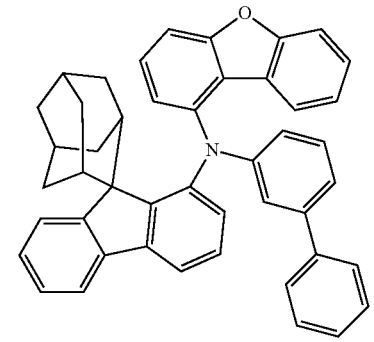
477
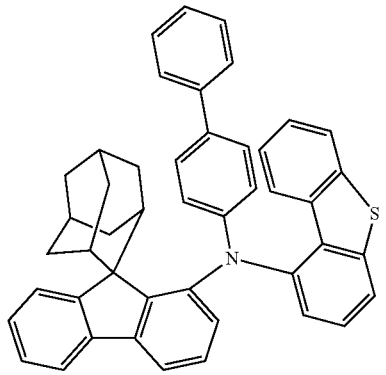
478
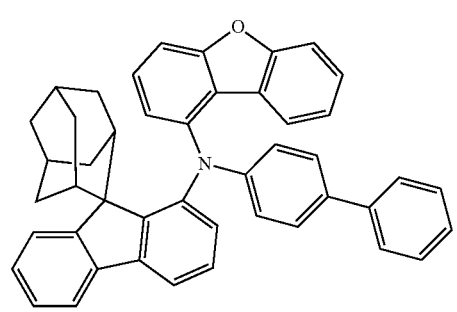

479
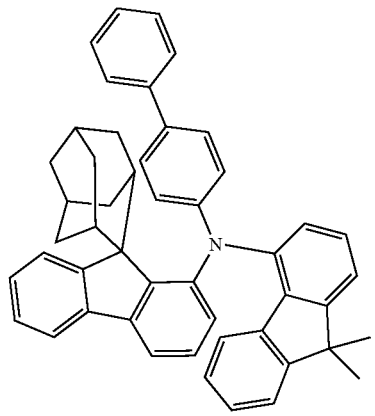
480
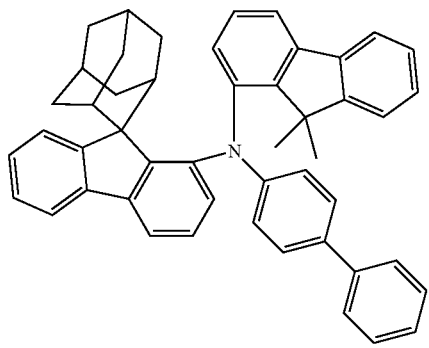
481
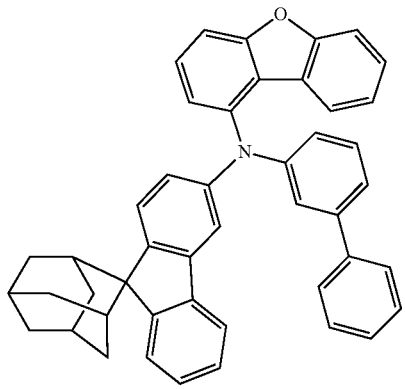
482
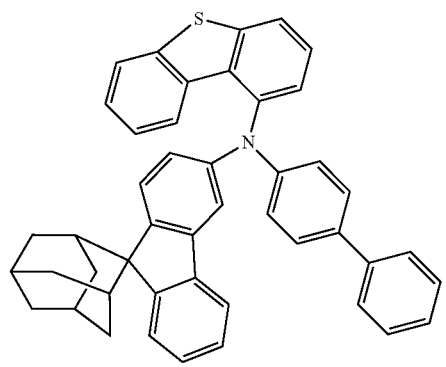
483
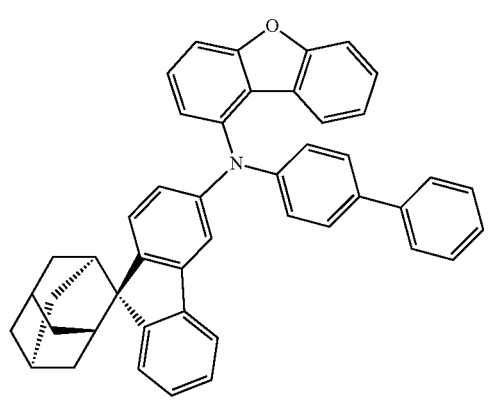
484
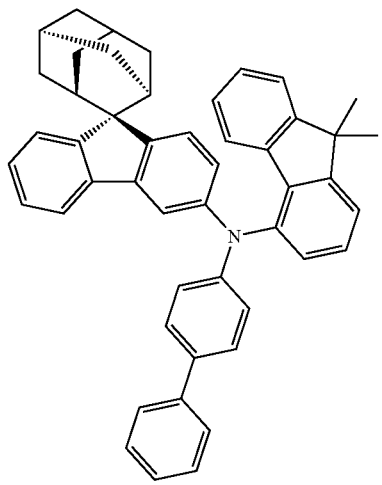
485
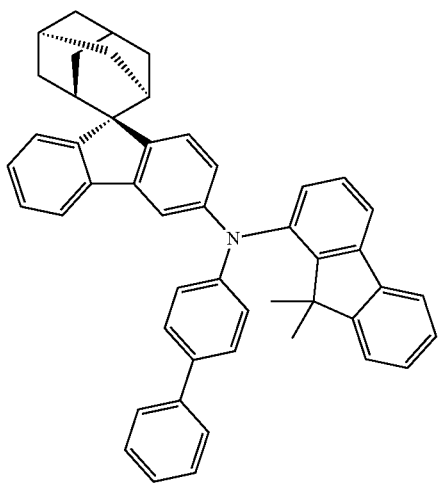

486
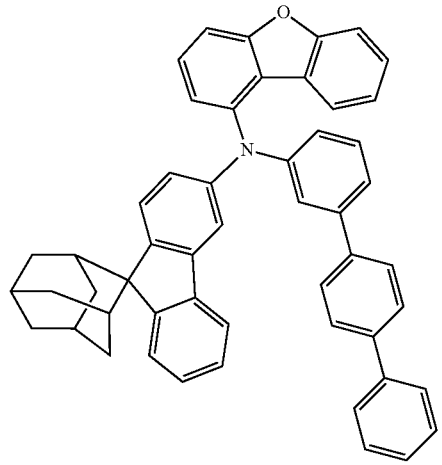
487
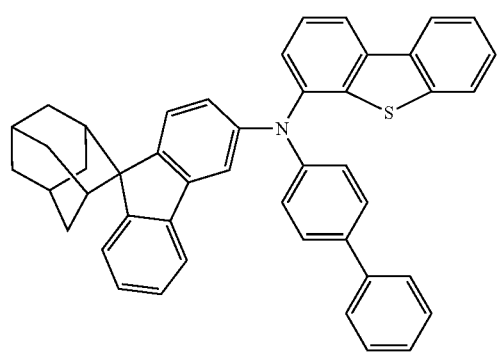
488
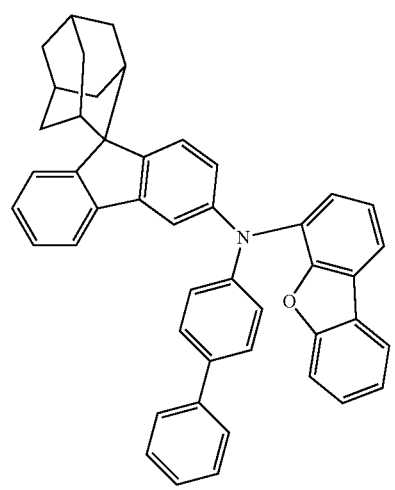
489
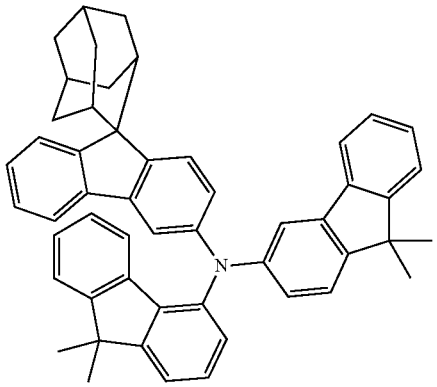
490
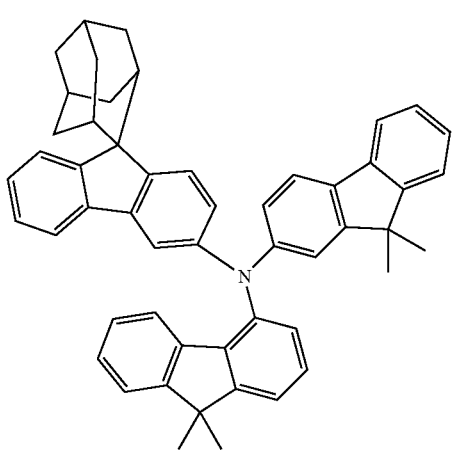
491
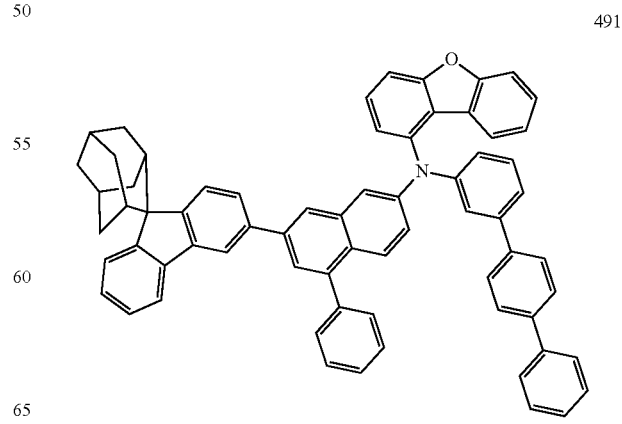

492
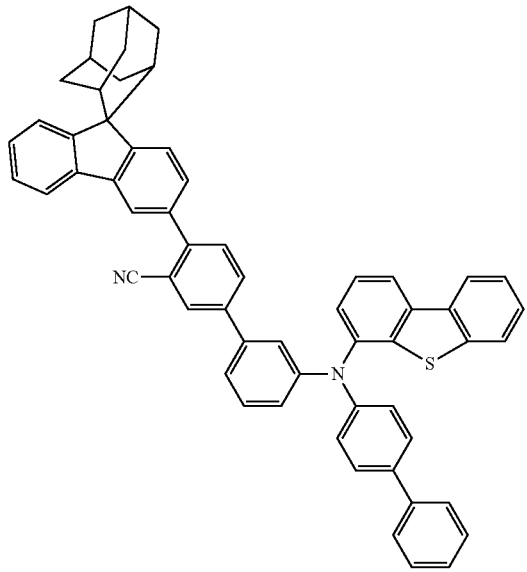
493
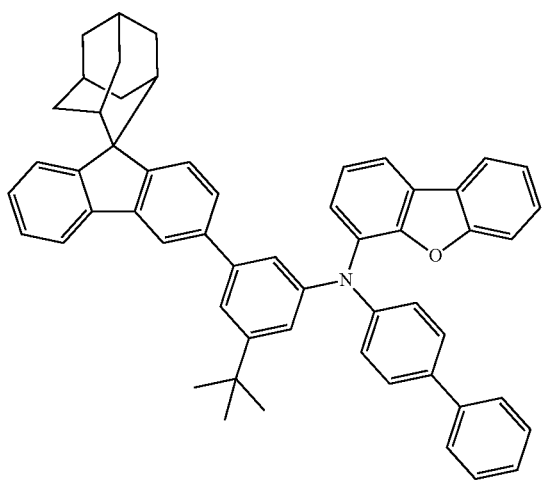
494
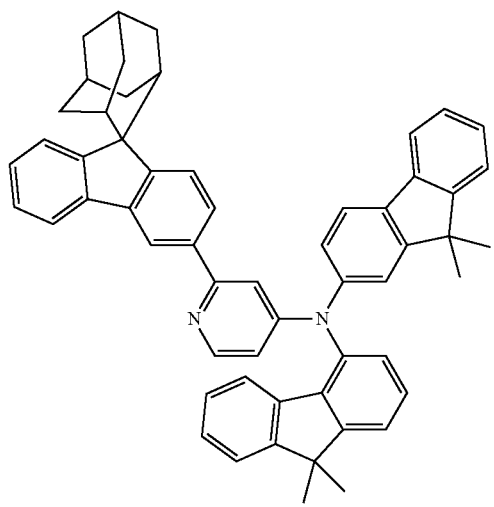
495
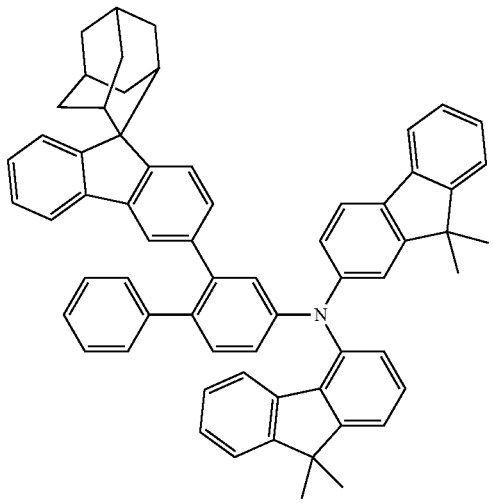
496
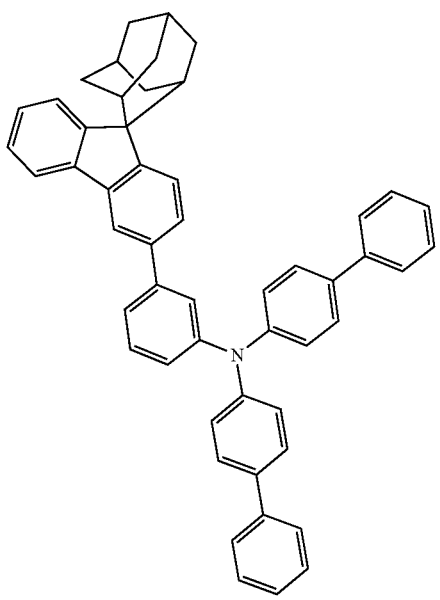
497
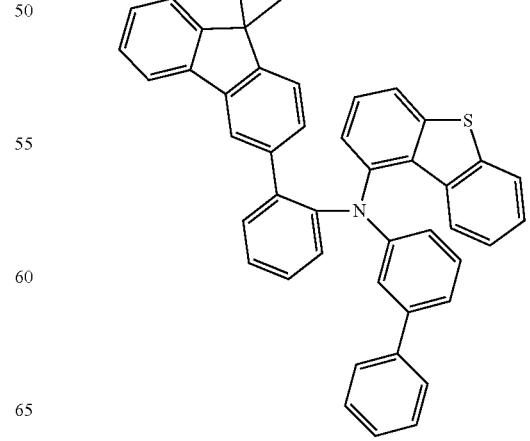

585
-continued
498
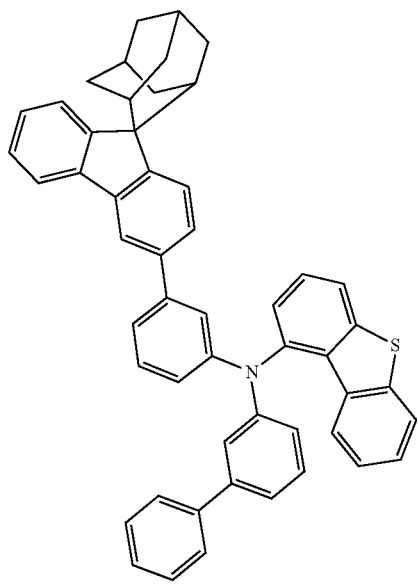
499
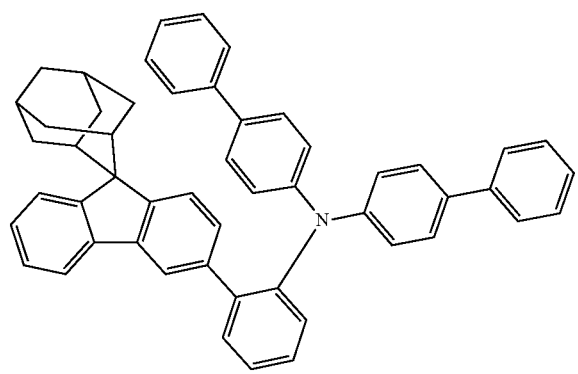
500
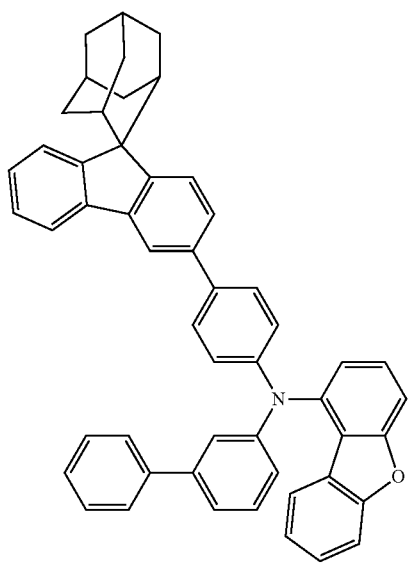
586
-continued
501
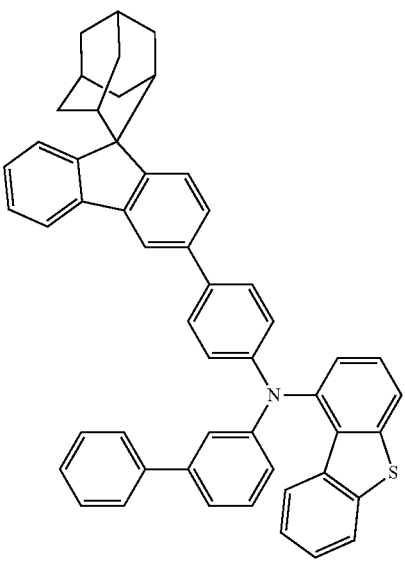
502
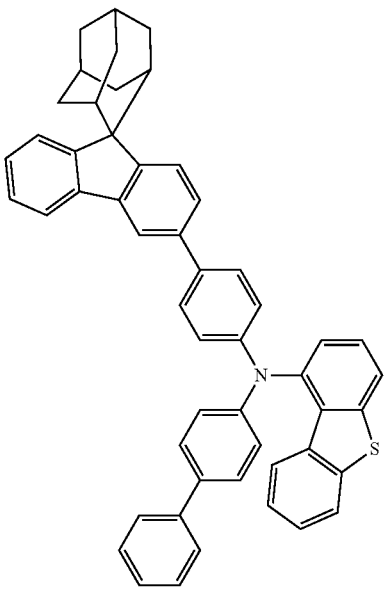

587
-continued
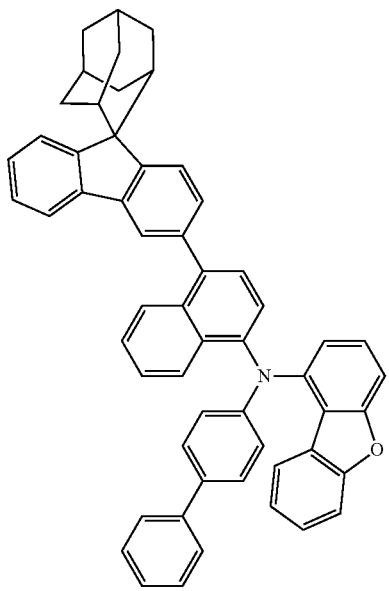
503
588
-continued
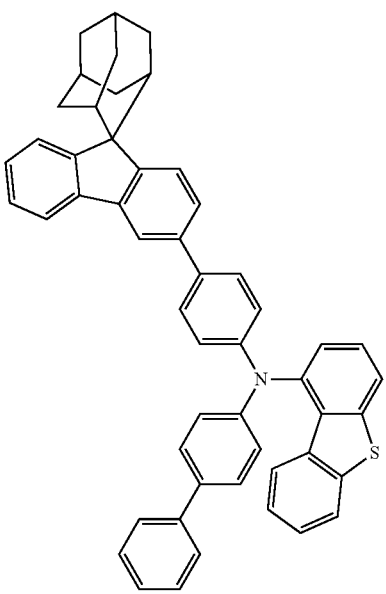
505
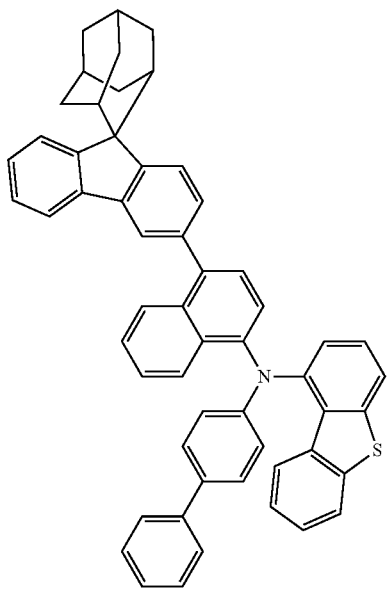
504
506

589
-continued
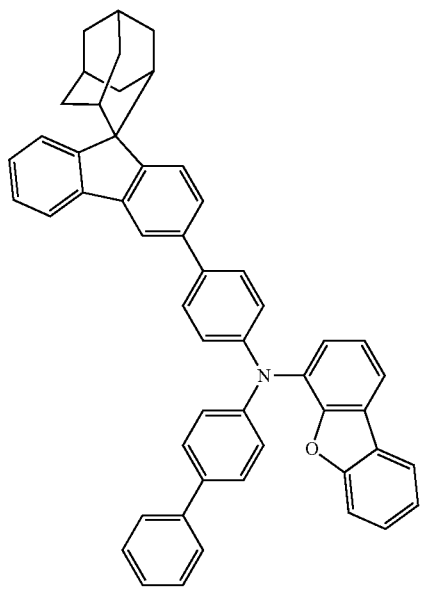
507
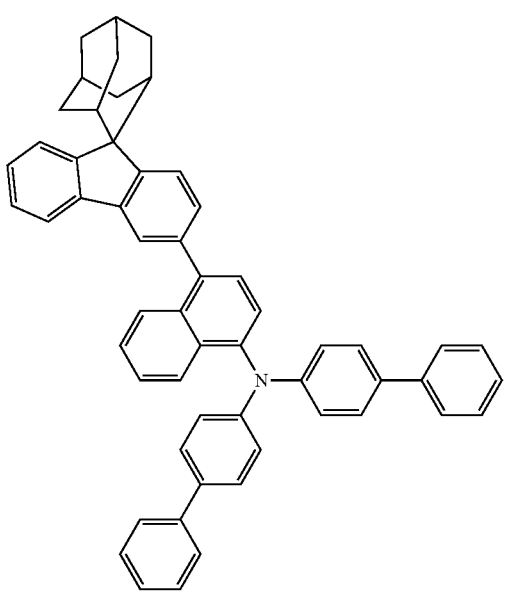
508
590
-continued
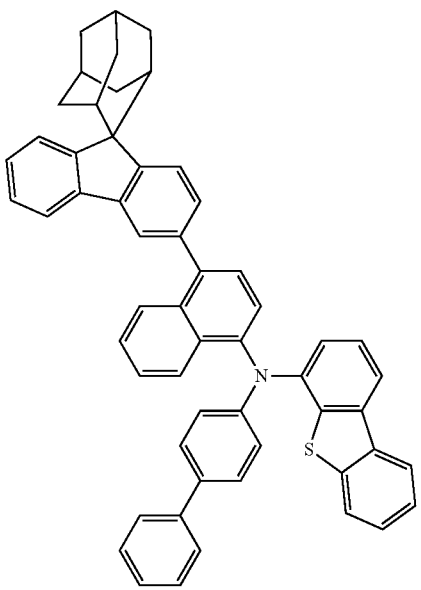
509
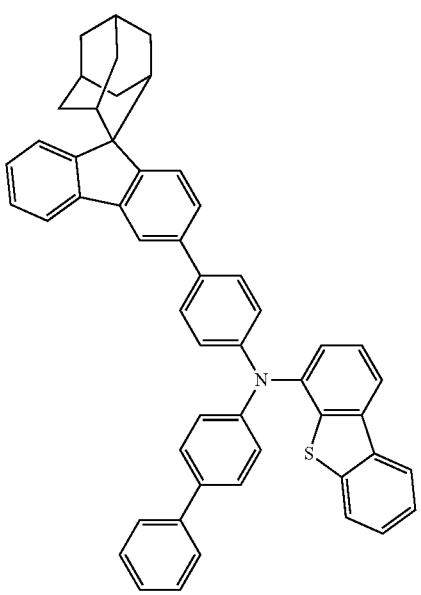
510

591
-continued
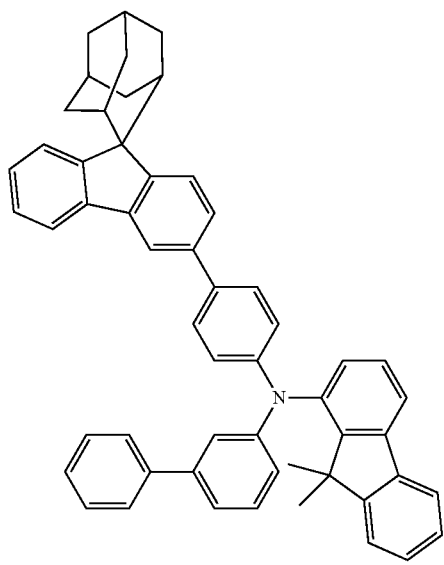
511
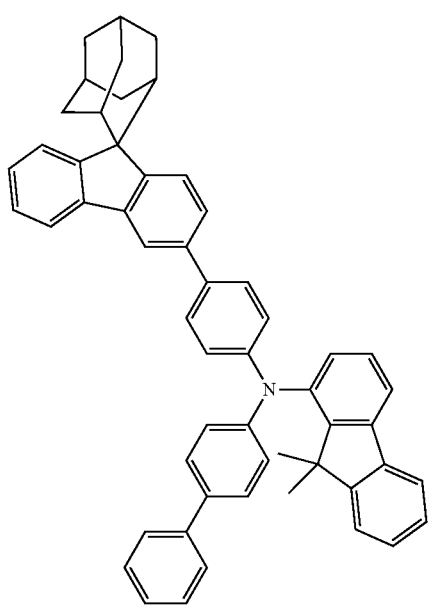
512
592
-continued
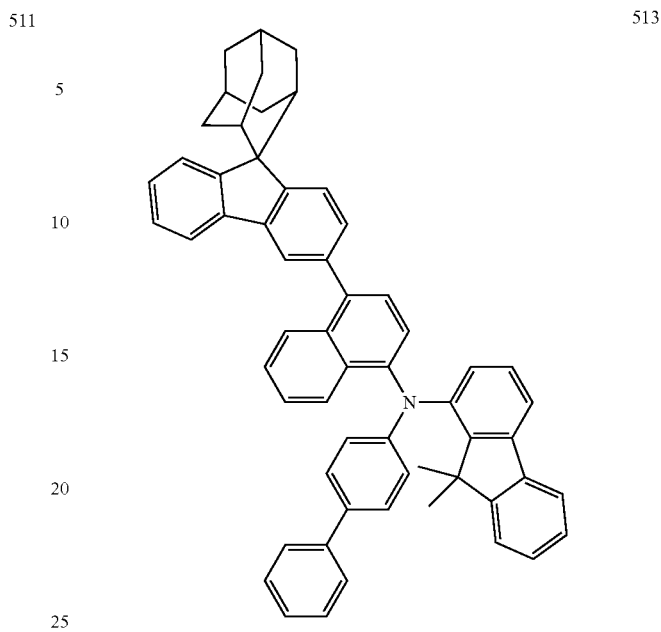
513
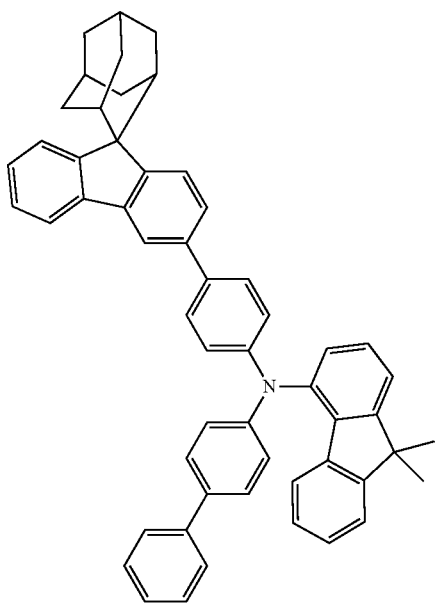
514

593
-continued
515
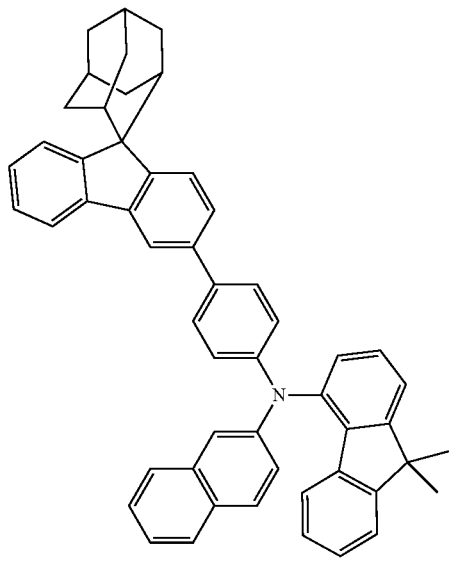
594
-continued
517
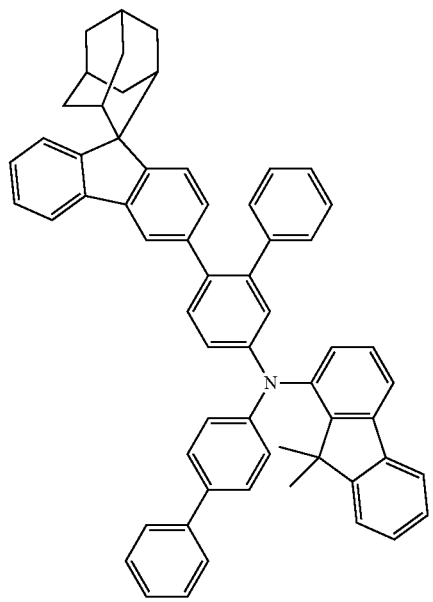
516
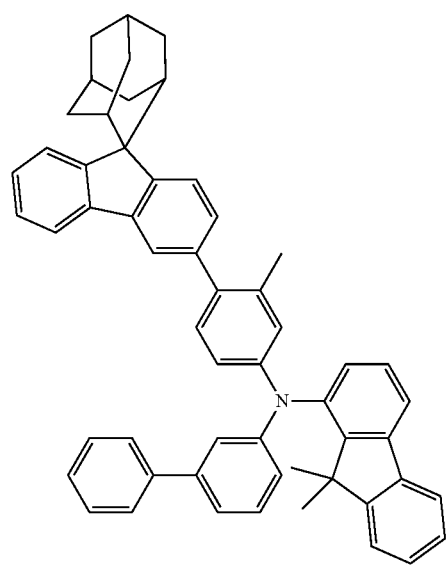
518
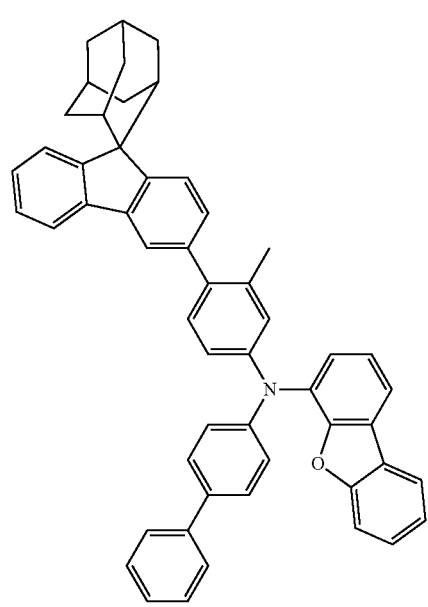

519
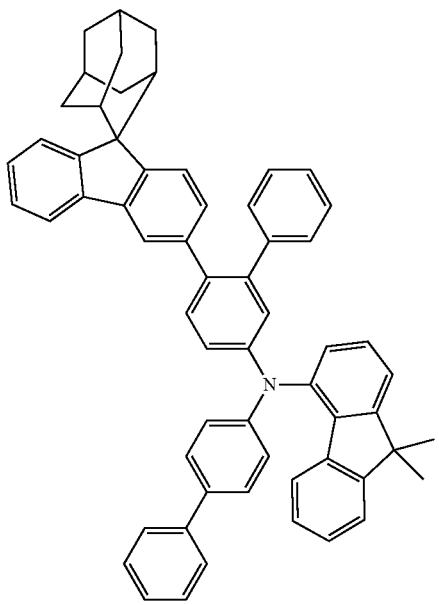
521
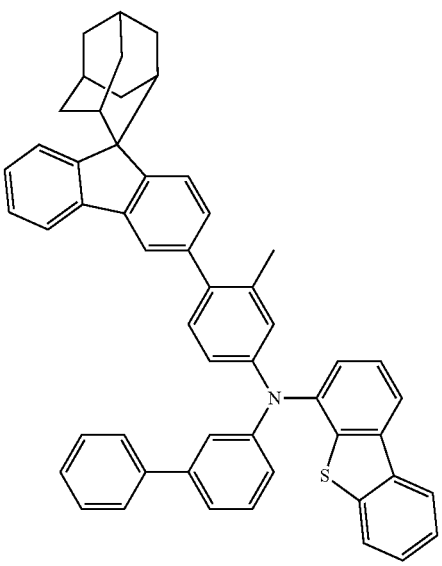
520
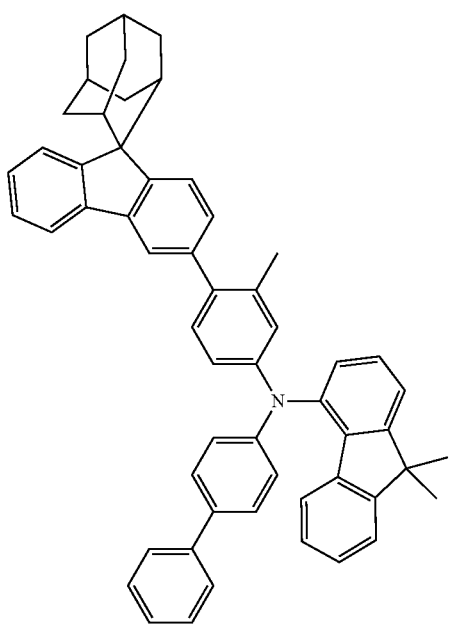
522
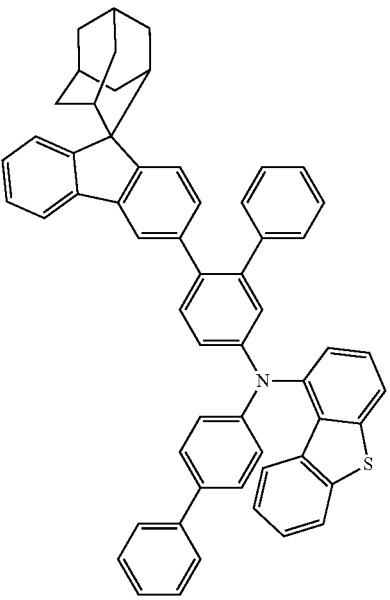

597
-continued
523
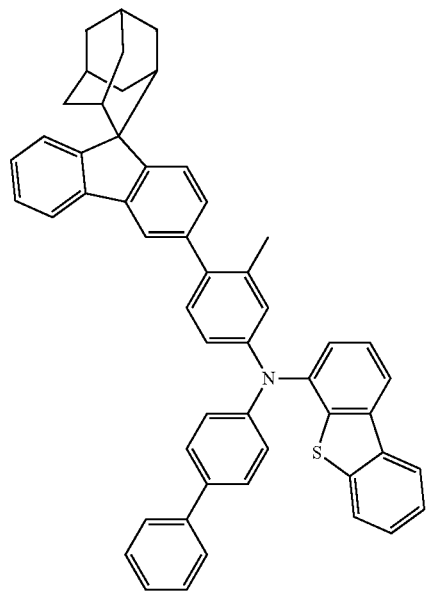
598
-continued
525
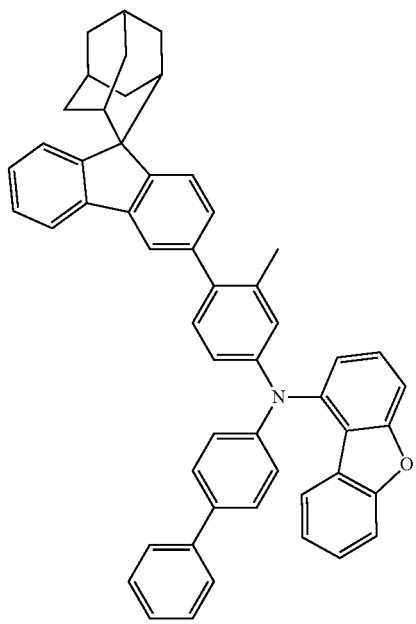
524
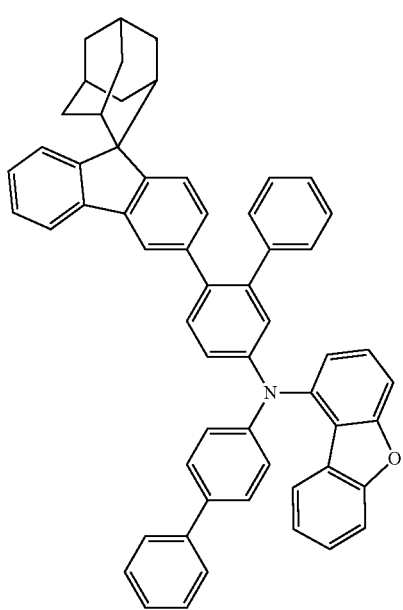
526
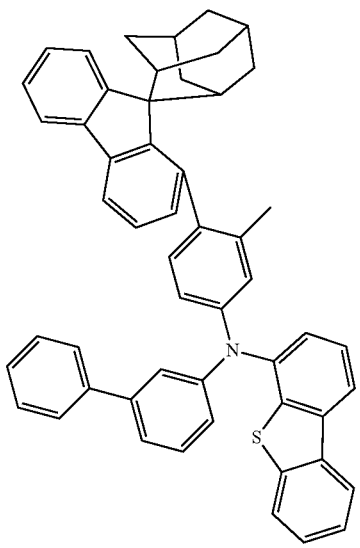

-continued
527
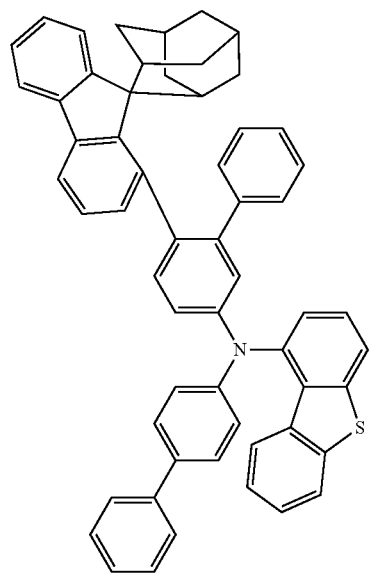
528
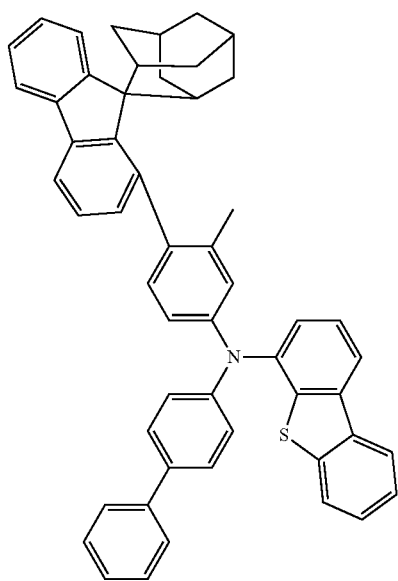
-continued
529
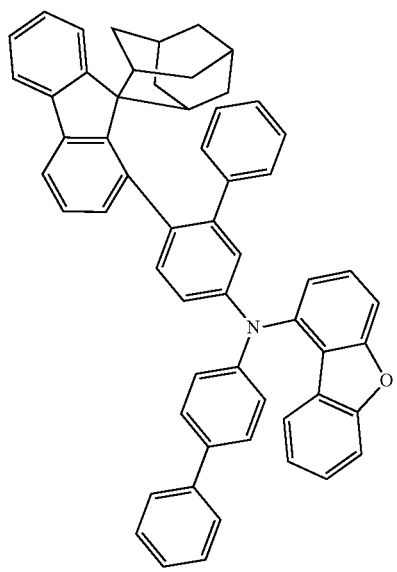
530
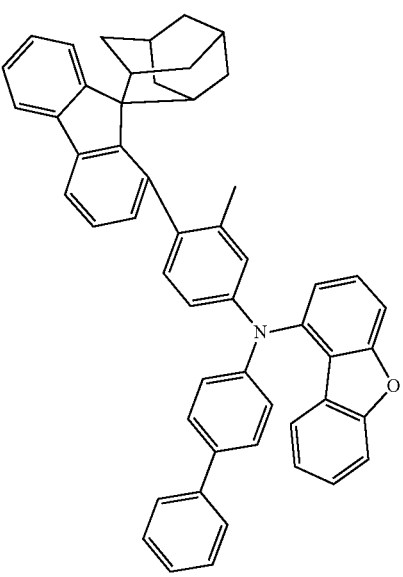
531

601
-continued
532
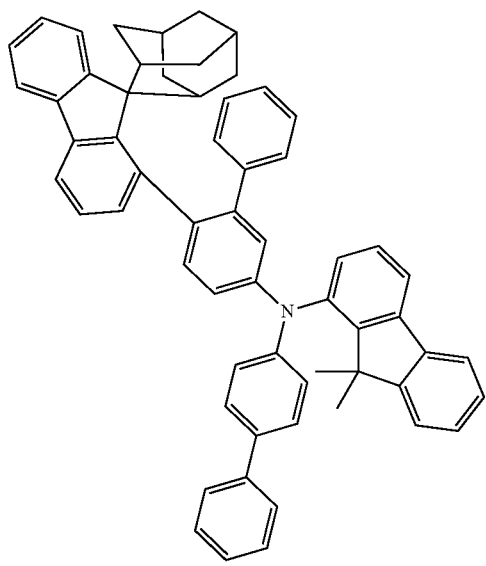
533
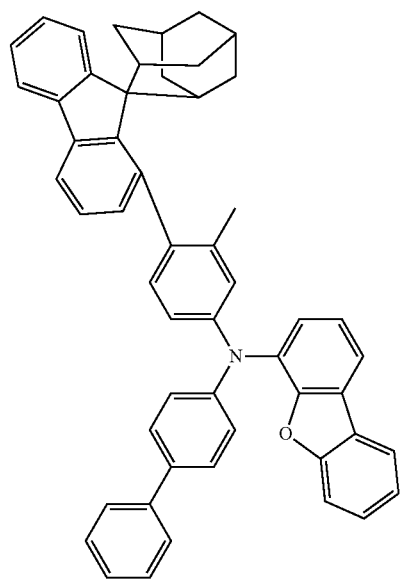
602
-continued
534
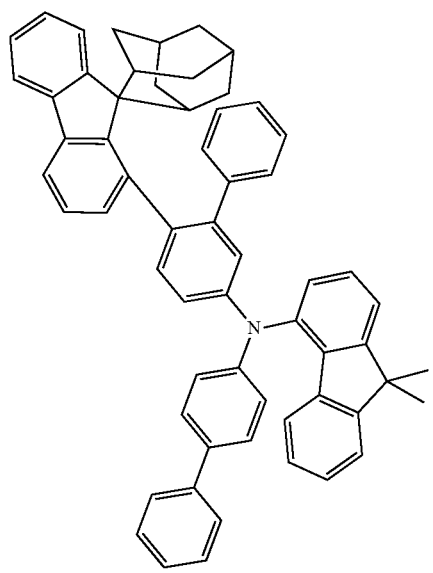
535
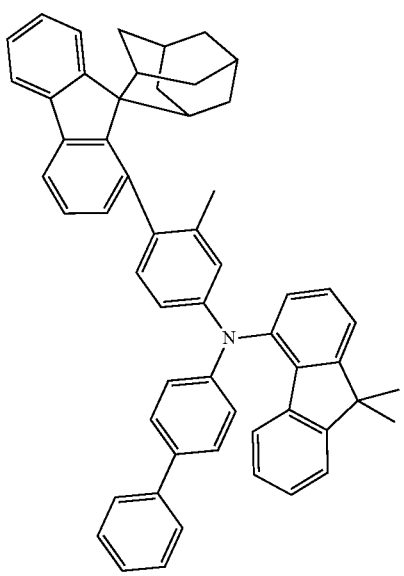
536
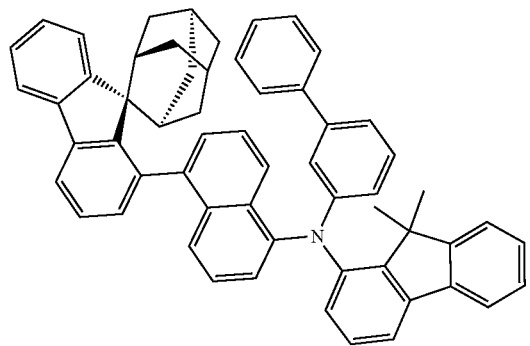

603
-continued
537
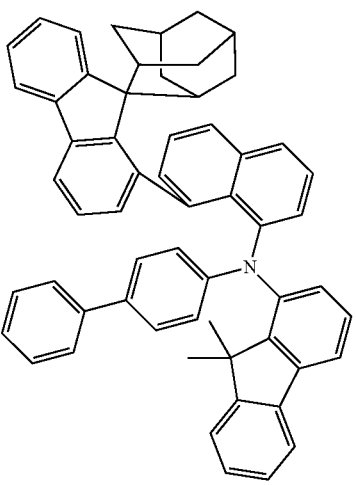
538
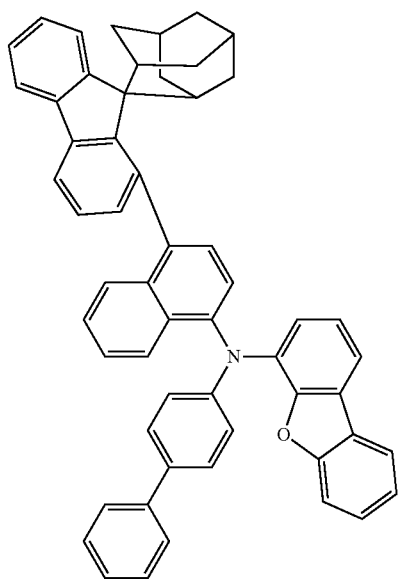
539
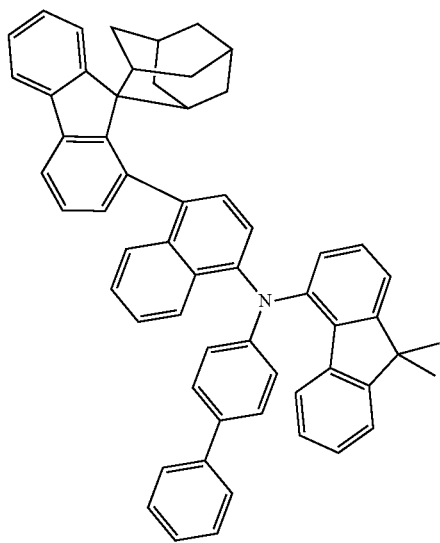
604
-continued
540
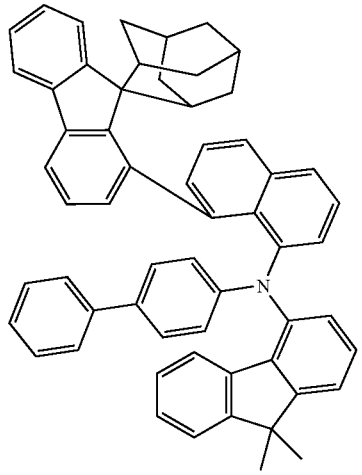
541
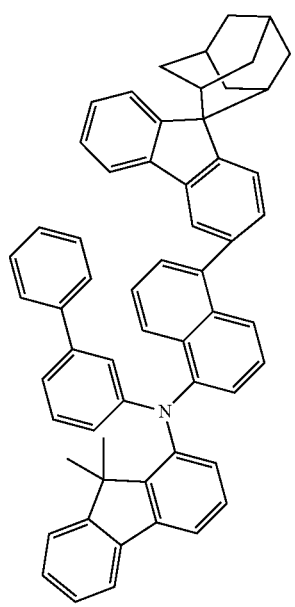
542
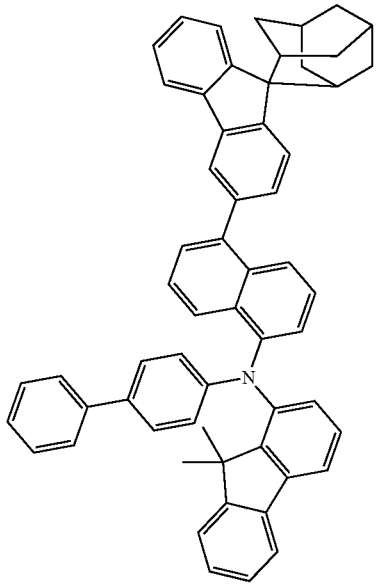

605
-continued
543
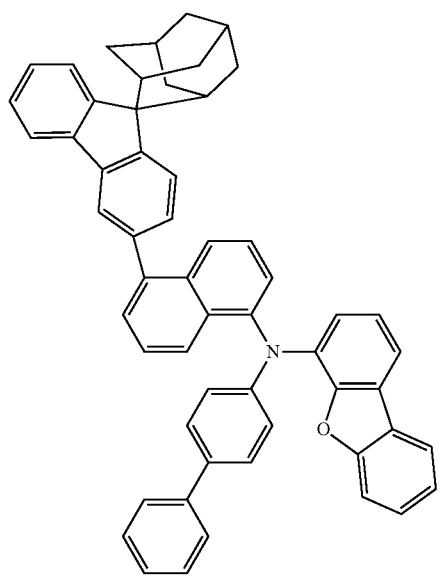
544
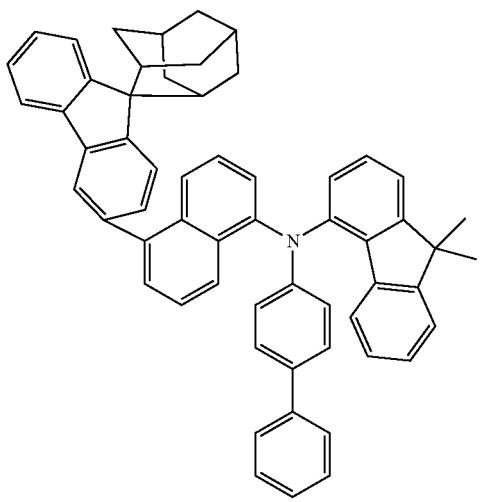
606
-continued
546
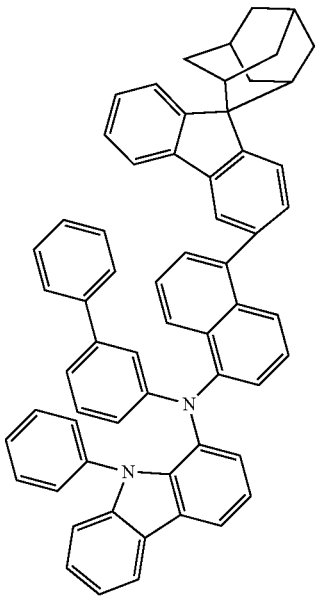
547
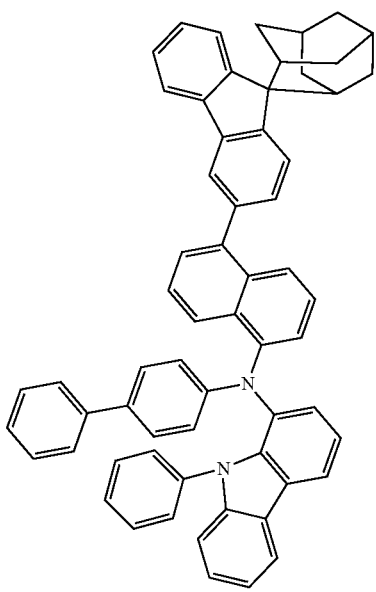

607
-continued
548
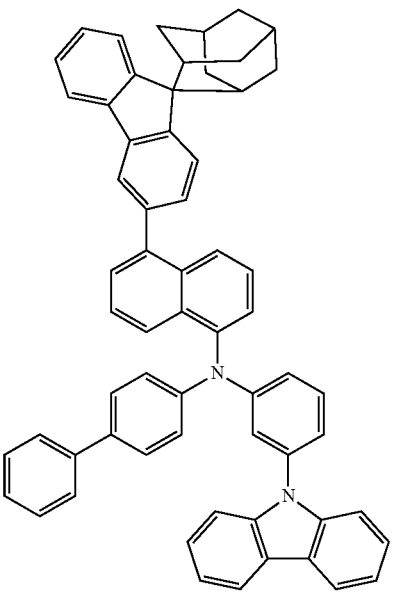
549
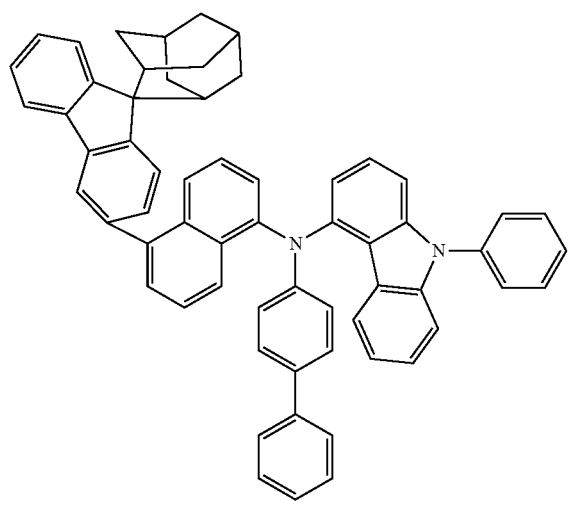
550
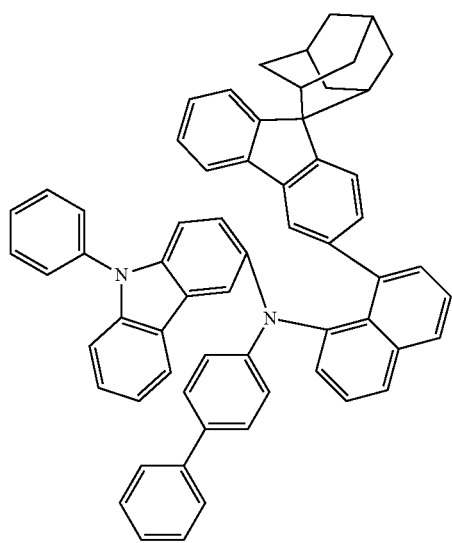
608
-continued
551
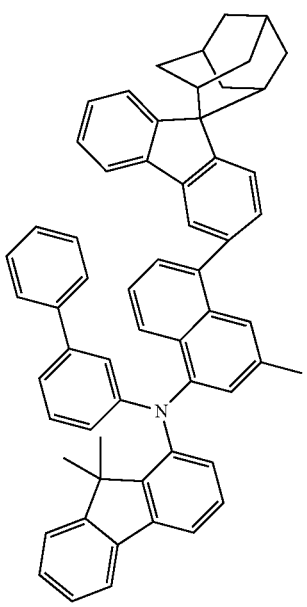
552
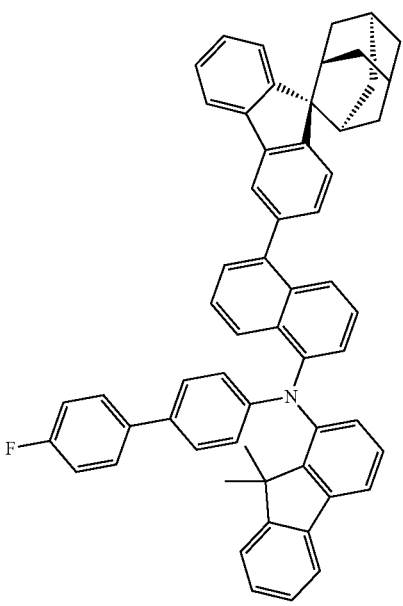

553
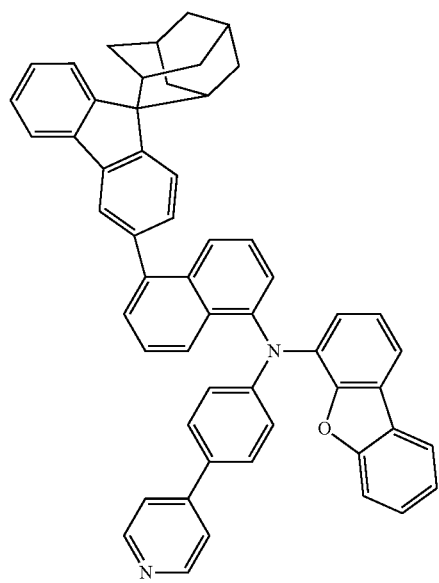
554
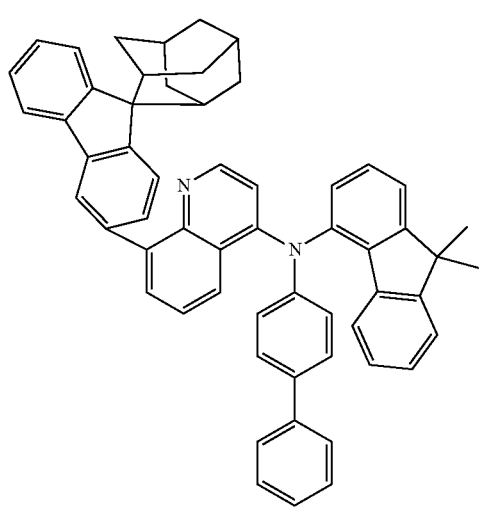
555
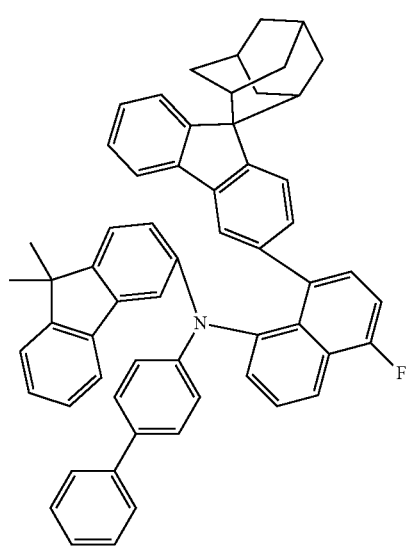
556
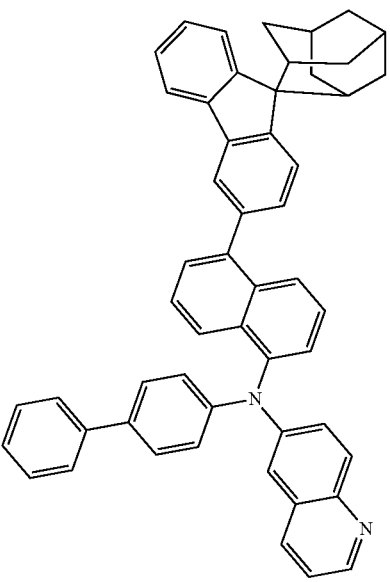
557
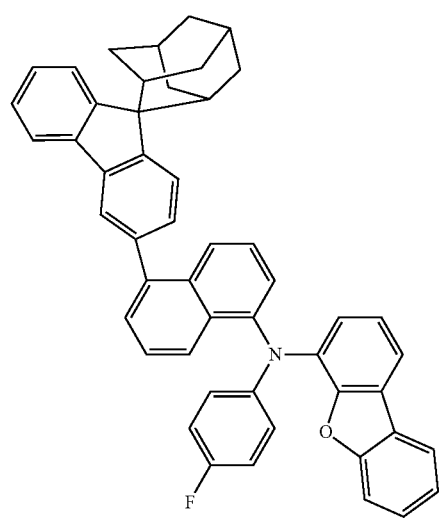
558
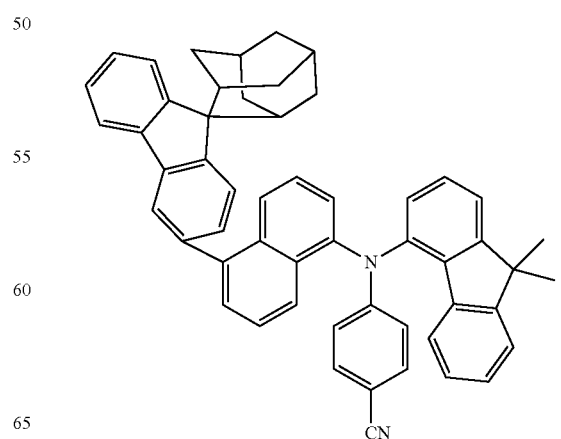

611
-continued
559
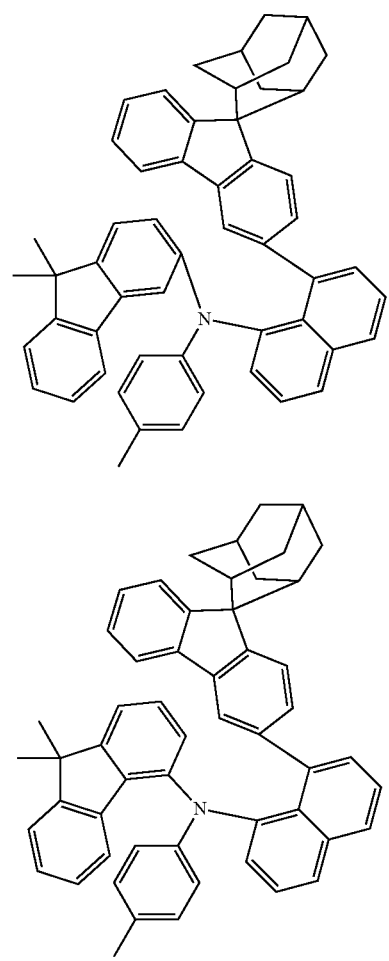
560
561
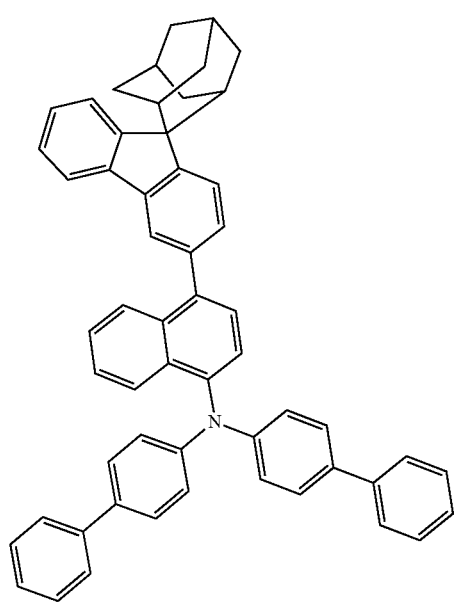
612
-continued
562
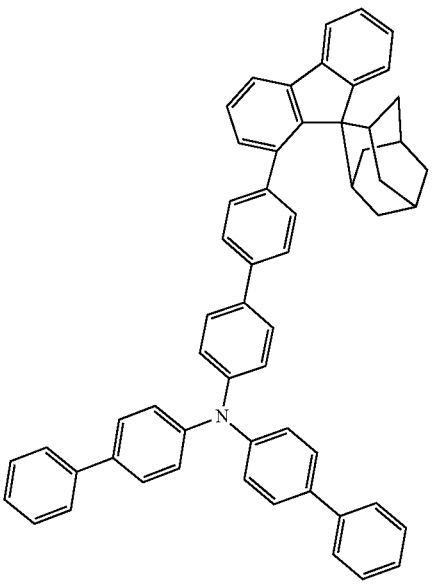
563
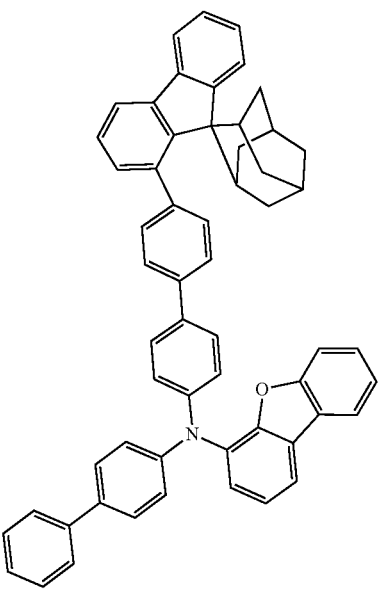

564
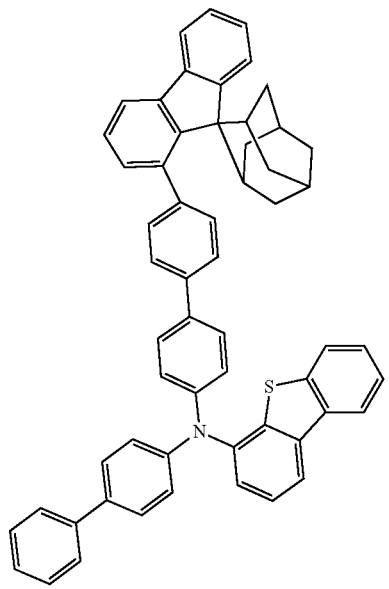
565
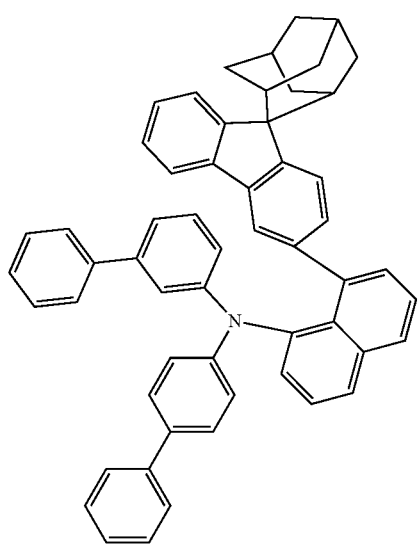
566
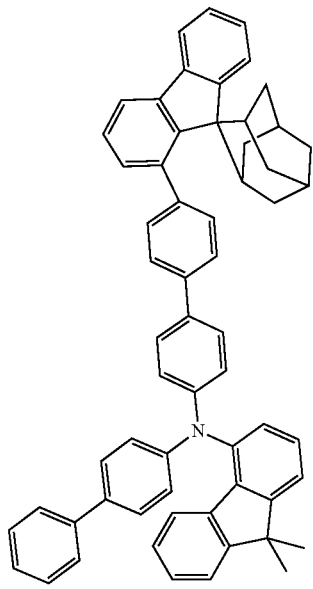
567
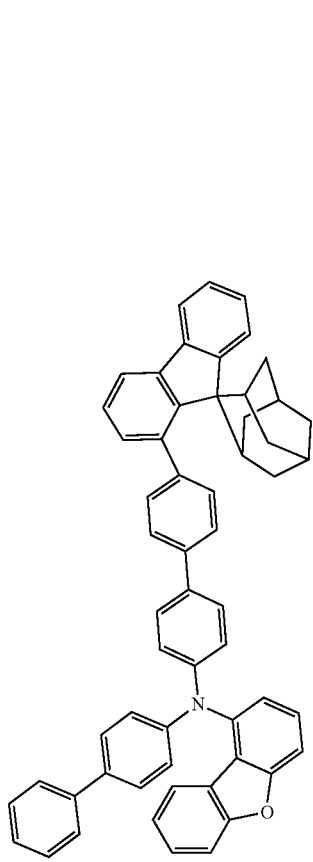

568
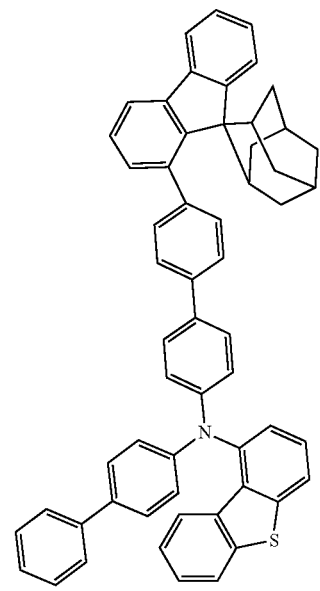
570
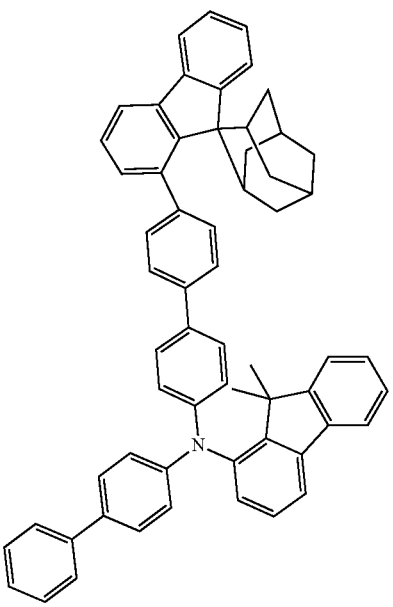
569
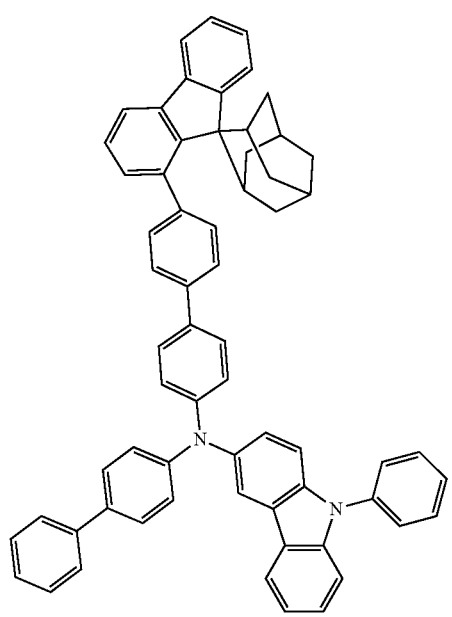
571
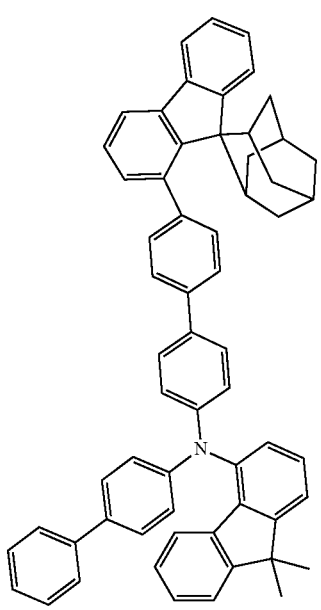

617
-continued
572
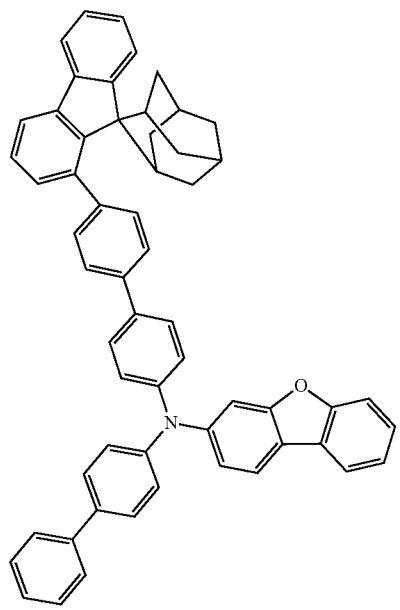
573
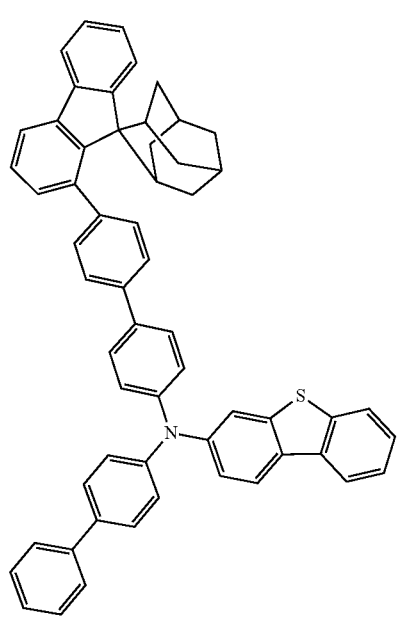
618
-continued
574
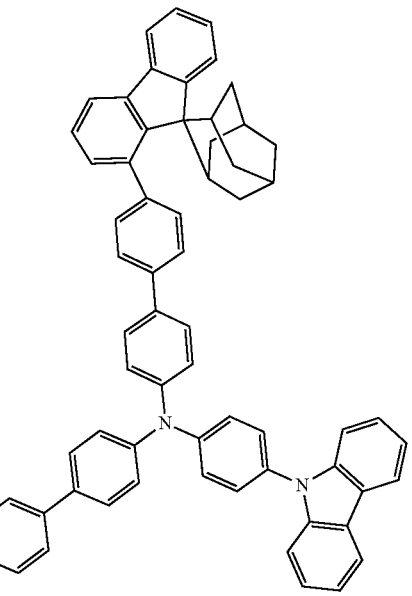
575
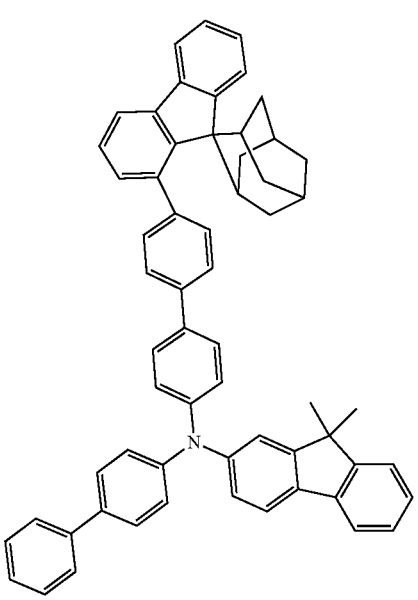

619
-continued
576
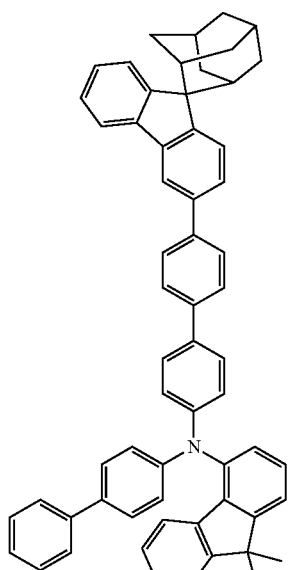
577
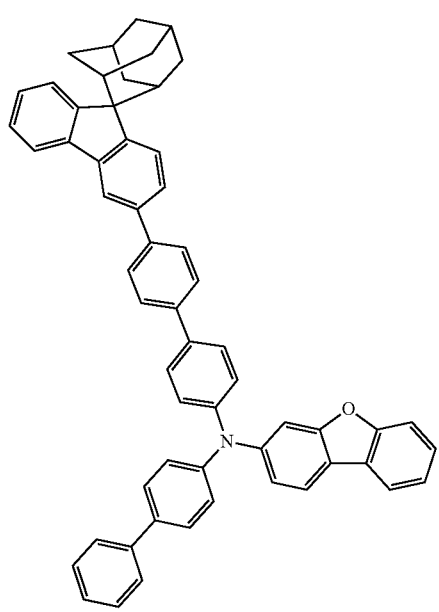
620
-continued
578
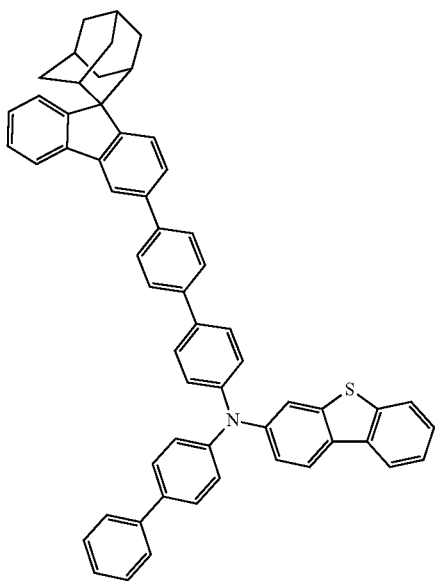
579
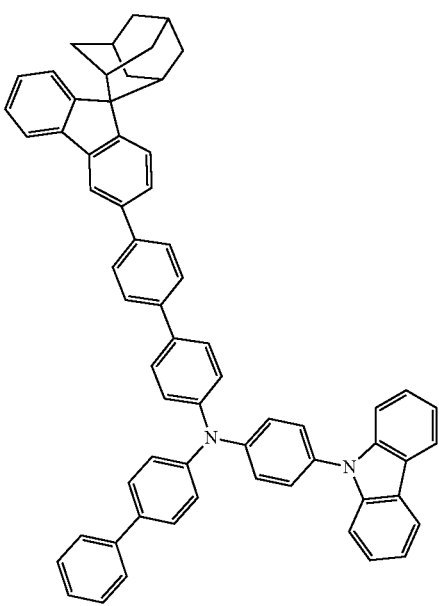

621
-continued
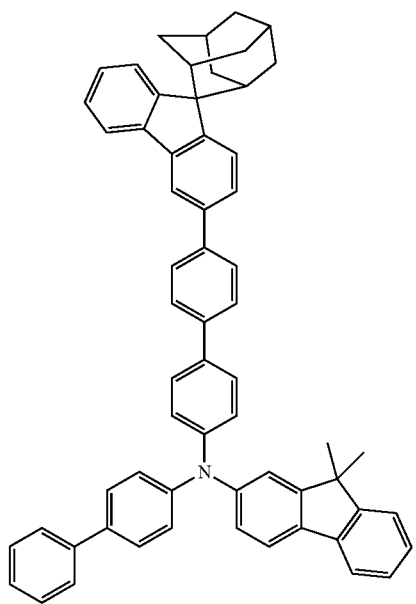
580
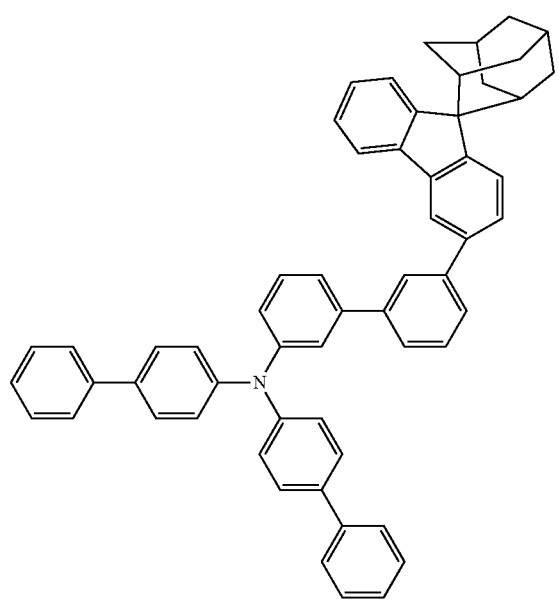
581
622
-continued
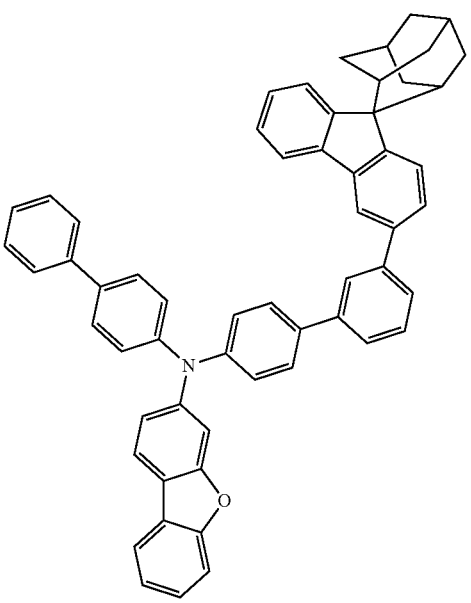
582
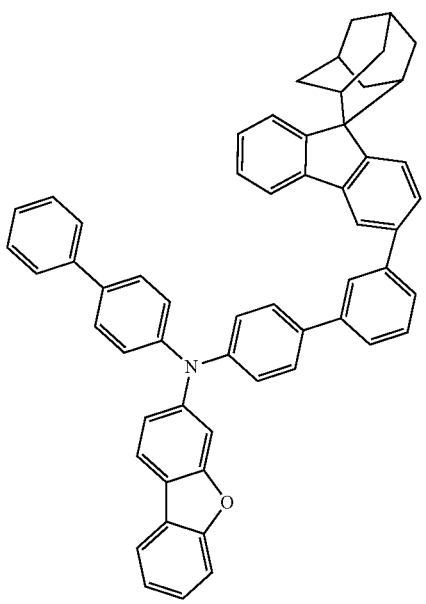
583

623
-continued
584
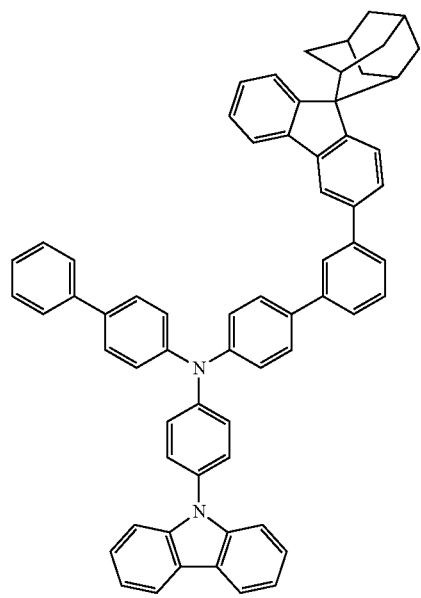
585
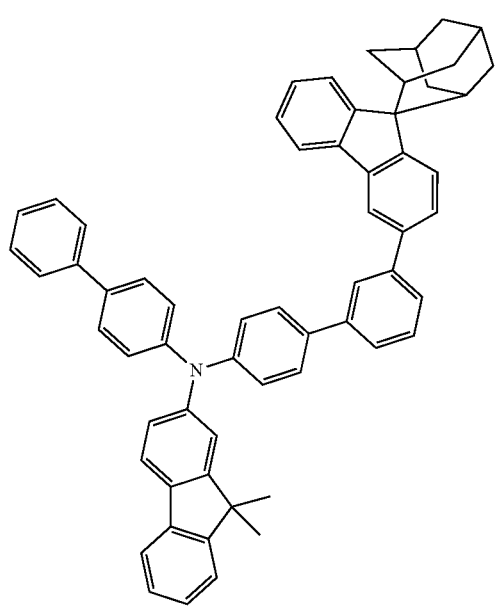
586
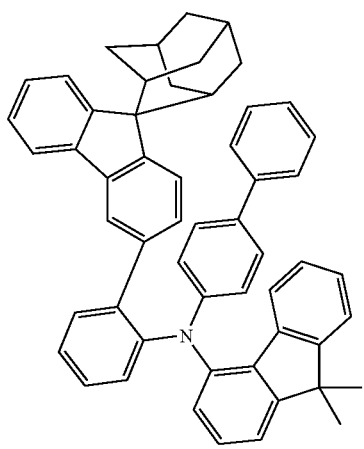
624
-continued
587
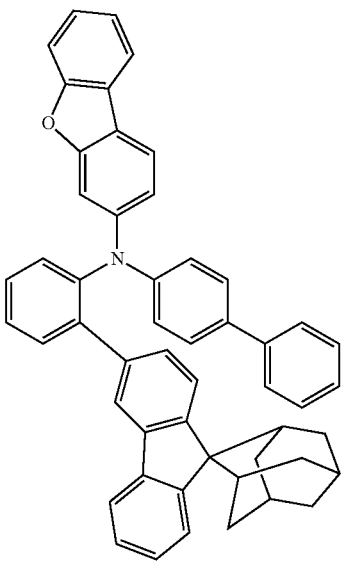
588
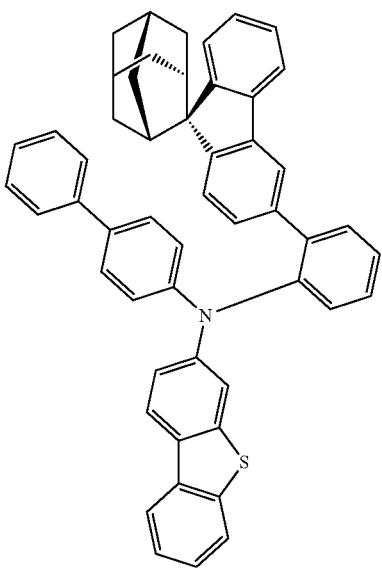

625
-continued
589
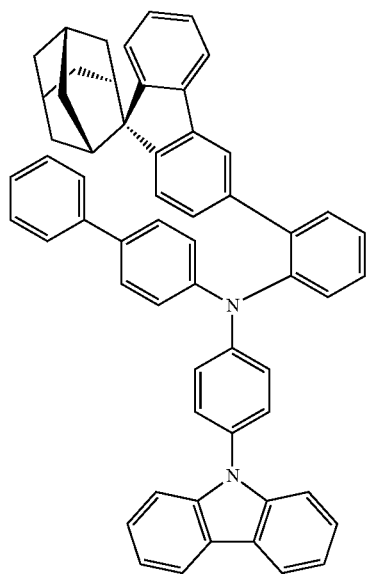
626
-continued
591
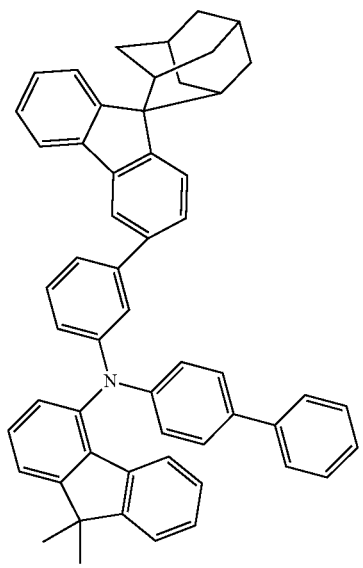
590
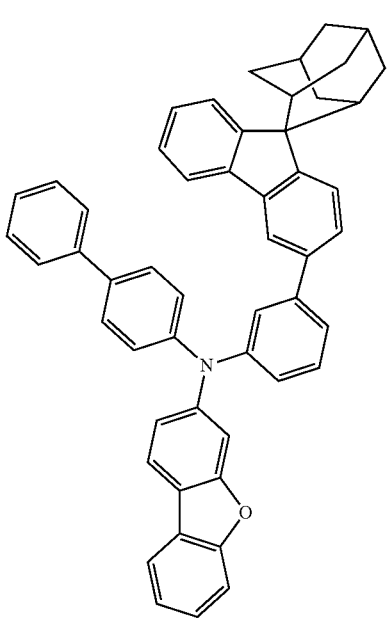
592

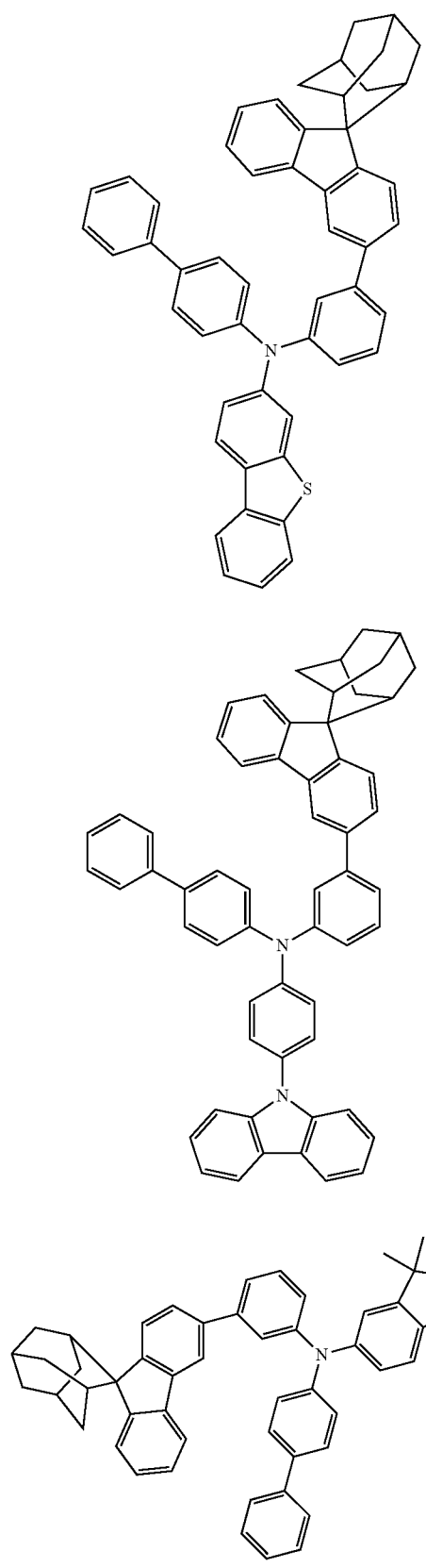
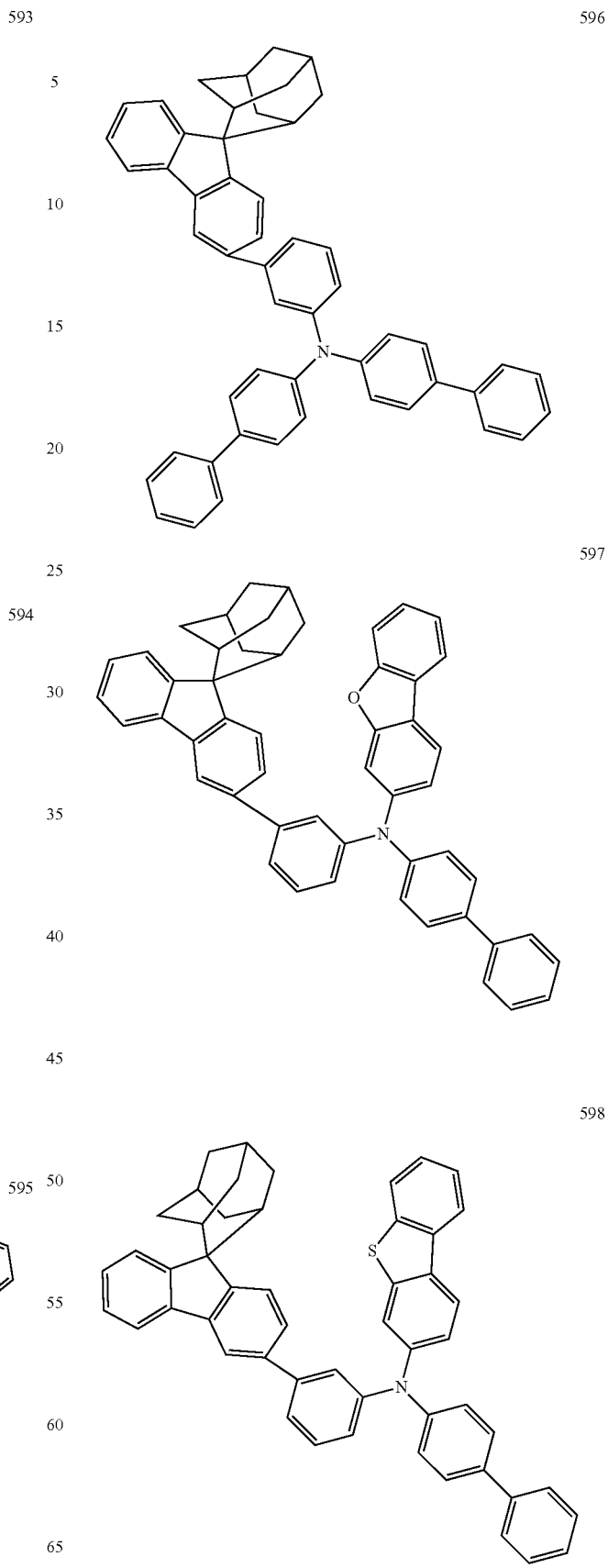

-continued
599
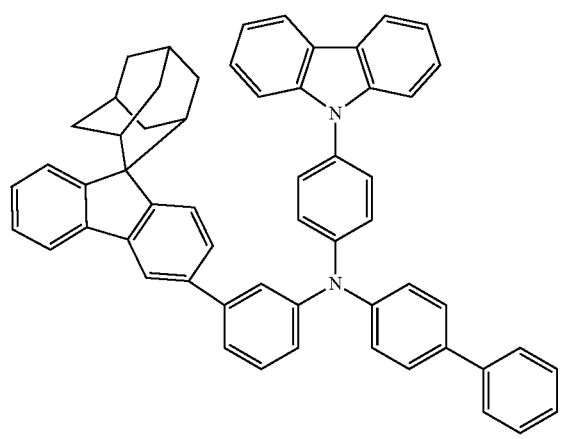
600
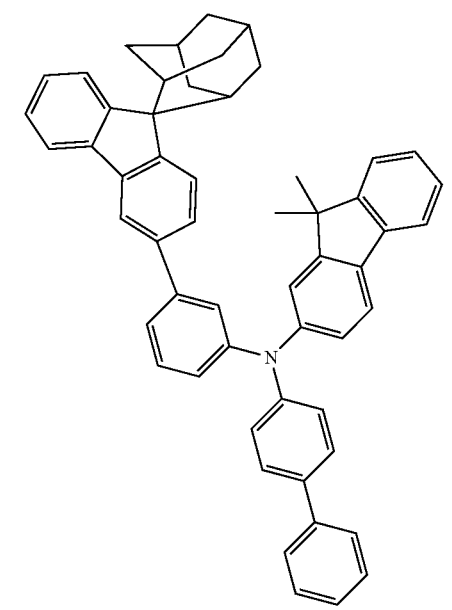
601
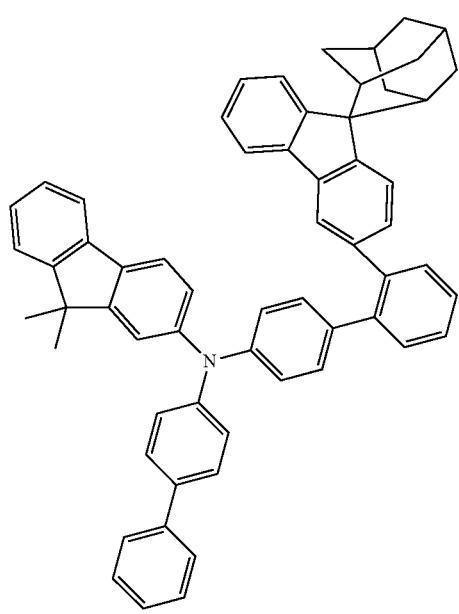
-continued
602
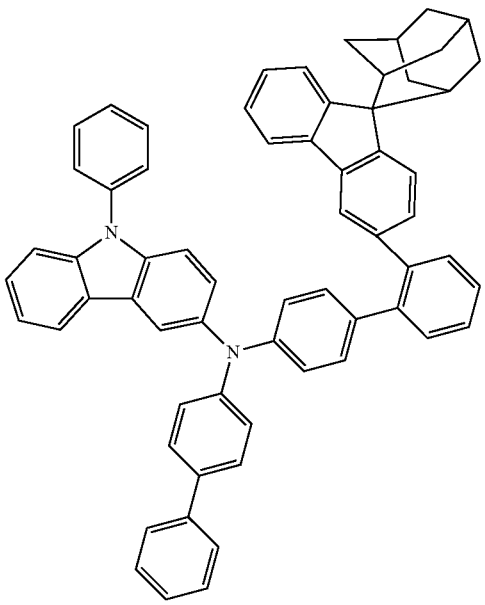
603
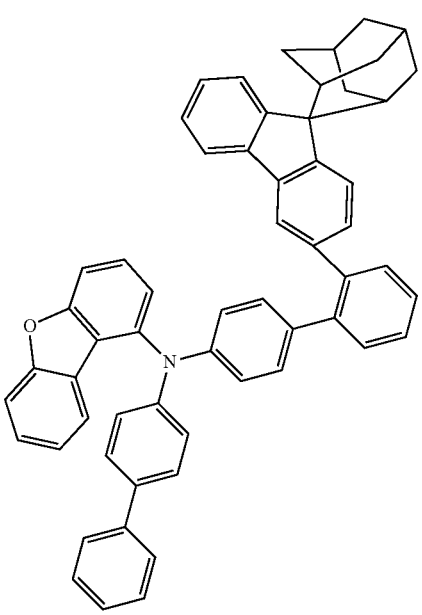

631
-continued
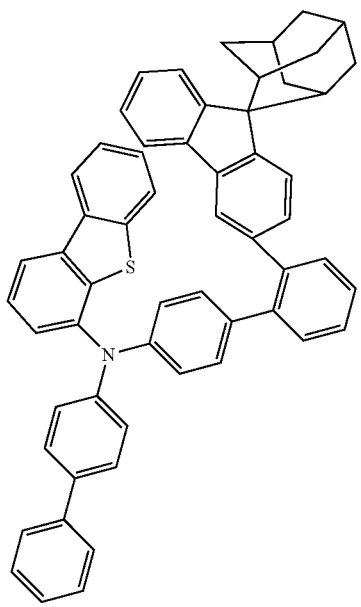
604
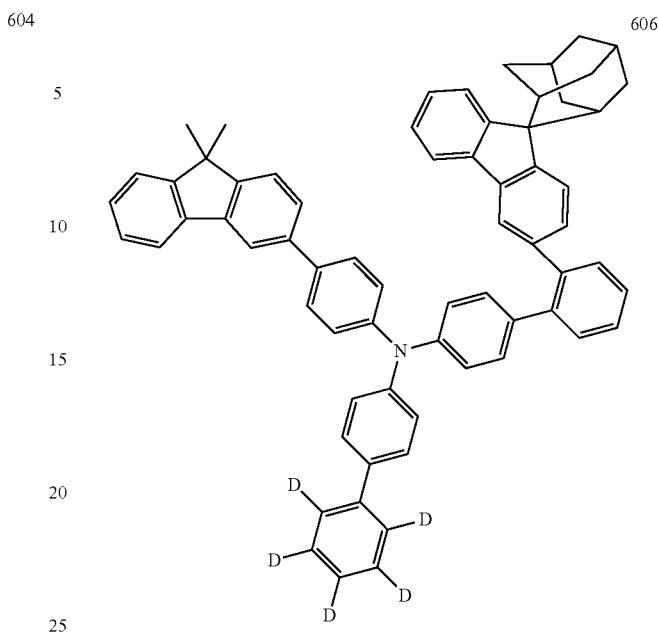
606
632
-continued
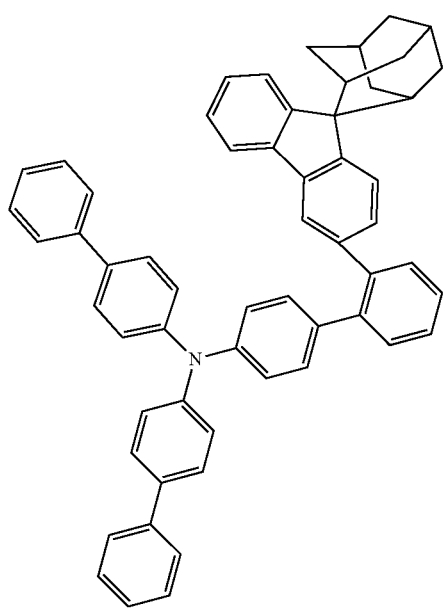
605
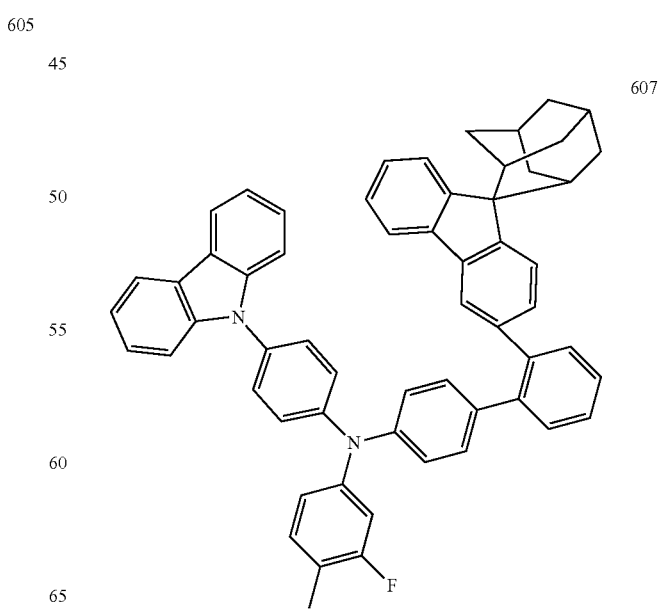
607

633
-continued
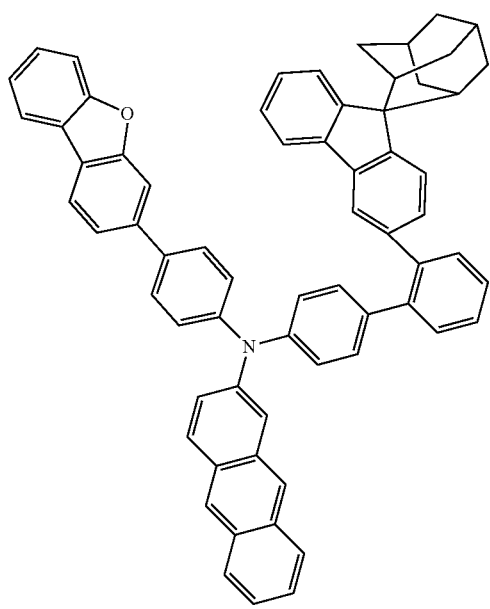
608
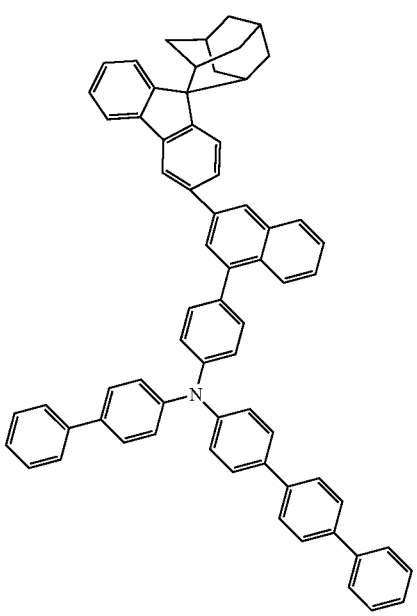
634
-continued
610
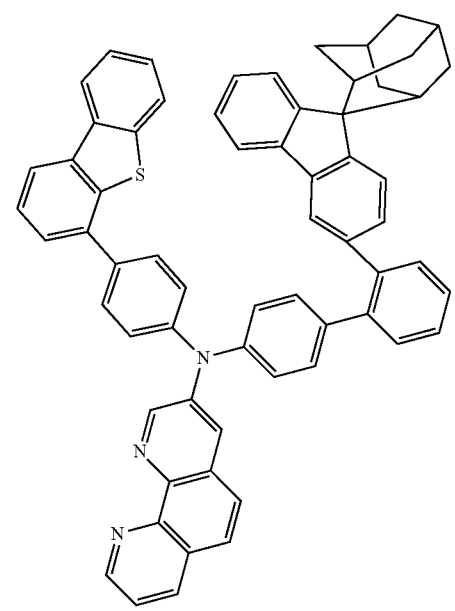
609
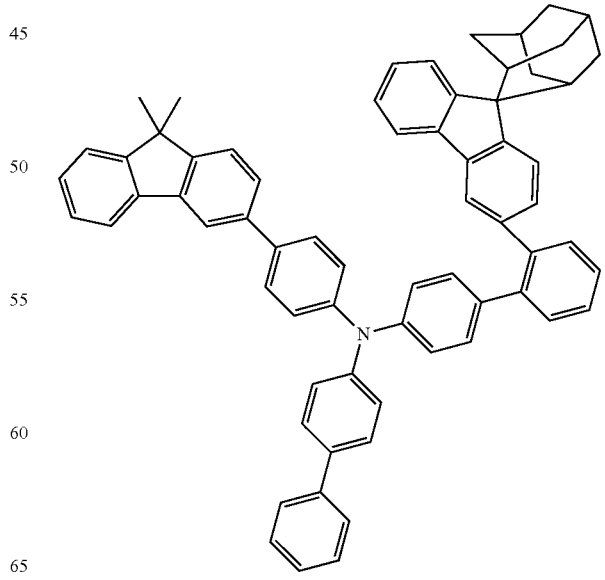
611

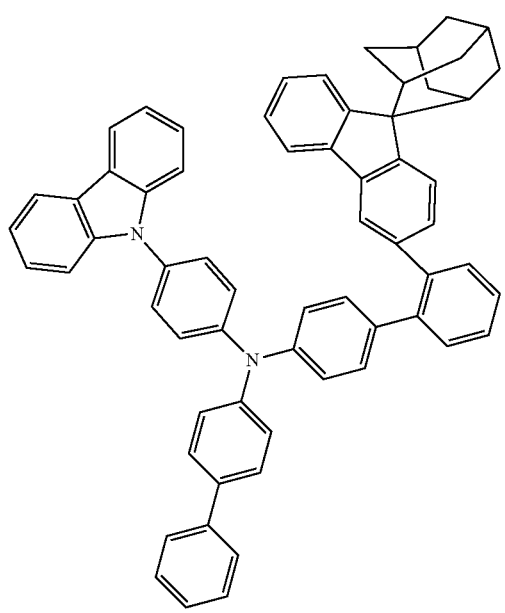
612
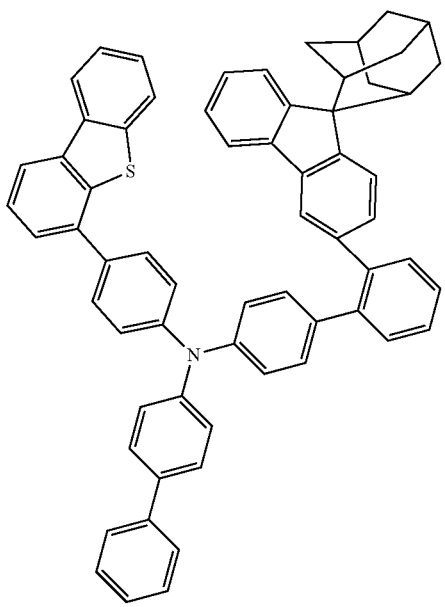
614
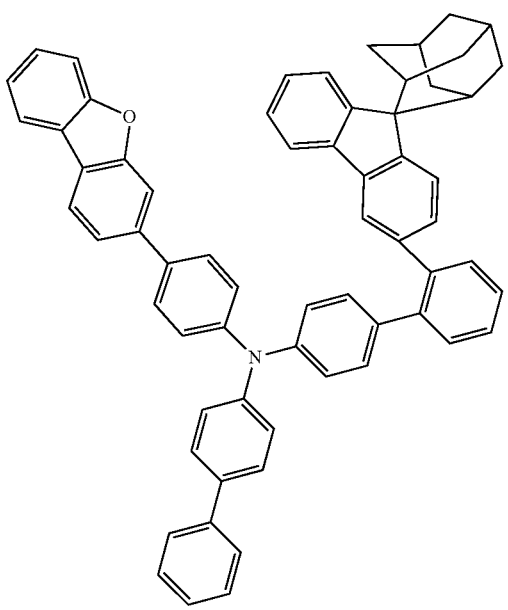
613
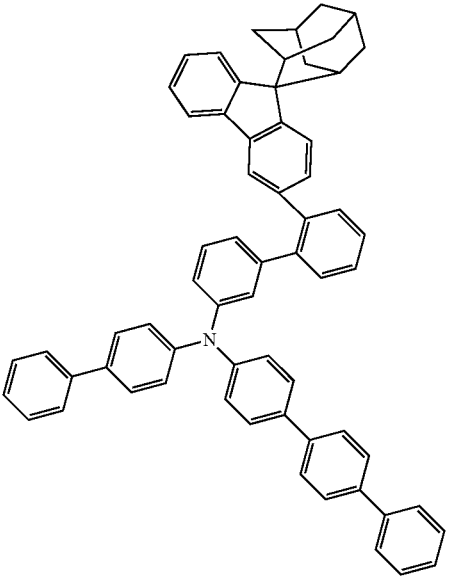
615

-continued
616
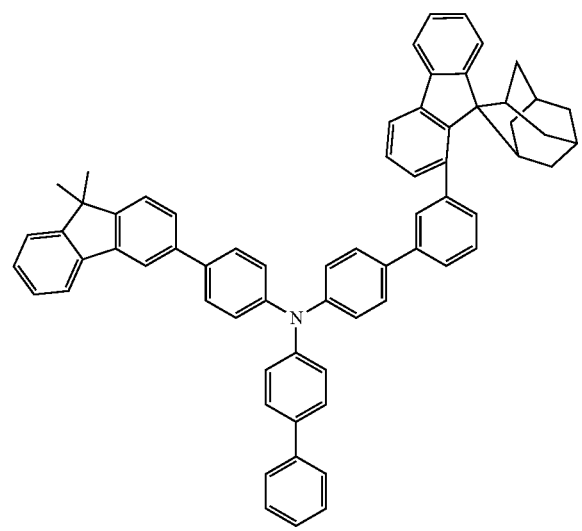
617
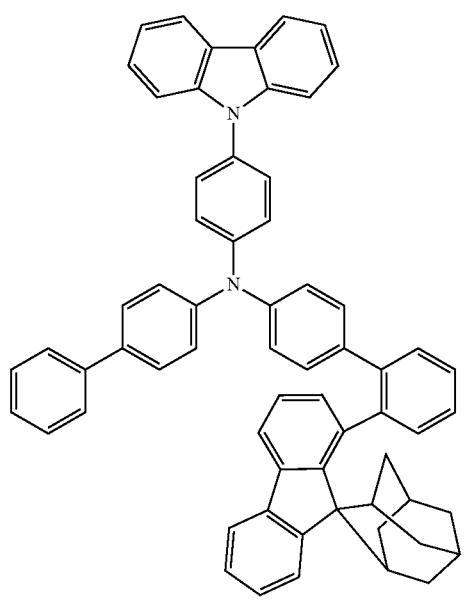
-continued
618
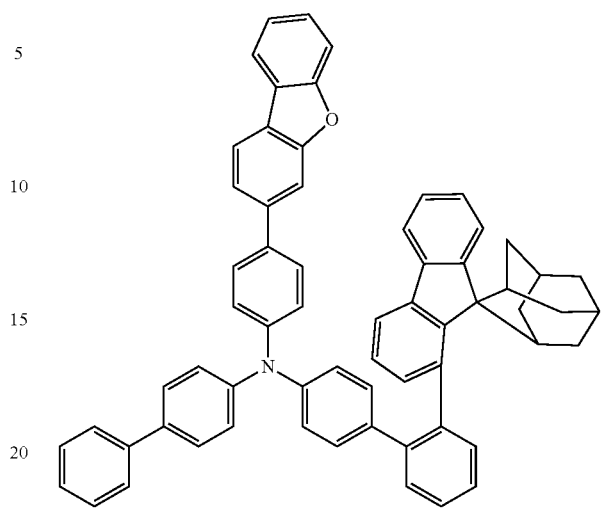
619
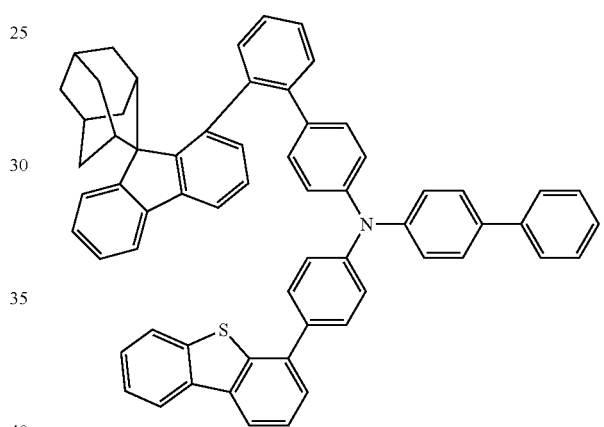
620
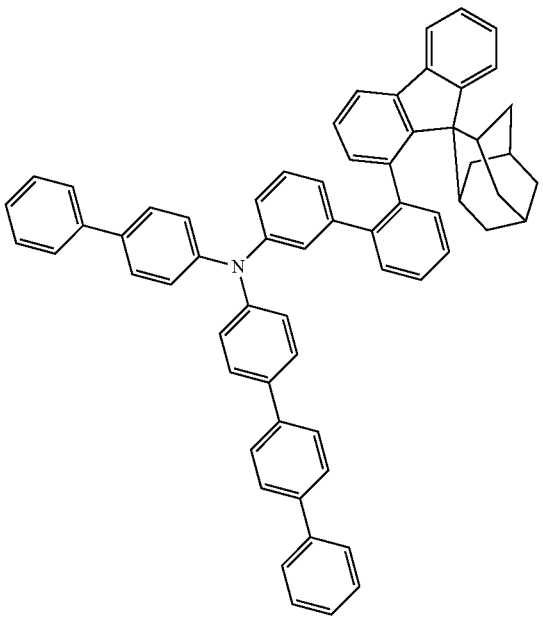

639
-continued
621
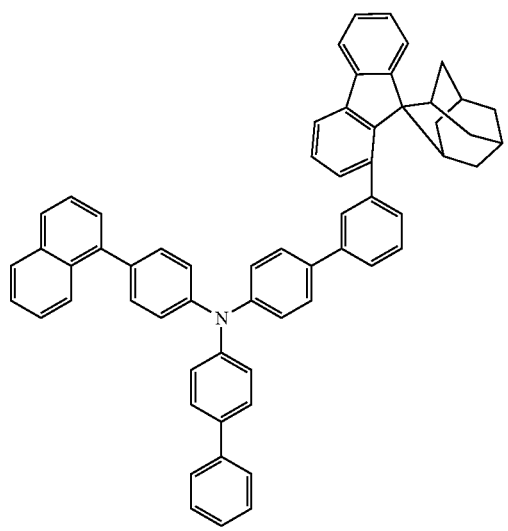
622
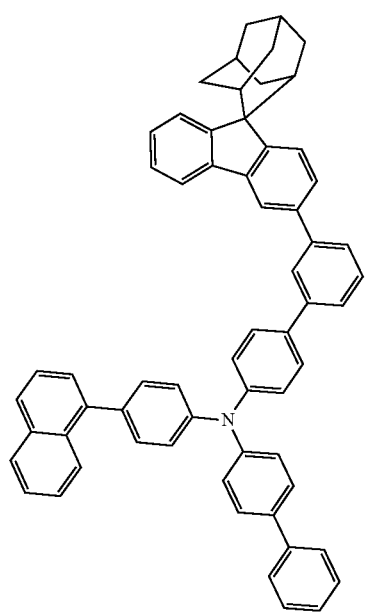
640
-continued
623
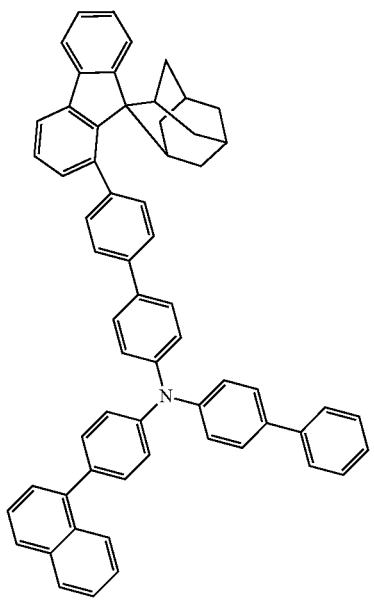
624
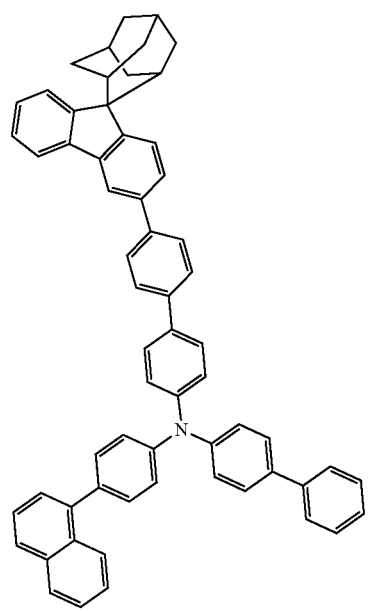

641
-continued
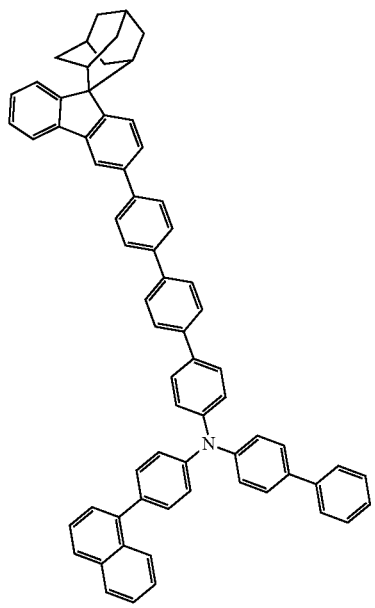
625
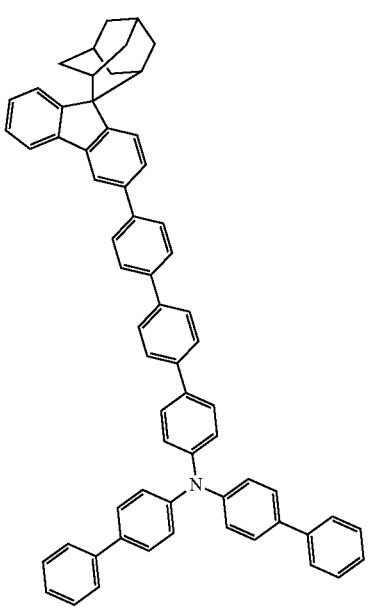
626
642
-continued
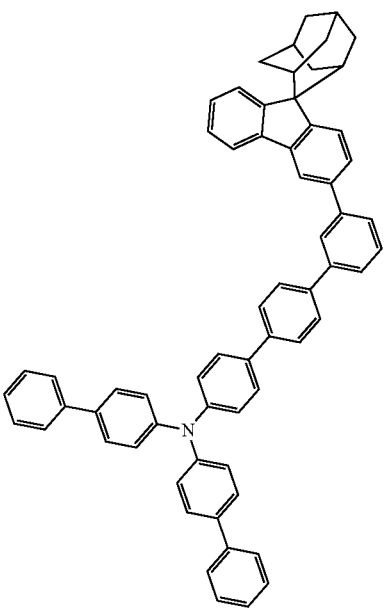
627
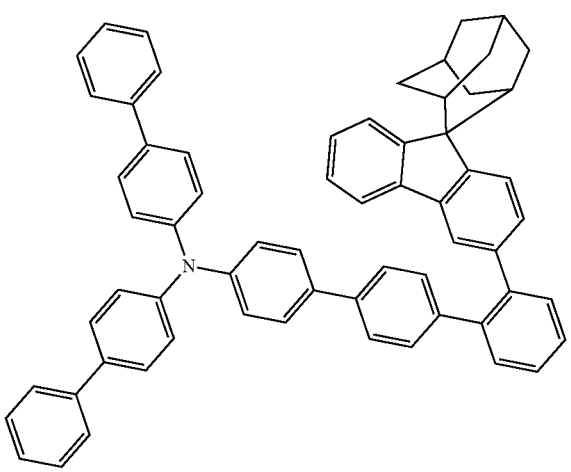
628

629
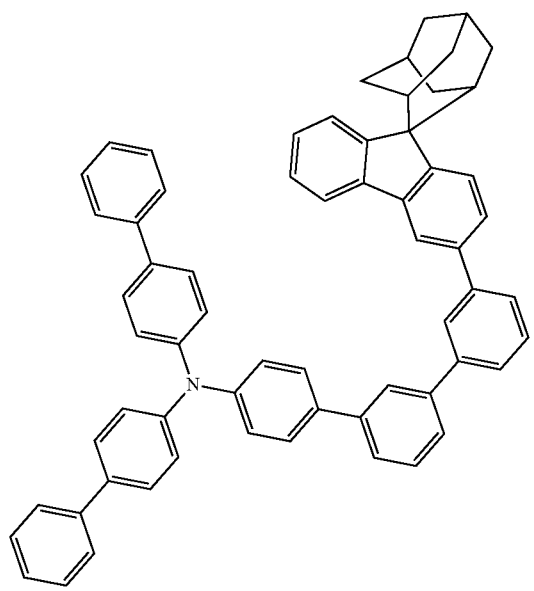
630
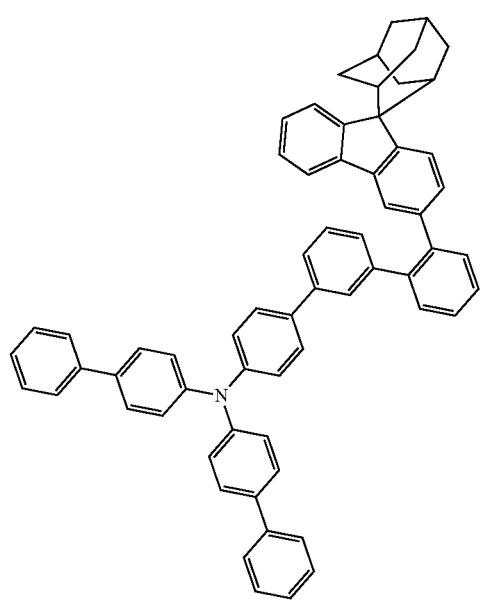
631
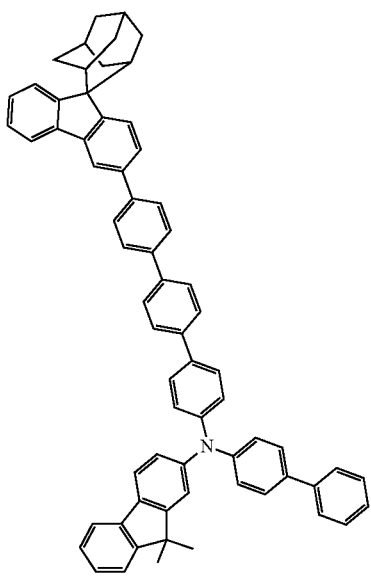
632
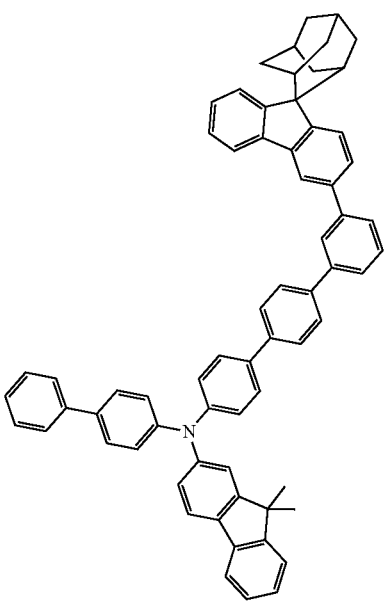

633
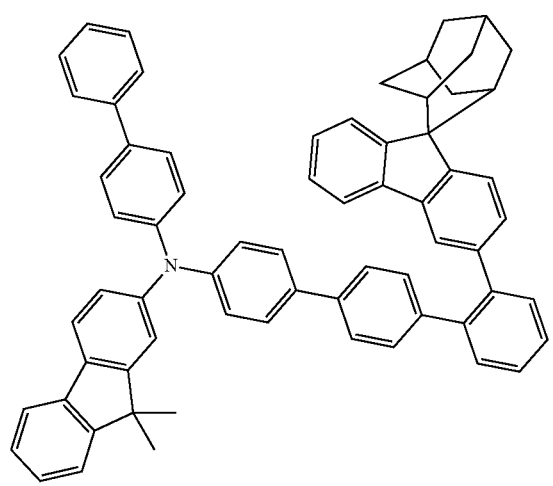
634
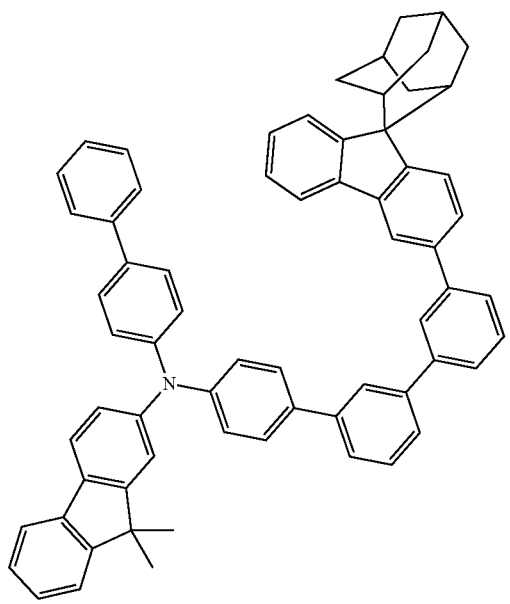
635
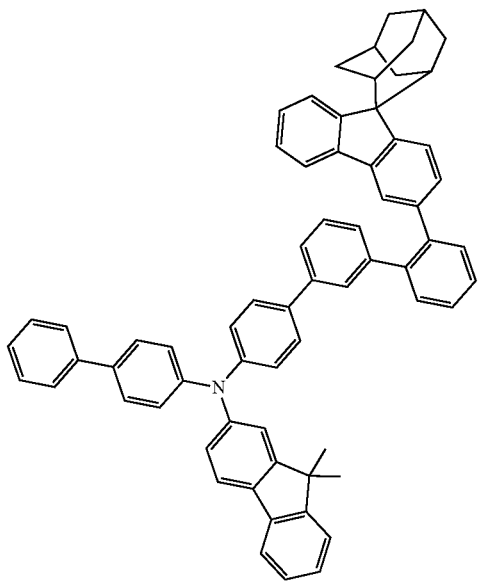
636
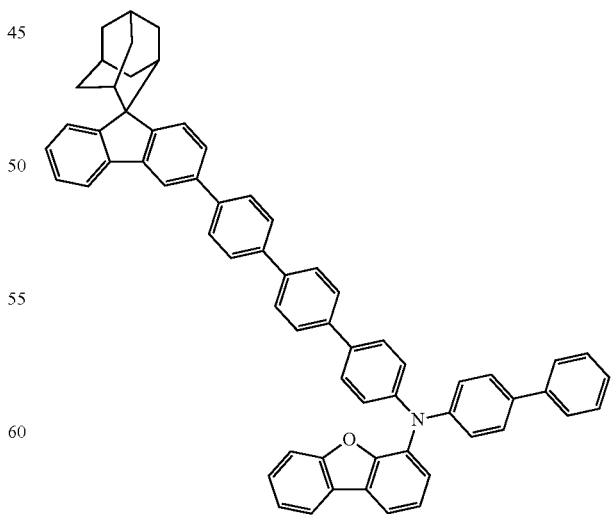

647
-continued
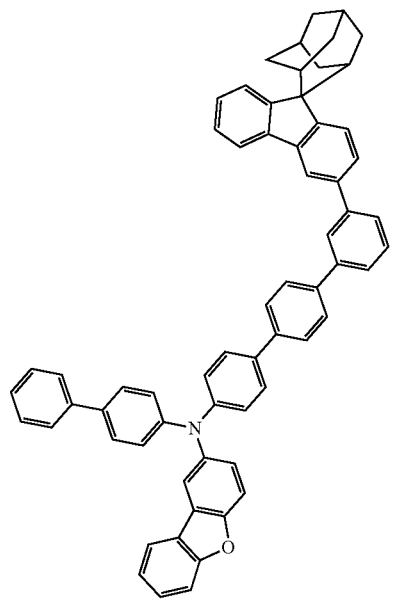
637
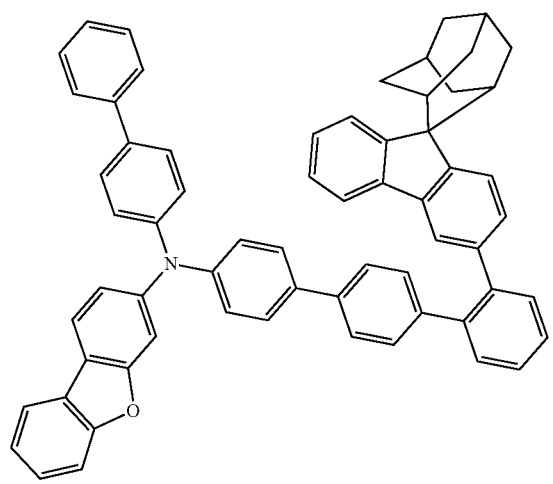
638
648
-continued
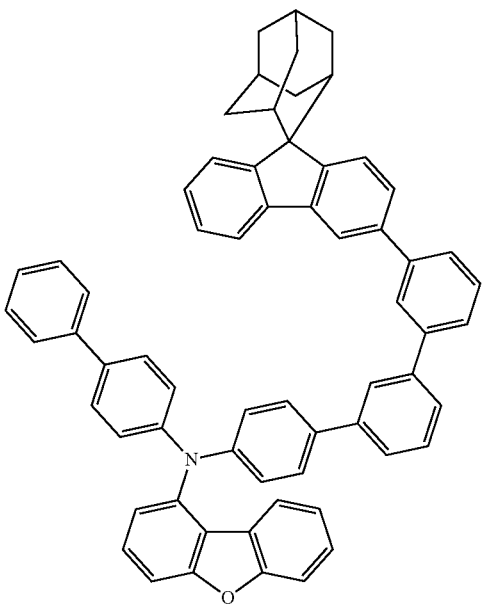
639
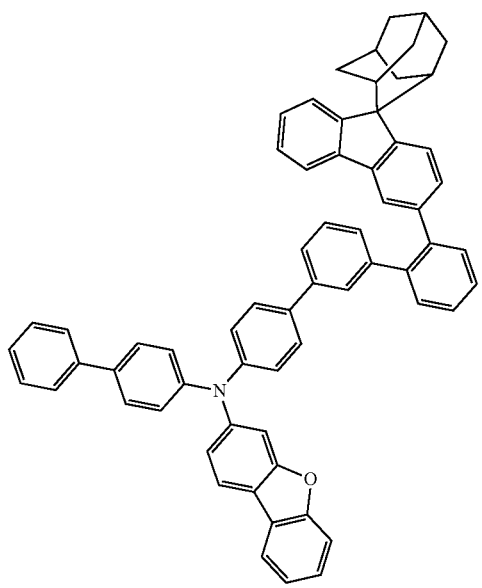
640

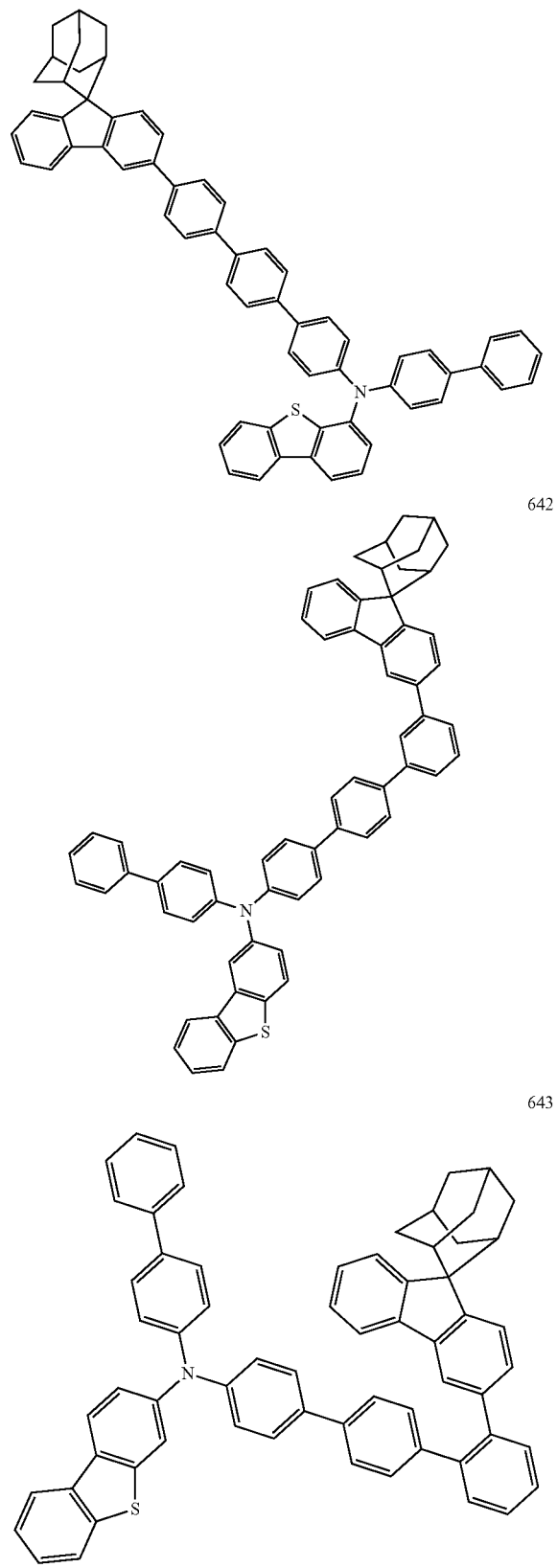

651
-continued
646
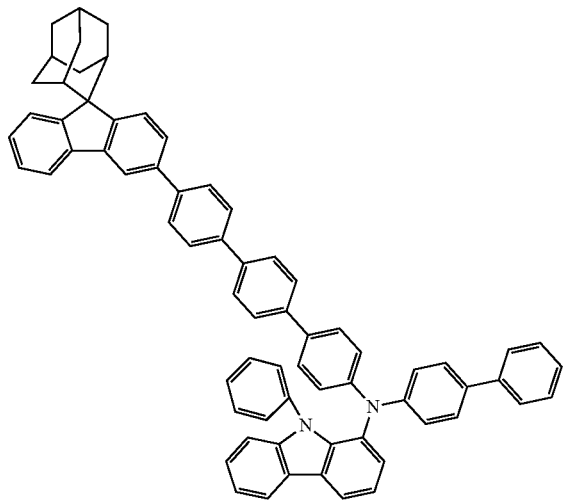
647
648
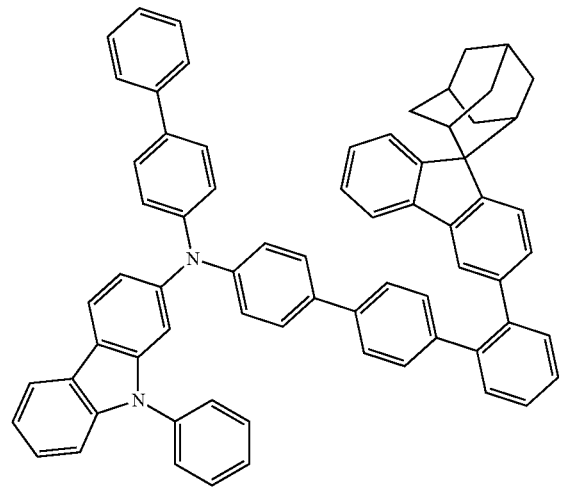
652
-continued
649
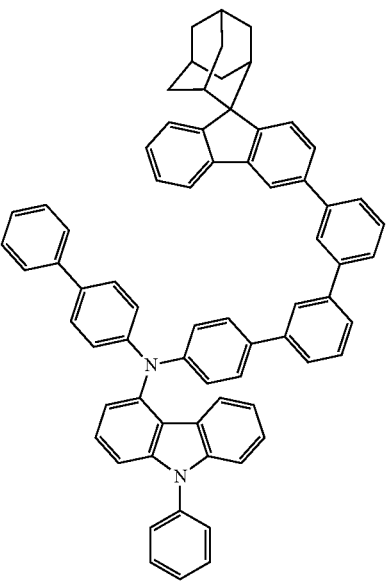
650
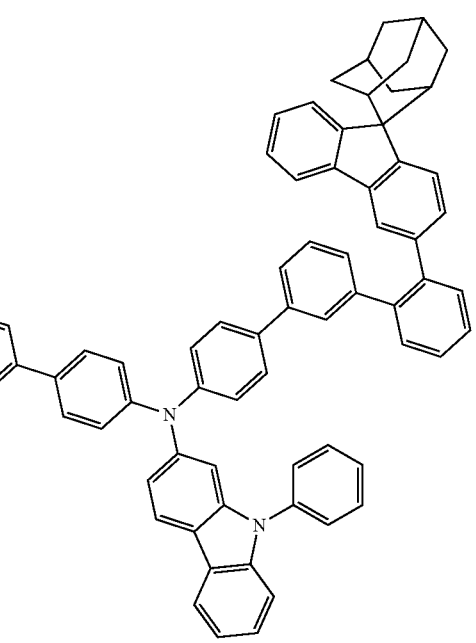
651

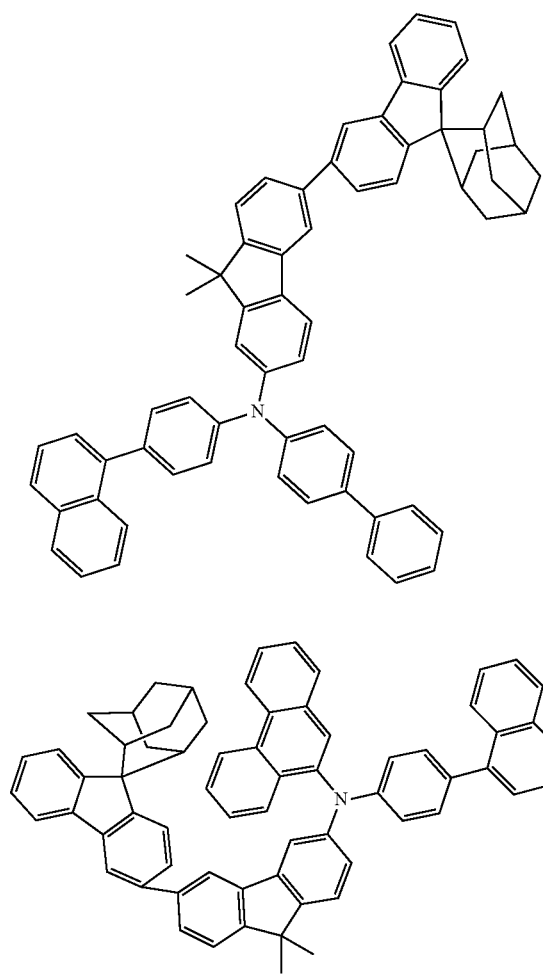
652
653
654
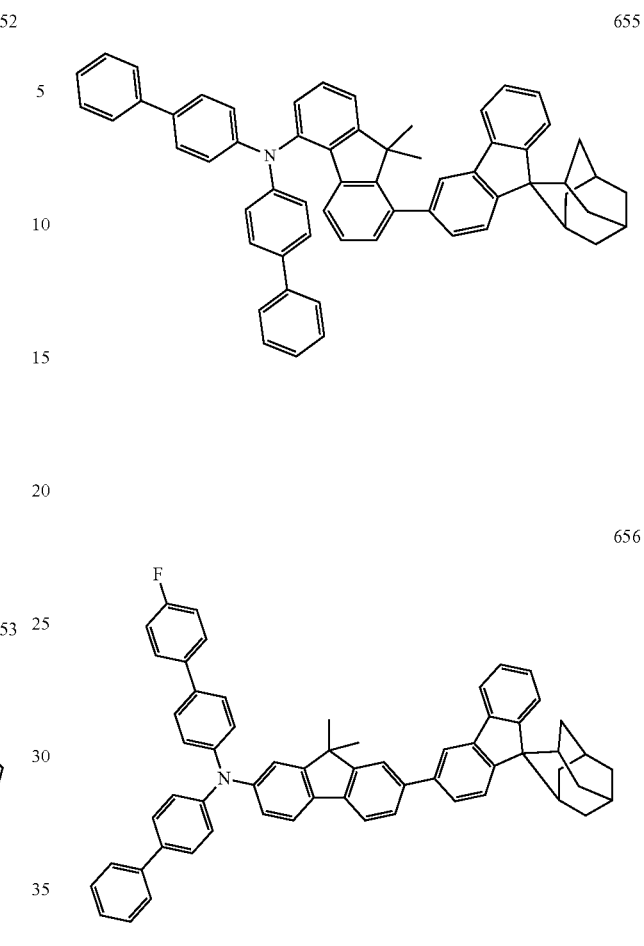
655
656
657
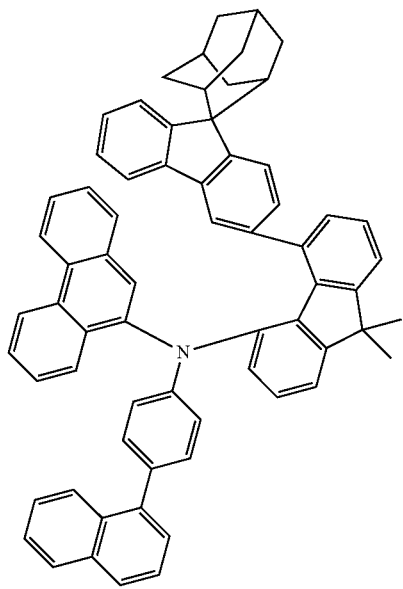
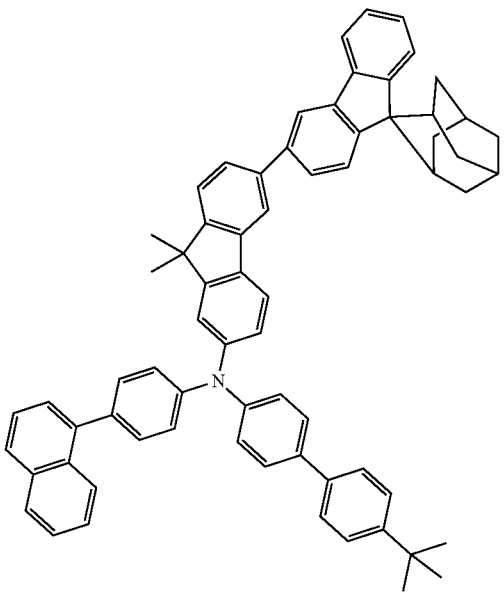

658
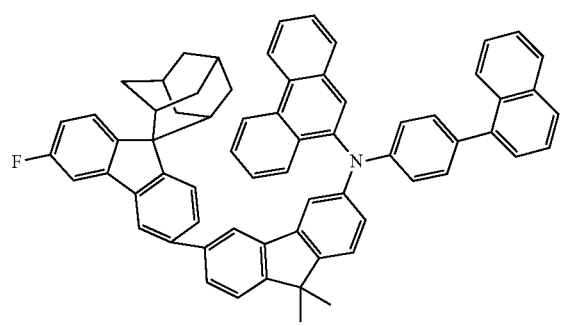
661
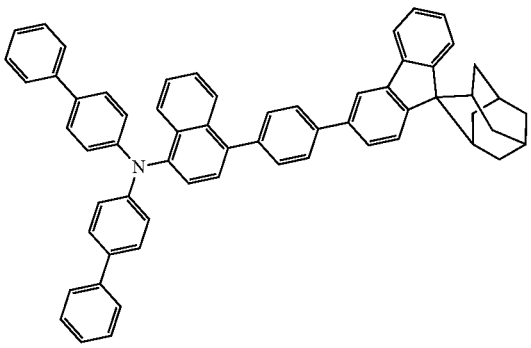
659
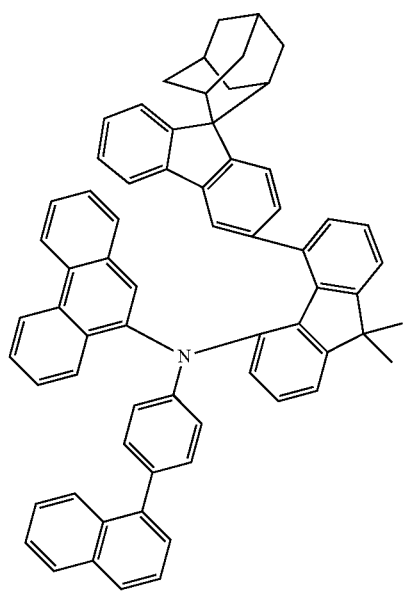
662
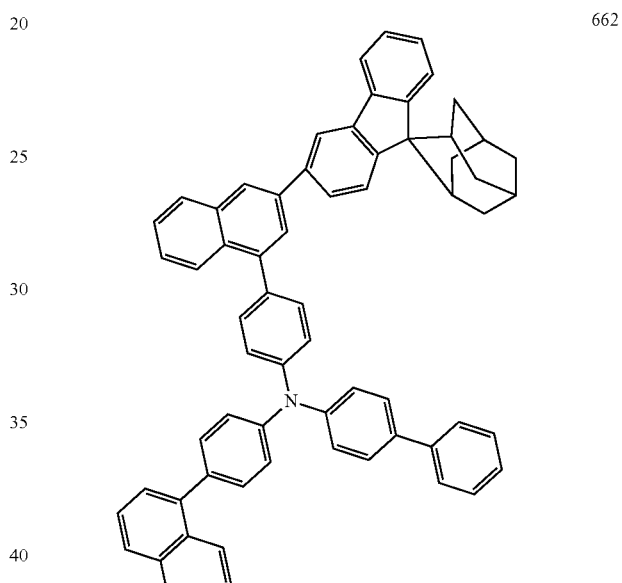
660
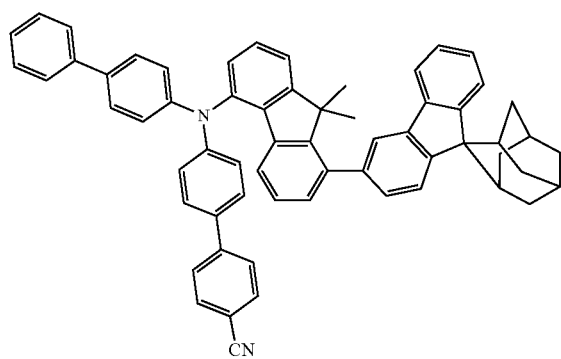
663
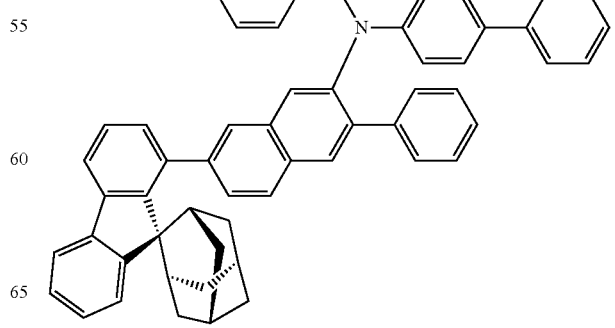

657
-continued
658
-continued
664
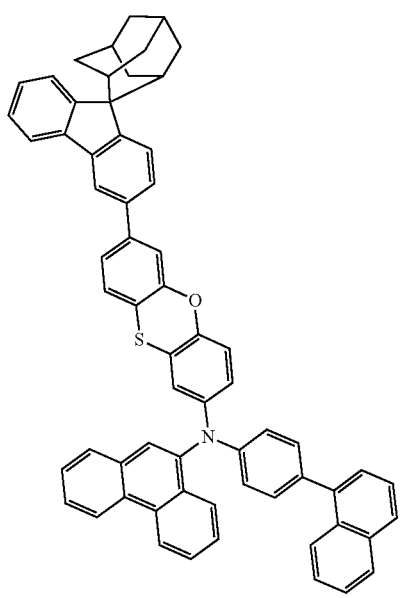
667
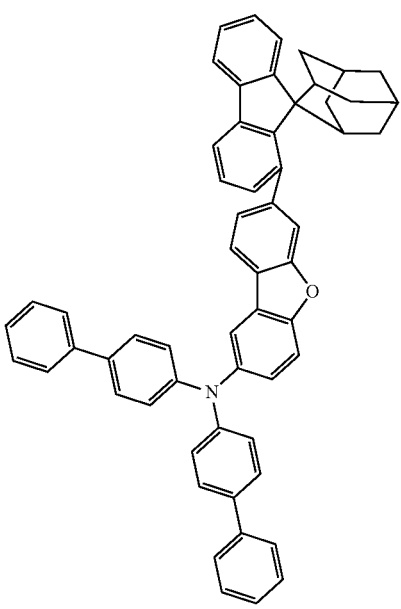
665
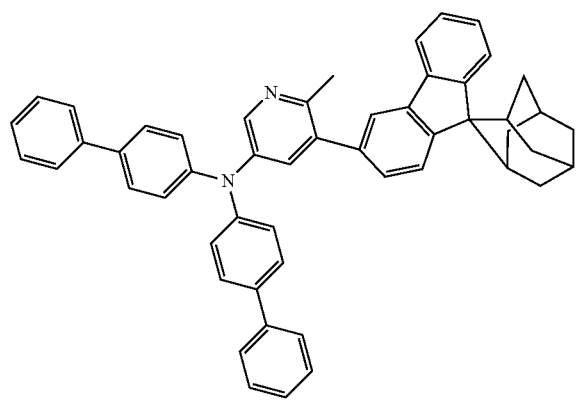
666
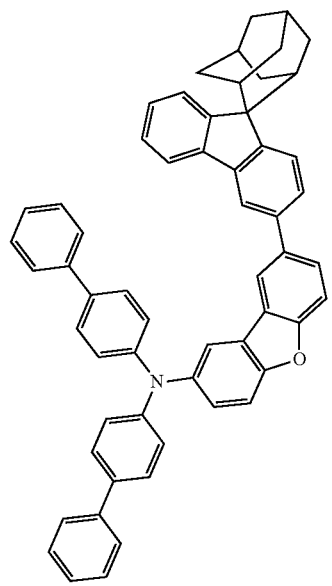
668
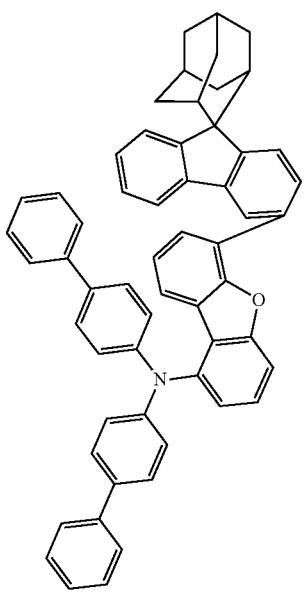

659
-continued
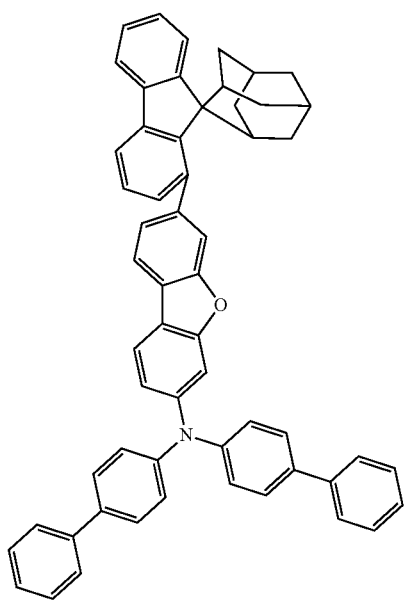
669
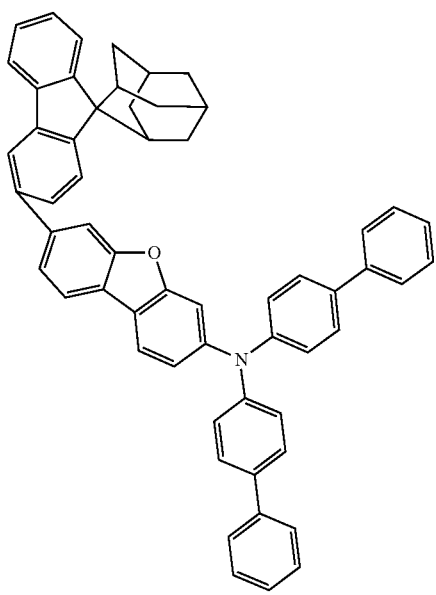
670
660
-continued
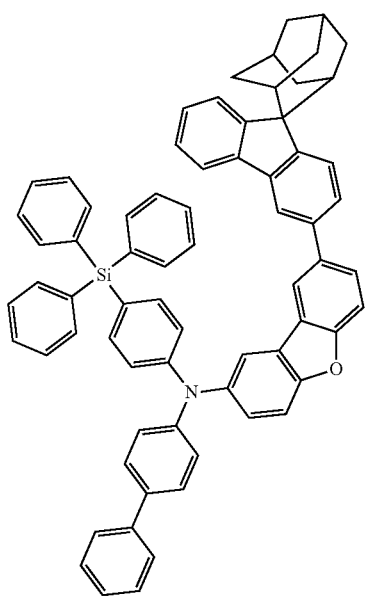
671
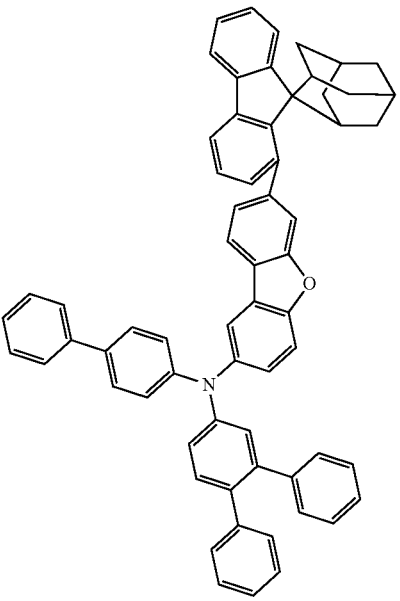
672

661
-continued
673
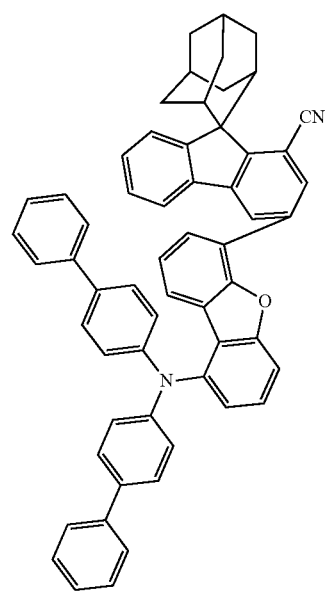
674
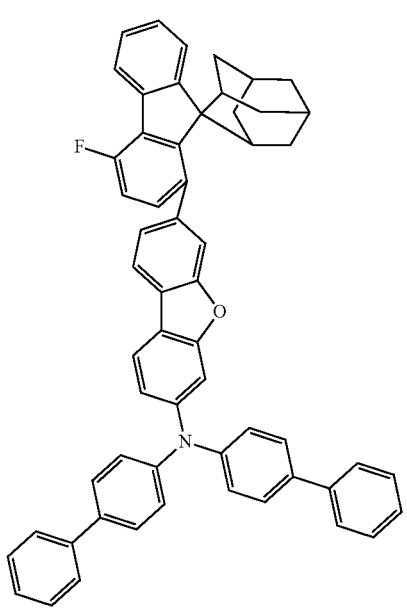
662
-continued
675
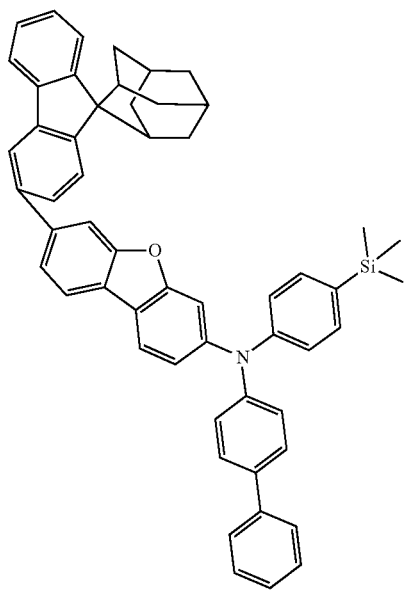
676
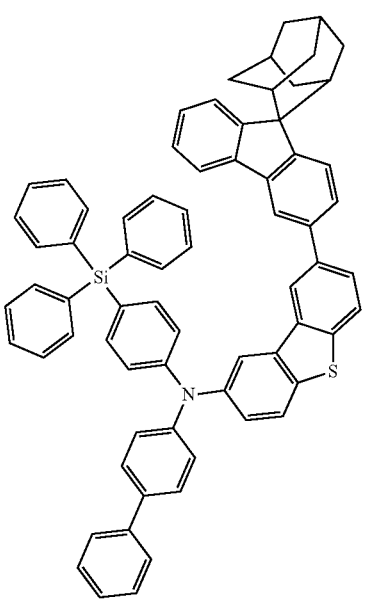

677
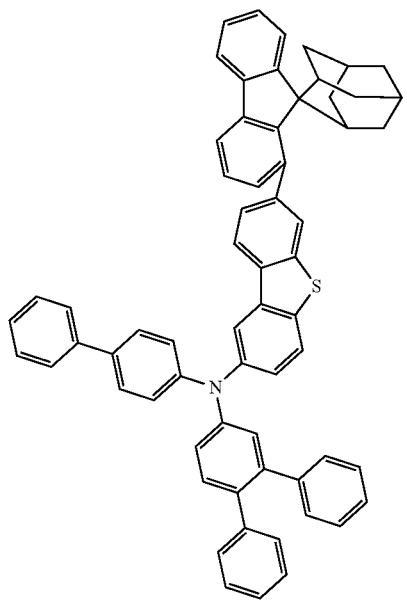
678
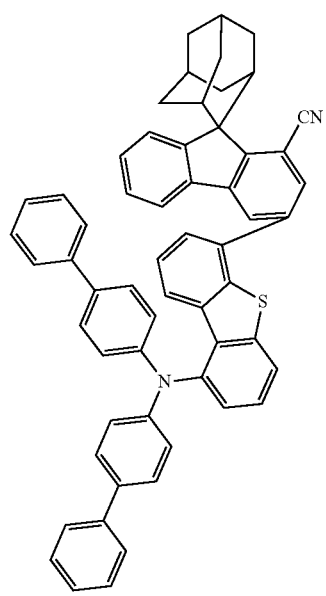
679
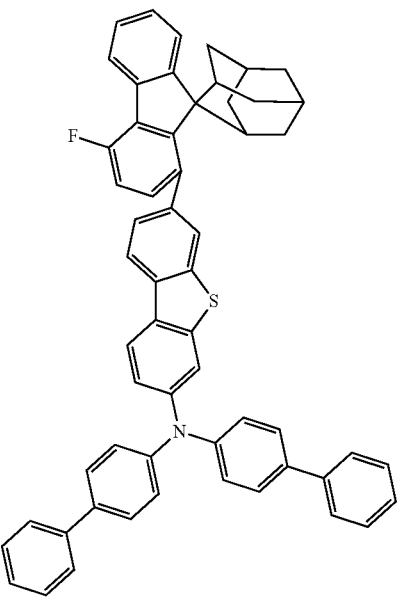
680
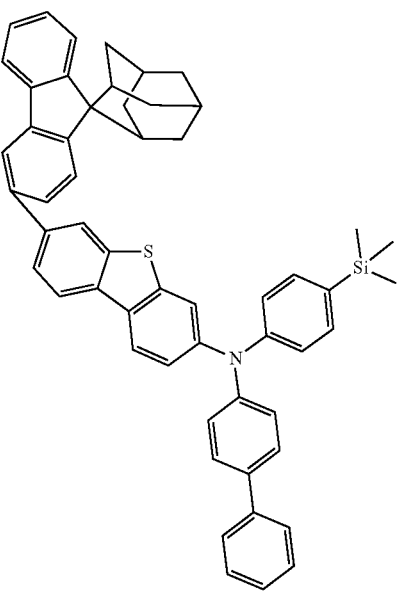

681 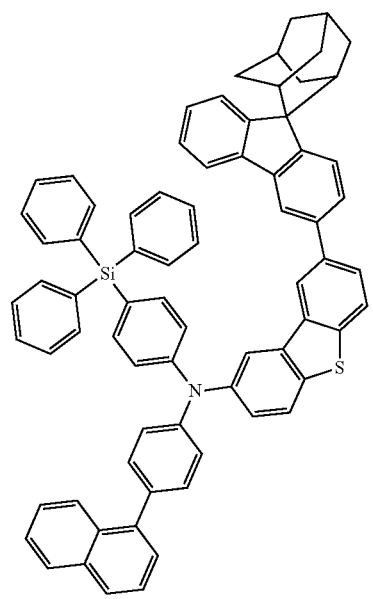
683 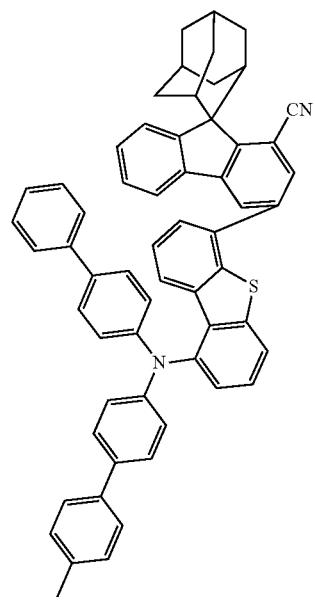
682 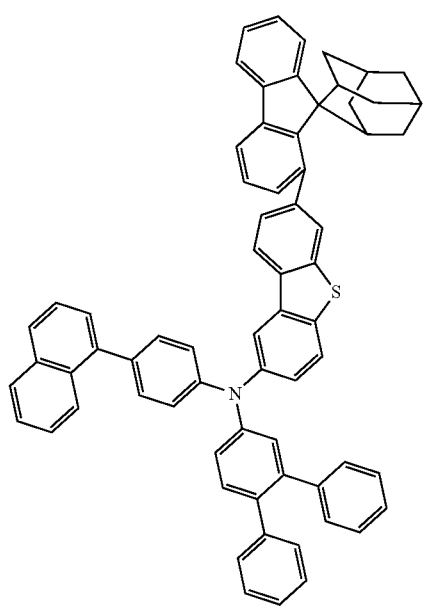
684

667
-continued
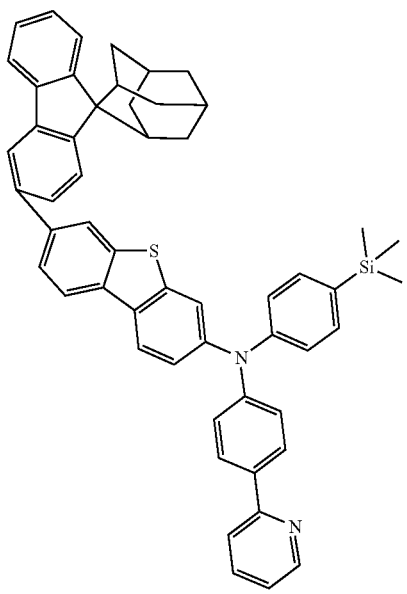
685
668
-continued
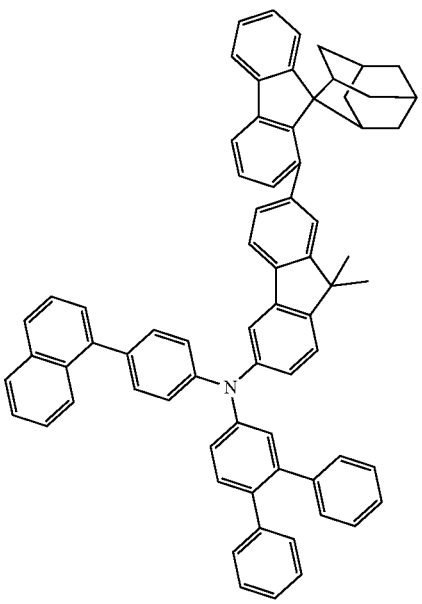
687
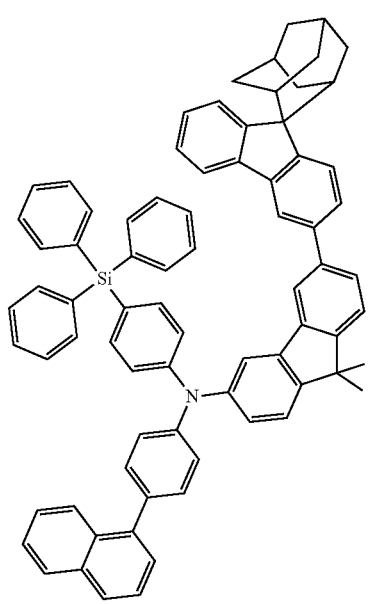
686
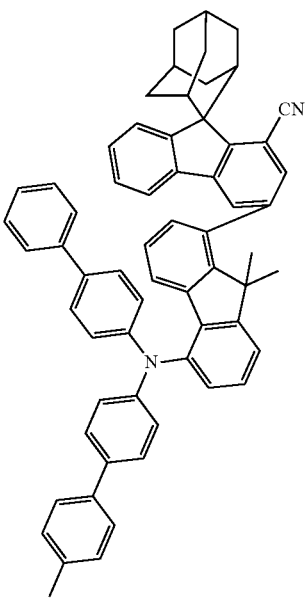
688

669
-continued
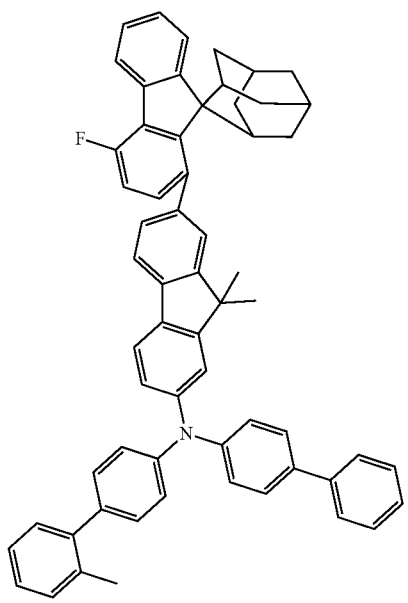
670
-continued
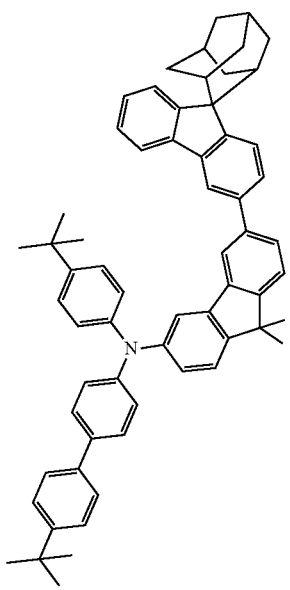
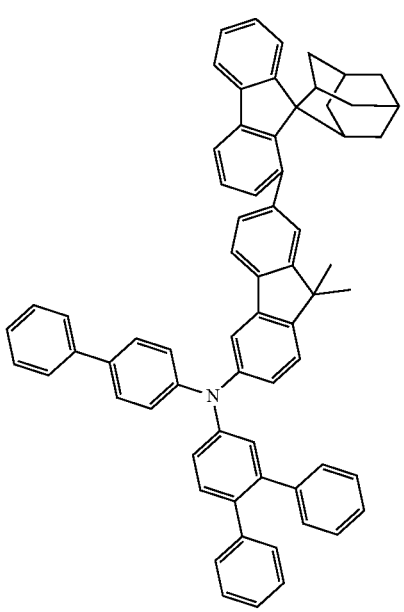

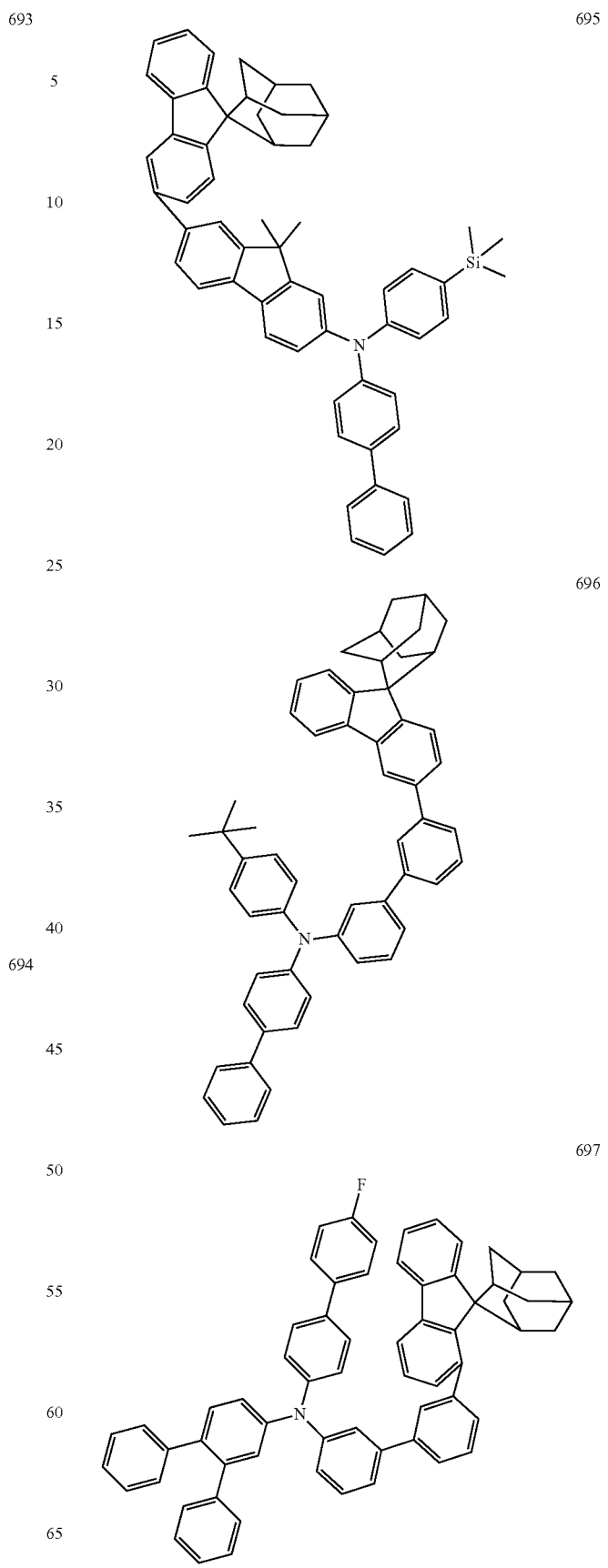

673
-continued
698
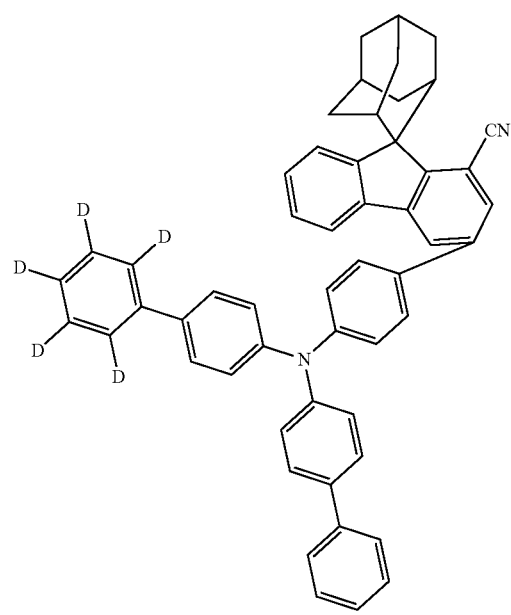
699
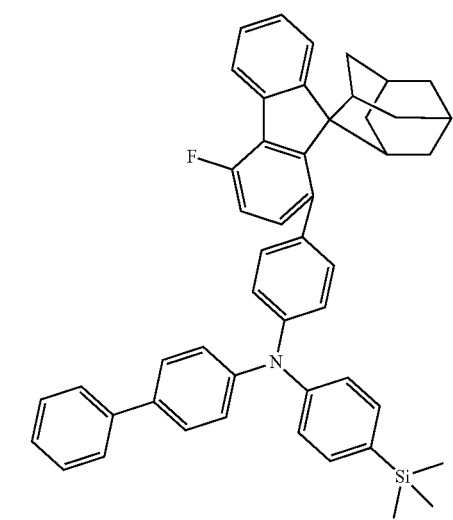
674
-continued
700
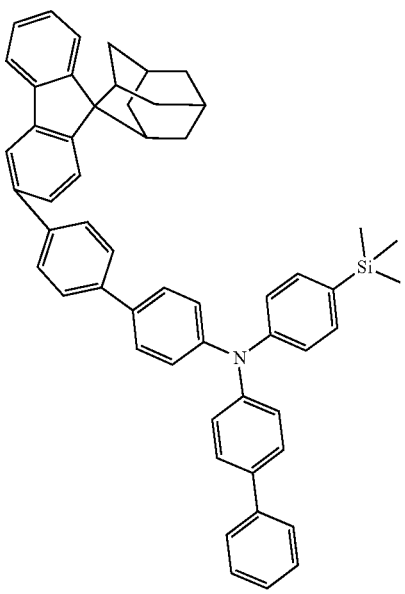
701
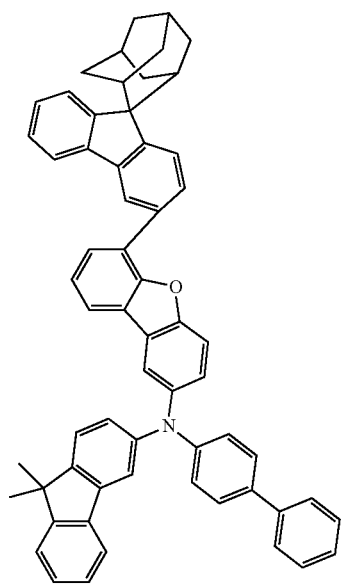

675
-continued
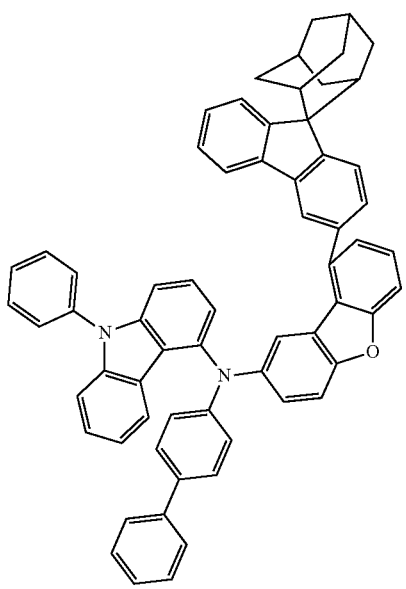
702
676
-continued
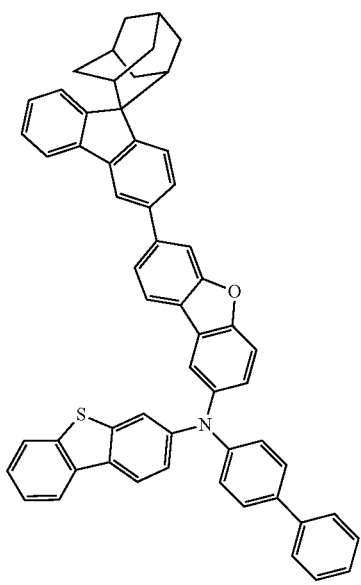
704
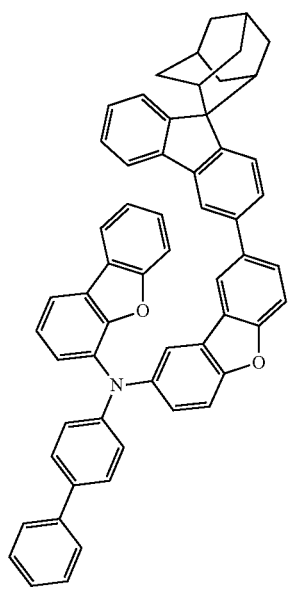
703
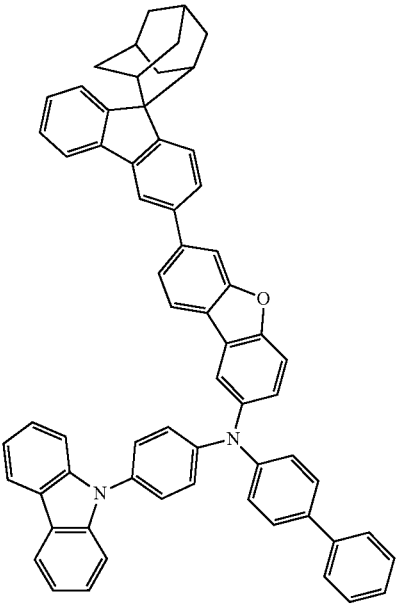
705

677
-continued
706
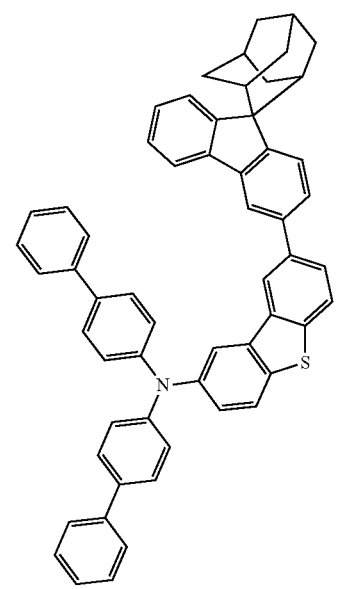
707
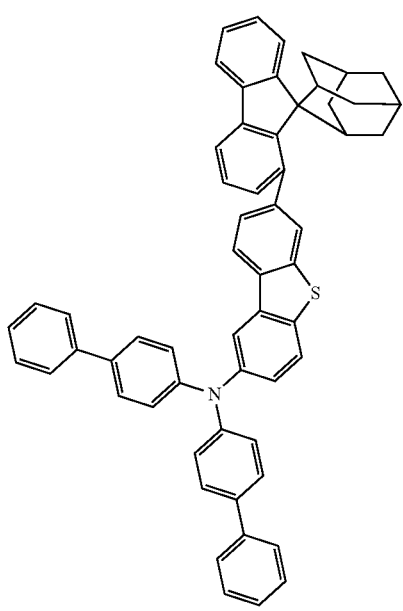
678
-continued
708
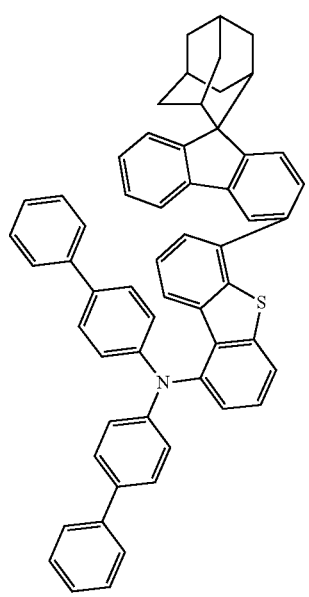
709
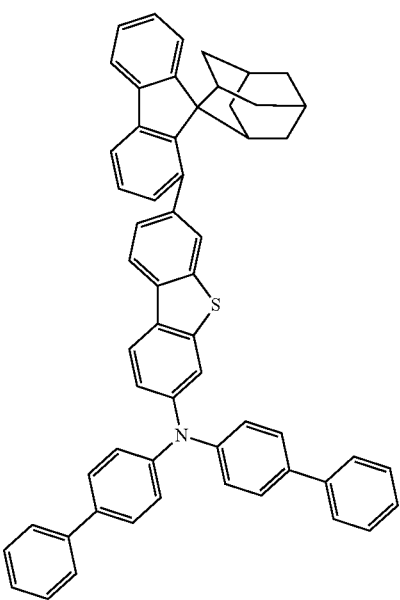

679
-continued
670
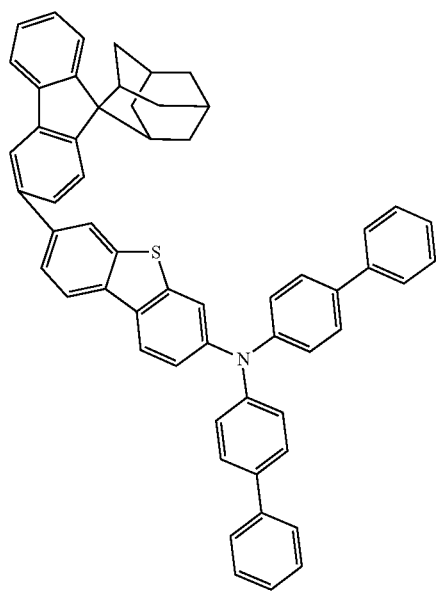
711
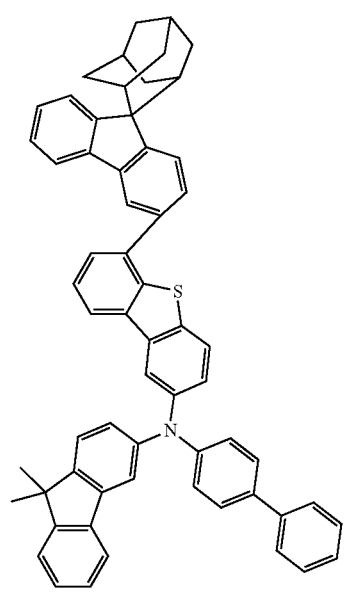
680
-continued
712
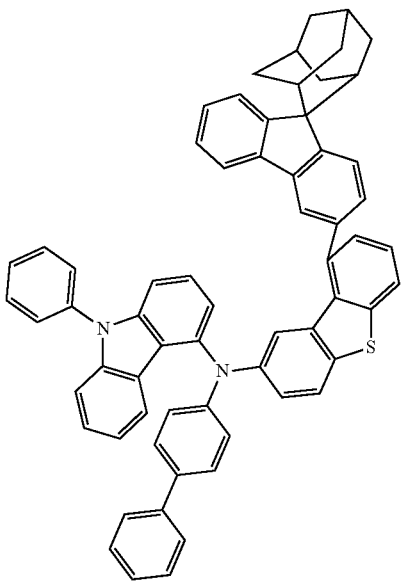
713
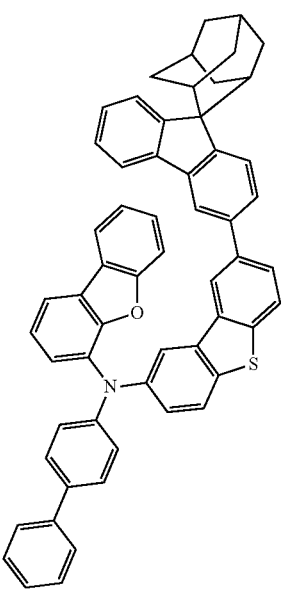

714
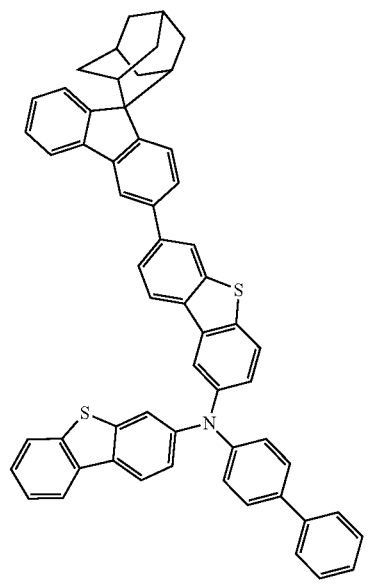
716
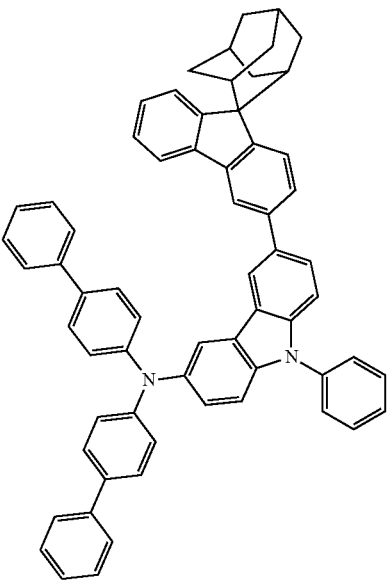
715
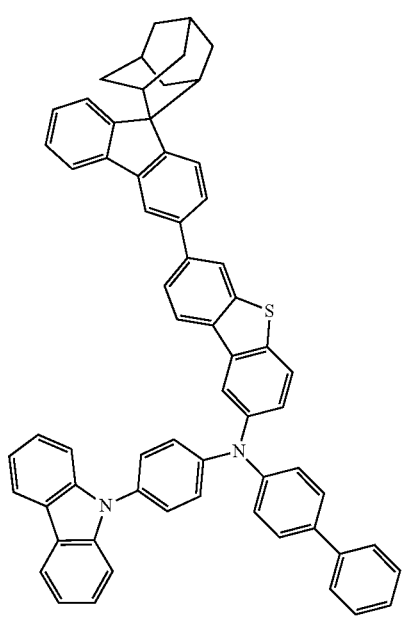
717
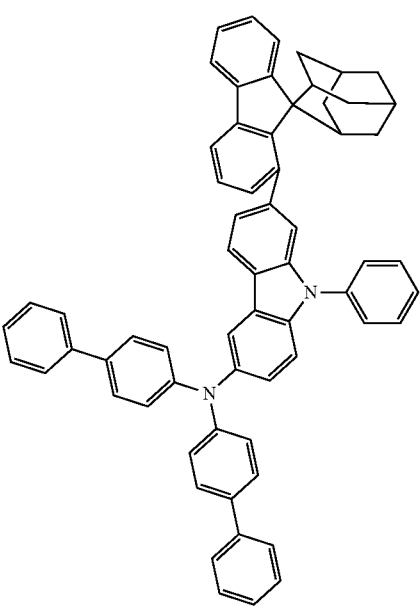

718
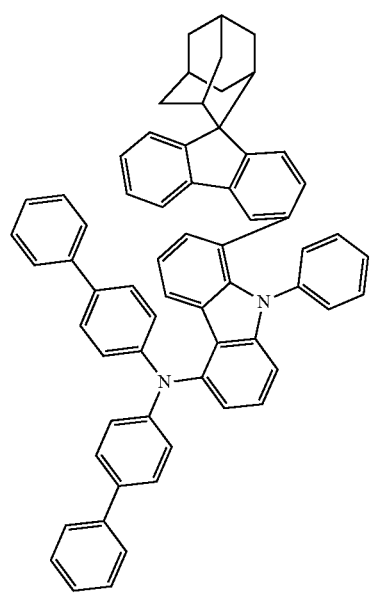
720
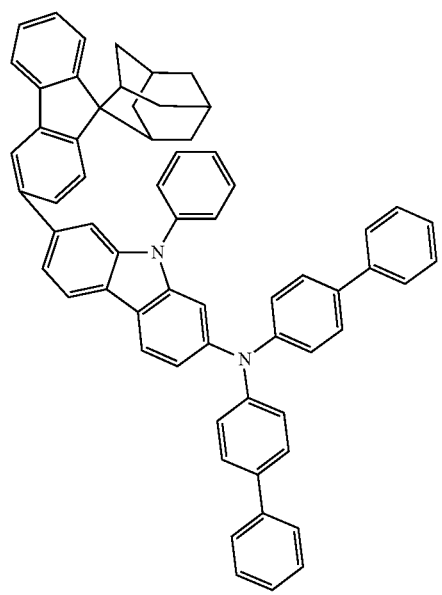
719
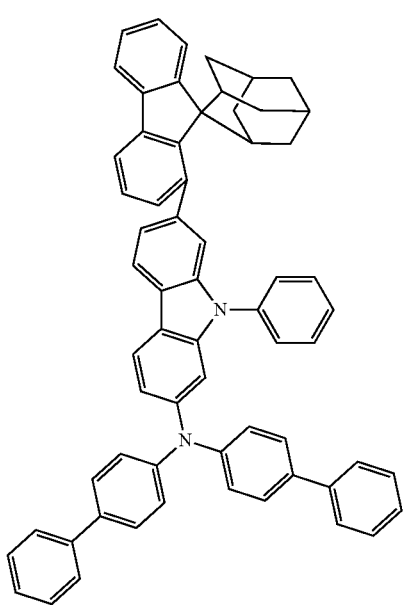
721
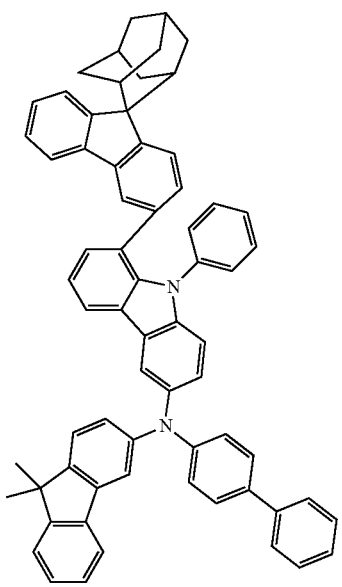

722
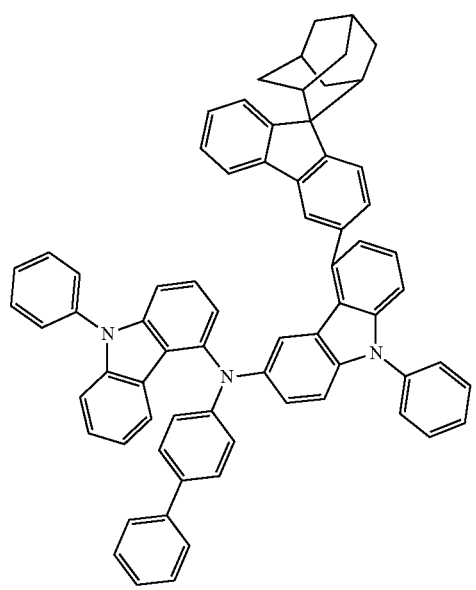
723
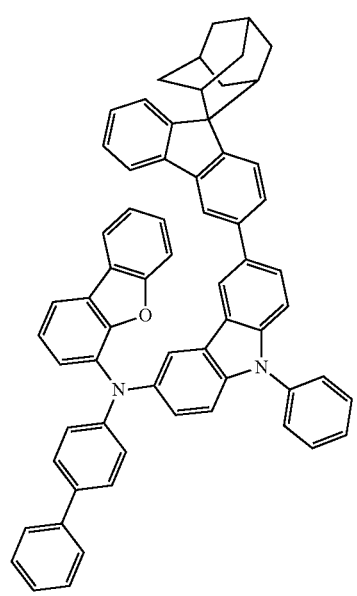
724
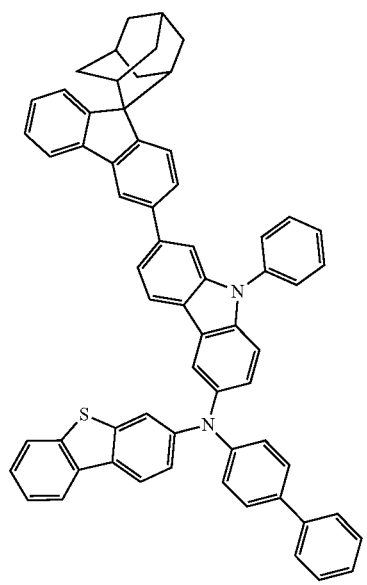
725
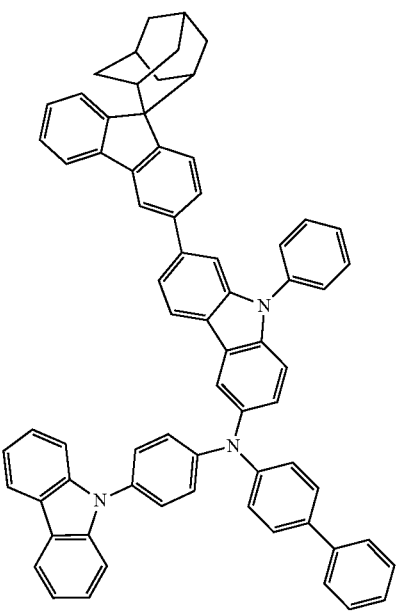

726
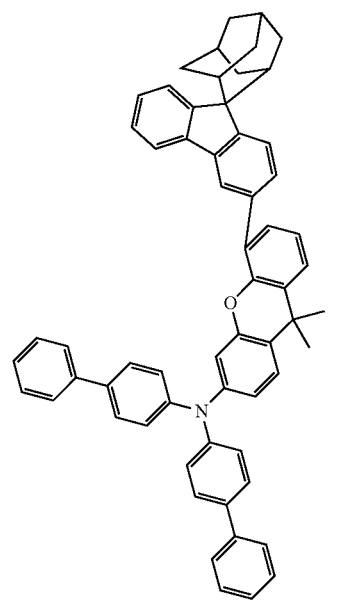
727
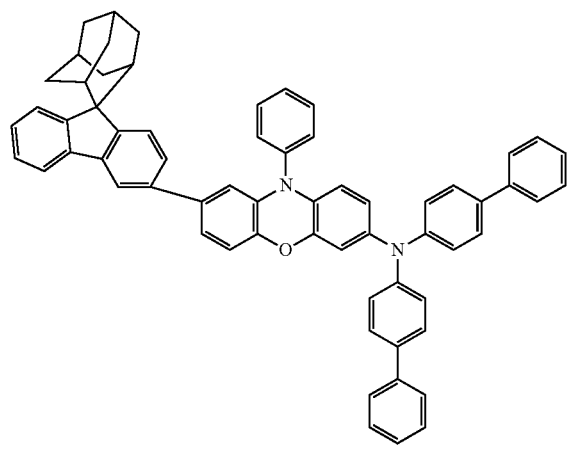
728
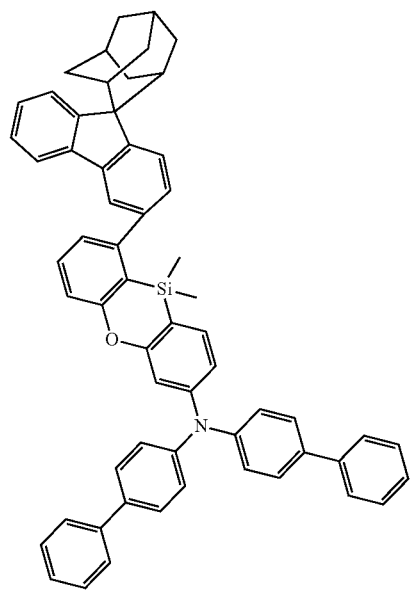
729
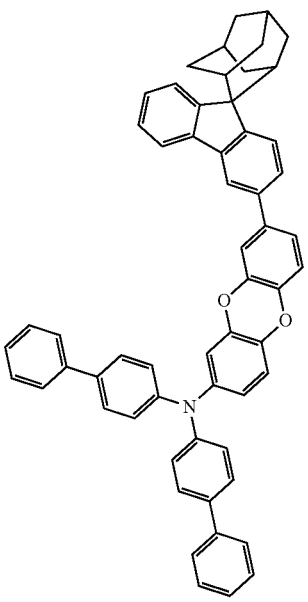
730
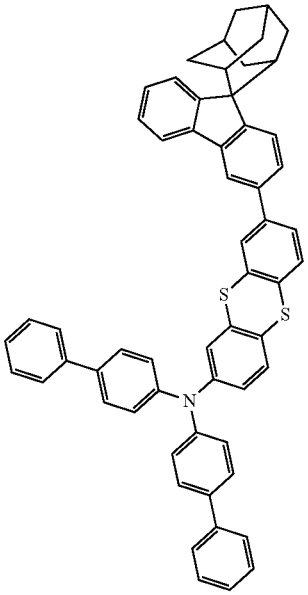

689
-continued
734
731
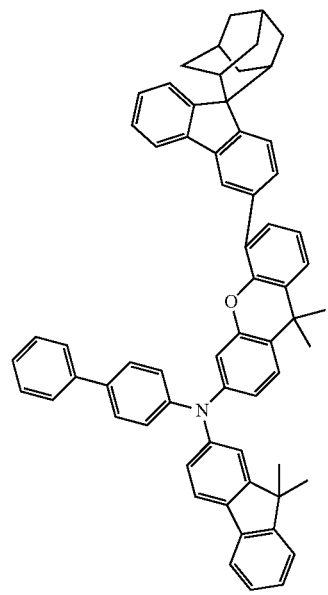
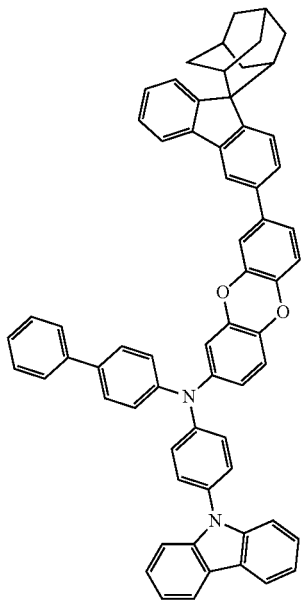
732
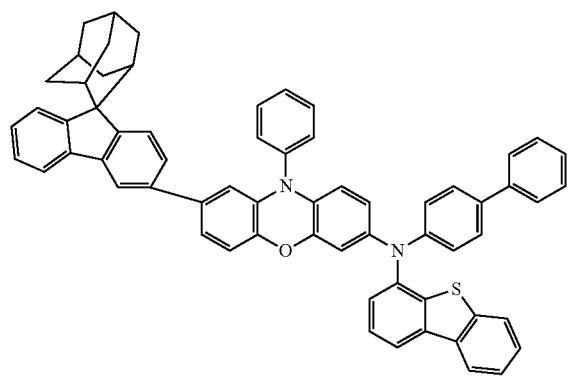
733
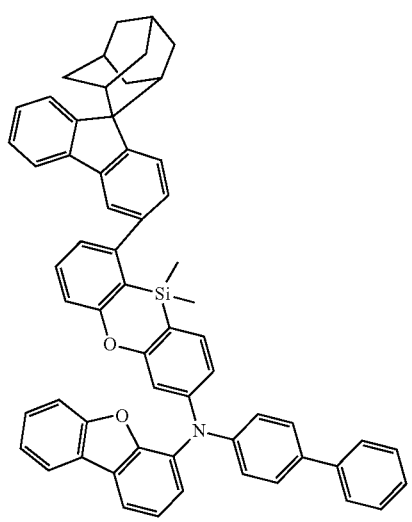
690
-continued
735
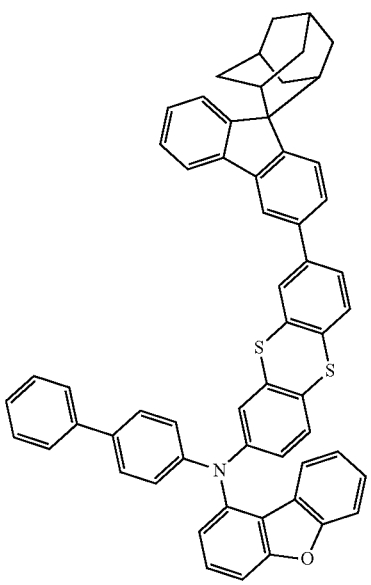

691
-continued
736
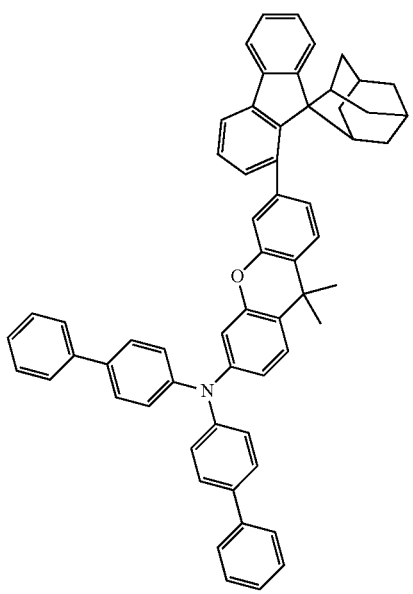
737
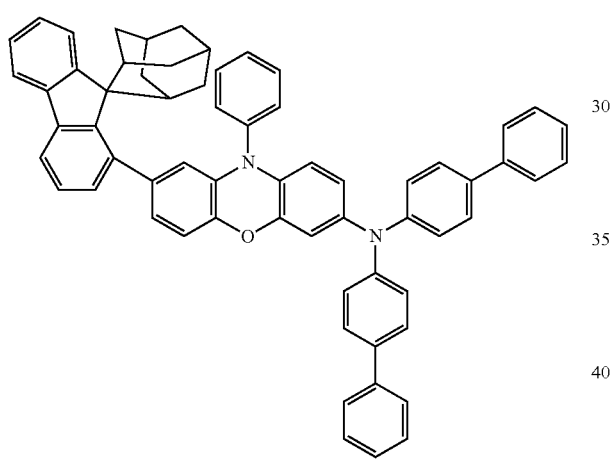
738
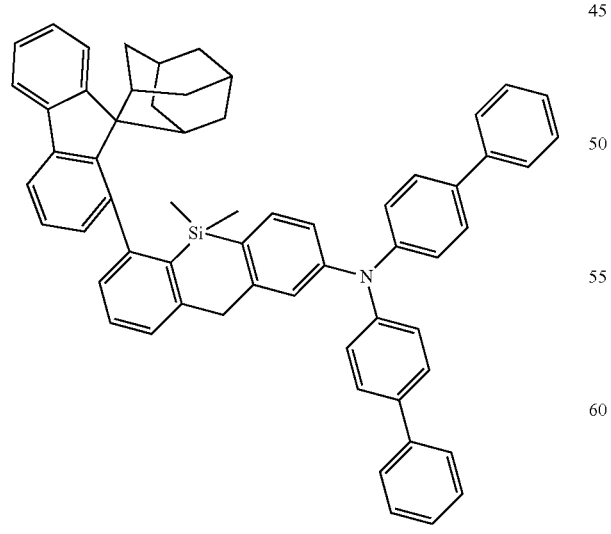
692
-continued
739
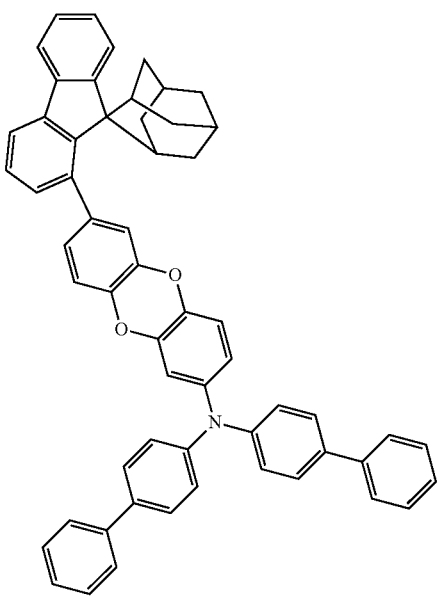
740
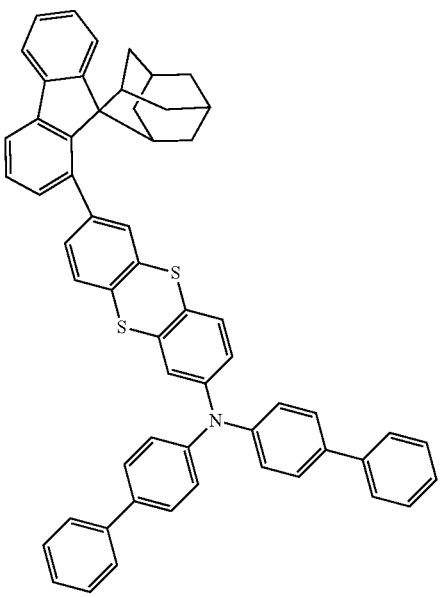

693
-continued
741
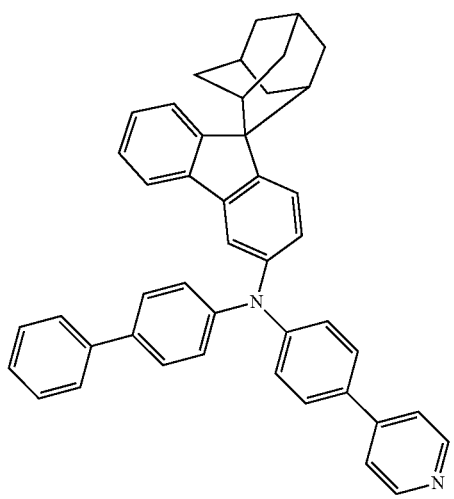
742
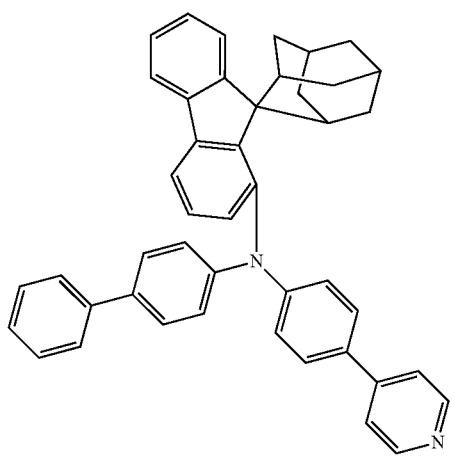
743
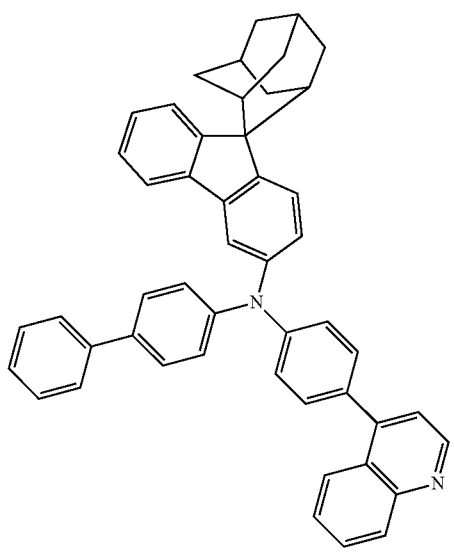
694
-continued
744
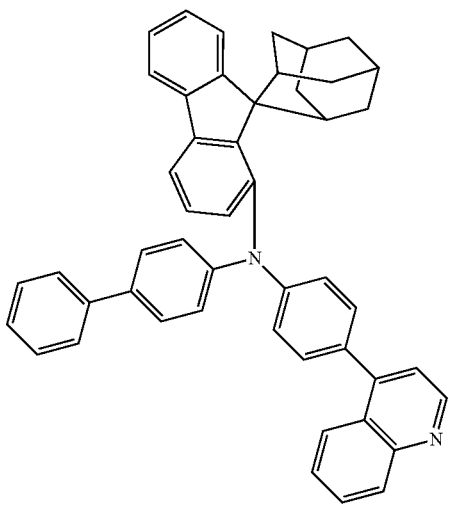
745
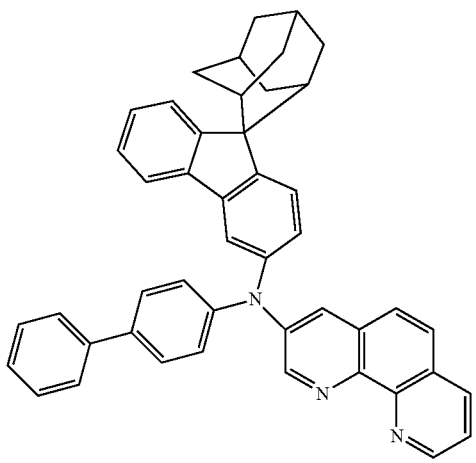
746
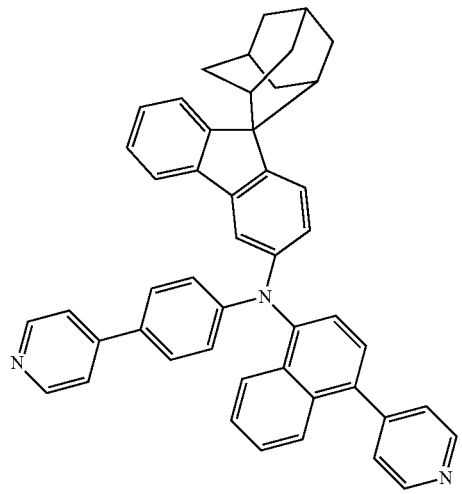

747 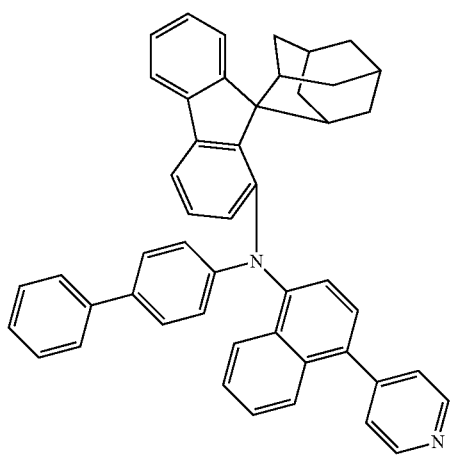
748 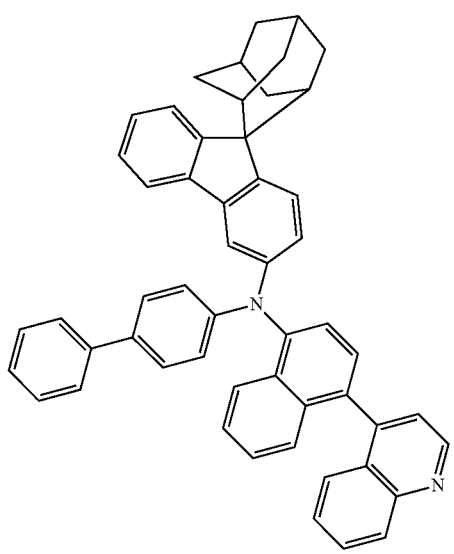
749 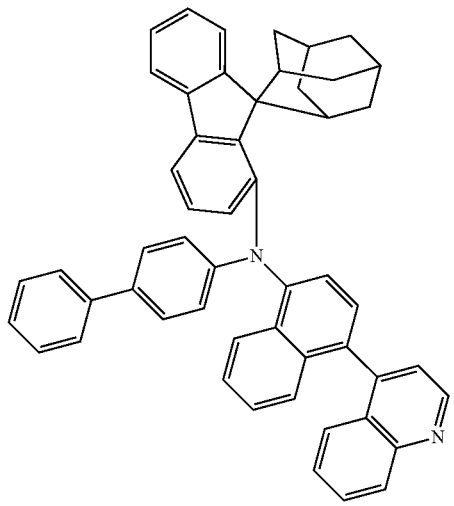
750 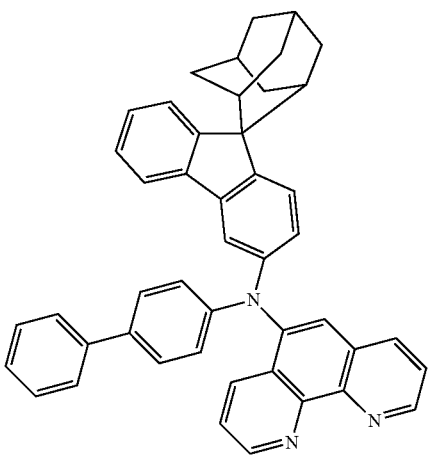
751 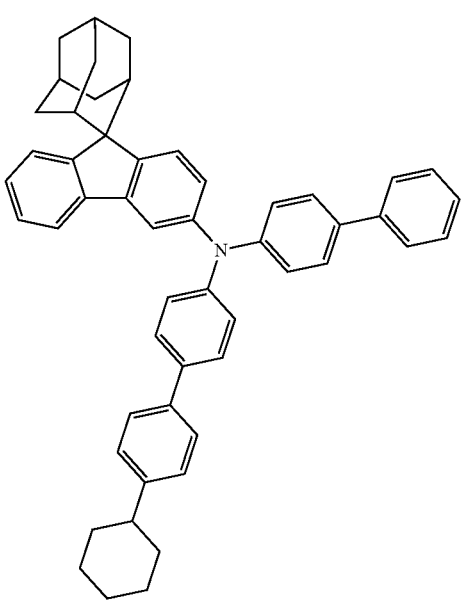
752 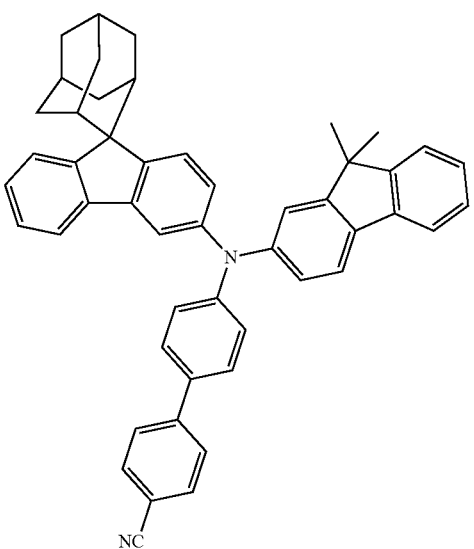

697
-continued
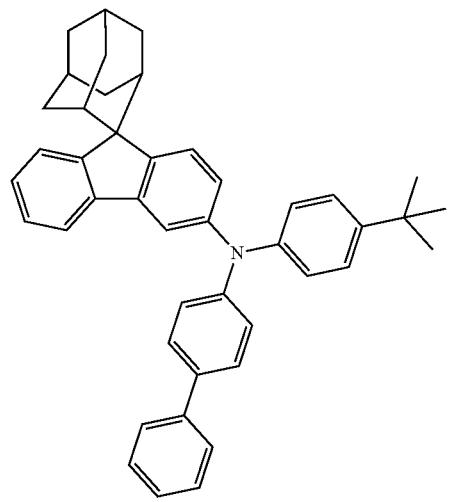
753
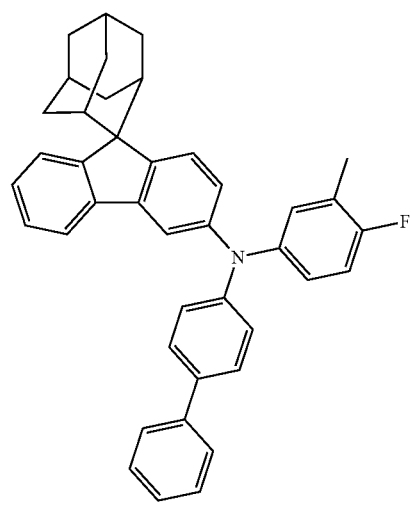
754
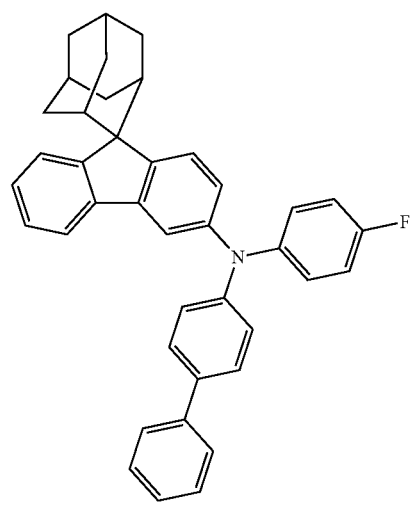
755
698
-continued
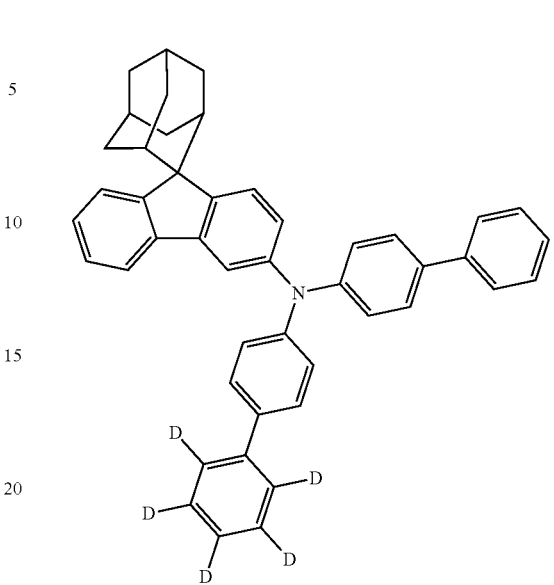
756
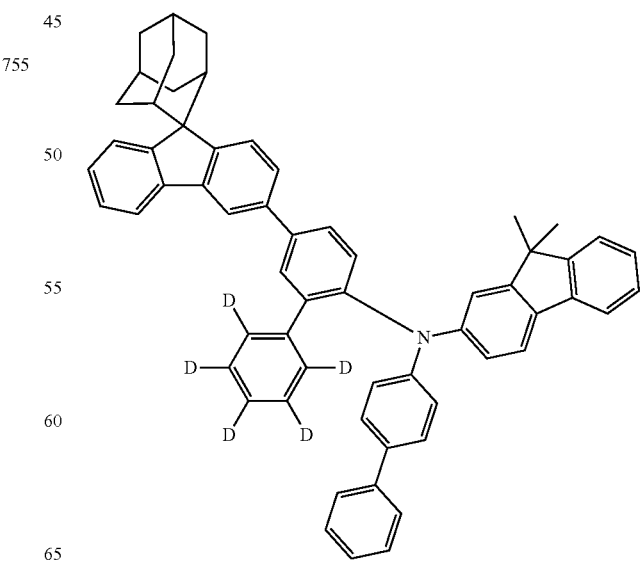
757

699
-continued
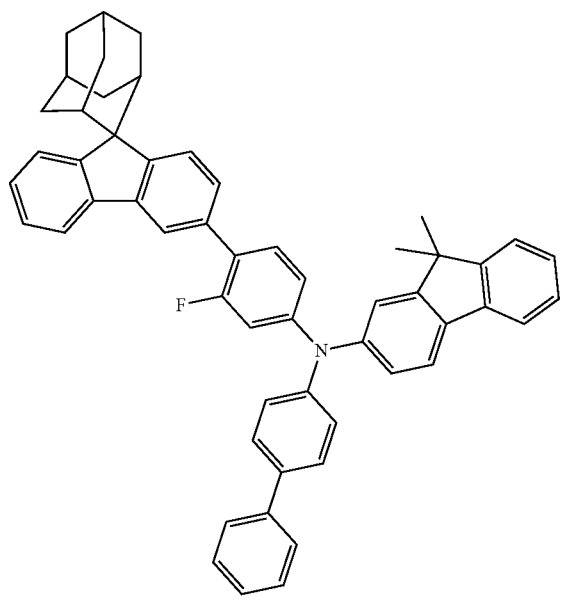
758
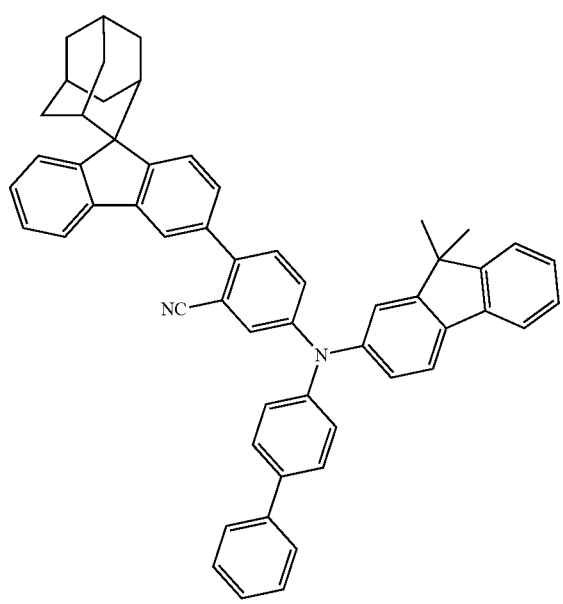
759
700
-continued
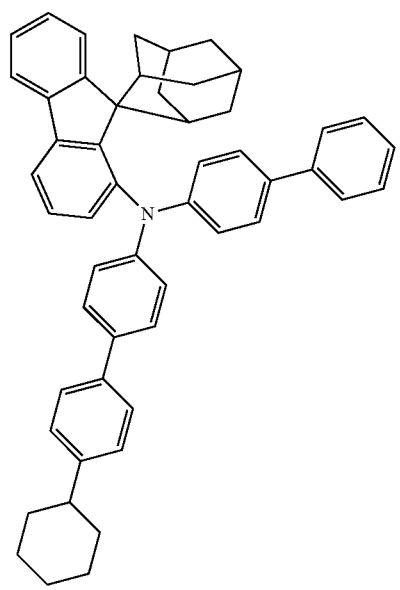
800
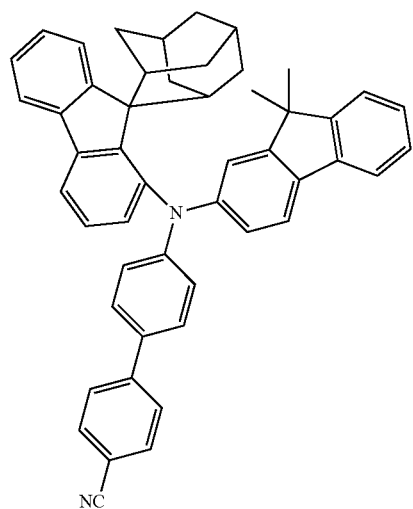
801
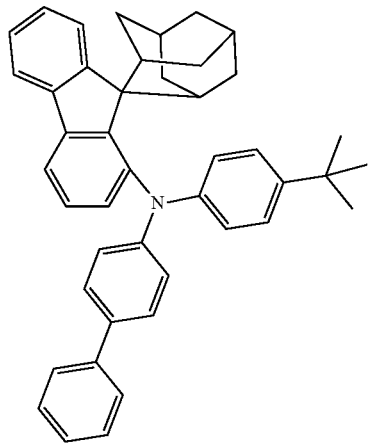
802

803 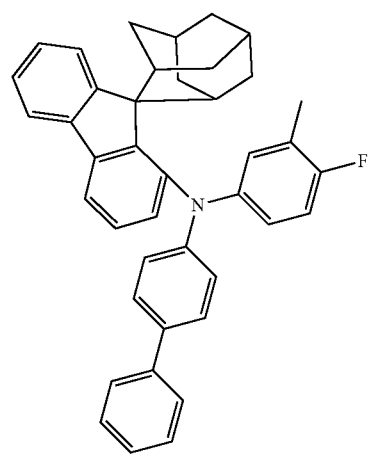
804 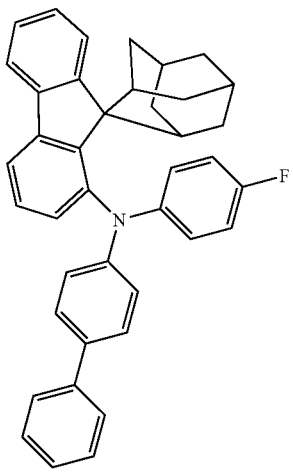
805 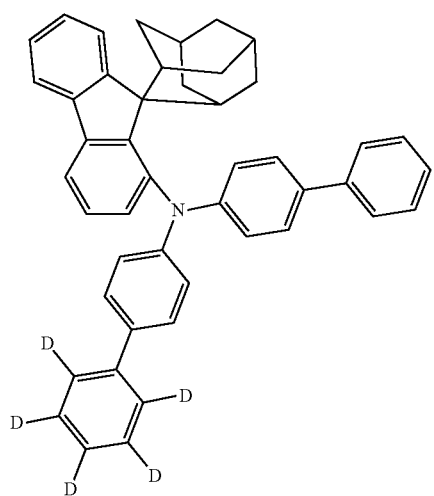
806 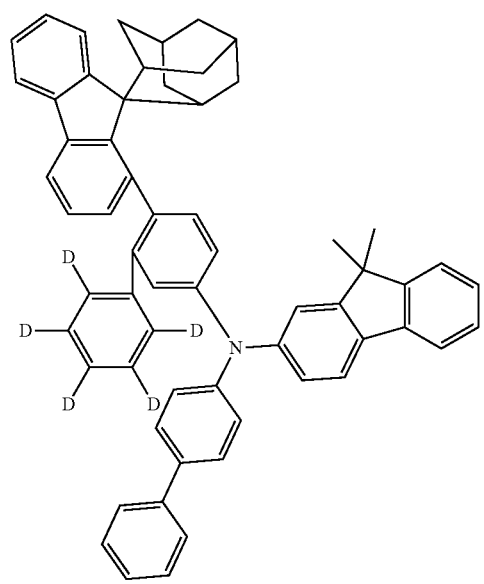
807 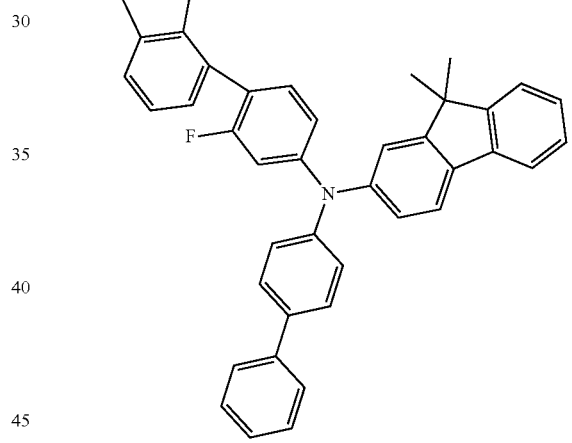
808 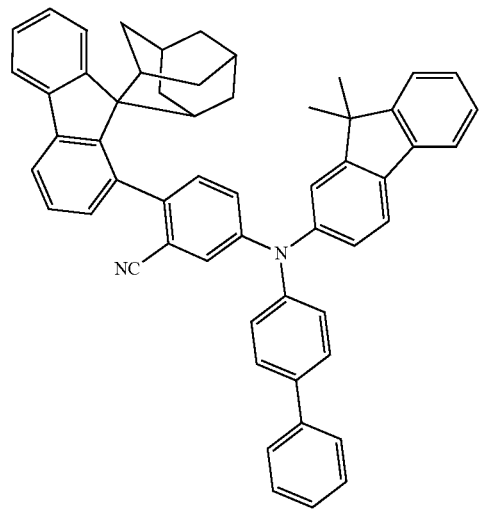

703
-continued
809
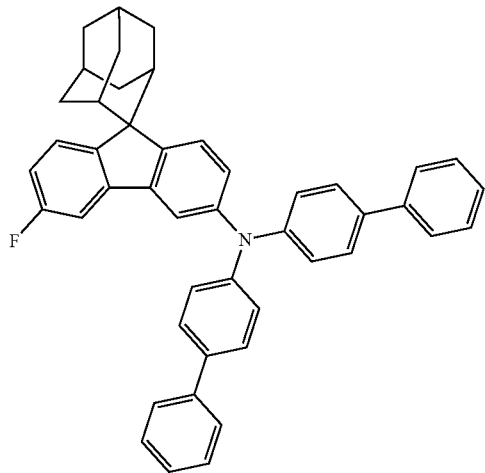
810
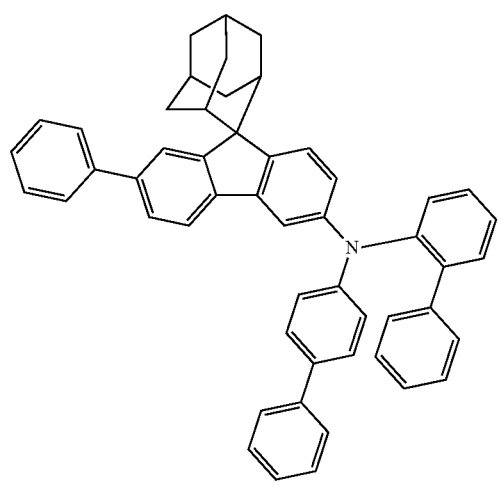
811
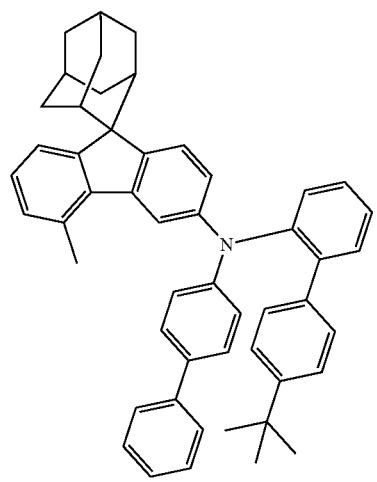
704
-continued
812
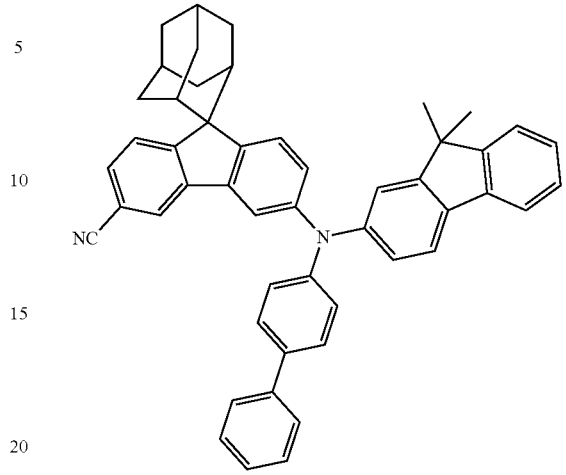
813
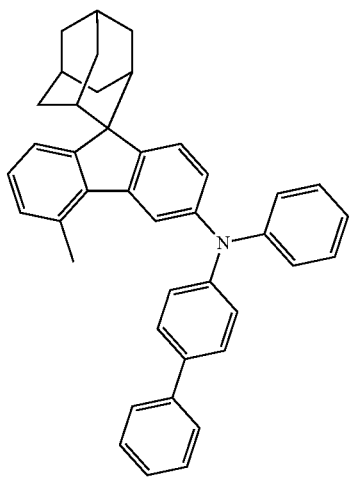
814
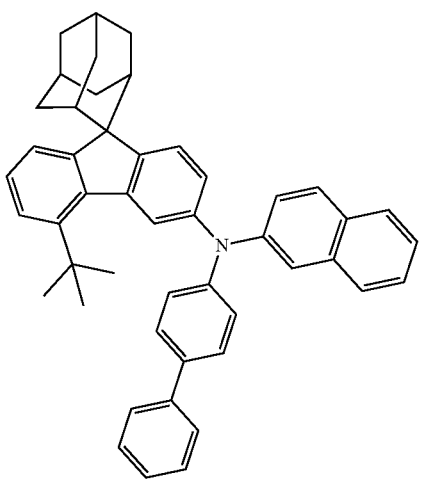

815
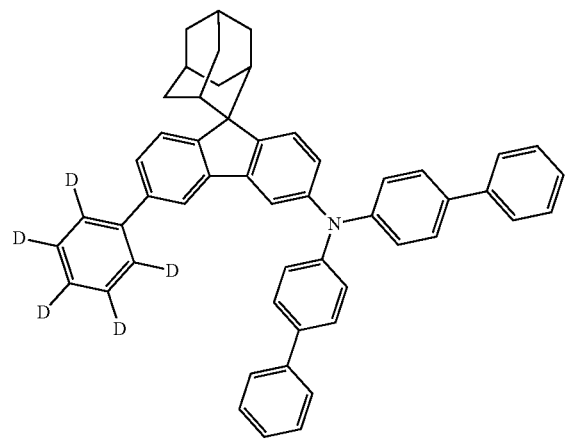
818
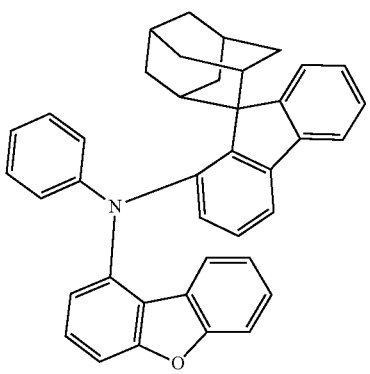
816
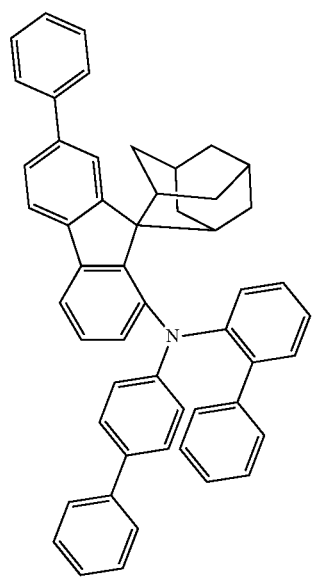
819
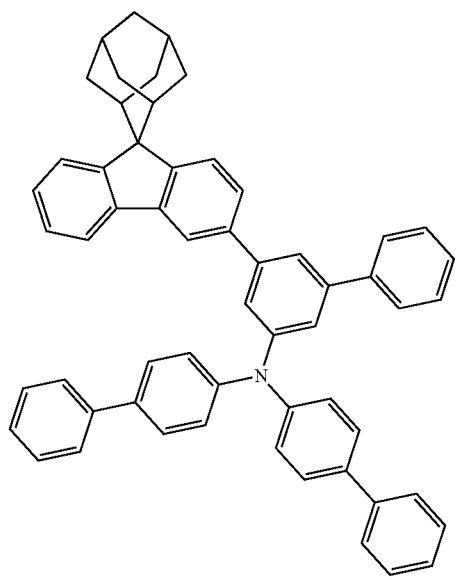
817
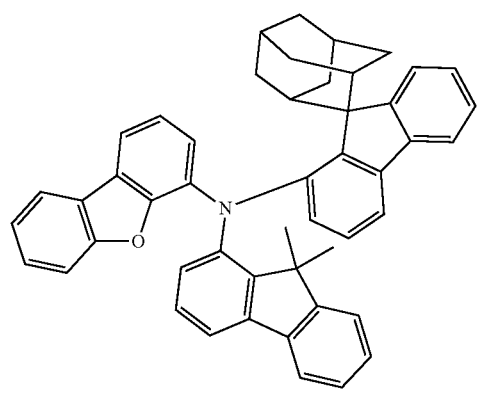
820
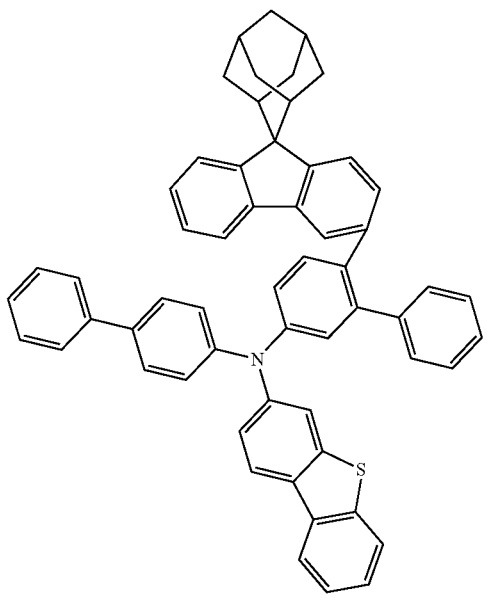

707
-continued
821
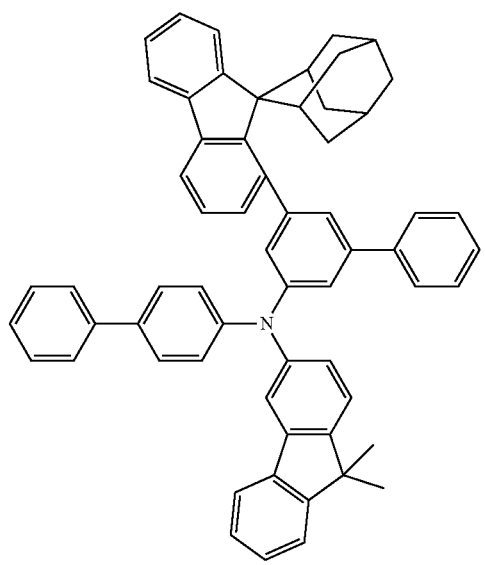
822
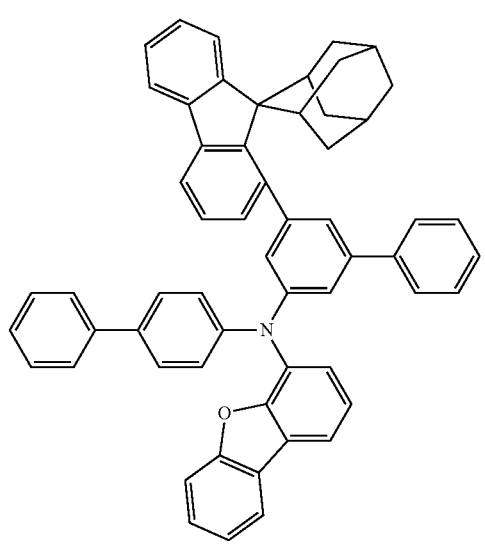
708
-continued
823
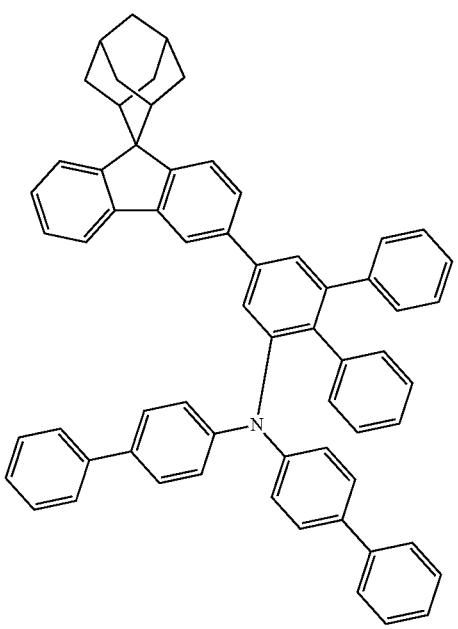
824
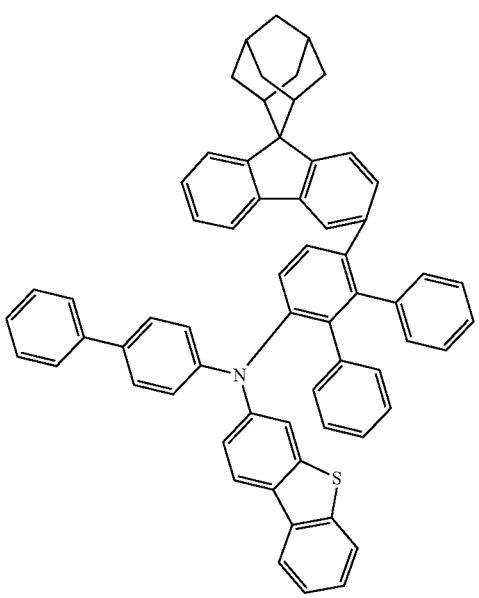

709
-continued
825
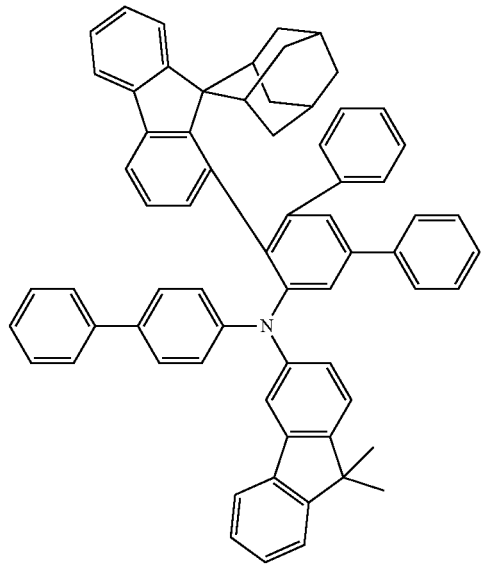
826
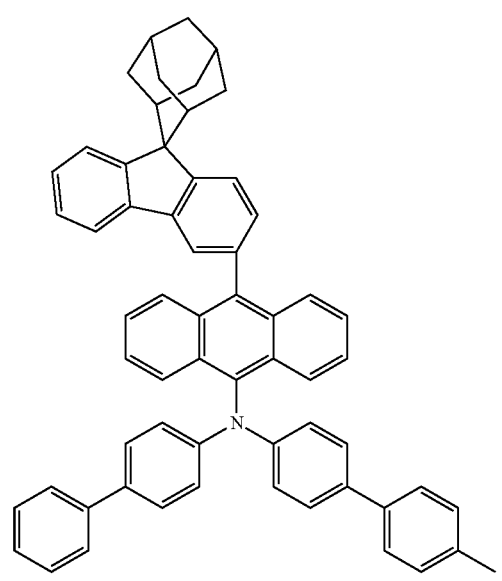
827
710
-continued
828
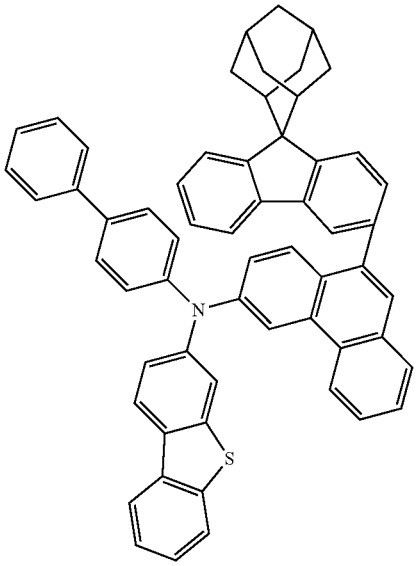
829
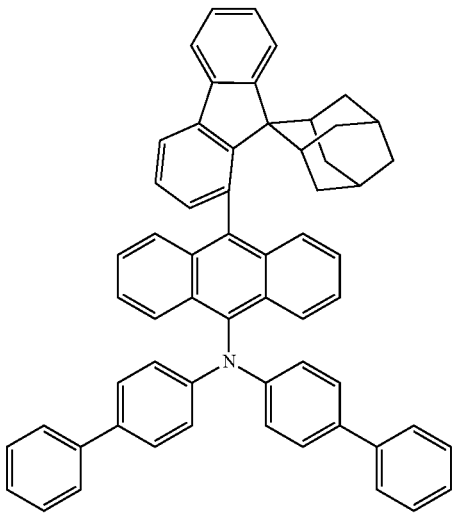
830
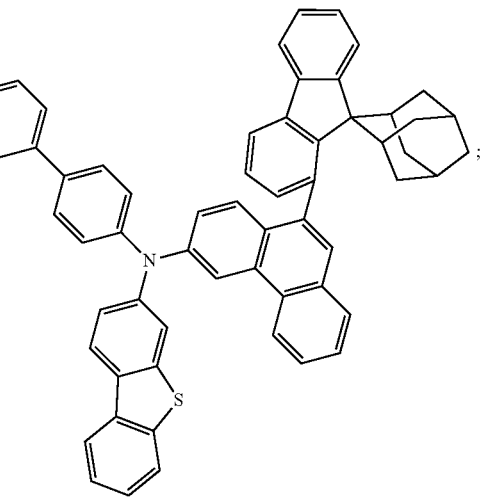
and
wherein the electronic element is a green light device.

4. The electronic element of claim 1, further comprising an anode and a cathode disposed opposite to each other, and a functional layer disposed between the anode and the cathode; wherein the functional layer contains the hole transporting layer and the electronic blocking layer.

5. An electronic device including the electronic element of claim 4.

\* \* \* \* \*